US008071592B2

(12) United States Patent
Ballell et al.

(10) Patent No.: US 8,071,592 B2
(45) Date of Patent: Dec. 6, 2011

(54) DERIVATIVES AND ANALOGS OF N-ETHYLQUINOLONES AND N-ETHYLAZAQUINOLONES

(75) Inventors: Lluis Ballell, Madrid (ES); David Barros, Madrid (ES); Gerald Brooks, Harlow (GB); Julia Castro Pichel, Madrid (ES); Steven Dabbs, Harlow (GB); Robert A Daines, Collegeville, PA (US); David Thomas Davies, Harlow (GB); Jose Maria Fiandor Roman, Madrid (ES); Israil Pendrak, Collegeville, PA (US); Modesto J Remuiñan Blanco, Madrid (ES); Jason Anthony Rossi, Collegeville, PA (US); Ilaria Giordano, Harlow (GB); Alan Joseph Hennessy, Harlow (GB); James B Hoffman, Collegeville, PA (US); Graham Elgin Jones, Harlow (GB); Timothy James Miles, Harlow (GB); Neil David Pearson, Harlow (GB); Lihua(lily) Zhang, Collegeville, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 252 days.

(21) Appl. No.: 12/374,389

(22) PCT Filed: Jul. 18, 2007

(86) PCT No.: PCT/EP2007/057422
  § 371 (c)(1),
  (2), (4) Date: Jan. 20, 2009

(87) PCT Pub. No.: WO2008/009700
  PCT Pub. Date: Jan. 24, 2008

(65) Prior Publication Data
  US 2009/0270374 A1    Oct. 29, 2009

Related U.S. Application Data

(60) Provisional application No. 60/807,850, filed on Jul. 20, 2006, provisional application No. 60/913,057, filed on Apr. 20, 2007.

(30) Foreign Application Priority Data

May 18, 2007    (EP) ...................................... 07381041

(51) Int. Cl.
  C07D 491/04    (2006.01)
  C07D 497/04    (2006.01)
  C07D 498/04    (2006.01)
  A61K 31/5383   (2006.01)
  A61K 31/519    (2006.01)

(52) U.S. Cl. ..................... 514/230.5; 544/105; 544/279; 514/264.1

(58) Field of Classification Search .................. 544/105, 544/279; 514/230.5, 264.1
  See application file for complete search history.

(56) References Cited

U.S. PATENT DOCUMENTS

2009/0198063 A1    8/2009 Kiyoto et al. ................. 546/122

FOREIGN PATENT DOCUMENTS

| WO | WO 2006/134378 A | 12/2006 |
| WO | WO 2006/137485 A | 12/2006 |
| WO | WO 2007/138974   | 5/2007 |
| WO | WO 2008071961    | 6/2008 |
| WO | WO 2008071962    | 6/2008 |
| WO | WO 2008071964    | 6/2008 |
| WO | WO 2008071981    | 6/2008 |
| WO | 2009001126 A1    | 12/2008 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Ali A. Y, et al.: "Synthesis and Antimicrobial activities of some quinoxalinonyl amino acid and peptide derivatives." Indian Journal of Chemistry, Section B: Organic, Inc. Medicinal, Publications and Informations directorate, New Delhi, In, vol. 42, No. 11, 2003, pp. 2835-2845, XP008085070; ISSN: 0019-5103; The whole document.
Deshmukh M. B. et al.: Synthesis of biological activity of some new 1-Substituted-quinolone Derivatives Journal of the Indian Chemical Society, The Indian Chemical Society, Calcutta, In. vol. 74, No. 1, 1997, pp. 52-53, XP008085069, ISSN: 0019-4522, the whole document.

* cited by examiner

*Primary Examiner* — Kahsay T Habte
(74) *Attorney, Agent, or Firm* — Robert H. Brink

(57) ABSTRACT

Bicyclic nitrogen containing compounds and their use as antibacterials.

16 Claims, No Drawings

DERIVATIVES AND ANALOGS OF N-ETHYLQUINOLONES AND N-ETHYLAZAQUINOLONES

This application is a 371 of International Application No. PCT/EP2007/057422, filed 18 Jul. 2007, which claims the priority of EP 07381041.8 filed 18 May 2007, and claims the benefit of U.S. Provisional Application No. 60/913,057, filed 20 Apr. 2007 and U.S. Provisional Application No. 60/807,850 filed 20 Jul. 2006 which are incorporated herein in their entirety.

This invention relates to novel compounds, compositions containing them and their use as antibacterials including the treatment of tuberculosis.

WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO06002047, WO06014580, WO06010040, WO06017326, WO06012396, WO06017468, WO06020561, WO01/25227, WO02/40474, WO02/07572, WO2004035569, WO2004089947, WO04024712, WO04024713, WO04087647, WO2005016916, WO2005097781, WO06010831, WO04035569, WO04089947, WO06021448, WO06032466, WO06038172, WO06046552, WO06134378 and WO06137485 disclose quinoline, naphthyridine, morpholine, cyclohexane, piperidine and piperazine derivatives having antibacterial activity.

This invention provides a compound of formula (I) or a pharmaceutically acceptable salt, solvate or N-oxide thereof:

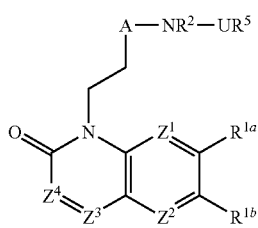

(I)

wherein:

two of $Z^1$, $Z^2$, $Z^3$ and $Z^4$ are independently $CR^{1c}$ or N and the remainder are independently $CR^{1c}$; or or $Z^3$ and $Z^4$ together represent S and one of $Z^1$ and $Z^2$ is $CR^{1c}$ or N and the other is independently $CR^{1c}$;

$R^{1a}$, $R^{1b}$ and $R^{1c}$ are independently selected from hydrogen; halogen; cyano; $(C_{1-6})$ alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted $(C_{1-6})$alkyl; $(C_{1-6})$alkoxy-substituted $(C_{1-6})$alkyl; hydroxy $(C_{1-6})$alkyl; an amino group optionally N-substituted by one or two $(C_{1-6})$ alkyl, formyl, $(C_{1-6})$alkylcarbonyl or $(C_{1-6})$alkylsulphonyl groups; or aminocarbonyl wherein the amino group is optionally substituted by $(C_{1-4})$alkyl; or two of $R^{1a}$, $R^{1b}$ and $R^{1c}$ on adjacent carbon atoms may together form an ethylenedioxy group;

$R^2$ is hydrogen, or $(C_{1-4})$alkyl, or together with $R^6$ forms Y as defined below;

A is a group (i):

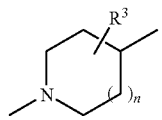

(ia)

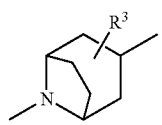

(ib)

in which: $R^3$ is as defined for $R^{1a}$, $R^{1b}$ and $R^{1c}$ or is oxo or aminomethyl and n is 1 or 2;

or A is a group (ii)

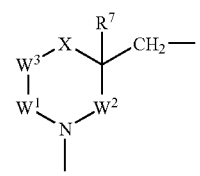

(ii)

$W^1$, $W^2$ and $W^3$ are $CR^4R^8$ or $W^2$ and $W^3$ are $CR^4R^8$ and $W^1$ represents a bond between $W^3$ and N.

X is O, $CR^4R^8$, or $NR^6$;

one $R^4$ is as defined for $R^{1a}$, $R^{1b}$ and $R^{1c}$ and the remainder and $R^8$ are hydrogen or one $R^4$ and $R^8$ are together oxo and the remainder are hydrogen;

$R^6$ is hydrogen or $(C_{1-6})$alkyl; or together with $R^2$ forms Y;

$R^7$ is hydrogen; halogen; hydroxy optionally substituted with $(C_{1-6})$alkyl; or $(C_{1-6})$ alkyl;

Y is $CR^4R^8CH_2$; $CH_2CR^4R^8$; (C=O); $CR^4R^8$; $CR^4R^8$(C=O); or (C=O)$CR^4R^8$;

or when X is $CR^4R^8$, $R^8$ and $R^7$ together represent a bond;

U is selected from CO, and $CH_2$ and $R^5$ is an optionally substituted bicyclic carbocyclic or heterocyclic ring system (B):

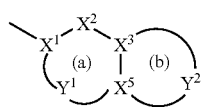

(B)

containing up to four heteroatoms in each ring in which
at least one of rings (a) and (b) is aromatic;

$X^1$ is C or N when part of an aromatic ring, or $CR^{14}$ when part of a non-aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring;

$Y^2$ is a 2 to 6 atom linker group, each atom of $Y^2$ being independently selected from N, $NR^{13}$, Q, $S(O)_x$, CO, $CR^{14}$ when part of an aromatic or non-aromatic ring or may additionally be $CR^{14}R^{15}$ when part of a non aromatic ring;

each of $R^{14}$ and $R^{15}$ is independently selected from: H; $(C_{1-4})$alkylthio; halo; carboxy$(C_{1-4})$alkyl; $(C_{1-4})$alkyl; $(C_{1-4})$alkoxycarbonyl; $(C_{1-4})$alkylcarbonyl; $(C_{1-4})$ alkoxy $(C_{1-4})$alkyl; hydroxy; hydroxy$(C_{1-4})$alkyl; $(C_{1-4})$alkoxy; nitro; cyano; carboxy; amino or aminocarbonyl optionally mono- or di-substituted by $(C_{1-4})$alkyl; or $R^{14}$ and $R^{15}$ may together represent oxo;

each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; $(C_{1-4})$alkoxycarbonyl; $(C_{1-4})$alkylcarbonyl; $(C_{1-6})$alkylsulphonyl; aminocarbonyl wherein the amino group is optionally mono or disubstituted by $(C_{1-4})$alkyl;

each x is independently 0, 1 or 2.

This invention further provides a compound of formula (I) other than a compound where:

$Z^3$ and $Z^4$ together represent S and one of $Z^1$ and $Z^2$ is $CR^{1c}$ or N and the other is independently $CR^{1c}$; and/or $R^3$ is aminomethyl;

or a pharmaceutically acceptable salt, solvate or N-oxide thereof.

This invention also provides a method of treatment of bacterial infections including tuberculosis in mammals, particularly in man, which method comprises the administration to a mammal in need of such treatment an effective amount of a compound of formula (I), or a pharmaceutically acceptable salt, solvate or N-oxide thereof.

The invention also provides the use of a compound of formula (I), or a pharmaceutically acceptable salt, solvate or N-oxide thereof, in the manufacture of a medicament for use in the treatment of bacterial infections including tuberculosis in mammals.

The invention also provides a pharmaceutical composition comprising a compound of formula (I), or a pharmaceutically acceptable salt, solvate or N-oxide thereof, and a pharmaceutically acceptable carrier.

This invention further provides a compound of formula (IA) or a pharmaceutically acceptable salt, solvate or N-oxide thereof:

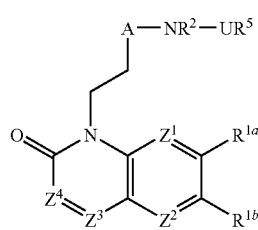

(IA)

wherein:

two of $Z^1$, $Z^2$ and $Z^3$ are independently $CR^{1c}$ or N and the remainder are independently $CR^{1c}$;

$Z^4$ is CH;

$R^{1a}$ is hydrogen, halogen, cyano or hydroxy substituted with $(C_{1-6})$alkyl;

$R^{1b}$ is hydrogen;

When $Z^3$ is $CR^{1c}$, $R^{1c}$ is hydrogen;

When $Z^1$ or $Z^2$ is $CR^{1c}$, $R^{1c}$ is hydrogen;

$R^2$ is hydrogen;

A is a group (ia):

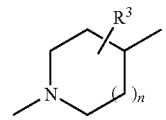

(ia)

in which: $R^3$ is hydrogen or hydroxy and n is 1;

or A is a group (ii)

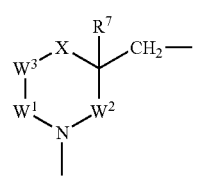

(ii)

$W^1$, $W^2$ and $W^3$ are $CH_2$;

or $W^2$ and $W^3$ are $CH_2$ and $W^1$ represents a bond between $W^3$ and N.

X is O or $CR^4R^8$;

$R^4$ is hydrogen or hydroxy;

$R^8$ is hydrogen;

$R^7$ is hydrogen;

U is selected from CO, and $CH_2$ and $R^5$ is an optionally substituted bicyclic heterocyclic ring system (B):

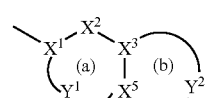

(B)

containing up to four heteroatoms in each ring in which ring (a) is aromatic and (b) is aromatic or non-aromatic;

$X^1$ is C;

$X^2$ is N, O, S or $CR^{14}$;

$X^3$ and $X^5$ are both C;

$Y^1$ is a 1 or 2 atom linker group each atom of which is independently selected from N and $CR^{14}$;

$Y^2$ is a 3 or 4 atom linker group, each atom of $Y^2$ being independently selected from $NR^{13}$, O, S, CO, or i) $CR^{14}$ when part of an aromatic ring, or ii) $CR^{14}R^{15}$ when part of a non aromatic ring;

each of $R^{14}$ and $R^{15}$ is independently selected from: H or halo; and $R^{13}$ is H; or $(C_{1-4})$alkyl.

In a particular aspect, in respect of formula (IA), one or two of $Z^1$, $Z^2$ and $Z^3$ are N.

In a particular aspect, in respect of formula (IA), $R^{1a}$ is hydrogen, halogen or hydroxy substituted with $(C_{1-6})$alkyl. In a further aspect, in respect of formula (IA), $R^{1a}$ is hydrogen, fluoro or methoxy. In a yet further aspect, in respect of formula (IA), $R^{1a}$ is methoxy.

In a particular aspect, in respect of formula (IA), A is a group (ia):

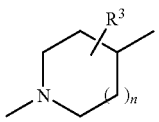

(ia)

in which: R³ is hydrogen or hydroxy and n is 1.

In a particular aspect, in respect of R⁵ in formula (IA):
X² is N or CR¹⁴, wherein R¹⁴ is selected from hydrogen or halo, for example chloro; and
Y¹ is a 2 atom linker group each atom of which is independently selected from N and CR¹⁴, provided that both atoms of Y¹ are not N.

In a particular aspect, in respect of R⁵ in formula (IA), Y² is a 4 atom linker group which is —NH—C(O)—CH₂-Q-, wherein Q is selected from O, S and CH₂.

In a particular aspect, in respect of R⁵ in formula (IA), Y² is other than —O—CH₂—CH₂—O—.

In particular aspects:
(1) each of Z¹, Z², Z³ and Z⁴ is independently CR¹ᶜ;
(2) Z¹ is N and each of Z², Z³ and Z⁴ is independently CR¹ᶜ;
(3) Z² is N and each of Z¹, Z³ and Z⁴ is independently CR¹ᶜ;
(4) Z³ is N and each of Z¹, Z² and Z⁴ is independently CR¹ᶜ;
(5) Z¹ and Z³ are N and Z² and Z⁴ are independently CR¹ᶜ;
(6) Z² and Z³ are N and Z¹ and Z⁴ are independently CR¹ᶜ;
(7) Z³ and Z⁴ are N and Z¹ and Z² are independently CR¹ᶜ;
(8) Z³ and Z⁴ together are S and Z¹ and Z⁴ are independently CR¹ᶜ;
(9) Z³ and Z⁴ together are S and Z¹ is CR¹ᶜ and Z⁴ is N;
(10) Z¹ and Z² are N and Z³ and Z⁴ are independently CR¹ᶜ.

In a particular aspect each R¹ᵃ, R¹ᵇ and R¹ᶜ is independently hydrogen, (C₁₋₄) alkoxy, (C₁₋₄)alkylthio, (C₁₋₄)alkyl, cyano, carboxy, hydroxymethyl or halogen; more particularly hydrogen, methoxy, methyl, ethyl, cyano, or halogen.

In some embodiments only one group R¹ᵃ, R¹ᵇ or R¹ᶜ is other than hydrogen. In a particular embodiment R¹ᵃ is methoxy, cyano or halo such as fluoro, chloro or bromo and R¹ᵇ and R¹ᶜ are hydrogen. In an alternative embodiment R¹ᵇ is other than hydrogen, for example fluoro.

In other embodiments two groups R¹ᵃ, R¹ᵇ or R¹ᶜ are other than hydrogen. In particular R¹ᵃ is fluoro and R¹ᵇ or R¹ᶜ are other than hydrogen, for example fluoro, ethyl or methoxy.

In further embodiments, Z¹ is R¹ᶜ and R¹ᵃ and R¹ᶜ together form an ethylenedioxy group.

In a particular aspect R² is hydrogen.

Particular examples of R³ include hydrogen; optionally substituted hydroxy; optionally substituted amino; halogen; (C₁₋₄) alkyl; 1-hydroxy-(C₁₋₄) alkyl; optionally substituted aminocarbonyl. More particular R³ groups are hydrogen; CONH₂; 1-hydroxyalkyl e.g. CH₂OH; optionally substituted hydroxy e.g. methoxy; optionally substituted amino; and halogen, in particular fluoro. Most particularly R³ is hydrogen or hydroxy.

In a particular aspect, when A is (ia), n is 1. In a further aspect, R³ is in the 3- or 4-position, more particularly in the 3-position. In a more particular aspect, A is (ia), n is 1 and R³ is in the 3-position, and more particularly is cis to the NR² group.

In particular embodiments, A is a group (ia) in which n is 1 and R³ is hydrogen or hydroxy. More particularly, where A is 3-hydroxy-piperidin-4-yl-amino the configuration is (3R, 4S).

In a particular aspect, when A is (ii), X is CR⁴R⁸, R⁸ is H and R⁴ is H or OH. More particularly when R⁴ is OH it is trans to R⁷. In a further aspect W¹ is a bond. In another aspect R⁷ is H. In an additional aspect W¹ is a bond, W² and W³ are both CH₂ and R⁷ is H. Where A is 3-hydroxypyrrolidin-4-ylmethyl, in a particular aspect the configuration is (3S,4S).

In a particular aspect, when A is (ii), X is CR⁴R⁸, R⁸ is H, R⁴ is OH, W¹, W² and W³ are all CH₂ and R⁷ is H, A is a 4-hydroxypiperidin-3-ylmethyl. More particularly R⁴OH is trans to R⁷H.

In a particular aspect, when A is (ii), X is O, R⁷ is H and W¹, W² and W³ are each CH₂.

In certain embodiments U is CH₂.

In certain embodiments R⁵ is an aromatic heterocyclic ring (B) having 8-11 ring atoms including 2-4 heteroatoms of which at least one is N or NR¹³ in which, in particular embodiments, Y² contains 2-3 heteroatoms, one of which is 5 and 1-2 are N, with one N bonded to X³.

In alternative embodiments the heterocyclic ring (B) has ring (a) aromatic selected from optionally substituted benzo, pyrido, pyridazino and pyrimidino and ring (b) non aromatic and Y² has 3-4 atoms including at least one heteroatom, with O, S, CH₂ or NR¹³ bonded to X⁵, where R¹³ is other than hydrogen, and either NHCO bonded via N to X³, or O, S, CH₂, or NH bonded to X³. In a particular aspect the ring (a) contains aromatic nitrogen, and more particularly ring (a) is pyridine, pyrazine or pyrimidine.

In certain embodiments R⁵ is:

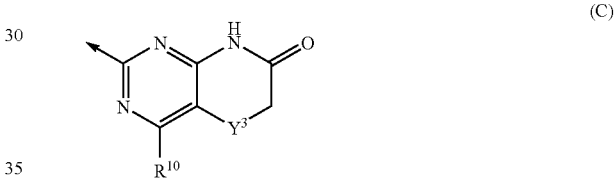

(C)

in which:
→ is the point of attachment;
Y³ is CH₂ or O; and
R¹⁰ is independently selected from hydrogen, halogen, (C₁₋₆)alkyl and (C₁₋₆) alkoxy.

More particularly R¹⁰ is selected from hydrogen, chloro, methyl and methoxy.

Examples of rings (B) include optionally substituted:
(a) and (b) Aromatic
1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, naphthalen-2-yl, 1,3-dioxo-isoindol-2-yl, benzimidazol-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-6-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimidin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo

[5,4-b]pyridin-6-yl, thiazolo[4,5-b]pyridin-5-yl, [1,2,3]thia-diazolo[5,4-b]pyridin-6-yl, 2H-isoquinolin-1-one-3-yl
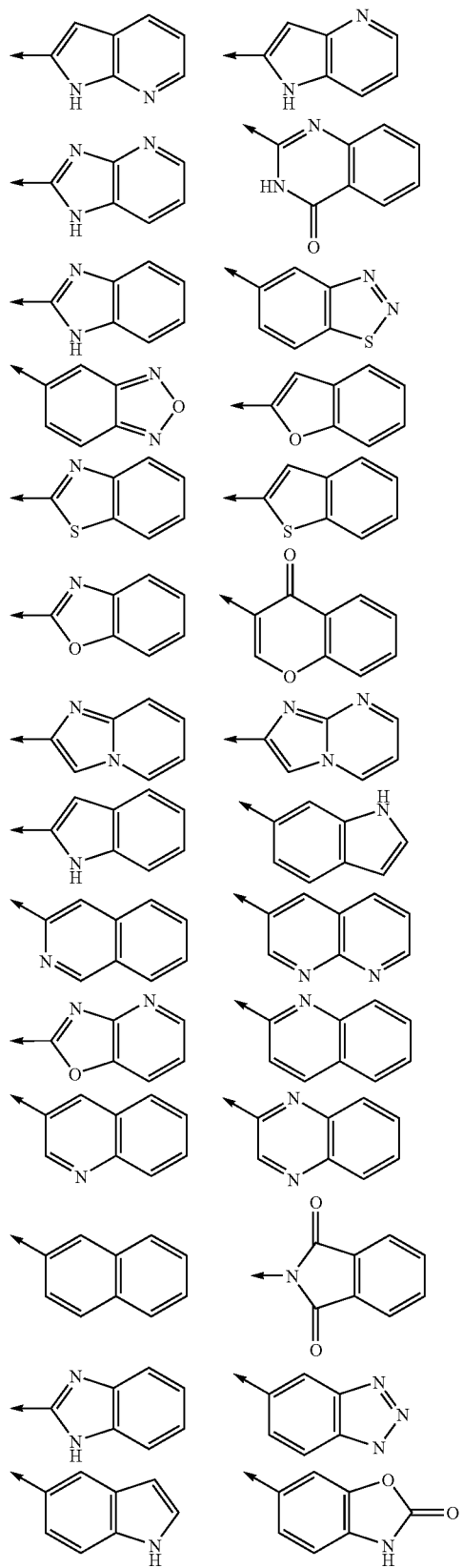
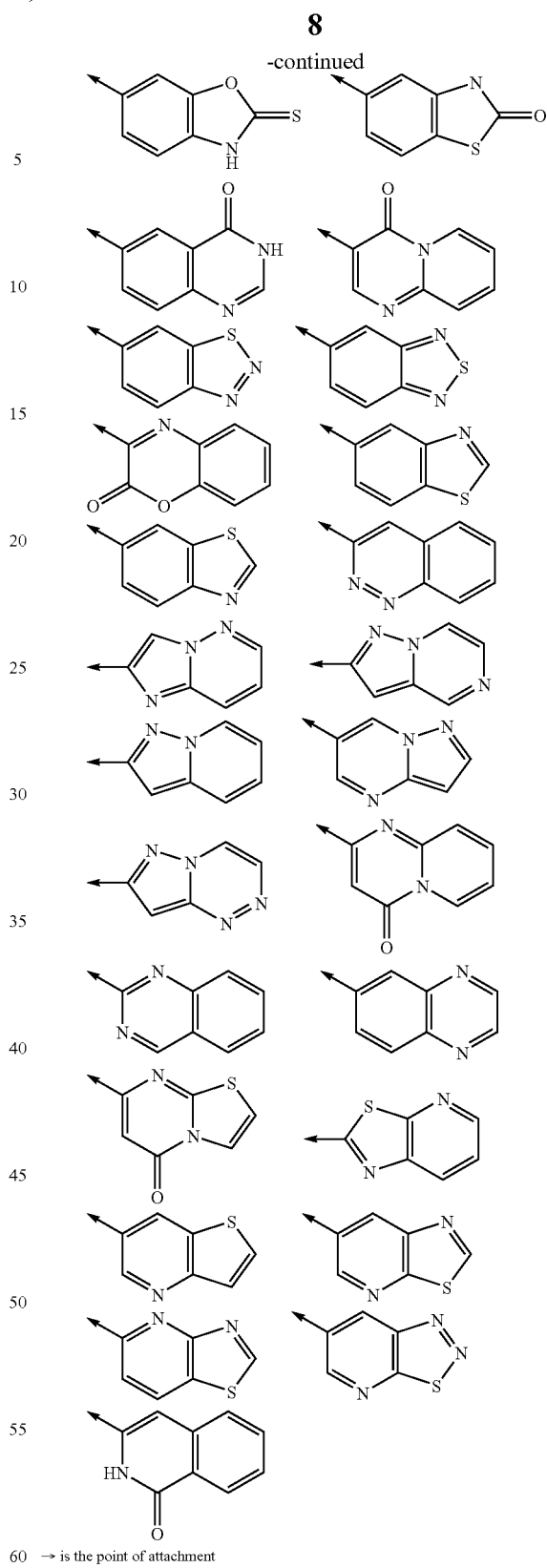
→ is the point of attachment
(a) is Non Aromatic
(2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3- yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, 5H-pyrano[2,3-d]pyrimidine, 8-substituted 2H-pyrido[1,2-a]pyrimidin-2-one, 2,3-dihydro-1-benzofuran-5-yl.

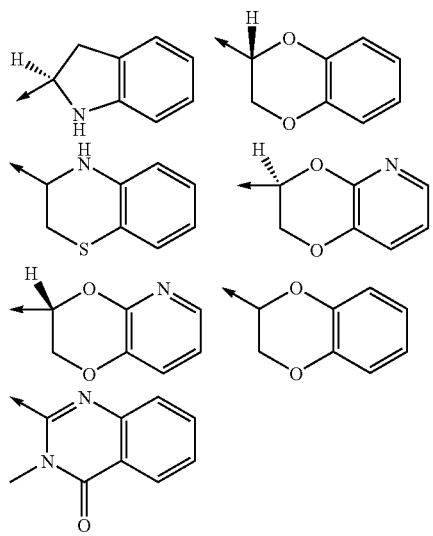

→ is the point of attachment (b) is Non Aromatic 1,1,3-trioxo-1,2,3,4-tetrahydrol $1^6$-benzo[1,4]thiazin-6-yl, benzo[1,3]dioxol-5-yl, 2,3-dihydro-benzo[1,4]dioxin-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, 1H-pyrido[2,3-b][1,4]thiazin-2-one-7-yl (2-oxo-2,3-dihydro-1H-pyrido[2,3-b][1,4]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 1,2,3,4-tetrahydro-[1,8]naphthyridin-7-yl, 2-oxo-3,4-dihydro-1H-[1,8]naphthyridin-6-yl, 6-oxo-6,7-dihydro-5H-8-thia-1,2,5-triaza-naphthalen-3-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6,7-dihydro-[1,4]dioxino[2,3-d]pyrimidin-2-yl, [1,3]oxathiolo[5,4-c]pyridin-6-yl, 3,4-dihydro-2H-pyrano[2,3-c]pyridine-6-yl, 2,3-dihydro[1,4]oxathiino[2,3-c]pyridine-7-yl, 6,7-dihydro[1,4]dioxino[2,3-c]pyridazin-3-yl, 6,7-dihydro[1,4]oxathiino[2,3-c]pyridazin-3-yl, 6,7-dihydro-5H-pyrano[2,3-c]pyridazin-3-yl, 5,6-dihydrofuro[2,3-c]pyridazin-3-yl, 2,3-dihydrofuro[2,3-c]pyridin-5-yl, 2-substituted 1H-pyrimido[5,4-b][1,4]oxazin-7(6H)-one, 2-substituted 5,6-dihydropyrido[2,3-d]pyrimidin-7(1H)-one, 7-substituted 2H-chromen-2-one, 7-substituted 2H-pyrano[2,3-b]pyridin-2-one, 2-substituted 6,7-dihydro-

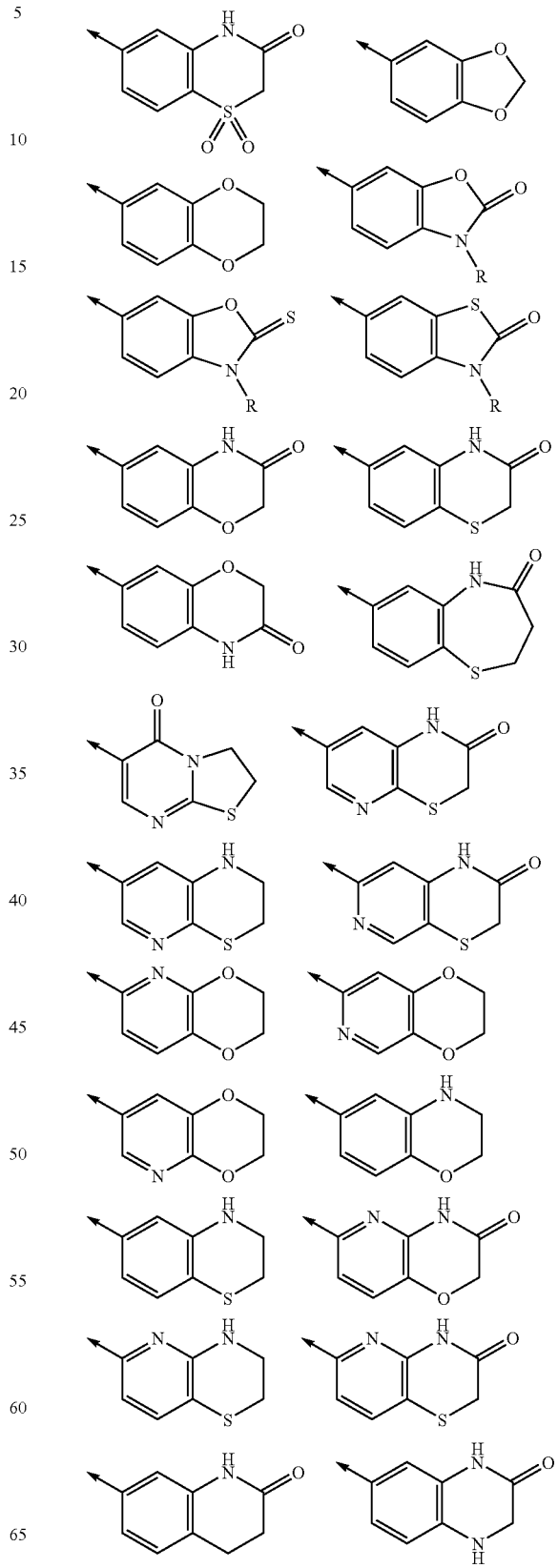

-continued

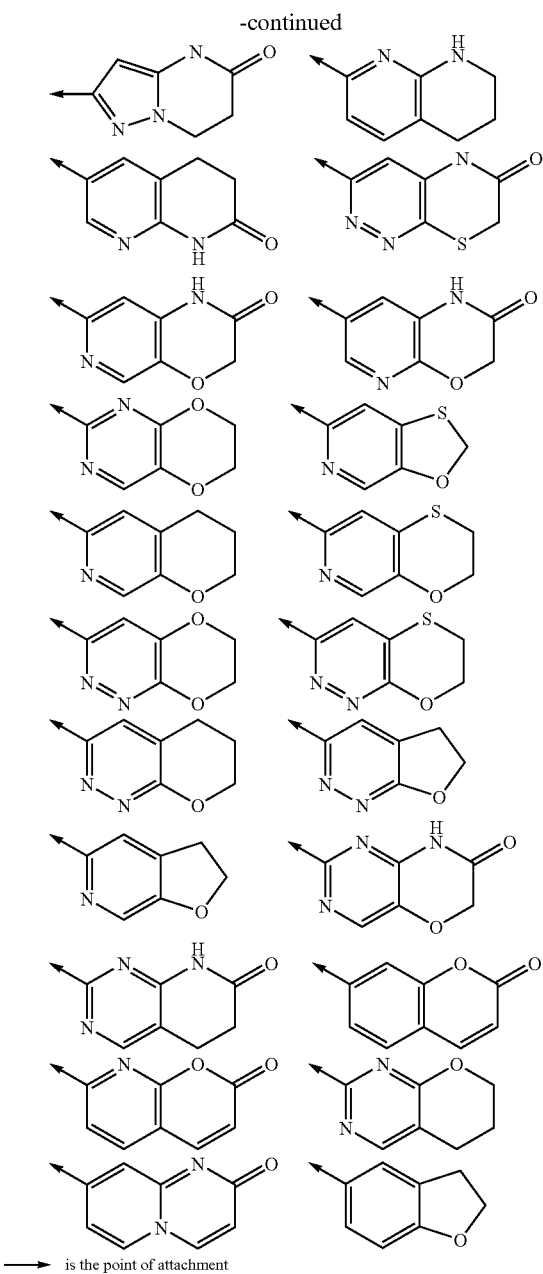

→ is the point of attachment

In some embodiments R[13] is H if in ring (a) or in addition $(C_{1-4})$alkyl such as methyl or isopropyl when in ring (b). More particularly, in ring (b) R[13] is H when NR[13] is bonded to X[3] and $(C_{1-4})$alkyl when NR[13] is bonded to X[5].

In further embodiments R[14] and R[15] are independently selected from hydrogen, halo, hydroxy, $(C_{1-4})$ alkyl, $(C_{1-4})$ alkoxy, nitro and cyano. More particularly R[15] is hydrogen.

More particularly each R[14] is selected from hydrogen, chloro, fluoro, hydroxy, methyl, methoxy, nitro and cyano. Still more particularly R[14] is selected from hydrogen, fluorine or nitro.

Most particularly R[14] and R[15] are each H.

Particular groups R[5] include:
[1,2,3]thiadiazolo[5,4-b]pyridin-6-yl
1H-pyrrolo[2,3-b]pyridin-2-yl
2,3-dihydro-[1,4]dioxino[2,3-b]pyridin-6-yl
2,3-dihydro-[1,4]dioxino[2,3-b]pyridin-7-yl
2,3-dihydro-[1,4]dioxino[2,3-c]pyridin-7-yl
2,3-dihydro-benzo[1,4]dioxin-6-yl
2-oxo-2,3-dihydro-1H-pyrido[2,3-b][1,4]oxazin-7-yl
2-oxo-2,3-dihydro-1H-pyrido[2,3-b][1,4]thiazin-7-yl
3,4-dihydro-2H-benzo[1,4]oxazin-6-yl
3-methyl-2-oxo-2,3-dihydro-benzooxazol-6-yl
3-oxo-3,4-dihydro-2H-benzo[1,4]oxazin-6-yl
3-oxo-3,4-dihydro-2H-pyrido[3,2-b][1,4]oxazin-6-yl
   (6-substituted 2H-pyrido[3,2-b][1,4]oxazin-3(4H)-one)
3-oxo-3,4-dihydro-2H-benzo[1,4]thiazin-6-yl (4H-benzo[1,4]thiazin-3-one-6-yl)
4-oxo-4H-pyrido[1,2-a]pyrimidin-2-yl
6-nitro-benzo[1,3]dioxol-5-yl
7-fluoro-3-oxo-3,4-dihydro-2H-benzo[1,4]oxazin-6-yl
8-hydroxy-1-oxo-1,2-dihydro-isoquinolin-3-yl
8-hydroxyquinolin-2-yl
benzo[1,2,3]thiadiazol-5-yl
benzo[1,2,5]thiadiazol-5-yl
benzothiazol-5-yl
thiazolo-[5,4-b]pyridin-6-yl
3-oxo-3,4-dihydro-2H-pyrido[3,2-b][1,4]thiazin-6-yl
   (6-substituted 2H-pyrido[3,2-b][1,4]thiazin-3(4H)-one)
7-chloro-3-oxo-3,4-dihydro-2H-pyrido[3,2-b][1,4]thiazin-6-yl
7-chloro-3-oxo-3,4-dihydro-2H-pyrido[3,2-b][1,4]oxazin-6-yl (6-substituted 7-chloro-2H-pyrido[3,2-b][1,4]oxazin-3(4H)-one)
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl
[1,3]oxathiolo[5,4-c]pyridin-6-yl
3,4-dihydro-2H-pyrano[2,3-c]pyridine-6-yl
2,3-dihydro-5-carbonitro-1,4-benzodioxin-7-yl (7-substituted 2,3-dihydro-1,4-benzodioxin-5-carbonitrile)
2,3-dihydro[1,4]oxathiino[2,3-c]pyridine-7-yl
2,3-dihydro-1-benzofuran-5-yl
6,7-dihydro[1,4]dioxino[2,3-c]pyridazin-3-yl
6,7-dihydro[1,4]oxathiino[2,3-c]pyridazin-3-yl
6,7-dihydro-5H-pyrano[2,3-c]pyridazin-3-yl
5,6-dihydrofuro[2,3-c]pyridazin-3-yl
2-substituted 1H-pyrimido[5,4-b][1,4]oxazin-7(6H)-one
2-substituted 4-chloro-1H-pyrimido[5,4-b][1,4]oxazin-7(6H)-one
2-substituted 5,6-dihydropyrido[2,3-d]pyrimidin-7(1H)-one
2-substituted 4-chloro-5,6-dihydropyrido[2,3-d]pyrimidin-7(1H)-one
2-substituted 4-methyl-5,6-dihydropyrido[2,3-d]pyrimidin-7(1H)-one
2-substituted 4-methyloxy-5,6-dihydropyrido[2,3-d]pyrimidin-7(1H)-one
7-substituted 2H-chromen-2-one
7-substituted 2H-pyrano[2,3-b]pyridin-2-one
4-chloro-6,7-dihydro-5H-pyrano[2,3-d]pyrimidin-2-yl
8-substituted 2H-pyrido[1,2-a]pyrimidin-2-one
6,7-dihydro-5H-pyrano[2,3-d]pyrimidin-2-yl)
5-chloro-1-benzothiophen-2-yl
6-chloro-1-benzothiophen-2-yl
1-benzothiophen-5-yl
1-methyl-1H-1,2,3-benzotriazol-6-yl imidazo[2,1-b][1,3]thiazol-6-yl
4-methyl-3,4-dihydro-2H-1,4-benzoxazin-7-yl
1-methyl-1H-indol-2-yl

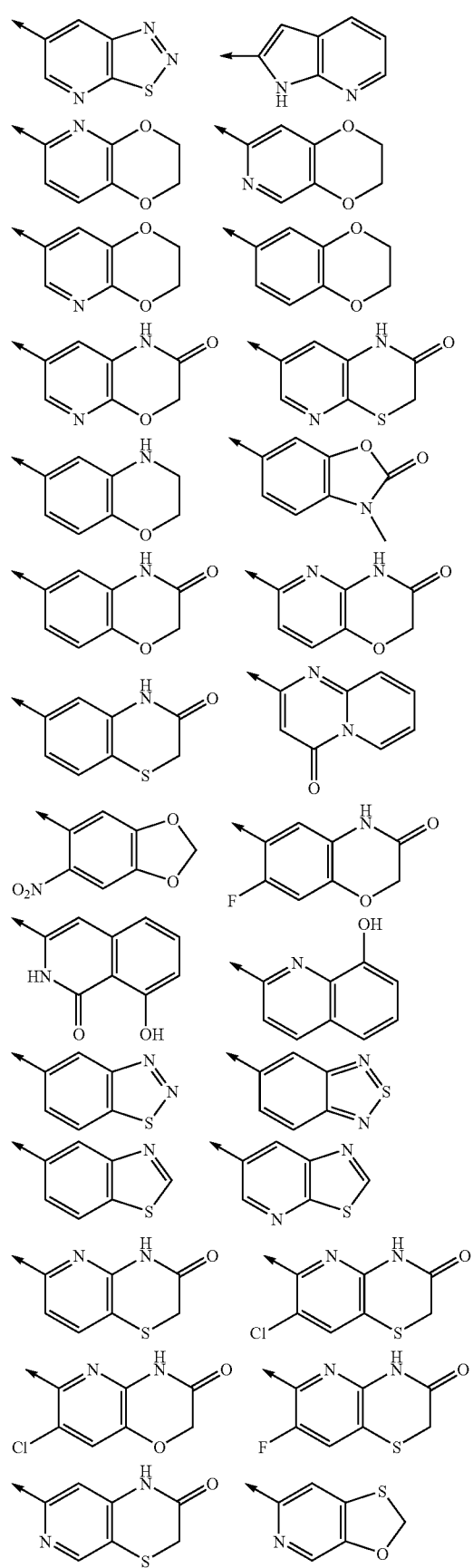
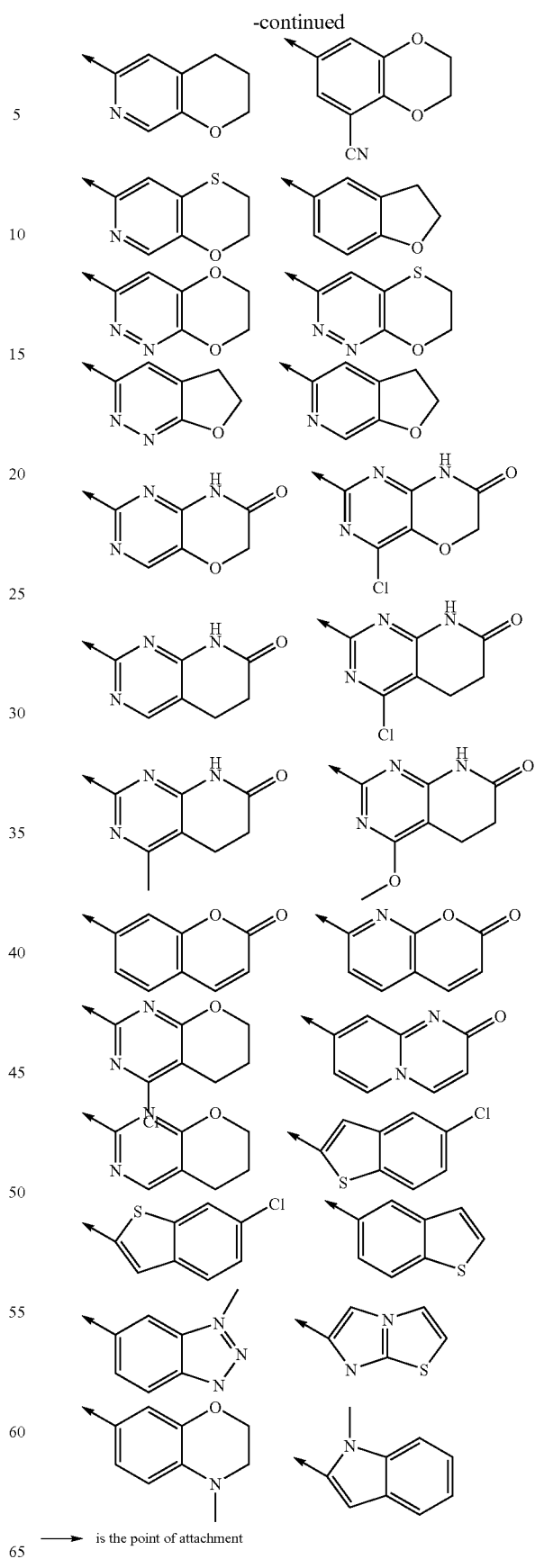
→ is the point of attachment especially
6-substituted 2H-pyrido[3,2-b][1,4]oxazin-3(4H)-one
2,3-dihydro-[1,4]dioxino[2,3-c]pyridin-7-yl
[1,3]oxathiolo[5,4-c]pyridin-6-yl
3,4-dihydro-2H-pyrano[2,3-c]pyridine-6-yl
6-substituted 2H-pyrido[3,2-b][1,4]thiazin-3(4H)-one
6-substituted 7-chloro-2H-pyrido[3,2-b][1,4]oxazin-3(4H)-one
6,7-dihydro[1,4]dioxino[2,3-c]pyridazin-3-yl
6,7-dihydro[1,4]oxathiino[2,3-c]pyridazin-3-yl
2-substituted 1H-pyrimido[5,4-b][1,4]oxazin-7(6H)-one
2-substituted 5,6-dihydropyrido[2,3-d]pyrimidin-7(1H)-one

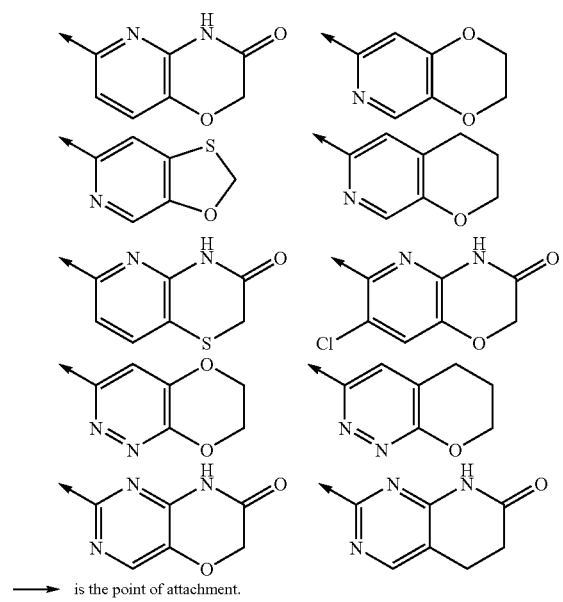

→ is the point of attachment.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo. Haloalkyl moieties include 1-3 halogen atoms.

Compounds within the invention contain a heterocyclyl group and may occur in two or more tautomeric forms depending on the nature of the heterocyclyl group; all such tautomeric forms are included within the scope of the invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Furthermore, it will be understood that phrases such as "a compound of formula (I) or a pharmaceutically acceptable salt, solvate or N-oxide thereof" are intended to encompass the compound of formula (I), an N-oxide of formula (I), a pharmaceutically acceptable salt of the compound of formula (I), a solvate of formula (I), or any pharmaceutically acceptable combination of these. Thus by way of non-limiting example used here for illustrative purpose, "a compound of formula (I) or a pharmaceutically acceptable salt or solvate thereof" may include a pharmaceutically acceptable salt of a compound of formula (I) that is further present as a solvate.

Since the compounds of formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of a compound of the formula (I) or pharmaceutically acceptable salt, solvate or N-oxide thereof.

Particular compounds according to the invention include those mentioned in the examples and their pharmaceutically acceptable N-oxides, salts and solvates.

Pharmaceutically acceptable salts of the above-mentioned compounds of formula (I) include the acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. The invention extends to all such derivatives.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Certain compounds of formula (I) may also exist in polymorphic forms and the invention includes such polymorphic forms.

In a further aspect of the invention there is provided a process for preparing compounds of formula (I), and pharmaceutically acceptable salt, solvate or N-oxides thereof, which process comprises reacting a compound of formula (II) with a compound of formula (III):

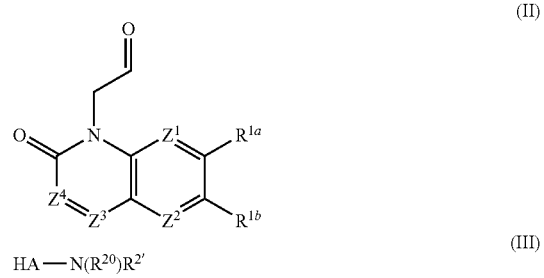

in which:
$R^{20}$ is $UR^5$ or a group convertible thereto and $R^{2'}$ is $R^2$ or a group convertible thereto, wherein $Z^1, Z^2, Z^3, Z^4, A, R^{1a}, R^{1b}, R^2, U$ and $R^5$ are as defined in formula (I), and thereafter optionally or as necessary converting $R^{20}$ and $R^{2'}$ to $UR^5$ and $R^2$, interconverting any variable groups, and/or forming a pharmaceutically acceptable salt, solvate or N-oxide thereof.

The reaction is a reductive alkylation (see for examples Smith, M. B.; March, J. M. *Advanced Organic Chemistry*, Wiley-Interscience 2001) with a suitable reducing agent such as sodium cyanoborohydride (in methanol/chloroform/acetic acid), triacetoxyborohydride or (polystyrylmethyl)trimethylammonium cyanoborohydride. If the amine is present as a hydrochloride salt it is preferable to have an excess of sodium acetate present to buffer the reaction. 3A Molecular sieves may also be used to help formation of the initial imine intermediate. The compound of formula (II) may be presented as a hemiacetal.

Conveniently one of $R^{20}$ and $R^{2'}$ is an N-protecting group, such as such as t-butoxycarbonyl, benzyloxycarbonyl, 9-fluorenylmethyloxycarbonyl or trifluoroacetyl. This may be removed by several methods well known to those skilled in the art (for examples see "*Protective Groups in Organic Synthesis*, T. W. Greene and P. G. M. Wuts, Wiley-Interscience, 1999), for example conventional acid hydrolysis (e.g. trifluoroacetic acid/dichloromethane, hydrochloric acid/dichloromethane/methanol), or potassium carbonate/methanol and the free amine converted to $NR^2UR^5$ by conventional means such as amide or sulphonamide formation with an acyl derivative $R^5COW$, for compounds where U is CO or, where U is $CH_2$, by alkylation with an alkyl halide $R^5CH_2$-halide in the presence of base, acylation/reduction with an acyl derivative $R^5COW$ or reductive alkylation with an aldehyde $R^5CHO$ under conventional conditions (see for examples Smith, M. B.; March, J. M. *Advanced Organic Chemistry*, Wiley-Interscience 2001). Suitable conditions include sodium cyanoborohydride (in methanol/chloroform/acetic acid). If the amine (III) is a hydrochloride salt then sodium acetate may be added to buffer the reaction. Sodium triacetoxyborohydride is an alternative reducing agent.

Alternatively, the compound of formula (III) may be replaced by a compound H-A-OH. After the coupling step with (II), the hydroxy group may be oxidised to the cyclic ketone using a suitable oxidising agent such as Dess-Martin periodinane (1,1,1-tris(acetyloxy)-1,1-dihydro-1,2-benziodoxol-3-(1H)-one. The ketone is reacted with an amine $HN(R^{20})R^{2'}$ by conventional reductive alkylation.

The appropriate reagents containing the required $R^5$ group are known compounds or may be prepared analogously to known compounds, see for example WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2006014580, WO2004/035569, WO2004/089947, WO2003082835, WO2002026723, WO06002047, WO06010040, WO06017326, WO06012396, WO06017468, WO06020561, WO06132739, WO06134378, WO06137485 and EP0559285.

The compound of formula (II) may be prepared by the following Scheme 1:

Scheme 1

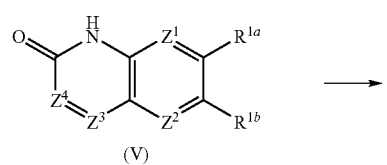

(V)

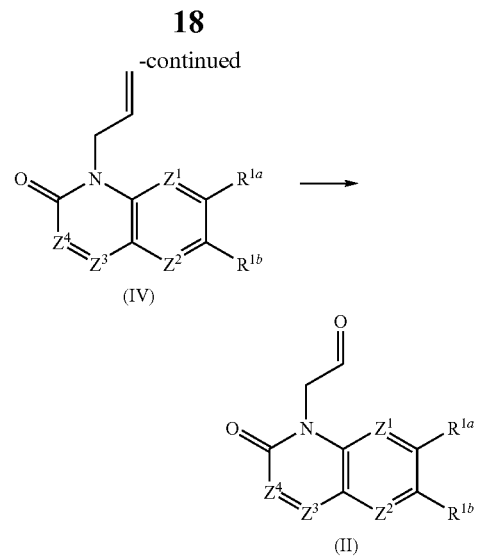

Compounds of formula (IV) may be made by allylation of compounds of type (V) under conventional conditions (see for examples Smith, M. B.; March, J. M. *Advanced Organic Chemistry*, Wiley-Interscience 2001). Conversion of (IV) to (II) may be effected by treatment with ozone or osmium tetroxide and sodium periodate under conventional conditions (see for examples Smith, M. B.; March, J. M. *Advanced Organic Chemistry*, Wiley-Interscience 2001).

The compound of formula (IV) may also be prepared by the following Scheme 2:

Scheme 2

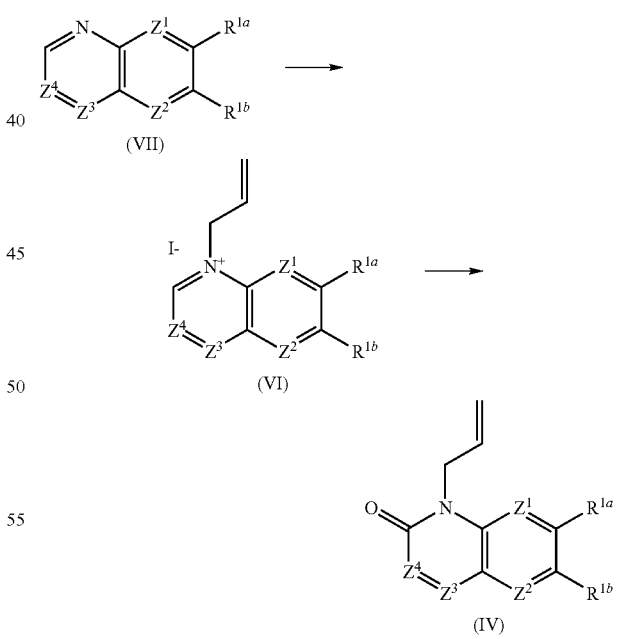

Conversion of a compound of formula (VII) to the quaternary salt (VI) may be effected by treatment with allyl iodide under conventional conditions (see for examples Smith, M. B.; March, J. M. *Advanced Organic Chemistry*, Wiley-Interscience 2001). Compound (IV) may then be prepared from (VI) by an oxidation using $K_3$-$[Fe(CN)_6]$ (for an example see Baxter, P. N. W.; Khoury, R. G.; Lehn, J. M.; Baum, G.; Fenske, D. Chemistry—A European Journal (2000), 6(22), 4140).

Compounds of formula (V) in which $Z^1$ is CH may be prepared by the following Scheme 3:

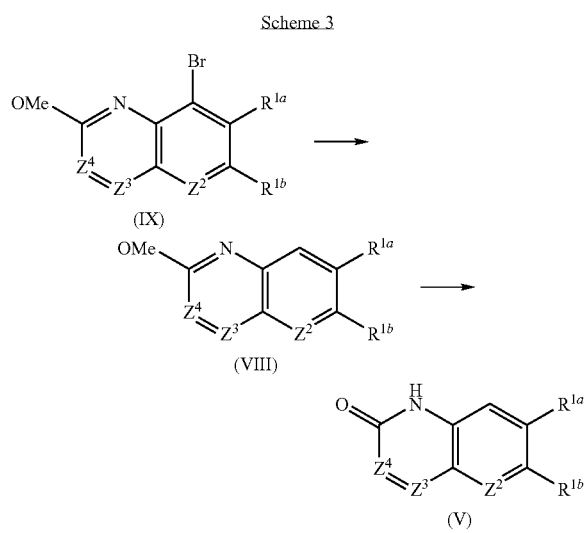

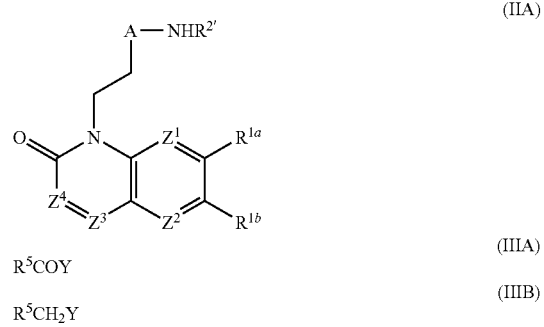

in which:
$R^{2'}$ is $R^2$ or a group convertible thereto and Y is H or a leaving group, wherein $Z^1$, $Z^2$, $Z^3$, $Z^4$, A, $R^{1a}$, $R^{1b}$, $R^2$, U and $R^5$ are as defined in formula (I), and thereafter optionally or as necessary converting $R^{2'}$ to $R^2$, interconverting any variable groups, and/or forming a pharmaceutically acceptable salt, solvate or N-oxide thereof.

The reaction is a reductive alkylation, acylation or alkylation as described above.

Compounds of formula (IIA) may be prepared by the reaction of compounds of formulae (II) and (III) described above, where $R^{20}$ is hydrogen. Alternatively, compounds of formula (IIA) where $Z^1$ and $Z^3$ are both nitrogen, may be prepared by the following Scheme 4:

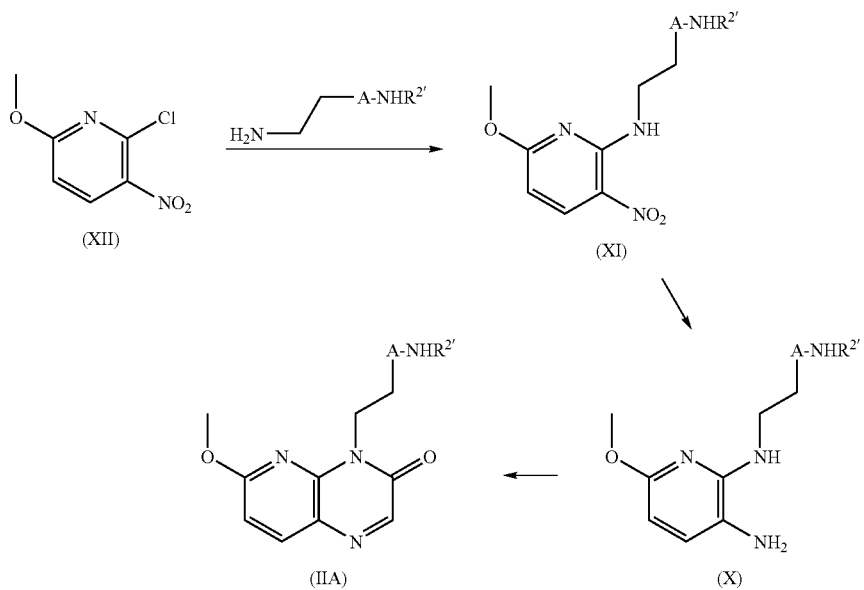

The bromo derivative (IX) may be hydrogenated using Pd/C to give (VIII). Demethylation with HBr affords the compound (V).

In an alternative aspect of the invention there is provided a process for preparing compounds of formula (I), and pharmaceutically acceptable salts, solvates and/or N-oxides thereof, which process comprises reacting a compound of formula (IIA) with a compound of formula (IIIA) or (IIIB):

Conversion of a compound of formula (XII) to (XI) takes place under conventional conditions (see for examples Smith, M. B.; March, J. M. Advanced Organic Chemistry, Wiley-Interscience 2001). Compound (X) may then be prepared from (XI) via catalytic hydrogenation under conventional conditions (see for examples Smith, M. B.; March, J. M. Advanced Organic Chemistry, Wiley-Interscience 2001). (X) can be converted to (IIA) by selective alkylation with ethyl bromoacetate, thermal cyclisation and then oxidation with manganese dioxide or oxygen under conventional conditions (see for examples Smith, M. B.; March, J. M. *Advanced Organic Chemistry*, Wiley-Interscience 2001).

Compounds of formula (II) in which $Z^1$ and $Z^3$ are both nitrogen may be prepared by a variant of Scheme 4 in which the compound of formula (XII) is reacted with aminoacetaldehyde dimethylacetal. Catalytic hydrogenation, selective alkylation with ethyl bromoacetate and thermal cyclisation yield the dimethylacetal of (II) which can be converted to the aldehyde (II) by treatment with trifluoroacetic acid.

Conversions of $R^{1a'}$ to $R^{1a}$ and interconversions of $R^{1a}$, $R^{1b}$, $R^{1c}$, $R^2$, A and $R^5$ are conventional. For example $R^{1a'}$ alkoxycarbonyl may be converted to $R^{1a}$ carboxy by hydrolysis, which in turn may be converted to $R^{1a}$ aminocarbonyl and cyano by conventional procedures. $R^{1a}$ halo may be introduced by conventional halogenation reactions eg chlorination with chlorosuccinimide in acetic acid to introduce a chloro group at $R^{1b}$. In compounds which contain an optionally protected hydroxy group, suitable conventional hydroxy protecting groups which may be removed without disrupting the remainder of the molecule include acyl and alkylsilyl groups. N-protecting groups are removed by conventional methods.

For example $R^{1a}$, $R^{1b}$ or $R^{1c}$ methoxy is convertible to $R^{1a}$, $R^{1b}$ or $R^{1c}$ hydroxy by treatment with lithium and diphenylphosphine (general method described in Ireland et al, *J. Amer. Chem. Soc.*, 1973, 7829) or HBr. Alkylation of the hydroxy group with a suitable alkyl derivative bearing a leaving group such as halide, yields $R^{1a}$, $R^{1b}$ or $R^{1c}$ substituted alkoxy. $R^{1a}$ halogen is convertible to other $R^{1a}$ by conventional means, for example to hydroxy, alkylthiol (via thiol) and amino using metal catalysed coupling reactions, for example using copper as reviewed in Synlett (2003), 15, 2428-2439 and Angewandte Chemie, International Edition, 2003, 42(44), 5400-5449.

Compounds of formula HA-N($R^{20}$)$R^{2'}$, (V), (VII) and (IX) are known compounds or may be prepared analogously to known compounds, for example quinazolinone and quinazolines may be prepared by standard routes as described by T. A. Williamson in *Heterocyclic Compounds*, 6, 324 (1957) Ed. R. C. Elderfield. Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

4-halogeno derivatives such as (IX) are commercially available, or may be prepared by methods known to those skilled in the art. A-4-bromo-substituent may be prepared from the quinolin- or naphthyridin-4-one by reaction with phosphorus tribromide ($PBr_3$) in DMF. A 4-chloroquinazoline is prepared from the corresponding quinazolin-4-one by reaction with phosphorus oxychloride ($POCl_3$) or phosphorus pentachloride, $PCl_5$.

For compounds of formula HA-N($R^{20}$)$R^{2'}$, (V), (VII) and (IX) see for example WO2004/035569, WO2004/089947, WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2003082835, WO2002026723, WO06002047, WO06014580, WO06134378 and WO06137485.

As shown in Scheme 5, the hydroxy-aminomethylpyrrolidines of formula (III) (A is (ii), X is $CR^4R^8$, $W^1$ is a bond, $W^2$ and $W^3$ are both $CH_2$, $R^4$ and $R^7$ are H and $R^8$ is OH) can be prepared from doubly protected chiral intermediate (XV), separated by preparative HPLC. The benzyloxycarbonyl protecting group is removed by hydrogenation to give (XIV) and the amino function converted to a trifluoroacetamide (XIII). The t-butoxycarbonyl (Boc) protecting group is removed with HCl to give the pyrrolidine hydrochloride salt (III).

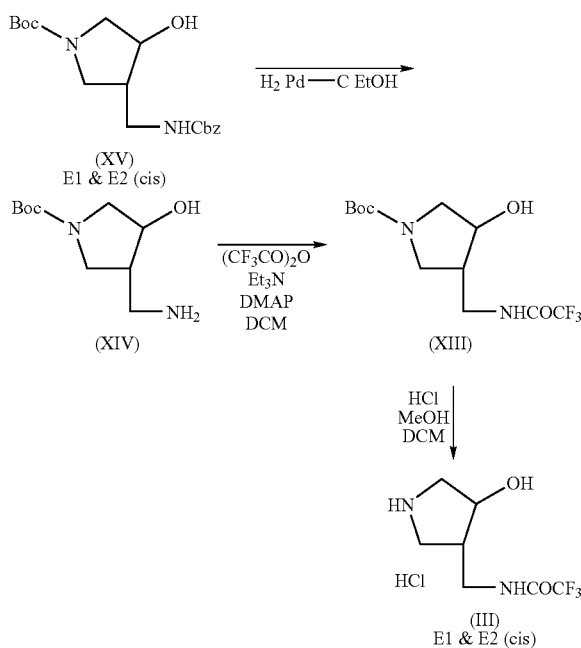

DMAP = dimethylaminopyridine

The intermediate (XV) may be prepared by the general method of Scheme 6:

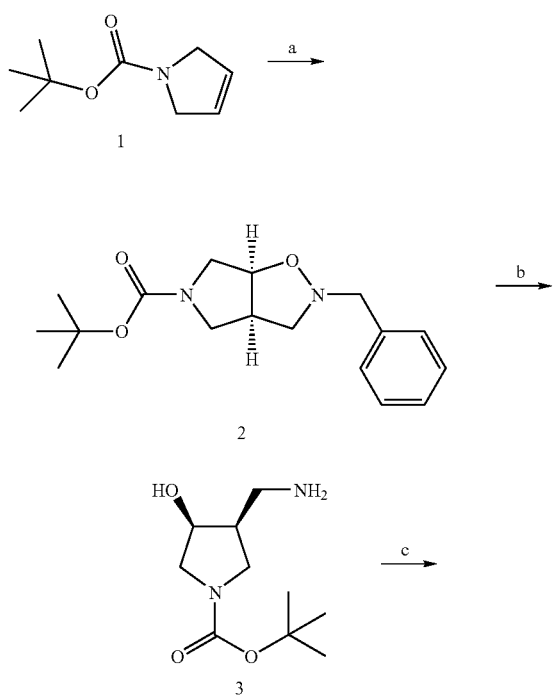

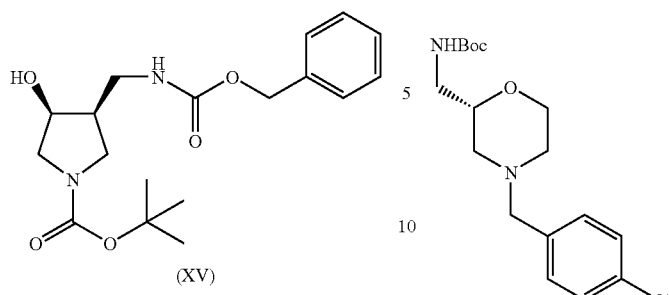

(XV)

Reagents and conditions: (a) N-Hydroxybenzylamine hydrochloride, paraformaldehyde, toluene, EtOH, 80° C.; (b) Pd(OH)$_2$, H$_2$ (50 psi), MeOH, room temperature; (c) Benzyloxycarbonyl-succinimide, Et$_3$N, dichloromethane, room temperature.

In Scheme 7 the aminomethylpyrrolidine of formula (III) (A is (ii), X is CR$^4$R$^8$, W$^1$ is a bond, W$^2$ and W$^3$ are both CH$_2$, R$^4$, R$^7$ and R$^8$ are all H) can be prepared from commercially available Boc-protected aminomethylpyrrolidine, and converted to the trifluoroacetamide.

Scheme 7

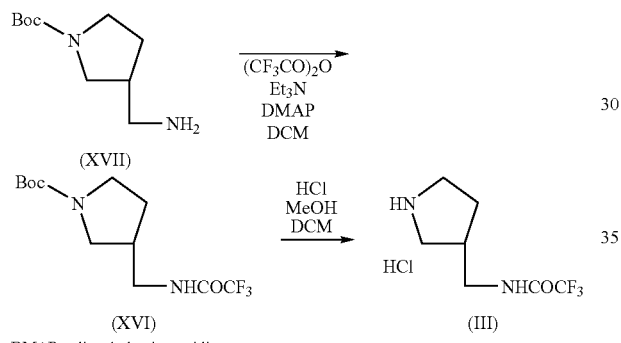

DMAP = dimethylaminopyridine

The aminomethylmorpholine intermediate of formula (III) (A is (ii), X is O, W$^1$, W$^2$ and W$^3$ are each CH$_2$) may be prepared from a chiral dichlorobenzyl intermediate (XX) (WO2003082835) (Scheme 8) by first protecting the amino function with a Boc-protecting group (XIX), removing the dichlorobenzyl group by hydrogenation to give (III), protecting the morpholine N-atom with a benzyloxycarbonyl group (to allow purification by chromatography) (XVIII), and hydrogenation to afford the required morpholine derivative (III).

Scheme 8

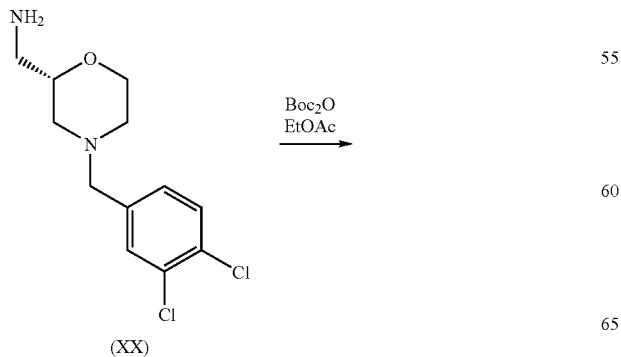

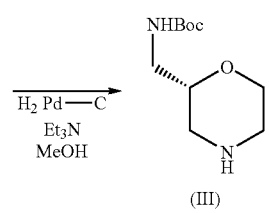

(XIX)

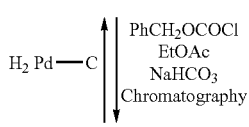

(XVIII)

A method to prepare the pyrimidinyloxazinone unit R$^5$ (C), where Y$^3$=O, R$^{10}$=H) is illustrated in Scheme 9.

Scheme 9

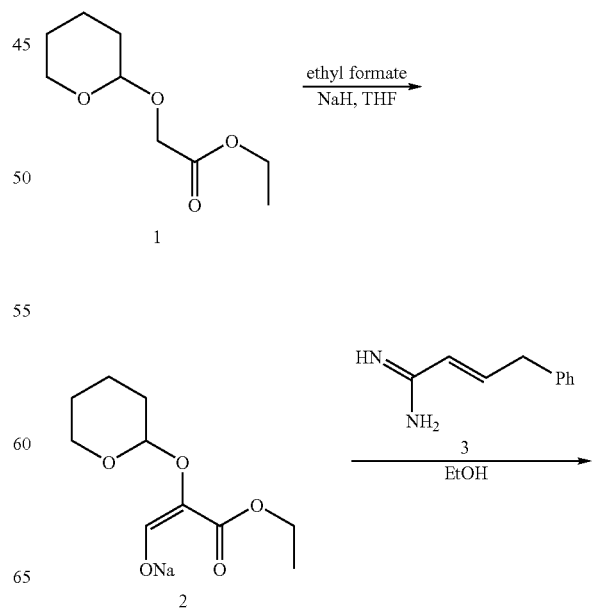

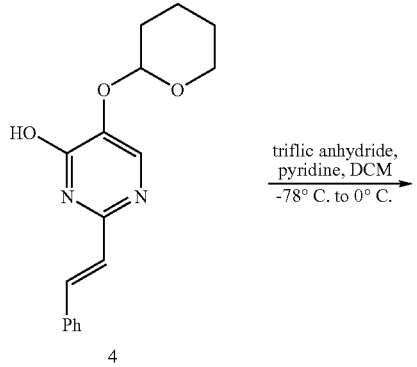

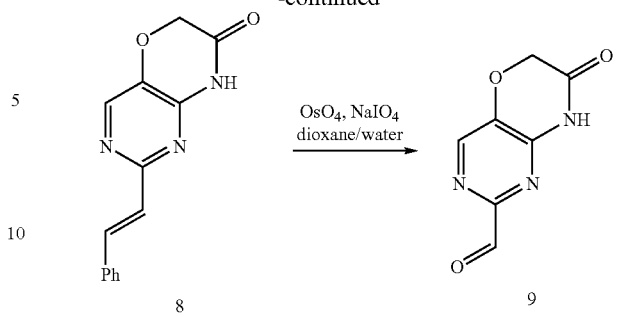

A suitably protected ethyl glycolate (THP-protected in this example, 1) is formylated using ethyl formate and a base such as NaH in THF or diethyl ether. The intermediate formyl enolate 2 is then directly reacted with an amidine, in this case the (2E)-3-phenyl-2-propenimidamide 3, giving the pyrimidinone 4. Pyrimidinone 4 is converted to a trifluoromethansulfonate ester (5) which is then reacted with ammonia in a suitable solvent, such as 1,4-dioxane, providing amine 6. The amino alcohol 7 is then obtained by removing the THP-protecting group of 6 with acid in methanol. Treatment of 7 with a base and an ester of a halo-acetate in an alcohol solvent such as absolute ethanol, provides the bicyclic intermediate 8 directly. This transformation may be accomplished using a base such as potassium tert-butoxide and the alkylating agent ethyl bromoacetate. An amine base such as triethylamine may also be employed as an alternative to the alkoxide base illustrated herein (for similar examples see N. V. Sazonov and T. S. Safonova, *Khimiya Geterotsiklicheskikh Soedinenii*, 1971, 1285-1288). The final aldehyde intermediate 9 is then obtained via oxidative cleavage of the phenylethenyl side chain. One method to achieve this is by reacting 8 with NaIO$_4$, in a mixture of 1,4-dioxane-water, with a catalytic amount of OsO$_4$. Other methods, such as ozonolysis, may also be suitable to achieve the desired transformation.

Pyrimidine dihydropyridone aldehyde (R$^5$ (C) where Y$^3$=CH$_2$ and R$^{10}$=Cl) may be prepared as illustrated in Scheme 10.

Scheme 10

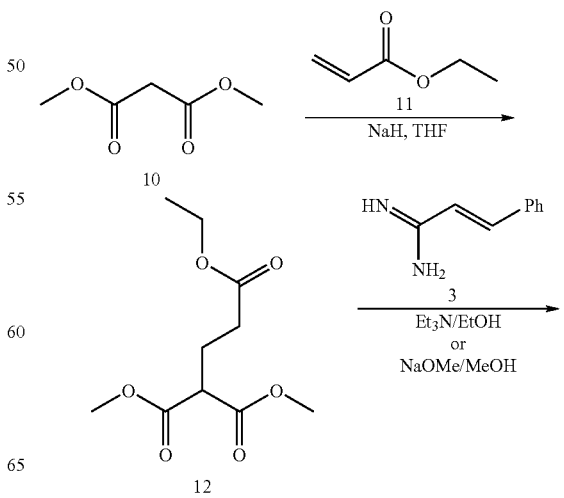

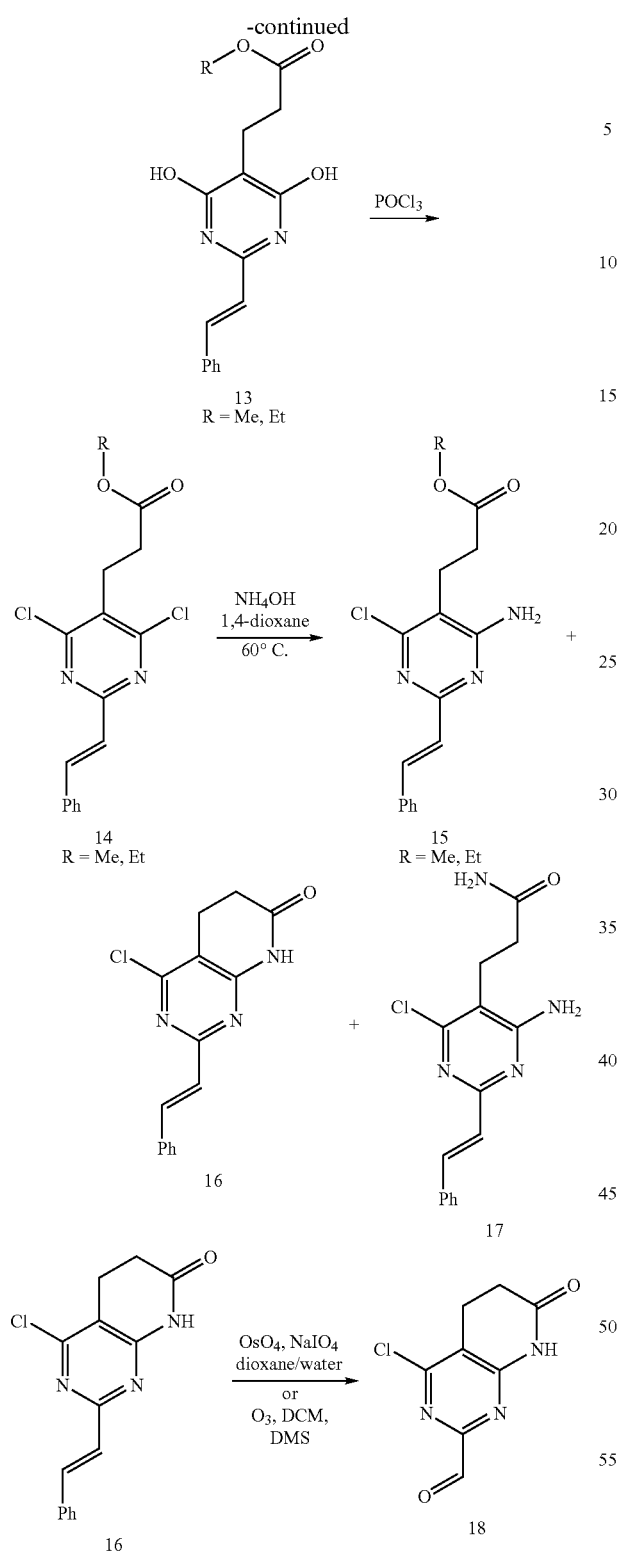

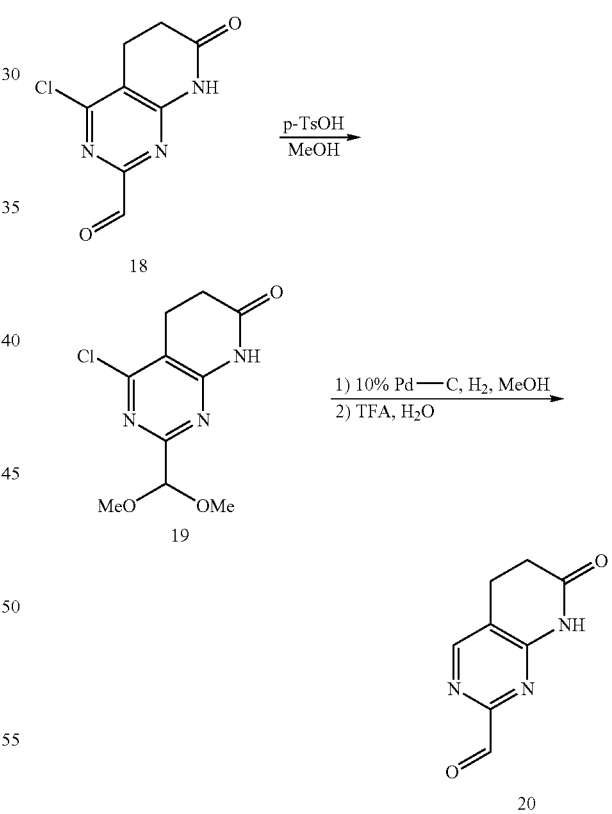

13 (R=Me) is obtained whereas the ethyl ester is preserved using the former conditions. Either ester form, methyl or ethyl, can be used to carry out the remaining steps of the synthesis. Treating 13 with POCl$_3$ provides the dichloropyrimidine 14. Heating 14 in a sealed tube in the presence of NH$_4$OH usually yields a mixture of the components 15, 16, and 17 with 15 and 16 predominating. Subsequently, intermediate 15 can be converted to 16 by treating with K$_2$CO$_3$ in MeOH. In addition, 17 can be recycled to 15 (R=Et) by treatment with ethanolic HCl. The preparation of the aldehyde 18 is then completed via oxidative cleavage of the olefin side chain of 16 using either OsO$_4$ and NaIO$_4$, or by ozonolysis.

Scheme 11 illustrates one convenient method to remove the chlorine substituent found in 18 in order to obtain the deschloro aldehyde 20 (R$^5$ (C) where Y$^3$=CH$_2$ and R$^{10}$=H). This can be achieved by first protecting the aldehyde group of 18 by forming the dimethyl acetal using p-toluene sulfonic acid (p-TsOH) and MeOH, providing 19. The chlorine is then be removed by hydrogenation using Pd—C catalysis under an atmosphere of H$_2$. Treatment with aqueous acid, such as TFA and water, once again liberates the aldehyde group, thus providing 20.

By reacting the anion of dimethyl malonate (10) with ethyl acrylate (11), the triester 12 is obtained. Condensing 12 with (2E)-3-phenyl-2-propenimidamide (3), in the presence of a base, leads to the dihydroxypyrimidine 13. Triethylamine in EtOH can be used to carry out this transformation, however the preferred conditions utilize NaOMe in MeOH. It should be noted that under these latter conditions the methyl ester of Scheme 12 illustrates a method to prepare analogs incorporating alternative substituents at the 4-position on the pyrimidine ring, for example for R$^5$ (C) where Y$^3$=CH$_2$ and R$^{10}$=OMe or Me. These analogs can be prepared from the previously described intermediate 16 using a variety of well known methods. Illustrated in Scheme 13 is the preparation of the 4-methoxy and the 4-methyl derivatives, however similar or other methods may be employed to incorporate a wide range of substituents. As shown below, 16 can be treated with NaOMe in refluxing methanol to provide the methoxy-containing intermediate 21A. The methyl group can be prepared from 16 via a Pd-mediated reaction with methyl boronic acid, thus affording 21B. The aldehyde functional group is once again liberated by oxidative cleavage of the olefin side chain using methods such as ozonolysis, or by reaction with $OsO_4$ and $NaIO_4$, to provide 22A and 22B.

Scheme 12

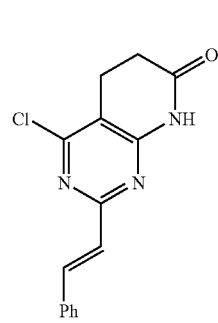

The pyrimidine oxazinone aldehyde unit needed to prepare examples of $R^5$ (C) where $Y^3$=O and $R^{10}$=Cl, is shown in Scheme 13 starting from dimethyl diazomalonate (23), prepared according to Peace, Carman, Wulfman, *Synthesis*, 658-661, (1971). Reaction of 23 with ethyl glycolate under rhodium catalysis provides the substituted malonate 24. The pyrimidine ring system is constructed through the reaction of 24 with (2E)-3-phenyl-2-propenimidamide (3), and sodium methoxide to give 25. Intermediate 25 is isolated as the carboxylic acid as the methyl ester is hydrolyzed under the sodium methoxide reaction conditions. Treatment of 25 with $POCl_3$ followed by the addition of MeOH provides dichloride-methyl ester 26. Exchanging one of the chlorines with ammonia can be accomplished by treating 26 with $NH_4OH$, also providing the primary amide, which is then converted to the ethyl ester 27 with HCl and EtOH. Formation of the oxazinone ring can be carried out by treating 27 with a base such as $K_2CO_3$ in a polar solvent such as DMF. Heating is usually required to complete the conversion to the bicyclic system 28. Conversion to the aldehyde can be achieved by oxidative cleavage of the 2-phenylethenyl side chain. In this particular example, the side chain of 28 is reacted with $OsO_4$ and $NaIO_4$ to give aldehyde 29.

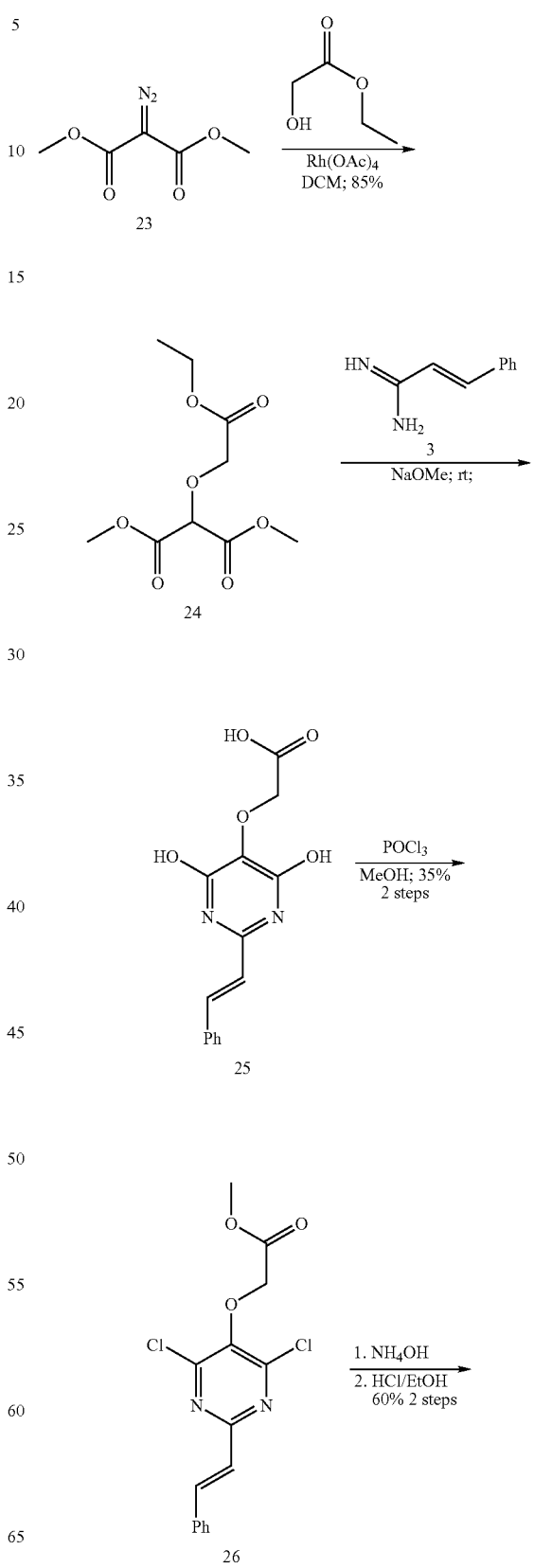

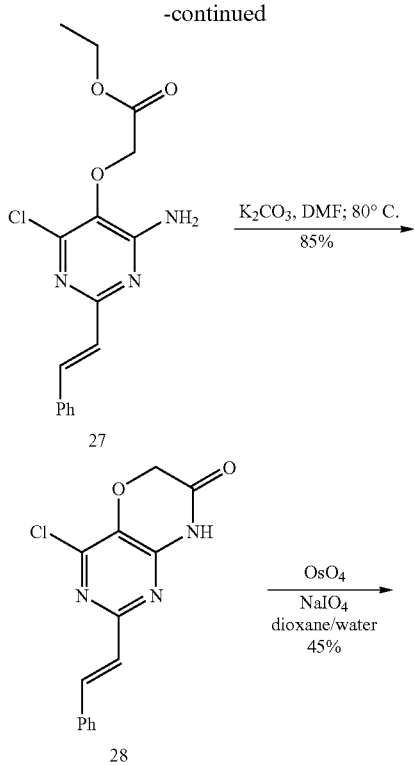

Further details for the preparation of compounds of formula (I) are found in the examples.

The antibacterial/antituberculosis compounds according to the invention may be formulated for administration in any convenient way for use in human or veterinary medicine, by analogy with other antibacterials/anti-tuberculosis compounds.

The pharmaceutical compositions of the invention include those in a form adapted for oral, topical or parenteral use and may be used for the treatment of bacterial infection including tuberculosis in mammals including humans.

The composition may be formulated for administration by any route. The compositions may be in the form of tablets, capsules, powders, granules, lozenges, suppositories, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-1000 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 30 mg/kg per day.

The compound of formula (I) may be the sole therapeutic agent in the compositions of the invention or a combination with other antibacterials, including anti-tuberculosis compounds. If the other antibacterial is a β-lactam then a β-lactamase inhibitor may also be employed.

Compounds of formula (I) may be used in the treatment of bacterial infections caused by a wide range of organisms including both Gram-negative and Gram-positive organisms, such as upper and/or lower respiratory tract infections, skin and soft tissue infections and/or urinary tract infections. Compounds of formula (I) may be also used in the treatment of tuberculosis caused by *Mycobacterium tuberculosis*. Some compounds of formula (I) may be active against more than one organism. This may be determined by the methods described herein.

The following examples illustrate the preparation of certain compounds of formula (I) and the activity of certain compounds of formula (I) against various bacterial organisms including *Mycobacterium tuberculosis*.

EXAMPLES AND EXPERIMENTAL

General

Abbreviations in the Examples:
PSI=pounds per square inch (1 PSI=0.069 bar)
RT/rt=room temperature
ES=Electrospray mass spectroscopy.
LCMS=Liquid chromatography mass spectroscopy
HPLC=High Performance Liquid Chromatography (Rt refers to retention time).
Certain reagents are also abbreviated herein. DCM refers to dichloromethane, DMF refers to dimethylformamide, DMSO refers to dimethylsulfoxide, MeOH refers to methanol, TFA refers to trifluoroacetic acid, THF refers to tetrahydrofuran, Pd/C refers to palladium on carbon catalyst. Boc refers to tert-butoxylcarbonyl. EtOH refers to ethanol. dppf is 1,1'-Bis(diphenylphosphino)ferrocene. EDC is N-[3-(dimethylamino)propyl]ethyl cabodiimide hydrochloride. HOBt is 1-hydroxybenzotriazole.
Proton nuclear magnetic resonance ($^1$H NMR) spectra were recorded at 400 or 250 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. All temperatures are reported in degrees Celsius. Celite® is a filter aid composed of acid-washed diatomaceous silica, and is a trademark of Manville Corp., Denver, Colo. MDAP or Mass directed autoprep=mass directed preparative HPLC (using a ZQ mass spectrometer (Waters)). The preparation of triethenylboroxin.pyridine complex is described in Kerins, Fergal; O'Shea, Donal F.; J. Org. Chem. (2002) 67(14) 4968. MP-carbonate refers to macroporous triethyammonium methylpolystyrene carbonate (Argonaut Technologies). Amberlyst®A21 is a weakly basic, macroreticular resin with alkyl amine functionality, ®Registered trademark of Rohm & Haas Co. SCX is an ion exchange column containing strong cation exchange resin (benzene sulfonic acid) supplied by Varian, USA. Chiralpak IA, Chiralpak AS-H and Chiralcel OD are polysaccharide based chiral HPLC columns (Chiral Technologies Inc.). Chiralpak AS-H column comprise of amylose tris [(S)-alpha-methylbenzylcarbamate) coated onto Sum silica. Chiralpak IA column comprise of silica for preparative column (Sum particle size, 21 mm ID×250 mm L) immobilized with Amylose tris(3,5-dimethylphenylcarbamate). Chiralpak AD and AD-H columns comprise of silica for preparative columns (Sum particle size AD-H and 10 um particle size AD, 21 mm ID×250 mm L; 20 uM particle size AD, 101 mm ID×250 mm L) coated with Amylose tris(3,5-dimethylphenylcarbamate) (Chiral Technologies USA). Measured retention times are dependent on the precise conditions of the chromatographic procedures. Where quoted below in the Examples they are indicative of the order of elution.

Reactions involving metal hydrides including lithium hydride, lithium aluminium hydride, di-isobutylaluminum hydride, sodium hydride, sodium borohydride, sodium triacetoxyborohydride, (polystyrylmethyl)trimethylammonium cyanoborohydride are carried out under argon or other inert gas.

As will be understood by the skilled chemist, references to preparations carried out according to or by the general method of other preparations, may encompass variations in routine parameters such as time, temperature, workup conditions, minor changes in reagent amounts, etc.

Example 1

1-(2-{4-[(2,3-Dihydro[1,4]dioxino[2,3-c]pyridin-7-ylmethyl)amino]-1-piperidinyl}ethyl)-7-(methyloxy)-2(1H)-quinolinone Hydrochloride

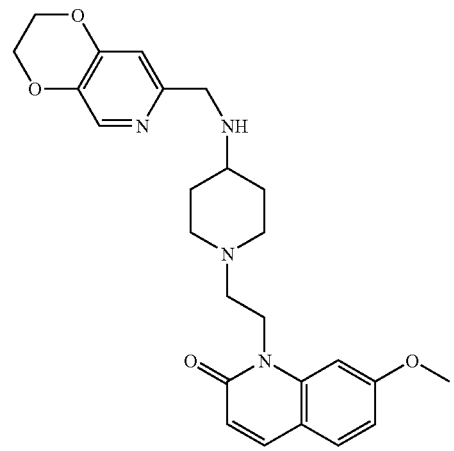

(a) 7-(Methyloxy)quinoline

A suspension of NaH (3.3 g; 137.93 mmol) in anhydrous DMF (160 ml) was cooled to 0° C. with stirring under argon. 7-Quinolinol (8 g; 55.17 mmol) dissolved in anhydrous DMF (320 ml) was added and the mixture was stirred at 0° C. under argon for 1 h. The mixture was then allowed to warm to rt and MeI (7.8 ml; 55.17 mmol) was added and the reaction was stirred for 1 h. Ice water was then added cautiously and the resulting mixture extracted with EtOAc (3×500 ml). The organic layer from this extraction was then washed with water (400 ml) and brine (400 ml). The resulting organic layer was dried with MgSO$_4$ and solvents removed to afford the desired compound (8.76 g; 99%)

MS (ES+) m/z 160 (MH$^+$).

(b) 7-(Methyloxy)-1-(2-propen-1-yl)quinolinium Iodide 7-(Methyloxy)quinoline (8.76 g; 55.09 mmol) and allyl iodide (19.72 ml; 110.18 mmol) were refluxed in toluene (120 ml) at 95° C. for 1 h, more allyl iodide (9.86 ml; 55.09 mmol) was added and the temperature of the reaction increased to 110° C. After a further 1 h the temperature of the reaction was increased to 120° C. and reaction continued for a further 0.5 h. The solvent was removed under vacuum and the resulting brown solid was washed with toluene and diethyl ether. The resultant solid were left to dry in a vacuum oven overnight to give the desired product (14.81 g; 82%)

MS (ES+) m/z 201 (MH+).

(c) 7-(Methyloxy)-1-(2-propen-1-yl)-2(1H)-quinolinone 7-(Methyloxy)-1-(2-propen-1-yl)quinolinium iodide (14.81 g; 45.43 mmol), KOH (11.20 g; 199.89 mmol) and $K_3$-[Fe(CN)$_6$] (32.78 g; 99.95 mmol) were stirred in 1:1 water: 1,4-dioxane (400 ml) at rt under Argon for 1 h. More KOH (1.1 g; 19.9 mmol) and $K_3$-[Fe(CN)$_6$] (3.28 g; 10.0 mmol) were added to the reaction and it was stirred under the same conditions for a further 0.5 h. EtOAc (500 ml) and water (500 ml) was then added. The layers were then separated and the combined organic layers were washed with water and then concentrated. The crude residue was then purified by column chromatography on silica gel using a 0-5% MeOH/DCM gradient to give the desired product (4.90 g; 51%).

MS (ES+) m/z 216 (MH+).

(d) [7-(Methyloxy)-2-oxo-1(2H)-quinolinyl]acetaldehyde 7-(Methyloxy)-1-(2-propen-1-yl)-2(1H)-quinolinone (2 g; 9.3 mmol) was dissolved in DCM (100 ml) and $O_3$ was bubbled through the reaction at −78° C. for 30 mins. Argon was then bubbled through for 10 mins to remove excess $O_3$ and then the reaction was quenched with dimethyl sulfide (2.3 ml, 37.2 mmol). The reaction was allowed to warm to rt and stirred for a further 20 mins. All the solvents were then removed to give the desired compound (2.31 g). For an alternative synthesis of this aldehyde see Example 52(a)-(e).

MS (ES+) m/z 218 (MH+).

(e) 1,1-Dimethylethyl (2,3-dihydro[1,4]dioxino[2,3-c]pyridin-7-ylmethyl)(1-{2-[7-(methyloxy)-2-oxo-1(2H)-quinolinyl]ethyl}-4-piperidinyl)carbamate A solution of [7-(methyloxy)-2-oxo-1(2H)-quinolinyl]acetaldehyde (65 mg, 0.3 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (105 mg, 0.3 mmol) in chloroform (3 ml) and MeOH (3 ml) was stirred at rt for 1 h. The mixture was then treated with NaBH(OAc)$_3$ (190.8 mg, 0.9 mmol), stirred at rt for 0.5 h. 1,1-dimethylethyl (2,3-dihydro[1,4]dioxino[2,3-c]pyridin-7-ylmethyl)-4-piperidinylcarbamate (52 mg, 0.15 mmol) and NaBH(OAc)$_3$ (127 mg, 0.6 mmol) were added and the reaction stirred at rt for 1 hour. The solvents were then removed and the residue was subjected to column chromatography on silica gel eluting with 0-10% methanol-DCM to afford the desired compound (92 mg, 56%).

MS (ES+) m/z 551 (MH+).

(f) Title Compound

To a solution of 1,1-dimethylethyl (2,3-dihydro[1,4]dioxino[2,3-c]pyridin-7-ylmethyl)(1-{2-[7-(methyloxy)-2-oxo-1(2H)-quinolinyl]ethyl}-4-piperidinyl)carbamate (92 mg) in chloroform (1.5 ml) was added 4N HCl in 1,4-dioxane (1.5 ml) and the reaction stirred at rt for 1 h. More 4N HCl in 1,4-dioxane (0.5 ml) was added and the reaction stirred at rt for 0.5 h then the solvents removed. The residue was dissolved in MeOH (25 ml) and treated with Amberlyst A21 basic resin until the pH was 6. The residue was filtered off and the solvent removed; the residue was subjected to column chromatography on silica gel eluting with 0-20% methanol-DCM to afford the free base of the title compound (67 mg, 89%).

$^1$H NMR (250 MHz) δ (CDCl$_3$) 1.72 (m, 2H), 2.06 (m, 2H), 2.38 (t, 2H), 2.76 (t, 2H), 3.15 (m, 2H), 3.80 (bs, 1H), 3.90 (s, 2H), 3.95 (s, 3H), 4.28-4.35 (m, 4H), 4.50 (t, 2H), 6.51 (d, 1H), 6.82 (dd, 1H), 6.90 (s, 1H), 7.01 (d, 1H), 7.45 (d, 1H), 7.59 (d, 1H), 8.09 (s, 1H)

MS (ES+) m/z 451 (MH+).

This material was converted to the hydrochloride by dissolving in DCM/methanol and adding 1 equivalent of 4M HCl/1,4-dioxane then evaporating to dryness to give a yellow solid was obtained.

Example 2

1-(2-{4-[(2,3-dihydro[1,4]dioxino[2,3-c]pyridin-7-ylmethyl)amino]-1-piperidinyl}ethyl)-7-fluoro-2(1H)-quinolinone Hydrochloride and

Example 3

1-(2-{4-[(2,3-dihydro[1,4]dioxino[2,3-c]pyridin-7-ylmethyl)amino]-1-piperidinyl}ethyl)-5-fluoro-2(1H)-quinolinone Hydrochloride

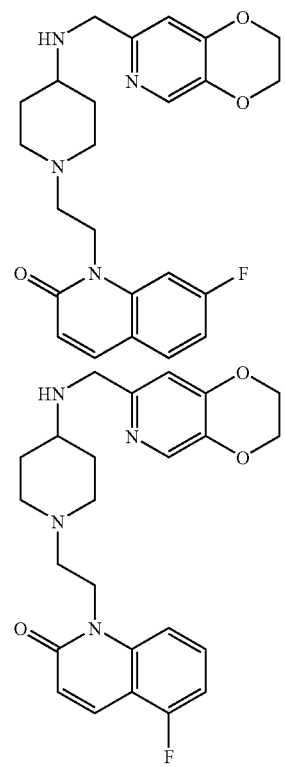

(a) N-(3-fluorophenyl)-3,3-bis(methyloxy)propanamide

3-Fluoroaniline (50 g, 450 mmol) was dissolved in toluene (500 ml) and 25% NaOMe in MeOH (120 ml) and methyl (2E)-3-(methyloxy)-2-propenoate (57.4 ml, 495 mmol) were added. The mixture was then heated to 70° C. and stirred at this temperature for 2.5 hours. The solvent was then reduced to around a quarter of the original volume and the reaction was then treated with NH₄Cl until pH 7 was reached (approx 500 ml used). EtOAc was added to the reaction and the layers separated, the aqueous layer was then extracted three times with EtOAc and the combined organic layers dried with MgSO₄. The solvents were removed and the crude residues were purified by column chromatography on silica gel using a 30-50% EtOAc/40-60 petroleum ether gradient. Fractions containing product were concentrated to afford the desired compound (40.68 g, 40%) and a less pure batch (6.17 g, 6%)

MS (ES+) m/z 228 (MH⁺).

(b) 7-Fluoro-2(1H)-quinolinone

A solution of 70% H₂SO₄ was made up by adding chilled H₂SO₄ (35 ml) to chilled water (15 ml) ensuring the temp remained between 10-20° C. Finely ground N-(3-fluorophenyl)-3,3-bis(methyloxy)propanamide (6.17 g, 27.2 mmol) was then added cautiously to this solution keeping the vessel in ice. This was stirred for 1 hour and then ice water (70 ml) was added. This was then diluted further with water (230 ml). The mixture was stirred for a further 30 mins. The precipitate was filtered off and dried in a vacuum oven overnight to give the desired product (3.67 g, 83%). This material contained approximately 10% of the isomeric 5-fluoro-2(1H)-quinolinone.

MS (ES+) m/z 164 (MH⁺).

(c) 7-Fluoro-1-(2-propen-1-yl)-2(1H)-quinolinone

To a suspension of 7-fluoro-2(1H)-quinolinone (1.53 g, 9.39 mmol) in DMF at 0° C. was added sodium hydride (0.83 g of a 60% w:w dispersion in oil, 20.65 mmol) and the reaction was allowed warm to rt over 0.5 h before addition of allyl iodide (1.91 ml, 20.65 mmol). The reaction was stirred at rt for a further 0.25 h before addition of water (100 ml). The aqueous phase was then extracted with 10% MeOH in DCM (3×200 ml) and the combined organic phases were dried, evaporated and the residue was subjected to column chromatography on silica gel using a 10% MeOH in DCM gradient to provide the desired compound (0.91 g, 48%). This material contained approximately 10% of the isomeric 5-fluoro-1-(2-propen-1-yl)-2(1H)-quinolinone.

MS (ES+) m/z 204 (MH⁺).

(d) (7-Fluoro-2-oxo-1(2H)-quinolinyl)acetaldehyde

A solution of 7-fluoro-1-(2-propen-1-yl)-2(1H)-quinolinone (0.909 g, 4.48 mmol) in 1,4-dioxane (50 ml) and water (30 ml) at 0° C. was treated with sodium periodate (2.20 g, 10.30 mmol) and OsO₄ (4% in water, 5 ml). The reaction was warmed to rt and stirred at rt for 1 h before an extra 30 ml of water was added, after another 1 h more sodium periodate (2.20 g, 10.30 mmol) was added and after a further 2 h more sodium periodate (4.20 g, 19.70 mmol) was added. The reaction was then stirred at rt for 0.5 h before evaporation, treatment with water and extraction with DCM (×3). The combined organics were dried and evaporated to give the desired product (0.50 g, 88%). This material contained approximately 10% of the isomeric (5-fluoro-2-oxo-1(2H)-quinolinyl)acetaldehyde.

MS (ES+) m/z 206 (MH⁺).

(e) 1,1-Dimethylethyl (2,3-dihydro[1,4]dioxino[2,3-c]pyridin-7-ylmethyl) {1-[2-(7-fluoro-2-oxo-1(2H)-quinolinyl)ethyl]-4-piperidinyl}carbamate A mixture of (7-fluoro-2-oxo-1(2H)-quinolinyl)acetaldehyde (123 mg, 0.602 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (210 mg, 0.602 mmol) in chloroform (5 ml) and MeOH (0.5 ml) was stirred for 2 h before addition of NaBH(OAc)₃ (383 mg, 1.806 mmol). The reaction was stirred for 0.5 h before addition of sat. aq NaHCO₃ (10 ml). The reaction was then extracted with 10% MeOH in DCM (3×200 ml). The combined organic phases were dried, evaporated and the crude residue purified by chromatography on silica gel using a 0-10% MeOH/DCM gradient to provide the desired compound (240 mg, 74% g). This material contained approximately 10% of the isomeric 1,1-dimethylethyl (2,3-dihydro[1,4]dioxino[2,3-c]pyridin-7-ylmethyl) {1-[2-(5-fluoro-2-oxo-1(2H)-quinolinyl)ethyl]-4-piperidinyl}carbamate.

MS (ES+) m/z 539 (MH⁺).

(f) Title Compounds

To a solution of 1,1-dimethylethyl (2,3-dihydro[1,4]dioxino[2,3-c]pyridin-7-ylmethyl) {1-[2-(7-fluoro-2-oxo-1(2H)-quinolinyl)ethyl]-4-piperidinyl}carbamate (240 mg, 0.446 mmol) in chloroform (5 ml) and MeOH (5 ml) was added 4M HCl in 1,4-dioxane (5 ml) and the reaction was stirred at rt for 0.5 h before evaporation, treatment with sat. aq NaHCO₃ (10 ml). The reaction was then extracted with 10% MeOH in DCM (3×200 ml). The combined organic phases were dried, evaporated and the crude residue purified by chromatography on silica gel using a 0-20% MeOH/DCM gradient to provide 1-(2-{4-[(2,3-dihydro[1,4]dioxino[2,3-c]pyridin-7-ylmethyl)amino]-1-piperidinyl}ethyl)-7-fluoro-2(1H)-quinolinone (178 mg, 91%). This material contained approximately 10% of the isomeric 1-(2-{4-[(2,3-dihydro[1,4]dioxino[2,3-c]pyridin-7-ylmethyl)amino]-1-piperidinyl}ethyl)-5-fluoro-2(1H)-quinolinone.

This material was separated by preparative HPLC through multiple injections on a luna C18(2) (3 microns) column eluting with H₂O (0.1% TFA) and CH₃CN (0.1% TFA) at a flow rate of 1.0 mL/minute with UV detection at 254 nm to give the free base of the title compounds 1-(2-{4-[(2,3-dihydro[1,4]dioxino[2,3-c]pyridin-7-ylmethyl)amino]-1-piperidinyl}ethyl)-7-fluoro-2(1H)-quinolinone (46 mg, 98% purity) and 1-(2-{4-[(2,3-dihydro[1,4]dioxino[2,3-c]pyridin-7-ylmethyl)amino]-1-piperidinyl}ethyl)-5-fluoro-2(1H)-quinolinone (4.6 mg, 98% purity).

Data for the major isomer (1-(2-{4-[(2,3-dihydro[1,4]dioxino[2,3-c]pyridin-7-ylmethyl)amino]-1-piperidinyl}ethyl)-7-fluoro-2(1H)-quinolinone):

MS (ES+) m/z 439 (MH⁺).

¹H NMR (400 MHz) δ (CDCl₃) 1.48-1.55 (2H, m), 1.58-2.00 (2H, m), 2.15-2.28 (2H, m), 2.51-2.71 (3H, m), 2.95-3.08 (2H, m), 3.70 (2H, s), 4.25-4.44 (m, 6H), 6.58-6.62 (1H, m), 6.82 (1H, s), 6.80-6.95 (1H, m), 7.70 (1H, d, J 11 Hz), 7.45-7.55 (1H, m), 7.62 (1H, d, J=10 Hz), 8.09 (s, 1H).

Data for the minor isomer 1-(2-{4-[(2,3-dihydro[1,4]dioxino[2,3-c]pyridin-7-ylmethyl)amino]-1-piperidinyl}ethyl)-5-fluoro-2(1H)-quinolinone MS (ES+) m/z 439 (MH⁺).

¹H NMR (500 MHz) 6(MeOD) 1.31-1.44 (2H, m), 1.80-1.88 (2H, m), 2.01-2.11 (2H, m), 2.39-2.58 (3H, m), 2.95-3.01 (2H, m), 3.68 (2H, s), 4.15-4.41 (m, 6H), 6.61 (1H, d,

J=10 Hz), 6.88 (1H, s), 6.95 (1H, t, J=9 Hz), 7.34 (1H, d, 9 Hz), 7.55 (1H, m), 7.90 (1H, s), 8.00 (1H, d, J=10 Hz).

These compounds were then converted to their HCl salts by dissolving in DCM/methanol and adding 1 equivalent of 4M HC/1,4-dioxane then evaporating to dryness.

Example 4

7-fluoro-1-(2-{4-[([1,3]oxathiolo[5,4-c]pyridin-6-ylmethyl)amino]-1-piperidinyl}ethyl)-2(1H)-quinolinone Dihydrochloride

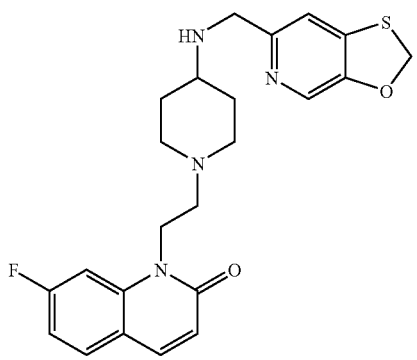

(a) 1,1-Dimethylethyl {1-[2-(7-fluoro-2-oxo-1(2H)-quinolinyl)ethyl]-4-piperidinyl}carbamate A mixture of (7-fluoro-2-oxo-1(2H)-quinolinyl)acetaldehyde (594 mg; 2.89 mmol) and 1,1-dimethylethyl 4-piperidinylcarbamate (578 mg; 2.89 mmol) in a 1:1 mixture of chloroform and methanol (20 ml:20 ml) was stirred at rt under argon for 1 h. The mixture was then treated with NaBH(OAc)$_3$ (1.83 g; 8.67 mmol) and stirred at rt for a 1 h. More 1,1-dimethylethyl 4-piperidinylcarbamate (297 mg; 1.45 mmol) was added and the reaction was stirred under the same conditions for a further 0.5 h. This was then again treated with NaBH(OAc)$_3$ (915 mg; 4.34 mmol) and stirred at rt for a further 0.75 h. More 1,1-dimethylethyl 4-piperidinylcarbamate (118 mg; 0.578 mmol) was then added, the reaction was stirred at rt for a further 10 mins, followed by addition of NaBH(OAc)$_3$ (366 mg; 1.73 mmol), the reaction was stirred for a further 25 mins. The solvents were removed and the crude residue purified by chromatography on silica gel using a 010% MeOH/DCM gradient to provide the impure desired compound (1.32 g, 117%)

MS (ES+) m/z 390 (MH$^+$).

(b) 1-[2-(4-Amino-1-piperidinyl)ethyl]-7-fluoro-2 (1H)-quinolinone 1,1-dimethylethyl {1-[2-(7-fluoro-2-oxo-1(2H)-quinolinyl)ethyl]-4-piperidinyl}carbamate (1.32 g; 3.39 mmol) was dissolved in a mixture of chloroform (10 ml) and HCl (12 ml) and stirred at rt under argon for 1 h. The salts were then dissolved in MeOH and all solvents removed. The residues were redissolved in MeOH and stirred with amberlyst ion exchange resin until a neutral pH was reached. This was then filtered and the solvent removed. The crude residue was subjected to chromatography on silica gel using a 0-20% 2M NH$_3$:MeOH/DCM gradient to provide the desired compound (632 mg; 64%)

MS (ES+) m/z 290 (MH$^+$).

(c) Title Compound

A mixture of 1-[2-(4-amino-1-piperidinyl)ethyl]-7-fluoro-2(1H)-quinolinone (100 mg; 0.364 mmol) and [1,3]oxathiolo[5,4-c]pyridine-6-carbaldehyde (for a synthesis see WO2004058144, Example 61) (57 mg; 0.364 mmol) were dissolved in a 5:1 mixture of chloroform and methanol (5 ml: 1 ml) and stirred at rt under argon for 1 h. The mixture was then treated with NaBH(OAc)$_3$ (231 mg; 1.092 mmol) and stirred for a further 1 h. The solvents were then removed and the crude residues purified by chromatography on silica gel using a 0-15% MeOH/DCM gradient to provide the title compound as free base (140 mg; 92%)

MS (ES+) m/z 441 (MH$^+$).

δH CDCl$_3$, (400 MHz) 1.68 (m, 2H), 2.01 (s, 2H), 2.04 (s, 3H), 2.34 (t, 2H), 2.74 (t, 3H), 3.15 (m, 2H), 3.92 (s, 2H), 4.43 (t, 2H), 5.48 (bs, 2H), 5.75 (s, 2H), 6.62 (d, 1H), 6.96 (m, 1H), 7.24 (m, 2H), 7.52 (m, 1H), 7.64 (d, 1H), 8.00 (s, 1H).

This compound was converted to the di-HCl salt by dissolving the obtained free base in MeOH adding 4M HCl in 1,4-dioxane. This was then evaporated to dryness.

Example 5

6-[({1-[2-(7-fluoro-2-oxo-1 (2H)-quinolinyl)ethyl]-4-piperidinyl}amino)methyl]-2H-pyrido[3,2-b][1,4]oxazin-3(4H)-one dihydrochloride

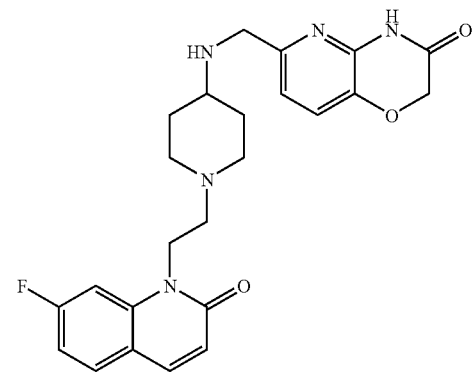

The title compound was prepared by the general method of Example 4(d) using 1-[2-(4-amino-1-piperidinyl)ethyl]-7-fluoro-2(1H)-quinolinone (100 mg; 0.346 mmol) and 3-oxo-3,4-dihydro-2H-pyrido[3,2-b][1,4]oxazine-6-carboxaldehyde (for a synthesis see WO2003087098, Example 31(e)) (66 mg; 0.346 mmol) and purified by chromatography on silica gel using a 0-20% MeOH/DCM gradient to obtain the title compound as free base (100 mg; 64%).

MS (ES+) m/z 453 (MH$^+$)

δH CDCl$_3$, (400 MHz) 1.76 (dd, 2H), 2.05 (m, 6H), 2.31 (t, 2H), 2.75 (m, 2H), 2.82 (bs, 1H), 3.19 (m, 2H), 3.95 (s, 2H), 4.43 (t, 2H), 4.62 (s, 2H), 6.62 (d, 1H), 6.95 (d, 2H), 7.21 (d, 2H), 7.53 (m, 1H), 7.63 (d, 1H).

This material was converted to the dihydrochloride by dissolving the free base in DCM/methanol and adding 4M HCl/1,4-dioxane then evaporating to dryness to give a yellow solid.

Example 6

1-(2-{4-[(6,7-dihydro[1,4]dioxino[2,3-c]pyridazin-3-ylmethyl)amino]-1-piperidinyl}ethyl)-7-fluoro-2(1H)-quinolinone Dihydrochloride

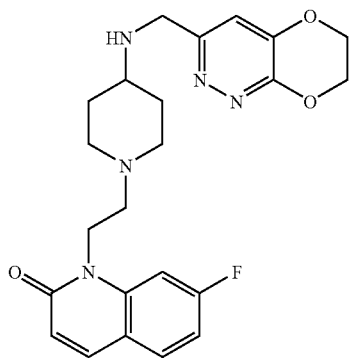

(a) 3,4,6-Trichloropyridazine

This was prepared by a slight variation on the method of Kasnar et al, Nucleosides & Nucleotides (1994), 13(1-3), 459-79.

Hydrazine sulphate salt (51 g) was suspended in water (250 ml), heated to reflux and bromomaleic anhydride (90.38 g) was added dropwise. The mixture was heated at reflux for 4 hours then cooled to room temperature. The reaction was repeated with 29 g hydrazine sulphate, 53 g bromomaleic anhydride and 130 ml water. The precipitates were collected by filtration, washed with water and acetone and dried as a combined batch in vacuo to afford 4-bromo-1,2-dihydro-3,6-pyridazinedione as a white solid (113 g).

The solid in two batches was treated with phosphorus oxychloride (2×200 ml) and heated to reflux for 3.5 hours. The mixture was cooled, evaporated and azeotroped with toluene. The residue was partitioned between dichloromethane and saturated aqueous sodium bicarbonate solution and extracted with DCM twice more. The organic extracts were dried and evaporated. This residue was re-dissolved in dichloromethane, and chromatographed on silica gel (300 g) (DCM as eluent) to give a white solid (101.5 g, 87%).

(LC/MS analysis showed ca 20-30% impurity, isomers of bromo-dichloropyridazine).

MS (+ve ion electrospray) m/z 184/185/186 (MH+), trichloropyridazine.

MS (+ve ion electrospray) m/z 228/229/231 (MH+), bromo-dichloropyridazine.

(b) 2-[(3,6-Dichloro-4-pyridazinyl)oxy]ethanol

A solution of ethylene glycol (55 ml) in tetrahydrofuran (200 ml) was treated at around 0° C. (ice bath cooling) with sodium hydride (60% dispersion in oil, 5.9 g) over 40 minutes. After the addition was complete, 3,4,6-trichloropyridazine (27 g) containing isomers of bromo-dichloropyridazine as impurity was added portionwise and washed in with more dry THF (50 ml) and the mixture was stirred at 0° C. for 1 hour and then at room temperature overnight. The mixture was concentrated (to ⅓ volume) then diluted with aqueous sodium bicarbonate solution and extracted with chloroform (5×) and ethyl acetate (3×). The combined organic extracts were washed with water, dried over sodium sulphate and evaporated and the solids filtered off and washed with CHCl₃ (×3) and dried in a vacuum oven overnight at 40° C. affording a white solid (25.5 g, 83%), containing some bromo-derivative (10-15%).

MS (+ve ion electrospray) m/z 209/211 (MH+).

MS (+ve ion electrospray) m/z 255/7 (MH+), bromo-derivative.

(c) 3-Chloro-6,7-dihydro[1,4]dioxino[2,3-c]pyridazine

A solution of 2-[(3,6-dichloro-4-pyridazinyl)oxy]ethanol containing some bromo-derivative (15.46 g; 0.0703 mol) in dry 1,4-dioxane (1.2 L) was treated with lithium hydride (2.3 g; 0.28 mol) in portions and stirred at room temperature for 1 hour under argon, then heated at 110° C. overnight. The reaction mixture was quenched with wet 1,4-dioxane, then iced-water. The solution was evaporated to half volume, taken to pH 8 with 5M hydrochloric acid and evaporated to dryness. Water was added and the residue was extracted 5× with chloroform, dried (sodium sulphate) and evaporated to afford a white solid (12.4 g, ca. 77%) (containing ca. 15% of a bromo species).

MS (+ve ion electrospray) m/z 173/5 (Cl MH+); 217/9 (Br MH+)

(d) 3-Ethenyl-6,7-dihydro[1,4]dioxino[2,3-c]pyridazine

A solution of 3-chloro-6,7-dihydro[1,4]dioxino[2,3-c]pyridazine (13.6 g, 0.079 mol) containing ca. 15% of a bromo species in dimethoxyethane (400 ml) was degassed under argon for 10 min then tetrakis(triphenylphosphine)palladium (0) (2 g), potassium carbonate (10.33 g), 2,4,6-trivinylcyclotriboroxane pyridine complex (11.32 g) and water (55 ml) were added. The mixture was heated at 95° C. for 48 hours and cooled and evaporated to dryness. The mixture was treated with aqueous sodium bicarbonate solution and extracted (5×) with DCM. Extracts were dried (sodium sulphate), evaporated and the residue chromatographed on silica gel (500 g), eluting with 0-100% ethyl acetate-hexane, affording the product (6.43 g, 50%); [also some impure fractions (1.8 g)].

MS (+ve ion electrospray) m/z 165 (MH+).

(e) 6,7-Dihydro[1,4]dioxino[2,3-c]pyridazine-3-carbaldehyde

A solution of 3-ethenyl-6,7-dihydro[1,4]dioxino[2,3-c]pyridazine (11.58 g) in 1,4-dioxane/water (600 ml/180 ml), cooled in ice, was treated with an aqueous solution of osmium tetroxide (4% w/v, 25 ml) and sodium periodate (43 g). This mixture was allowed to warm to room temperature and after 7 hours under stirring the mixture was evaporated to dryness and azeotroped with 1,4-dioxane. Silica gel, 1,4-dioxane and chloroform were added and the mixture was evaporated to dryness overnight, then added to a silica column (400 g) and chromatographed, eluting with chloroform then 0-100% ethyl acetate in hexane, to afford a white solid (7.55 g, 64%).

MS (+ve ion electrospray) m/z 167 (MH+).

(f) Title Compound

The title compound was prepared by the general method of Example 4(d) using 1-[2-(4-amino-1-piperidinyl)ethyl]-7-fluoro-2(1H)-quinolinone (100 mg, 0.346 mmol) and 6,7-dihydro[1,4]dioxino[2,3-c]pyridazine-3-carbaldehyde (57 mg, 0.346 mmol) and purified by column chromatography on silica gel using a 0-12% MeOH/DCM gradient to obtain the title compound as free base (86 mg, 66%). δH CDCl$_3$, (400 MHz) 1.65 (m, 2H), 2.03 (s, 1H), 2.06 (s, 4H), 2.40 (t, 2H), 2.75 (m, 3H), 3.17 (d, 2H), 3.93 (bs, 2H), 4.05 (s, 2H), 4.38 (m, 2H), 4.47 (m, 2H), 4.53 (m, 2H), 6.62 (d, 1H), 6.97 (m, 1H), 7.08 (s, 1H), 7.31 (d, 1H), 7.53 (m, 1H), 7.65 (d, 1H)

MS (ES+) m/z 440 (MH$^+$).

This material was converted to the dihydrochloride by dissolving the free base in DCM/methanol and adding 4M HCl/dioxane then evaporating to dryness to give a yellow solid.

Example 7

1-(2-{4-[(2,3-Dihydro[1,4]dioxino[2,3-c]pyridin-7-ylmethyl)amino]-1-piperidinyl}ethyl)-7-fluoro-1,5-naphthyridin-2(1H)-one Hydrochloride

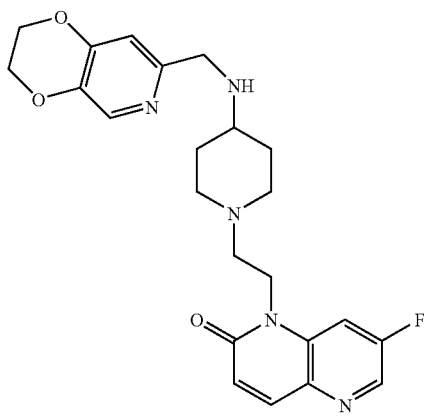

(a) 7-Fluoro-2-(methoxy)-1,5-naphthyridine

8-Bromo-7-fluoro-2-(methoxy)-1,5-naphthyridine (for a synthesis see WO2004058144, Example 53(g)) (5.040 g, 19.61 mmol) was stirred in MeOH (200 ml) with sodium hydrogen carbonate (3.29 g, 39.22 mmol) and 10% palladium on carbon (2.5 g), and the resulting suspension was hydrogenated at 1 atmosphere of hydrogen pressure under for 4 h. The mixture was filtered with suction through celite and the solids were washed with MeOH (500 ml). The combined filtrate plus washings were concentrated to about 50 ml under reduced pressure and then treated with water (200 ml) and DCM (300 ml). The aqueous phase was separated and extracted twice more with DCM (300 ml). The combined organic phases were separated, dried over anhydrous magnesium sulphate, filtered and evaporated to give the desired compound as an off-white solid (3.044 g, 87%).

MS (ES+) m/z 179 (MH$^+$).

(b). 7-Fluoro-1,5-naphthyridin-2(1H)-one

A suspension of 7-fluoro-2-(methoxy)-1,5-naphthyridine (3.044 g, 17.101 mmol) in glacial acetic acid (50 ml) at rt under argon, was treated with 33% HBr in acetic acid (50 ml). After stirring at rt for 18 h, the solvents were evaporated (copious fumes of HBr were produced). The residue was treated with acetic acid (100 ml) and re-evaporated, then stirred with water (200 ml) and the pH of the suspension was adjusted to pH 4 by addition of solid sodium hydrogen carbonate. The mixture was then stirred at rt for 1 hour then the solid was isolated by filtration with suction to give an off-white damp solid. The product was dried on the sinter with suction for 2 hours then dried in a vacuum desiccator over P$_2$O$_5$ overnight to give the desired compound as a white solid (2.412 g, 86%).

MS (ES+) m/z 165 (MH$^+$).

(c) 7-Fluoro-1-(2-propen-1-yl)-1,5-naphthyridin-2(1H)-one

7-Fluoro-1,5-naphthyridin-2(1H)-one (2.152 g, 13.122 mmol) was suspended in dry DMF (40 ml) under argon at 0° C., and the stirred suspension was treated with sodium hydride (1.155 g of a 60% w:w dispersion in oil, 2.2 eq.) added in portions. The suspension was allowed to warm to rt. After stirring for 30 mins at rt, the mixture was treated with allyl iodide (2.67 ml, 2.2 eq) and then stirred for a further 30 min before addition of water (100 ml). The mixture was then extracted with DCM (3×200 ml). The organic extracts were combined, dried over anhydrous magnesium sulphate, filtered and evaporated to give a residue which was purified by column chromatography on silica with a 0-10% methanol in DCM gradient to give the desired product as a light brown solid (1.683 g, 63%).

MS (ES+) m/z 205 (MH$^+$).

(d) (7-Fluoro-2-oxo-1,5-naphthyridin-1(2H)-yl)acetaldehyde (as the Methyl Hemiacetal)

7-Fluoro-1-(2-propen-1-yl)-1,5-naphthyridin-2(1H)-one (1.683 g, 8.25 mmol) was dissolved in 1,4-dioxane (100 ml) and water (50 ml) was added. The solution was cooled to 0° C. and sodium periodate (5.29 g, 24.75 mmol) was added, followed by osmium tetroxide (9 mL of 4% aqueous solution). The stirred mixture was allowed to warm to rt, then stirred at rt for 1 h. The mixture was then treated with a further 100 ml of water and sodium periodate (10.58 g, 49.5 mmol) and stirred at rt for 1 h. The mixture was evaporated to approximately 50 ml and the residue was extracted with 20% methanol in DCM (3×300 ml). The organic extracts were combined, dried over anhydrous magnesium sulphate, filtered and evaporated to give (7-fluoro-2-oxo-1,5-naphthyridin-1(2H)-yl)acetaldehyde (mainly as the methyl hemiacetal) as an off-white solid (1.531 g, 90%).

MS (ES+) m/z 239 (MH$^+$) consistent with the proposed hemiacetal structure, NMR (400 MHz, methanol-d$_4$) was also consistent with the proposed hemiacetal structure.

(e) 1,1-Dimethylethyl (2,3-dihydro[1,4]dioxino[2,3-c]pyridin-7-ylmethyl) {1-[2-(7-fluoro-2-oxo-1,5-naphthyridin-1(2H)-yl)ethyl]-4-piperidinyl}carbamate A mixture of (7-fluoro-2-oxo-1,5-naphthyridin-1(2H)-yl)acetaldehyde (mainly as the methyl hemiacetal) (441 mg) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (747 mg, 2.141 mmol) in chloroform (20 ml) and MeOH (1 ml) was stirred for 2 h before addition of NaBH(OAc)$_3$ (1.36 g, 6.422 mmol). The reaction was stirred for 0.5 h before addition of sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the desired compound as a white foam (900 mg, 78%).

MS (ES+) m/z 540 (MH$^+$).

(f) Title Compound

A solution of 1,1-dimethylethyl (2,3-dihydro[1,4]dioxino[2,3-c]pyridin-7-ylmethyl) {1-[2-(7-fluoro-2-oxo-1,5-naphthyridin-1(2H)-yl)ethyl]-4-piperidinyl}carbamate (900 mg, 1.67 mmol) in chloroform (10 ml) and MeOH (10 ml) was added 4M HCl in 1,4-dioxane (10 ml) and the reaction was stirred under argon at rt for 0.5 h before evaporation, treatment with sat. aq NaHCO$_3$. The reaction was then extracted with 10% MeOH in DCM (3×200 ml). The combined organic phases were dried, evaporated and the crude residue purified by chromatography on silica gel using a 0-20% MeOH/DCM gradient to provide the free base of the title compound (595 mg, 81%).

MS (ES+) m/z 440 (MH$^+$).
$^1$H NMR (250 MHz) δ (CDCl$_3$) 1.25-1.42 (2H, m), 1.81-1.98 (2H, m), 2.01-2.21 (2H, m), 2.40-2.55 (1H, m), 2.62-2.74 (2H, t), 3.00-3.12 (2H, m), 3.78 (2H, s), 4.25-4.35 (m, 4H), 4.63 (2H, t), 6.81 (1H, s), 6.84 (1H, d, J=10 Hz), 7.51 (1H, d, J=8 Hz), 7.68 (1H, d, J=10 Hz), 7.98 (1H, d, J=8 Hz), 8.08 (1H, s).

This compound was converted to the HCl salt by dissolving the obtained free base in 1:1 DCM:MeOH and adding 1 equivalent of 4M HCl in 1,4-dioxane. This was then evaporated to dryness to give a white solid (597 mg).

Example 8

1-(2-{4-[(3,4-dihydro-2H-pyrano[2,3-c]pyridin-6-ylmethyl)amino]-1-piperidinyl}ethyl)-7-fluoro-1,5-naphthyridin-2(1H)-one hydrochloride

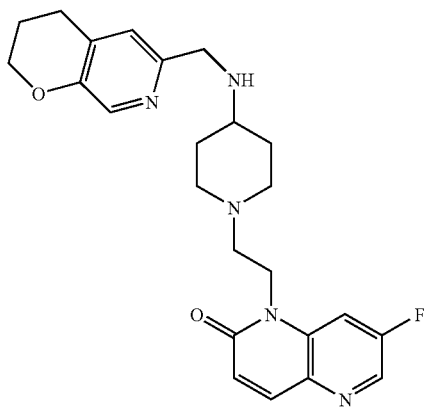

(a) 1,1-Dimethylethyl {1-[2-(7-fluoro-2-oxo-1,5-naphthyridin-1(2H)-yl)ethyl]-4-piperidinyl}carbamate A mixture of (7-fluoro-2-oxo-1,5-naphthyridin-1(2H)-yl) acetaldehyde (as the methyl hemiacetal) (1.09 g, 5.291 mmol) and 1,1-dimethylethyl 4-piperidinylcarbamate (1.06 g, 5.291 mmol) in chloroform (50 ml) and MeOH (2.5 ml) was stirred for 2 h before addition of NaBH(OAc)$_3$ (3.37 g, 15.873 mmol). The reaction was stirred for 0.5 h before addition of sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the desired compound (1.591 g, 77%).

MS (ES+) m/z 391 (MH$^+$).

(b) 1-[2-(4-Amino-1-piperidinyl)ethyl]-7-fluoro-1,5-naphthyridin-2(1H)-one Dihydrochloride To a solution of 1,1-dimethylethyl {1-[2-(7-fluoro-2-oxo-1,5-naphthyridin-1(2H)-yl)ethyl]-4-piperidinyl}carbamate (1.591 g, 4.079 mmol) in chloroform (15 ml) and MeOH (15 ml) was added 4M HCl in 1,4-dioxane (15 ml). The reaction was stirred at rt for 0.5 h before evaporation to provide the desired compound as a slightly impure white solid which was used without further purification (1.633 g, 110%).

MS (ES+) m/z 291 (MH$^+$).

(c) Title Compound

A mixture of 1-[2-(4-amino-1-piperidinyl)ethyl]-7-fluoro-1,5-naphthyridin-2(1H)-one dihydrochloride (145 mg, 0.399 mmol) in chloroform (5 ml) and MeOH (0.1 ml) was treated with triethylamine (161 μl, 1.162 mmol) and stirred for 0.25 h before addition of 3,4-dihydro-2H-pyrano[2,3-c]pyridine-6-carbaldehyde (for a synthesis see WO2004058144, Example 126(e)) (59 mg, 0.363 mmol). The reaction was stirred for 0.5 h before addition of NaBH(OAc)$_3$ (231 mg, 1.089 mmol). The reaction was stirred for 0.5 h before addition of sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (132 mg, 76%).

MS (ES+) m/z 438 (MH$^+$).

$^1$H NMR (250 MHz) δ (CDCl$_3$) 1.39-1.58 (2H, m), 1.88-2.09 (4H, m), 2.11-2.28 (2H, m), 2.50-2.72 (3H, m), 2.72-2.82 (2H, t), 2.92-3.03 (2H, m), 3.82 (2H, s), 4.21 (2H, t), 4.33 (2H, t) 6.86 (1H, d, J=10 Hz), 6.99 (1H, s), 7.58 (1H, dd, J 10.5, 2 Hz), 7.90 (1H, d, J=10 Hz), 8.08 (1H, s), 8.42 (1H, d J 2.5 Hz).

Example 9

1-(2-{4-[(3,4-dihydro-2H-pyrano[2,3-c]pyridin-6-ylmethyl)amino]-1-piperidinyl}ethyl)-7-fluoro-1,5-naphthyridin-2(1H)-one Hydrochloride

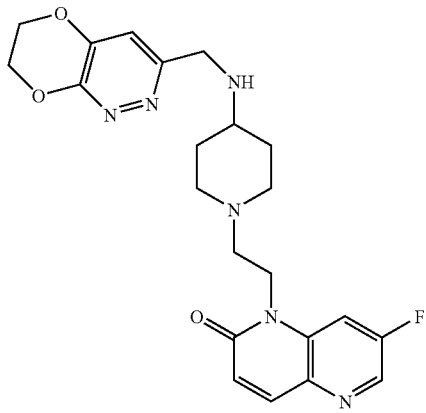

A mixture of 1-[2-(4-amino-1-piperidinyl)ethyl]-7-fluoro-1,5-naphthyridin-2(1H)-one dihydrochloride (127 mg, 0.350 mmol) in chloroform (5 ml) and MeOH (0.1 ml) was treated with triethylamine (154 μl, 1.018 mmol) and stirred for 0.25 h before addition of 6,7-dihydro[1,4]dioxino[2,3-c]pyridazine-3-carbaldehyde (53 mg, 0.318 mmol). The reaction was stirred for 0.5 h before addition of NaBH(OAc)₃ (202 mg, 0.954 mmol). The reaction was stirred for 0.5 h before addition of sat. aq NaHCO₃ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (46 mg, 30%).

MS (ES+) m/z 441 (MH⁺).

¹H NMR (250 MHz) δ (CDCl₃) 1.39-1.58 (2H, m), 1.88-2.09 (4H, m), 2.11-2.28 (2H, m), 2.50-2.72 (3H, m), 2.72-2.82 (2H, t), 2.92-3.03 (2H, m), 3.82 (2H, s), 4.21 (2H, t), 4.33 (2H, t) 6.86 (1H, d, J=10 Hz), 6.99 (1H, s), 7.58 (1H, dd, J 10.5, 2 Hz), 7.90 (1H, d, J=10 Hz), 8.08 (1H, s), 8.42 (1H, d J 2.5 Hz).

This compound was converted to the HCl salt by dissolving the obtained free base in 1:1 DCM:MeOH and adding 1 equivalent of 4M HCl in 1,4-dioxane. This was then evaporated to dryness.

Example 10

1-(2-{4-[(3,4-dihydro-2H-pyrano[2,3-c]pyridin-6-ylmethyl)amino]-1-piperidinyl}ethyl)-7-fluoro-1,5-naphthyridin-2(1H)-one hydrochloride

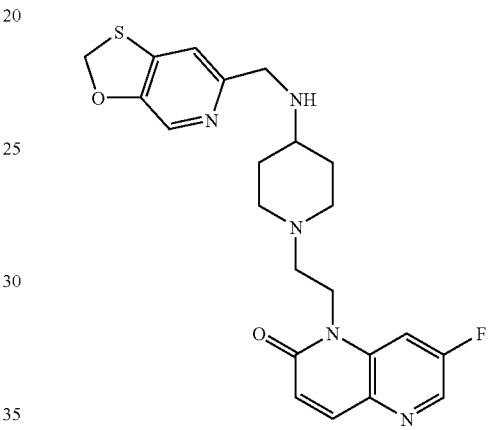

A mixture of 1-[2-(4-amino-1-piperidinyl)ethyl]-7-fluoro-1,5-naphthyridin-2(1H)-one dihydrochloride (141 mg, 0.388 mmol) in chloroform (5 ml) and MeOH (0.1 ml) was treated with triethylamine (156 μl, 1.130 mmol) and stirred for 0.25 h before addition of [1,3]oxathiolo[5,4-c]pyridine-6-carbaldehyde (for a synthesis see WO2004058144, Example 61) (59 mg, 0.353 mmol). The reaction was stirred for 0.5 h before addition of NaBH(OAc)₃ (224 mg, 1.058 mmol). The reaction was stirred for 0.5 h before addition of sat. aq NaHCO₃ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (110 mg, 64%).

MS (ES+) m/z 442 (MH⁺).

¹H NMR (250 MHz) δ (CDCl₃) 1.38-1.56 (2H, m), 1.85-2.01 (2H, m), 2.11-2.30 (2H, m), 2.49-2.72 (3H, m), 2.91-3.03 (2H, m), 3.84 (2H, s), 4.30-4.36 (m, 2H), 5.74 (2H, s), 6.85 (1H, d, J=10 Hz), 7.21 (1H, s), 7.61 (1H, dd, J 10.5, 2 Hz), 7.88 (1H, d, J=10 Hz), 8.00 (1H, s), 8.42 (1H, d J 2.5 Hz).

This compound was converted to the HCl salt by dissolving the obtained free base in 1:1 DCM:MeOH and adding 1 equivalent of 4M HCl in 1,4-dioxane. This was then evaporated to dryness.

Example 11

1-(2-{4-[(2,3-dihydro[1,4]dioxino[2,3-c]pyridin-7-ylmethyl)amino]-1-piperidinyl}ethyl)-7-(methyloxy)-1,5-naphthyridin-2(1H)-one Hydrochloride

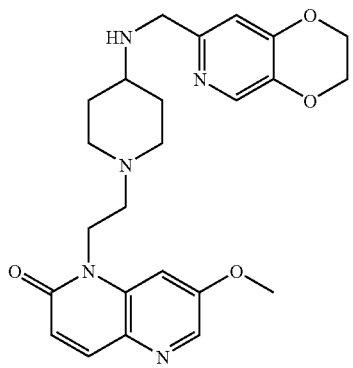

(a) 8-Bromo-2,7-bis(methoxy)-1,5-naphthyridine

8-Bromo-7-fluoro-2-(methoxy)-1,5-naphthyridine (for a synthesis see WO2004058144, example 53(g) (11.215 g, 43.64 mmol) was stirred in methanol (100 mL) at rt under argon and a solution of sodium methoxide in methanol (94 ml of a ca. 25% solution, 10 eq.) was added. The mixture was heated at 50° C. for 1 h. The mixture was allowed to cool to rt, then was diluted with water (500 ml) and brine (500 ml), and extracted with DCM (2×300 ml). The DCM extracts were combined, dried over anhydrous magnesium sulphate, filtered and evaporated under reduced pressure to give 8-bromo-2,7-bis(methoxy)-1,5-naphthyridine as a cream solid (11.21 g, 95%).

MS (ES+) m/z 269/271 (MH$^+$).

(b) 2,7-Bis(methoxy)-1,5-naphthyridine

8-Bromo-2,7-bis(methoxy)-1,5-naphthyridine (11.21 g, 41.673 mmol) was stirred in MeOH (400 mL) with sodium hydrogen carbonate (7.00 g, 83.35 mmol) and 10% palladium on carbon (2.8 g), and the resulting suspension was hydrogenated at 1 atmosphere of hydrogen pressure for 18 h. The mixture was filtered with suction through celite and the solids were washed with ethanol (300 ml). The filtrate was concentrated under reduced pressure and the residue treated with DCM (300 ml) and water (300 ml). The aqueous phase was extracted with DCM (2×300 ml). The combined organic phases were separated, dried over anhydrous magnesium sulphate, filtered and evaporated under reduced pressure to give 2,7-bis(methoxy)-1,5-naphthyridine as a cream solid (7.45 g, 94%).

MS (ES+) m/z 191 (MH$^+$).

(c) 7-(Methoxy)-1,5-naphthyridin-2(1H)-one 2,7-bis(methoxy)-1,5-naphthyridine (7.45 g, 39.210 mmol) stirred in glacial acetic acid (100 ml) at rt under argon, was treated with 33% HBr in acetic acid (100 ml). After stirring at rt for 18 h, the solvents were evaporated under reduced pressure (copious fumes of HBr were produced). The orange solid residue was stirred with water (ca. 250 ml) and the pH of the suspension was adjusted to ca. pH 6 by addition of solid sodium hydrogen carbonate. The mixture was then filtered and dried in a vacuum desiccator over P$_2$O$_5$ overnight to give 7-(methoxy)-1,5-naphthyridin-2(1H)-one as an off-white solid (5.958 g, 86%).

MS (ES+) m/z 177 (MH$^+$).

(d) 7-(Methoxy)-1-(2-propen-1-yl)-1,5-naphthyridin-2(1H)-one 7-(Methoxy)-1,5-naphthyridin-2(1H)-one (5.958 g, 33.852 mmol) was suspended in dry DMF (100 ml) under argon at rt, and the stirred suspension was treated with sodium hydride (2.98 g, 60% suspension in oil, 74.48 mmol) and stirred at rt for 0.5 h. Allyl iodide (6.88 ml, 74.475 mmol) was then added. The reaction was stirred at rt for 0.5 h and then the mixture was diluted with water to 300 ml and extracted with DCM (3×300 ml). The DCM extracts were combined, dried over anhydrous magnesium sulphate, filtered and evaporated under reduced pressure to give a brown gum which was purified by chromatography on silica gel using a 0-10% MeOH/DCM gradient to provide the desired compound (4.096 g, 56%). Mixed fractions could be triturated with diethyl ether to provide further compound (0.95 g, 13%).

MS (ES+) m/z 217 (MH$^+$).

(e) [7-(Methoxy)-2-oxo-1,5-naphthyridin-1(2H)-yl]acetaldehyde (as the methyl Hemiacetal)

7-(Methoxy)-1-(2-propen-1-yl)-1,5-naphthyridin-2(1H)-one (5.046 g, 23.361 mmol) was dissolved in 1,4-dioxane (100 mL) and water (100 ml). Sodium periodate (12.49 g, 58.402 mmol) was added, followed by osmium tetroxide (5 mL of 4% aqueous solution). The mixture stirred at rt for 1 h, water (200 ml) was added the mixture was stirred for a further 1 h. The reaction was concentrated to about 300 ml and extracted with 20% MeOH/DCM (3×400 ml). The organic extracts were combined, dried over anhydrous magnesium sulphate, filtered and evaporated under reduced pressure to give [7-(methoxy)-2-oxo-1,5-naphthyridin-1(2H)-yl]acetaldehyde (as the methyl hemiacetal) as a yellow solid (3.807 g, 75%).

MS (ES+) m/z 219, 251 (MH$^+$) (consistent with the proposed hemiacetal structure).

(f) 1,1-Dimethylethyl (2,3-dihydro[1,4]dioxino[2,3-c]pyridin-7-ylmethyl)(1-{2-[7-(methyloxy)-2-oxo-1,5-naphthyridin-1(2H)-yl]ethyl}-4-piperidinyl)carbamate A mixture of [7-(methoxy)-2-oxo-1,5-naphthyridin-1(2H)-yl]acetaldehyde (as the methyl hemiacetal) (530 mg, 2.431 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (848 mg, 2.431 mmol) in chloroform (20 ml) and MeOH (1 ml) was stirred for 2 h before addition of NaBH(OAc)$_3$ (1.546 mg, 7.293 mmol). The reaction was stirred for 0.5 h before addition of sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the desired compound (833 mg, 62%).

MS (ES+) m/z 552 (MH+).

(g) Title Compound

A solution of 1,1-dimethylethyl (2,3-dihydro[1,4]dioxino[2,3-c]pyridin-7-ylmethyl)(1-{2-[7-(methyloxy)-2-oxo-1,5-naphthyridin-1(2H)-yl]ethyl}-4-piperidinyl)carbamate (833 mg, 1.512 mmol) in chloroform (10 ml) and MeOH (10 ml) was added 4M HCl in 1,4-dioxane (10 ml) and the reaction was stirred at rt for 0.5 h before evaporation and treatment with sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (462 mg, 68%).

MS (ES+) m/z 452 (MH+).

$^1$H NMR (250 MHz) δ (CDCl$_3$) 1.35-1.53 (2H, m), 1.85-2.00 (2H, m), 2.11-2.28 (2H, m), 2.43-2.71 (3H, m), 2.92-3.05 (2H, m), 3.78 (2H, s), 3.98 (3H, s), 4.26-4.40 (m, 6H), 6.74 (1H, d, J=10 Hz), 6.82 (1H, s), 7.25 (1H, s), 7.82 (1H, d, J 10 Hz), 8.10 (1H, s), 8.28 (1H, d J 2.5 Hz).

This compound was converted to the HCl salt by dissolving the obtained free base in 1:1 DCM:MeOH and adding 1 equivalent of 4M HCl in 1,4-dioxane. This was then evaporated to dryness.

Example 12

1-(2-{4-[(6,7-dihydro[1,4]dioxino[2,3-c]pyridazin-3-ylmethyl)amino]-1-piperidinyl}ethyl)-7-(methyloxy)-2(1H)-quinolinone Dihydrochloride

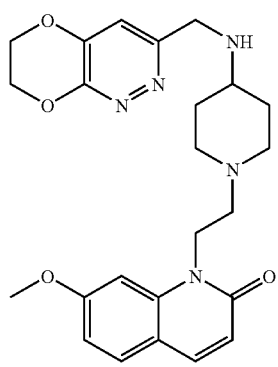

(a) 1,1-Dimethylethyl (1-{2-[7-(methyloxy)-2-oxo-1(2H)-quinolinyl]ethyl}-4-piperidinyl)carbamate

[7-(Methyloxy)-2-oxo-1(2H)-quinolinyl]acetaldehyde (2.31 g, 10.65 mmol) and 1,1-dimethylethyl 4-piperidinylcarbamate (3.15 g, 15.98 mmol) were stirred in a 1:1 mixture of chloroform and methanol (140 ml) for 1 h at rt under argon. This mixture was then treated with NaBH(OAc)$_3$ (10.16 g, 47.93 mmol) and stirred for a further 45 mins. The solvents were then removed from the reaction and crude residues purified by column chromatography on silica gel using a 0-35% MeOH/DCM gradient, to give the desired product (2.0 g; 47%).

MS (ES+) m/z 402 (MH+).

(b) 1-[2-(4-Amino-1-piperidinyl)ethyl]-7-(methyloxy)-2(1H)-quinolinone 1,1-Dimethylethyl (1-{2-[7-(methyloxy)-2-oxo-1(2H)-quinolinyl]ethyl}-4-piperidinyl)carbamate (2.25 g; 5.61 mmol) was dissolved in a mixture of chloroform (20 ml) and HCl (15 ml) and stirred at rt under argon for 1 hour. The salts were dissolved in MeOH and a small amount of toluene added, all the solvents were then removed. The residues were redissolved in MeOH and stirred with amberlyst ion exchange resin until a neutral pH was reached. The resin was filtered off and the solvent removed and the crude residues were purified by column chromatography on silica gel using a 0-20% 2M NH$_3$:MeOH/DCM gradient, to give the desired product (900 mg; 54%).

(c) Title Compound

1-[2-(4-Amino-1-piperidinyl)ethyl]-7-(methyloxy)-2(1H)-quinolinone (300 mg; 0.99 mmol) and 6,7-dihydro[1,4]dioxino[2,3-c]pyridazine-3-carbaldehyde (164 mg; 0.99 mmol) were dissolved in a 5:1 mixture of chloroform and methanol (10 ml:2 ml) and stirred at rt under argon for 4 days. This was then treated with NaBH(OAc)$_3$ (634 mg, 2.97 mmol) and left to stir for 1 h. More 6,7-dihydro[1,4]dioxino[2,3-c]pyridazine-3-carbaldehyde (25 mg; 0.15 mmol) was then added and the mixture stirred overnight at rt. More NaBH(OAc)$_3$ (300 mg; 1.38 mmol) was then added and stirred for 30 mins. The solvents were then removed and the crude residues were purified by column chromatography on silica gel using a 0-30% MeOH/DCM gradient. Fractions containing desired were concentrated to afford the product as the acetate salt (306 mg; 68%). δH CDCl$_3$, (400 MHz) 1.57 (m, 2H), 2.0 (m, 3H), 2.33 (t, 2H), 2.63 (m, 1H), 2.74 (t, 2H), 3.12 (d, 2H), 3.94 (s, 3H), 4.01 (s, 2H), 4.37 (m, 2H), 4.51 (m, 4H), 6.51 (d, 1H), 6.82 (dd, 1H), 6.99 (d, 1H), 7.04 (s, 1H), 7.45 (d, 1H), 7.59 (d, 1H).

MS (ES+) m/z 452 (MH+).

This compound was converted to the diHCl salt by dissolving the free base in MeOH and treating it with 4M HCl in 1,4-dioxane. This was then evaporated to dryness.

Example 13

1-(2-{4-[(2,3-dihydro[1,4]dioxino[2,3-c]pyridin-7-ylmethyl)amino]-1-piperidinyl}ethyl)-7-(methyloxy)-1,8-naphthyridin-2(1H)-one Dihydrochloride

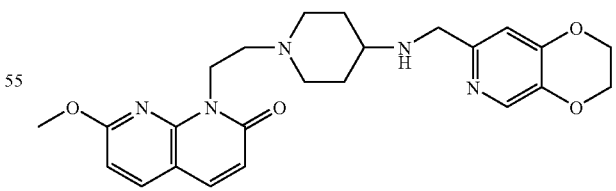

(a) 1-(2-Propen-1-yl)-7-(2-propen-1-yloxy)-1,8-naphthyridin-2(1H)-one

A suspension of 1,8-naphthyridine-2,7(1H,8H)-dione (8.0 g, 49.4 mmol)(prepared according to the method of Newkome, George R et al, Journal of Organic Chemistry

53

(1981), 46(5), 833-9) in DMF (200 ml) was treated under argon with sodium hydride (2.2 g of 60% dispersion with mineral oil, 1.3 g, 55 mmol) then heated to 40° C. for 20 minutes. Allyl bromide (~5 ml) was added. After 2 hours at 40° C. more sodium hydride (2.2 g of 60% dispersion with mineral oil, 1.3 g, 55 mmol) and allyl iodide (~5 ml) were added. After a further 1 hour at 40° C. the mixture was cooled to room temperature and quenched with saturated aqueous ammonium chloride (5 ml). The mixture was evaporated and the residue chromatographed eluting with 0-10% ethyl acetate in hexane affording the product as a yellow oil (5.2 g, 45%).

MS (ES+) m/z 243 (MH+).

(b) 1-(2-Propen-1-yl)-1,8-naphthyridine-2,7(1H,8H)-dione

A solution of 1-(2-propen-1-yl)-7-(2-propen-1-yloxy)-1,8-naphthyridin-2(1H)-one (440 mg, 1.8 mmol) in acetic acid (1 ml) was treated with 33% hydrogen bromide in acetic acid (1 ml) and heated for 1 hour at 50° C. and 10 hours at 80° C. The mixture was evaporated to dryness and taken to pH4 with saturated aqueous sodium bicarbonate (~5 ml). The mixture was extracted with ethyl acetate, dried and evaporated. The residue was chromatographed eluting with 0-100% ethyl acetate in hexane affording the product as a yellow oil (123 mg, 34%).

MS (ES+) m/z 203 (MH+).

(c) 7-(Methyloxy)-1-(2-propen-1-yl)-1,8-naphthyridin-2(1H)-one

A solution of 1-(2-propen-1-yl)-1,8-naphthyridine-2,7 (1H,8H)-dione (123 mg, 0.61 mmol) in DMF (2 ml) was treated under argon with a solution of potassium t-butoxide in THF (1M; 0.7 ml, 0.7 mmol) then methyl iodide (0.06 ml, 142 mg, 1 mmol) was added. After 30 minutes the mixture was evaporated and the residue chromatographed eluting with 0-100% ethyl acetate in hexane affording an oil (120 mg, 92%).

MS (ES+) m/z 217 (MH+).

(d) 1,1-Dimethylethyl (2,3-dihydro[1,4]dioxino[2,3-c]pyridin-7-ylmethyl)(1-{2-[7-(methyloxy)-2-oxo-1,8-naphthyridin-1(2H)-yl]ethyl}-4-piperidinyl)carbamate A solution of 7-(methyloxy)-1-(2-propen-1-yl)-1,8-naphthyridin-2(1H)-one (110 mg, 0.51 mmol) in 1,4-dioxane/water (6 ml/6 ml) was treated with osmium tetroxide solution (4% in water, 0.6 ml) followed by sodium periodate (500 mg, 2.3 mmol). After 2 hours more water (6 ml) was added. After a further 2 hours more sodium periodate (1.3 g, 6 mmol) and more water (6 ml) was added. After 1 hour the mixture was concentrated and partitioned between brine (30 ml) and 10% methanol in dichloromethane (30 ml). The aqueous phase was further extracted with 10% methanol in dichloromethane (2×30 ml). The combined organic extracts were dried and evaporated to give a brown oil (100 mg) which was dissolved in dichloromethane/methanol (3 ml/0.3 ml) then treated with 1,1-dimethylethyl (2,3-dihydro[1,4]dioxino[2,3-c]pyridin-7-ylmethyl)-4-piperidinylcarbamate (for a synthesis see WO2004/058144 Example 99(h)) (160 mg, 0.46 mmol) and sodium triacetoxyborohydride (320 mg, 1.5 mmol). After 1 hour the mixture was treated with saturated aqueous sodium bicarbonate. The organic extract was added to a silica column eluting with 0-30% methanol in dichloromethane affording an oil (170 mg, 67% over the two stages).

MS (ES+) m/z 552 (MH+).

(e) Title Compound

A solution of 1,1-dimethylethyl (2,3-dihydro[1,4]dioxino[2,3-c]pyridin-7-ylmethyl)(1-{2-[7-(methyloxy)-2-oxo-1,8-naphthyridin-1(2H)-yl]ethyl}-4-piperidinyl)carbamate (160 mg, 0.3 mmol) in TFA/dichloromethane (2 ml/2 ml) was allowed to stand at room temperature for 1 hour then evaporated to dryness, azeotroping with chloroform. The residue was dissolved in dichloromethane/methanol (10 ml/10 ml) and treated with MP-carbonate resin (2.5 mmol of carbonate per gramme, 4 g, 10 mmol). After 15 minutes the mixture was filtered, washing with dichloromethane then methanol (twice) followed by evaporation affording the free base of the title compound.

MS (ES+) m/z 452 (MH+).

δH CDCl₃, (250 MHz) 1.35-1.55 (2H, m), 1.60-2.25 (4H, m), 2.45-2.60 (1H, m), 2.65-2.75 (2H, m), 3.00-3.15 (2H, m), 3.95-4.20 (5H, m), 4.25-4.40 (4H, m), 4.55-4.70 (2H, m), 6.50-6.60 (2H, m), 6.80 (1H, s), 7.55 (1H, d), 7.70 (1H, d), 8.10 (1H, s).

The residue was suspended in dichloromethane/methanol (1 ml/1 ml) and a small amount of insoluble material was removed by centrifugation followed by decanting off the supernatant. The supernatant was treated with a solution of 1M hydrochloric acid in ether (1 ml) and diluted with ether. The title compound was isolated by centrifugation as a solid (115 mg).

Example 14

1-(2-{4-[(6,7-dihydro[1,4]dioxino[2,3-c]pyridazin-3-ylmethyl)amino]-1-piperidinyl}ethyl)-2-oxo-1,2-dihydro-7-quinolinecarbonitrile Diformate

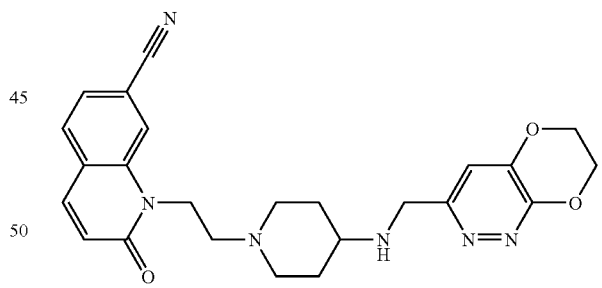

(a) 7-Quinolinyl trifluoromethanesulfonate

A suspension of 7-hydroxy quinoline (1 g, 6.9 mmol) in DCM (50 ml) was treated with pyridine (1.22 mL, 15.2 mmol) under Argon. The reaction mixture was then cooled to 0° C. and trifluoromethansulfonic anhydride was added. The reaction was then stirred at rt for 0.5 h. A saturated solution of ammonium chloride was then added and the two phases were separated. The aqueous phase was re-extracted with DCM twice more. The combined organic phases were dried on magnesium sulphate, filtered and evaporated to give the desired product as a solid (1.88 g, 98%).

MS (ES+) m/z 278 (MH+).

(b) 7-Quinolinecarbonitrile

A solution of 7-quinolinyl trifluoromethanesulfonate (1.88 g, 6.8 mmol) in DMF (40 ml) was degassed for 10 minutes with Argon. Zinc(II) cyanide (0.48 g, 4.08 mmol), tris(dibenzylideneacetone)dipalladium(0) (155 mg, 2.5% mmol) and 1,1'-bis(diphenylphospino)ferrocene (188 mg, 5% mmol) was then added and the mixture was heated at 100° C. under argon for 1.5 h. The solvent was evaporated and residue dissolved in DCM and organic phase washed with a saturated solution of sodium bicarbonate. The aqueous phase was extracted with DCM (3×80 ml). The combined organic phases were dried, evaporated and the residue was chromatographed on silica gel, eluting with 0-10% methanol-DCM to afford the desired compound (1.01 g, 97%).

MS (ES+) m/z 155 (MH+).

(c) 7-Cyano-1-(2-propen-1-yl)quinolinium iodide

7-Quinolinecarbonitrile (1.01 g, 6.6 mmol) and allyl iodide (1.2 mL, 13.2 mmol) in toluene (10 ml) was heated at 90° C. then at 120° C. for 2 h. More allyl iodide was then added (1.2 ml, 13.2 mmol). After other 2 h more allyl iodide was added (1.2 ml, 13.2 mmol). After 2 h more the reaction was cooled to rt. The solid was filtered off, washed with toluene and dried in vacuo at 45° C. overnight to afford the desired compound (1.75 g, 82%).

MS (ES+) m/z 195 (MH+).

(d) 2-Oxo-1-(2-propen-1-yl)-1,2-dihydro-7-quinolinecarbonitrile

A mixture of 7-cyano-1-(2-propen-1-yl)quinolinium iodide (1.75 g, 5.4 mmol), potassium hydroxide (1.33 g, 23.76 mmol) and potassium ferricyanide (3.9 g, 11.9 mmol) in 50% 1,4-dioxane/water was stirred at rt for 2 h. Water (50 ml) was then added and the organic phase was extracted with 10% methanol/DCM (2×100 ml). The combined organic phases were washed with water (100 ml) then dried and evaporated. The residue was chromatographed on silica gel, eluting with 0-5% methanol-DCM to afford the desired compound (0.6 g, 55%).

MS (ES+) m/z 211 (MH+).

(e) 2-Oxo-1-(2-oxoethyl)-1,2-dihydro-7-quinolinecarbonitrile

A solution of 2-oxo-1-(2-propen-1-yl)-1,2-dihydro-7-quinolinecarbonitrile (600 mg, 2.9 mmol) in 1,4-dioxane (30 ml) and water (20 ml) was cooled to 0° C. and treated with $OsO_4$ (4% in water, 3 ml) and sodium periodate (1.4 g, 6.67 mmol). The reaction was warmed to rt; 0.6 g and then 3.7 g more of sodium periodate were added. After 4 h in total, the solvent was evaporated and residue partitioned between water and 20% methanol-DCM. The phases were separated and the organic phase was dried and evaporated to afford the desired compound (660 mg, 107%).

MS (ES+) m/z 213 (MH+).

(f) 1,1-Dimethylethyl {1-[2-(7-cyano-2-oxo-1(2H)-quinolinyl)ethyl]-4-piperidinyl}carbamate A solution of 2-oxo-1-(2-oxoethyl)-1,2-dihydro-7-quinolinecarbonitrile (0.60 g, 2.8 mmol) and 4-t-butoxycarbonylaminopiperidine (0.68 g, 2.8 mmol) in chloroform (30 ml) and MeOH (20 ml) was stirred at 60° C. for 1 h. The mixture was then treated with NaBH(OAc)₃ (1.8 g, 8.5 mmol), stirred at rt for 1 h, more 4-t-butoxycarbonylaminopiperidine (340 mg, 1.4 mmol) and NaBH(OAc)₃ (1.2 g, 5.7 mmol) were then added and the reaction stirred at rt for 1 h. The solvents were then removed and the residue was subjected to column chromatography on silica gel eluting with 0-10% methanol-DCM to afford the desired compound (1.1 g, 98%).

MS (ES+) m/z 397 (MH+).

(g) 1-[2-(4-Amino-1-piperidinyl)ethyl]-2-oxo-1,2-dihydro-7-quinolinecarbonitrile To a solution of 1,1-dimethylethyl {1-[2-(7-cyano-2-oxo-1(2H)-quinolinyl)ethyl]-4-piperidinyl}carbamate (1.1 g, 2.8 mmol) in chloroform (15 ml) was added 4N HCl in 1,4-dioxane (15 ml) and the reaction stirred at rt for 45 mins. Toluene was then added and the solution was evaporated, dissolved in MeOH and treated with Amberlyst A21 basic resin for 30 m until pH of the solution is basic. The resine was filtered off and the solvent removed; the residue was subjected to column chromatography on silica gel eluting with 0-15% 2M ammonia in methanol-DCM to afford the desired compound (0.82 g, 99%).

MS (ES+) m/z 297 (MH+).

(h) Title Compound

A solution of 1-[2-(4-Amino-1-piperidinyl)ethyl]-2-oxo-1,2-dihydro-7-quinolinecarbonitrile (200 mg, 0.68 mmol) and 6,7-dihydro[1,4]dioxino[2,3-c]pyridazine-3-carbaldehyde (113 mg, 0.68 mmol) in chloroform (15 ml) and methanol (10 ml) was stirred at rt under argon overnight and then NaBH(OAc)₃ (432 mg, 2.04 mmol) was added. After 2 h at rt, DMF (1 ml) was added to the mixture. After 1 h, 6,7-dihydro[1,4]dioxino[2,3-c]pyridazine-3-carbaldehyde (113 mg, 0.68 mmol) and DMF (1 mL) were added then reaction stirred at rt overnight. The solvents were then removed and the residue was subjected to column chromatography on silica gel eluting with a 20% 2M ammonia in methanol-DCM to afford 70 mg of impure compound which was subjected to MDAP to afford the title compound (15 mg) directly as the diformate salt.

¹H NMR (400 MHz) δ (CDCl₃) 1.81 (m, 2H), 2.15 (m, 2H), 2.59 (t, 2H), 2.9-3.00 (m, 3H), 3.32 (m, 2H), 4.17 (s, 2H), 4.40-4.64 (m, 10H), 6.81 (d, 1H), 7.10 (s, 1H), 7.49 (d, 1H), 7.65 (d, 1H), 7.71 (d, 1H), 7.93 (s, 1H), 8.31 (s, 2H).

MS (ES+) m/z 447 (MH+).

Example 15A 1-(2-{4-[(2,3-dihydro[1,4]dioxino[2,3-c]pyridin-7-ylmethyl)amino]-1-piperidinyl}ethyl)-2-oxo-1,2-dihydro-7-quinolinecarbonitrile Hydrochloride

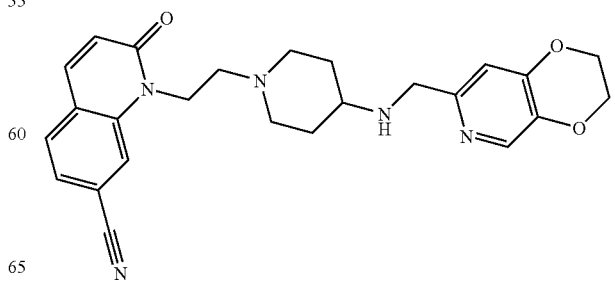

A suspension of 1-[2-(4-amino-1-piperidinyl)ethyl]-2-oxo-1,2-dihydro-7-quinolinecarbonitrile (300 mg, 1.01 mmol) and 2,3-dihydro[1,4]dioxino[2,3-c]pyridine-7-carboxaldehyde (for a synthesis see WO2004058144, Example 2(c) or WO03/087098, Example 19(d)) (167 mg, 1.01 mmol) in chloroform (10 mL), methanol (15 mL) and DMF (20 mL) was stirred at rt for 30 min then NaBH(OAc)$_3$ (642 mg, 3.03 mmol) was added. The reaction was stirred at rt overnight. The solvents were removed and residue dried in vacuo. The residue was subjected to column chromatography on silica gel eluting with 0-20% methanol-DCM to afford the free base of the title compound (247 mg, 55%).

MS (ES+) m/z 446 (MH+).

$^1$H NMR (400 MHz) δ (CDCl$_3$) 1.55 (m, 2H), 1.97 (d, 2H), 2.23 (t, 2H), 2.6-2.7 (m, 3H), 3.04 (d, 2H), 3.37 (bs, 1H), 3.85 (s, 2H), 4.20-4.35 (m, 4H), 4.41 (m, 2H), 6.81 (d, 1H), 6.85 (s, 1H), 7.46 (dd, 1H), 7.64 (d, 1H), 7.69 (d, 1H), 7.80, (s, 1H), 8.10 (s, 1H).

This material was converted to the hydrochloride by dissolving in DCM/methanol and adding 1 equivalent of 4M HCl/1,4-dioxane then evaporating to dryness. Salt dissolved in minimum amount of methanol and diethyl ether added to precipitate it; after trituration, solvent decanted and solid dried in vacuum oven at 40° C.

Example 15B 1-(2-{4-[(2,3-dihydro[1,4]dioxino[2,3-c]pyridin-7-ylmethyl)amino]-1-piperidinyl}ethyl)-2-oxo-1,2-dihydro-7-quinolinecarbonitrile Diformate Purification of 1-(2-{4-[(2,3-dihydro[1,4]dioxino[2,3-c]pyridin-7-ylmethyl)amino]-1-piperidinyl}ethyl)-2-oxo-1,2-dihydro-7-quinolinecarbonitrile by MDAP provided the title compound directly as the diformate salt.

Example 16

1-(2-{4-[(6,7-dihydro[1,4]dioxino[2,3-c]pyridazin-3-ylmethyl)amino]-1-piperidinyl}ethyl)-7-(methyloxy)-1,5-naphthyridin-2(1H)-one Hydrochloride

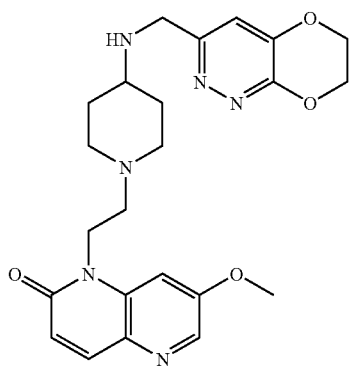

(a) 1,1-Dimethylethyl (1-{2-[7-(methyloxy)-2-oxo-1,5-naphthyridin-1(2H)-yl]ethyl}-4-piperidinyl)carbamate A mixture of [7-(methoxy)-2-oxo-1,5-naphthyridin-1(2H)-yl]acetaldehyde (as the methyl hemiacetal) (3.807 g, 17.463 mmol) and 1,1-dimethylethyl 4-piperidinylcarbamate (3.493 g, 17.463 mmol) in chloroform (100 ml) and MeOH (5 ml) was stirred for 1 h before addition of NaBH(OAc)$_3$ (11.11 g, 52.39 mmol). The reaction was stirred for 0.5 h before addition of water (100 ml) and sat. aq NaHCO$_3$ (100 ml). The reaction was then extracted with 20% MeOH in DCM (3×200 ml). The combined organic phases were dried, evaporated and the crude residue purified by chromatography on silica gel using a 0-10% MeOH/DCM gradient to provide the desired compound (5.453 g, 78%).

MS (ES+) m/z 403 (MH+).

(b) 1-[2-(4-Amino-1-piperidinyl)ethyl]-7-(methyloxy)-1,5-naphthyridin-2(1H)-one dihydrochloride A solution of 1,1-dimethylethyl (1-{2-[7-(methyloxy)-2-oxo-1,5-naphthyridin-1(2H)-yl]ethyl}-4-piperidinyl)carbamate (5.453 g, 13.565 mmol) in chloroform (30 ml) was added 4M HCl in 1,4-dioxane (30 ml) and the reaction was stirred at rt for 0.5 h before addition of MeOH (30 ml). The reaction was stirred for a further 1 h before evaporation to provide the desired compound as a slightly impure white solid (5.323 g, 105%), which was used without further purification.

MS (ES+) m/z 303 (MH+).

(c) Title Compound

A mixture of 1-[2-(4-amino-1-piperidinyl)ethyl]-7-(methyloxy)-1,5-naphthyridin-2(1H)-one dihydrochloride (145 mg, 0.399 mmol) in chloroform (20 ml) and MeOH (2 ml) was treated with triethylamine (0.62 ml, 4.49 mmol) and stirred for 0.25 h before addition of 6,7-dihydro[1,4]dioxino[2,3-c]pyridazine-3-carbaldehyde (226 mg, 1.360 mmol). The reaction was stirred for 0.5 h before addition of NaBH(OAc)$_3$ (577 mg, 2.72 mmol). After 1 h of stirring at rt more NaBH(OAc)$_3$ (577 mg, 2.72 mmol) was added. After a further 1 h still more NaBH(OAc)$_3$ (577 mg, 2.72 mmol) was added. The reaction was then stirred for a further 0.5 h before addition of sat. aq NaHCO$_3$ (20 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (473 mg, 70%).

MS (ES+) m/z 453 (MH+).

$^1$H NMR (250 MHz) δ (CDCl$_3$) 1.45-1.62 (2H, m), 1.90-2.08 (2H, m), 2.25-2.42 (2H, m), 2.52-2.79 (3H, m), 2.95-3.15 (2H, m), 4.01 (5H, m), 4.30-4.56 (m, 6H), 6.73 (1H, d, J=10 Hz), 7.04 (1H, s), 7.35 (1H, s), 7.85 (1H, d, J=10 Hz), 8.28 (1H, d J 2 Hz).

This compound was converted to the HCl salt by dissolving the obtained free base in 1:1 DCM:MeOH and adding 1 equivalent of 4M HCl in 1,4-dioxane. This was then evaporated to dryness.

Example 17

1-(2-{4-[(6,7-dihydro[1,4]dioxino[2,3-c]pyridazin-3-ylmethyl)amino]-1-piperidinyl}ethyl)-7-(methyloxy)-1,8-naphthyridin-2(1H)-one Dihydrochloride

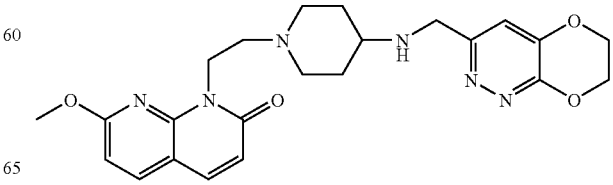

(a) 1,1-Dimethylethyl (1-{2-[7-(methyloxy)-2-oxo-1,8-naphthyridin-1(2H)-yl]ethyl}-4-piperidinyl)carbamate A solution of 7-(methyloxy)-1-(2-propen-1-yl)-1,8-naphthyridin-2(1H)-one (240 mg, 1.1 mmol) in 1,4-dioxane/water (12 ml/20 ml) was treated with osmium tetroxide solution (4% in water, 1 ml) followed by sodium periodate (2.1 g, 10 mmol). After 30 minutes more water (15 ml) was added. After a further 1 hour the mixture was diluted with an equal mixture of brine and extracted twice with ethyl acetate. The dried extracts were evaporated to give a yellow oil. This was dissolved in dichloromethane/methanol (6 ml/0.6 ml) and treated with 1,1-dimethylethyl 4-piperidinylcarbamate (240 mg, 1.2 mmol) then sodium triacetoxyborohydride (626 mg, 3 mmol). After 2 hours the mixture was treated with saturated aqueous sodium bicarbonate and dichloromethane. The organic extract was added to a silica column, eluting with 0-100% ethyl acetate in hexane then 0-20% methanol in ethyl acetate, affording a brown foam (320 mg, 72% over 2 steps).

MS (ES+) m/z 403 (MH+).

(b) Title Compound

A solution of 1,1-dimethylethyl (1-{2-[7-(methyloxy)-2-oxo-1,8-naphthyridin-1(2H)-yl]ethyl}-4-piperidinyl)carbamate (310 mg, 0.77 mmol) in TFA/dichloromethane (10 ml/0 ml) was allowed to stand at room temperature for 1 hour then evaporated to dryness, azeotroping with chloroform then triturating with ether. The resulting solid was dried in vacuo for 1 hour then dissolved in dichloromethane/methanol (10 ml/10 ml) and treated with MP-carbonate resin (2.5 mmol of carbonate per gram, 2.7 g, 7.3 mmol). After 15 minutes the mixture was filtered, washing with dichloromethane then methanol (twice) followed by evaporation to give an oil. This was dissolved in dichloromethane/methanol (5 ml/0.5 ml) then treated with 6,7-dihydro[1,4]dioxino[2,3-c]pyridazine-3-carbaldehyde (172 mg, 1.04 mmol) and sodium triacetoxyborohydride (500 mg, 2.4 mmol). After 1 hour more 6,7-dihydro[1,4]dioxino[2,3-c]pyridazine-3-carbaldehyde (85 mg, 0.5 mmol) was added. After a further 1 hour the mixture was treated with saturated aqueous sodium bicarbonate and dichloromethane. The organic extract was dried and evaporated. The residue was added to a silica column eluting with 0-20% (2M ammonia in methanol) in dichloromethane affording the free base of the title compound as an oil (210 mg, 60% over the two stages).

MS (ES+) m/z 453 (MH+).

δH CDCl₃, (250 MHz) 1.35-1.55 (2H, m), 1.70-2.00 (2H, m), 2.10-2.25 (2H, m), 2.45-2.55 (1H, m), 2.65-2.75 (2H, m), 3.00-3.10 (2H, m), 4.00 (2H, s), 4.03 (3H, s), 4.38 (2H, m), 4.50 (3H, m), 4.60-4.70 (2H, m), 6.57 (1H, d), 6.62 (1H, d), 7.08 (1H, s), 7.60 (1H, d), 7.74 (1H, d).

This oil was dissolved in chloroform and treated with a solution of 1M hydrochloric acid in ether (5 ml) and diluted with ether. The title compound was isolated by centrifugation as a solid (250 mg).

Example 18

6-{[(1-{2-[7-(methyloxy)-2-oxo-1,5-naphthyridin-1(2H)-yl]ethyl}-4-piperidinyl)amino]methyl}-2H-pyrido[3,2-b][1,4]oxazin-3(4H)-one Hydrochloride

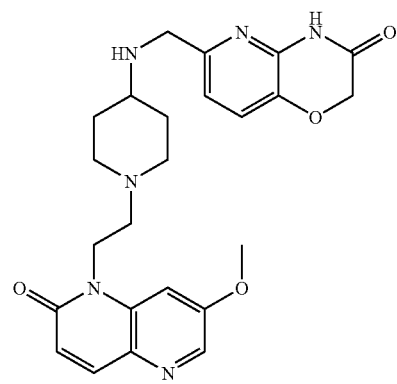

A mixture of 1-[2-(4-amino-1-piperidinyl)ethyl]-7-(methyloxy)-1,5-naphthyridin-2(1H)-one dihydrochloride (164 mg, 0.440 mmol) in chloroform (5 ml) and MeOH (0.5 ml) was treated with triethylamine (194 μl, 1.40 mmol) and stirred for 0.25 h before addition of 3-oxo-3,4-dihydro-2H-pyrido[3,2-b][1,4]oxazine-6-carboxaldehyde (for a synthesis see WO2003087098, Example 31(e)) (71 mg, 0.40 mmol). The reaction was stirred for 0.5 h before addition of NaBH(OAc)₃ (254 mg, 1.20 mmol). The reaction was stirred for a further 0.5 h before addition of sat. aq NaHCO₃ (20 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (144 mg, 71%).

MS (ES+) m/z 465 (MH+).

¹H NMR (250 MHz) δ (CDCl₃) 1.39-1.53 (2H, m), 1.85-1.99 (2H, m), 2.12-2.28 (2H, m), 2.48-2.72 (3H, m), 2.92-3.05 (2H, m), 3.81 (2H, s), 3.98 (3H, s), 4.34-4.40 (m, 2H), 4.64 (2H, s), 6.73 (1H, d, J=10 Hz), 6.93 (1H, d, J=8 Hz), 7.20 (1H, d, J=8 Hz), 7.23 (1H, d, J=2 Hz), (7.84 (1H, d, J=10 Hz), 8.28 (1H, d J 2.5 Hz).

This compound was converted to the HCl salt by dissolving the obtained free base in 1:1 DCM:MeOH and adding 1 equivalent of 4M HCl in 1,4-dioxane. This was then evaporated to dryness.

Example 19

6-[({1-[2-(7-fluoro-2-oxo-1,5-naphthyridin-1(2H)-yl)ethyl]-4-piperidinyl}amino)methyl]-2H-pyrido[3,2-b][1,4]oxazin-3(41H)-one Hydrochloride

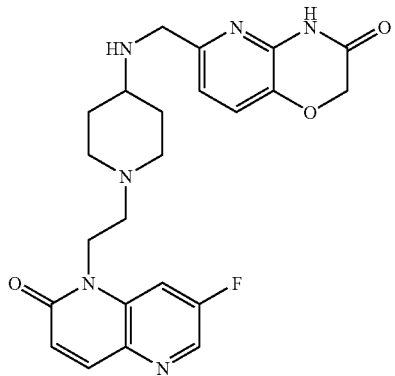

A mixture of 1-[2-(4-amino-1-piperidinyl)ethyl]-7-fluoro-1,5-naphthyridin-2(1H)-one dihydrochloride (180 mg, 0.496 mmol) in chloroform (5 ml) and MeOH (0.1 ml) was treated with triethylamine (218 μl, 1.58 mmol) and stirred for 0.25 h before addition of 3-oxo-3,4-dihydro-2H-pyrido[3,2-b][1,4]oxazine-6-carboxaldehyde (for a synthesis see WO2003087098, Example 31(e)) (80 mg, 0.451 mmol). The reaction was stirred for 0.5 h before addition of NaBH(OAc)$_3$ (315 mg, 1.49 mmol). The reaction was stirred for 0.5 h before addition of sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (187 mg, 83%).

MS (ES+) m/z 453 (MH$^+$).

$^1$H NMR (250 MHz) δ (CDCl$_3$) 1.34-1.65 (2H, m), 1.72-1.99 (2H, m), 2.10-2.28 (2H, m), 2.48-2.72 (3H, m), 2.89-3.03 (2H, m), 3.84 (2H, s), 4.30-4.36 (m, 2H), 4.63 (2H, s), 6.84 (1H, d, J=10 Hz), 6.93 (1H, d, J=8 Hz), 7.19 (1H, d J 8 Hz), 7.55 (1H, dd, J 10, 2 Hz), 7.88 (1H, d, J=10 Hz), 8.41 (1H, d J 2 Hz).

This compound was converted to the HCl salt by dissolving the obtained free base in 1:1 DCM:MeOH and adding 1 equivalent of 4M HCl in 1,4-dioxane. This was then evaporated to dryness.

Example 20

1-(2-{4-[(2,3-dihydro[1,4]dioxino[2,3-c]pyridin-7-ylmethyl)amino]-1-piperidinyl}ethyl)-7-fluoro-2(1H)-quinoxalinone Dihydrochloride

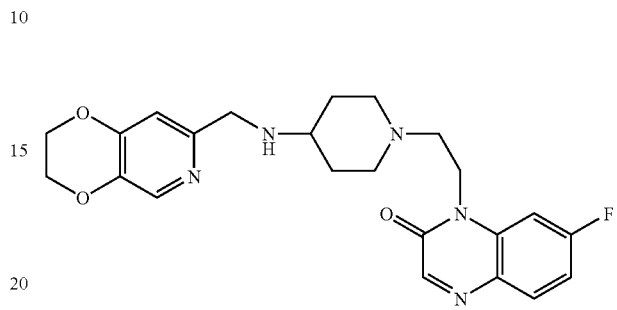

(a) 1,1-Dimethylethyl (2,3-dihydro[1,4]dioxino[2,3-c]pyridin-7-ylmethyl) {1-[2-(7-fluoro-2-oxo-1(2H)-quinoxalinyl)ethyl]-4-piperidinyl}carbamate A solution of 7-fluoro-2-oxo-1(2H)-quinoxalinyl)acetaldehyde (approx. 70% pure, 0.63 g; 2.16 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (0.75 g, 2.16 mmol) in dry methanol (1 mL) and chloroform (20 mL) was stirred at rt for 2 h. Sodium triacetoxyborohydride (1.37 g, 6.49 mmol) was added and the mixture was stirred for 1.5 h. Aqueous sodium bicarbonate was added to basify and the phases were separated. The aqueous phase was extracted with DCM several times, and the organic fractions were dried and evaporated. Chromatography on silica, eluting with 0-20% methanol/DCM, followed by a second chromatography eluting with 50-100% ethyl acetate/hexane, gave the product (0.43 g, 37%).

MS (+ve ion electrospray) m/z 540 (MH+).

(b) Title Compound

A solution of 1,1-dimethylethyl (2,3-dihydro[1,4]dioxino[2,3-c]pyridin-7-ylmethyl) {1-[2-(7-fluoro-2-oxo-1(2H)-quinoxalinyl)ethyl]-4-piperidinyl}carbamate (0.43 g, 0.80 mmol) in DCM (8 ml) and methanol (5 ml) was treated with 4M hydrogen chloride in 1,4-dioxane (8 ml), stirred at rt for 1.5 h and evaporated to dryness (finally dried at 50° C. under vacuum) to give the free base of the title compound (0.41 g, 100%).

δH (DMSO-d$_6$), (250 MHz) 2.07 (2H, m), 2.38 (2H, br.d), 3.10 (2H, m), 3.32 (3H, broad), 3.53 (2H, m), 4.25 (2H, br. s), 4.38 (2H, m), 4.44 (2H, m), 4.62 (2H, m), 5.30 (3H, v. Broad), 7.29 (1H, td). 7.39 (1H, s), 7.82 (1H, dd), 7.92 (1H, dd), 8.22 (1H, s), 8.30 (1H, s), 9.88 (2H, broad), 10.89 (2H broad).

MS (+ve ion electrospray) m/z 440 (MH+).

Example 21

1-(2-{4-[(3,4-dihydro-2H-pyrano[2,3-c]pyridin-6-ylmethyl)amino]-1-piperidinyl}ethyl)-7-(methyloxy)-1,5-naphthyridin-2(1H)-one Hydrochloride

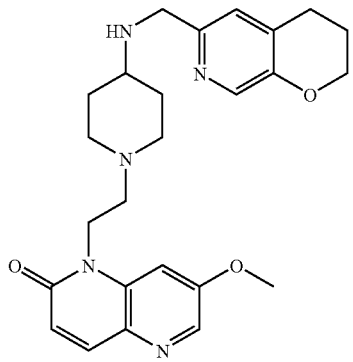

(a) Title Compound

A mixture of 1-[2-(4-amino-1-piperidinyl)ethyl]-7-(methyloxy)-1,5-naphthyridin-2(1H)-one dihydrochloride (174 mg, 0.466 mmol) in chloroform (5 ml) and MeOH (0.1 ml) was treated with triethylamine (205 μl, 1.484 mmol) and stirred for 0.25 h before addition of 3,4-dihydro-2H-pyrano[2,3-c]pyridine-6-carbaldehyde (for a synthesis see WO2004058144, Example 126(e)) (69 mg, 0.424 mmol). The reaction was stirred for 0.5 h before addition of NaBH(OAc)$_3$ (270 mg, 1.272 mmol). The reaction was stirred for 0.5 h before addition of sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (157 mg, 75%).

MS (ES+) m/z 450 (MH+).

$^1$H NMR (250 MHz) δ (CDCl$_3$) 1.37-1.58 (2H, m), 1.82-2.10 (4H, m), 2.11-2.29 (2H, m), 2.40-2.82 (5H, m), 3.80 (2H, m), 3.78 (2H, s), 3.98 (3H, s), 4.19-4.23 (m, 2H), 4.35-4.41 (m, 2H), 6.73 (1H, d, J=10 Hz), 6.97 (1H, s), 7.27 (1H, s), 7.82 (1H, d, J=10 Hz), 8.08 (1H, s), 8.28 (1H, s).

This compound was converted to the HCl salt by dissolving the obtained free base in 1:1 DCM:MeOH and adding 1 equivalent of 4M HCl in 1,4-dioxane. This was then evaporated to dryness.

This compound was converted to the di-HCl salt by dissolving the obtained free base in 1:1 DCM:MeOH and adding 4M HCl in 1,4-dioxane. This was then evaporated to dryness.

Example 22

1-(2-{4-[(2,3-dihydro[1,4]dioxino[2,3-c]pyridin-7-ylmethyl)amino]-1-piperidinyl}ethyl)-6-fluoro-2(1H)-quinoxalinone Dihydrochloride

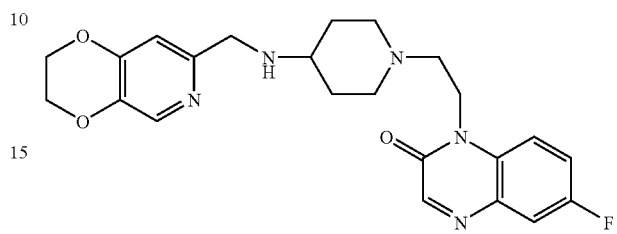

(a) 6-Fluoro-2-oxo-1(2H)-quinoxalinyl)acetaldehyde

A solution of 6-fluoro-1-(2-propen-1-yl)-2(1H)-quinoxalinone (0.86 g; 4.22 mmol) in 1,4-dioxane (50 ml) and water (100 ml) was treated with osmium tetroxide (4% solution in water; 5.1 ml) and sodium periodate (4.14 g) and the mixture was stirred at rt for 3.5 h. Dioxane was removed by evaporation and the residue was extracted several times with 10% methanol/DCM. The extracts were dried and evaporated, and the crude product was chromatographed on silica, eluting with 50-100% ethyl acetate/hexane to give the aldehyde (0.54 g, 62%. Spectra show a mixture of aldehyde and methyl hemiacetal).

MS (+ve ion electrospray) m/z 207 (MH+), 221 (M.CH$_3$+ from hemiacetal).

(b) 1,1-Dimethylethyl (2,3-dihydro[1,4]dioxino[2,3-c]pyridin-7-ylmethyl) {1-[2-(6-fluoro-2-oxo-1(2H)-quinoxalinyl)ethyl]-4-piperidinyl}carbamate A solution of 6-fluoro-2-oxo-1(2H)-quinoxalinyl)acetaldehyde (0.54 g; 2.62 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (0.92 g, 2.62 mmol) in dry methanol (0.5 ml) and chloroform (10 ml) was stirred at rt for 1 h. Sodium triacetoxyborohydride (1.66 g, 7.87 mmol) was added and the mixture was stirred for 2.5 h. Aqueous sodium bicarbonate was added to basify and the phases were separated. The aqueous phase was extracted with DCM several times, and the organic fractions were dried and evaporated. Chromatography on silica, eluting with 0-15% methanol/ethyl acetate, gave the product (0.66 g, 47%).

MS (+ve ion electrospray) m/z 540 (MH+).

(c) Title Compound

A solution of 1,1-dimethylethyl (2,3-dihydro[1,4]dioxino[2,3-c]pyridin-7-ylmethyl) {1-[2-(6-fluoro-2-oxo-1(2H)-quinoxalinyl)ethyl]-4-piperidinyl}carbamate (0.66 g, 1.22 mmol) in DCM (12 ml) and methanol (8 ml) was treated with 4M hydrogen chloride in 1,4-dioxane (12 ml), stirred at rt for 1.5 h and evaporated to dryness (finally dried at 50° C. under vacuum) to give the title compound (0.66 g, 106%).

MS (+ve ion electrospray) m/z 440 (MH+).

A small portion (15 mg) of the dihydrochloride salt was treated with aqueous sodium bicarbonate and extracted three times with DCM. The extracts were dried and evaporated to give a small sample of the free base.

δH (CDCl$_3$), (250 MHz) 1.42 (2H, m), 1.90 (2H, br.d), 2.17 (2H, td), 2.50 (1H, m), 2.63 (2H, t), 2.95 (2H, br. d), 3.79 (2H, s), 4.32 (4H, m), 6.82 (1H, s). 7.32 (1H, td), 7.39 (1H, dd), 7.58 (1H, dd), 8.10 (1H, s), 8.31 (1H, s).

Addition of one equivalent of 4M hydrogen chloride in 1,4-dioxane to a DCM/MeOH solution of the free base of 1-(2-{4-[(2,3-dihydro[1,4]dioxino[2,3-c]pyridin-7-ylmethyl)amino]-1-piperidinyl}ethyl)-6-fluoro-2(1H)-quinoxalinone, followed by evaporation, provided the mono-hydrochloride salt.

Example 23

1-(2-{4-[(6,7-dihydro[1,4]dioxino[2,3-c]pyridazin-3-ylmethyl)amino]-1-piperidinyl}ethyl)-8-ethyl-7-fluoro-1,5-naphthyridin-2(1H)-one Dihydrochloride

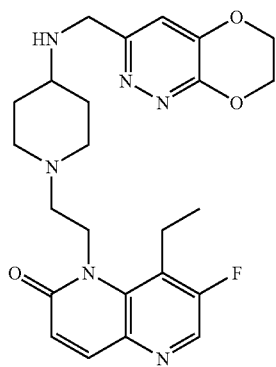

1-[2-(4-amino-1-piperidinyl)ethyl]-8-ethyl-7-fluoro-1,5-naphthyridin-2(1H)-one (0.117 g, 0.368 mmol) and 6,7-dihydro[1,4]dioxino[2,3-c]pyridazine-3-carbaldehyde (0.061 g, 0.368 mmol) were dissolved in CHCl$_3$ (2 ml) and MeOH (0.2 ml) at rt under argon. NaBH(OAc)$_3$ (0.234 g, 1.10 mmol) was added and the reaction was allowed to stir at rt for 16 h. After which it was purified by chromatography on silica gel using a 0-30% MeOH in DCM gradient to give the free base of the title compound as a clear oil (0.045 g, 26%).

MS (ES+) m/z 469 (MH$^+$).

$^1$H NMR (250 MHz) δ (MeOD) 1.38 (3H, t), 1.58-1.70 (2H, m), 2.03-2.14 (2H, m), 2.16-2.35 (2H, m), 2.76-2.87 (2H, m), 2.91-3.21 (5H, m), 4.30 (2H, s), 4.38-4.63 (6H, m), 6.82 (1H, d), 7.33 (1H, d), 7.90 (1H, d), 8.44 (1H, s).

This compound was converted to the HCl salt by dissolving the obtained free base in MeOH (1 ml) and adding 1M HCl in MeOH (0.3 ml). This solution was then evaporated to dryness to give the di-HCl salt.

Example 24

1-(2-{4-[(2,3-dihydro[1,4]dioxino[2,3-c]pyridin-7-ylmethyl)amino]-1-piperidinyl}ethyl)-8-ethyl-7-fluoro-1,5-naphthyridin-2(1H)-one Dihydrochloride

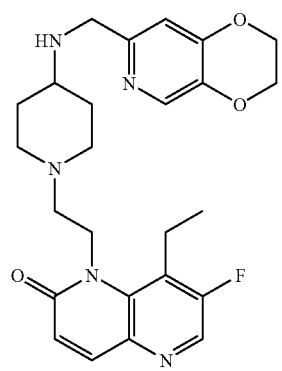

(a) 8-Ethyl-7-fluoro-2-(methyloxy)-1,5-naphthyridine

8-Ethenyl-7-fluoro-2-(methoxy)-1,5-naphthyridine (for a synthesis see WO2004/058144 Example 53(h)) (1.0 g, 4.90 mmol) was stirred in EtOH (50 ml) with 10% palladium on carbon (0.2 g) and the resulting suspension was hydrogenated under 1 atmosphere of hydrogen pressure for 3 h. The mixture was filtered with suction through celite and the solids were washed with MeOH (500 ml). The combined filtrate plus washings were concentrated to give the title compound as a clear oil (1.045 g, 103%).

MS (ES+) m/z 207 (MH$^+$).

(b) 8-Ethyl-7-fluoro-1,5-naphthyridin-2(1H)-one

A suspension of 8-ethyl-7-fluoro-2-(methyloxy)-1,5-naphthyridine (1.045 g, 5.07 mmol) in glacial acetic acid (10 ml) at rt under argon, was treated with 33% HBr in acetic acid (10 mL). After stirring at rt for 18 h, the solvents were evaporated under reduced pressure. More glacial acetic acid (10 ml) was added to the reaction mixture and the solvent was removed to give a yellow solid. As this residue was placed in water (ca. 50 ml) a white precipitate came out of solution. The pH was adjusted to pH 6-7 by addition of solid sodium hydrogen carbonate. The mixture was then stirred at rt for 2 h, after which the solid was isolated by filtration with suction to give a white damp solid. This product was dried on the sinter with suction for 2 h then dried in a vacuum oven over 18 h at 40° C. to give the title compound as an white solid (0.81 g, 83%).

MS (ES+) m/z 193 (MH$^+$).

(c) 8-Ethyl-7-fluoro-2-(2-propen-1-yloxy)-1,5-naphthyridine

8-Ethyl-7-fluoro-1,5-naphthyridin-2(1H)-one (0.810 g, 4.22 mmol) was suspended in dry DMF (12.5 mL) under argon at 0° C., this was then treated with sodium hydride

67

(0.371 g of a 60% w:w dispersion in oil, 2.2 eq.) added in portions. The suspension was allowed to warm to rt; after stirring for 30 mins at rt, the mixture was treated with allyl iodide (0.858 ml, 2.2 eq). It was then stirred for a further 30 mins before addition of water (10 ml). The mixture was then extracted with 10% MeOH/DCM (3×20 ml). The organic extracts were combined, dried over anhydrous sodium sulphate, filtered and evaporated under reduced pressure to give a brown oil. This residue was then purified by column chromatography on silica gel (50 g) eluting with 0-100% EtOAc in hexane gradient to give title compound as a brown oil (0.9588 g, 98%).

MS (ES+) m/z 233 (MH$^+$).

(d) 8-Ethyl-7-fluoro-1-(2-propen-1-yl)-1,5-naphthyridin-2(1H)-one

8-Ethyl-7-fluoro-2-(2-propen-1-yloxy)-1,5-naphthyridine (0.660 g, 2.84 mmol) was dissolved in xylene (14 ml) at rt under argon, whereupon tetrakis(triphenylphosphine)palladium (0.329 g, 0.284 mmol) was added. The reaction was then heated to 150° C. for 30 mins. Reaction was then cooled, a solid then precipitated out which was filtered. The filtrate was then purified by column chromatography on silica gel eluting with 0-100% EtOAc in hexane then 0-20% MeOH in EtOAc gradient to give title compound as a white solid (0.181 g, 27%).

MS (ES+) m/z 233 (MH$^+$)

(e) (8-Ethyl-7-fluoro-2-oxo-1,5-naphthyridin-1(2H)-yl)acetaldehyde 8-ethyl-7-fluoro-1-(2-propen-1-yl)-1,5-naphthyridin-2(1H)-one (0.181 g, 0.781 mmol) was dissolved in 1,4-dioxane (4.0 mL) and water (3.5 ml) at rt under argon. Then sodium periodate (0.418 g, 1.95 mmol) was added followed by osmium tetroxide (0.175 mL of 4% aqueous solution). After 10 mins a white precipitate came out of solution, further addition of water (2 ml) was required to re-dissolve everything. After the reaction had been left stirring at rt overnight, it was then diluted with brine (20 ml) and EtOAc (20 ml). The aqueous was then separated and washed a further with EtOAc (3×20 ml). The organic layers were then combined, dried using sodium sulphate, filtered and solvent removed to give the crude product as a yellow solid (0.168 g).

(f) 1,1-Dimethylethyl {1-[2-(8-ethyl-7-fluoro-2-oxo-1,5-naphthyridin-1(2H)-yl)ethyl]-4-piperidinyl}carbamate (8-Ethyl-7-fluoro-2-oxo-1,5-naphthyridin-1(2H)-yl)acetaldehyde (0.168 g, 0.718 mmol) and 1,1-dimethylethyl 4-piperidinylcarbamate (0.172 g, 0.860 mmol) was dissolved in CHCl$_3$ (6 ml) and MeOH (0.6 ml) at rt under argon, whereupon NaBH(OAc)$_3$ (0.497 g, 2.34 mmol) was added, after which it was stirred for 3 h. The reaction was then purified by chromatography on silica gel using a 0-20% MeOH in EtOAc gradient to give the title compound as a yellow oil (0.234 g, 72%).

MS (ES+) m/z 419 (MH$^+$).

(g) 1-[2-(4-amino-1-piperidinyl)ethyl]-8-ethyl-7-fluoro-1,5-naphthyridin-2(1H)-one To a solution of 1,1-dimethylethyl {1-[2-(8-ethyl-7-fluoro-2-oxo-1,5-naphthyridin-1(2H)-yl)ethyl]-4-piperidinyl}carbamate (0.234 g, 0.559 mmol) in DCM (2 ml) was added TFA

68

(1 ml) and the reaction was allowed to stirred at rt for 1 h before evaporation of solvent. The residue was dissolved in 1:1 DCM and MeOH (2 ml) and then treated with MP-Carbonate resin until the pH reached 8. The reaction was then filtered, resin washed with MeOH and the filtrate was evaporated to dryness to give a yellow oil (0.176 g, 99%).

MS (ES+) m/z 319 (MH$^+$).

(h) Title Compound

1-[2-(4-amino-1-piperidinyl)ethyl]-8-ethyl-7-fluoro-1,5-naphthyridin-2(1H)-one (0.056 g, 0.184 mmol) and 2,3-dihydro[1,4]dioxino[2,3-c]pyridine-7-carboxaldehyde (for a synthesis see WO2004058144, Example 2(c) or WO03/087098, Example 19(d)) (0.030 g, 0.184 mmol) was dissolved in CHCl$_3$ (1 ml) and MeOH (0.1 ml) at rt under argon. NaBH(OAc)$_3$ (0.117 g, 0.552 mmol) was then added and the reaction was allowed to stir at rt for 16 h. After which it was purified by chromatography on silica gel (10 g) using a 0-30% MeOH in DCM gradient to give the free base of the title compound as a yellow oil (0.041 g, 48%).

MS (ES+) m/z 468 (MH$^+$).

$^1$H NMR (250 MHz) δ(MeOD) 1.38 (3H, t), 1.51-1.67 (2H, m), 2.03-2.10 (2H, m), 2.18-2.27 (2H, m), 2.65-2.85 (2H, m), 3.00-3.21 (5H, m), 4.18 (2H, s), 4.30-4.41 (4H, m), 4.55 (2H, t), 6.84 (1H, d), 6.99 (1H, s), 7.93 (1H, d), 8.13 (1H, s), 8.45 (1H, s).

This compound was converted to the HCl salt by dissolving the obtained free base in MeOH (1 ml) and adding 1M HCl in MeOH (0.1 ml). This solution was then evaporated to dryness to give the di-HCl salt.

Example 25

10-(2-{4-[(2,3-dihydro[1,4]dioxino[2,3-c]pyridin-7-ylmethyl)amino]-1-piperidinyl}ethyl)-2,3-dihydro[1,4]dioxino[2,3-h]quinolin-9(10H)-one Hydrochloride

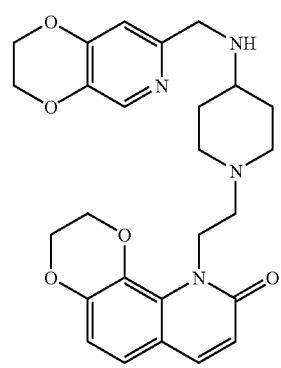

(a) 5-Nitro-2,3-dihydro-1,4-benzodioxin

3-Nitro-1,2-benzenediol (5 g; 32.26 mmol), dibromoethane (12.13 ml; 64.52 mmol), tetra(n-butyl)ammonium bromide (1.1 g; 32.26 mmol) and K$_2$CO$_3$ (13.35 g; 96.78 mmol) were stirred at reflux in toluene overnight. The reaction was then poured onto water (150 ml) and twice extracted with diethyl ether (2×150 ml). The combined organics were washed with water (100 ml) and brine (100 ml) then dried with MgSO$_4$ and the solvents removed to afford the desired product (5.4 g; 93%).

(b) 2,3-Dihydro-1,4-benzodioxin-5-amine

5-Nitro-2,3-dihydro-1,4-benzodioxin (5.4 g; 29.83 mmol) was dissolved in ethanol (130 ml) and conc.HCl added (1.13 ml; 29.83 mmol) this was then stirred with 10% Pd/C under hydrogen at rt and atmospheric pressure overnight. The catalyst was then filtered off and washed with MeOH. The solvents were removed and the crude purified by SCX. Fractions containing product were concentrated to give the desired product (4.6 g).

MS (ES+) m/z 153 (MH$^+$).

(c) 2,3-Dihydro[1,4]dioxino[2,3-h]quinoline

A mixture of concentrated sulphuric acid (30 ml), boric acid (2.29 g; 47.20 mmol) iron (II) sulphate heptahydrate (1.09 g; 3.93 mmol) and 3-nitrobenzene sulphonic acid sodium salt (9.5 g; 42.36 mmol) was cooled to 0° C. before addition of glycerol (11 ml; 151.31 mmol) and 2,3-dihydro-1,4-benzodioxin-5-amine (4.6 g; 30.26 mmol) followed by water (30 ml). The mixture was then heated to 140° C. and stirred for 4 hours. The reaction was then cooled to rt before being poured onto ice water (150 ml) and filtered. The resulting mixture was then basified to pH 8 with 6N NaOH and stirred with EtOAc for 30 mins. The organics were separated and the aqueous layer extracted with EtOAc×3. The combined organic layers were filtered through kieselguhr, washed with brine and dried with MgSO$_4$. The solvents were removed to afford the desired product (3.65 g; 65%).

MS (ES+) m/z 188 (MH$^+$).

(d) 10-(2-Propen-1-yl)-2,3-dihydro[1,4]dioxino[2,3-h]quinolin-10-ium Iodide 2,3-Dihydro[1,4]dioxino[2,3-h]quinoline (3.65 g; 19.52 mmol) and allyl iodide (6.52 ml; 39.04 mmol) were refluxed in toluene (50 ml) at 100° C. After 2.5 h more allyl iodide (0.65 ml; 3.9 mmol) was added to the mixture and the reaction continued under the same conditions for a further 0.5 h. The solvent was removed and the tar like product washed with toluene. This was dried under high vacuum overnight to afford the desired product (5.91 g; 85%).

MS (ES+) m/z 229 (MH$^+$)

(e) 10-(2-propen-1-yl)-2,3-dihydro[1,4]dioxino[2,3-h]quinolin-9(10H)-one 10-(2-Propen-1-yl)-2,3-dihydro[1,4]dioxino[2,3-h]quinolin-10-ium iodide (5.91 g; 16.65 mmol), KOH (4.10 g; 73.26 mmol) and K$_3$-[Fe(CN)$_6$] (12.05 g; 36.63 mmol) were stirred in 50% aqueous 1,4-dioxane at RT for 1.5 h. Water (250 ml) was added and the aqueous layer was extracted with 10% MeOH/DCM (150 ml) and the organics were washed with water (250 ml). The organics were dried with MgSO$_4$ and the solvents removed. The crude residues were purified by column chromatography on silica gel using a 0-7% MeOH/DCM gradient to give the desired product (2.6 g; 65%). MS (ES+) m/z 244 (MH$^+$).

(f) (9-Oxo-2,3-dihydro[1,4]dioxino[2,3-h]quinolin-10(9H)-yl)acetaldehyde 10-(2-Propen-1-yl)-2,3-dihydro[1,4]dioxino[2,3-h]quinolin-9(10H)-one (1.3 g; 5.35 mmol) was dissolved in DCM (70 ml) and cooled to −78° C. This mixture was then stirred under O$_3$ for 65 mins before addition of DMS (1.4 ml; 21.4 mmol) and warmed to rt. Once at rt this was stirred for a further 20 mins. The solvents were then removed to afford the desired product (1.5 g).

MS (ES+) 246 (MH$^+$).

(g) 1,1-dimethylethyl {1-[2-(9-oxo-2,3-dihydro[1,4]dioxino[2,3-h]quinolin-10(9H)-yl)ethyl]-4-piperidinyl}carbamate (9-oxo-2,3-dihydro[1,4]dioxino[2,3-h]quinolin-10(9H)-yl)acetaldehyde (1.5 g; 6.12 mmol) and 1,1-dimethylethyl 4-piperidinylcarbamate (1.84 g; 9.18 mmol) were dissolved in a 1:1 mixture of chloroform and MeOH (50 ml:50 ml) and stirred at rt for 30 mins. NaBH(OAc)$_3$ (5.81 g; 27.54 mmol) was added and the reaction left overnight. The solvents were then removed and the residues purified by column chromatography on silica gel using a 0-12% MeOH/DCM gradient to give the desired product (1 g; 38%).

MS (ES+) m/z 430 (MH$^+$).

(h) 10-[2-(4-amino-1-piperidinyl)ethyl]-2,3-dihydro[1,4]dioxino[2,3-h]quinolin-9(10H)-one 1,1-dimethylethyl {1-[2-(9-oxo-2,3-dihydro[1,4]dioxino[2,3-h]quinolin-10(9H)-yl)ethyl]-4-piperidinyl}carbamate (1 g; 2.34 mmol) was dissolved in chloroform (8 ml) and 4M HCl in 1,4-dioxane (10 ml) added. This was then stirred at rt for 1 h. The salts from the reaction were dissolved in MeOH and all solvents then removed. The residues were redissolved in MeOH and stirred with amberlyst ion exchange resin until a neutral pH was reached. The resin was filtered off and all solvents were removed. The crude residues were subjected to column chromatography on silica gel using a 0-20% 2M NH$_3$: MeOH/DCM gradient to give the desired product (425 mg; 55%).

MS (ES+) m/z 330 (MH$^+$).

(i) Title Compound

10-[2-(4-amino-1-piperidinyl)ethyl]-2,3-dihydro[1,4]dioxino[2,3-h]quinolin-9(10H)-one (100 mg; 0.304 mmol) and 2,3-dihydro[1,4]dioxino[2,3-c]pyridine-7-carboxaldehyde (for a synthesis see WO2004058144, Example 2(c) or WO03/087098, Example 19(d)) (50 mg; 0.304 mmol) were dissolved in a 5:1 mixture of chloroform and MeOH (5 ml:1 ml) and stirred at rt for 2.5 h. More 2,3-dihydro[1,4]dioxino[2,3-c]pyridine-7-carbaldehyde (10 mg; 0.031 mmol) was added to the reaction and stirred for 20 mins. This was then treated with NaBH(OAc)$_3$ (20 mg; 0.092 mmol) and stirred for 30 mins. More 2,3-dihydro[1,4]dioxino[2,3-c]pyridine-7-carbaldehyde (10 mg; 0.031 mmol) was added to the reaction and stirred for 15 mins. This was then treated with NaBH(OAc)$_3$ (20 mg; 0.092 mmol) and stirred for 15 mins. The solvents were then removed and the crude residues purified by column chromatography on silica gel using a 0-20% 2M NH$_3$:MeOH/DCM gradient. Fractions containing the desired were concentrated to afford the free base of the title compound. (140 mg; 96%). δH CDCl$_3$, (400 MHz) 1.49 (m, 2H), 1.8-2.6 (m, 8H), 2.76 (m, 2H), 3.04 (d, 2H), 3.81 (s, 2H), 4.2-4.4 (m, 8H), 4.71 (m, 2H), 6.51 (d, 1H), 6.78 (d, 1H), 6.83 (s, 1H), 7.01 (d, 1H), 7.49 (d, 1H), 8.1 (s, 1H).

MS (ES+) m/z 479 (MH$^+$).

Example 26

10-(2-{4-[(6,7-dihydro[1,4]dioxino[2,3-c]pyridazin-3-ylmethyl)amino]-1-piperidinyl}ethyl)-2,3-dihydro[1,4]dioxino[2,3-h]quinolin-9(10H)-one hydrochloride

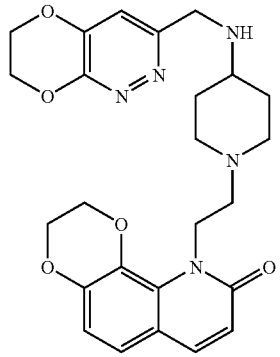

10-[2-(4-Amino-1-piperidinyl)ethyl]-2,3-dihydro[1,4]dioxino[2,3-h]quinolin-9(10H)-one (100 mg; 0.304 mmol) and 6,7-dihydro[1,4]dioxino[2,3-c]pyridazine-3-carbaldehyde (50 mg; 0.304 mmol) were dissolved in a 5:1 mixture of chloroform and MeOH (5 ml: 1 ml) and stirred at rt for 7 h. This was then treated with NaBH(OAc)$_3$ (194 mg; 0.912 mmol) and left stirring overnight. More 6,7-dihydro[1,4]dioxino[2,3-c]pyridazine-3-carbaldehyde (25 mg; 0.152 mmol) was added and stirred for a further 20 mins then the mixture was treated with NaBH(OAc)$_3$ (32 mg; 0.152 mmol) and stirred for 1 h. The solvents were then removed and the crude residues were purified by column chromatography on silica gel using a 0-15% 2M NH$_3$:MeOH/DCM and fractions containing desired product were concentrated to afford the title compound as free base (110 mg, 75%).

MS (ES+) m/z 480 (MH$^+$).

δH CDCl$_3$, (400 MHz) 1.44 (m, 2H), 1.91 (d, 2H), 2.06 (bs, 1H), 2.20 (m, 2H), 2.52 (m, 1H), 2.74 (m, 2H), 3.02 (d, 2H), 4.00 (s, 2H), 4.3-4.4 (m, 6H), 4.51 (m, 2H), 6.50 (d, 1H), 6.77 (d, 1H), 7.01 (d, 1H), 7.05 (s, 1H), 7.49 (d, 1H).

This compound was converted to the HCl salt by dissolving the free base in MeOH and treating it with 1 equivalent of 4M HCl in 1,4-dioxane. This was then evaporated to dryness.

Example 27

5-(2-{4-[(2,3-dihydro[1,4]dioxino[2,3-c]pyridin-7-ylmethyl)amino]-1-piperidinyl}ethyl)-6-oxo-5,6-dihydro-1,5-naphthyridine-3-carbonitrile Dihydrochloride

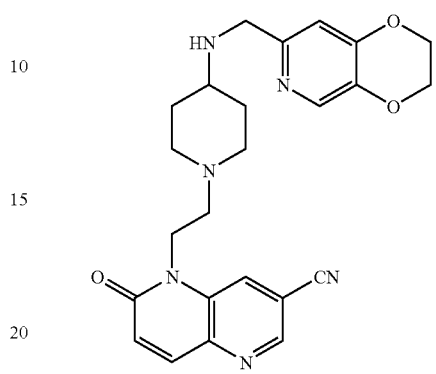

(a) Methyl 4-bromo-6-(methyloxy)-1,5-naphthyridine-3-carboxylate

To a solution of 4-bromo-6-(methoxy)-[1,5]naphthyridine-3-carboxylic acid (for a synthesis see WO2004058144, Example 53(d)) (8.28 g, 29.3 mmol) in DMF (200 ml) was added K$_2$CO$_3$ (5.934 g, 43 mmol) and iodomethane (2.18 ml, 35 mmol) and the reaction was stirred at rt for 72 h. The reaction was partitioned between EtOAc and water. The organic phase was separated and washed twice more with water. The aqueous phases were re-extracted with EtOAc and this EtOAc phase separated and washed with water. The combined organic phases were dried and evaporated to give the desired product as a solid (7 g, 80%).

MS (ES+) m/z 297/299 (MH$^+$).

(b) Methyl 6-(methyloxy)-1,5-naphthyridine-3-carboxylate

To a mixture of methyl 4-bromo-6-(methyloxy)-1,5-naphthyridine-3-carboxylate (1.67 g, 5.64 mmol)) and NaHCO$_3$ (0.84 g, 10 mmol) in MeOH (20 ml) and 1,4-dioxane (15 ml) was added 10% Pd/C (0.75 g) and the mixture was then stirred at rt under 1 atmosphere of hydrogen for 3 h. The reaction mixture was then filtered through a thin pad of Celite, washing through with EtOH. The filtrate was evaporated and stirred in 50 ml of water, the solid was then filtered off and dried in vacuo to give the desired product (1.19 g, 96%).

MS (ES+) m/z 219 (MH$^+$).

(c) Methyl 6-oxo-5,6-dihydro-1,5-naphthyridine-3-carboxylate

A mixture of methyl 6-(methyloxy)-1,5-naphthyridine-3-carboxylate (1.45 g, 6.65 mmol) in 30% HBr in acetic acid (40 ml) was stirred at rt for 18 h before evaporation and drying in vacuo. The solid was washed with Et$_2$O and dried in vacuo to give the desired product as the dihydrobromide salt (2.425 g, 99%).

MS (ES+) m/z 205 (MH$^+$).

(d) Methyl 6-oxo-5-(2-propen-1-yl)-5,6-dihydro-1,5-naphthyridine-3-carboxylate A solution of methyl 6-oxo-5,6-dihydro-1,5-naphthyridine-3-carboxylate (1.963 g, 5.36 mmol) in DMF (32 ml) was treated with $K_2CO_3$ (2.95 g, 21.3 mmol), stirred for 10 mins and then treated with allyl iodide (0.535 ml, 5.88 mmol), heated for 7 h at 75° C., further allyl iodide (0.15 ml, 0.89 mmol) was added and the reaction heated for a further 2 h. The reaction was treated with EtOAc, washed with water three times. The combined aqueous phases were then re-extracted with EtOAc and this washed with water twice. The combined organic phases were dried, evaporated and the residue was subjected to column chromatography on silica gel using a 1:1 EtOAc:hexane gradient to provide the desired compound (0.809 g, 62%).

MS (ES+) m/z 245 (MH$^+$).

(e) 6-Oxo-5-(2-propen-1-yl)-5,6-dihydro-1,5-naphthyridine-3-carboxylic Acid

To a solution of methyl 6-oxo-5-(2-propen-1-yl)-5,6-dihydro-1,5-naphthyridine-3-carboxylate (0.809 g, 3.32 mmol) in 1,4-dioxane (10 ml) and water (5 ml) was added 2M NaOH (2 ml) and the reaction was stirred at rt for 2 h. The pH of the mixture was then adjusted to 2-3 with 2M HCl and extracted three times with EtOAc. The combined organic phases were then dried and evaporated to give the desired product as a solid (0.689 g, 90%).

MS (ES+) m/z 231 (MH$^+$).

(f) 6-Oxo-5-(2-propen-1-yl)-5,6-dihydro-1,5-naphthyridine-3-carboxamide

A suspension of 6-oxo-5-(2-propen-1-yl)-5,6-dihydro-1,5-naphthyridine-3-carboxylic acid (0.689 g, 3 mmol) in DCM (20 ml) and DMF (2 drops) was cooled to 0° C. and treated with oxalyl chloride (0.306 mg, 3.5 mmol), allowed to warm to rt and stirred at rt for 18 h. The mixture was evaporated to a low volume and treated with aqueous ammonia and the resultant solid was filtered off and dried in vacuo to give the desired product (690 mg, 100%).

MS (ES+) m/z 230 (MH$^+$).

(g) 6-Oxo-5-(2-propen-1-yl)-5,6-dihydro-1,5-naphthyridine-3-carbonitrile

To a suspension of 6-oxo-5-(2-propen-1-yl)-5,6-dihydro-1,5-naphthyridine-3-carboxamide (0.69 g, 3 mmol) in DCM (30 ml) at 0° C. was added triethylamine (1.0 ml, 7.2 mmol) and trifluoromethanesulfonic anhydride (0.605 ml, 3.6 mmol) and the reaction was allowed warm to rt and stirred for 1 h at rt. Another four sequential treatments of triethylamine (1.0 ml, 7.2 mmol) and trifluoromethanesulfonic anhydride (0.605 ml, 3.6 mmol) over the next 6 h were necessary to drive the reaction almost to completion. The reaction mixture was treated with sat. aq NaHCO$_3$ and the aqueous extracted twice more with DCM. The combined organic phases were then dried, evaporated and the residue was subjected to column chromatography on silica gel using a EtOAc:hexane gradient to provide the desired compound (0.570 g, 90%).

MS (ES+) m/z 212 (MH$^+$).

(h) 6-Oxo-5-(2-oxoethyl)-5,6-dihydro-1,5-naphthyridine-3-carbonitrile (as the Methyl hemiacetal 5-[2-hydroxy-2-(methyloxy)ethyl]-6-oxo-5,6-dihydro-1,5-naphthyridine-3-carbonitrile)

A solution of 6-oxo-5-(2-propen-1-yl)-5,6-dihydro-1,5-naphthyridine-3-carbonitrile (0.465 mg, 2.20 mmol) in 1,4-dioxan (22 ml) and water (4.4 ml) was cooled to 0° C. and treated with sodium periodate (1.10 g, 5.14 mmol) and OsO$_4$ (4% in water, 1.99 ml). The reaction was warmed to rt and stirred at rt for 18 h before treatment with water and extraction with DCM and 20% MeOH/DCM (×20). The combined organics were dried and evaporated to give the product existing mostly as the slightly impure methyl hemiacetal (0.50 g, 93%)

MS (ES+) m/z 214 (MH$^+$), 246(methylhemiacetalH$^+$)

(i) 1,1-Dimethylethyl {1-[2-(7-cyano-2-oxo-1,5-naphthyridin-1(2H)-yl)ethyl]-4-piperidinyl}carbamate A mixture of 6-oxo-5-(2-oxoethyl)-5,6-dihydro-1,5-naphthyridine-3-carbonitrile (0.50 g, 2.05 mmol), 4-t-butoxycarbonylaminopiperidine (0.80 g, 4.00 mmol) and 3A molecular sieves in DCM (4.5 ml) and MeOH (4.5 ml) was stirred at rt for 4 h. The mixture was then treated with NaBH(OAc)$_3$ (0.94 g, 4.43 mmol), stirred at rt for 18 h, filtered through a thin pad of celite, evaporated, dissolved in 10% MeOH/DCM and washed with sat. aq NaHCO$_3$. The aqueous phase was re-extracted twice with 10% MeOH/DCM, the combined organics dried, and the residue was subjected to column chromatography on silica gel using a DCM:MeOH:aq NH$_3$ gradient to provide the desired compound (0.411 g, 50%).

MS (ES+) m/z 398 (MH$^+$).

(j) 5-[2-(4-Amino-1-piperidinyl)ethyl]-6-oxo-5,6-dihydro-1,5-naphthyridine-3-carbonitrile To a solution of 1,1-dimethylethyl {1-[2-(7-cyano-2-oxo-1,5-naphthyridin-1(2H)-yl)ethyl]-4-piperidinyl}carbamate (0.411 g, 1.03 mmol) in DCM (16 ml) was added TFA (9 ml) and the reaction stirred at rt for 1 h. The solution was evaporated, dissolved in MeOH and passed through a column of Amberlyst A21 basic resin. The fractions containing the desired product were evaporated and the residue was subjected to column chromatography on silica gel using a DCM:MeOH:aq NH$_3$ gradient to provide the desired compound (0.214 g, 70%).

MS (ES+) m/z 298 (MH$^+$).

(k) Title Compound

A solution of 5-[2-(4-amino-1-piperidinyl)ethyl]-6-oxo-5,6-dihydro-1,5-naphthyridine-3-carbonitrile (44 mg, 0.148 mmol) and 2,3-dihydro[1,4]dioxino[2,3-c]pyridine-7-carboxaldehyde (for a synthesis see WO2004058144, Example 2(c) or WO03/087098, Example 19(d)) (24.5 mg, 0.148 mmol) and 3A molecular sieves in chloroform (1 ml) and MeOH (1 ml) was heated at 65° C. for 5 h, cooled and then NaBH(OAc)$_3$ (63 mg, 0.30 mmol) was added. The reaction was stirred at rt for 18 h, filtered through Celite and evaporated. The residue was treated with sat. aq NaHCO$_3$ solution and a 4:1 DCM:MeOH mixture. The aqueous phase was extracted twice with a 4:1 DCM:MeOH mixture and then the combined organic phases were dried and the solvent was removed under reduced pressure. The residue was subjected to column chromatography on silica gel using a DCM, MeOH and aqueous ammonia gradient to provide the free base of the title compound (0.061 g, 92%).

MS (ES+) m/z 447 (MH+).

$^1$H NMR (400 MHz) δ (CDCl$_3$) 1.35-1.58 (2H, m), 1.85-1.95 (2H, m), 2.12-2.22 (2H, m), 2.45-2.56 (1H, m), 2.62-2.68 (2H, t), 2.90-2.96 (2H, m), 3.80 (2H, s), 4.26-4.35 (m, 6H), 6.68 (1H, s), 7.05 (1H, d, J=10 Hz), 7.94 (1H, d, J=10 Hz), 8.10 (2H, s), 8.72 (1H, s).

This material was converted to the dihydrochloride by dissolving in DCM/MeOH and adding 1M HCl/diethyl ether then evaporating to dryness. MS as that of free base.

Addition of one equivalent of benzoic acid to a solution of 5-(2-{4-[(2,3-dihydro[1,4]dioxino[2,3-c]pyridin-7-ylmethyl)amino]-1-piperidinyl}ethyl)-6-oxo-5,6-dihydro-1,5-naphthyridine-3-carbonitrile, followed by evaporation, provided the benzoate salt.

Example 28

8-(2-{4-[(2,3-dihydro[1,4]dioxino[2,3-c]pyridin-7-ylmethyl)amino]-1-piperidinyl}ethyl)-7-oxo-7,8-dihydro-1,8-naphthyridine-2-carbonitrile Hydrochloride

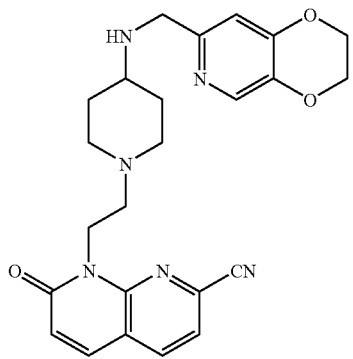

(a) 7-Oxo-8-(2-propen-1-yl)-7,8-dihydro-1,8-naphthyridin-2-yl Trifluoromethanesulfonate To a solution of 1-(2-propen-1-yl)-1,8-naphthyridine-2,7(1H,8H)-dione (1.172 g, 5.80 mmol) in DMF (100 ml) at 0° C. was added sodium hydride (60% dispersion in oil, 278 mg, 6.96 mmol) and the reaction was allowed warm to rt and stirred at rt for 0.5 h. N-phenyltrifluoromethanesulfonimide (2.48 g, 6.96 mmol) was then added and the reaction was stirred at rt for 1 h before addition of water (5 ml) and evaporation. The residue was treated with water (500 ml) and then extracted with diethyl ether (3×200 ml). The combined organic phases were dried, evaporated and the crude residue purified by chromatography on silica gel using an ethyl acetate/hexane gradient to provide the desired compound (697 mg, 36%).

MS (ES+) m/z 335 (MH+).

(b) 7-Oxo-8-(2-propen-1-yl)-7,8-dihydro-1,8-naphthyridine-2-carbonitrile

To a degassed solution of 7-oxo-8-(2-propen-1-yl)-7,8-dihydro-1,8-naphthyridin-2-yl trifluoromethanesulfonate (697 mg, 2.087 mmol) in DMF (10 ml) was added Zn(CN)$_2$, (147 mg, 1.252 mmol) Pd$_2$(dba)$_3$ (48 mg, 0.052 mmol), and 1,1'-bis(diphenylphosphino)ferrocene (58 mg, 0.104 mmol). The reaction was then heated at 50° C. for 1 h and then at 70° C. for a further 1 h and at 100° C. for a further 1 h. More Zn(CN)$_2$, (147 mg, 1.252 mmol) Pd$_2$(dba)$_3$ (48 mg, 0.052 mmol), and 1,1'-bis(diphenylphosphino)ferrocene (58 mg, 0.104 mmol) was then added and the reaction was heated at 100° C. for a further 1 h. The reaction was then cooled and treated with water (200 ml). The reaction was then extracted with DCM (3×200 ml). The combined organic phases were dried, evaporated and the crude residue purified by chromatography on silica gel using an ethyl acetate/hexane gradient to provide the desired compound (374 mg, 85%).

MS (ES+) m/z 212 (MH+).

(c) 7-Oxo-8-(2-oxoethyl)-7,8-dihydro-1,8-naphthyridine-2-carbonitrile

7-Oxo-8-(2-propen-1-yl)-7,8-dihydro-1,8-naphthyridine-2-carbonitrile (374 mg, 1.773 mmol) was dissolved in 1,4-dioxane (10 ml) and water (10 ml). Sodium periodate (948 mg, 4.433 mmol) was added, followed by osmium tetroxide (0.38 ml of 4% aqueous solution). The mixture stirred at rt for 1 h, water (40 ml) was added the mixture was stirred for a further 1 h. The reaction was concentrated to about 50 ml and extracted with 20% MeOH/DCM (3×100 ml). The organic extracts were combined, dried over anhydrous magnesium sulphate, filtered and evaporated under reduced pressure to give 7-oxo-8-(2-oxoethyl)-7,8-dihydro-1,8-naphthyridine-2-carbonitrile as an impure brown solid (423 mg, 112%).

MS (ES+) m/z 214 (MH+).

(d) 1,1-Dimethylethyl {1-[2-(7-cyano-2-oxo-1,8-naphthyridin-1(2H)-yl)ethyl]-4-piperidinyl}(2,3-dihydro[1,4]dioxino[2,3-c]pyridin-7-ylmethyl)carbamate A mixture of 7-oxo-8-(2-oxoethyl)-7,8-dihydro-1,8-naphthyridine-2-carbonitrile (329 mg, 1.545 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (539 mg, 1.545 mmol) in chloroform (15 ml) and MeOH (1 ml) was stirred for 2 h before addition of NaBH(OAc)$_3$ (982 mg, 4.635 mmol). The reaction was stirred for 0.5 h before addition of sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the desired compound (620 mg, 73%).

MS (ES+) m/z 547 (MH+).

(e) Title Compound

A solution of 1,1-dimethylethyl {1-[2-(7-cyano-2-oxo-1,8-naphthyridin-1(2H)-yl)ethyl]-4-piperidinyl}(2,3-dihydro

[1,4]dioxino[2,3-c]pyridin-7-ylmethyl)carbamate (600 mg, 1.100 mmol) in DCM (10 ml) at 0° C. was added 1M HCl in diethyl ether (10 ml) and the reaction was stirred at 0° C. for 0.5 h and then allowed warm to rt and stirred at rt for 2 h before evaporation, treatment with sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (314 mg, 64%).

MS (ES+) m/z 447 (MH$^+$).

$^1$H NMR (250 MHz) δ (CDCl$_3$) 1.22-1.41 (2H, m), 1.81-1.92 (2H, m), 2.11-2.20 (2H, m), 2.42-2.58 (1H, m), 2.60-2.72 (2H, t), 2.59-3.12 (2H, m), 3.78 (2H, m), 4.25-4.62 (4H, m), 4.62 (2H, t), 6.81 (1H, s), 6.73 (1H, d, J=10 Hz), 7.51 (1H, d, J=8 Hz), 7.66 (1H, d, J=10 Hz), 7.97 (1H, d, J=8 Hz), 8.08 (1H, s).

This compound was converted to the HCl salt by dissolving the obtained free base in 1:1 DCM:MeOH and adding 1 equivalent of 4M HCl in 1,4-dioxane. This was then evaporated to dryness.

Example 29

5-(2-{4-[(6,7-dihydro[1,4]dioxino[2,3-c]pyridazin-3-ylmethyl)amino]-1-piperidinyl}ethyl)-6-oxo-5,6-dihydro-1,5-naphthyridine-3-carbonitrile Dihydrochloride

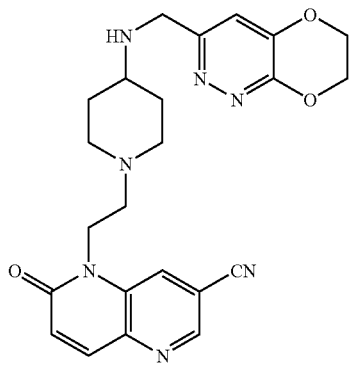

The title compound was prepared by the general method of Example 27(k) from 5-[2-(4-amino-1-piperidinyl)ethyl]-6-oxo-5,6-dihydro-1,5-naphthyridine-3-carbonitrile (20 mg) and 6,7-dihydro[1,4]dioxino[2,3-c]pyridazine-3-carbaldehyde (11.2 mg) to give the free base of the title compound (16 mg, 53%).

MS (ES+) m/z 448 (MH$^+$).

$^1$H NMR (400 MHz) δ (CDCl$_3$) 1.31-1.45 (2H, m), 1.85-1.95 (2H, m), 2.11-2.22 (2H, m), 2.51-2.60 (1H, m), 2.65 (2H, t), 2.88-2.98 (2H, m), 4.00 (2H, s), 4.31-4.42 (4H, m), 4.52 (2H, t), 7.04 (2H, m), 7.92 (1H, d, J=10 Hz), 8.12 (1H, s), 8.72 (1H, s).

This material was converted to the dihydrochloride by dissolving in DCM/MeOH and adding 1M HCl/diethyl ether then evaporating to dryness. MS as that of free base.

Example 30

5-(2-{4-[(6,7-dihydro[1,4]oxathiino[2,3-c]pyridazin-3-ylmethyl)amino]-1-piperidinyl}ethyl)-6-oxo-5,6-dihydro-1,5-naphthyridine-3-carbonitrile Dihydrochloride

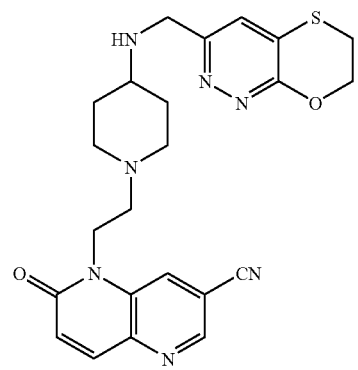

The title compound was prepared by the general method of Example 27(k) from 5-[2-(4-amino-1-piperidinyl)ethyl]-6-oxo-5,6-dihydro-1,5-naphthyridine-3-carbonitrile (20 mg) and 6,7-dihydro[1,4]oxathiino[2,3-c]pyridazine-3-carbaldehyde (13.3 mg) to give the free base of the title compound (17 mg, 45%).

MS (ES+) m/z 464 (MH$^+$).

$^1$H NMR (400 MHz) δ (CDCl$_3$) 1.31-1.46 (2H, m), 1.85-1.95 (2H, m), 2.12-2.22 (2H, m), 2.49-2.51 (1H, m), 2.57 (2H, t), 2.88-2.95 (2H, m), 3.23 (2H, t), 3.98 (2H, s), 4.30 (2H, t), 4.65 (2H, t), 7.04 (1H, d, J=10 Hz), 7.34 (1H, s), 7.93 (1H, d, J=10 Hz), 8.13 (1H, s), 8.72 (1H, s).

This material was converted to the dihydrochloride by dissolving in DCM/MeOH and adding 1M HCl/diethyl ether then evaporating to dryness. MS as that of free base.

Example 31

7-Bromo-1-(2-{4-[(2,3-dihydro[1,4]dioxino[2,3-c]pyridin-7-ylmethyl)amino]-1-piperidinyl}ethyl)pyrido[2,3-b]pyrazin-2(1H)-one Formate

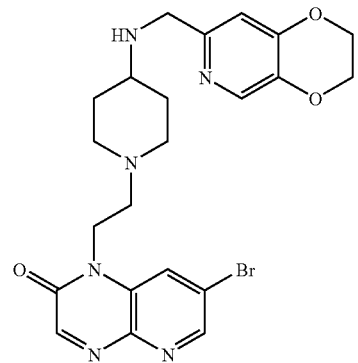

(a) 7-Bromopyrido[2,3-b]pyrazin-2(1H)-one

A solution of 5-bromo-2,3-pyridinediamine (465 mg, 2.473 mmol) and glyoxylic acid monohydrate (284 mg, 3.09 mmol) in water (5 ml) was stirred at rt for 3 h and the resultant precipitate was filtered and washed with water (50 ml), MeOH (20 ml) and finally diethyl ether (20 ml) before drying in vacuo gave the desired product as a light brown solid (368 mg, 66%).

MS (ES+) m/z 226/228 (MH+).

(b) 7-bromo-1-(2-propen-1-yl)pyrido[2,3-b]pyrazin-2(1H)-one

7-Bromopyrido[2,3-b]pyrazin-2(1H)-one (368 mg, 1.628 mmol) was suspended in dry DMF (10 ml) under argon at rt, and the stirred suspension was treated with $K_2CO_3$ (741 mg, 5.372 mmol) and allyl iodide (331 μL, 3.581 mmol). It was then stirred for 2 h before addition of water (100 ml). The mixture was then extracted with DCM (3×200 ml). The DCM extracts were combined, dried over anhydrous magnesium sulphate, filtered and evaporated under reduced pressure to give a brown solid which was purified by column chromatography on silica with a 0-10% MeOH in DCM gradient to give the desired product as a light brown solid (278 mg, 64%).

MS (ES+) m/z 266/268 (MH+).

(c) (7-Bromo-2-oxopyrido[2,3-b]pyrazin-1(2H)-yl)acetaldehyde (as the hydrate)

7-Bromo-1-(2-propen-1-yl)pyrido[2,3-b]pyrazin-2(1H)-one (278 mg, 1.045 mmol) was dissolved in 1,4-dioxane (10 ml) and water (10 ml). Sodium periodate (559 mg, 2.613 mmol) was added, followed by osmium tetroxide (0.22 ml of 4% aqueous solution). The mixture stirred at rt for 1 h, water 40 ml was added the mixture was stirred for a further 1 h. The reaction was concentrated to about 50 ml and extracted with 20% MeOH/DCM (3×100 ml). The organic extracts were combined, dried over anhydrous magnesium sulphate, filtered and evaporated under reduced pressure to give (7-bromo-2-oxopyrido[2,3-b]pyrazin-1(2H)-yl)acetaldehyde (existing mostly as the hydrate) as an impure brown oil (423 mg, 107%).

MS (ES+) m/z 268/270 (MH+) 286/288 (hydrateH+).

(d) 1,1-Dimethylethyl {1-[2-(6-bromo-3-oxopyrido[2,3-b]pyrazin-4(3H)-yl)ethyl]-4-piperidinyl}(2,3-dihydro[1,4]dioxino[2,3-c]pyridin-7-ylmethyl)carbamate A mixture of (7-bromo-2-oxopyrido[2,3-b]pyrazin-1(2H)-yl)acetaldehyde (as a mixture of aldehyde and the hydrate of the aldehyde) (299 mg, 1.116 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (389 mg, 1.116 mmol) in chloroform (15 ml) and MeOH (1 ml) was stirred for 2 h before addition of NaBH(OAc)$_3$ (709 mg, 3.348 mmol). The reaction was stirred for 0.5 h before addition of sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient to provide the desired compound as an impure yellow foam (298 mg, 44%).

MS (ES+) m/z 601/603 (MH+).

(e) Title Compound

A solution of 1,1-dimethylethyl {1-[2-(6-bromo-3-oxopyrido[2,3-b]pyrazin-4(3H)-yl)ethyl]-4-piperidinyl}(2,3-dihydro[1,4]dioxino[2,3-c]pyridin-7-ylmethyl)carbamate (900 mg, 1.67 mmol) in chloroform (5 ml) and MeOH (5 ml) was added 4M HCl in 1,4-dioxane (5 ml) and the reaction was stirred at rt for 0.5 h before evaporation, treatment with sat. aq NaHCO$_3$ (50 ml). The reaction was then extracted with 20% MeOH in DCM (3×200 ml). The combined organic phases were dried, evaporated and the crude residue purified by chromatography on silica gel using a 0-20% MeOH/DCM gradient and then by MDAP to provide the title compound directly as the formate salt (595 mg, 81%).

MS (ES+) m/z 501/303 (MH+).
$^1$H NMR (400 MHz) δ (CDCl$_3$) 1.59-1.72 (2H, m), 1.92-2.08 (2H, m), 2.22-2.43 (2H, m), 2.32-2.42 (1H, m), 2.73 (2H, t), 3.01-3.08 (2H, m), 3.99 (2H, s), 4.28-4.36 (m, 6H), 6.84 (1H, s), 8.10 (2H, s), 8.51 (1H, s), 8.66 (1H, s).

Example 32

1-(2-{4-[(2,3-dihydro[1,4]dioxino[2,3-c]pyridin-7-ylmethyl)amino]-1-piperidinyl}ethyl)-5,7-difluoro-2(1H)-quinolinone Diformate

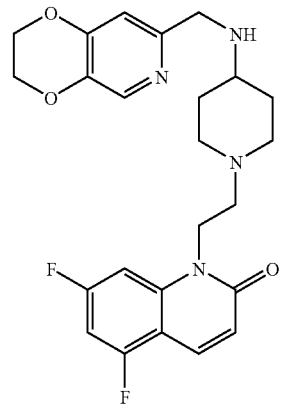

(a) N-(3,5-difluorophenyl)-3,3-bis(methyloxy)propanamide

A solution of 3,5-difluoroaniline (5 g, 38.8 mmol), methyl-3-methoxyacrylate (4.6 ml, 42.7 mmol) and sodium methoxide solution (25% in MeOH, 12 ml) in toluene (50 ml) under Argon was stirred at 70° C. for 3 h. More sodium methoxide solution (25% in MeOH, 6 mL) added and reaction stirred overnight. Still more sodium methoxide solution (25% in MeOH, 12 mL) and methyl-3-methoxyacrylate (5 mL, 46.4 mmol) were then added and reaction was heated at 70° C. for 5 h. MeOH was added and volume of toluene was reduced to about 10 ml. The residue was acidified to pH 7 using a saturated solution of ammonium chloride, solid ammonium chloride and 5N HCl. The aqueous phase was extracted using ethyl acetate (2×500 ml). The combined organic phases were dried, evaporated and the residue was chromatographed on silica gel, eluting with 0-100% ethyl acetate-40-60° C. petroleum ether to afford the impure desired compound (12 g, 126%).

δH DMSO, (400 MHz) 2.64 (2H, d), 3.27 (6H, s), 4.78 (2H, t), 6.90 (1H, m), 7.30 (2H, m), 10.4 (1H, s).

(b) 5,7-Difluoro-2(1H)-quinolinone

A solution of 70% H$_2$SO$_4$ was made up by adding chilled H$_2$SO$_4$ (70 ml) to chilled water (30 ml) ensuring the temp remained between 10-20° C. The acid was then slowly added to the water keeping the temperature between 10 and 20° C. Finely ground N-(3,5-difluorophenyl)-3,3-bis(methyloxy)propanamide (12 g, 49 mmol) was added to the chilled solution over 1 h and then stirred at 5° C. for 1.5 h. An ice-water mixture (100 ml) was added carefully, followed by water (400 ml). The mixture was stirred for 0.5 h then the solid formed was filtered off and dried in the vacuum-oven at 40° C. over the weekend. The solid was still wet so it was dried in the desiccator with $P_2O_5$ to afford the impure desired compound (12 g, 136%).

MS (ES+) m/z 182 (MH$^+$).

(c) 5,7-Difluoro-1-(2-propen-1-yl)-2(1H)-quinolinone

A suspension of 5,7-difluoro-2(1H)-quinolinone (640 mg, 3.54 mmol) in DMF (15 ml) under argon at 0° C. was treated with sodium hydride (60% in mineral oil, 312 mg, 7.8 mmol) and then it was warmed up at rt. After 0.5 h at rt allyl iodide (0.72 mL, 7.8 mmol) was added. After 0.5 h sodium hydride (60% in mineral oil, 200 mg, 5 mmol) and allyl iodide (0.35 ml, 3.8 mmol) were added. Water (15 ml) was added and the aqueous was extracted using DCM (3×50 ml). The combined organic phases were dried, evaporated and the residue was chromatographed on silica gel, eluting with 0-4% MeOH-DCM to afford 350 mg of the desired compound (45%).

MS (ES+) m/z 222 (MH$^+$).

(d) (5,7-Difluoro-2-oxo-1 (2H)-quinolinyl)acetaldehyde 5,7-Difluoro-1-(2-propen-1-yl)-2(1H)-quinolinone (1.65 g; 7.46 mmol) was dissolved in DCM (80 ml) in a 3 necked flask and cooled to −78° C. This was then stirred under O3 for 1.5 hours before Argon was bubbled through the reaction to remove any excess O3 and the reaction then quenched with DMS (2 ml; 29.84 mmol). This was then left to warm to rt and stirred overnight. The solvents were removed to afford the impure product (2.1 g).

(e) 1,1-Dimethylethyl {1-[2-(5,7-difluoro-2-oxo-1 (2H)-quinolinyl)ethyl]-4-piperidinyl}carbamate (5,7-Difluoro-2-oxo-1(2H)-quinolinyl)acetaldehyde (2.1 g; 9.4 mmol) and 1,1-dimethylethyl 4-piperidinylcarbamate (2.82 g; 14.1 mmol) were dissolved in a 1:1 mixture of chloroform and MeOH (60 ml:60 ml) and stirred at rt for 1 h. This was then treated with NaBH(OAc)$_3$ (8.92 g; 42.3 mmol) and stirred for a further 1 h. More 1,1-dimethylethyl 4-piperidinylcarbamate (470 mg; 2.35 mmol) was added and the reaction stirred under the same conditions for 20 mins, this was then treated with NaBH(OAc)$_3$ (1.98 g; 9.4 mmol) and stirred for 25 mins. More 1,1-dimethylethyl 4-piperidinylcarbamate (470 mg; 2.35 mmol) was then added and the reaction stirred for 20 mins. More NaBH(OAc)$_3$ (500 mg; 2.38 mmol) was then added to the reaction and it was stirred overnight at rt. The solvents were then removed and the crude residue purified by column chromatography on silica gel using a 0-15% MeOH/DCM gradient to give the desired product (2 g; 52%).

MS (ES+) m/z 408 (MH$^+$).

(f) 1-[2-(4-Amino-1-piperidinyl)ethyl]-5,7-difluoro-2(1H)-quinolinone 1,1-Dimethylethyl {1-[2-(5,7-difluoro-2-oxo-1(2H)-quinolinyl)ethyl]-4-piperidinyl}carbamate (2 g; 4.9 mmol) was dissolved in chloroform (20 ml) and 4M HCl in 1,4-dioxane added (20 ml), this was stirred at rt for 1 h. The salts were then dissolved in MeOH and all solvents removed. The residues were redissolved in MeOH and stirred with amberlyst ion exchange resin until neutral pH was reached, the resin was filtered off and solvents removed. The crude residues were purified by column chromatography on silica gel using a 0-20% 2M $NH_3$:MeOH/DCM gradient to give the desired product (970 mg; 65%).

MS (ES+) m/z 308 (MH$^+$).

(g) Title Compound

1-[2-(4-Amino-1-piperidinyl)ethyl]-5,7-difluoro-2(1H)-quinolinone (150 mg; 0.49 mmol) and 2,3-dihydro[1,4]dioxino[2,3-c]pyridine-7-carboxaldehyde (for a synthesis see WO2004058144, Example 2(c) or WO03/087098, Example 19(d)) (80 mg; 0.49 mmol) were dissolved in a 5:1 mixture of chloroform and MeOH (5 ml: 1 ml) and stirred at rt for 1 h. This was then treated with NaBH(OAc)$_3$ (310 mg; 1.47 mmol) and stirred for a further 2 h under the same conditions. The solvents were then removed from the reaction and the crude residues purified by column chromatography on silica gel using a 0-20% 2M $NH_3$:MeOH/DCM gradient. Fractions containing the desired product were concentrated to afford the free base of the title compound (200 mg; 89%) however this was shown to be impure so was further purified by MDAP to afford the title compound (30 mg; 14%) directly as the diformate salt.

MS (ES+) m/z 457 (MH$^+$).

δH MeOD, (400 MHz) 1.74 (m, 2H), 2.17 (d, 2H), 2.37 (m, 2H), 2.83 (t, 2H), 3.19 (m, 1H), 3.25-3.40 (m, 2H), 4.21 (d, 2H), 4.35 (m, 2H), 4.38 (m, 2H), 4.49 (t, 2H), 6.66 (d, 1H), 6.96-7.02 (m, 2H), 7.29 (d, 1H), 8.05 (d, 1H), 8.13 (s, 1H), 8.28 (bs, 2H).

Example 33

1-(2-{4-[(6,7-dihydro[1,4]dioxino[2,3-c]pyridazin-3-ylmethyl)amino]-1-piperidinyl}ethyl)-5,7-difluoro-2 (1H)-quinolinone Diformate

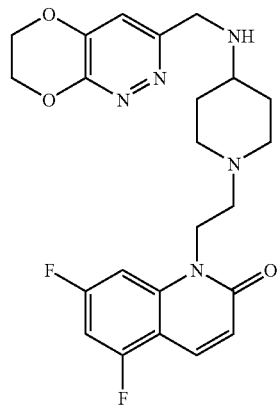

The title compound was prepared by the general method of Example 32(g) using 1-[2-(4-amino-1-piperidinyl)ethyl]-5,7-difluoro-2(1H)-quinolinone and 6,7-dihydro[1,4]dioxino[2,3-c]pyridazine-3-carbaldehyde to give the desired product directly as the diformate salt (34 mg; 15%).

δH MeOD, (400 MHz) 1.75 (m, 2H), 2.19 (d, 2H), 2.45 (t, 2H), 2.90 (t, 2H), 3.19 (m, 1H), 3.25-3.4 (m, 2H), 4.36 (s, 2H), 4.45-4.52 (m, 4H), 4.59 (m, 2H), 6.67 (d, 1H), 7.00 (m, 1H), 7.25 (s, 1H), 7.30 (d, 1H), 8.05 (d, 1H), 8.28 (bs, 2H).

MS (ES+) m/z 458 (MH+).

Example 34

6-[({1-[2-(7-Fluoro-2-oxo-1(2H)-quinoxalinyl)ethyl]-4-piperidinyl}amino)methyl]-2H-pyrido[3,2-b][1,4]thiazin-3(4H)-one dihydrochloride

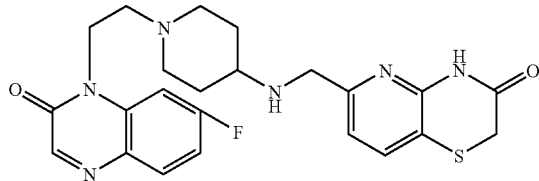

(a) 7-Fluoro-2(1H)-quinoxalinone (and 6-fluoro-2(1H)-quinoxalinone)

A mixture of 4-fluoro-1,2-benzenediamine (44.9 g) and 50% ethyl glyoxalate in toluene (74.53 ml) in ethanol (1 L) was heated under reflux for 3.5 hours, cooled in an ice bath, and the resulting solid was collected and washed twice with ethanol and dried under vacuum at 40° C., to give a solid (51.4 g; 88%) which was a 1:2 mixture of 7-fluoro-2(1H)-quinoxalinone and 6-fluoro-2(1H)-quinoxalinone.

MS (+ve ion electrospray) m/z 165 (MH+).

(b) 7-Fluoro-1-(2-propen-1-yl)-2(1H)-quinoxalinone

A 1:2 mixture of 7-fluoro-2(1H)-quinoxalinone and 6-fluoro-2(1H)-quinoxalinone (20 g, 0.122 mol) in dry DMF (250 ml) and anhydrous potassium carbonate (50.5 g, 0.38 mol) was treated with allyl iodide (12.3 ml, 0.134 mol) and the mixture was stirred at rt for 2 hours. The reaction mixture was evaporated to dryness, water was added and the mixture was extracted (3×) with DCM, washed with water, dried (sodium sulphate) and evaporated. It was chromatographed, twice, on silica gel, eluting with 0-40% ethyl acetate-hexane. The early fractions gave 7-fluoro-1-(2-propen-1-yl)-2(1H)-quinoxalinone (4.7 g) [later fractions contained the isomeric 6-fluoro-isomer (6.7 g)].

MS (+ve ion electrospray) m/z 205 (MH+).

(c) 7-Fluoro-2-oxo-1(2H)-quinoxalinyl)acetaldehyde

A solution of 7-fluoro-1-(2-propen-1-yl)-2(1H)-quinoxalinone (2.4 g, 11.77 mmol) in 1,4-dioxane (140 ml) and water (250 ml) was treated with osmium tetroxide (4% solution in water; 14.5 ml) and sodium periodate (11.9 g) and the mixture was stirred at rt for 1.5 hours. It was evaporated to dryness onto silica gel and chromatographed on a 300 g silica gel column, eluting with 1:1 ethyl acetate-hexane then ethyl acetate. The early fractions gave (7-fluoro-2-oxo-1(2H)-quinoxalinyl)acetaldehyde which was triturated with ether/DCM 3:1 to give product (1.56 g).

MS (+ve ion electrospray) m/z 207 (MH+).

(d) 1,1-Dimethylethyl {1-[2-(7-fluoro-2-oxo-1(2H)-quinoxalinyl)ethyl]-4-piperidinyl}carbamate A solution of 7-fluoro-2-oxo-1(2H)-quinoxalinyl)acetaldehyde (2.48 g, 12 mmol) and 1,1-dimethylethyl 4-piperidinylcarbamate (3.61 g, 18 mmol) in MeOH (10 ml) and chloroform (20 ml) was stirred at rt overnight and sodium triacetoxyborohydride (7.6 g, 36 mmol) was added and the mixture was stirred at rt overnight. Water and sodium carbonate solution were added and the mixture was extracted (3×) with DCM, dried (sodium sulphate), evaporated, and chromatographed on silica gel, eluting with 0-10% MeOH-DCM to give the product as a foam (4.0 g).

MS (+ve ion electrospray) m/z 391 (MH+).

(e) 1-[2-(4-Amino-1-piperidinyl)ethyl]-7-fluoro-2(1H)-quinoxalinone Dihydrochloride A solution of 1,1-dimethylethyl {1-[2-(7-fluoro-2-oxo-1(2H)-quinoxalinyl)ethyl]-4-piperidinyl}carbamate (4.0 g) in dry MeOH (15 ml) and dry DCM (30 ml) was treated with 4 M hydrogen chloride in 1,4-dioxane (30 ml) and stirred at rt for 3 h. It was evaporated to dryness and the insoluble product was heated in MeOH (50 ml), cooled, filtered, washed with cold MeOH, then ether, to give a solid (3.05 g).

MS (+ve ion electrospray) m/z 291 (MH+).

(f) Title Compound

A solution of 1-[2-(4-amino-1-piperidinyl)ethyl]-7-fluoro-2(1H)-quinoxalinone dihydrochloride (60 mg; 0.166 mmol) and 3-oxo-3,4-dihydro-2H-pyrido[3,2-b][1,4]thiazine-6-carboxaldehyde (for a synthesis, see WO2004058144, Example 7(d)) (32 mg, 0.166 mmol) in MeOH (3 ml), chloroform (3 ml) and triethylamine (0.06 ml) was stirred at rt for 1 h then heated at 70° C. overnight. It was cooled and sodium triacetoxyborohydride (0.106 g; 0.5 mmol) was added and the mixture was stirred at rt for 5 h. More 3-oxo-3,4-dihydro-2H-pyrido[3,2-b][1,4]thiazine-6-carbaldehyde (4 mg) was added and the mixture was stirred for 3 h at rt. Sodium triacetoxyborohydride (53 mg) was added and the mixture was stirred at rt for 72 h. Water and sodium carbonate solution were added and the mixture was extracted (3×) with 10% MeOH-DCM, dried (sodium sulphate), evaporated, and chromatographed on silica gel, eluting with 0-15% MeOH-DCM to give the free base of the title compound.

MS (+ve ion electrospray) m/z 469 (MH+).

δH (CDCl3), (400 MHz) 1.40-1.53 (2H, m), 1.92 (2H, br.d), 2.20 (2H, t), 2.55 (1H, m), 2.65-2.70 (2H, m), 2.98 (2H, m), 3.49 (2H, s), 3.83 (2H, s), 4.30 (2H, m), 6.98 (1H, d), 7.06 (1H, m), 7.12 (1H, m), 7.58 (1H, d), 7.86 (1H, m), 8.20 (1H, s), 8.30 (1H, br.s).

This material was converted to the dihydrochloride by dissolving in DCM/MeOH and adding 1M HCl/diethyl ether then evaporating to dryness. MS as that of free base.

Example 35

1-(2-{4-[(2,3-dihydro[1,4]dioxino[2,3-c]pyridin-7-ylmethyl)amino]-1-piperidinyl}ethyl)-7-fluoropyrido[2,3-b]pyrazin-2(1H)-one Hydrochloride

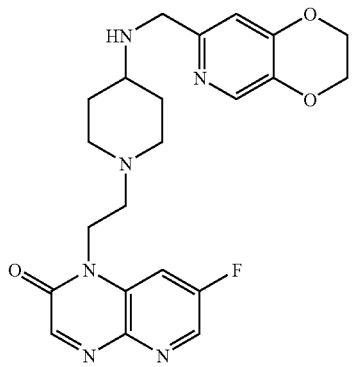

(a) 5-Fluoro-3-nitro-2-pyridinamine

A solution of 2-bromo-5-fluoro-3-nitropyridine (1.176 g, 5.321 mmol) in 2M $NH_3$ in MeOH (20 ml) was sealed in an autoclave and then heated at 75° C. for 6 h and then at 90° C. for a further 18 h. The reaction mixture was then cooled and evaporated, treated with sat. aq. $NaHCO_3$ (100 ml) and then extracted with 5% MeOH/DCM (3×200 ml). The combined organic phases were dried and the solvent was removed. The residue was subjected to column chromatography on silica gel using a 0-5% MeOH in DCM gradient to provide the desired compound as a yellow solid (561 mg, 67%).

MS (ES+) m/z 158 ($MH^+$).

(b) 5-Fluoro-2,3-pyridinediamine

A suspension of 5-fluoro-3-nitro-2-pyridinamine (561 mg, 3.573 mmol) in ethanol (100 ml) was treated with added 10% Pd/C (100 mg) and the mixture was then stirred at rt under 1 atmosphere of hydrogen for 5 h. The reaction mixture was then filtered through a thin pad of Celite, washing through with EtOH (500 ml). The filtrate was evaporated to give the desired product as a grey solid (435 mg, 96%).

MS (ES+) m/z 128 ($MH^+$).

(c) 7-Fluoropyrido[2,3-b]pyrazin-2(1H)-one and 7-fluoropyrido[2,3-b]pyrazin-3(4H)-one A solution of 5-fluoro-2,3-pyridinediamine (435 mg, 3.425 mmol) and glyoxylic acid monohydrate (410 mg, 4.453 mmol) in water (30 ml) was stirred at rt for 18 h. The reaction was then concentrated to about 5 ml and resultant precipitate was filtered and triturated with ethyl acetate, refiltered and washed with diethyl ether before drying in vacuo gave the desired product as a slightly impure brown solid (306 mg, 54%).

MS (ES+) m/z 166 ($MH^+$).

The isomeric 7-fluoropyrido[2,3-b]pyrazin-3(4H)-one was obtained as an impure brown solid by evaporating the organics used in the trituration.

(d) 7-Fluoro-1-(2-propen-1-yl)pyrido[2,3-b]pyrazin-2(1H)-one

7-Fluoropyrido[2,3-b]pyrazin-2(1H)-one (306 mg, 1.855 mmol) was suspended in dry DMF (10 mL) under argon at rt, and the stirred suspension was treated with $K_2CO_3$ (845 mg, 6.12 mmol) and allyl iodide (223 μl, 2.41 mmol). It was then stirred for 1 h before addition of water (100 ml). The mixture was then extracted with DCM (2×200 ml) and 5% MeOH/DCM (100 ml). The combined organic extracts were dried over anhydrous magnesium sulphate, filtered and evaporated and purified by column chromatography on silica with a 0-10% MeOH in DCM gradient to give the desired product as a yellow solid (177 mg, 47%).

MS (ES+) m/z 206 ($MH^+$).

(e) (7-Fluoro-2-oxopyrido[2,3-b]pyrazin-1(2H)-yl)acetaldehyde (as the Methyl Hemiacetal)

7-Fluoro-1-(2-propen-1-yl)pyrido[2,3-b]pyrazin-2(1H)-one (163 mg, 0.795 mmol) was dissolved in 1,4-dioxane (5 ml) and water (5 ml). Sodium periodate (426 mg, 1.99 mmol) was added, followed by osmium tetroxide (0.17 ml of 4% aqueous solution). The mixture stirred at rt for 2 h, and then treated with water (20 ml) and extracted with 20% MeOH/DCM (3×100 ml). The organic extracts were combined, dried over anhydrous magnesium sulphate, filtered and evaporated to give (7-fluoro-2-oxopyrido[2,3-b]pyrazin-1(2H)-yl)acetaldehyde (existing mostly as the methyl hemiacetal) as an impure brown oil (193 mg, 117%).

MS (ES+) m/z 207 ($MH^+$) 240 (methyl hemiacetal$H^+$).

(f) 1,1-Dimethylethyl (2,3-dihydro[1,4]dioxino[2,3-c]pyridin-7-ylmethyl) {1-[2-(6-fluoro-3-oxopyrido[2,3-b]pyrazin-4(3H)-yl)ethyl]-4-piperidinyl}carbamate A mixture of (7-fluoro-2-oxopyrido[2,3-b]pyrazin-1(2H)-yl)acetaldehyde (exists mostly as the methyl hemiacetal) (193 mg, presumed 0.795 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (277 mg, 0.795 mmol) in chloroform (10 ml) and MeOH (0.5 ml) was stirred at rt under argon for 2 h before addition of $NaBH(OAc)_3$ (377 mg, 1.59 mmol). The reaction was stirred for 1 h before addition of more $NaBH(OAc)_3$ (377 mg, 1.59 mmol). The reaction was stirred for 1 h more before addition of sat. aq $NaHCO_3$ (50 ml). The reaction was then extracted with DCM (3×100 ml). The combined organic phases were dried, evaporated and the crude residue purified by chromatography on silica gel using a 0-10% MeOH/DCM gradient to provide the desired compound as an impure oil (195 mg, 45%).

MS (ES+) m/z 541 ($MH^+$).

(g) Title Compound

A solution of 1,1-dimethylethyl (2,3-dihydro[1,4]dioxino[2,3-c]pyridin-7-ylmethyl) {1-[2-(6-fluoro-3-oxopyrido[2,3-b]pyrazin-4(3H)-yl)ethyl]-4-piperidinyl}carbamate (195 mg, 0.361 mmol) in chloroform (5 ml) and MeOH (5 ml) was added 4M HCl in 1,4-dioxane (5 ml) and the reaction was stirred at rt for 0.5 h before evaporation and treatment with saturated aq NaHCO₃ (30 ml). The reaction was then extracted with 20% MeOH in DCM (3×100 ml). The combined organic phases were dried, evaporated and the crude residue purified by chromatography on silica gel using a 0-20% MeOH/DCM gradient to provide the title compound as a yellow oil (58 mg, 37%).

MS (ES+) m/z 441 (MH⁺).

$^1$H NMR (250 MHz) δ(CDCl₃) 1.32-1.65 (2H, m), 1.85-2.00 (2H, m), 2.10-2.30 (2H, m), 2.51-2.72 (3H, m), 2.85-3.05 (2H, m), 3.81 (2H, s), 4.26-4.63 (m, 6H), 6.83 (1H, s), 7.62 (1H, dd, J 9, 3 Hz), 8.10 (1H, s), 8.46 (1H, s), 8.51 (1H, d, J=2.5 Hz).

This compound was converted to the HCl salt by dissolving the obtained free base in 1:1 DCM:MeOH and adding 1 equivalent of 1M HCl in diethyl ether. This was then evaporated to dryness to give a yellow solid (33 mg).

Example 36

1-(2-{4-[(6,7-Dihydro-5H-pyrano[2,3-c]pyridazin-3-ylmethyl)amino]-1-piperidinyl}ethyl)-7-fluoro-2(1H)-quinoxalinone Dioxalate

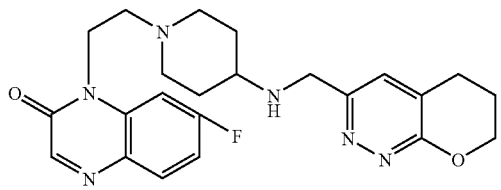

(a) 4-Bromo-2-{[4-(methyloxy)phenyl]methyl}-6-({[4-(methyloxy)phenyl]methyl}oxy)-3(2H)-pyridazinone and 5-bromo-2-{[4-(methyloxy)phenyl]methyl}-6-({[4-(methyloxy)phenyl]methyl}oxy)-3(2H)-pyridazinone A solution of 4-methoxybenzyl alcohol (6.2 ml, 50 mmol) in dry ether (120 ml) was treated dropwise with phosphorus tribromide (2.07 ml, 22 mmol). The mixture was heated under reflux for 1 h, cooled, washed twice with water, dried and the solvent was evaporated. The 4-methoxybenzyl bromide thus produced was added to a mixture of 4-bromo-1,2-dihydro-3,6-pyridazinedione (for a preparation see Example 6(a)) (4 g, 21 mmol) and potassium carbonate (8.28 g, 60 mmol) in dry DMF (60 ml) and stirred overnight at rt. The mixture was diluted with ethyl acetate, washed 3 times with water, dried over magnesium sulfate and evaporated to low volume. Some solid was filtered off and washed with ethyl acetate. The filtrate was evaporated to dryness and the residue chromatographed on silica, eluting with 20% ethyl acetate/hexane and then 100% ethyl acetate. This gave the less polar of the two desired products (3.233 g), the more polar of the two desired products (1.626 g) and a mixture of these (1.351 g). Total yield: 6.30 g, 70%.

Less polar product: MS (+ve ion electrospray) m/z 431 and 433 (MH⁺, 15%), 121 (100%).

More polar product: MS (+ve ion electrospray) m/z 431 and 433 (MH⁺, 15%), 121 (100%).

(b) Butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate and butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate Argon was bubbled through a mixture of 4-bromo-2-{[4-(methyloxy)phenyl]methyl}-6-({[4-(methyloxy)phenyl]methyl}oxy)-3(2H)-pyridazinone and 5-bromo-2-{[4-(methyloxy)phenyl]methyl}-6-({[4-(methyloxy)phenyl]methyl}oxy)-3(2H)-pyridazinone (1.35 g, 3.14 mmol) in dry 1,4-dioxane (7.5 ml) for 20 minutes. The solution was then treated with bis(tri-t-butylphosphine)palladium(0) (32 mg, 0.0628 mmol), tris(dibenzylideneacetone)dipalladium(0) (29 mg, 0.0314 mmol), dicyclohexylmethylamine (0.74 ml, 3.45 mmol) and n-butyl acrylate (0.543 ml, 3.78 mmol), stirred under argon at rt for 1 hour and at 95° C. overnight. The mixture was partitioned between ethyl acetate and water, separated, and the aqueous re-extracted with ethyl acetate. The combined organic solution was dried and evaporated and the residue was chromatographed, eluting with 15% ethyl acetate/hexane and then 35% ethyl acetate/hexane.

Less polar product (butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate) (838 mg, 55%).

MS (+ve ion electrospray) m/z 479 (MH⁺, 70%), 121 (100%).

More polar product (butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate) (580 mg, 39%).

MS (+ve ion electrospray) m/z 479 (MH⁺, 70%), 121 (100%).

(c) 6,7-Dihydro-2H-pyrano[2,3-c]pyridazin-3(5H)-one

Method A (1) Butyl 3-(2-{[4-(methyloxy)phenyl]methyl}-3,6-dioxo-1,2,3,6-tetrahydro-4-pyridazinyl)propanoate A solution of butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate) (838 mg) in ethanol (15 ml)/1,4-dioxane (10 ml) was treated with 10% Pd/C (400 mg) and stirred under hydrogen at atmospheric pressure and rt for 2 h. The catalyst was filtered off using kieselguhr and the filtrate was evaporated and redissolved in 1,4-dioxane and the solution evaporated to dryness to give the product as a colourless oil (0.56 g, 89%).

MS (+ve ion electrospray) m/z 361 (MH⁺, 60%), 121 (100%).

(2) 5-(3-Hydroxypropyl)-1-{[4-(methyloxy)phenyl]methyl}-1,2-dihydro-3,6-pyridazinedione Butyl 3-(2-{[4-(methyloxy)phenyl]methyl}-3,6-dioxo-1,2,3,6-tetrahydro-4-pyridazinyl)propanoate (0.56 g, 1.56 mmol) was dissolved in dry THF (30 ml). The solution under argon was cooled to −30° C., treated dropwise with a 1M solution of lithium aluminium hydride in THF (1.8 ml, 1.8 mmol), allowed to warm gradually to 0° C. and stirred in an ice bath for 30 minutes. 2M Hydrochloric acid was added until pH 3 was obtained, and the mixture was partitioned between water and ethyl acetate. The aqueous was re-extracted with ethyl acetate and the combined organic solution dried and evaporated. Chromatography of the residue on silica, eluting with ethyl acetate, gave the product as a white solid (300 mg, 67%).

MS (+ve ion electrospray) m/z 291 (MH$^+$, 30%), 121 (100%).

(3) 4-(3-Hydroxypropyl)-1,2-dihydro-3,6-pyridazinedione 5-(3-Hydroxypropyl)-1-{[4-(methyloxy)phenyl]methyl}-1,2-dihydro-3,6-pyridazinedione (2.734 g) was treated with anisole (10 ml) and TFA (100 ml) and stirred at 40° C. overnight. The solution was cooled, evaporated to dryness and kept under high vacuum for 30 minutes. The residue was taken up in MeOH (150 ml), refluxed for 12 hours, cooled and evaporated. The residue was kept for 1 hour under high vacuum, triturated under ether and the solid was filtered off. Drying under vacuum gave the product as a solid (1.48 g, 92%).

MS (+ve ion electrospray) m/z 171 (MH$^+$, 100%).

(4) Title Compound

A suspension of 4-(3-hydroxypropyl)-1,2-dihydro-3,6-pyridazinedione (1.48 g, 8.7 mmol) in THF (105 ml) was held in an ultrasound bath for 5 minutes, then cooled under argon in an ice bath. Triphenylphosphine (3.67 g, 14 mmol) was added, followed by diisopropyl azodicarboxylate (2.76 ml, 14 mmol). After 30 minutes the solvent was evaporated and the residue kept under high vacuum overnight. Chromatography on silica, eluting first with 2.5% MeOH/DCM until triphenylphosphine oxide was removed and then with 5% MeOH/DCM, gave the product as an off-white solid (1.049 g, 79%).

MS (+ve ion electrospray) m/z 153 (MH$^+$, 100%).
Method B

(5) Butyl 3-(1-{[4-(methyloxy)phenyl]methyl}-3,6-dioxo-1,2,3,6-tetrahydro-4-pyridazinyl)propanoate A solution of butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate) (580 mg) in ethanol (15 ml)/1,4-dioxane (5 ml) was treated with 10% Pd/C (400 mg) and stirred under hydrogen at atmospheric pressure and rt for 2 h. The catalyst was filtered off using kieselguhr and the filtrate was evaporated and redissolved in 1,4-dioxane and the solution evaporated to dryness to give the product (0.43 g, 98%).

MS (+ve ion electrospray) m/z 361 (MH$^+$, 50%), 121 (100%).

(6) 4-(3-Hydroxypropyl)-1-{[4-(methyloxy)phenyl]methyl}-1,2-dihydro-3,6-pyridazinedione Butyl 3-(1-{[4-(methyloxy)phenyl]methyl}-3,6-dioxo-1,2,3,6-tetrahydro-4-pyridazinyl)propanoate (0.43 g, 1.19 mmol) was dissolved in dry THF (20 ml). The solution under argon was cooled to −30° C., treated dropwise with a 1M solution of lithium aluminium hydride in THF (1.4 ml, 1.4 mmol), allowed to warm gradually to 0° C. and stirred in an ice bath for 30 minutes. 2M hydrochloric acid was added until the pH was 3 and the mixture was partitioned between water and ethyl acetate. The aqueous phase was re-extracted with ethyl acetate and the combined organic solution dried and evaporated. The resulting solid was triturated under ethyl acetate, filtered off, washed with ethyl acetate and dried under vacuum to give the product (241 mg, 70%).

MS (+ve ion electrospray) m/z 291 (MH$^+$, 10%), 121 (100%).

(7) 2-{[4-(Methyloxy)phenyl]methyl}-6,7-dihydro-2H-pyrano[2,3-c]pyridazin-3(5H)-one A suspension of 4-(3-hydroxypropyl)-1-{[4-(methyloxy)phenyl]methyl}-1,2-dihydro-3,6-pyridazinedione (2.624 g, 9.1 mmol) in THF (100 ml) was held in an ultrasound bath for 15 minutes. Triphenylphosphine (3.57 g, 13.6 mmol) was added under argon, the reaction mixture was then cooled to −10° C. and diisopropyl azodicarboxylate (2.68 ml, 13.6 mmol) was added, and the mixture was allowed to warm gradually to rt. After 1 h the solvent was evaporated. Chromatography on silica, eluting first with ethyl acetate to remove by-products and then with 10% ethanol/ethyl acetate, gave the product (2.55 g) contaminated with a little triphenylphosphine oxide (2.55 g).

MS (+ve ion electrospray) m/z 273 (MH$^+$, 50%), 121 (100%).

(8) Title Compound

2-{[4-(Methyloxy)phenyl]methyl}-6,7-dihydro-2H-pyrano[2,3-c]pyridazin-3(5H)-one (2.75 g, 10.1 mmol) was treated with anisole (10 ml) and TFA (100 ml) and heated at 70° C. for 24 hours. The solution was cooled and evaporated and the residue taken up in 2.5% MeOH/DCM. This was applied to a column of silica, and then elution with this solvent mixture followed by 5% MeOH/DCM gave the product as an off white solid (1.36 g, 88%).

MS (+ve ion electrospray) m/z 153 (MH$^+$, 100%).

(d) 6,7-Dihydro-5H-pyrano[2,3-c]pyridazin-3-yl trifluoromethanesulfonate

A solution of 6,7-dihydro-2H-pyrano[2,3-c]pyridazin-3(5H)-one (152 mg, 1 mmol) in DMF (2.5 ml) under argon was ice-cooled, treated with sodium hydride (60 mg of a 60% dispersion in oil, 1.5 mmol) and stirred for 1 hour, allowing to warm to RT. N-Phenyl-bis(trifluoromethanesulfonimide) (505 mg, 1 mmol) was added and stirring continued for 2 hours. The mixture was diluted with ethyl acetate, washed with saturated aqueous sodium bicarbonate solution and water (twice), dried over magnesium sulfate and evaporated. Chromatography, eluting with 40% ethyl acetate/hexane, gave the product as a white solid (228 mg, 80%).

MS (+ve ion electrospray) m/z 285 (MH$^+$, 100%).

(e) 3-Ethenyl-6,7-dihydro-5H-pyrano[2,3-c]pyridazine

Argon was bubbled for 15 minutes through a solution of 6,7-dihydro-5H-pyrano[2,3-c]pyridazin-3-yl trifluoromethanesulfonate (228 mg, 0.8 mmol) in 1,2-dimethoxyethane (6.5 ml). Tetrakis(triphenylphosphine)palladium(0) (50 mg, 0.0475 mmol) was added and the solution stirred for 20 minutes under argon. The mixture was then treated with potassium carbonate (111 mg, 0.8 mmol), water (1.9 ml) and triethenylboroxin pyridine complex (180 mg, 0.75 mmol). After stirring for 2 hours at 80° C., the mixture was cooled and partitioned between DCM and saturated aqueous sodium bicarbonate solution. Layers were separated and the aqueous was extracted twice with 20% MeOH/DCM. The combined organic solution was dried over magnesium sulfate, evaporated and the residue chromatographed on silica, eluting with ethyl acetate to give the product as a white solid (100 mg, 77%).

MS (+ve ion electrospray) m/z 163 (MH⁺, 100%).

(f) 6,7-Dihydro-5H-pyrano[2,3-c]pyridazine-3-carbaldehyde

A solution of 3-ethenyl-6,7-dihydro-5H-pyrano[2,3-c]pyridazine (100 mg, 0.617 mmol) in 1,4-dioxane (5.5 ml)/water (1.1 ml) was cooled in ice/water and treated with sodium periodate (306 mg, 1.43 mmol) and a 4% aqueous solution of osmium tetroxide (0.55 ml). The mixture was allowed to warm to rt after an hour, and after a total of 4.75 h stirring, the solvent was evaporated. 1,4-Dioxane was added and evaporated, a few ml of DCM were added and the mixture briefly held in an ultrasonic bath. The whole mixture was applied to a silica column and eluted with ethyl acetate to give the product (55 mg, 54%).

MS (+ve ion electrospray) m/z 165 (MH⁺, 100%).

(g) Title Compound

A solution of 1-[2-(4-amino-1-piperidinyl)ethyl]-7-fluoro-2(1H)-quinoxalinone dihydrochloride (60 mg; 0.166 mmol) and 6,7-dihydro-5H-pyrano[2,3-c]pyridazine-3-carbaldehyde (30 mg, 0.183 mmol) in MeOH (3 ml), chloroform (3 ml) and triethylamine (0.06 ml) was stirred at rt overnight. It was cooled and sodium triacetoxyborohydride (0.106 g; 0.5 mmol) was added and the mixture was stirred at rt overnight. More 6,7-dihydro-5H-pyrano[2,3-c]pyridazine-3-carbaldehyde (10 mg) was added and the mixture was stirred for 2 h at rt. Sodium triacetoxyborohydride (53 mg) was added and the mixture was stirred at rt for 18 hours. Water and sodium carbonate solution were added and the mixture was extracted (3×) with 10% MeOH-DCM, dried (sodium sulphate), evaporated, and chromatographed on silica gel, eluting with 0-20% MeOH-DCM to give the free base (25 mg) of the title compound.

MS (+ve ion electrospray) m/z 439 (MH+).

δH (CDCl₃), (400 MHz) 1.40-1.52 (2H, m), 1.92 (2H, br.d), 2.10 (2H, m), 2.20 (2H, t), 2.65 (1H, m), 2.70 (2H, m), 2.85 (2H, m), 3.01 (2H, d), 4.02 (2H, s), 4.33 (2H, m), 4.42 (2H, m), 7.06 (1H, m). 7.12 (1H, m), 7.28 (1H, s), 7.86 (1H, m), 8.22 (1H, s).

The free base in chloroform/DCM was treated with an excess of oxalic acid (~20 mg) in ether (2 ml) and the solution was evaporated to dryness. Ether was added and the pale yellow solid was collected and washed with ether, giving the title compound (31 mg).

Example 37

4-(2-{4-[(2,3-dihydro[1,4]dioxino[2,3-c]pyridin-7-ylmethyl)amino]-1-piperidinyl}ethyl)-6-(methyloxy)pyrido[2,3-b]pyrazin-3(4H)-one Dihydrochloride

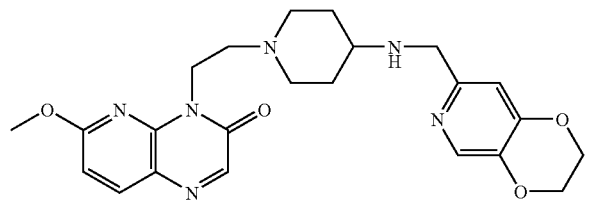

(a) 1,1-Dimethylethyl {1-[2-({[(phenylmethyl)oxy]carbonyl}amino)ethyl]-4-piperidinyl}carbamate A mixture of phenylmethyl (2-bromoethyl)carbamate (12.9 g, 50 mmol) (prepared from phenylmethyl (2-bromoethyl)carbamate and phenylmethyl chloridocarbonate according to the method of A. J. Brouwer and R. M. J. Liskamp, *European Journal of Organic Chemistry* (2005), (3), 487-495), 1,1-dimethylethyl 4-piperidinylcarbamate (10 g, 50 mmol), potassium carbonate (6.9 g, 50 mmol), acetonitrile (100 ml) and DMF (30 ml) was heated at 40° C. for 2.5 days. The solvents were decanted from inorganic residues and evaporated. The residue was partitioned between ethyl acetate and dilute brine. The organic extract was dried (MgSO₄) and evaporated affording a white solid (17.6 g, 93%).

MS (+ve ion electrospray) m/z: 378 (MH⁺).

(b) 1,1-Dimethylethyl [1-(2-aminoethyl)-4-piperidinyl]carbamate

A solution of 1,1-dimethylethyl {1-[2-({[(phenylmethyl)oxy]carbonyl}amino)ethyl]-4-piperidinyl}carbamate (8.2 g, 21.8 mmol) in ethanol (500 ml) was hydrogenated overnight over 10% palladium on charcoal (50% dispersion with water, 4.0 g). The mixture was filtered, evaporated, and azeotroped with chloroform to afford the title intermediate (5.4 g, 100%).

MS (+ve ion electrospray) m/z: 244 (MH⁺).

(c) 1,1-Dimethylethyl [1-(2-{[6-(methyloxy)-3-nitro-2-pyridinyl]amino}ethyl)-4-piperidinyl]carbamate A mixture of 2-chloro-6-(methyloxy)-3-nitropyridine (1.9 g, 10 mmol), 1,1-dimethylethyl [1-(2-aminoethyl)-4-piperidinyl]carbamate (2.43 g, 10 mmol) and potassium carbonate (1.4 g, 10 mmol) in acetonitrile (35 ml) and DMF (10 ml) was heated at 40° C. for 30 minutes. The mixture was filtered, washing with acetonitrile, and evaporated. The residue was dissolved in the minimum volume of DCM (15 ml) and washed with water (1 ml). The organic extract was added to a silica column which was then eluted with 0-100% ethyl acetate in hexane affording a yellow solid (3.1 g, 78%).

MS (+ve ion electrospray) m/z: 396 (MH⁺).

(d) 1,1-Dimethylethyl [1-(2-{[3-amino-6-(methyloxy)-2-pyridinyl]amino}ethyl)-4-piperidinyl]carbamate A solution of 1,1-dimethylethyl [1-(2-{[6-(methyloxy)-3-nitro-2-pyridinyl]amino}ethyl)-4-piperidinyl]carbamate (3.0 g, 7.6 mmol) in ethanol (500 ml) was hydrogenated for 2 hours over 10% palladium on charcoal (50% dispersion with water, 1.5 g). The mixture was filtered, evaporated, and azeotroped with chloroform to afford a purple oil (2.8 g, 100%).

MS (+ve ion electrospray) m/z: 366 (MH⁺).

(e) Ethyl N-[2-({2-[4-({[(1,1-dimethylethyl)oxy]carbonyl}amino)-1-piperidinyl]ethyl}amino)-6-(methyloxy)-3-pyridinyl]glycinate A mixture of 1,1-dimethylethyl [1-(2-{[3-amino-6-(methyloxy)-2-pyridinyl]amino}ethyl)-4-piperidinyl]carbamate (2.8 g, 7.6 mmol), ethyl bromoacetate (0.85 ml, 1.3 g, 7.6 mmol) and potassium carbonate (2 g, 15.2 mmol) in acetonitrile (40 ml) and DMF (20 ml) was stirred under argon overnight. The mixture was filtered, washing with acetonitrile, and evaporated. The residue was dissolved in the minimum volume of DCM (20 ml) and washed with water (20 ml). The organic extract was added to a silica column which was then eluted with 0-100% ethyl acetate in hexane affording a brown oil (1.3 g, 38%).

MS (+ve ion electrospray) m/z: 452 (MH⁺).

(f) 1,1-Dimethylethyl (1-{2-[6-(methyloxy)-3-oxopyrido[2,3-b]pyrazin-4(3H)-yl]ethyl}-4-piperidinyl)carbamate A solution of ethyl N-[2-({2-[4-({[(1,1-dimethylethyl)oxy]carbonyl}amino)-1-piperidinyl]ethyl}amino)-6-(methyloxy)-3-pyridinyl]glycinate (1.2 g, 2.7 mmol) in toluene (400 ml) was heated to reflux under argon for 24 hours. This solution was treated at rt with manganese dioxide (2.0 g, 23 mmol). After 7 h the mixture was filtered, washing with warm toluene then evaporated affording a dark oil. Chromatography on silica eluting with 0-100% ethyl acetate in hexane afforded a yellow solid (470 mg, 43%).

MS (+ve ion electrospray) m/z: 404 (MH+).

(g) 4-[2-(4-Amino-1-piperidinyl)ethyl]-6-(methyloxy)pyrido[2,3-b]pyrazin-3(4H)-one A solution of 1,1-dimethylethyl (1-{2-[6-(methyloxy)-3-oxopyrido[2,3-b]pyrazin-4(3H)-yl]ethyl}-4-piperidinyl)carbamate (470 mg, 1.2 mmol) in DCM/trifluoroacetic acid (10 ml/10 ml) was stirred at rt for 30 minutes then evaporated to dryness. The residue was triturated with ether and then resultant solid dried in vacuo. The solid was dissolved in DCM/MeOH (20 ml/20 ml) and treated with MP-carbonate resin (2.3 mmol of carbonate per gram, 3 g, ca 8 mmol). After 1.5 hours the mixture was filtered, washing alternatively with small volumes of DCM and MeOH. The combined filtrates were evaporated affording a yellow oil (contaminated with particulate material from the resin). This residue was treated with 20% MeOH in DCM (20 ml) filtered and evaporated affording a yellow oil (350 mg, 100%).

MS (+ve ion electrospray) m/z: 304 (MH+).

(h) Title Compound

A solution of 4-[2-(4-amino-1-piperidinyl)ethyl]-6-(methyloxy)pyrido[2,3-b]pyrazin-3(4H)-one (150 mg, 0.494 mmoles) and 2,3-dihydro[1,4]dioxino[2,3-c]pyridine-7-carboxaldehyde (for a synthesis see WO2004058144, Example 2(c) or WO03/087098, Example 19(d)) (82 mg, 0.496 mmoles) in anhydrous DCM (10 ml) and anhydrous MeOH (1 ml) was stirred at rt for 5 minutes. Sodium triacetoxyborohydride (316 mg, 1.49 mmoles) was added and the mixture was stirred, under argon, for 18 h, treated with sat. aq. NaHCO₃ solution (5 ml) and 10:1 DCM:MeOH (10 ml). The layers were separated and the aqueous layer was washed with 10:1 DCM:MeOH (5 ml). The organic extracts were combined, washed with brine, passed through a hydrophobic frit and evaporated to an orange gum. Purification on a 20 g silica column eluted with a 0% to 30% DCM/MeOH gradient elution gave the free base of the title compound as a colourless gum (128 mg, 57%).

MS (ES+) m/z 453 (MH+).

¹H NMR δ (CDCl₃) 1.44 (2H, m). 1.90 (2H, m), 2.18 (2H, m), 2.58 (1H, m), 2.74 (2H, m), 3.04 (2H, m), 3.81 (2H, s), 4.03 (3H, s), 4.27 (2H, m), 4.32 (2H, m), 4.58 (2H, t, J=7.2 Hz), 6.73 (1H, d, J=8.4 Hz), 6.82 (1H, s), 8.01 (1H, d, J=8.4 Hz), 8.09 (1H, s), 8.15 (1H, s).

A solution of the free base (128 mg, 0.283 mmoles) in chloroform (3.5 ml) was treated with 1M HCl in diethyl ether (1 ml) and anhydrous diethyl ether (4 ml). After centrifugation the solvent was decanted off and the solid dried to give the title compound as a cream solid (154 mg).

Example 38

1-(2-{4-[(2,3-dihydrofuro[2,3-c]pyridin-5-ylmethyl)amino]-1-piperidinyl}ethyl)-7-fluoro-2(1H)-quinoxalinone Dihydrochloride

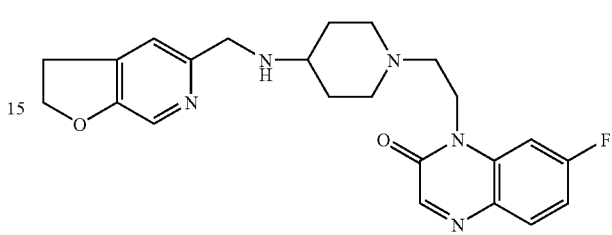

(a) {5-({[4-(Methyloxy)phenyl]methyl}oxy)-4-[(trimethylsilyl)ethynyl]-2-pyridinyl}methyl Acetate (5-({[4-(Methoxy)phenyl]methyl}oxy)-4-{[(trifluoromethyl)sulfonyl]oxy}-2-pyridinyl)methyl acetate (for a synthesis, see WO2004058144 Example 60(d)) (10 g, 23 mmol) was dissolved in acetonitrile (400 ml) and triethylamine (65 ml) and copper (I) iodide (0.44 g, 2.3 mmol) were added. The mixture was degassed and placed under a blanket of argon. Trimethylsilylacetylene (10 ml, 69 mmol) and bis(triphenylphosphine)palladium(II) dichloride (0.645 g, 0.9 mmol) were added and the mixture heated to 45° C. for 18 h. The mixture was then allowed to cool and filtered. The filtrate was evaporated to dryness and the residue partitioned between ethyl acetate and water. The organic layer was separated and dried (sodium sulphate). Chromatography on silica gel, eluting with a gradient of 20-75% ethyl acetate in 40-60° C. petroleum ether, gave an oil (8.4 g, 96%).

MS (+ve ion electrospray) m/z 384 (MH+).

(b) {5-Hydroxy-4-[(trimethylsilyl)ethynyl]-2-pyridinyl}methyl Acetate, Trifluoroacetate {5-({[4-(Methyloxy)phenyl]methyl}oxy)-4-[(trimethylsilyl)ethynyl]-2-pyridinyl}methyl acetate (8.45 g, 22 mmol) in DCM (70 ml) was treated with trifluoroacetic acid (9.4 ml) and triethylsilane (3.33 ml) and stirred at ambient temperature for 18 h. The mixture was evaporated to dryness and chromatographed on silica gel, eluting with a gradient of 2-8% MeOH in DCM. This gave an oil (10 g, 100%).

MS (+ve ion electrospray) m/z 264 (MH+).

(c) Furo[2,3-c]pyridin-5-ylmethyl Acetate

{5-Hydroxy-4-[(trimethylsilyl)ethynyl]-2-pyridinyl}methyl acetate, trifluoroacetate) (10 g, 22 mmol) was dissolved in pyridine (200 ml) and treated with copper(I) iodide (5.2 g, 27 mmol) then heated under reflux for 18 h. The mixture was allowed to cool, evaporated to dryness and the residue partitioned between ethyl acetate and water. This mixture was filtered through kieselguhr to remove copper residues. The organic layer was separated from the filtrate, dried and chromatographed on silica gel, eluting with a gradient of 10-60% ethyl acetate in 40-60° C. petroleum ether. This gave furo[2,3-c]pyridin-5-ylmethyl acetate (1.15 g, 27%) and a less polar product [2-(trimethylsilyl)furo[2,3-c]pyridin-5-yl]methyl acetate (1.3 g, 23%) as oils.

MS (+ve ion electrospray) m/z 192 (MH+) and MS (+ve ion electrospray) m/z 264 (MH+).

(d) Furo[2,3-c]pyridin-5-ylmethanol

A solution of furo[2,3-c]pyridin-5-ylmethyl acetate (1.15 g) in 1,4-dioxane (30 ml) and water (10 ml) was treated with 2M sodium hydroxide (12 ml) then stirred at ambient temperature for 18 h. The mixture was then partitioned between ethyl acetate and water. The organic fractions were separated and dried then evaporated to dryness. This gave an oil (0.63 g, 70%).

MS (+ve ion electrospray) m/z 150 (MH+).

(e) 2,3-Dihydrofuro[2,3-c]pyridin-5-ylmethanol

Furo[2,3-c]pyridin-5-ylmethanol (1.29 g, 8.7 mmol) was dissolved in ethanol (50 ml) and hydrogenated at rt, 1 atmosphere over 10% palladium on charcoal paste for 18 h. The mixture was filtered through kieselguhr and the filtrate evaporated to dryness, to give (1.31 g, 100%).

MS (+ve ion electrospray) m/z 152 (MH+).

(f) 2,3-Dihydrofuro[2,3-c]pyridine-5-carbaldehyde 2,3-Dihydrofuro[2,3-c]pyridin-5-ylmethanol (1.31 g, 8.7 mmol) was dissolved in DCM (100 ml), treated with manganese (IV) dioxide (6 g, 69 mmol) and heated under reflux for 18 h. Filtration through kieselguhr and evaporation of the filtrate to dryness gave an oil (0.9 g, 70%).

MS (+ve ion electrospray) m/z 150 (MH+).

(g) Title Compound

A solution of 1-[2-(4-amino-1-piperidinyl)ethyl]-7-fluoro-2(1H)-quinoxalinone dihydrochloride (60 mg; 0.166 mmol) and 2,3-dihydrofuro[2,3-c]pyridine-5-carbaldehyde (30 mg, 0.20 mmol) in MeOH (3 ml), chloroform (3 ml) and triethylamine (0.06 ml) was heated under reflux with 3A molecular sieves overnight. It was cooled and sodium triacetoxyborohydride (0.11 g; 0.52 mmol) was added, and the mixture was stirred at rt overnight. Aqueous sodium bicarbonate solution was added to basify and the aqueous phase was extracted several times with 10% MeOH-DCM. The organic fractions were dried and evaporated. Chromatography on silica gel, eluting with 0-20% MeOH-DCM gave the free base of the title compound (50 mg, 71%).

MS (+ve ion electrospray) m/z 424 (MH+).

δH (CDCl₃), (250 MHz) 1.49 (2H, m), 1.93 (2H, br.d), 2.19 (2H, t), 2.59 (1H, m), 2.67 (2H, t), 2.98 (2H, br. d), 3.22 (2H, t), 3.87 (2H, s), 4.31 (2H, t), 4.61 (2H, t), 7.08 (1H, m), 7.13 (1H, m), 7.21 (1H, s), 7.86 (1H, dd), 8.07 (1H, s), 8.22 (1H, s)

The free base in chloroform/DCM was treated with 0.4M hydrogen chloride in 1,4-dioxane (0.6 mL) and evaporated to dryness to give the dihydrochloride salt.

Example 39

1-(2-{4-[(2,3-dihydrofuro[2,3-c]pyridin-5-ylmethyl)amino]-1-piperidinyl}ethyl)-7-fluoro-2(1H)-quinoxalinone Dihydrochloride

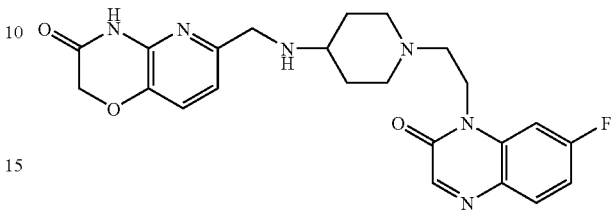

A solution of 1-[2-(4-amino-1-piperidinyl)ethyl]-7-fluoro-2(1H)-quinoxalinone dihydrochloride (60 mg; 0.166 mmol) and 3-oxo-3,4-dihydro-2H-pyrido[3,2-b][1,4]oxazine-6-carboxaldehyde (for a synthesis see WO2003087098, Example 31(e))(35 mg, 0.20 mmol) in MeOH (3 ml), chloroform (3 ml) and triethylamine (0.06 ml) was heated under reflux with 3A molecular sieves overnight. It was cooled and sodium triacetoxyborohydride (0.11 g; 0.52 mmol) was added, and the mixture was stirred at rt for 7-8 h. Aqueous sodium bicarbonate solution was added to basify and the aqueous phase was extracted several times with 10% MeOH-DCM. The organic fractions were dried and evaporated. Chromatography on silica gel, eluting with 0-20% MeOH-DCM gave the free base of the title compound (68 mg, 91%).

δH (CDCl₃), (250 MHz) 1.49 (2H, m), 1.92 (2H, br.d), 2.19 (2H, t), 2.55 (1H, m), 2.69 (2H, t), 2.99 (2H, br. d), 3.83 (2H, s), 4.31 (2H, t), 4.63 (2H, s), 6.95 (1H, d), 7.08 (1H, m), 7.14 (1H, m), 7.20 (1H, d), 7.85 (1H, dd), 8.22 (1H, s)

MS (+ve ion electrospray) m/z 453 (MH+).

The free base in chloroform/DCM was treated with 0.4M hydrogen chloride in 1,4-dioxane (0.75 mL) and evaporated to dryness to give the dihydrochloride salt.

Example 40

1-(2-{4-[(6,7-dihydro[1,4]oxathiino[2,3-c]pyridazin-3-ylmethyl)amino]-1-piperidinyl}ethyl)-7-fluoro-2(1H)-quinoxalinone Dihydrochloride

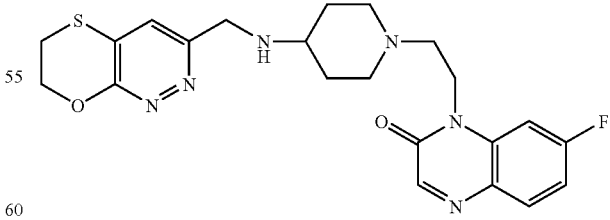

(a) 2-[(3,6-Dichloro-4-pyridazinyl)thio]ethanol

A solution of 3,4,6-trichloropyridazine (25 g) in tetrahydrofuran (200 ml) and triethylamine (19 ml) was treated at 0°

C. (ice bath cooling) with 2-mercaptoethanol (8.33 ml) over 5 minutes: After the addition was complete, the mixture was stirred at rt for 72 hours. The mixture was stirred with aqueous sodium bicarbonate solution and DCM and the solid was collected, washed with water, ether and pentane and dried in vacuo, giving (22.9 g). The combined aqueous and organic fraction was evaporated to half volume giving further solid, which was washed and dried as above (5.0 g). The total yield of solid (27.9 g; 91%) contained some bromo-analogue (5-10%) by NMR.

(b) 3-Chloro-6,7-dihydro[1,4]oxathiino[2,3-c]pyridazine

A solution of 2-[(3,6-dichloro-4-pyridazinyl)thio]ethanol (13 g) (previously dried at 50° C. in vacuo) in dry 1,4-dioxane (250 ml) was treated with lithium hydride (3 g) in portions and heated at 105-110° C. for 24 h. The reaction mixture was cooled and quenched with iced-water. The solution was taken to pH 10-11 with 5M hydrochloric acid and evaporated. Water was added and the mixture was extracted 4× with DCM, dried (sodium sulphate), evaporated, and chromatographed on silica gel, eluting with 0-100% ethyl acetate-hexane, to afford a white solid (1.61 g) (containing ca. 10% of the bromo species).

MS (+ve ion electrospray) m/z 189/91 (Cl MH+); 233/5 (Br MH+).

δH (CDCl$_3$, 400 MHz) 3.23 (2H, m), 4.67 (2H, m), 7.26 (1H, s) (for major chloro-compound).

(c) 3-Ethenyl-6,7-dihydro[1,4]oxathiino[2,3-c]pyridazine

A solution of 3-chloro-6,7-dihydro[1,4]oxathiino[2,3-c]pyridazine (1.0 g) in dimethoxyethane (2 ml) was degassed under argon then tetrakis(triphenylphosphine)palladium (0) (135 mg), potassium carbonate (0.695 g), triethenylboroxin pyridine complex (0.8 g) and water (3.7 ml) were added. The mixture was heated overnight at 105° C. More triethenylboroxin pyridine complex (0.4 g) and tetrakis(triphenylphosphine)palladium (0) (30 mg) were added and heating was continued for 24 hours. The mixture was cooled, treated with aqueous sodium bicarbonate solution, extracted (4×) with DCM, dried (sodium sulphate), evaporated and chromatographed on silica gel (70 g), eluting with 0-100% ethyl acetate-hexane, affording a solid (0.56 g) (87% pure by LC-MS).

MS (+ve ion electrospray) m/z 181 (MH+).

(d) 6,7-Dihydro[1,4]oxathiino[2,3-c]pyridazine-3-carbaldehyde

A solution of 3-ethenyl-6,7-dihydro[1,4]oxathiino[2,3-c]pyridazine (320 mg) in 1,4-dioxane/water (20 ml/5 ml) was treated with an aqueous solution of osmium tetroxide (4% w/v, 2 ml) and sodium periodate (1.0 g), initially stirred in an ice-bath, then allowed to warm to rt. After 2.5 h the mixture was evaporated to dryness and dissolved in 1,4-dioxane and chloroform. Silica gel was added and the mixture was evaporated to dryness, added to a silica column (50 g) and chromatographed, eluting with 0-100% ethyl acetate in hexane, to afford a white solid (116 mg, 36%).

MS (+ve ion electrospray) m/z 183 (MH+).

(e) Title Compound

A solution of 1-[2-(4-amino-1-piperidinyl)ethyl]-7-fluoro-2(1H)-quinoxalinone dihydrochloride (60 mg; 0.166 mmol) and 3-oxo-3,4-dihydro-2H-pyrido[3,2-b][1,4]oxazine-6-carbaldehyde (35 mg, 0.20 mmol) in MeOH (3 ml), chloroform (3 ml) and triethylamine (0.06 ml) was heated under reflux with 3A molecular sieves overnight. It was cooled and sodium triacetoxyborohydride (0.1 μg; 0.52 mmol) was added, and the mixture was stirred at rt for 7-8 h. More triacetoxyborohydride (100 mg) was added and stirring was continued overnight. A further addition of triacetoxyborohydride (100 mg) was made, followed by another 50 mg, together with more aldehyde (5 mg) after 8 h. Stirring was again continued overnight. Aqueous sodium bicarbonate solution was added to basify and the aqueous phase was extracted several times with 10% MeOH-DCM. The organic fractions were dried and evaporated. Chromatography on silica gel, eluting with 0-20% MeOH-DCM gave the free base of the title compound (25 mg, 33%).

δH (CDCl$_3$), (250 MHz) 1.54 (2H, m), 1.99 (2H, br.d), 2.28 (2H, t), 2.66 (1H, m), 2.72 (2H, t), 3.05 (2H, br. d), 3.21 (2H, m), 4.02 (2H, s), 4.37 (2H, t), 4.67 (2H, m), 7.07 (1H, m), 7.21 (1H, dd), 7.36 (1H, s), 7.85 (1H, dd), 8.22 (1H, s).

MS (+ve ion electrospray) m/z 457 (MH+).

The free base in chloroform/DCM was treated with 0.4M hydrogen chloride in 1,4-dioxane (0.25 ml) and evaporated to dryness to give the dihydrochloride salt Example 41

1-(2-{(3R,4S)-4-[(2,3-dihydro[1,4]dioxino[2,3-c]pyridin-7-ylmethyl)amino]-3-hydroxy-1-piperidinyl}ethyl)-7-fluoro-1,5-naphthyridin-2(1H)-one Hydrochloride

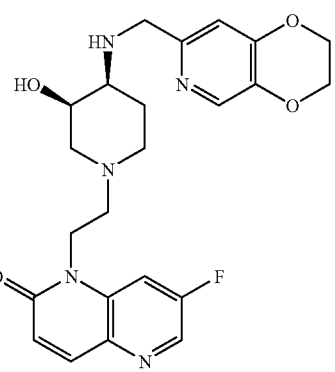

(a) 1,1-dimethylethyl {(3R,4S)-1-[2-(7-fluoro-2-oxo-1,5-naphthyridin-1(2H)-yl)ethyl]-3-hydroxy-4-piperidinyl}carbamate (7-Fluoro-2-oxo-1,5-naphthyridin-1(2H)-yl)acetaldehyde methyl hemiacetal (200 mg, 0.8396 mmol) and 1,1-dimethylethyl[(3R,4S)-3-hydroxy-4-piperidinyl]carbamate (for a synthesis see WO2004058144, Example 5(c), cis-(3-hydroxy-piperidin-4-yl)-carbamic acid tert-butyl ester Enantiomer 1) (182 mg, 1 eq.) were stirred in chloroform (10 ml) plus MeOH (0.5 ml) under argon for 2 hours. Sodium triacetoxyborohydride (534 mg, 3 eq.) was added in one portion and the mixture was stirred at rt overnight, then quenched by addition of saturated aqueous sodium hydrogen cabonate (20 ml) and extracted with 20% v:v MeOH in DCM (3×200 ml). The organic extractes were combined, dried over anhydrous magnesium sulphate, filtered and evaporated under reduced pressure to give the crude product, which was purified by column chromatography on silica, eluted with 0-20% (2M ammonia in MeOH) in DCM. Appropriate fractions were combined and evaporated under reduced pressure to give title compound (247 mg) as an off-white foam.

MS (ES+) m/z 407 (MH$^+$).

(b) 1-{2-[(3R,4S)-4-amino-3-hydroxy-1-piperidinyl]ethyl}-7-fluoro-1,5-naphthyridin-2(1H)-one Dihydrochloride 1,1-Dimethylethyl {(3R,4S)-1-[2-(7-fluoro-2-oxo-1,5-naphthyridin-1(2H)-yl)ethyl]-3-hydroxy-4-piperidinyl}carbamate (240 mg, 0.5905 mmol) was dissolved in DCM (10 ml) and the solution was treated with 4M hydrogen chloride in 1,4-dioxane (2 mL). Effervescence and formation of a precipitate was observed. After 2 h, the solvents were removed under reduced pressure and the residue was dried under reduced pressure overnight, to give 1-{2-[(3R,4S)-4-amino-3-hydroxy-1-piperidinyl]ethyl}-7-fluoro-1,5-naphthyridin-2(1H)-one dihydrochloride as an off-white solid (220 mg).

MS (ES+) m/z 307 (MH$^+$).

(c) Title Compound

1-{2-[(3R,4S)-4-Amino-3-hydroxy-1-piperidinyl]ethyl}-7-fluoro-1,5-naphthyridin-2(1H)-one dihydrochloride (100 mg, 0.2637 mmol) was stirred in 9:1 v:v chloroform:MeOH (5 ml) at rt under argon and triethylamine (129 µl, 3.5 eq.) was added. The mixture was stirred at rt for 10 mins, then 2,3-dihydro[1,4]dioxino[2,3-c]pyridine-7-carboxaldehyde (for a synthesis see WO2004058144, Example 2(c) or WO03/087098, Example 19(d)) (44 mg, 0.264 mmol) was added and the mixture was stirred at rt for 1 h before being treated with sodium triacetoxyborohydride (168 mg) added in one portion. The mixture was then stirred at rt over the weekend. Saturated aqueous sodium hydrogen cabonate (2 ml) was then added and the organic phase was diluted with DCM to bring the total volume to ca. 20 ml. The organic phase was separated using a hydrophobic frit and the aqueous phase was extracted with DCM (2×20 ml). The combined DCM extracts were evaporated under reduced pressure and purified by MDAP to give the free base of the title compound as an off-white foam (66 mg).

$^1$H NMR δ (400 MHz, CDCl$_3$): 8.44 (1H, d, J=2 Hz), 8.34 (1H, s), 8.11 (1H, s), 7.91 (1H, d, J=10 Hz), 7.54 (1H, dd, J=8 Hz, 2 Hz), 6.89-6.86 (2H, m), 4.53-4.44 (1H, m), 4.36-4.20 (5H, m), 4.12 (1H, s), 4.08 (2H, s), 3.32-3.28 (1H, m), 3.03-2.99 (2H, m), 2.80-2.71 (2H, m), 2.39 (1H, d, J 11 Hz), 2.32-2.25 (1H, m), 1.95-1.84 (2H, m).

MS (ES+) m/z 456 (MH$^+$).

This material was converted to the hydrochloride by dissolving in DCM and adding 1 equivalent of 1M HCl/diethyl ether then evaporating to dryness. MS as that of the free base.

Example 42

1-(2-{(3R,4S)-4-[(2,3-dihydro[1,4]dioxino[2,3-c]pyridin-7-ylmethyl)amino]-3-hydroxy-1-piperidinyl}ethyl)-7-(methyloxy)-1,5-naphthyridin-2(1H)-one Hydrochloride

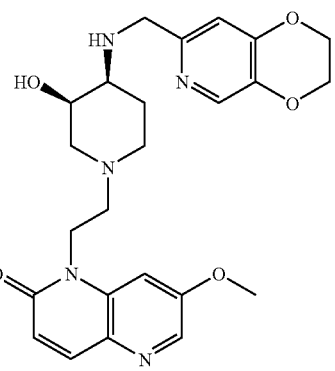

(a) 1,1-dimethylethyl ((3R,4S)-3-hydroxy-1-{2-[7-(methyloxy)-2-oxo-1,5-naphthyridin-1(2H)-yl]ethyl}-4-piperidinyl)carbamate

[7-(methoxy)-2-oxo-1,5-naphthyridin-1(2H)-yl]acetaldehyde methyl hemiacetal (200 mg, 0.7992 mmol) and 1,1-dimethylethyl[(3R,4S)-3-hydroxy-4-piperidinyl]carbamate (for a synthesis see WO2004058144, Example 5(c), cis-(3-hydroxy-piperidin-4-yl)-carbamic acid tert-butyl ester Enantiomer 1) (173 mg, 1 eq.) were stirred in chloroform (10 ml) plus MeOH (0.5 ml) under argon for 2 h. Sodium triacetoxyborohydride (508 mg, 3 eq.) was added in one portion and the mixture was stirred at rt over the weekend, then quenched by addition of saturated aqueous sodium hydrogen cabonate (20 ml) and extracted with 20% v:v MeOH in DCM (3×200 ml). The organic extractes were combined, dried over anhydrous magnesium sulphate, filtered and evaporated under reduced pressure to give the crude product, which was purified by column chromatography on silica, eluted with 0-20% (2M ammonia in MeOH) in DCM. Appropriate fractions were combined and evaporated under reduced pressure to give 1,1-dimethylethyl ((3R,4S)-3-hydroxy-1-{2-[7-(methyloxy)-2-oxo-1,5-naphthyridin-1(2H)-yl]ethyl}-4-piperidinyl)carbamate (263 mg) as an off-white foam.

MS (ES+) m/z 419 (MH$^+$).

(b) 1-{2-[(3R,4S)-4-amino-3-hydroxy-1-piperidinyl]ethyl}-7-(methyloxy)-1,5-naphthyridin-2(1H)-one Dihydrochloride 1,1-dimethylethyl ((3R,4S)-3-hydroxy-1-{2-[7-(methyloxy)-2-oxo-1,5-naphthyridin-1 (2H)-yl]ethyl}-4-piperidinyl)carbamate (258 mg, 0.6165 mmol) was dissolved in DCM (10 mL) and the solution was treated with 4M hydrogen chloride in 1,4-dioxane (2 ml). Effervescence and formation of a precipitate was observed. After 2 h, the solvents were removed under reduced pressure and the residue was dried under reduced pressure overnight, to give the title compound as a pale pink solid (223 mg).

MS (ES+) m/z 319 (MH$^+$).

(c) Title Compound

1-{2-[(3R,4S)-4-amino-3-hydroxy-1-piperidinyl]ethyl}-7-(methyloxy)-1,5-naphthyridin-2(1H)-one dihydrochloride (100 mg, 0.2556 mmol) was stirred in 9:1 v:v chloroform:MeOH (5 mL) at rt under argon and triethylamine (125 uL, 3.5 eq.) was added. The mixture was stirred at rt for 10 mins., then 2,3-dihydro[1,4]dioxino[2,3-c]pyridine-7-carboxaldehyde (for a synthesis see WO2004058144, Example 2(c) or WO03/087098, Example 19(d)) was added and the mixture was stirred at rt for 1 h before being treated with sodium triacetoxyborohydride (163 mg) added in one portion. The mixture was then stirred at rt over the weekend. Saturated aqueous sodium hydrogen cabonate (3 ml) was then added and the organic phase was diluted with DCM to bring the total volume to ca. 20 ml. The organic phase was separated using a hydrophobic frit and the aqueous phase was extracted with DCM (2×20 ml). The combined DCM extracts were evaporated under reduced pressure and purified by MDAP to give the free base of the title compound as an off-white foam (45 mg).

$^1$H NMR δ (CDCl$_3$, 400 MHz) 8.71 (1H, s), 8.294 (1H, d, J=2 Hz), 8.10 (1H, s), 7.87 (1H, d, J 10 Hz), 7.21 (1H, d, J=2 Hz), 6.85 (1H, s), 6.75 (1H, d, J 10 Hz), 4.58-4.46 (2H, m), 4.39-4.28 (4H, m), 4.08 (1H, s), 4.02 (2H, s), 4.00 (3H, s), 3.33-3.29 (1H, m), 3.00-2.90 (2H, m), 2.83-2.70 (2H, m), 2.42 (1H, d, J 11 Hz), 2.35-2.28 (1H, m), 1.92-1.81 (2H, m).

MS (ES+) m/z 468 (MH$^+$).

This material was converted to the hydrochloride by dissolving in DCM and adding 1 equivalent of 1M HCl/diethyl ether then evaporating to dryness. MS as that of the free base.

Example 43

1-(2-{4-[(2,3-dihydro[1,4]dioxino[2,3-c]pyridin-7-ylmethyl)amino]-1-piperidinyl}ethyl)-6,7-difluoro-2(1H)-quinoxalinone Dihydrochloride

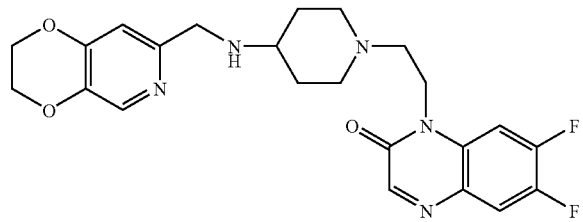

(a) 6,7-Difluoro-2(1H)-quinoxalinone

A mixture of 4,5-difluoro-1,2-benzenediamine (0.60 g) and 50% ethyl glyoxalate in toluene (0.87 ml) in ethanol (25 ml) was heated under reflux for 2 hours then cooled. After refrigeration overnight, the resulting solid was collected and washed with ice-cold ethanol and dried under vacuum to give a solid (0.57 g; 75%).

MS (+ve ion electrospray) m/z 183 (MH+).

(b) 6,7-Difluoro-1-(2-propen-1-yl)-2(1H)-quinoxalinone

A solution of 6,7-difluoro-2(1H)-quinoxalinone (0.57 g; 3.13 mmol) in dry DMF (10 ml) containing anhydrous potassium carbonate (1.3 g; 9.4 mmol) was treated with allyl iodide (0.31 ml; 3.45 mmol) and the mixture was stirred at rt for 2 h. The solvents were evaporated, water was added and the mixture was extracted (3×) with DCM. The extracts were dried and evaporated, and the residue was chromatographed on silica gel, eluting with 0-50% ethyl acetate/hexane to give the product (0.44 g, 63%).

MS (+ve ion electrospray) m/z 223 (MH+).

(c) 6,7-Difluoro-2-oxo-1(2H)-quinoxalinyl)acetaldehyde

A solution of 6,7-difluoro-1-(2-propen-1-yl)-2(1H)-quinoxalinone (0.44 g; 1.98 mmol) in 1,4-dioxane (25 ml) and water (50 ml) was treated with osmium tetroxide (4% solution in water; 2.49 ml) and sodium periodate (1.95 g) and the mixture was stirred at rt for 2.75 hours. 1,4-Dioxane was removed by evaporation and the aqueous residue was extracted several times with DCM/MeOH. The extracts were dried and evaporated and the residue was chromatographed on a silica gel column, eluting with 50-100% ethyl acetate/hexane to give a mixture of the aldehyde and the corresponding methyl hemiacetal (approx. 1:1, 0.38 g, 80%).

MS (+ve ion electrospray) m/z 225 (MH+), 239 (M.CH$_3$+ from hemiacetal).

(d) 1,1-Dimethylethyl (2,3-dihydro[1,4]dioxino[2,3-c]pyridin-7-ylmethyl) {1-[2-(6,7-difluoro-2-oxo-1(2H)-quinoxalinyl)ethyl]-4-piperidinyl}carbamate A solution of 6,7-difluoro-2-oxo-1(2H)-quinoxalinyl)acetaldehyde/methyl hemiacetal mixture (approx. 1:1, 0.19 g; 0.79 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (0.2 g, 0.8 mmol) in dry MeOH (0.2 ml) and chloroform (5 ml) was stirred at rt for 1.5 h. Sodium triacetoxyborohydride (0.5 g, 2.37 mmol) was added and the mixture was stirred for 7 h. Aqueous sodium bicarbonate was added to basify and the phases were separated. The aqueous phase was extracted with DCM a few times, and the organic fractions were dried and evaporated. Chromatography on silica, eluting with 0-10% MeOH/ethyl acetate, gave the product (0.26 g, 59%).

MS (+ve ion electrospray) m/z 558 (MH+).

(e) Title Compound

A solution of 1,1-dimethylethyl (2,3-dihydro[1,4]dioxino[2,3-c]pyridin-7-ylmethyl) {1-[2-(6,7-difluoro-2-oxo-1(2H)-quinoxalinyl)ethyl]-4-piperidinyl}carbamate (0.26 g, 0.46 mmol) in DCM (5 ml) and MeOH (3 ml) was treated with 4M hydrogen chloride in 1,4-dioxane (5 ml), stirred at rt for 2.5 h and evaporated to dryness (finally dried at 50° C. under vacuum) to give the title compound (0.256 g, 105%).

MS (+ve ion electrospray) m/z 458 (MH+).

A small portion (6-7 mg) of the dihydrochloride salt was treated with aqueous sodium bicarbonate and extracted three times with DCM. The extracts were dried and evaporated to give a small sample of the free base δH (CDCl$_3$), (250 MHz) 1.43 (2H, m), 1.90 (2H, br.d), 2.18 (2H, td), 2.55 (1H, m), 2.65 (2H, t), 2.94 (2H, br. d), 3.79 (2H, s), 4.30 (4H, m), 6.82 (1H, s). 7.29 (1H, m), 7.68 (1H, dd), 8.10 (1H, s), 8.25 (1H, s).

Example 44A 1-(2-{4-[(6,7-dihydro[1,4]dioxino[2,3-c]pyridazin-3-ylmethyl)amino]-1-piperidinyl}ethyl)-7-fluoro-2(1H)-quinoxalinone Dihydrochloride

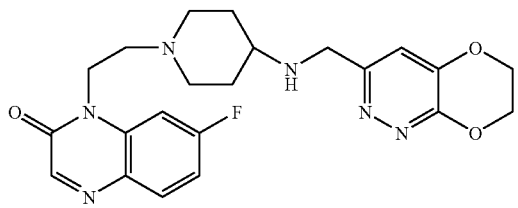

(a) Phenylmethyl 4-[(6,7-dihydro[1,4]dioxino[2,3-c]pyridazin-3-ylmethyl)amino]-1-piperidinecarboxylate A mixture of phenylmethyl 4-amino-1-piperidinecarboxylate (for a synthesis see WO 2004/058144 Example 99(e)) (14.4 g crude, equivalent to 11 g, 47 mmol) and 6,7-dihydro[1,4]dioxino[2,3-c]pyridazine-3-carbaldehyde (for a preparation see Example 6(e)) (6.46 g, 39 mmol) in DCM (200 ml) and MeOH (10 ml) was stirred for 4 h at rt, then cooled in ice as sodium triacetoxyborohydride (12.4 g) was added over 15 min. After stirring for another 2 h, the mixture was treated with aqueous sodium bicarbonate to neutralise. The aqueous phase was extracted with DCM and the organic fractions were dried and evaporated. Chromatography on silica (750 g), eluting with 0-10% MeOH/DCM, gave the product (11.1 g, 62%).

MS (+ve ion electrospray) m/z 385 (MH+).

(b) Phenylmethyl 4-((6,7-dihydro[1,4]dioxino[2,3-c]pyridazin-3-ylmethyl){[(1,1-dimethylethyl)oxy]carbonyl}amino)-1-piperidinecarboxylate Sodium bicarbonate (7.34 g) was added slowly to a solution of phenylmethyl 4-[(6,7-dihydro[1,4]dioxino[2,3-c]pyridazin-3-ylmethyl)amino]-1-piperidinecarboxylate (11.1 g, 29 mmol) in MeOH (200 ml) and the mixture was cooled in an ice-bath before portion-wise addition of di-tert-butyl dicarbonate (6.98 g, 32 mmol). The mixture was stirred at rt for approx. 3 days, then filtered and evaporated. Chromatography on silica (500 g), eluting with 0-100% ethyl acetate/hexane gave the product as a white solid (11.89 g, 85%).

MS (+ve ion electrospray) m/z 485 (MH+).

(c) 1,1-Dimethylethyl (6,7-dihydro[1,4]dioxino[2,3-c]pyridazin-3-ylmethyl)-4-piperidinylcarbamate Phenylmethyl 4-((6,7-dihydro[1,4]dioxino[2,3-c]pyridazin-3-ylmethyl) {[(1,1-dimethylethyl)oxy]carbonyl}amino)-1-piperidinecarboxylate (11.89 g. 25 mmol) in ethanol (90 ml) was hydrogenated with 10% palladium on charcoal (aqueous paste, 2 g) for 21 h. The mixture was filtered and evaporated to give a white solid (8.5 g, 97%).

MS (+ve ion electrospray) m/z 351 (MH+).

(d) 1,1-Dimethylethyl (6,7-dihydro[1,4]dioxino[2,3-c]pyridazin-3-ylmethyl) {1-[2-(7-fluoro-2-oxo-1(2H)-quinoxalinyl)ethyl]-4-piperidinyl}carbamate A solution of 1,1-dimethylethyl (6,7-dihydro[1,4]dioxino[2,3-c]pyridazin-3-ylmethyl)-4-piperidinylcarbamate (0.68 g, 1.94 mmol) and 7-fluoro-2-oxo-1(2H)-quinoxalinyl)acetaldehyde (for a preparation see Example 34(c)) (0.4 g, 1.94 mmol) in dry MeOH (0.5 ml) and chloroform (10 ml) was stirred at rt for 2 h. Sodium triacetoxyborohydride (1.23 g, 5.82 mmol) was added and the mixture was stirred for 2.5 h. Aqueous sodium bicarbonate was added to basify and the phases were separated. The aqueous phase was extracted with DCM several times, and the organic fractions were dried and evaporated. Chromatography on silica (50 g), eluting with 0-20% MeOH/ethyl acetate, gave the product (0.37 g, 35%).

MS (+ve ion electrospray) m/z 541 (MH+).

(e) Title Compound

A solution of 1,1-dimethylethyl (6,7-dihydro[1,4]dioxino[2,3-c]pyridazin-3-ylmethyl) {1-[2-(7-fluoro-2-oxo-1(2H)-quinoxalinyl)ethyl]-4-piperidinyl}carbamate (0.37 g, 0.68 mmol) in DCM (7 ml) and MeOH (5 ml) was treated with 4M hydrogen chloride in 1,4-dioxane (7 ml), stirred at rt for 1 h and evaporated to dryness (finally dried at 50° C. under vacuum) to give the title compound as a light yellow solid (0.35 g, 100%). A portion of the salt (10 mg) was treated with aqueous NaHCO$_3$ and extracted with 110% MeOH/DCM and the organic layer was separated, dried and evaporated to give the free base.

δH (CDCl$_3$), (250 MHz) 1.44 (2H, m), 1.91 (2H, br.d), 2.18 (2H, t), 2.54 (1H, m), 2.65 (2H, t), 2.96 (2H, br. d), 4.00 (2H, s), 4.30 (2H, t), 4.35 (2H, m), 4.50 (2H, m), 7.03 (1H, s), 7.09 (2H, m), 7.86 (1H, dd), 8.22 (1H, s). Small impurity signals also at δ 3.90 (t), 6.66 (s).

MS (+ve ion electrospray) m/z 441 (MH+).

Example 44B 1-(2-{4-[(6,7-dihydro[1,4]dioxino[2,3-c]pyridazin-3-ylmethyl)amino]-1-piperidinyl}ethyl)-7-fluoro-2(1H)-quinoxalinone benzoate Further purification of 1-(2-{4-[(6,7-dihydro[1,4]dioxino[2,3-c]pyridazin-3-ylmethyl)amino]-1-piperidinyl}ethyl)-7-fluoro-2(1H)-quinoxalinone dihydrochloride dissolved in methanol:isopropanol:acetonitrile (0.2:0.2:1.2) with excess isopropylamine by HPLC (Chiralpak IA 5 u, 21×250 mm column, eluting with 80:20:0.1-acetonitrile:isopropanol:isopropylamine at 20 ml/min, 330 mg in 50 mg injections, uv detection at 254 nm) gave the free base of the title compound (177 mg).

The free base was slurried in MeOH, and 1.0 equiv. benzoic acid added to give a complete solution. Concentration to a semi-solid, addition of methyl t-butyl ester and re-concentration (5×), and drying of the yellow solid at 45° C. gave the benzoate salt (226 mg).

δH (CD$_3$OD), (400 MHz) 1.57 (2H, m), 2.05 (2H, m), 2.25 (2H, m), 2.78 (2H, m), 2.95 (1H, m), 3.19 (2H, m), 4.22 (22H, s), 4.45 (4H, m), 4.59 (2H, m), 7.20 (1H, m), 7.26 (1H, s), 7.42 (3H, m), 7.52 (1H, m), 7.91 (1H, m), 8.00 (2H, m), 8.18 (1H, s).

Example 44C

1-(2-{4-[(6,7-dihydro[1,4]dioxino[2,3-c]pyridazin-3-ylmethyl)amino]-1-piperidinyl}ethyl)-7-fluoro-2(1H)-quinoxalinone Fumarate Method 1

Addition of one equivalent of 0.5M fumaric acid in MeOH (5.9 mL) to a solution of 1-(2-{4-[(6,7-dihydro[1,4]dioxino[2,3-c]pyridazin-3-ylmethyl)amino]-1-piperidinyl}ethyl)-7-fluoro-2(1H)-quinoxalinone (1.30 g, 2.95 mmol) in DCM, followed by evaporation, provided the fumarate salt of the title compound as an off-white solid (1.55 g).

Method 2

(a) Methyl N-(4-fluoro-2-nitrophenyl)glycinate

A mixture of 2,5-difluoronitrobenzene (54.6 g, 343 mmol), glycine methyl ester hydrochloride (47.3 g, 374 mmol) and triethylamine (114.5 mL, 818 mmol) was heated at 65° C. (internal temperature) in THF (1500 mL) over a 3 night period. Additional glycine methyl ester hydrochloride (30 g) and triethylamine (20 mL) were added and the heating continued for a further 2 nights. The mixture was cooled, filtered and evaporated to dryness. The residue was treated with 5M hydrochloric acid and the orange solid was filtered off, washed well with water (total ~2 L) and dried under vacuum to give the product (58.5 g). The product was then extracted with ethyl acetate (600 ml total), filtered and evaporated. The residue was slurried with water (1 L), filtered and dried to give product (40 g, 51%).

MS (+ve ion electrospray) 229 (MH+)

(b) 7-Fluoro-3,4-dihydro-2(1H)-quinoxalinone

Methyl N-(4-fluoro-2-nitrophenyl)glycinate (40 g, 175 mmol) in water (2000 mL) was heated to 90° C. Sodium dithionite (243.8 g, 1401 mmol) was added in portions. The resulting mixture was heated at 100° C. for 2 h, then allowed to cool. The solid was filtered off, washed with water and dried to give the product (13.75, 47%). Concentration of the liquor by evaporation to ~700 mL gave a further precipitate which was filtered off, washed and dried as before to give more product (1.90 g: total yield 15.65 g, 54%).

MS (+ve ion electrospray) 167 (MH+)

(c) 7-Fluoro-2(1H)-quinoxalinone

A solution of 7-fluoro-3,4-dihydro-2(1H)-quinoxalinone (15.65 g, 92.88 mmol) in dichloromethane/methanol (1:1, 600 mL) was stirred with manganese dioxide (78.25 g) at room temperature for 1.5 h. The mixture was filtered through kieselguhr, washing through several times with 10% methanol/dichloromethane (~1 L), and the filtrate was evaporated to give the product (7.27 g). Extraction of the residual filtration solids several times with dimethylformamide at 60-70° C., followed by filtration and evaporation of the extracts, gave more product (6.66 g), the total yield being 13.93 g (91.5%).

MS (+ve ion electrospray) 165 (MH+)

(d) 7-Fluoro-1-(2-propen-1-yl)-2(1H)-quinoxalinone

A mixture of 7-fluoro-2(1H)-quinoxalinone (3.84 g, 23 mmol), allyl iodide (2.39 mL, 25.5 mmol) and potassium carbonate (9.56 g, 69.3 mmol) in dimethylformamide (60 mL) was stirred at room temp. for 3 h., then evaporated. The residue was dissolved in dichloromethane/water and the phases were separated. The aqueous phase was extracted (3×) with dichloromethane and the organic fractions were dried and evaporated.

The crude product was chromatographed on 200 g silica, eluting with 0-50% ethyl acetate/hexane to give the product (3.29 g, 70%).

MS (+ve ion electrospray) 205 (MH+)

(e) 7-Fluoro-2-oxo-1(2H)-quinoxalinyl)acetaldehyde

A solution of 7-fluoro-1-(2-propen-1-yl)-2(1H)-quinoxalinone (7.9 g, 38.7 mmol) and sodium periodate (38.15 g, 178.3 mmol)) in 2-butanol (500 mL) and water (920 mL) was treated with osmium tetroxide (4% solution in water; 10 mL) and the mixture was stirred at room temperature for 24 hours. It was evaporated to dryness and the residue was dissolved in water and extracted with dichloromethane/tetrahydrofuran. The organic extracts were dried and evaporated under vacuum at rt to give the aldehyde (7.82 g, 80%, 82% pure by LCMS).

MS (+ve ion electrospray) m/z 207 (MH+).

The oxidation may alternatively be carried out by ozonolysis in 3:1 DCM/MeOH, followed by treatment with methyl sulfide, generating a mixture of aldehyde and hemiacetal which can be used in the next step.

(f) 1,1-Dimethylethyl {1-[2-(7-fluoro-2-oxo-1(2H)-quinoxalinyl)ethyl]-4-piperidinyl}carbamate A solution of 7-fluoro-2-oxo-1(2H)-quinoxalinyl)acetaldehyde (9.56 g, 46.4 mmol) and 1,1-dimethylethyl 4-piperidinylcarbamate (10.2 g, 51 mmol) in methanol (200 mL) and chloroform (400 mL) was stirred with 3A molecular sieves at room temperature for 2 h. Sodium triacetoxyborohydride (30 g, 140 mmol) was added and the mixture was stirred at room temperature for 4 h. A further portion of sodium triacetoxyborohydride (15 g) was added and stirring was continued overnight. Aqueous sodium bicarbonate solution was added to basify and the phases were separated. The aqueous phase was brought to pH8 by addition of 2M sodium hydroxide, and then extracted four times with 10% methanol/dichloromethane. Organic fractions were dried and evaporated. The crude product was chromatographed on silica gel (1 Kg), eluting with 50-70% ethyl acetate/hexane, to give the product (6.25 g). Impure material (6.7 g) was chromatographed again, together with another 1.08 g of impure material from a similar preparation, on silica (600 g), eluting as above to give further product (3.65 g)

MS (+ve ion electrospray) m/z 391 (MH+).

The use of 1,2-dichloroethane as solvent and maintaining the temperature below 5° C. during the reaction with sodium triacetoxyborohydride may prevent the formation of a ring reduction product.

(g) 1-[2-(4-Amino-1-piperidinyl)ethyl]-7-fluoro-2(1H)-quinoxalinone Dihydrochloride A solution of 1,1-dimethylethyl {1-[2-(7-fluoro-2-oxo-1(2H)-quinoxalinyl)ethyl]-4-piperidinyl}carbamate (8.72 g, 22.36 mmol) in methanol (90 ml) and dichloromethane (150 mL) was treated with 4 M hydrogen chloride in 1,4-dioxane (150 mL) (added in a slow stream, some exotherm and rapid precipitation observed) and stirred at room temperature for 2.5 h. The mixture was evaporated to dryness and the residue was triturated with ether. The solid was filtered off, washed with ether and dried to give the amine salt as a grey-green solid (8.06 g, 99%).

MS (+ve ion electrospray) m/z 291 (MH+).

TFA in DCM may be used instead of HCl and results in the trifluoroacetate salt which can be used in the next step.

(h) Title Compound

1-[2-(4-Amino-1-piperidinyl)ethyl]-7-fluoro-2(1H)-quinoxalinone dihydrochloride (8.06 g, 22.2 mmol), 6,7-dihydro[1,4]dioxino[2,3-c]pyridazine-3-carbaldehyde (4.08 g, 24.45 mmol) and triethylamine (8.03 mL, 55.5 mmol) were mixed in dry chloroform (250 mL) and dry methanol (200 mL) and heated under reflux with 3A molecular sieves for 6-7 h. After cooling, sodium triacetoxyborohydride (18.9 g, 89.1 mmol) was added and the mixture was stirred at room temperature overnight. A further portion of acetoxyborohydride (10 g) was added, followed by another (5 g) after 6 h. After a further 2 h of stirring, aqueous sodium bicarbonate was added to basify. The phases were separated, and the aqueous phase was extracted several times with 10% methanol/dichloromethane. The organic fractions were dried and evaporated, and the crude product was chromatographed on silica (500 g), eluting with 0-20% methanol/dichloromethane to give the product free base (eluted as two sets of fractions at approx. 10 and 20% methanol, 5.98 g, 61%).

TFA salt may be used in place of HCl salt, and dimethylacetamide/isopropanol as solvent in place of chloroform/methanol, with a further equivalent of TFA added after addition of the borohydride.

A solution of fumaric acid (1.58 g, 1 eq.) in methanol (approx. 40 mL) was added to the free base in dichloromethane/methanol (approx. 200 mL). Evaporation of the solvent gave the fumarate salt as an off white solid (7.41 g).

A small portion of fumarate salt was dissolved in a minimal amount of methanol with heating. The solution was filtered and allowed to evaporate slowly at room temperature to give off-white fine crystals. Crystallisation may also be achieved from ethanol, to give crystalline fumarate salt (melting point 230-232° C.).

Crude 1,1-dimethylethyl (6,7-dihydro[1,4]dioxino[2,3-c]pyridazin-3-ylmethyl) {1-[2-(7-fluoro-2-oxo-1(2H)-quinoxalinyl)ethyl]-4-piperidinyl}carbamate free base (266.6 g, ranging in purity from 77%-99%) was purified chemically to 99.5% purity by preparative chiral HPLC using Chiralpak AD (20 microns, 101.6 mm×250 mm) with 50:50:0.1 acetonitrile: methanol:isopropylamine as the mobile phase. The desired fraction solutions were combined and concentrated under high vacuum at 50-55° C. to a minimum stir volume until the product crystallized to give a thick white slurry. After cooling to ambient temperature, the product was collected by filtration and rinsed with methanol. After drying to a constant weight at 50-55° C./<5 mm Hg, a total of 215.5 g of pure free base was obtained. Melting onset 187.84° C. by Differential Scanning Calorimetry (conducted on a TA Instrument model Q100 Differential Scanning Calorimeter. The sample is placed and weighed in a A1 DSC pan. The pan is sealed using the hand press supplied by the vendor. The sample is ramped from 35° C. to 300° C. at 15° C./minute).

Example 44D 1-(2-{4-[(6,7-dihydro[1,4]dioxino[2,3-c]pyridazin-3-ylmethyl)amino]-1-piperidinyl}ethyl)-7-fluoro-2 (1H)-quinoxalinone Hydrochloride 30 mg of 1-(2-{4-[(6,7-dihydro[1,4]dioxino[2,3-c]pyridazin-3-ylmethyl)amino]-1-piperidinyl}ethyl)-7-fluoro-2 (1H)-quinoxalinone fumarate was slurried in 0.25 ml methanol and 3 drops isopropylamine were added followed by 0.25 ml isopropanol and 11.0 ml acetonitrile and the mixture heated to 60° C. to dissolve the sample and then cooled to 30° C. The mixture was eluted on a Chiralpak IA column (5 um, 21×250 mm) with 80:20:0.1 acetonitrile:isopropanol:isopropylamine and the major fraction concentrated to a white solid (20 mg). This was dissolved in warm methanol (5 ml) and 1 eq aqueous 6N HCl added. The mixture was concentrated and dried at 50° C. under high vacuum to give the monohydrochloride salt (22 mg).

Example 44E 1-(2-{4-[(6,7-dihydro[1,4]dioxino[2,3-c]pyridazin-3-ylmethyl)amino]-1-piperidinyl}ethyl)-7-fluoro-2 (1H)-quinoxalinone Citrate Acetone (7.0 mL) was added to crystalline 1,1-dimethylethyl (6,7-dihydro[1,4]dioxino[2,3-c]pyridazin-3-ylmethyl) {1-[2-(7-fluoro-2-oxo-1(2H)-quinoxalinyl)ethyl]-4-piperidinyl}carbamate free base (152.90 mg, 0.3471 mmoles). The slurry was heated to 50° C. for an hour and cooled to room temperature. To the slurry, citric acid (3.0M solution in water, 1.0 equivalent) was added at room temperature. Addition of acid produced a thick slurry that was combined with a second aliquot of acetone (3.0 mL). The slurry was then heated to 50° C. for 12 hours, cooled slowly to 23° C. (cooling rate of 0.1° C./min) and left stirring at 23° C. for 6 hours. The slurry was cooled further to 5° C. (cooling rate of 0.1° C./min) and left stirring at 5° C. for 12 hours. The slurry was filtered, washed with acetone and air-dried for 15 minutes. The weight of the crystalline citrate salt obtained was 187.3 mg.

Example 44F 1-(2-{4-[(6,7-dihydro[1,4]dioxino[2,3-c]pyridazin-3-ylmethyl)amino]-1-piperidinyl}ethyl)-7-fluoro-2 (1H)-quinoxalinone L-tartrate Isopropanol (500 μL) was added to crystalline 1,1-dimethylethyl (6,7-dihydro[1,4]dioxino[2,3-c]pyridazin-3-ylmethyl) {1-[2-(7-fluoro-2-oxo-1(2H)-quinoxalinyl)ethyl]-4-piperidinyl}carbamate free base (20.40 mg, 0.0463 mmoles). The slurry was heated to 40° C. for an hour and cooled to room temperature. To the slurry, L-tartaric acid (1.0M solution in methanol, 2.0 equivalent) was added at room temperature. The slurry was then heated to 40° C. for 5 hours, cooled slowly to 23° C. (cooling rate of 0.1° C./min) and left stirring at 23° C. for 5 hours. The slurry was cooled further to 5° C. (cooling rate of 0.1° C./min) and left stirring at 5° C. for 48 hours. A sample of the L-tartrate salt was obtained by filtering an aliquot (75 μL) of the slurry.

Example 45

6-{[(1-{2-[6-(methyloxy)-3-oxopyrido[2,3-b]pyrazin-4(3H)-yl]ethyl}-4-piperidinyl)amino]methyl}-2H-pyrido[3,2-b][1,4]oxazin-3(4H)-one

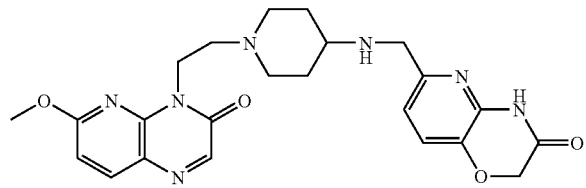

A solution of 4-[2-(4-amino-1-piperidinyl)ethyl]-6-(methyloxy)pyrido[2,3-b]pyrazin-3(4H)-one (50 mg, 0.1648 mmoles) and 3-oxo-3,4-dihydro-2H-pyrido[3,2-b][1,4]oxazine-6-carboxaldehyde (for a synthesis see WO2003087098, Example 31(e)) (29.4 mg, 0.1648 mmoles) in anhydrous DCM (5 ml) and anhydrous MeOH (0.5 ml) was stirred at rt for 5 mins. Sodium triacetoxyborohydride (104.7 mg, 0.494 mmoles) was added and the mixture was stirred, under argon, for 24 h. The reaction was treated with sat. aq. NaHCO₃ solution (2 ml) and 9:1 DCM:MeOH (5 ml). The layers were separated and the aqueous layer was washed with 9:1 DCM:MeOH (10 ml) and 5:1 DCM:MeOH (2×20 ml). The organic extracts were combined, passed through a hydrophobic frit and evaporated to an orange gum. Purification on a 10 g silica column eluted with an 80:20 DCM:MeOH elution gave the product as a yellow gum (39.8 mg, 52%).

MS (ES+) m/z 466 (MH$^+$).

$^1$H NMR δ (CDCl$_3$, 400 MHz) 1.49 (2H, m). 1.93 (2H, m), 2.18 (2H, m), 2.59 (1H, m), 2.77 (2H, m), 3.10 (2H, m), 3.85 (2H, s), 4.03 (3H, s), 4.58 (4H, m), 6.71 (1H, d, J=8.4 Hz), 6.94 (1H, d, J=8 Hz), 7.18 (1H, d, J=8 Hz), 8.00 (1H, d, J=8.4 Hz), 8.12 (1H, s).

Example 46A 4-(2-{4-[(6,7-dihydro[1,4]dioxino[2,3-c]pyridazin-3-ylmethyl)amino]-1-piperidinyl}ethyl)-6-(methyloxy)pyrido[2,3-b]pyrazin-3(4H)-one Dihydrochloride

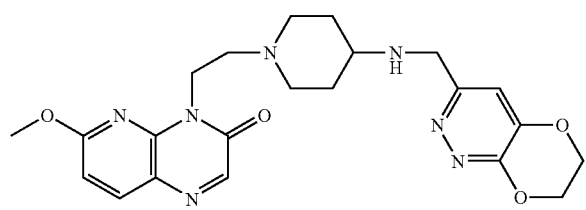

A solution of 4-[2-(4-amino-1-piperidinyl)ethyl]-6-(methyloxy)pyrido[2,3-b]pyrazin-3(4H)-one (50 mg, 0.1648 mmoles) and 6,7-dihydro[1,4]dioxino[2,3-c]pyridazine-3-carbaldehyde (30.1 mg, 0.181 mmoles) in anhydrous DCM (5 ml) and anhydrous MeOH (0.5 ml) was stirred at rt for 5 minutes. Sodium triacetoxyborohydride (115 mg, 0.543 mmoles) was added and the mixture was stirred, under argon, for 24 hours. A further 6,7-dihydro[1,4]dioxino[2,3-c]pyridazine-3-carbaldehyde (15 mg, 0.09 mmoles) and sodium triacetoxyborohydride (50 mg, 0.236 mmoles) were added and reaction was stirred for 5 hours, treated with sat. aq. NaHCO₃ solution (2 ml) and 9:1 DCM:MeOH (5 ml). The layers were separated and the aqueous layer was washed with 9:1 DCM:MeOH (10 ml) and 5:1 DCM:MeOH (2×20 ml). The organic extracts were combined, passed through a hydrophobic frit and evaporated to an orange gum. Purification on a 20 g silica column eluted with a 20:1 to 10:1 DCM:MeOH gradient elution gave the free base of the title compound as a pale yellow gum (26.1 mg, 35%)

MS (ES+) m/z 454 (MH$^+$).

$^1$H NMR δ (CDCl$_3$) 1.42 (2H, m). 1.92 (2H, m), 2.19 (2H, m), 2.55 (1H, m), 2.75 (2H, m), 3.06 (2H, m), 4.00 (2H, s), 4.03 (3H, s), 4.37 (2H, m), 4.51 (2H, m), 4.58 (2H, m), 6.73 (1H, d, J=8.4 Hz), 7.03 (1H, s), 8.01 (1H, d, J=8.4 Hz), 8.15 (1H, s).

A solution of the free base (26.1 mg, 0.058 mmoles) in chloroform (2 ml) was treated with 1M HCl in diethyl ether (1 ml) and anhydrous diethyl ether (1 ml) and evaporated to give the dihydrochloride as a light green foam, MS as that of the free base.

Example 46B 4-(2-{4-[(6,7-dihydro[1,4]dioxino[2,3-c]pyridazin-3-ylmethyl)amino]-1-piperidinyl}ethyl)-6-(methyloxy)pyrido[2,3-b]pyrazin-3(4H)-one Fumarate Addition of one equivalent of fumaric acid to a solution of 4-(2-{4-[(6,7-dihydro [1,4]dioxino[2,3-c]pyridazin-3-ylmethyl)amino]-1-piperidinyl}ethyl)-6-(methyloxy)pyrido[2,3-b]pyrazin-3(4H)-one, followed by evaporation, provided the title compound.

Example 47

1-(2-{4-[(6,7-dihydro[1,4]dioxino[2,3-c]pyridazin-3-ylmethyl)amino]-1-piperidinyl}ethyl)-7-(methyloxy)-2(1H)-quinoxalinone dihydrochloride

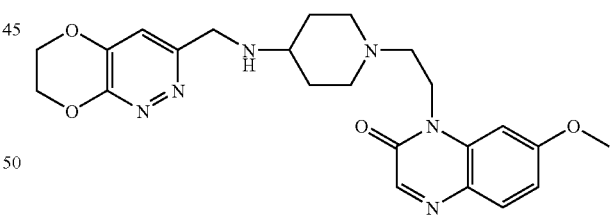

(a) 1-[2-(4-Amino-1-piperidinyl)ethyl]-7-(methyloxy)-2(1H)-quinoxalinone

To a solution of 1-[2-(4-amino-1-piperidinyl)ethyl]-7-fluoro-2(1H)-quinoxalinone dihydrochloride (0.363 g, 1 mmol) in dry MeOH (5 ml) was added a 25 wt. % solution of sodium methoxide in MeOH (0.87 ml, 4 mmol). After heating under reflux overnight, a further portion of sodium methoxide solution (0.22 ml) was added and heating was continued for 24 h. Aqueous ammonium chloride 96 drops) was added and the mixture was evaporated to dryness. The residue was extracted several times with 10% MeOH/DCM, and the extracts were filtered and evaporated. The residue was chromatographed on silica, eluting with 0-20% (2M ammonia/MeOH)/DCM to give the product (0.20 g, 66%).

MS (+ve ion electrospray) m/z 303 (MH+).

(b) Title Compound

A solution of 1-[2-(4-amino-1-piperidinyl)ethyl]-7-(methyloxy)-2(1H)-quinoxalinone (200 mg; 0.66 mmol) and 6,7-dihydro[1,4]dioxino[2,3-c]pyridazine-3-carbaldehyde (116 mg, 0.70 mmol) in MeOH (8 mL) and chloroform (8 mL) was heated under reflux with 3A molecular sieves overnight. It was cooled and sodium triacetoxyborohydride (0.54 g; 2.55 mmol) was added, and the mixture was stirred at rt overnight. More aldehyde (20 mg) and acetoxyborohydride (100 mg) were added, and this was repeated after 7 h. The mixture was left stirring for three days, then aqueous sodium bicarbonate solution was added to basify and the phases were separated. The aqueous phase was extracted three times with 10% MeOH-DCM, and the organic fractions were dried and evaporated. Chromatography on silica gel, eluting with 0-20% MeOH-DCM gave the free base of the title compound (155 mg, 52%).

δH (CDCl$_3$), (250 MHz) 1.45 (2H, m), 1.92 (2H, br.d, part, obscured by water), 2.21 (2H, t), 2.56 (1H, m), 2.68 (2H, t), 2.99 (2H, br. d), 3.93 (3H, s), 4.00 (2H, s), 4.35 (4H, m), 4.52 (2H, m), 6.88 (1H, m), 6.93 (1H, dd), 7.03 (1H, s), 7.78 (1H, d), 8.12 (1H, s).

MS (+ve ion electrospray) m/z 453 (MH+).

The free base in chloroform/DCM/MeOH was treated with 0.4M hydrogen chloride in 1,4-dioxane (1.7 mL) and evaporated to dryness to give the title compound, dihydrochloride salt.

Addition of one equivalent of benzoic acid to a solution of 1-(2-{4-[(6,7-dihydro[1,4]dioxino[2,3-c]pyridazin-3-ylmethyl)amino]-1-piperidinyl}ethyl)-7-(methyloxy)-2(1H)-quinoxalinone, followed by evaporation, provided the benzoate salt.

Example 48

1-(2-{4-[(2,3-dihydro[1,4]dioxino[2,3-b]pyridin-7-ylmethyl)amino]-1-piperidinyl}ethyl)-7-fluoro-2(1H)-quinoxalinone Fumarate

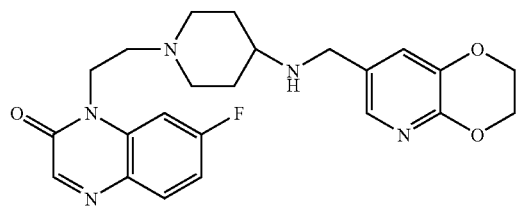

A solution of 1-[2-(4-amino-1-piperidinyl)ethyl]-7-fluoro-2(1H)-quinoxalinone dihydrochloride (60 mg; 0.166 mmol) and 2,3-dihydro[1,4]dioxino[2,3-b]pyridine-7-carbaldehyde (for a synthesis see WO 2003/087098 Example 20(e)) (33 mg, 0.197 mmol) in MeOH (3 ml), chloroform (3 ml) and triethylamine (0.06 ml) was heated under reflux with 3A molecular sieves overnight. It was cooled and sodium triacetoxyborohydride (0.11 g; 0.52 mmol) was added, and the mixture was stirred at rt for 7 h. Sodium triacetoxyborohydride (0.1 µg) was added and the mixture was stirred for another 5 days, with addition of two more portions of triacetoxyborohydride (0.11 g). Aqueous sodium bicarbonate solution was added to basify and the aqueous phase was extracted several times with 10% MeOH/DCM. The organic fractions were dried and evaporated. Chromatography on silica gel, eluting with 0-20% MeOH-DCM gave the free base of the title compound (20 mg, 27%).

δH (CDCl$_3$), (250 MHz) 1.42 (2H, m), 1.90 (2H, br.d), 2.18 (2H, t), 2.52 (1H, m), 2.66 (2H, t), 2.98 (2H, br. d), 3.73 (2H, s), 4.25 (2H, m), 4.31 (2H, t), 4.41 (2H, m), 7.08 (1H, td), 7.13 (1H, dd), 7.21 (1H, d), 7.86 (1H, dd), 8.22 (1H, s).

MS (+ve ion electrospray) m/z 440 (MH+).

The free base in DCM was treated with one equivalent of 0.5M fumaric acid (0.1 mL) and evaporated to dryness. The solid was triturated with ether and MeOH and dried to give the title compound.

Example 49

1-(2-{4-[(6,7-dihydro[1,4]dioxino[2,3-c]pyridazin-3-ylmethyl)amino]-1-piperidinyl}ethyl)-6,7-difluoro-2(1H)-quinoxalinone Trifluoroacetate

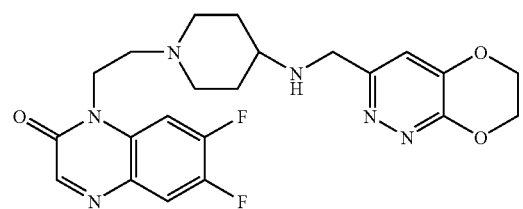

(a) 1,1-Dimethylethyl {1-[2-(6,7-difluoro-2-oxo-1(2H)-quinoxalinyl)ethyl]-4-piperidinyl}(6,7-dihydro[1,4]dioxino[2,3-c]pyridazin-3-ylmethyl)carbamate A solution of 1,1-dimethylethyl (6,7-dihydro[1,4]dioxino[2,3-c]pyridazin-3-ylmethyl)-4-piperidinylcarbamate (0.31 g, 0.89 mmol) and 6,7-difluoro-2-oxo-1(2H)-quinoxalinyl)acetaldehyde/methyl hemiacetal mixture (approx. 1:1, 0.2 g, 0.89 mmol) in dry MeOH (0.25 ml) and chloroform (5 ml) was stirred at rt for 2 h. Sodium triacetoxyborohydride (0.57 g, 2.67 mmol) was added and the mixture was stirred for 6 h. Aqueous sodium bicarbonate was added to basify and the phases were separated. The aqueous phase was extracted with DCM several times, and the organic fractions were dried and evaporated. Chromatography on silica, eluting with 0-20% MeOH/ethyl acetate, gave the product (0.17 g, 34%).

MS (+ve ion electrospray) m/z 559 (MH+).

(b) Title Compound

A solution of 1,1-dimethylethyl {1-[2-(6,7-difluoro-2-oxo-1(2H)-quinoxalinyl)ethyl]-4-piperidinyl}(6,7-dihydro[1,4]dioxino[2,3-c]pyridazin-3-ylmethyl)carbamate (0.17 g, 0.305 mmol) in DCM (0.65 ml) was treated with trifluoroacetic acid (0.43 ml, 5.78 mmol) stirred at rt for 1 h and evaporated. The residue was triturated with ether and dried at 50° C. under vacuum to give the title compound (0.149 g).

δH (CD₃OD), (250 MHz) 2.04 (2H, m), 2.49 (2H, br.d), 3.15 (2H, t), 3.55 (2H, m), 3.60 (1H, m), 4.02 (2H, br. d), 4.46 (4H, m), 4.59 (2H, m), 4.676 (2H, t), 7.24 (1H, s). 7.69 (1H, dd), 7.83 (1H, dd)), 8.23 (1H, s).

MS (+ve ion electrospray) m/z 459 (MH+).

Example 50

7-Chloro-6-{[({(3S,4S)-1-[2-(7-fluoro-2-oxo-1(2H)-quinolinyl)ethyl]-4-hydroxy-3-pyrrolidinyl}methyl)amino]methyl}-2H-pyrido[3,2-b][1,4]oxazin-3(4H)-one

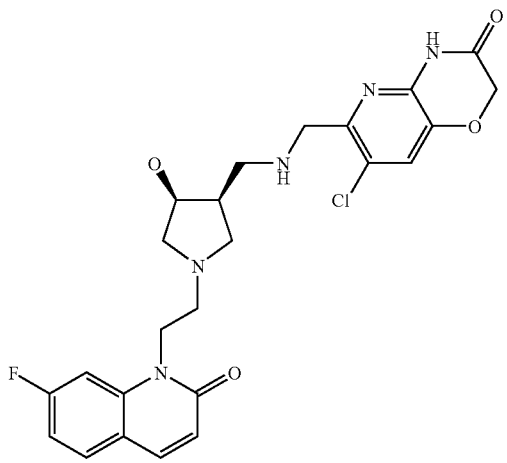

A solution of 1-{2-[(3S,4S)-3-(aminomethyl)-4-hydroxy-1-pyrrolidinyl]ethyl}-7-fluoro-2(1H)-quinolinone (100 mg; 0.33 mmol) and 7-chloro-3-oxo-3,4-dihydro-2H-pyrido[3,2-b][1,4]oxazine-6-carboxaldehyde (for a synthesis see WO2003064421, Example 15(c)) (70 mg, 0.33 mmol) in methanol (2 mL), methylene chloride (4 mL) was stirred at room temperature overnight. Sodium triacetoxyborohydride (130 mg; 0.6 mmol) was added and the mixture was stirred at room temperature for 1 hour. The reaction was evaporated and chromatographed on silica gel, eluting with 0-10% methanol-DCM-1% NH₄OH to give the title compound as a solid (80 mg).

1H NMR (400 MHz, CD₃OD) δ ppm 2.38-2.48 (m, 1H) 2.58-2.67 (m, 2H) 2.73 (dd, J=11.75, 6.44 Hz, 1H) 2.76-2.88 (m, 2H) 2.90-2.99 (m, 2H) 3.12 (dd, J=10.36, 5.56 Hz, 1H) 3.31 (dt, J=3.28, 1.64 Hz, 2H) 3.35 (s, 3H) 3.85-3.95 (m, 2H) 4.36 (td, J=6.06, 3.28 Hz, 1H) 4.43 (ddd, J=8.21, 6.06, 5.94 Hz, 2H) 4.66 (s, 2H) 6.59 (d, J=9.60 Hz, 1H) 7.08 (td, J=8.46, 2.27 Hz, 1H) 7.36 (s, 1H) 7.39 (dd, J=11.49, 2.15 Hz, 1H) 7.72 (dd, J=8.59, 6.32 Hz, 1H) 7.85-7.91 (m, 2H).

MS (+ve ion electrospray) m/z 502 (M+H)+.

Addition of 1 equivalent of benzoic acid to a solution of 7-chloro-6-{[({(3S,4S)-1-[2-(7-fluoro-2-oxo-1(2H)-quinolinyl)ethyl]-4-hydroxy-3-pyrrolidinyl}methyl)amino]methyl}-2H-pyrido[3,2-b][1,4]oxazin-3(4H)-one in MeOH, followed by evaporation, provided the benzoate salt of the title compound.

Example 51A 1-(2-{4-[(2,3-dihydro[1,4]dioxino[2,3-c]pyridin-7-ylmethyl)amino]-1-piperidinyl}ethyl)-7-(methyloxy) pyrido[2,3-b]pyrazin-2(1H)-one Hydrochloride

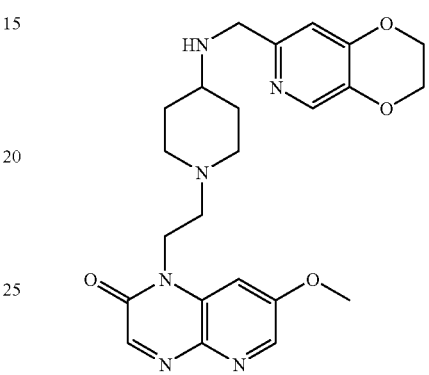

(a) 7-(Methyloxy)-1-(2-propen-1-yl)pyrido[2,3-b]pyrazin-2(1H)-one

A solution of 7-fluoro-1-(2-propen-1-yl)pyrido[2,3-b]pyrazin-2(1H)-one (196 mg, 0.956 mmol) in MeOH (5 ml) was treated with sodium methoxide (25% w/v in MeOH, 1.03 ml. 4.780 mmol) and stirred at rt for 1 h. The reaction was repeated with more 7-fluoro-1-(2-propen-1-yl)pyrido[2,3-b]pyrazin-2(1H)-one (657 mg, 3.204 mmol) in MeOH (15 ml) and sodium methoxide (25% w/v in MeOH, 3.45 ml. 16.02 mmol). This reaction was also stirred for 1 h after which time both reaction mixtures were combined and treated with water (100 ml). The mixture was then extracted with DCM (3×100 ml). The combined organic extracts were dried over anhydrous magnesium sulphate, filtered and evaporated under reduced pressure to give a yellow solid which was purified by column chromatography on silica with ethyl acetate to give the desired product as a brown solid (846 mg, 94%).

MS (ES+) m/z 218 (MH⁺).

(b) [7-(Methyloxy)-2-oxopyrido[2,3-b]pyrazin-1 (2H)-yl]acetaldehyde (as the Methyl Hemiacetal)

7-(Methyloxy)-1-(2-propen-1-yl)pyrido[2,3-b]pyrazin-2 (1H)-one (846 mg, 3.900 mmol) was dissolved in 1,4-dioxane (20 ml) and water (10 ml). Sodium periodate (20.09 g, 9.75 mmol) was added, followed by osmium tetroxide (0.83 ml of 4% aqueous solution). The mixture stirred at rt for 4 h, and then extracted with 20% MeOH/DCM (3×200 ml). The organic extracts were combined, dried over anhydrous magnesium sulphate, filtered and evaporated under reduced pressure to give [7-(methyloxy)-2-oxopyrido[2,3-b]pyrazin-1 (2H)-yl]acetaldehyde (existing mostly as the methyl hemiacetal) as an impure brown solid (969 mg, 113%).

MS (ES+) m/z 220 (MH⁺) 252 (methyl hemiacetalH⁺).

(c) 1,1-Dimethylethyl (2,3-dihydro[1,4]dioxino[2,3-c]pyridin-7-ylmethyl)(1-{2-[6-(methyloxy)-3-oxopyrido[2,3-b]pyrazin-4(3H)-yl]ethyl}-4-piperidinyl)carbamate A mixture of [7-(methyloxy)-2-oxopyrido[2,3-b]pyrazin-1(2H)-yl]acetaldehyde (as the methyl hemiacetal) (969 mg, 3.510 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (1.22 g, 3.510 mmol) in chloroform (40 ml) was stirred for 1 h before addition of NaBH(OAc)$_3$ (377 mg, 1.59 mmol). The reaction was stirred for 1 h more before addition of sat. aq NaHCO$_3$ (100 ml). The reaction was then extracted with 10% MeOH in DCM (3×200 ml). The combined organic phases were dried, evaporated and the crude residue purified by chromatography on silica gel using a 0-10% MeOH/DCM gradient to provide the desired compound as an impure yellow foam (1.408 g, 73%).

MS (ES+) m/z 553 (MH$^+$).

(d) Title Compound

A solution of 1,1-dimethylethyl (2,3-dihydro[1,4]dioxino[2,3-c]pyridin-7-ylmethyl)(1-{2-[6-(methyloxy)-3-oxopyrido[2,3-b]pyrazin-4(3H)-yl]ethyl}-4-piperidinyl)carbamate (1.408 g, 2.551 mmol) in chloroform (20 ml) and MeOH (5 ml) was added 4M HCl in 1,4-dioxane (10 ml) and the reaction was stirred at rt for 0.5 h before evaporation, treatment with sat. aq NaHCO$_3$ (50 ml). The reaction was then extracted with 20% MeOH in DCM (3×100 ml). The combined organic phases were dried, evaporated and the crude residue purified by chromatography on silica gel using a 0-20% MeOH/DCM gradient to provide the free base of the title compound as a yellow solid (266 mg, 23%).

MS (ES+) m/z 453 (MH$^+$).

$^1$H NMR (250 MHz) δ (CDCl$_3$) 1.32-1.52 (2H, m), 1.82-1.98 (2H, m), 2.09-2.25 (2H, m), 2.42-2.2.61 (1H, m), 2.61-2.72 (2H, t), 2.85-3.01 (2H, m), 3.78 (2H, s), 4.00 (3H, s), 4.26-4.34 (m, 6H), 6.81 (1H, s), 7.21 (1H, d, J=2.5 Hz), 8.10 (1H, s), 8.34 (1H, s), 8.51 (1H, d, J=2.5 Hz).

This compound was converted to the HCl salt by dissolving the obtained free base in 1:1 DCM:MeOH and adding 1 equivalent of 4M HCl in 1,4-dioxane. This was then evaporated to dryness.

Example 51B

1-(2-{4-[(2,3-dihydro[1,4]dioxino[2,3-c]pyridin-7-ylmethyl)amino]-1-piperidinyl}ethyl)-7-(methyloxy)pyrido[2,3-b]pyrazin-2(1H)-one diformate Purification of 1-(2-{4-[(2,3-dihydro[1,4]dioxino[2,3-c]pyridin-7-ylmethyl)amino]-1-piperidinyl}ethyl)-7-(methyloxy)pyrido[2,3-b]pyrazin-2(1H)-one by MDAP gave the title compound.

Example 52

6-({[((3R,4R)-4-hydroxy-1-{2-[7-(methyloxy)-2-oxo-1(2H)-quinolinyl]ethyl}-3-pyrrolidinyl)methyl]amino}methyl)-2H-pyrido[3,2-b][1,4]thiazin-3(4H)-one dihydrochloride

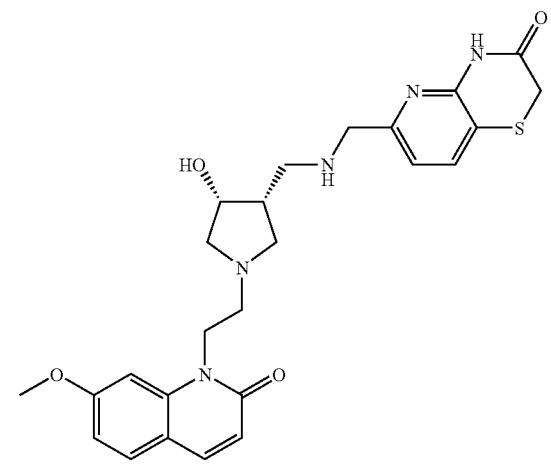

(a) (2E)-3-(Ethyloxy)-2-propenoyl Chloride

To a solution of oxayl chloride (40 ml, 0.453 mol) cooled to 0° C. under N$_2$ was added via addition funnel ethyl vinyl ether (29 ml, 0.302 mol) at such a rate as to keep the internal temperature at 0° C. After addition was complete, the reaction mixture was allowed to warm to ambient temperature and stirred for 18 h. The reaction mixture was heated to 90° C. for 90 min. then 120° C. for 1 h. The product was isolated as a yellow oil by vacuum distillation to yield 22 g (54%).

1H NMR (400 MHz, CHLOROFORM-d) δ ppm 1.37 (t, J=7.07 Hz, 3H) 4.04 (q, J=7.07 Hz, 2H) 5.48 (d, J=12.13 Hz, 1H) 7.77 (d, J=12.13 Hz, 1H).

(b)(2E)-3-(Ethyloxy)-N-[3-(methyloxy)phenyl]-2-propenamide

To a mixture of m-anisidine (18.ml, 0.163 mol) in DCM (400 ml) at 0° C. under N$_2$ was added pyridine (15.8 ml, 0.196 mol). To this reaction mixture was added via addition funnel (2E)-3-(ethyloxy)-2-propenoyl chloride (22 g, 0.163 mol). After warming to ambient temperature the reaction was stirred for 18 h, then diluted with sat. NaHCO$_3$ (400 ml). The crude product was washed successively with sat. NaHCO$_3$ (2×400 ml), brine (1×250 ml), and 0.25 M HCl (1×250 ml). The organic layer was dried over magnesium sulphate, filtered, and concentrated to a brown oil which solidified upon standing to yield 34 g (94%) of the title compound as a brown solid.

MS (ES+) m/z 222 (MH$^+$).

(c) 7-(Methyloxy)-2(1H)-quinolinone (2E)-3-(Ethyloxy)-N-[3-(methyloxy)phenyl]-2-propenamide (25 g; 0.113 mol) was dissolved in conc. $H_2SO_4$ and stirred for 1 h. The reaction mixture was poured onto ice and filtered. The crude product was washed with water and dried to yield the title compound (12 g; 60%) as a tan solid.

MS (ES+) m/z 175.6 (MH+).

1H NMR (400 MHz, DMSO-$d_6$) δ ppm 3.80 (s, 3H), 6.30 (d, J=9.35 Hz, 1H) 6.77-6.83 (m, 2H) 7.55 (d, J=8.34 Hz, 1H) 7.81 (d, J=9.35 Hz, 1H) 11.63 (s, 1H).

(d) 7-(Methyloxy)-1-(2-propen-1-yl)-2(1H)-quinolinone

A solution of 7-(methyloxy)-2(1H)-quinolinone (5 g, 0.029 mol) in DMF (70 ml) at 0° C. under $N_2$ was added NaH (60% dispersion in oil; 2.5 g, 0.063 mol) stirred for 10 min, warmed to ambient temperature and stirred for a further 30 min. To this reaction mixture was added allyl iodide (3.13 ml, 0.034 mol) and stirred overnight. The reaction was quenched with water (20 ml) and concentrated. The product was obtained after column chromatography (gradient-5% MeOH in DCM) to yield 4.2 g (68%).

MS (ES+) m/z 215.8 (MH+).

(e) [7-(Methyloxy)-2-oxo-1(2H)-quinolinyl]acetaldehyde

To a stirred solution of 7-(methyloxy)-1-(2-propen-1-yl)-2(1H)-quinolinone (4.14 g, 0.019 mol) in 1,4-dioxane (80 ml) and water (40 ml) under $N_2$ was added sodium periodate (9.5 g; 0.044 mol) and osmium tetroxide (10 ml, 4% aqueous solution) and stirred overnight. The reaction was concentrated and partitioned in 20% MeOH/DCM (300 ml) and water (200 ml). The organic layer was dried over magnesium sulphate, filtered, and concentrated. The product was obtained after column chromatography (neat ethyl acetate) to yield g (71%) of the title compound as a green solid.

MS (ES+) m/z 217.8 (MH+).

(f) Phenylmethyl {[(3S,4R)-4-hydroxy-3-pyrrolidinyl]methyl}carbamate

To a stirred solution of 1,1-dimethylethyl (3R,4R)-3-hydroxy-4-[({[(phenylmethyl)oxy]carbonyl}amino)methyl]-1-pyrrolidinecarboxylate (for a synthesis see WO2006002047, Preparation 24(c) (±)-1,1-dimethylethyl cis-3-hydroxy-4-[({[(phenylmethyl)oxy]carbonyl}amino) methyl]-1-pyrrolidinecarboxylate E2 isomer) (2 g, 5.7 mmol) in DCM (50 ml) was added trifluoracetic acid (50 mL) and stirred for 2 h. The reaction mixture was concentrated and placed under high-vac for 3 h. To the TFA salt dissolved in 100 ml of 10:1 CHCl$_3$:MeOH was added MP-carbonate resin (8 g; 22.8 mmol) and stirred overnight. The reaction mixture was filtered and concentrated to provide the title compound as a pale yellow oil (1.4 g; 100%).

MS (ES+) m/z 251.3 (MH+).

(g) Phenylmethyl [((3R,4R)-4-hydroxy-1-{2-[7-(methyloxy)-2-oxo-1(2H)-quinolinyl]ethyl}-3-pyrrolidinyl)methyl]carbamate Phenylmethyl {[(3S,4R)-4-hydroxy-3-pyrrolidinyl] methyl}carbamate (300 mg, 1.20 mmol) and [7-(methyloxy)-2-oxo-1(2H)-quinolinyl]acetaldehyde (260 mg, 1.12 mmol) were combined in anhydrous DCM (5 ml) and anhydrous MeOH (1 ml) with a spatula of solid sodium carbonate. The reaction mixture was stirred under nitrogen for 1 h then sodium triacetoxyborohydride (762 mg, 3.6 mmol) was added and stirred overnight. The reaction mixture was concentrated and the title compound was obtained as a pale yellow oil (337 mg, 62%) after column chromatography (90:10:1: DCM:MeOH:NH$_4$OH).

MS (ES+) m/z 452.3 (MH+).

(h) 1-{2-[(3R,4R)-3-(Aminomethyl)-4-hydroxy-1-pyrrolidinyl]ethyl}-7-(methyloxy)-2(1H)-quinolinone To a solution of phenylmethyl [((3R,4R)-4-hydroxy-1-{2-[7-(methyloxy)-2-oxo-1(2H)-quinolinyl]ethyl}-3-pyrrolidinyl)methyl]carbamate (337 mg, 0.746 mmol) was added 20% Pd(OH)$_2$/C, degassed and placed under 1 atm of H$_2$ for 18 h. The reaction mixture was filtered through Celite and concentrated to obtain the title compound as a yellow oil (235 mg, 100%).

MS (ES+) m/z 318.3 (MH+).

(i) Title Compound

1-{2-[(3R,4R)-3-(Aminomethyl)-4-hydroxy-1-pyrrolidinyl]ethyl}-7-(methyloxy)-2(1H)-quinolinone (118 mg, 0.372 mmol) and 3-oxo-3,4-dihydro-2H-pyrido[3,2-b][1,4]thiazine-6-carboxaldehyde (for a synthesis, see WO2004058144, Example 7(d)) (77 mg, 0.398 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (241 mg, 1.09 mmol) was added and stirred for 1 h. The reaction mixture was concentrated and purified to obtain the free base of the title compound as a pale yellow oil (148 mg, 82%) after column chromatography (90:10:1:DCM:MeOH:NH$_4$OH).

MS (ES+) m/z 496.5 (MH+).

1H NMR (400 MHz, CD$_3$OD) δ ppm 3.45-3.56 (m, 3H) 3.74 (s, 4H) 4.00 (s, 5H) 4.24 (dd, J 5.68, 2.15 Hz, 1H) 4.39 (s, 3H) 4.66 (s, 1H) 4.73-4.82 (m, 3H) 6.58 (d, J=9.35 Hz, 1H) 7.01 (dd, J 8.59, 2.02 Hz, 1H) 7.08 (d, J=1.77 Hz, 1H) 7.16 (d, J=7.83 Hz, 1H) 7.69 (d, J=8.59 Hz, 1H) 7.84 (d, J=7.83 Hz, 1H) 7.92 (d, J=9.35 Hz, 1H).

The dihydrochloride salt was made by addition of 149 μl of 4N HCl/1,4-dioxane to a solution of the free base.

Example 53

6-({[((3R,4R)-4-hydroxy-1-{2-[7-(methyloxy)-2-oxo-1(2H)-quinolinyl]ethyl}-3-pyrrolidinyl)methyl] amino}methyl)-2H-pyrido[3,2-b][1,4]oxazin-3(4H)-one dihydrochloride

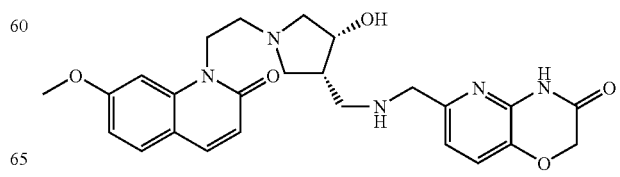

1-{2-[(3R,4R)-3-(Aminomethyl)-4-hydroxy-1-pyrrolidinyl]ethyl}-7-(methyloxy)-2(1H)-quinolinone (111 mg, 0.350 mmol) and 3-oxo-3,4-dihydro-2H-pyrido[3,2-b][1,4]oxazine-6-carboxaldehyde (for a synthesis see WO2003087098, Example 31(e)) (68 mg; 0.385 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (233 mg, 1.05 mmol) was added and stirred for 1 h. The reaction mixture was concentrated and purified to obtain the free base as a pale yellow oil (97 mg, 58%) after column chromatography (90:10:1: DCM:MeOH:NH$_4$OH).

MS (ES+) m/z 496.5 (MH$^+$).

1H NMR (400 MHz, CD$_3$OD) δ ppm 3.49 (dd, J 10.99, 1.64 Hz, 3H) 3.69-3.81 (m, 4H) 3.96-4.02 (m, 4H) 4.23 (dd, J 5.56, 2.02 Hz, 1H) 4.34 (s, 3H) 4.66 (s, 1H) 4.71 (s, 2H) 4.73-4.82 (m, 3H) 6.59 (d, J=8.84 Hz, 1H) 7.00 (d, J=8.59 Hz, 1H) 7.07 (s, 1H) 7.14 (d, J=8.08 Hz, 1H) 7.39 (d, J=8.08 Hz, 1H) 7.68 (d, J=8.59 Hz, 1H) 7.90 (d, J=9.60 Hz, 1H).

The dihydrochloride salt was made by addition of 102 uL of 4N HCl/1,4-dioxane to a solution of the free base.

Example 54

6-({[((3R,4R)-4-hydroxy-1-{2-[7-(methyloxy)-2-oxo-1,5-naphthyridin-1(2H)-yl]ethyl}-3-pyrrolidinyl)methyl]amino}methyl)-2H-pyrido[3,2-b][1,4]oxazin-3(4H)-one Fumarate

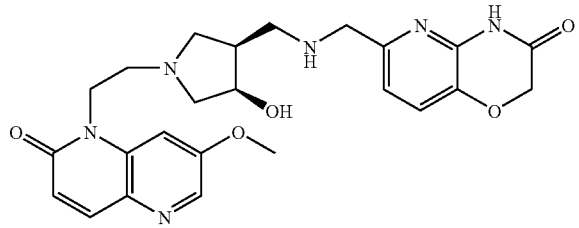

(a) Phenylmethyl [((3R,4R)-4-hydroxy-1-{2-[7-(methyloxy)-2-oxo-1,5-naphthyridin-1 (2H)-yl]ethyl}-3-pyrrolidinyl)methyl]carbamate To a solution of [7-(methoxy)-2-oxo-1,5-naphthyridin-1(2H)-yl]acetaldehyde (as the methyl hemiacetal) (0.500 g, 2.29 mmol) in 1:1 (MeOH/CHCl$_3$) (40 mL) were added phenylmethyl {[(3S,4R)-4-hydroxypyrrolidin-3-yl]methyl}carbamate (0.658 g, 2.29 mmol) and triethylamine (0.351 mL, 2.52 mmol). The resulting solution was stirred at ambient temperature for 1 h. Na(OAc)$_3$BH (1.46 g, 6.87 mmol) was added and the solution stirred at rt for an additional 18 h. The reaction mixture was concentrated onto silica gel and chromatographed on a silica gel column [0-100% CHCl$_3$/(90:10:1) CHCl$_3$/MeOH/NH$_4$OH)] to yield a colorless oil (0.760 g, 73%).

LCMS: m/z 453 (M+H)+.

(b) 1-{2-[(3R,4R)-3-(Aminomethyl)-4-hydroxy-1-pyrrolidinyl]ethyl}-7-(methyloxy)-1,5-naphthyridin-2(1H)-one To a solution of phenylmethyl [((3R,4R)-4-hydroxy-1-{2-[7-(methyloxy)-2-oxo-1,5-naphthyridin-1(2H)-yl]ethyl}-3-pyrrolidinyl)methyl]carbamate (0.76 g, 1.68 mmol) in MeOH (10 mL) was added 10% Palladium on carbon (0.20 g) and the resulting solution subjected to H$_2$ at 20 PSI on a Parr shaker for 1 hour. No reaction was observed. The solution was then subjected to H$_2$ at 50 PSI on a Parr shaker. The solution was filtered through a pad of Celite® and concentrated under reduced pressure (0.408 g, 76%).

LCMS: m/z 319.2 (M+H)+.

(c) Title Compound

To a solution of 1-{2-[(3R,4R)-3-(aminomethyl)-4-hydroxy-1-pyrrolidinyl]ethyl}-7-(methyloxy)-1,5-naphthyridin-2(1H)-one (0.140 g, 0.44 mmol) in 1:1 (MeOH/CH$_2$Cl$_2$) (25 mL) were added 3-oxo-3,4-dihydro-2H-pyrido[3,2-b][1,4]oxazine-6-carboxaldehyde (for a synthesis see WO2003087098, Example 31(e)) (0.078 g, 0.44 mmol) and sodium sulphate (0.100 g) and the resulting solution stirred for 18 hours at ambient temperature. Na(OAc)$_3$BH (0.28 g, 1.32 mmol) was then added and the solution stirred at room temperature for an additional 2 hours. The reaction mixture was concentrated onto silica gel and chromatographed on a silica gel column [0-100% CHCl$_3$/(90:10:1) CHCl$_3$/MeOH/NH$_4$OH)] to yield a colorless oil. The material was further purified by HPLC(CH$_3$CN/H$_2$O w 1% TFA) to yield the title compound as the trifluoroacetate salt (0.066 g). The free base was obtained by treating with excess polymer supported carbonate resin in MeOH for 3 hours.

LCMS: m/z 481 (M+H)+.

1H NMR (400 MHz, CD$_3$OD) δ ppm 2.70-2.79 (m, 1H) 3.04-3.12 (m, 3H) 3.14-3.24 (m, 3H) 3.26 (d, J=5.05 Hz, 1H) 3.37 (s, 5H) 4.02-4.07 (m, 3H) 4.27 (d, J=2.27 Hz, 2H) 4.46-4.57 (m, 2H) 4.60-4.68 (m, 1H) 4.70 (d, J=1.26 Hz, 2H) 6.63 (d, J=9.60 Hz, 1H) 6.68 (s, 3H) 7.09 (d, J=8.08 Hz, 1H) 7.37 (d, J=8.08 Hz, 1H) 7.46 (d, J=2.27 Hz, 1H) 7.87 (d, J=9.60 Hz, 1H) 8.31 (d, J=2.27 Hz, 1H).

The fumarate salt was formed by treating 6-({[((3R,4R)-4-hydroxy-1-{2-[7-(methyloxy)-2-oxo-1,5-naphthyridin-1(2H)-yl]ethyl}-3-pyrrolidinyl)methyl]amino}methyl)-2H-pyrido[3,2-b][1,4]oxazin-3(4H)-one with 1 equivalent of fumaric acid in MeOH yielding an off white solid (0.026 g, 10%).

Example 55

6-({[((3R,4R)-4-hydroxy-1-{2-[7-(methyloxy)-2-oxo-1,5-naphthyridin-1(2H)-yl]ethyl}-3-pyrrolidinyl)methyl]amino}methyl)-2H-pyrido[3,2-b][1,4]thiazin-3(4H)-one fumarate

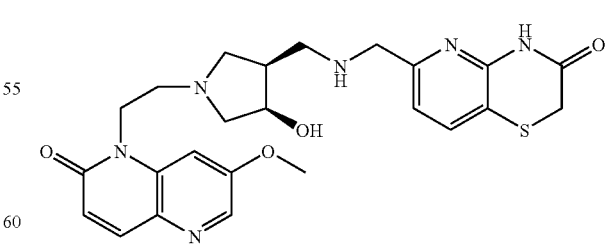

To a solution of 1-{2-[(3R,4R)-3-(aminomethyl)-4-hydroxy-1-pyrrolidinyl]ethyl}-7-(methyloxy)-1,5-naphthyridin-2(1H)-one (0.140 g, 0.44 mmol) in 1:1 (MeOH/CH$_2$Cl$_2$) (25 mL) were added 3-oxo-3,4-dihydro-2H-pyrido[3,2-b][1,4]thiazine-6-carboxaldehyde (for a synthesis, see WO2004058144, Example 7(d)) (0.085 g, 0.44 mmol) and sodium sulphate (0.100 g) and the resulting solution stirred for 18 hours at ambient temperature. Na(OAc)₃BH (0.28 g, 1.32 mmol) was added and the reaction stirred an additional 2 hours. The reaction mixture was concentrated onto silica gel and chromatographed on a silica gel column) [0-100% CHCl₃/(90:10:1) CHCl₃/MeOH/NH₄OH)] to yield a colorless oil. The material was purified by HPLC(CH₃CN/H₂O w 1% TFA) to yield the title compound as the trifluoroacetate salt (0.090 g). The free base was obtained by treating with excess polymer supported carbonate resin in MeOH for 3 hours The silica gel was then filtered off and the solution concentrated down.

LCMS: m/z 497 (M+H)+.

¹H NMR (400 MHz, CDCl₃) δ 8.49 (s, 1H), 7.90 (d, J=9.2 Hz, 1H), 7.45 (d, J=7.8 Hz, 1H), 7.22 (dd, J=9.2 Hz, 1H), 7.10 (s, 1H), 6.81 (d, J=7.8 Hz, 1H), 3.95 (d, J=14.4 Hz, 1H), 3.85 (s, 3H), 3.77 (d, J=14.3 Hz, 1H), 3.59 (m, 1H), 3.31 (s, 2H), 3.21 (dd, J=10.34 Hz, 1H), 3.14 (t, J=7.7 Hz, 2H), 2.95 (d, J=11.1 Hz, 1H), 2.63 (m, 2H), 2.39 (m, 1H), 2.10 (m, 1H), 2.07 (m, 1H), 2.04 (m, 1H), 1.94 (m, 1H), 1.46 (m, 1H).

The fumarate salt was formed by treating 6-({[((3R,4R)-4-hydroxy-1-{2-[7-(methyloxy)-2-oxo-1,5-naphthyridin-1(2H)-yl]ethyl}-3-pyrrolidinyl)methyl]amino}methyl)-2H-pyrido[3,2-b][1,4]thiazin-3(4H)-one with 1 equivalent of fumaric acid to yield an off white solid (0.035 g, 13%)

Example 56

1-(2-{(3S,4R)-4-[(2,3-dihydro[1,4]dioxino[2,3-c]pyridin-7-ylmethyl)amino]-3-hydroxy-1-piperidinyl}ethyl)-7-fluoro-1,5-naphthyridin-2(1H)-one hydrochloride

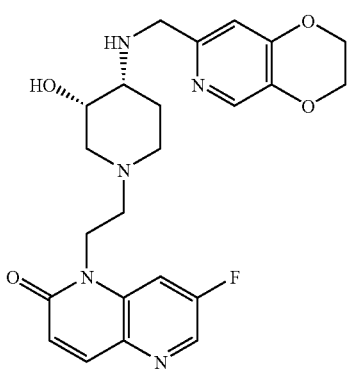

(a) 1,1-dimethylethyl {(3S,4R)-1-[2-(7-fluoro-2-oxo-1,5-naphthyridin-1(2H)-yl)ethyl]-3-hydroxy-4-piperidinyl}carbamate (7-Fluoro-2-oxo-1,5-naphthyridin-1(2H)-yl)acetaldehyde methyl hemiacetal (200 mg, 0.8396 mmol) and 1,1-dimethylethyl[(3S,4R)-3-hydroxy-4-piperidinyl]carbamate (for a synthesis see WO2004058144, Example 5(c), cis-(3-hydroxy-piperidin-4-yl)-carbamic acid tert-butyl ester Enantiomer 2) (192 mg, 1 eq.) were stirred in chloroform (10 ml) plus MeOH (0.5 ml) under argon for 2 h. Sodium triacetoxyborohydride (534 mg, 3 eq.) was added in one portion and the mixture was stirred at rt over the weekend, then quenched by addition of saturated aqueous sodium hydrogen cabonate (2 mL). The organic phase was separated using a hydrophobic frit and the aqueous phase was extracted with DCM (2×20 ml). The organic extracts were combined, dried over anhydrous magnesium sulphate, filtered and evaporated under reduced pressure to give the crude product, which was purified by column chromatography on silica, eluted with 0-20% (2M ammonia in MeOH) in DCM. Appropriate fractions were combined and evaporated under reduced pressure to give 1,1-dimethylethyl {(3S,4R)-1-[2-(7-fluoro-2-oxo-1,5-naphthyridin-1(2H)-yl)ethyl]-3-hydroxy-4-piperidinyl}carbamate (310 mg) as a tan foam.

MS (ES+) m/z 407 (MH⁺).

(b) 1-{2-[(3S,4R)-4-amino-3-hydroxy-1-piperidinyl]ethyl}-7-fluoro-1,5-naphthyridin-2(1H)-one Dihydrochloride 1,1-Dimethylethyl {(3S,4R)-1-[2-(7-fluoro-2-oxo-1,5-naphthyridin-1(2H)-yl)ethyl]-3-hydroxy-4-piperidinyl}carbamate (310 mg, 0.7627 mmol) was dissolved in DCM (1 ml) and the solution was treated with 4M hydrogen chloride in 1,4-dioxane (1 ml). Effervescence and formation of a precipitate was observed. After 2 h, the solvents were removed under reduced pressure and the residue was dried under reduced pressure overnight, to give 1-{2-[(3S,4R)-4-amino-3-hydroxy-1-piperidinyl]ethyl}-7-fluoro-1,5-naphthyridin-2(1H)-one dihydrochloride as an off-white solid (253 mg).

MS (ES+) m/z 307 (MH⁺).

(c) Title Compound

1-{2-[(3S,4R)-4-Amino-3-hydroxy-1-piperidinyl]ethyl}-7-fluoro-1,5-naphthyridin-2(1H)-one dihydrochloride (247 mg, 0.6513 mmol) was stirred in 9:1 v:v chloroform:MeOH (10 ml) at rt under argon and triethylamine (318 µL, 3.5 eq.) was added. The mixture was stirred at rt for 10 mins., then 2,3-dihydro[1,4]dioxino[2,3-c]pyridine-7-carboxaldehyde (108 mg, for a synthesis see WO2004058144, Example 2(c) or WO03/087098, Example 19(d)) was added and the mixture was stirred at rt for 2 hours before being treated with sodium triacetoxyborohydride (414 mg) added in one portion. The mixture was then stirred at rt overnight. Saturated aqueous sodium hydrogen cabonate (5 ml) was then added and the organic phase was diluted with DCM to bring the total volume to ca. 100 ml. The organic phase was separated using a hydrophobic frit and the aqueous phase was extracted with DCM (2×50 ml). The combined DCM extracts were evaporated under reduced pressure and purified by MDAP to give the free base of the title compound as a white foam (130 mg).

NMR δ (400 MHz, CDCl₃): 8.44 (1H, d, J=2 Hz), 8.34 (1H, s), 8.11 (1H, s), 7.91 (1H, d, J=10 Hz), 7.54 (1H, dd, J=8 Hz, 2 Hz), 6.89-6.86 (2H, m), 4.53-4.44 (1H, m), 4.36-4.20 (5H, m), 4.12 (1H, s), 4.08 (2H, s), 3.32-3.28 (1H, m), 3.03-2.99 (2H, m), 2.80-2.71 (2H, m), 2.39 (1H, d, J 11 Hz), 2.32-2.25 (1H, m), 1.95-1.84 (2H, m).

MS (ES+) m/z 456 (MH⁺).

Example 57

10-(2-{4-[(2,3-dihydro[1,4]dioxino[2,3-c]pyridin-7-ylmethyl)amino]-1-piperidinyl}ethyl)-6-fluoro-2,3-dihydro[1,4]dioxino[2,3-h]quinolin-9(10H)-one hydrochloride

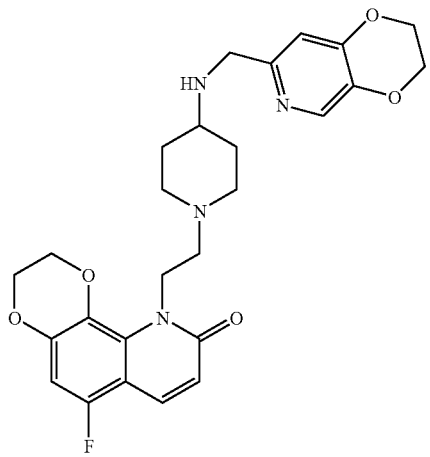

(a) 5-Fluoro-3-nitro-1,2-benzenediol

Boric acid (20.45 g, 330.7 mmol), and hydrogen peroxide (35%, 36.8 mL) in tetrahydrofuran (150 ml) was treated with concentrated sulfuric acid (15 ml) and the mixture was stirred at rt for 30 min. 1-(5-Fluoro-2-hydroxy-3-nitrophenyl)ethanone (15 g, 75.4 mmol) in tetrahydrofuran (45 ml) was added and reaction heated for 48 h at 75° C. The reaction mixture was cooled to rt, diluted with water and extracted with DCM (3×500 ml). The combined organic phases were dried on magnesium sulphate, evaporated and the residue was subjected to column chromatography on silica gel using a 20%-80% EtOAc: 40-60 petroleum ether gradient to provide the desired compound (6.55 g, 50%), a 5:1 mixture of desired product and 1-(5-fluoro-2-hydroxy-3-nitrophenyl)ethanone (4 g) and recovered 1-(5-fluoro-2-hydroxy-3-nitrophenyl)ethanone (1.5 g).

$^1$H NMR (250 MHz) δ(DMSO) 6.91-6.97 (m, 1H), 7.17-7.22 (m, 1H), 10.5 (bs, 2H).

(b) 7-Fluoro-5-nitro-2,3-dihydro-1,4-benzodioxin

A mixture of 5-fluoro-3-nitro-1,2-benzenediol (6.55 g, 37.9 mmol), anhydrous potassium carbonate (21 g, 151.6 mmol) and 1,2-dibromoethane (8.2 mL) in DMF (70 ml) was heated at 80° C. under argon for 5 h. The reaction was cooled to rt, water (200 ml) added and the aqueous phase extracted with ethyl acetate (3×200 ml). The organics were washed with brine, dried, filtered and evaporated to afford the desired compound (6.96 g, 93%).

$^1$H NMR (250 MHz) δ (CDCl$_3$) 4.38 (m, 4H), 6.88 (m, 1H), 7.25 (m 1H).

(c) 7-Fluoro-2,3-dihydro-1,4-benzodioxin-5-amine

7-Fluoro-5-nitro-2,3-dihydro-1,4-benzodioxin (6.96 g, 35 mmol) and 5% Pd/C (4 g) in MeOH (500 ml) was stirred overnight in the presence of hydrogen at atmospheric pressure at rt. The catalyst was filtered off and solvent removed; the residue was dissolved in MeOH (100 ml), more 5% Pd/C (paste, 3 g) was added and mixture stirred overnight in presence of hydrogen (45 psi) at rt. The catalyst was filtered off and solvent removed; the residue treated with DCM (20 ml), the solid filtered off and compound in DCM loaded on silica (pre-wet with petroleum ether) and purified using a 10%-50% EtOAc: 40-60 petroleum ether gradient to provide the desired compound (3 g, 51%).

MS (ES+) m/z 170 (MH$^+$).

(d) 6-Fluoro-2,3-dihydro[1,4]dioxino[2,3-h]quinoline

Concentrated sulfuric acid (25 ml), boric acid (2.22 g, 35.6 mmol), iron (II) sulfate heptahydrate (831 mg, 2.99 mmol) and 3-nitrobenzene sulfonic acid sodium salt (7.25 g, 32.2 mmol) were stirred in a flask cooled with an ice-bath; glycerol (8.4 ml, 23 mmol) and 7-fluoro-2,3-dihydro-1,4-benzodioxin-5-amine (3.9 g, 23 mmol) were added followed by water (25 ml). The reaction was heated at 140° C. for 3 h, then cooled to rt. The mixture was poured onto ice-water (100 ml) and filtered. The filtrate was basified to pH 8 with 6N sodium hydroxide (130 ml) and then stirred with ethyl acetate (300 ml) for 0.5 h. The mixture was then filtered through celite and the phases separated. The aqueous layer was extracted with ethyl acetate (3×300 ml), the combined organics washed with brine, dried on magnesium sulphate, filtered and reduced to afford a crude which dissolved in ethyl acetate and purified by filtration over a silica pad to afford the compound as a pale green solid (2.78 g, 60%).

MS (ES+) m/z 206 (MH$^+$).

(e) 6-Fluoro-10-(2-propen-1-yl)-2,3-dihydro[1,4]dioxino[2,3-h]quinolin-10-ium Iodide 6-fluoro-2,3-dihydro[1,4]dioxino[2,3-h]quinoline (2.78 g, 13.6 mmol) and allyl iodide (2.5 ml, 27.2 mmol) in toluene (50 ml) under argon was heated at 90° C. than at 120° C. for 5 h. The reaction was cooled to rt, the solvent decanted and the solid dried in the vacuum oven at 40° C. overnight to afford the desired product (4 g, 80%).

MS (ES+) m/z 246 (MH$^+$).

(f) 7-Fluoro-10-(2-propen-1-yl)-2,3-dihydro[1,4]dioxino[2,3-h]quinolin-9(10H)-one 6-Fluoro-10-(2-propen-1-yl)-2,3-dihydro[1,4]dioxino[2,3-h]quinolin-10-ium iodide (4 g; 10.7 mmol), KOH (2.6 g; 47.1 mmol) and K$_3$-[Fe(CN)$_6$] (7 g; 21.4 mmol) were stirred in 50% aqueous 1,4-dioxane (100 mL) at rt, then at 45° C. overnight. Water (100 ml) was added and the aqueous layer was extracted with 15% MeOH/DCM. The organics were dried with MgSO$_4$ and the solvents removed. The residue was purified by column chromatography on silica gel using a 0-4% MeOH/DCM gradient to give the desired product (0.62 g; 22%).

MS (ES+) m/z 261 (MH$^+$).

125

(g) (7-Fluoro-9-oxo-2,3-dihydro[1,4]dioxino[2,3-h]quinolin-10(9H)-yl)acetaldehyde 7-Fluoro-10-(2-propen-1-yl)-2,3-dihydro[1,4]dioxino[2,3-h]quinolin-9(10H)-one (0.62 g, 2.4 mmol) was dissolved in DCM (20 ml) and cooled to −78° C. This mixture was then stirred with O3 bubbling for 25 mins before addition of DMS (0.79 ml; 5.5 mmol) and the reaction was then warmed to rt. Once at rt this was stirred for a further 30 mins. The solvents were then removed to afford the desired product (0.75 g, >100%).

MS (ES+) 264 (MH+)

(h) 1,1-Dimethylethyl (2,3-dihydro[1,4]dioxino[2,3-c]pyridin-7-ylmethyl) {1-[2-(7-fluoro-9-oxo-2,3-dihydro[1,4]dioxino[2,3-h]quinolin-10(9H)-yl)ethyl]-4-piperidinyl}carbamate A solution of (7-fluoro-9-oxo-2,3-dihydro[1,4]dioxino[2,3-h]quinolin-10(9H)-yl)acetaldehyde (375 mg, 1.4 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (489 mg, 1.4 mmol) in chloroform (10 ml) and MeOH (2 ml) was stirred at rt for 0.5 h. The mixture was then treated with NaBH(OAc)3 (594 mg, 2.8 mmol), stirred at rt for 1 h. The solvents were then removed and the residue partitioned between saturated solution of sodium bicarbonate and 10% MeOH/DCM. The phases were separated and aqueous layer extracted with 10% MeOH/DCM (2×100 ml). The combined organics were dried on magnesium sulphate, filtered and evaporated. The residue was subjected to column chromatography on silica gel eluting with 0-20% MeOH-DCM and after to afford 330 mg of the desired compound.

MS (ES+) m/z 597 (MH+).

(i) Title Compound

To a solution of 1,1-Dimethylethyl (2,3-dihydro[1,4]dioxino[2,3-c]pyridin-7-ylmethyl) {1-[2-(7-fluoro-9-oxo-2,3-dihydro[1,4]dioxino[2,3-h]quinolin-10(9H)-yl)ethyl]-4-piperidinyl}carbamate (330 mg) in chloroform (6 ml) was added 4N HCl in 1,4-dioxane (6 ml) and the reaction was stirred at rt for 30 min. Toluene (10 ml) was then added and the solution was evaporated, dissolved in MeOH and treated with Amberlyst A21 basic resin for 30 min. The resin was filtered off and the solvent removed; the residue was subjected to column chromatography on silica gel eluting with 0-30% MeOH-DCM to afford the free base of the title compound (200 mg, 73%).

δH CD3OD, (250 MHz) 1.57 (m, 2H), 2.04 (d, 2H), 2.30 (m, 2H), 2.81 (m, 3H) 3.15 (d, 2H), 3.96 (s, 2H), 4.30-4.41 (m, 8H), 4.73 (m, 2H), 6.51 (d, 1H), 6.67 (d, 1H), 6.99 (s, 1H), 7.93 (d, 1H), 8.06 (s, 1H).

MS (ES+) m/z 497 (MH+).

This compound was converted to the HCl salt by dissolving the free base in MeOH and treating with 1 equivalent of 4M HCl in 1,4-dioxane. This was then evaporated to dryness to afford an off-white solid. LCMS as of the free base.

126

Example 58

7-[({1-[2-(7-fluoro-2-oxo-1(2H)-quinoxalinyl)ethyl]-4-piperidinyl}amino)methyl]-1H-pyrido[2,3-b][1,4]thiazin-2(3H)-one Fumarate

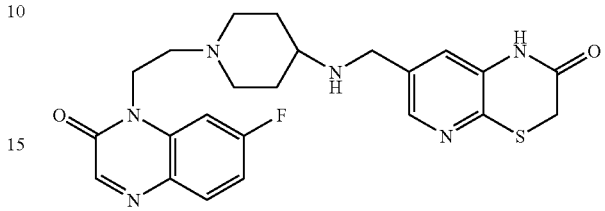

A solution of 1-[2-(4-amino-1-piperidinyl)ethyl]-7-fluoro-2(1H)-quinoxalinone dihydrochloride (60 mg; 0.166 mmol) and 2-oxo-2,3-dihydro-1H-pyrido[2,3-b][1,4]thiazine-7-carboxaldehyde (for a synthesis see WO 2004/058144 Example 48(e)) (85% pure, 44 mg, 0.197 mmol) in MeOH (3 ml), chloroform (3 ml) and triethylamine (0.06 ml) was heated under reflux with 3A molecular sieves overnight. It was cooled and sodium triacetoxyborohydride (0.11 g; 0.52 mmol) was added, and the mixture was stirred at rt overnight. Sodium triacetoxyborohydride (0.11 g) was added and the mixture was stirred for another 4 days, with addition of two more portions of triacetoxyborohydride (0.1 μg and 0.22 g). Aqueous sodium bicarbonate solution was added to basify and the aqueous phase was extracted several times with 10% MeOH/DCM. The organic fractions were dried and evaporated. Chromatography on silica gel, eluting with 0-20% MeOH-DCM gave the free base of the title compound (16 mg, 21%).

δH (CDCl3), (250 MHz) 1.40 (2H, m), 1.90 (2H, br.d), 2.18 (2H, t), 2.52 (1H, m), 2.68 (2H, t), 2.98 (2H, br. d), 3.57 (2H, s), 3.80 (2H, s), 4.31 (2H, t), 7.07 (2H, m), 7.15 (1H, d), 7.87 (1H, dd), 8.13 (1H, d), 8.23 (1H, s).

MS (+ve ion electrospray) m/z 440 (MH+).

The free base in DCM was treated with 0.5M fumaric acid (0.07 mL, one equivalent) and evaporated to dryness. The solid was triturated with ether and dried to give the fumarate salt.

Example 59

7-fluoro-1-[2-(4-{[(7-oxo-1,5,6,7-tetrahydro-1,8-naphthyridin-2-yl)methyl]amino}-1-piperidinyl)ethyl]-2(1H)-quinoxalinone Fumarate

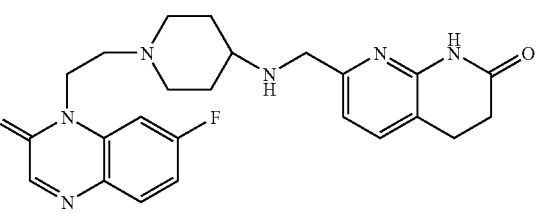

A solution of 1-[2-(4-amino-1-piperidinyl)ethyl]-7-fluoro-2(1H)-quinoxalinone dihydrochloride (60 mg; 0.166 mmol) and 7-oxo-1,5,6,7-tetrahydro-[1,8]-naphthyridine-2-carboxaldehyde (for a synthesis see WO 2003/087098 Example 307(f)) (35 mg, 0.197 mmol) in MeOH (3 ml), chloroform (3 ml) and triethylamine (0.06 ml) was heated under reflux with 3A molecular sieves overnight. Chloroform (2 ml) and MeOH (2 ml) were added, the mixture was cooled and sodium triacetoxyborohydride (0.11 g; 0.52 mmol) was added, and the mixture was stirred at rt overnight. Sodium triacetoxyborohydride (0.1 µg) was added and the mixture was stirred overnight again. Aqueous sodium bicarbonate solution was added to basify and the aqueous phase was extracted several times with 10% MeOH/DCM. The organic fractions were dried and evaporated. Chromatography on silica gel, eluting with 0-20% MeOH-DCM gave the free base of the title compound (23 mg, 31%).

δH (CDCl$_3$), (250 MHz) 1.46 (2H, m), 1.95 (presumed 2H, m, mostly obscured by water), 2.19 (2H, t), 2.56 (1H, m), 2.66 (4H, m), 2.97 (4H, m), 3.84 (2H, s), 4.31 (2H, t), 6.94 (1H, d), 7.07 (1H, td), 7.14 (1H, dd), 7.43 (1H, d), 7.86 (1H, dd), 8.03 (1H, br. s), 8.22 (1H, s).

MS (+ve ion electrospray) m/z 451 (MH+).

The free base in DCM was treated with 0.5M fumaric acid (0.1 mL, one equivalent) and evaporated to dryness. The solid was triturated with ether, dissolved in MeOH, evaporated and dried to give the fumarate salt.

Example 60

6-chloro-4-(2-{4-[(2,3-dihydro[1,4]dioxino[2,3-c]pyridin-7-ylmethyl)amino]-1-piperidinyl}ethyl)-1,2,4-benzotriazin-3(4H)-one 1-oxide Hydrochloride

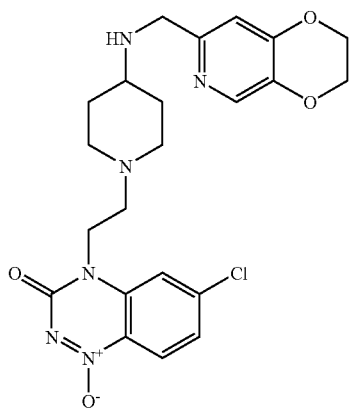

(a) N-(5-chloro-2-nitrophenyl)urea

To a solution of triphosgene (3.613 g, 12.175 mmol) in toluene (15 ml) was added a solution of 5-chloro-2-nitroaniline (2.100 g, 12.175 mmol) in toluene (15 ml) over 0.5 h and then the reaction was heated at 80° C. for 24 h. The reaction was then cooled and carefully poured onto aqueous NH$_3$. This mixture was stirred for 1 h, filtered, washed with water (100 ml), MeOH (50 ml) and ethyl acetate (50 ml) to leave the desired product as a yellow solid (1.558 g, 60%).

(b) 6-Chloro-1,2,4-benzotriazin-3(4H)-one 1-oxide

A suspension of N-(5-chloro-2-nitrophenyl)urea (1.558 g, 7.230 mmol) in an aqueous NaOH solution (4.34 g NaOH in 15 ml water) was heated at reflux for 0.5 h before cooling and treatment with water (100 ml). The mixture was then heated to reflux again and the hot mixture filtered through a Buchner funnel. The filtrate was then acidified with conc. HCl and the resultant solid was filtered, washed with water (20 ml) and dried in vacuo to give the desired product (700 mg, 49%).

MS (ES+) m/z 198/200 (MH$^+$).

(c) 6-Chloro-4-(2-propen-1-yl)-1,2,4-benzotriazin-3(4H)-one 1-oxide

6-Chloro-1,2,4-benzotriazin-3(4H)-one 1-oxide (700 mg, 3.544 mmol) was suspended in dry DMF (20 ml) under argon at rt, and the stirred suspension was treated with K$_2$CO$_3$ (1.614 mg, 11.695 mmol) and allyl iodide (0.43 ml, 4.607 mmol). It was then stirred at rt for 2 h before addition of further allyl iodide (0.86 ml, 9.214 mmol) and then the reaction was heated at 60° C. for 1 h before addition of water (100 ml). The mixture was then extracted with DCM (3×200 ml). The combined organic extracts were dried over anhydrous magnesium sulphate, filtered and evaporated under reduced pressure to give a yellow solid which was purified by column chromatography on silica with a 0-5% MeOH in DCM gradient to give the desired product as a light brown solid (472 mg, 56%).

MS (ES+) m/z 238/240 (MH+).

(d) (6-Chloro-1-oxido-3-oxo-1,2,4-benzotriazin-4(3H)-yl)acetaldehyde

6-Chloro-4-(2-propen-1-yl)-1,2,4-benzotriazin-3(4H)-one 1-oxide (104 mg, 0.438 mmol) was dissolved in 1,4-dioxane (4 ml) and water (2 ml). Sodium periodate (234 mg, 1.096 mmol) was added, followed by osmium tetroxide (0.09 ml of 4% aqueous solution). The mixture stirred at rt for 6 h, and then extracted with 20% MeOH/DCM (3×100 ml). The organic extracts were combined, dried over anhydrous magnesium sulphate, filtered and evaporated under reduced pressure to give (6-Chloro-1-oxido-3-oxo-1,2,4-benzotriazin-4(3H)-yl)acetaldehyde as an impure yellow oil (89 mg, 85%).

MS (ES+) m/z 240/242 (MH+).

(e) 1,1-Dimethylethyl {1-[2-(6-chloro-1-oxido-3-oxo-1,2,4-benzotriazin-4(3H)-yl)ethyl]-4-piperidinyl}(2,3-dihydro[1,4]dioxino[2,3-c]pyridin-7-ylmethyl)carbamate A mixture of (6-chloro-1-oxido-3-oxo-1,2,4-benzotriazin-4(3H)-yl)acetaldehyde (89 mg, 0.372 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (117 mg, 0.334 mmol) in chloroform (5 ml) and MeOH (0.5 ml) was stirred for 2 h before addition of NaBH(OAc)$_3$ (212 mg, 1.002 mmol). The reaction was stirred for 1 h before addition of sat. aq NaHCO$_3$ (50 ml). The reaction was then extracted with 10% MeOH in DCM (3×200 ml). The combined organic phases were dried, evaporated and the crude residue purified by chromatography on silica gel using a 0-10% MeOH/DCM gradient to provide the desired compound as a yellow oil (81 mg, 42%).

MS (ES+) m/z 573/574 (MH$^+$).

(f) Title Compound

A solution of 1,1-dimethylethyl {1-[2-(6-chloro-1-oxido-3-oxo-1,2,4-benzotriazin-4(3H)-yl)ethyl]-4-piperidinyl}(2,3-dihydro[1,4]dioxino[2,3-c]pyridin-7-ylmethyl)carbamate (81 mg, 0.141 mmol) in chloroform (1 ml) and MeOH (1 ml) was added 4M HCl in 1,4-dioxane (1 ml) and the reaction was stirred at rt for 0.5 h before evaporation, treatment with sat. aq NaHCO₃ (50 ml). The reaction was then extracted with 20% MeOH in DCM (3×100 ml). The combined organic phases were dried, evaporated and the crude residue purified by chromatography on silica gel using a 0-20% MeOH/DCM gradient to provide the free base of the title compound as a yellow foam (60 mg, 90%).

MS (ES+) m/z 473/475 (MH⁺).

¹H NMR (250 MHz) δ (CDCl₃) 1.38-1.51 (2H, m), 1.85-1.99 (2H, m), 2.12-2.26 (2H, m), 2.52-2.82 (3H, m), 2.92-3.02 (2H, m), 3.81 (2H, s), 4.27-4.38 (m, 6H), 6.81 (1H, s), 7.28 (1H, d, J=10 Hz), 7.58 (1H, s), 8.08 (1H, s), 8.27 (1H, d, J=10.5 Hz).

This compound was converted to the HCl salt by dissolving the obtained free base in 1:1 DCM:MeOH and adding 1 equivalent of 4M HCl in 1,4-dioxane. This was then evaporated to dryness.

Example 61

6-({[((3S,4S)-4-hydroxy-1-{2-[7-(methyloxy)-2-oxo-1(2H)-quinolinyl]ethyl}-3-pyrrolidinyl)methyl]amino}methyl)-2H-pyrido[3,2-b][1,4]thiazin-3(4H)-one Dihydrochloride

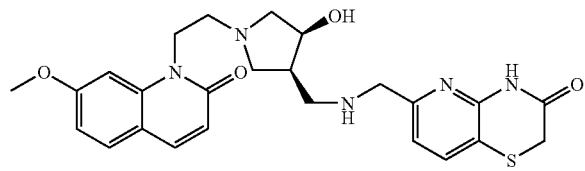

(a) Phenylmethyl {[(3R,4S)-4-hydroxy-3-pyrrolidinyl]methyl}carbamate

To a stirred solution of 1,1-dimethylethyl (3S,4S)-3-hydroxy-4-[({[(phenylmethyl)oxy]carbonyl}amino)methyl]-1-pyrrolidinecarboxylate (for a synthesis see WO2006002047 preparation 24(c), (±)-1,1-dimethylethyl cis-3-hydroxy-4-[({[(phenylmethyl)oxy]carbonyl}amino)methyl]-1-pyrrolidinecarboxylate E1 isomer) (1 g, 2.85 mmol) in DCM (50 ml) was added trifluoroacetic acid (50 ml) and stirred for 2 h. The reaction mixture was concentrated and placed under high vacuum for 3 h. To the TFA salt dissolved in DCM (50 ml) was added MP-carbonate resin (4 g; 11.4 mmol) and stirred overnight. The reaction mixture was filtered and concentrated to provide the title compound as a pale yellow oil (840 mg, 100%)

MS (ES+) m/z 251.3 (MH⁺).

(b) Phenylmethyl [((3S,4S)-4-hydroxy-1-{2-[7-(methyloxy)-2-oxo-1(2H)-quinolinyl]ethyl}-3-pyrrolidinyl)methyl]Carbamate Phenylmethyl {[(3R,4S)-4-hydroxy-3-pyrrolidinyl]methyl}carbamate (840 mg, 3.35 mmol) and [7-(methyloxy)-2-oxo-1(2H)-quinolinyl]acetaldehyde (663 mg, 3.05 mmol) were combined in anhydrous DCM (10 ml) and anhydrous MeOH (2 ml) with a spatula of solid sodium carbonate. The reaction mixture was stirred under nitrogen for 1 h then sodium triacetoxyborohydride (2.03 g, 9.12 mmol) was added and stirred overnight. The reaction mixture was concentrated and the title compound was obtained as a pale yellow oil (1 g, 71%) after column chromatography (90:10:1: DCM:MeOH:NH₄OH).

MS (ES+) m/z 452.8 (MH⁺).

(c) 1-{2-[(3S,4S)-3-(Aminomethyl)-4-hydroxy-1-pyrrolidinyl]ethyl}-7-(methyloxy)-2(1H)-quinolinone To a solution of phenylmethyl [((3S,4S)-4-hydroxy-1-{2-[7-(methyloxy)-2-oxo-1(2H)-quinolinyl]ethyl}-3-pyrrolidinyl)methyl]carbamate (1 g, 2.21 mmol) was added 20% Pd(OH)₂/C, degassed and placed under 1 atm of H₂ for 2 h. The reaction mixture was filtered through Celite and concentrated to obtain the title compound as a yellow oil (622 mg, 89%).

MS (ES+) m/z 318.3 (MH⁺).

(d) Title Compound

1-{2-[(3S,4S)-3-(Aminomethyl)-4-hydroxy-1-pyrrolidinyl]ethyl}-7-(methyloxy)-2(1H)-quinolinone (146 mg, 0.460 mmol) and 3-oxo-3,4-dihydro-2H-pyrido[3,2-b][1,4]thiazine-6-carboxaldehyde (for a synthesis, see WO2004058144, Example 7(d)) (98 mg, 0.506 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (306 mg, 1.38 mmol) was added and stirred for 1 h. The reaction mixture was concentrated and purified to obtain the free base of the title compound as a pale yellow oil (91 mg, 40%) after column chromatography (90:10:1: DCM:MeOH:NH₄OH).

MS (ES+) m/z 496.4 (MH⁺).

1H NMR (400 MHz, CD₃OD) δ ppm 3.43-3.55 (m, 3H) 3.58 (s, 2H) 3.68 (s, 3H) 3.73 (s, 3H) 4.00 (s, 4H) 4.38 (s, 2H) 4.65 (s, 1H) 4.76 (t, J=5.94 Hz, 3H) 6.59 (d, J=9.35 Hz, 1H) 7.02 (dd, J 8.59, 2.02 Hz, 1H) 7.07 (s, 1H) 7.16 (d, J=7.83 Hz, 1H) 7.70 (d, J=8.59 Hz, 1H) 7.85 (d, J=7.83 Hz, 1H) 7.92 (d, J=9.35 Hz, 1H).

The dihydrochloride salt was made by addition of 92 μL of 4N HCl/1,4-dioxane to a solution of the free base.

Example 62

7-chloro-6-({[((3S,4S)-4-hydroxy-1-{2-[7-(methyloxy)-2-oxo-1(2H)-quinolinyl]ethyl}-3-pyrrolidinyl)methyl]amino}methyl)-2H-pyrido[3,2-b][1,4]oxazin-3(4H)-one dihydrochloride

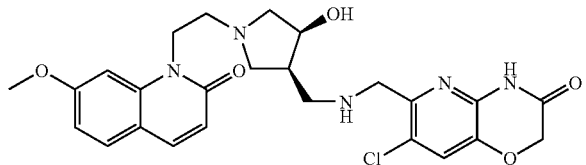

1-{2-[(3S,4S)-3-(Aminomethyl)-4-hydroxy-1-pyrrolidinyl]ethyl}-7-(methyloxy)-2(1H)-quinolinone (68 mg, 0.214 mmol) and 7-chloro-3-oxo-3,4-dihydro-2H-pyrido[3,2-b][1,4]oxazine-6-carboxaldehyde (for a synthesis see WO2003064421, Example 15(c)) (50 mg, 0.236 mmol) were combined in anhydrous DCM (5 mL) and anhydrous MeOH (1 ml) with a spatula of solid sodium carbonate. The reaction mixture was stirred under nitrogen for 18 h then sodium triacetoxyborohydride (143 mg, 0.643 mmol) was added and stirred for 1 h. The reaction mixture was concentrated and purified to obtain the free base of the title compound as a pale oil (96 mg; 87%) after column chromatography (90:10:1: DCM:MeOH:NH$_4$OH).

MS (ES+) m/z 514 (MH$^+$).

1H NMR (400 MHz, CD$_3$OD) δ ppm 3.40 (dd, J 12.63, 6.06 Hz, 2H) 3.57 (dd, J 12.38, 6.57 Hz, 2H) 3.68 (s, 1H) 3.75 (t, J=5.43 Hz, 3H) 4.00 (s, 4H) 4.47 (s, 2H) 4.68 (s, 1H) 4.73-4.82 (m, 5H) 6.61 (d, J=9.35 Hz, 1H) 7.01 (dd, J 8.72, 1.89 Hz, 1H) 7.08 (d, J=1.52 Hz, 1H) 7.54 (s, 1H) 7.69 (d, J=8.84 Hz, 1H) 7.91 (d, J=9.35 Hz, 1H).

The dihydrochloride salt was made by addition of 93 μL of 4N HCl/1,4-dioxane to a solution of the free base.

Example 63

3-{[({(3S,4S)-1-[2-(7-fluoro-2-oxo-1(2H)-quinolinyl)ethyl]-4-hydroxy-3-pyrrolidinyl}methyl)amino]methyl}-5H-pyridazino[3,4-b][1,4]thiazin-6(7H)-one

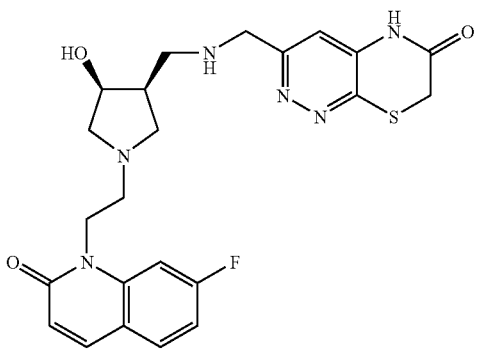

A solution of 1-{2-[(3S,4S)-3-(aminomethyl)-4-hydroxy-1-pyrrolidinyl]ethyl}-7-fluoro-2(1H)-quinolinone (100 mg; 0.33 mmol) and 6-oxo-6,7-dihydro-5H-pyridazino[3,4-b][1,4]thiazine-3-carbaldehyde (for a synthesis see WO2004058144, Example 58) (65 mg, 0.33 mmol) in methanol (2 mL), DCM (4 mL) was stirred at room temperature overnight. Sodium triacetoxyborohydride (210 mg; 1.0 mmol) was added and the mixture was stirred at room temperature for 4 h. The reaction was evaporated and chromatographed on silica gel, eluting with 0-10% methanol-DCM-1% NH$_4$OH to give 42 mg of the title compound as an oil which solidified to an off-white powder upon standing.

1H NMR (400 MHz, CD$_3$OD) δ ppm 2.39-2.50 (m, 1H) 2.68-2.80 (m, 3H) 2.86-2.99 (m, 4H) 3.13 (dd, J=10.5, 5.6 Hz, 1H) 3.49 (dd, J=14.1, 7.1 Hz, 2H) 3.73-3.81 (m, 2H) 4.35-4.49 (m, 3H) 6.60 (d, J=9.49 Hz, 1H) 7.07-7.10 (m, 2H) 7.43 (d, J=11.9 Hz, 1H) 7.76 (dd, J=8.6, 6.3 Hz, 1H) 7.89 (d, J=9.5 Hz, 1H) MS (+ve ion electrospray) m/z 485 (M+H)+.

Example 64

1-[2-((3S,4S)-3-{[(2,3-dihydro[1,4]dioxino[2,3-c]pyridin-7-ylmethyl)amino]methyl}-4-hydroxy-1-pyrrolidinyl)ethyl]-7-fluoro-2(1H)-quinolinone Dihydrochloride

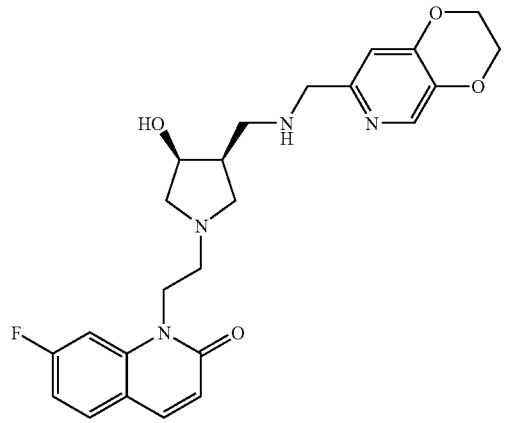

A solution of 1-{2-[(3S,4S)-3-(aminomethyl)-4-hydroxy-1-pyrrolidinyl]ethyl}-7-fluoro-2(1H)-quinolinone (60 mg; 0.2 mmol) and 2,3-dihydro[1,4]dioxino[2,3-c]pyridine-7-carboxaldehyde (for a synthesis see WO2004058144, Example 2(c) or WO03/087098, Example 19(d)) (32 mg, 0.2 mmol) in methanol (1 mL), DCM (3 mL) was stirred at room temperature overnight. Sodium triacetoxyborohydride (85 mg; 0.4 mmol) was added and the mixture was stirred at room temperature for 1 hour. The reaction was evaporated and chromatographed on silica gel, eluting with 0-10% methanol-DCM-1% NH$_4$OH to give an oil. The oil was treated with 1M HCl in Et$_2$O to give the title compound (50 mg) as a hydrochloride salt.

1H NMR (400 MHz, CD$_3$OD) δ ppm 2.35-2.45 (m, 1H) 2.57 (t, J=8.84 Hz, 1H) 2.62-2.70 (m, 2H) 2.76-2.86 (m, 2H) 2.96 (dd, J=9.09, 7.83 Hz, 1H) 3.14 (dd, J=10.36, 5.56 Hz, 1H) 3.33 (dt, J=3.28, 1.64 Hz, 1H) 3.73-3.81 (m, 2H) 4.31 (dd, J=5.05, 2.78 Hz, 2H) 4.35-4.46 (m, 5H) 6.61 (d, J=9.35 Hz, 1H) 6.97 (s, 1H) 7.10 (td, J=8.53, 2.40 Hz, 1H) 7.42 (dd, J=11.37, 2.27 Hz, 1H) 7.75 (dd, J=8.59, 6.32 Hz, 1H) 7.90 (d, J=9.35 Hz, 1H) 7.92 (s, 1H) 8.00 (s, 1H).

MS (+ve ion electrospray) m/z 455 (M+H)+.

Example 65

3-[({1-[2-(7-fluoro-2-oxo-1(2H)-quinoxalinyl)ethyl]-4-piperidinyl}amino)methyl]-5H-pyridazino[3,4-b][1,4]thiazin-6(7H)-one Fumarate

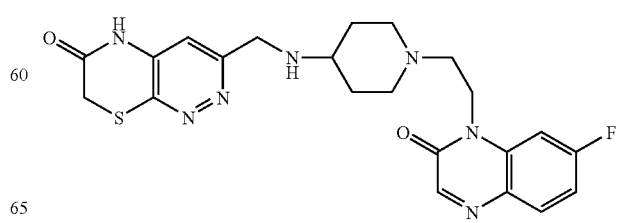

A solution of 1-[2-(4-amino-1-piperidinyl)ethyl]-7-fluoro-2(1H)-quinoxalinone dihydrochloride (90 mg; 0.25 mmol) and 6-oxo-6,7-dihydro-5H-pyridazino[3,4-b][1,4]thiazine-3-carbaldehyde (for a synthesis see WO 2004/058144 Example 58(d)) (48 mg, 0.25 mmol) in MeOH (5 ml), chloroform (5 ml) and triethylamine (0.09 ml) was heated under reflux with 3A molecular sieves overnight. It was cooled and sodium triacetoxyborohydride (0.166 g; 0.78 mmol) was added, and the mixture was stirred at rt for 8 h. Further triacetoxyborohydride (0.166 g) was added and stirring continued overnight. Aqueous sodium bicarbonate solution was added to basify and the aqueous phase was extracted several times with 10% MeOH-DCM. The organic fractions were dried and evaporated. Chromatography on silica gel, eluting with 0-20% MeOH-DCM gave the free base of the title compound (61 mg, 52%).

δH (CDCl$_3$), (250 MHz) 1.41 (2H, m), 1.90 (2H, br.d), 2.18 (2H, t), 2.57 (1H, m), 2.68 (2H, t), 2.97 (2H, br. d), 3.65 (2H, s), 4.09 (2H, s), 4.31 (2H, t), 7.08 (3H, m), 7.20 (1H, d), 7.86 (1H, dd), 8.23 (1H, s)

MS (+ve ion electrospray) m/z 470 (MH+).

The free base in chloroform was treated with one equivalent of 0.5M fumaric acid in MeOH and evaporated to dryness to give the fumarate salt.

Example 66

1-(2-{(3S,4R)-4-[(2,3-dihydro[1,4]dioxino[2,3-c]pyridin-7-ylmethyl)amino]-3-hydroxy-1-piperidinyl}ethyl)-7-(methyloxy)-1,5-naphthyridin-2(1H)-one hydrochloride

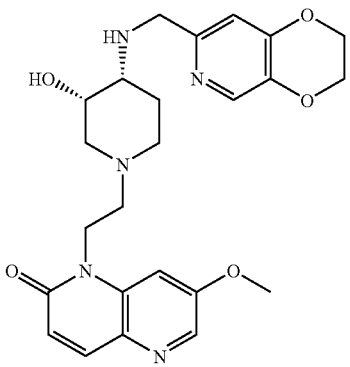

(a) 1,1-Dimethylethyl ((3S,4R)-3-hydroxy-1-{2-[7-(methyloxy)-2-oxo-1,5-naphthyridin-1(2H)-yl]ethyl}-4-piperidinyl)carbamate

[7-(methoxy)-2-oxo-1,5-naphthyridin-1(2H)-yl]acetaldehyde methyl hemiacetal (200 mg) and 1,1-dimethylethyl[(3S,4R)-3-hydroxy-4-piperidinyl]carbamate (for a synthesis see WO2004058144, Example 5(c), cis-(3-hydroxy-piperidin-4-yl)-carbamic acid tert-butyl ester Enantiomer 2) (182 mg) were stirred in chloroform (10 ml) plus MeOH (0.5 ml) under argon for 2 h. Sodium triacetoxyborohydride (534 mg) was added in one portion and the mixture was stirred at rt overnight, then quenched by addition of saturated aqueous sodium hydrogen cabonate (2 ml). The organic phase was separated using a hydrophobic frit and the aqueous phase was extracted with DCM (2×20 ml). The organic extracts were combined, dried over anhydrous magnesium sulphate, filtered and evaporated under reduced pressure to give the crude product, which was purified by column chromatography on silica, eluted with 0-20% (2M ammonia in MeOH) in DCM. Appropriate fractions were combined and evaporated under reduced pressure to give the title compound (226 mg) as an off-white foam.

MS (ES+) m/z 419 (MH$^+$)

(b) 1-{2-[(3S,4R)-4-amino-3-hydroxy-1-piperidinyl]ethyl}-7-(methyloxy)-1,5-naphthyridin-2(1H)-one Dihydrochloride 1,1-dimethylethyl ((3S,4R)-3-hydroxy-1-{2-[7-(methyloxy)-2-oxo-1,5-naphthyridin-1(2H)-yl]ethyl}-4-piperidinyl)carbamate (223 mg) was dissolved in DCM (2 ml) and the solution was treated with 4M hydrogen chloride in 1,4-dioxane (2 ml). Effervescence and formation of a precipitate was observed. After 2 h, the solvents were removed under reduced pressure and the residue was dried under reduced pressure overnight, to give the title compound as a pale yellow solid (209 mg).

MS (ES+) m/z 319 (MH$^+$)

(c) Title Compound

1-{2-[(3S,4R)-4-amino-3-hydroxy-1-piperidinyl]ethyl}-7-(methyloxy)-1,5-naphthyridin-2(1H)-one dihydrochloride (209 mg) was stirred in 9:1 v:v chloroform:MeOH (5 ml) at rt under argon and triethylamine (250 11) was added. The mixture was stirred at rt for 10 mins., then 2,3-dihydro[1,4]dioxino[2,3-c]pyridine-7-carboxaldehyde (88 mg, for a synthesis see WO2004058144, Example 2(c) or WO03/087098, Example 19(d)) was added and the mixture was stirred at rt for 4 hours before being treated with sodium triacetoxyborohydride (360 mg) added in one portion. The mixture was then stirred at rt overnight. Saturated aqueous sodium hydrogen cabonate (2 ml) was then added and the organic phase was diluted with DCM to bring the total volume to ca. 50 ml. The organic phase was separated using a hydrophobic frit and the aqueous phase was extracted with DCM (2×10 ml). The combined organic extracts were evaporated under reduced pressure and purified by MDAP to give the free base of the title compound as colourless gum (30 mg).

NMR δ (400 MHz, CDCl$_3$): 8.71 (1H, s), 8.29 (1H, d, J=2 Hz), 8.10 (1H, s), 7.87 (1H, d, J=10 Hz), 7.21 (1H, d, J=2 Hz), 6.85 (1H, s), 6.75 (1H, d, J=10 Hz), 4.58-4.46 (2H, m), 4.39-4.28 (4H, m), 4.08 (1H, s), 4.02 (2H, s), 4.00 (3H, s), 3.33-3.29 (1H, m), 3.00-2.90 (2H, m), 2.83-2.70 (2H, m), 2.42 (1H, d, J=11 Hz), 2.35-2.28 (1H, m), 1.92-1.81 (2H, m).

MS (ES+) m/z 468 (MH$^+$).

This material was converted to the hydrochloride by dissolving in DCM and adding 1 equivalent of 1M HCl/diethyl ether then evaporating to dryness. MS as that of the free base.

Example 67

1-[2-((3S,4S)-3-{[(2,3-dihydro[1,4]dioxino[2,3-c]pyridin-7-ylmethyl)amino]methyl}-4-hydroxy-1-pyrrolidinyl)ethyl]-7-(methyloxy)-1,5-naphthyridin-2(1H)-one Fumarate

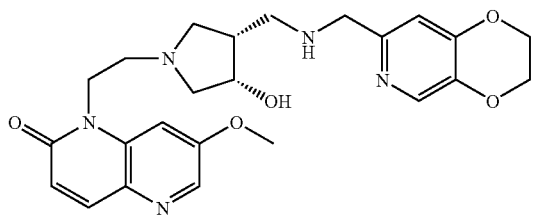

(a) Phenylmethyl [((3S,4S)-4-hydroxy-1-{2-[7-(methyloxy)-2-oxo-1,5-naphthyridin-1(2H)-yl]ethyl}-3-pyrrolidinyl)methyl]carbamate To a solution of [7-(methoxy)-2-oxo-1,5-naphthyridin-1(2H)-yl]acetaldehyde (as the methyl hemiacetal) (0.654 g, 3.0 mmol) in 1:1 (MeOH/CHCl$_3$) (50 mL) were added phenylmethyl {[(3R,4S)-4-hydroxy-3-pyrrolidinyl]methyl}carbamate (0.750 g, 3.0 mmol) and Na$_2$SO$_4$ (0.100 g) and the resulting solution stirred at ambient temperature for 18 hours. Na(OAc)$_3$BH (1.91 g, 9.0 mmol) was added and the solution stirred an additional 2 hours. The reaction mixture was concentrated onto silica gel and chromatographed on a silica gel column [0-100% CHCl$_3$/(90:10:1) CHCl$_3$/MeOH/NH$_4$OH)] to yield a colorless oil. (0.897 g, 66%).

LCMS: m/z 453 (M+H)+.

(b) 1-{2-[(3S,4S)-3-(Aminomethyl)-4-hydroxy-1-pyrrolidinyl]ethyl}-7-(methyloxy)-1,5-naphthyridin-2(1H)-one To a solution of phenylmethyl [((3S,4S)-4-hydroxy-1-{2-[7-(methyloxy)-2-oxo-1,5-naphthyridin-1(2H)-yl]ethyl}-3-pyrrolidinyl)methyl]carbamate (0.90 g, 1.99 mmol) in MeOH (30 mL) was added catalytic 10% Palladium on carbon (0.20 g) and the resulting solution subjected to H$_2$ at 50 PSI on a Parr shaker. The solution was filtered through a pad of Celite® and concentrated under reduced pressure to give the product (0.571 g, 90%).

LCMS: m/z 319 (M+H)+.

(c) Title Compound

To a solution of 1-{2-[(3S,4S)-3-(aminomethyl)-4-hydroxy-1-pyrrolidinyl]ethyl}-7-(methyloxy)-1,5-naphthyridin-2(1H)-one (0.114 g, 0.358 mmol) in 1:1 (MeOH/CH$_2$Cl$_2$) (25 mL) were added 2,3-dihydro[1,4]dioxino[2,3-c]pyridine-7-carboxaldehyde (for a synthesis see WO2004058144, Example 2(c) or WO03/087098, Example 19(d)) (0.059 g, 0.358 mmol) and sodium sulphate (0.100 g) and the resulting solution stirred for 18 h at ambient temperature. Na(OAc)$_3$BH (0.228 g, 1.07 mmol) was added and the solution stirred an additional 2 h. The reaction mixture was concentrated onto silica gel and chromatographed on a silica gel column [0-100% CHCl$_3$/(90:10:1) CHCl$_3$/MeOH/NH$_4$OH)] to yield a colorless oil. The title compound as fumarate salt was formed by treating with 1 equivalent of fumaric acid to yield an off white solid (0.048 g, 23%).

LCMS: m/z 468 (M+H)+.

1H NMR (400 MHz, CD$_3$OD) δ ppm 2.64-2.73 (m, 1H) 3.04-3.14 (m, 6H) 3.24 (ddd, J=18.44, 12.51, 5.94 Hz, 2H) 3.33 (dt, J=3.28, 1.64 Hz, 2H) 4.05 (s, 3H) 4.19 (s, 2H) 4.31-4.36 (m, 2H) 4.36-4.41 (m, 2H) 4.51-4.62 (m, 3H) 6.64-6.68 (m, 3H) 6.98 (s, 1H) 7.47 (d, J=2.27 Hz, 1H) 7.84 (d, J=9.60 Hz, 1H) 7.93 (s, 1H) 8.30 (d, J=2.27 Hz, 1H).

Example 68

6-({[((3S,4S)-4-hydroxy-1-{2-[7-(methyloxy)-2-oxo-1,5-naphthyridin-1(2H)-yl]ethyl}-3-pyrrolidinyl)methyl]amino}methyl)-2H-pyrido[3,2-b][1,4]oxazin-3(4H)-one fumarate

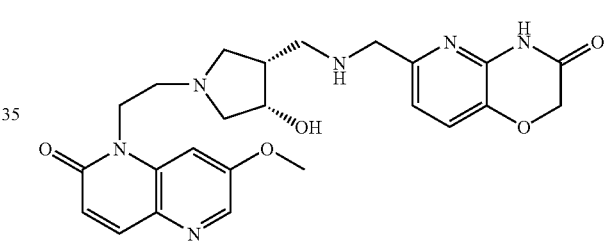

To a solution of 1-{2-[(3S,4S)-3-(aminomethyl)-4-hydroxy-1-pyrrolidinyl]ethyl}-7-(methyloxy)-1,5-naphthyridin-2(1H)-one (0.114 g, 0.358 mmol) in 1:1 (MeOH/CH$_2$Cl$_2$) (25 mL) were added 3-oxo-3,4-dihydro-2H-pyrido[3,2-b][1,4]oxazine-6-carboxaldehyde (for a synthesis see WO2003087098, Example 31(e) (0.064 g, 0.358 mmol) and sodium sulphate (0.10 g) and the resulting solution stirred for 18 hours at ambient temperature. Na(OAc)$_3$BH (0.228 g, 1.07 mmol) was added and the solution stirred an additional 2 hours. The reaction mixture was concentrated onto silica gel and chromatographed on a silica gel column [0-100% CHCl$_3$/(90:10:1) CHCl$_3$/MeOH/NH$_4$OH)] to yield a colorless oil. A fumarate salt was formed by treating with 1 equivalent of fumaric acid to yield the title compound as an off white solid (0.038 g, 18%).

LCMS: m/z 481 (M+H)+.

1H NMR (400 MHz, CD$_3$OD) δ ppm 2.68-2.78 (m, 1H) 2.96-3.06 (m, 3H) 3.06-3.16 (m, 3H) 3.23 (dd, J=12.51, 5.18 Hz, 1H) 3.33 (dt, J=3.28, 1.64 Hz, 3H) 4.01-4.07 (m, 3H) 4.26 (d, J=1.77 Hz, 2H) 4.45-4.57 (m, 2H) 4.59-4.67 (m, 1H) 4.69 (d, J=1.26 Hz, 2H) 6.62 (d, J=9.60 Hz, 1H) 6.66 (s, 2H) 7.09 (d, J=8.08 Hz, 1H) 7.36 (d, J=8.08 Hz, 1H) 7.46 (d, J=2.27 Hz, 1H) 7.86 (d, J=9.60 Hz, 1H) 8.29 (d, J=2.27 Hz, 1H)

Example 69

6-({[((3S,4S)-4-hydroxy-1-{2-[7-(methyloxy)-2-oxo-1,5-naphthyridin-1(2H)-yl]ethyl}-3-pyrrolidinyl)methyl]amino}methyl)-2H-pyrido[3,2-b][1,4]thiazin-3(4H)-one Fumarate

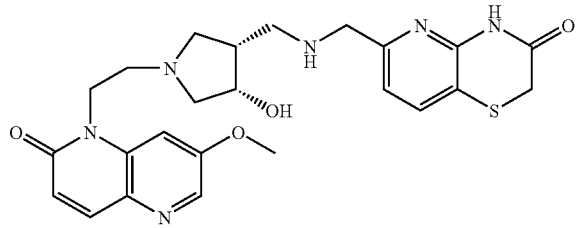

To a solution of 1-{2-[(3S,4S)-3-(aminomethyl)-4-hydroxy-1-pyrrolidinyl]ethyl}-7-(methyloxy)-1,5-naphthyridin-2(1H)-one (0.114 g, 0.358 mmol) in 1:1 (MeOH/CH$_2$Cl$_2$) (25 mL) were added 3-oxo-3,4-dihydro-2H-pyrido[3,2-b][1,4]thiazine-6-carboxaldehyde (for a synthesis, see WO2004058144, Example 7(d)) (0.070 g, 0.358 mmol) and sodium sulphate (0.100 g) and the resulting solution stirred for 18 hours at ambient temperature. Na(OAc)$_3$BH (0.228 g, 1.07 mmol) was added and the solution stirred an additional 2 hours. The reaction mixture was concentrated onto silica gel and chromatographed on a silica gel column [0-100% CHCl$_3$/(90:10:1) CHCl$_3$/MeOH/NH$_4$OH)] to yield a colorless oil. A fumarate salt was formed by treating with 1 equivalent of fumaric acid to yield the title compound as an off white solid (0.053 g, 24%).

LCMS: m/z 497 (M+H)+.

1H NMR (400 MHz, CD$_3$OD) δ ppm 2.70-2.79 (m, 1H) 2.96-3.07 (m, 3H) 3.07-3.17 (m, 3H) 3.24 (dd, J=12.63, 5.05 Hz, 1H) 3.33 (dt, J=3.28, 1.64 Hz, 3H) 3.37 (m, 1H) 3.51-3.59 (m, 2H) 4.01-4.07 (m, 3H) 4.27-4.35 (m, 2H) 4.45-4.57 (m, 2H) 4.58-4.69 (m, 1H) 6.59 (d, J=9.60 Hz, 1H) 6.66 (s, 2H) 7.12 (d, J=7.83 Hz, 1H) 7.46 (d, J=2.02 Hz, 1H) 7.80 (d, J=7.83 Hz, 1H) 7.87 (d, J=9.60 Hz, 1H) 8.30 (d, J=2.53 Hz, 1H).

Example 70

1-[2-((3S,4S)-3-{[(6,7-dihydro[1,4]dioxino[2,3-c]pyridazin-3-ylmethyl)amino]methyl}-4-hydroxy-1-pyrrolidinyl)ethyl]-7-(methyloxy)-1,5-naphthyridin-2(1H)-one Fumarate

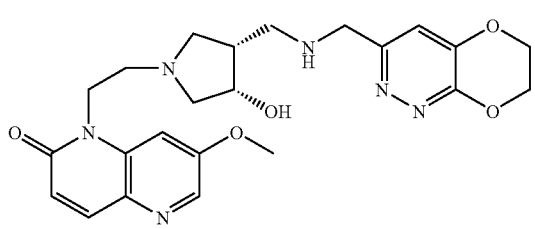

To a solution of 1-{2-[(3S,4S)-3-(aminomethyl)-4-hydroxy-1-pyrrolidinyl]ethyl}-7-(methyloxy)-1,5-naphthyridin-2(1H)-one (0.114 g, 0.358 mmol) in 1:1 (MeOH/CH$_2$Cl$_2$) (25 mL) were added 6,7-dihydro[1,4]dioxino[2,3-c]pyridazine-3-carbaldehyde (0.060 g, 0.358 mmol) and sodium sulphate (0.100 g) and the resulting solution stirred for 18 h at ambient temperature. Na(OAc)$_3$BH (0.228 g, 1.07 mmol) was added and the solution stirred an additional 2 hours. The reaction mixture was concentrated onto silica gel and chromatographed on a silica gel column [0-100% CHCl$_3$/(90:10:1) CHCl$_3$/MeOH/NH$_4$OH)] to yield a colorless oil.

LCMS: m/z 469 (M+H)+.

1H NMR (400 MHz, CD$_3$OD) δ ppm 2.41 (d, J=7.83 Hz, 1H) 2.61 (t, J=8.72 Hz, 1H) 2.66-2.74 (m, 2H) 2.81-2.90 (m, 3H) 2.92-2.98 (m, 1H) 3.13 (dd, J=10.36, 5.56 Hz, 1H) 3.96 (d, J=2.53 Hz, 2H) 4.06 (s, 3H) 4.38 (td, J=6.00, 3.16 Hz, 1H) 4.43-4.52 (m, 4H) 4.54-4.61 (m, 2H) 6.74 (d, J=9.60 Hz, 1H) 7.24 (s, 1H) 7.52 (d, J=2.27 Hz, 1H) 7.92 (d, J=9.60 Hz, 1H) 8.30 (d, J=2.27 Hz, 1H).

A fumarate salt was formed by treating with 1 equivalent of fumaric acid to yield the title compound as an off white solid (0.018 g, 8%).

Example 71

7-chloro-6-({[((3S,4S)-4-hydroxy-1-{2-[7-(methyloxy)-2-oxo-1,5-naphthyridin-1(2H)-yl]ethyl}-3-pyrrolidinyl)methyl]amino}methyl)-2H-pyrido[3,2-b][1,4]oxazin-3(4H)-one Fumarate

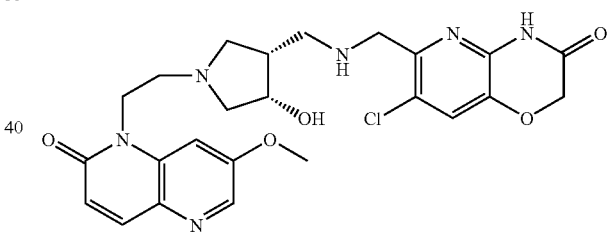

To a solution of 1-{2-[(3S,4S)-3-(aminomethyl)-4-hydroxy-1-pyrrolidinyl]ethyl}-7-(methyloxy)-1,5-naphthyridin-2(1H)-one (0.114 g, 0.358 mmol) in 1:1 (MeOH/CH$_2$Cl$_2$) (25 mL) were added 7-chloro-3-oxo-3,4-dihydro-2H-pyrido[3,2-b][1,4]oxazine-6-carboxaldehyde (for a synthesis see WO2003064421, Example 15(c))(0.076 g, 0.358 mmol) and sodium sulphate (0.100 g) and the resulting solution stirred for 18 h at ambient temperature. Na(OAc)$_3$BH (0.228 g, 1.07 mmol) was added and the solution stirred an additional 2 h. The reaction mixture was concentrated onto silica gel and chromatographed on a silica gel column [0-100% CHCl$_3$/(90:10:1) CHCl$_3$/MeOH/NH$_4$OH)] to yield a colorless oil. A fumarate salt was formed by treating with 1 equivalent of fumaric acid to yield the title compound as an off white solid (0.078 g, 34%).

LCMS: m/z 515 (M+H)+.

1H NMR (400 MHz, DMSO-d$_6$) δ ppm 2.23-2.34 (m, 1H) 2.63-2.71 (m, 2H) 2.71-2.80 (m, 2H) 2.85 (dd, J=11.75, 7.20 Hz, 1H) 2.90-2.95 (m, 1H) 3.08 (dd, J=10.11, 5.81 Hz, 1H) 3.81-3.91 (m, 3H) 3.98 (s, 4H) 4.20 (td, J=6.13, 3.66 Hz, 1H) 4.31-4.41 (m, 2H) 4.68 (s, 3H) 6.56 (s, 3H) 6.64 (d, J=9.85

Hz, 1H) 7.40 (d, J=2.27 Hz, 1H) 7.56 (s, 1H) 7.85 (d, J=9.85 Hz, 1H) 8.28 (d, J=2.53 Hz, 1H).

Example 72

6-({[((3S)-1-{2-[7-(methyloxy)-2-oxo-1,5-naphthyridin-1(2H)-yl]ethyl}-3-pyrrolidinyl)methyl]amino}methyl)-2H-pyrido[3,2-b][1,4]oxazin-3(4H)-one

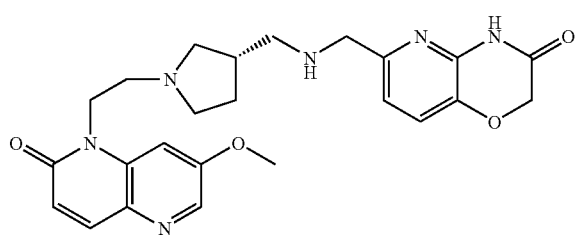

(a) Phenylmethyl [((3S)-1-{2-[7-(methyloxy)-2-oxo-1,5-naphthyridin-1(2H)-yl]ethyl}-3-pyrrolidinyl)methyl]carbamate To a solution of [7-(methoxy)-2-oxo-1,5-naphthyridin-1(2H)-yl]acetaldehyde (as the methyl hemiacetal) (0.500 g, 2.29 mmol) 1:4 (MeOH/CH$_2$Cl$_2$) (40 mL) were added phenylmethyl [(3R)-3-pyrrolidinyl-methyl]carbamate (for a synthesis see WO2006002047 Preparation 23(b)) (0.536 g, 2.29 mmol) and triethylamine (0.351 mL, 2.52 mmol) and the resulting solution stirred at ambient temperature for 1 h. Na(OAc)$_3$BH (1.46 g, 6.87 mmol) was added and the solution stirred an additional 18 hours. The reaction mixture was concentrated onto silica gel and chromatographed on a silica gel column [0-100% CHCl$_3$/(90:10:1) CHCl$_3$/MeOH/NH$_4$OH)] to yield a colorless oil, (0.333 g, 33%).

LCMS: m/z 437 (M+H)+.

(b) 1-{2-[(3S)-3-(Aminomethyl)-1-pyrrolidinyl]ethyl}-7-(methyloxy)-1,5-naphthyridin-2(1H)-one To a solution of phenylmethyl [((3S)-1-{2-[7-(methyloxy)-2-oxo-1,5-naphthyridin-1(2H)-yl]ethyl}-3-pyrrolidinyl)methyl]carbamate (0.33 g, 0.761 mmol) in MeOH (30 mL) was added catalytic 10% Palladium on carbon (0.20 g) and the resulting solution was subjected to H$_2$ at 50 PSI on a Parr shaker. The solution was filtered through a pad of Celite® and concentrated under reduced pressure to yield a colorless oil, (0.100 g, 43%).

LCMS: m/z 303 (M+H)+.

(c) Title Compound

To a solution of 1-{2-[(3S)-3-(aminomethyl)-1-pyrrolidinyl]ethyl}-7-(methyloxy)-1,5-naphthyridin-2(1H)-one (0.050 g, 0.165 mmol) in 1:1 (MeOH/CH$_2$Cl$_2$) (15 mL) were added 3-oxo-3,4-dihydro-2H-pyrido[3,2-b][1,4]oxazine-6-carboxaldehyde (for a synthesis see WO2003087098, Example 31(e)) (0.029 g, 0.165 mmol) and sodium sulphate (0.05 g) and the resulting solution stirred for 18 hours at ambient temperature. Na(OAc)$_3$BH (0.105 g, 0.496 mmol) was added and the solution stirred an additional 2 hours. The reaction mixture was concentrated onto silica gel and chromatographed on a silica gel column) [0-100% CHCl$_3$/(90:10:1) CHCl$_3$/MeOH/NH$_4$OH)] to yield a colorless oil. The oil was purified by HPLC(CH$_3$CN/H$_2$O) to yield the title compound as a white solid, (0.0065 g, 9%).

LCMS: m/z 465 (M+H)+.

1H NMR (400 MHz, CD$_3$OD) δ ppm 1.53 (dd, J=13.01, 6.19 Hz, 1H) 2.02-2.12 (m, 1H) 2.40-2.52 (m, 2H) 2.63 (d, J=7.07 Hz, 2H) 2.72-2.81 (m, 3H) 2.82-2.86 (m, 1H) 2.87-2.95 (m, 1H) 3.74-3.82 (m, 2H) 4.05 (s, 3H) 4.49 (t, J=7.45 Hz, 2H) 4.65 (s, 2H) 6.76 (d, J=9.85 Hz, 1H) 6.98 (d, J=8.08 Hz, 1H) 7.28 (d, J=8.08 Hz, 1H) 7.50 (d, J=2.27 Hz, 1H) 7.93 (d, J=9.60 Hz, 1H) 8.30 (d, J=2.53 Hz, 1H).

Example 73

6-({[((3S,4S)-4-hydroxy-1-{2-[7-(methyloxy)-2-oxo-1(2H)-quinolinyl]ethyl}-3-pyrrolidinyl)methyl]amino}methyl)-2H-pyrido[3,2-b][1,4]oxazin-3(4H)-one hydrochloride

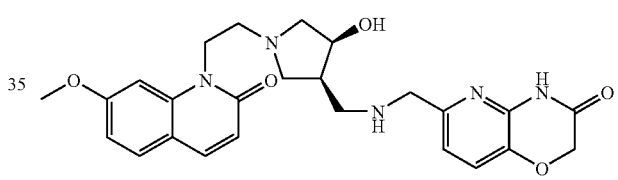

1-{2-[(3S,4S)-3-(Aminomethyl)-4-hydroxy-1-pyrrolidinyl]ethyl}-7-(methyloxy)-2(1H)-quinolinone (116 mg, 0.365 mmol) and 3-oxo-3,4-dihydro-2H-pyrido[3,2-b][1,4]oxazine-6-carboxaldehyde (for a synthesis see WO2003087098, Example 31(e)) (72 mg, 0.402 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (243 mg, 1.1 mmol) was added and stirred for 1 h. The reaction mixture was concentrated and purified to obtain the free base of the title compound as a pale yellow oil (91 mg, 40%) after column chromatography (90:10:1:DCM:MeOH:NH$_4$OH).

MS (ES+) m/z 480.3 (MH$^+$).

1H NMR (400 MHz, CD$_3$OD) δ ppm 2.72 (d, J=5.05 Hz, 1H) 2.99 (d, J=17.68 Hz, 3H) 3.06-3.14 (m, 1H) 3.14-3.20 (m, 1H) 3.22-3.30 (m, 1H) 3.33 (s, 4H) 3.38 (s, 1H) 3.96 (s, 3H) 4.23-4.33 (m, 2H) 4.41-4.51 (m, 1H) 4.55 (s, 1H) 4.63-4.73 (m, 3H) 6.34 (d, J=9.35 Hz, 1H) 6.96-7.05 (m, 2H) 7.11 (d, J=7.83 Hz, 1H) 7.39 (d, J=7.83 Hz, 1H) 7.65 (d, J=8.59 Hz, 1H) 7.80 (d, J=9.35 Hz, 1H).

The title compound hydrochloride salt was made by addition of 43 µL (one equivalent) of 4N HCl/1,4-dioxane to a solution of the free base.

Example 74

1-[2-((3S,4S)-3-{[(2,3-dihydro[1,4]dioxino[2,3-c]pyridin-7-ylmethyl)amino]methyl}-4-hydroxy-1-pyrrolidinyl)ethyl]-7-(methyloxy)-2(1H)-quinolinone Hydrochloride

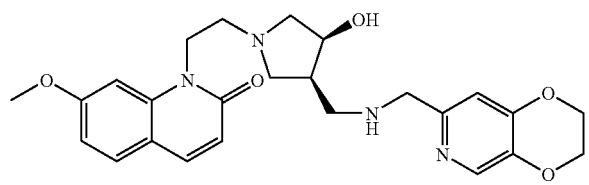

1-{2-[(3S,4S)-3-(Aminomethyl)-4-hydroxy-1-pyrrolidinyl]ethyl}-7-(methyloxy)-2(1H)-quinolinone (94 mg, 0.296 mmol) and 2,3-dihydro[1,4]dioxino[2,3-c]pyridine-7-carboxaldehyde (for a synthesis see WO2004058144, Example 2(c) or WO03/087098, Example 19(d)) (54 mg, 0.326 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (197 mg, 0.884 mmol) was added and stirred for 1 h. The reaction mixture was concentrated and purified to obtain the free base of the title compound as a pale oil (62 mg, 45%) after column:chromatography (90:10:1: DCM:MeOH:NH$_4$OH).

MS (ES+) m/z 467.5 (MH$^+$).

1H NMR (400 MHz, CD$_3$OD) δ ppm 2.62-2.72 (m, 1H) 2.87 (dd, J 9.60, 7.58 Hz, 1H) 2.94-3.00 (m, 3H) 3.02-3.06 (m, 2H) 3.23 (d, J=5.56 Hz, 2H) 3.33 (dt, J 3.28, 1.64 Hz, 1H) 3.94-4.00 (m, 3H) 4.19 (s, 2H) 4.31-4.41 (m, 5H) 4.50-4.60 (m, 3H) 6.37 (d, J=9.35 Hz, 1H) 6.94-7.03 (m, 3H) 7.60 (d, J=8.84 Hz, 1H) 7.75 (d, J=9.35 Hz, 1H) 7.92 (s, 1H).

The title compound hydrochloride salt was made by addition of 33 uL (one equivalent) of 4N HCl/1,4-dioxane to a solution of the free base.

Example 75

1-[2-((3S,4S)-3-{[(6,7-dihydro[1,4]dioxino[2,3-c]pyridazin-3-ylmethyl)amino]methyl}-4-hydroxy-1-pyrrolidinyl)ethyl]-7-(methyloxy)-2(1H)-quinolinone hydrochloride

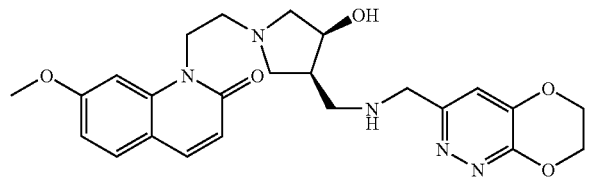

1-{2-[(3S,4S)-3-(Aminomethyl)-4-hydroxy-1-pyrrolidinyl]ethyl}-7-(methyloxy)-2(1H)-quinolinone (118 mg, 0.372 mmol) and 6,7-dihydro[1,4]dioxino[2,3-c]pyridazine-3-carbaldehyde (68 mg, 0.409 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (247 mg, 1.12 mmol) was added and stirred for 1 h. The reaction mixture was concentrated and purified to obtain the free base of the title compound as a pale oil (35 mg, 20%) after column:chromatography (90:10:1: DCM:MeOH:NH$_4$OH).

MS (ES+) m/z 468.3 (MH$^+$).

1H NMR (400 MHz, CD$_3$OD) δ ppm 2.65 (d, J=5.05 Hz, 1H) 3.07 (s, 1H) 3.12-3.20 (m, 3H) 3.20-3.29 (m, 4H) 3.97 (s, 3H) 4.31 (d, J=2.02 Hz, 2H) 4.48 (d, J=4.04 Hz, 2H) 4.53 (s, 1H) 4.59 (s, 5H) 6.40 (d, J=9.35 Hz, 1H) 6.96-7.06 (m, 2H) 7.21 (s, 1H) 7.62 (d, J=8.59 Hz, 1H) 7.78 (d, J=9.35 Hz, 1H).

The title compound, hydrochloride salt was made by addition of 19 μL (one equivalent) of 4N HCl/1,4-dioxane to a solution of the free base.

Example 76

6-{[({(3S,4S)-1-[2-(7-fluoro-2-oxo-1(2H)-quinolinyl)ethyl]-4-hydroxy-3-pyrrolidinyl}methyl)amino]methyl}-2H-pyrido[3,2-b][1,4]thiazin-3(4H)-one Hydrochloride

A solution of 1-{2-[(3S,4S)-3-(aminomethyl)-4-hydroxy-1-pyrrolidinyl]ethyl}-7-fluoro-2(1H)-quinolinone (100 mg; 0.33 mmol) and 3-oxo-3,4-dihydro-2H-pyrido[3,2-b][1,4]thiazine-6-carboxaldehyde (for a synthesis, see WO2004058144, Example 7(d) (64 mg, 0.33 mmol) in methanol (2 mL), DCM (4 mL) was stirred at room temperature overnight. Sodium triacetoxyborohydride (0.13 g; 0.6 mmol) was added and the mixture was stirred at room temperature for 1 hours. The reaction was evaporated and chromatographed on silica gel, eluting with 0-10% methanol-DCM-1% NH$_4$OH to give an oil. The oil was treated with 1M HCl in Et$_2$O to give the title compound (60 mg) as the dihydrochloride salt.

1H NMR (400 MHz, CD$_3$OD) δ ppm 2.37-2.46 (m, 1H) 2.59 (t, J=8.72 Hz, 1H) 2.63-2.71 (m, 2H) 2.77-2.89 (m, 2H) 2.93-3.00 (m, 1H) 3.15 (dd, J=10.48, 5.43 Hz, 1H) 3.33 (dt, J=3.28, 1.64 Hz, 3H) 3.52 (s, 2H) 3.77-3.85 (m, 2H) 4.37 (td, J=5.94, 3.28 Hz, 1H) 4.42-4.48 (m, 2H) 6.62 (d, J=9.60 Hz, 1H) 7.03 (d, J=7.83 Hz, 1H) 7.10 (td, J=8.46, 2.27 Hz, 1H) 7.42 (dd, J=11.62, 2.27 Hz, 1H) 7.69 (d, J=7.58 Hz, 1H) 7.75 (dd, J=8.72, 6.19 Hz, 1H) 7.90 (d, J=9.35 Hz, 1H).

MS (+ve ion electrospray) m/z 484 (M+H)+.

Addition of one equivalent of benzoic acid to a solution of 6-{[({(3S,4S)-1-[2-(7-fluoro-2-oxo-1(2H)-quinolinyl)ethyl]-4-hydroxy-3-pyrrolidinyl}methyl)amino]methyl}-2H-pyrido[3,2-b][1,4]thiazin-3(4H)-one, followed by evaporation, provided the benzoate salt.

Example 77

6-{[({(3S,4S)-1-[2-(7-fluoro-2-oxo-1(2H)-quinolinyl)ethyl]-4-hydroxy-3-pyrrolidinyl}methyl)amino]methyl}-2H-pyrido[3,2-b][1,4]oxazin-3(4H)-one dihydrochloride

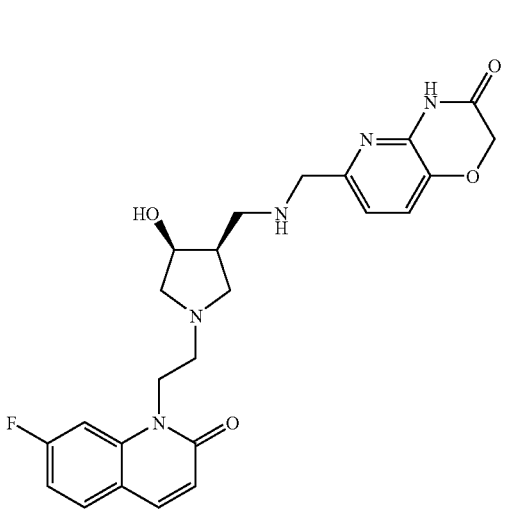

(a) 1-{2-[(3S,4S)-3-(aminomethyl)-4-hydroxy-1-pyrrolidinyl]ethyl}-7-fluoro-2(1H)-quinolinone Prepared as for Example 78 (a)-(b) using 7-fluoro-2-oxo-1(2H)-quinolinyl)acetaldehyde (0.205 g, 1 mmol) and phenylmethyl {[(3R,4S)-4-hydroxy-3-pyrrolidinyl]methyl}carbamate (b) 6-{[({(3S,4S)-1-[2-(7-fluoro-2-oxo-1(2H)-quinolinyl)ethyl]-4-hydroxy-3-pyrrolidinyl}methyl)amino]methyl}-2H-pyrido[3,2-b][1,4]oxazin-3(4H)-one A solution of 1-{2-[(3S,4S)-3-(aminomethyl)-4-hydroxy-1-pyrrolidinyl]ethyl}-7-fluoro-2(1H)-quinolinone (100 mg; 0.33 mmol) and 3-oxo-3,4-dihydro-2H-pyrido[3,2-b][1,4]oxazine-6-carboxaldehyde (for a synthesis see WO2003087098, Example 31(e)) (60 mg, 0.33 mmol) in methanol (2 mL), DCM (4 mL) was stirred at room temperature overnight. Sodium triacetoxyborohydride (0.13 g; 0.6 mmol) was added and the mixture was stirred at room temperature for 1 hour. The reaction was evaporated and chromatographed on silica gel, eluting with 0-20% methanol-DCM-2% NH$_4$OH to give an oil. The oil was treated with 1M HCl in Et$_2$O to give the title compound (73 mg) as the dihydrochloride salt.

1H NMR (400 MHz, CD$_3$OD) δ ppm 2.36-2.46 (m, 1H) 2.58 (t, J=8.84 Hz, 1H) 2.62-2.71 (m, 2H) 2.78-2.84 (m, 1H) 2.85-2.88 (m, 1H) 2.98 (dd, J=9.09, 7.83 Hz, 1H) 3.15 (dd, J=10.36, 5.56 Hz, 1H) 3.33 (dt, J=3.28, 1.64 Hz, 3H) 3.73-3.81 (m, 2H) 4.36 (td, J=6.06, 3.28 Hz, 1H) 4.42-4.47 (m, 2H) 4.64 (s, 2H) 6.62 (d, J=9.60 Hz, 1H) 6.98 (d, J=8.08 Hz, 1H) 7.10 (td, J=8.46, 2.27 Hz, 1H) 7.27 (d, J=8.08 Hz, 1H) 7.42 (dd, J=11.49, 2.15 Hz, 1H) 7.75 (dd, J=8.59, 6.32 Hz, 1H) 7.90 (d, J=9.60 Hz, 1H).

MS (+ve ion electrospray) m/z 468 (M+H)+.

Example 78

6-{[({(3R,4R)-1-[2-(7-fluoro-2-oxo-1(2H)-quinolinyl)ethyl]-4-hydroxy-3-pyrrolidinyl}methyl)amino]methyl}-2H-pyrido[3,2-b][1,4]oxazin-3(4H)-one Dihydrochloride

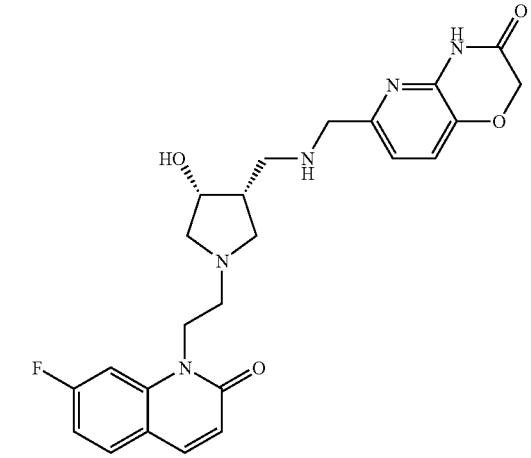

(a) Phenylmethyl ({(3R,4R)-1-[2-(7-fluoro-2-oxo-1(2H)-quinolinyl)ethyl]-4-hydroxy-3-pyrrolidinyl}methyl)carbamate A solution of 7-fluoro-2-oxo-1(2H)-quinolinyl)acetaldehyde (0.205 g, 1 mmol) and phenylmethyl {[(3S,4R-4-hydroxy-3-pyrrolidinyl]methyl}carbamate (for a synthesis see Example 52(f) or WO2006002047 Preparation 24(d) (±)-phenylmethyl {[cis-4-hydroxy-3-pyrrolidinyl]methyl}carbamate E2 isomer) (0.25 g, 1 mmol) in methanol (1 mL) and chloroform (3 mL) was stirred at room temperature overnight and sodium triacetoxyborohydride (0.636 g; 3 mmol) was added and the mixture was stirred at room temperature for 2 hours. The mixture was extracted (3×) with DCM, dried (Na$_2$SO$_4$), evaporated, and chromatographed on silica gel, eluting with 0-10% methanol-DCM-1% NH$_4$OH to give the product as a foam (0.3 g).

MS (+ve ion electrospray) m/z 440 (M+H)+.

(b) 1-{2-[(3R,4R)-3-(aminomethyl)-4-hydroxy-1-pyrrolidinyl]ethyl}-7-fluoro-2(1H)-quinolinone A solution of phenylmethyl ({(3R,4R)-1-[2-(7-fluoro-2-oxo-1(2H)-quinolinyl)ethyl]-4-hydroxy-3-pyrrolidinyl}methyl)carbamate (0.3 g) in dry methanol (15 mL) was treated with 10% Pd/C (0.08 g) and shaken under 15 psi at room temperature for 2 hours. The Pd catalyst was filtered through Celite®. The filtrate was evaporated to dryness to give an oil (0.2 g).

MS (+ve ion electrospray) m/z 305 (M+H)+.

(c) Title Compound

A solution of 1-{2-[(3R,4R)-3-(aminomethyl)-4-hydroxy-1-pyrrolidinyl]ethyl}-7-fluoro-2(1H)-quinolinone (90 mg;

0.3 mmol) and 3-oxo-3,4-dihydro-2H-pyrido[3,2-b][1,4]oxazine-6-carboxaldehyde (for a synthesis see WO2003087098, Example 31(e)) (53 mg, 0.3 mmol) in methanol (2 mL), DCM (4 mL) was stirred at room temperature overnight. Sodium triacetoxyborohydride (0.127 g; 0.6 mmol) was added and the mixture was stirred at room temperature for 1 hour. The reaction was evaporated and chromatographed on silica gel, eluting with 0-15% methanol-DCM-1% NH₄OH to give an oil. The oil was treated with 1M HCl in Et₂O to give the title compound (36 mg) as the dihydrochloride salt.

1H NMR (400 MHz, CD₃OD) δ ppm 2.38-2.46 (m, 1H) 2.58 (t, J=8.84 Hz, 1H) 2.63-2.71 (m, 2H) 2.79-2.84 (m, 1H) 2.86-2.91 (m, 1H) 2.98 (dd, J=8.97, 7.96 Hz, 1H) 3.15 (dd, J=10.48, 5.43 Hz, 1H) 3.33 (dt, J=3.28, 1.64 Hz, 5H) 3.78 (d, J=1.52 Hz, 2H) 4.36 (td, J=6.06, 3.28 Hz, 1H) 4.43-4.48 (m, 2H) 4.65 (s, 2H) 6.62 (d, J=9.35 Hz, 1H) 6.98 (d, J=8.08 Hz, 1H) 7.11 (td, J=8.46, 2.27 Hz, 1H) 7.27 (d, J=8.08 Hz, 1H) 7.42 (dd, J=11.49, 2.15 Hz, 1H) 7.76 (dd, J=8.59, 6.32 Hz, 1H) 7.91 (d, J=9.60 Hz, 1H).

MS (+ve ion electrospray) m/z 468 (M+H)+.

Example 79

6-{[({(3R,4R)-1-[2-(7-fluoro-2-oxo-1(2H)-quinolinyl)ethyl]-4-hydroxy-3-pyrrolidinyl}methyl)amino]methyl}-2H-pyrido[3,2-b][1,4]thiazin-3(4H)-one Dihydrochloride

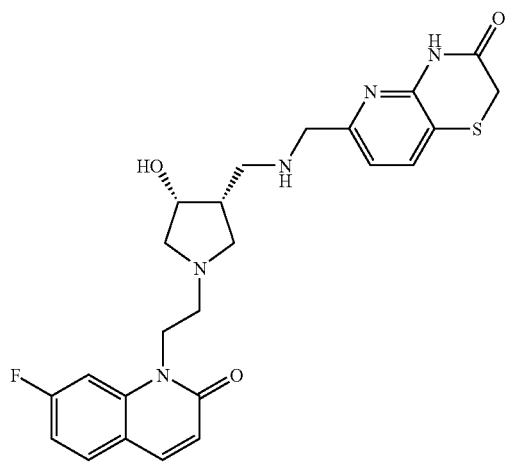

A solution of 1-{2-[(3R,4R)-3-(aminomethyl)-4-hydroxy-1-pyrrolidinyl]ethyl}-7-fluoro-2(1H)-quinolinone (90 mg; 0.3 mmol) and 3-oxo-3,4-dihydro-2H-pyrido[3,2-b][1,4]thiazine-6-carboxaldehyde (for a synthesis, see WO2004058144, Example 7(d) (60 mg, 0.3 mmol) in methanol (2 mL), DCM (4 mL) was stirred at room temperature overnight. Sodium triacetoxyborohydride (0.127 g; 0.6 mmol) was added and the mixture was stirred at room temperature for 1 hour. The reaction was evaporated and chromatographed on silica gel, eluting with 0-15% methanol-DCM-1% NH₄OH to give an oil. The oil was treated with 1M HCl in Et₂O to give the title compound (40 mg) as the dihydrochloride salt.

1H NMR (400 MHz, CD₃OD) δ ppm 3.37 (none, 21H) 2.38-2.47 (m, 1H) 2.59 (t, J=8.84 Hz, 1H) 2.63-2.71 (m, 2H) 2.77-2.87 (m, 2H) 2.88-2.91 (m, 1H) 2.97 (dd, J=9.09, 7.83 Hz, 1H) 3.15 (dd, J=10.36, 5.56 Hz, 1H) 3.33 (dt, J=3.28, 1.64 Hz, 3H) 3.52 (s, 2H) 3.77-3.85 (m, 2H) 4.34-4.40 (m, 1H) 4.42-4.49 (m, 2H) 6.62 (d, J=9.35 Hz, 1H) 7.03 (d, J=7.83 Hz, 1H) 7.10 (td, J=8.46, 2.27 Hz, 1H) 7.42 (dd, J=11.49, 2.15 Hz, 1H) 7.69 (d, J=7.83 Hz, 1H) 7.75 (dd, J=8.59, 6.32 Hz, 1H) 7.90 (d, J=9.35 Hz, 1H).

MS (+ve ion electrospray) m/z 484 (M+H)+.

Example 80

6-{[({(3S,4S)-1-[2-(7-fluoro-2-oxo-1,5-naphthyridin-1(2H)-yl)ethyl]-4-hydroxy-3-pyrrolidinyl}methyl)amino]methyl}-2H-pyrido[3,2-b][1,4]oxazin-3(4H)-one Hydrochloride

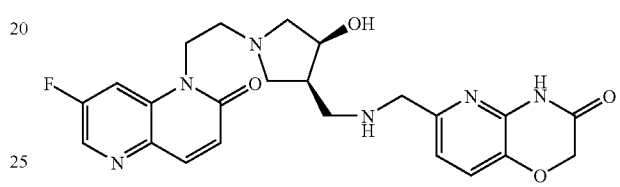

(a) Phenylmethyl ({(3S,4S)-1-[2-(7-fluoro-2-oxo-1,5-naphthyridin-1(2H)-yl)ethyl]-4-hydroxy-3-pyrrolidinyl}methyl)carbamate Phenylmethyl {[(3R,4S)-4-hydroxy-3-pyrrolidinyl]methyl}carbamate (1.17 g; 4.560 mmol) and (7-fluoro-2-oxo-1,5-naphthyridin-1(2H)-yl)acetaldehyde (as the methyl hemiacetal)) (855 mg, 4.17 mmol) were combined in anhydrous DCM (5 ml) and anhydrous MeOH (1 ml) with a spatula of solid sodium carbonate. The reaction mixture was stirred under nitrogen for 1 h then sodium triacetoxyborohydride (2.76 g; 12.44 mmol) was added and stirred overnight. The reaction mixture was concentrated and the title compound was obtained as a pale yellow oil (1.69 mg, 87%) after column:chromatography (90:10: DCM:MeOH).

MS (ES+) m/z 442.4 (MH+).

(b) 1-{2-[(3S,4S)-3-(aminomethyl)-4-hydroxy-1-pyrrolidinyl]ethyl}-7-fluoro-1,5-naphthyridin-2(1H)-one To a solution of phenylmethyl ({(3S,4S)-1-[2-(7-fluoro-2-oxo-1,5-naphthyridin-1(2H)-yl)ethyl]-4-hydroxy-3-pyrrolidinyl}methyl)carbamate (1.7 g; 3.85 mmol) was added 10% Pd/C, degassed and placed under 1 atm of H₂ for 18 h. The reaction mixture was filtered through Celite and concentrated to obtain the title compound as a yellow oil (1.3 g; 100%).

MS (ES+) m/z 307.3 (MH+).

(c) Title Compound

1-{2-[(3S,4S)-3-(Aminomethyl)-4-hydroxy-1-pyrrolidinyl]ethyl}-7-fluoro-1,5-naphthyridin-2(1H)-one (108 mg; 0.353 mmol) and 3-oxo-3,4-dihydro-2H-pyrido[3,2-b][1,4]oxazine-6-carboxaldehyde (for a synthesis see WO2003087098, Example 31(e)) (69 mg; 0.388 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (235 mg; 1.06 mmol) was added and stirred for 1 h. The reaction mixture was concentraed and purified to obtain the free base of the title compound as a pale yellow oil (80 mg; 48%) after column chromatography (90:10:1: DCM:MeOH:NH$_4$OH).

MS (ES+) m/z 470.5 (MH$^+$).

1H NMR (400 MHz, CD$_3$OD) δ ppm 2.69 (d, J=6.06 Hz, 1H) 2.84 (d, J=7.07 Hz, 1H) 2.88-2.95 (m, 2H) 2.99-3.09 (m, 1H) 3.12 (dd, J 9.60, 4.80 Hz, 1H) 3.19-3.29 (m, 1H) 3.68 (s, 2H) 4.24-4.31 (m, 2H) 4.32-4.42 (m, 1H) 4.47-4.55 (m, 1H) 4.57-4.68 (m, 1H) 4.71 (d, J=1.77 Hz, 2H) 6.72 (d, J=9.85 Hz, 1H) 7.11 (d, J=7.83 Hz, 1H) 7.39 (d, J=8.08 Hz, 1H) 7.89-8.00 (m, 2H) 8.52 (d, J 2.02 Hz, 1H).

The title compound, hydrochloride salt was made by addition of 43 μL (one equivalent) of 4N HCl/1,4-dioxane to a solution of the free base.

Example 81

6-{[({(3S,4S)-1-[2-(7-fluoro-2-oxo-1,5-naphthyridin-1(2H)-yl)ethyl]-4-hydroxy-3-pyrrolidinyl}methyl)amino]methyl}-2H-pyrido[3,2-b][1,4]thiazin-3(4H)-one Hydrochloride

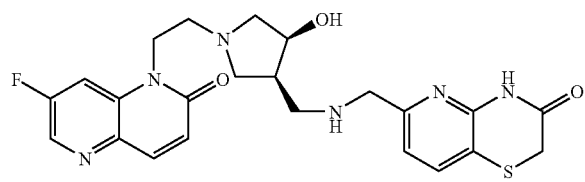

1-{2-[(S,4S)-3-(Aminomethyl)-4-hydroxy-1-pyrrolidinyl]ethyl}-7-fluoro-1,5-naphthyridin-2(1H)-one (130 mg, 0.423 mmol) and 3-oxo-3,4-dihydro-2H-pyrido[3,2-b][1,4]thiazine-6-carboxaldehyde (for a synthesis, see WO2004058144, Example 7(d)) (90 mg, 0.465 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (282 mg, 1.27 mmol) was added and stirred for 1 h. The reaction mixture was concentrated and purified to obtain the free base of the title compound as a pale yellow oil (95 mg, 46%) after column chromatography (90:10:1: DCM:MeOH:NH$_4$OH).

MS (ES+) m/z 485.5 (MH$^+$).

1H NMR (400 MHz, CD$_3$OD) δ ppm 2.61-2.70 (m, 1H) 2.72-2.82 (m, 3H) 2.84-2.89 (m, 2H) 2.94-3.06 (m, 2H) 3.17-3.26 (m, 1H) 3.57 (s, 2H) 3.68 (s, 2H) 4.29 (d, J=9.85 Hz, 2H) 4.36 (ddd, J 14.65, 5.81, 5.56 Hz, 1H) 4.51 (ddd, J 7.52, 4.04, 3.85 Hz, 1H) 4.54-4.65 (m, 1H) 6.68 (d, J 9.85 Hz, 1H) 7.11-7.17 (m, 1H) 7.80-7.86 (m, 1H) 7.91-7.98 (m, 2H) 8.52 (d, J=2.27 Hz, 1H).

The title compound, hydrochloride salt was made by addition of 49 uL (one equivalent) of 4N HCl/1,4-dioxane to a solution of the free base.

Example 82

7-chloro-6-{[({(3S,4S)-1-[2-(7-fluoro-2-oxo-1,5-naphthyridin-1(2H)-yl)ethyl]-4-hydroxy-3-pyrrolidinyl}methyl)amino]methyl}-2H-pyrido[3,2-b][1,4]oxazin-3(4H)-one Hydrochloride

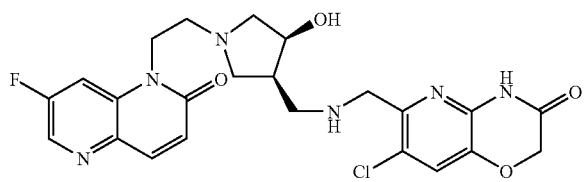

1-{2-[(3S,4S)-3-(Aminomethyl)-4-hydroxy-1-pyrrolidinyl]ethyl}-7-fluoro-1,5-naphthyridin-2(1H)-one (118 mg, 0.386 mmol) and 7-chloro-3-oxo-3,4-dihydro-2H-pyrido[3,2-b][1,4]oxazine-6-carboxaldehyde (for a synthesis see WO2003064421, Example 15(c)) (90 mg, 0.425 mmol) were combined in anhydrous DCM (5 ml) and anhydrous MeOH (1 ml) with a spatula of solid sodium carbonate. The reaction mixture was stirred under nitrogen for 18 h then sodium triacetoxyborohydride (257 mg, 1.16 mmol) was added and stirred for 1 h. The reaction mixture was concentrated and purified to obtain the free base of the title compound as a pale yellow oil (83 mg; 43%) after column chromatography (90:10:1: DCM:MeOH:NH$_4$OH).

MS (ES+) m/z 503.3 (MH$^+$).

1H NMR (400 MHz, CD$_3$OD) δ ppm 2.69-2.78 (m, 3H) 2.86 (dd, J 10.74, 6.19 Hz, 1H) 2.91-3.00 (m, 1H) 3.01-3.12 (m, 2H) 3.23 (dd, J 9.22, 3.66 Hz, 1H) 3.68 (s, 2H) 4.29-4.39 (m, 3H) 4.56 (td, J 6.63, 2.40 Hz, 1H) 4.64 (ddd, J 14.78, 8.72, 6.32 Hz, 1H) 4.71-4.75 (m, 2H) 6.63 (d, J=9.60 Hz, 1H) 7.54 (s, 1H) 7.87 (d, J=9.60 Hz, 1H) 7.95 (dd, J=10.48, 2.15 Hz, 1H) 8.51 (d, J=2.27 Hz, 1H).

The title compound, hydrochloride salt was made by addition of 41 uL (one equivalent) of 4N HCl/1,4-dioxane to a solution of the free base.

Example 83

1-[2-((3S,4S)-3-{[(2,3-dihydro[1,4]dioxino[2,3-c]pyridin-7-ylmethyl)amino]methyl}-4-hydroxy-1-pyrrolidinyl)ethyl]-7-fluoro-1,5-naphthyridin-2(1H)-one Hydrochloride

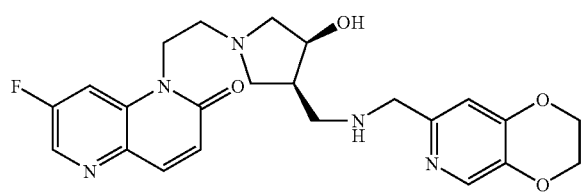

1-{2-[(3S,4S)-3-(Aminomethyl)-4-hydroxy-1-pyrrolidinyl]ethyl}-7-fluoro-1,5-naphthyridin-2(1H)-one (110 mg, 0.359 mmol) and 2,3-dihydro[1,4]dioxino[2,3-c]pyridine-7- carboxaldehyde (for a synthesis see WO2004058144, Example 2(c) or WO03/087098, Example 19(d)) (65 mg; 0.395 mmol) were combined in anhydrous DCM (ml) and anhydrous MeOH (1 ml) with a spatula of solid sodium carbonate. The reaction mixture was stirred under nitrogen for 18 h then sodium triacetoxyborohydride (239 mg, 1.08 mmol) was added and stirred for 1 h. The reaction mixture was concentrated and purified to obtain the free base of the title compound as a pale yellow oil (46 mg, 28%) after column chromatography (90:10:1: DCM:MeOH:NH$_4$OH).

MS (ES+) m/z 456.4 (MH$^+$).

1H NMR (400 MHz, CD$_3$OD) δ ppm 2.54 (d, J=5.81 Hz, 1H) 2.78 (dd, J 9.47, 7.20 Hz, 1H) 2.82-2.91 (m, 5H) 3.09 (d, J=5.56 Hz, 2H) 3.33 (dt, J=3.28, 1.64 Hz, 1H) 4.03-4.12 (m, 2H) 4.33 (dd, J 5.31, 2.53 Hz, 2H) 4.37-4.41 (m, 2H) 4.44-4.51 (m, 3H) 6.78 (d, J=9.60 Hz, 1H) 6.97 (s, 1H) 7.87-7.92 (m, 2H) 7.96 (dd, J 10.61, 2.02 Hz, 1H) 8.51 (d, J=2.27 Hz, 1H).

The title compound, hydrochloride salt was made by addition of 25 uL (one equivalent) of 4N HCl/1,4-dioxane to a solution of the free base.

Example 84

1-(2-{4-[(2,3-dihydro[1,4]dioxino[2,3-c]pyridin-7-ylmethyl)amino]-1-piperidinyl}ethyl)-5-fluoro-7-(methyloxy)-2(1H)-quinolinone Benzoate and Example 85

1-(2-{4-[(2,3-dihydro[1,4]dioxino[2,3-c]pyridin-7-ylmethyl)amino]-1-piperidinyl}ethyl)-7-fluoro-5-(methyloxy)-2(1H)-quinolinone Benzoate

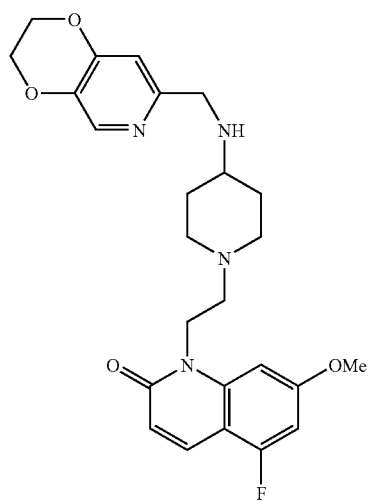

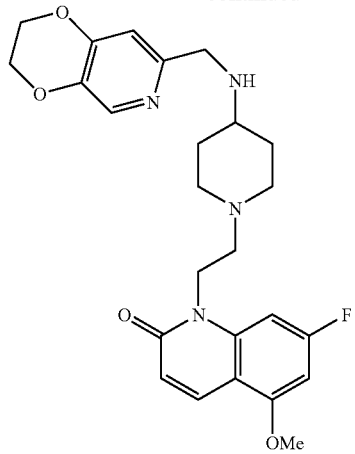

(a) 7-Fluoro-5-(methyloxy)-1-(2-propen-1-yl)-2 (1H)-quinolinone and 5-fluoro-7-(methyloxy)-1-(2-propen-1-yl)-2(1H)-quinolinone (1:1 Mixture)

5,7-difluoro-1-(2-propen-1-yl)-2(1H)-quinolinone (350 mg, 1.58 mmol) was dissolved in dry MeOH (7 ml). Sodium methoxide (85 mg, 1.58 mmol) was added slowly and the reaction heated to reflux under argon overnight. More sodium methoxide (42.5 mg, 0.79 mmol) was added and then after 3 h more sodium methoxide (63.8 mg, 1.18 mmol) was added. The reaction was stirred overnight at reflux and then more sodium methoxide (85 mg, 1.58 mmol) was added and the reaction stirred at reflux overnight. The MeOH was removed and residue partitioned between water and ethyl acetate. The organics dried (sodium sulphate) and evaporated to afford a pale yellow oil which was chromatographed on silica gel, eluting with 0-50% ethyl acetate-40-60° C. petroleum ether to afford 240 mg of the mixture of the two isomers (62%).

MS (ES+) m/z 222 (MH$^+$).

(b) [7-fluoro-5-(methyloxy)-2-oxo-1(2H)-quinolinyl] acetaldehyde and [5-fluoro-7-(methyloxy)-2-oxo-1 (2H)-quinolinyl]acetaldehyde (1:1 Mixture)

7-fluoro-5-(methyloxy)-1-(2-propen-1-yl)-2(1H)-quinolinone and 5-fluoro-7-(methyloxy)-1-(2-propen-1-yl)-2(1H)-quinolinone (1:1 mixture) (240 mg; 1.03 mmol) was dissolved in DCM (8 ml) in a 3 necked flask and cooled to −78° C. This was then stirred under O$_3$ for 20 min and the reaction then quenched with DMS (0.29 ml; 4.12 mmol). This was then left to warm to rt. The solvents were removed to afford the impure products (304 mg).

MS (ES+) m/z 236 (MH$^+$).

(c) 1,1-Dimethylethyl (2,3-dihydro[1,4]dioxino[2,3-c]pyridin-7-ylmethyl)(1-{2-[5-fluoro-7-(methyloxy)-2-oxo-1 (2H)-quinolinyl]ethyl}-4-piperidinyl)carbamate and 1,1-dimethylethyl (2,3-dihydro[1,4] dioxino[2,3-c]pyridin-7-ylmethyl)(1-{2-[7-fluoro-5-(methyloxy)-2-oxo-1(2H)-quinolinyl]ethyl}-4-piperidinyl)carbamate (1:1 Mixture)

[7-fluoro-5-(methyloxy)-2-oxo-1(2H)-quinolinyl]acetaldehyde and [5-fluoro-7-(methyloxy)-2-oxo-1(2H)-quinolinyl]acetaldehyde (1:1 mixture) (304 mg; 1.29 mmol) and 1,1-dimethylethyl (2,3-dihydro[1,4]dioxino[2,3-c]pyridin- 7-ylmethyl)-4-piperidinylcarbamate (for a synthesis see WO2004/058144 Example 99(h)) (848 mg, 2.431 mmol) (450 mg; 1.29 mmol) were dissolved in a 5:1 mixture of chloroform and MeOH (25 ml:5 ml) and stirred at rt under argon for 1 hour. This was then treated with NaBH(OAc)₃ (820 mg; 3.87 mmol) and stirred for a further hour. Solvents were then removed and the crude residue purified by column chromatography on silica gel using a 0-10% MeOH/DCM gradient. Fractions containing the desired were concentrated (300 mg; 41%).

MS (ES+) m/z 569 (MH⁺).

(d) Title Compounds 1,1-dimethylethyl (2,3-dihydro[1,4]dioxino[2,3-c]pyridin-7-ylmethyl)(1-{2-[5-fluoro-7-(methyloxy)-2-oxo-1(2H)-quinolinyl]ethyl}-4-piperidinyl)carbamate and 1,1-dimethylethyl (2,3-dihydro[1,4]dioxino[2,3-c]pyridin-7-ylmethyl)(1-{2-[7-fluoro-5-(methyloxy)-2-oxo-1(2H)-quinolinyl]ethyl}-4-piperidinyl)carbamate (1:1 mixture) (300 mg, 0.53 mmol) were dissolved in chloroform (5 ml) and 4M HCl in 1,4-dioxane solution was added (1 ml). The reaction was stirred at rt under argon for 1 h. Solid formed was dissolved in MeOH and the solvents removed. The solids were redissolved in MeOH and stirred with Amberlyst resin until neutral pH reached. The resin was filtered and solvent removed to afford 220 mg of crude material which was purified by chromatography to afford 82 mg of a 1:1 mixture of the free bases of the title compounds.

MS (ES+) m/z 469 (MH⁺).

This material was separated by preparative HPLC through single injection on a Chiralpak AS-H column eluting with MeOH (0.1% isopropylamine) at a flow rate of 20.0 mL/minute with UV detection at 254 nm to give the free bases of the title compounds 1-(2-{4-[(2,3-dihydro[1,4]dioxino[2,3-c]pyridin-7-ylmethyl)amino]-1-piperidinyl}ethyl)-5-fluoro-7-(methyloxy)-2(1H)-quinolinone (39 mg, >99.8% purity) and 1-(2-{4-[(2,3-dihydro[1,4]dioxino[2,3-c]pyridin-7-ylmethyl)amino]-1-piperidinyl}ethyl)-7-fluoro-5-(methyloxy)-2(1H)-quinolinone (32 mg, >99.8% purity).

1-(2-{4-[(2,3-dihydro[1,4]dioxino[2,3-c]pyridin-7-ylmethyl)amino]-1-piperidinyl}ethyl)-5-fluoro-7-(methyloxy)-2(1H)-quinolinone ¹H NMR (400 MHz) δ (CD₃OD) 1.65 (1H, m), 2.10 (2H, d), 2.25 (2H, t), 2.73 (2H, t), 2.98 (1H, m), 3.19 (2H, d), 3.96 (3H, s), 4.1 (2H, s), 4.33 (2H, m), 4.39 (2H, m), 4.49 (2H, t), 6.54 (1H, d), 6.78 (1H, m), 6.90 (1H, s), 7.00 (1H, s), 7.39 (2H, m), 7.46 (1H, m), 7.99 (3H, m), 8.11 (1H, s).

1-(2-{4-[(2,3-dihydro[1,4]dioxino[2,3-c]pyridin-7-ylmethyl)amino]-1-piperidinyl}ethyl)-7-fluoro-5-(methyloxy)-2(1H)-quinolinone ¹H NMR (400 MHz) 6(CD₃OD) 1.65 (2H, m), 2.10 (2H, d), 2.24 (2H, t), 2.72 (2H, t), 2.99 (1H, m), 3.18 (2H, d), 3.99 (3H, s), 4.11 (2H, s), 4.33 (2H, m), 4.39 (2H, m), 4.44 (2H, m), 6.55 (1H, d), 6.75 (1H, m), 7.00 (2H, m), 7.40 (2H, m), 7.46 (1H, m), 7.99 (2H, m), 8.12 (1H, s), 8.20 (1H, d).

These compounds were converted to the title compounds, mono-benzoic acid salts by treatment with 1 equivalent of benzoic acid.

Example 86

5-Chloro-3-(2-{4-[(2,3-dihydro[1,4]dioxino[2,3-c]pyridin-7-ylmethyl)amino]-1-piperidinyl}ethyl)-1,3-benzothiazol-2(3H)-one Dihydrochloride

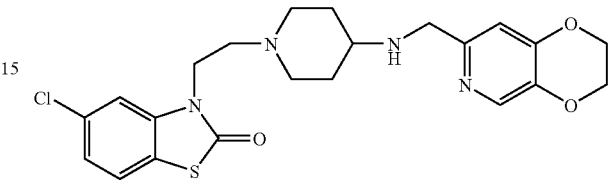

(a) 5-Chloro-3-(2-propen-1-yl)-1,3-benzothiazol-2(3H)-one

5-Chloro-1,3-benzothiazol-2(3H)-one (1.85 g, 10 mmol) was dissolved in DMF (50 ml) and treated with potassium carbonate (1.66 g, 12 mmol) and allyl iodide (1.1 ml, 12 mmol) then heated at 100° C. for 18 hrs. The solvent was then removed in-vacuo and the residue partitioned between water (100 ml) and ethyl acetate (2×100 ml). The organic layer was washed with saturated brine, separated and dried. Chromatography on silica gel eluting with a gradient of 10-50% ethyl acetate/40-60 petroleum ether gave the title compound as an oil that crystalised on standing (2.14 g, 95%).

MS (ES+) m/z 226 and 228 (MH⁺, 100 and 30% respectively).

(b) (5-Chloro-2-oxo-1,3-benzothiazol-3(2H)-yl)acetaldehyde 5-chloro-3-(2-propen-1-yl)-1,3-benzothiazol-2(3H)-one (0.43 g, 1.9 mmol) (0.43 g, 1.9 mmole) was dissolved in 1,4-dioxane (20 ml) and water (22 ml) was added. Sodium periodate (0.94 g, 4.4 mmol) was added followed by 4% osmium tetroxide in water (2.1 ml) and stirred at rt for 30 mins after which time a heavy precipitate had formed. Water (20 ml) was added followed by more sodium periodate (1.9 g, 8.9 mmol) and the mixture stirred at rt for 18 h. The mixture was concentrated in-vacuo to a small volume and partitioned between water (50 ml) and DCM (2×50 ml). The organics were separated and dried. Chromatography on silica gel eluting with a gradient of 25-100% ethyl acetate/40-60 petroleum ether gave 0.21 g, 48%) of the title compound.

MS (ES+) m/z 226 and 228 (M–H, 100 and 35% respectively).

(c) Title Compound (5-chloro-2-oxo-1,3-benzothiazol-3(2H)-yl)acetaldehyde (0.10 g, 0.44 mmol) and 1,1-dimethylethyl (2,3-dihydro[1,4]dioxino[2,3-c]pyridin-7-ylmethyl)-4-piperidinylcarbamate (0.154 g, 0.44 mmole) (for a synthesis see WO2004/058144 Example 99(h)) were dissolved in chloroform (10 ml) and MeOH (1.5 ml) and treated with acetic acid (8 drops) and (polystyrylmethyl)trimethylammonium cyanoborohydride (Novabiochem) (4.1 mmol/g, 0.87 g), and the mixture stirred at rt for 60 h. The reaction was filtered and evaporated to dryness. Chromatography on silica gel eluting with a gradient of 0-12% MeOH/DCM gave 1,1-dimethylethyl {1-[2-(5-chloro-2-oxo-1,3-benzthiazol-3(2H)-yl)ethyl]-4-piperidinyl}(2,3-dihydro[1,4]dioxino[2,3-c]pyridin-7-ylmethyl)carbamate as an oil (0.25 g, 100%). MS (ES+) m/z 561 and 563 (MH+). This was dissolved in DCM (10 ml) and treated with trifluoroacetic acid (3 ml) at rt for 18 h then evaporated to dryness. The residue was partitioned between 10% potassium carbonate in water (30 ml) and 10% MeOH in DCM (3×30 ml). The organics were dried, filtered and evaporated to dryness. Chromatography on silica gel eluting with a gradient of 0-10% 2M ammonia in MeOH/DCM gave the free base of the title compound as an oil (0.138 g, 67%).

¹H NMR δ (CDCl₃) 1.29-1.45 (2H, m), 1.73 (2H, s), 1.80-1.93 (2H, m), 2.05-2.18 (2H, m), 2.42-2.55 (1H, m), 2.66 (2H, t, J=6.5 Hz), 2.85-2.96 (2H, m), 3.75 (2H, s), 3.99 (2H, t, J=6.5 Hz), 4.22-4.35 (4H, m), 6.82 (1H, s), 7.07-7.13 (2H, m), 7.33 (1H, d, J=4.8 Hz), 8.10 (1H, s).

MS (ES+) m/z 461 and 463 (MH+, 30 and 10% respectively).

This was dissolved in MeOH and treated with excess 1M HCl in ether. The solution was evaporated to dryness to give the title compound, dihydrochloride as a white solid.

Example 87

1-(2-{4-[(2,3-dihydro[1,4]dioxino[2,3-c]pyridin-7-ylmethyl)amino]-1-piperidinyl}ethyl)-6-fluoro[1,3]thiazolo[5,4-b]pyridin-2(1H)-one Dihydrochloride

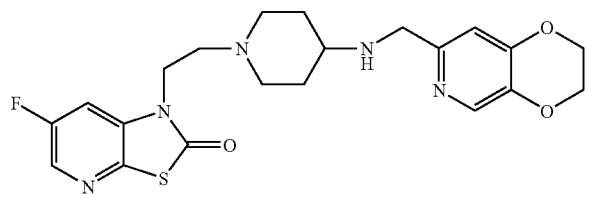

(a) 2-Chloro-5-fluoro-3-nitropyridine

The title compound was prepared from 5-fluoro-3-nitro-2(1H)-pyridinone (1.0 g, 6.3 mmole) by the general method of Sugimoto et al, Tetrahedron Letters (1999), 40, 7477-7478 to give (0.7 g, 62%) of a brown oil that crystallised on standing.

¹H NMR δ (CDCl₃) 7.99-8.05 (1H, m), 8.55 (1H, d, J=2.8 Hz).

(b) 6-Fluoro[1,3]thiazolo[5,4-b]pyridin-2(1H)-one

2-Chloro-5-fluoro-3-nitropyridine (0.7 g, 3.9 mmole) was suspended in THF (20 ml) and treated with water (0.43 ml) triethylamine (2.3 ml) and sulphur flakes (0.63 g). This mixture was placed in a Bergoff pressure bomb and pressurised to 1500 kPa (15 bar) with carbon monoxide then heated to 90° C. for 18 hrs. The reaction was allowed to cool and excess carbon monoxide was vented, the solution/suspension was evaporated to dryness and the residue partitioned between DCM and water. The organic phase was dried, filtered and evaporated to dryness. Chromatography on silica gel eluting with a gradient of 0-10% MeOH/DCM followed by further chromatography with a 0-100% ethyl acetate/40-60 petroleum ether gradient gave the title compound (0.05 g, 7.4%).

MS (ES+) m/z 171 (MH+, 100%).

(c) 6-Fluoro-1-(2-propen-1-yl)[1,3]thiazolo[5,4-b]pyridin-2(1H)-one

6-Fluoro[1,3]thiazolo[5,4-b]pyridin-2(1H)-one (0.045 g, 0.31 mmol) was dissolved in DMF (3 ml) and treated with potassium carbonate (0.043 g, 0.31 mmol) and allyl iodide (0.03 ml, 0.33 mmol) then heated at 100° C. for 18 hrs. The solvent was then removed in-vacuo and the residue partitioned between water and ethyl acetate. The organic layer was washed with saturated brine, separated and dried. Chromatography on silica gel eluting with a gradient of 10-50% ethyl acetate/40-60 petroleum ether gave the title compound (0.046 g, 83%) as an oil.

MS (ES+) m/z 211 (MH+, 100%).

(d) (6-Fluoro-2-oxo[1,3]thiazolo[5,4-b]pyridin-1(2H)-yl)acetaldehyde

6-Fluoro-1-(2-propen-1-yl)[1,3]thiazolo[5,4-b]pyridin-2(1H)-one (0.046 g, 0.22 mmole) was dissolved in DCM (8 ml) and MeOH (1 ml) and the solution cooled to −70° C. A gas mixture containing ozone in oxygen was bubbled through the solution for 20 mins to give a pale green solution. Argon was then bubbled through the solution for 5 mins then dimethyl sulphide (0.064 ml, 0.87 mmole) added. The mixture was allowed to warm to rt then evaporated to dryness to give a crude product which was used without further purification.

MS (ES+) m/z 245 (MH+ for MeOH hemiacetal, 100%).

(e) Title Compound (6-fluoro-2-oxo[1,3]thiazolo[5,4-b]pyridin-1(2H)-yl)acetaldehyde (0.046 g, 0.22 mmole) and 1,1-dimethylethyl (2,3-dihydro[1,4]dioxino[2,3-c]pyridin-7-ylmethyl)-4-piperidinylcarbamate (0.069 g, 0.2 mmole) (for a synthesis see WO2004/058144 Example 99(h)) were dissolved in chloroform (5 ml) and MeOH (1 ml) and treated with acetic acid (10 drops) and (polystyrylmethyl)trimethylammonium cyanoborohydride (Novabiochem) (4.1 mmol/g, 0.39 g), and the mixture stirred at rt for 60 h. The reaction was filtered and evaporated to dryness to give 1,1-dimethylethyl (2,3-dihydro[1,4]dioxino[2,3-c]pyridin-7-ylmethyl) {1-[2-(6-fluoro-2-oxo[1,3]thiazolo[5,4-b]pyridin-1(2H)-yl)ethyl]-4-piperidinyl}. This was dissolved in DCM (3 ml) and treated with trifluoroacetic acid (1 ml) at rt for 4 h then evaporated to dryness. The residue was dissolved in MeOH, stirred with polymer supported carbonate resin and then filtered and evaporated. Chromatography on silica gel of the residue, eluting with a gradient of 0-12% 2M ammonia in MeOH/DCM gave the free base of the title compound (0.05 g, 51%)

¹H NMR δ (CDCl₃) 1.29-1.45 (2H, m), 1.73 (2H, s), 1.80-1.93 (2H, m), 2.05-2.18 (2H, m), 2.42-2.55 (1H, m), 2.66 (2H, t, J=6.5 Hz), 2.80-2.92 (2H, m), 3.75 (2H, s), 3.99 (2H, t, J=6.5 Hz), 4.22-4.35 (4H, m), 6.80 (1H, s), 7.16 (1H, dd, J 2.5 and 9 Hz), 8.10 (1H, s), 8.18 (1H, dd, J 1 and 2.5 Hz).

MS (ES+) m/z 446 (MH+, 100%).

Example 88

6-{[({(3S)-1-[2-(7-Fluoro-2-oxo-1(2H)-quinolinyl)ethyl]-3-pyrrolidinyl}methyl)amino]methyl}-2H-pyrido[3,2-b][1,4]oxazin-3(4H)-one

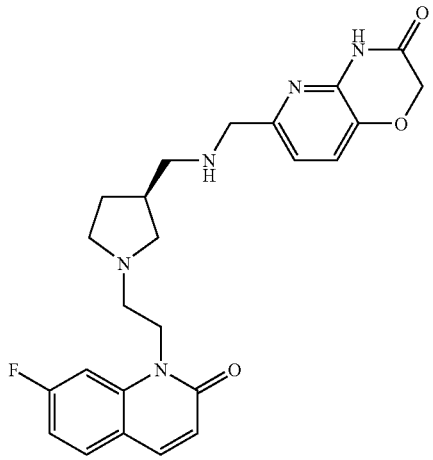

(a) (7-Fluoro-2-oxo-1(2H)-quinolinyl)acetaldehyde

A solution of 7-fluoro-1-(2-propen-1-yl)-2(1H)-quinolinone (5.0 g, 0.025 mmol) in 3:1 $CH_2Cl_2$:MeOH (500 mL) was cooled to −70° and O3 was bubbled through the solution for 20 min. Dimethyl sulfide (19 mL, 0.25 mol) were added and the reaction was stirred for 90 min at −70° C., then allowed to warm to room temperature overnight. The solvents were removed under reduced pressure yielding a thick orange oil. Purification by column chromatography on silica gel (1% to 100% hexane:ethyl acetate gradient) yielded a dark yellow solid (4.2 g, 82%).

MS (ES) m/z 206 $[M+H]^+$.

(b) Phenylmethyl ({(3S)-1-[2-(7-fluoro-2-oxo-1(2H)-quinolinyl)ethyl]-3-pyrrolidinyl}methyl)carbamate To a solution of (7-fluoro-2-oxo-1(2H)-quinolinyl)acetaldehyde (1.17 g, 5.71 mmol) and phenylmethyl [(3R)-3-pyrrolidinylmethyl]carbamate (may be prepared analogously to the 3R isomer of Preparation 23(b) in WO2006002047, from (R)-3-(aminomethyl)-1-N-Boc-pyrrolidine) (1.34 g, 5.71 mmol) in 1:1 $CH_2Cl_2$:MeOH (80 mL) were added 8 eq. $Na_2SO_4$ (6.5 g, 46 mmol) and the reaction was stirred at ambient temperature for 18 h. The intermediate imine was treated with sodium triacetoxyborohydride (3.63 g, 17.0 mmol) and stirred for an additional 16 h. The solvents were removed under reduced pressure; the residue was partitioned between ethyl acetate and aqueous saturated $NaHCO_3$, and the organic layer was dried over $Na_2SO_4$. Purification by column chromatography on silica gel, (1% to 20% methanol:dichloromethane gradient) yielded a light amber oil. (820 mg, 34%).

MS (ES) m/z 424 $[M+H]^+$.

(c) 1-{2-[(3S)-3-(Aminomethyl)-1-pyrrolidinyl]ethyl}-7-fluoro-2(1H)-quinolinone To a solution of phenylmethyl ({(3S)-1-[2-(7-fluoro-2-oxo-1(2H)-quinolinyl)ethyl]-3-pyrrolidinyl}methyl)carbamate (820 mg, 1.94 mmol) in MeOH (30 mL) was added 5% palladium on carbon (200 mg, 50% by weight with water). The mixture was hydrogenated at 15 psi for 2.5 h, filtered through a pad of Celite®, and concentrated to give a clear oil which darkened and solidified on standing (555 mg, 99%).

MS (ES) m/z 290 $[M+H]^+$.

(d) 6-{[({(3S)-1-[2-(7-fluoro-2-oxo-1(2H)-quinolinyl)ethyl]-3-pyrrolidinyl}methyl)amino]methyl}-2H-pyrido[3,2-b][1,4]oxazin-3(4H)-one To a solution of 1-{2-[(3S)-3-(aminomethyl)-1-pyrrolidinyl]ethyl}-7-fluoro-2(1H)-quinolinone (87 mg, 0.30 mmol) and 3-oxo-3,4-dihydro-2H-pyrido[3,2-b][1,4]oxazine-6-carboxaldehyde (for a synthesis see WO2003087098, Example 31(e)) (54 mg, 0.302 mmol) was added $Na_2SO_4$ (355 mg, 2.50 mmol) and the reaction was stirred at ambient temperature for 18 h. The intermediate imine was treated with sodium triacetoxyborohydride (160 mg, 0.75 mmol) and stirred for an additional 16 h. The solvents were removed under reduced pressure; the residue was partitioned between dichloromethane and aqueous sodium bicarbonate, and the organic layer was dried ($Na_2SO_4$). Purification by column chromatography on silica gel, (1% to 20% methanol:dichloromethane gradient) yielded the title compound as an amorphous off-white solid (69 mg, 51%).

1H NMR (400 Mz, $CDCl_3$) δ 7.65 (d, J=9.5 Hz, 1H), 7.56-7.53 (m, 1H), 7.21 (d, J=8.1 Hz, 1H), 7.16 (dd, J=9.6 Hz, J=2.2 Hz, 1H), 6.99-6.95 (m, 1H), 6.92, (d, J=8.1 Hz, 1H), 6.71 (d, J=9.5 Hz), 4.65 (s, 2H), 4.46-4.37 (m, 2H), 3.83 (s, 2H), 2.95 (apparent t, 1H), 2.80 (t, J=7.63 Hz, 2H), 2.73 (t, J=6.91 Hz, 2H), 2.67 (d, J=6.92 Hz, 1H), 2.58-2.54 (m, 1H), 2.48-2.07 (m, 1H), 2.07-2.00 (m, 1H), 1.58-1.28 (m, 1H).

MS (ES) m/z 452 $[M+H]^+$.

Example 89

6-({[((2S)-4-{2-[7-(Methyloxy)-2-oxo-1,5-naphthyridin-1(2H)-yl]ethyl}-2-morpholinyl)methyl]amino}methyl)-2H-pyrido[3,2-b][1,4]thiazin-3(4H)-one Hydrochloride

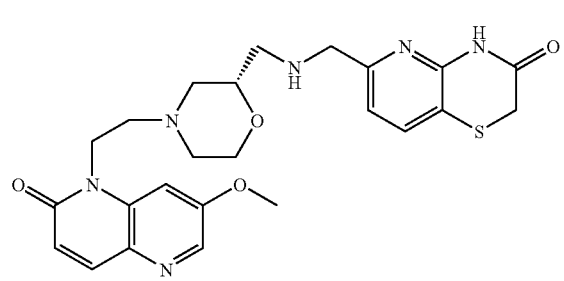

(a) Racemic 2-{[(2R,S)-4-(phenylmethyl)-2-morpholinyl]methyl}-1H-isoindole-1,3(2H)-dione To a solution of 4-benzyl-2-(chloromethyl)morpholine (2.0 g, 8.86 mmol) in DMF (10 mL) was added potassium phthalimide (1.96 g, 10.6 mmol) and the mixture was heated at 165° C. for 4 h. Upon cooling, the reaction mixture was poured into water (20 mL) and the product was extracted into CHCl$_3$ (3×) and the combined organic layers were washed with a small amount of water, brine, and dried (Na$_2$SO$_4$). Evaporation of the solvent gave a light tan solid which was used directly in next step.

LC/MS (ES) m/e 337 (M+H)$^+$.

(b) Racemic {[(2R,S)-4-(phenylmethyl)-2-morpholinyl]methyl}amine

Crude 2-{[(2R,S)-4-(phenylmethyl)-2-morpholinyl]methyl}-1H-isoindole-1,3(2H)-dione (~8.8 mmol) was suspended in absolute ethanol (15 mL) and treated with hydrazine monohydrate (0.75 mL, 15.4 mmol). The reaction mixture was heated to reflux during which time the reaction solution turned yellow and homogeneous followed by precipitation of a white solid. After 2 h, the reaction was cooled to room temperature, diluted with CHCl$_3$, and the solids were filtered off. The filtrate was evaporated and the residue was taken up in CHCl$_3$ and washed with a small amount of water, brine, and dried (Na$_2$SO$_4$). Evaporation of the solvent gave a yellow oil (1.69 g) which was used directly in next step.

LC/MS (ES) m/e 207 (M+H)$^+$.

(c) Racemic 1,1-Dimethylethyl {[(2R,S)-4-(phenylmethyl)-2-morpholinyl]methyl}carbamate To a solution of crude {[(2R,S)-4-(phenylmethyl)-2-morpholinyl]methyl}amine (1.69 g, 8.2 mmol) in DCM (15 mL) at 0° C. was added di-tert-butyl dicarbonate (1.88 g, 8.6 mmol). The cooling bath was removed and the reaction was stirred at room temperature for 2 h. The solvent was removed in vacuo and the resulting oil was purified on silica gel eluting with CHCl$_3$-MeOH—NH$_4$OH, 96:4:1, providing the title compound as a white solid (1.94 g, 71% over 3 steps): LC/MS (ES) m/e 307 (M+H)$^+$.

(d) 1,1-Dimethylethyl {[(2S)-4-(phenylmethyl)-2-morpholinyl]methyl}carbamate and 1,1-dimethylethyl {[(2R)-4-(phenylmethyl)-2-morpholinyl]methyl}carbamate 1,1-Dimethylethyl {[(2R,S)-4-(phenylmethyl)-2-morpholinyl]methyl}carbamate (10 g) was resolved via chiral preparative HPLC (Chiralcel OD 77 mm×240 mm column, 95:5 hexane:ethanol, 280 mL/min flow rate, 0.5 g per injection, UV (254 nm) to provide 1,1-dimethylethyl {[(2S)-4-(phenylmethyl)-2-morpholinyl]methyl}carbamate (4.9 g, 99% ee, ret. time=4.194 min, [α]$_D$=−14.6°) as a colorless oil and 1,1-dimethylethyl {[(2R)-4-(phenylmethyl)-2-morpholinyl]methyl}carbamate (4.9 g, >98% ee, ret. time=3.477 min, [α]$_D$=+14.60) as a colorless oil.

(e) 1,1-Dimethylethyl [(2R)-2-morpholinylmethyl]carbamate

To a solution of 1,1-dimethylethyl {[(2S)-4-(phenylmethyl)-2-morpholinyl]methyl}carbamate (4.9 g, 16 mmol) in ethanol (160 mL) was added 10% Pd/C (1.5 g). The suspension was hydrogenated at 50 psi using a Parr Shaker apparatus for 8 h. The reaction was filtered through a pad of Celite® and the pad was washed several times with methanol. The filtrate was concentrated to afford the title compound (3.35 g, 97%) as a colorless solid which was not purified further: LC/MS (ES) m/e 217 (M+H)$^+$. The absolute stereochemistry of the title compound was determined by vibrational circular dichroism (VCD).

(f) 1,1-Dimethylethyl [((2S)-4-{2-[7-(methyloxy)-2-oxo-1,5-naphthyridin-1(2H)-yl]ethyl}-2-morpholinyl)methyl]carbamate To a solution of [7-(methoxy)-2-oxo-1,5-naphthyridin-1(2H)-yl]acetaldehyde (as the methyl hemiacetal) (0.500 g, 2.29 mmol) in 1:1 (MeOH/CHCl$_3$) (25 mL) were added 1,1-dimethylethyl [(2R)-2-morpholinyl-methyl]carbamate (0.500 g, 2.29 mmol) and Na$_2$SO$_4$ (0.100 g) and the resulting solution stirred at ambient temperature for 18 h. Na(OAc)$_3$BH (1.46 g, 6.87 mmol) was added and the solution stirred an additional 2 g. The reaction mixture was concentrated onto silica gel and chromatographed on a silica gel column) [0-100% Hexanes/EtOAc] to yield a yellowish oil. (0.460 g, 48%)

LCMS: m/z 419 (MH+)+.

(g) 1-{2-[(2S)-2-(Aminomethyl)-4-morpholinyl]ethyl}-7-(methyloxy)-1,5-naphthyridin-2(1H)-one To a solution of 1,1-dimethylethyl [((2S)-4-{2-[7-(methyloxy)-2-oxo-1,5-naphthyridin-1(2H)-yl]ethyl}-2-morpholinyl)methyl]carbamate (0.46 g, 1.10 mmol) in CH$_2$Cl$_2$ (10 mL) was added HCl in 1,4-dioxane (1.10 mL, 4.40 mmol) and the resulting solution stirred at ambient temperature for 16 h. After concentration under reduced pressure, the free base was formed by treating with excess MP carbonate to yield a yellow oil. (0.300 g, 85%).

LCMS: m/z 319 (M+H)+.

(h) Title Compound

To a solution of 1-{2-[(2S)-2-(aminomethyl)-4-morpholinyl]ethyl}-7-(methyloxy)-1,5-naphthyridin-2(1H)-one (0.100 g, 0.314 mmol) in 1:1 (MeOH/CH$_2$Cl$_2$) (25 mL) were added 3-oxo-3,4-dihydro-2H-pyrido[3,2-b][1,4]thiazine-6-carboxaldehyde (for a synthesis, see WO2004058144, Example 7(d) (0.061 g, 0.314 mmol) and sodium sulphate (0.100 g) and the resulting solution stirred for 18 hours at ambient temperature. Na(OAc)$_3$BH (0.200 g, 0.942 mmol) was added and the solution stirred an additional 2 h. The reaction mixture was concentrated onto silica gel and chromatographed on a silica gel column) [0-100% CHCl$_3$/(90:10:1) CHCl$_3$/MeOH/NH$_4$OH)] to yield a colorless oil. The mono-HCl salt was formed by treating with 1N HCl (one equivalent) in ether which yielded the title compound as an off white solid (0.094 g, 56%).

LCMS: m/z 497 (M+H)+.

1H NMR (400 MHz, CD$_3$OD) δ ppm 1.26 (t, J=7.07 Hz, 1H) 1.98-2.04 (m, 2H) 2.28 (td, J=11.37, 3.28 Hz, 1H) 2.61-2.72 (m, 4H) 2.92 (dd, J=18.82, 11.24 Hz, 2H) 3.52 (s, 2H) 3.58-3.69 (m, 2H) 3.75-3.83 (m, 2H) 3.83-3.91 (m, 1H) 4.04 (s, 3H) 4.12 (q, J=7.16 Hz, 1H) 4.50 (t, J=7.20 Hz, 2H) 6.75

(d, J=9.60 Hz, 1H) 7.01 (d, J=7.83 Hz, 1H) 7.50 (d, J=2.27 Hz, 1H) 7.68 (d, J=7.83 Hz, 1H) 7.92 (d, J=9.85 Hz, 1H) 8.29 (d, J=2.27 Hz, 1H).

Example 90

7-Chloro-6-({[((2S)-4-{2-[7-(methyloxy)-2-oxo-1,5-naphthyridin-1(2H)-yl]ethyl}-2-morpholinyl)methyl]amino}methyl)-2H-pyrido[3,2-b][1,4]oxazin-3(4I)-one Hydrochloride

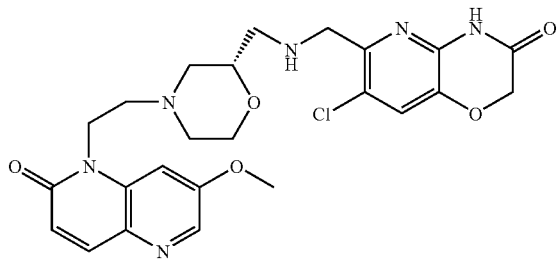

To a solution of 1-{2-[(2S)-2-(aminomethyl)-4-morpholinyl]ethyl}-7-(methyloxy)-1,5-naphthyridin-2(1H)-one (0.100 g, 0.314 mmol) in 1:1 (MeOH/CH$_2$Cl$_2$) (25 mL) were added 7-chloro-3-oxo-3,4-dihydro-2H-pyrido[3,2-b][1,4]oxazine-6-carboxaldehyde (for a synthesis see WO2003064421, Example 15(c)) (0.067 g, 0.314 mmol) and sodium sulphate (0.100 g) and the resulting solution stirred for 18 h at rt. Na(OAc)$_3$BH (0.200 g, 0.942 mmol) was added and the solution stirred an additional 2 h. The reaction mixture was concentrated onto silica gel and chromatographed on a silica gel column [0-100% CHCl$_3$/(90:10:1) CHCl$_3$/MeOH/NH$_4$OH)] to yield a colorless oil. The mono-HCl salt was formed by treating with 1N HCl (one equivalent) in ether which yielded the title compound as an off white solid (0.095 g, 54%)

LCMS: m/z 515 (M+H)+.

1H NMR (400 MHz, CD$_3$OD) δ ppm 2.02 (t, J=10.61 Hz, 1H) 2.28 (td, J=11.37, 3.28 Hz, 1H) 2.64-2.74 (m, 4H) 2.88-2.98 (m, 2H) 3.62 (td, J=11.37, 2.27 Hz, 1H) 3.67 (td, J=4.99, 2.65 Hz, 1H) 3.84-3.92 (m, 3H) 4.04 (s, 3H) 4.43-4.53 (m, 2H) 4.67 (s, 2H) 6.74 (d, J=9.60 Hz, 1H) 7.35 (s, 1H) 7.48 (d, J=2.27 Hz, 1H) 7.90 (d, J=9.60 Hz, 1H) 8.27 (d, J=2.27 Hz, 1H).

Example 91

1-[2-((2S)-2-{[(2,3-Dihydro[1,4]dioxino[2,3-c]pyridin-7-ylmethyl)amino]methyl}-4-morpholinyl)ethyl]-7-(methyloxy)-1,5-naphthyridin-2(1H)-one

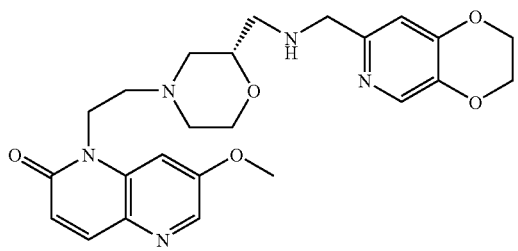

To a solution of 1-{2-[(2S)-2-(aminomethyl)-4-morpholinyl]ethyl}-7-(methyloxy)-1,5-naphthyridin-2(1H)-one (0.100 g, 0.314 mmol) in 1:1 (MeOH/CH$_2$Cl$_2$) (25 mL) were added 2,3-dihydro[1,4]dioxino[2,3-c]pyridine-7-carboxaldehyde) (for a synthesis see WO2004/058144 Example 2(c) or WO03/087098, Example 19(d)) (0.052 g, 0.314 mmol) and sodium sulphate (0.100 g) and the resulting solution stirred for 18 hours at ambient temperature. Na(OAc)$_3$BH (0.200 g, 0.942 mmol) was added and the solution stirred an additional 2 h. The reaction mixture was concentrated onto silica gel and chromatographed to yield a colorless oil and further purified by HPLC(CH$_3$CN/H$_2$O) to yield the title compound as a white powder (0.049 g, 33%).

LCMS: m/z 468 (M+H)+.

1H NMR (400 MHz, CD$_3$OD) δ ppm 1.98-2.06 (m, 1H) 2.28 (td, J=11.31, 3.16 Hz, 1H) 2.61-2.72 (m, 4H) 2.92 (dd, J=17.68, 11.12 Hz, 2H) 3.58-3.67 (m, 2H) 3.70-3.80 (m, 2H) 3.89 (ddd, J=9.98, 1.52, 1.39 Hz, 1H) 4.05 (s, 3H) 4.30-4.40 (m, 4H) 4.51 (td, J=7.07, 1.52 Hz, 2H) 6.75 (d, J=9.60 Hz, 1H) 6.96 (s, 1H) 7.52 (d, J=2.27 Hz, 1H) 7.93 (d, J=9.85 Hz, 1H) 8.01 (s, 1H) 8.30 (d, J=2.53 Hz, 1H).

Example 92

7-Chloro-6-({[((3S)-1-{2-[7-(methyloxy)-2-oxo-1,5-naphthyridin-1(2H)-yl]ethyl}-3-piperidinyl)methyl]amino}methyl)-2H-pyrido[3,2-b][1,4]oxazin-3(4H)-one

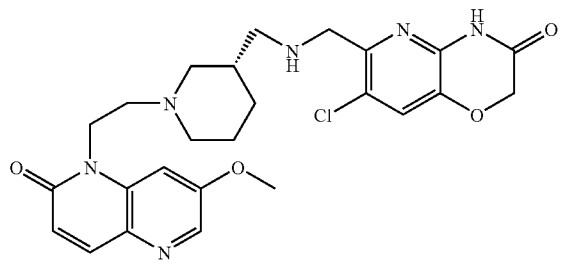

(a) 1,1-Dimethylethyl (3S)-3-[({[(phenylmethyl)oxy]carbonyl}amino)methyl]-1-piperidinecarboxylate To a solution of 1,1-dimethylethyl (3S)-3-(aminomethyl)-1-piperidinecarboxylate (2.0 g, 9.33 mmol) in DCM (12 mL) at 0° C. were added triethylamine (1.7 mL, 12.1 mmol) followed by N-(benzyloxycarbonyloxy)succinimide (2.56 g, 10.3 mmol). After a few minutes the cooling bath was removed and the reaction was stirred at room temperature for 2 h. The reaction was diluted with ethyl acetate and washed with water (2×), 1N HCl, saturated aq. NaHCO$_3$, brine, dried (Na$_2$SO$_4$) and concentrated. The product was purified on silica gel eluting with 10% ethyl acetate-DCM to give 3.48 g of material containing a small amount of N-(benzyloxycarbonyloxy)succinimide which was used directly in next step.

LC/MS (ES) m/e 349 (M+H)+.

(b) Phenylmethyl [(3R)-3-piperidinylmethyl]carbamate 1,1-Dimethylethyl (3S)-3-[({[(phenylmethyl)oxy]carbonyl}amino)methyl]-1-piperidinecarboxylate (·9.3 mmol) was dissolved in DCM (25 mL) and treated with a 4M HCl solution in 1,4-dioxane (24 mL, 96 mmol). The reaction was stirred at room temperature for 3 h, at which time LC/MS indicated that all starting material was consumed. The reaction was concentrated in vacuo to give a thick gum. This material was dissolved in water and extracted with ethyl acetate. The aqueous phase was separated and treated with solid $Na_2CO_3$ to bring the pH to ~10. The product was then extracted into $CHCl_3$ (3×) and the combined organic phases were dried ($Na_2SO_4$) and concentrated to yield the desired product as an orange oil (2.3 g, 100% for two steps).

LC/MS (ES) m/e 249 (M+H)+.

(c) Phenylmethyl [((3S)-1-{2-[7-(methyloxy)-2-oxo-1,5-naphthyridin-1(2H)-yl]ethyl}-3-piperidinyl)methyl]carbamate To a solution of [7-(methoxy)-2-oxo-1,5-naphthyridin-1(2H)-yl]acetaldehyde (as the methyl hemiacetal) (0.250 g, 1.15 mmol) in 1:1 (MeOH/CHCl$_3$) (25 mL) were added phenylmethyl [(3R)-3-piperidinyl-methyl]carbamate (0.210 g, 0.90 mmol) and $Na_2SO_4$ (0.100 g) and the resulting solution stirred at ambient temperature for 18 hours. Na(OAc)$_3$BH (0.57 g, 2.7 mmol) was added and solution stirred an additional 2 hours. The reaction mixture was concentrated onto silica gel and chromatographed on a silica gel column) [0-100% Hexanes/EtOAc] to yield a colorless oil. (0.207 g, 51%) LCMS: m/z 451 (M+H)+.

(d) 1-{2-[(3S)-3-(Aminomethyl)-1-piperidinyl]ethyl}-7-(methyloxy)-1,5-naphthyridin-2(1H)-one To a solution of phenylmethyl [((3S)-1-{2-[7-(methyloxy)-2-oxo-1,5-naphthyridin-1(2H)-yl]ethyl}-3-piperidinyl)methyl]carbamate (0.21 g, 0.44 mmol) in MeOH (30 mL) was added 10% Palladium on carbon (0.20 g) and the solution subjected to $H_2$ at 50 PSI on a Parr shaker. The solution was filtered through a pad of Celite® and concentrated under reduced pressure to give desired product (0.149 g, 100%)

LCMS: m/z 317.3 (MH+).

(e) Title Compound

To a solution of 1-{2-[(3S)-3-(Aminomethyl)-1-piperidinyl]ethyl}-7-(methyloxy)-1,5-naphthyridin-2(1H)-one (0.149 g, 0.472 mmol) in 1:1 (MeOH/CH$_2$Cl$_2$) (25 mL) were added 7-chloro-3-oxo-3,4-dihydro-2H-pyrido[3,2-b][1,4]oxazine-6-carboxaldehyde (for a synthesis see WO2003064421, Example 15(c)) (0.100 g, 0.472 mmol) and sodium sulphate (0.100 g) and the resulting solution stirred for 18 hours at ambient temperature. Na(OAc)$_3$BH (0.300 g, 1.42 mmol) was added and the solution stirred an additional 2 h. The reaction mixture was concentrated onto silica gel and chromatographed on a silica gel column [0-100% CHCl$_3$/(90:10:1) CHCl$_3$/MeOH/NH$_4$OH)] to yield a colorless oil and then further purified by HPLC(CH$_3$CN/H$_2$O) to yield the title compound as a white powder (0.041 g, 17%).

LCMS: m/z 513 (M+H)+.

1H NMR (400 MHz, CD$_3$OD) δ ppm 1.04 (t, J=6.95 Hz, 1H) 1.57-1.68 (m, 1H) 1.73-1.78 (m, J=10.01, 3.46, 3.46, 3.28 Hz, 1H) 1.80-1.91 (m, 3H) 2.12-2.23 (m, 1H) 2.56 (d, J=6.06 Hz, 2H) 2.65-2.76 (m, 2H) 2.97 (s, 1H) 3.10-3.16 (m, 1H) 3.85-3.93 (m, 2H) 4.05 (s, 3H) 4.48-4.56 (m, 2H) 4.69 (s, 2H) 6.79 (d, J=9.60 Hz, 1H) 7.41 (s, 1H) 7.54 (d, J=2.27 Hz, 1H) 7.93 (d, J=9.60 Hz, 1H) 8.30 (d, J=2.27 Hz, 1H).

Example 93

7-chloro-6-{[({(3S)-1-[2-(7-fluoro-2-oxo-1(2H)-quinolinyl)ethyl]-3-piperidinyl}methyl)amino]methyl}-2H-pyrido[3,2-b][1,4]oxazin-3(4H)-one Dihydrochloride

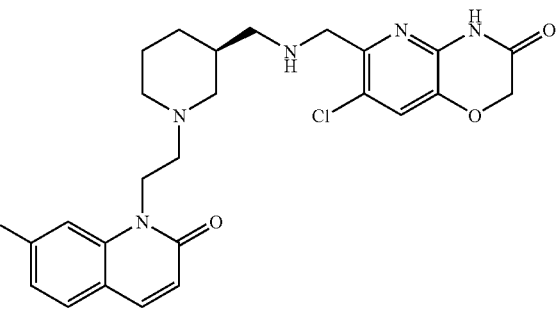

(a) 1-{2-[(3S)-3-(aminomethyl)-1-piperidinyl]ethyl}-7-fluoro-2(1H)-quinolinone

A solution of (7-fluoro-2-oxo-1(2H)-quinolinyl)acetaldehyde (0.205 g, 1 mmol) and phenylmethyl [(3R)-3-piperidinylmethyl]carbamate (0.275 g, 1 mmol) in methanol (1 ml) and DCM (3 ml) was stirred at rt overnight and sodium triacetoxyborohydride (0.424 g; 2 mmol) was added and the mixture was stirred at room temperature for 2 h. The mixture was extracted (3×) with DCM, dried (sodium sulphate), evaporated, and chromatographed on silica gel, eluting with 0-10% methanol-DCM-1% NH$_3$.H$_2$O to give the product as a foam (0.2 g). The foam (0.2 g) in dry methanol (15 mL) was treated with 10% Pd/C (0.08 g) and shaken under 15 psi at room temperature for 2 hours. The Pd catalyst was removed by filtration through Celite®. The filtrate was evaporated to dryness to give an oil (0.18 g).

MS (+ve ion electrospray) m/z 304 (M+H)+.

(b) 7-chloro-6-{[({(3S)-1-[2-(7-fluoro-2-oxo-1(2H)-quinolinyl)ethyl]-3-piperidinyl}methyl)amino]methyl}-2H-pyrido[3,2-b][1,4]oxazin-3(4H)-one A solution of 1-{2-[(3S)-3-(aminomethyl)-1-piperidinyl]ethyl}-7-fluoro-2(1H)-quinolinone (90 mg; 0.3 mmol) and 7-chloro-3-oxo-3,4-dihydro-2H-pyrido[3,2-b][1,4]oxazine-6-carboxaldehyde (for a synthesis see WO2003064421, Example 15(c)) (64 mg, 0.3 mmol) in methanol (2 ml), DCM (4 ml) was stirred at rt overnight. Sodium triacetoxyborohydride (0.127 g; 0.6 mmol) was added and the mixture was stirred at room temperature for 1 h. The reaction was evaporated and chromatographed on silica gel, eluting with 0-15% methanol-DCM-1% NH$_4$OH to give an oil. The oil was treated with 1M HCl in Et$_2$O to give the title compound (14 mg) as the dihydrochloride salt. 1H NMR (400 MHz, CD$_3$OD) δ ppm 1.07 (s, 1H) 1.59-1.69 (m, 1H) 1.71-1.83 (m, 2H) 1.83-1.94 (m, 2H) 2.15-2.23 (m, 1H) 2.56-2.61 (m, 21H) 2.63-2.75 (m, 3H) 2.97 (s, 1H) 3.13-3.20 (m, 1H) 3.90 (s, 2H) 4.49 (td, J=14.21, 7.71 Hz, 2H) 6.67 (d, J=9.60 Hz, 1H) 7.11 (td, J=8.46, 2.27 Hz, 1H) 7.38-7.50 (m, 2H) 7.75 (dd, J=8.72, 6.19 Hz, 1H) 7.91 (d, J=9.60 Hz, 1H)

MS (+ve ion electrospray) m/z 500 (M+H)+.

Example 94

5-(2-{4-[(2,3-dihydro[1,4]dioxino[2,3-c]pyridin-7-ylmethyl)amino]-1-piperidinyl}ethyl)-3-(methyloxy)pyrido[2,3-b]pyrazin-6(5H)-one Hydrochloride

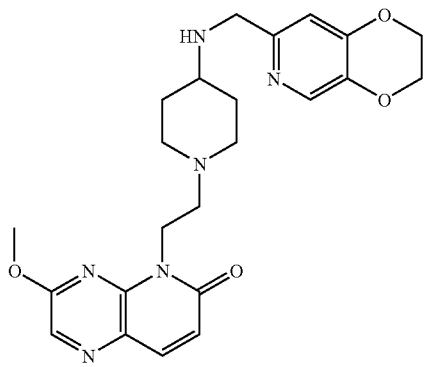

(a) 6-Chloro-3-nitro-2-pyridineamine

To an ice-cooled solution of 2,6-dichloro-3-nitropyridine (55.65 g, 288 mmol) in EtOH (500 ml) was added sodium carbonate (76.32 g, 720 mmol) followed by aqueous ammonia (35%, 21 ml). The reaction was then allowed to warm to rt, stirred at rt for 1 h, then at 50° C. for 1 h and then at 90° C. for 1 h. Another 20 ml of aqueous ammonia was added and heating continued at 90° C. for a further 1 h. Another 50 ml of aqueous ammonia was added and heating continued at 90° C. for a further 1 h. The reaction was cooled to rt, and the solid was filtered, washed with water (500 ml) and dried in vacuo to give the title compound as a yellow solid (37.25 g, 75%).

$^1$H NMR (250 MHz) δ(CDCl$_3$) 6.94 (2H, d, J=8.5 Hz), 8.38 (2H, d, J=8.5 Hz).

(b) 6-({[4-(Methyloxy)phenyl]methyl}oxy)-3-nitro-2-pyridineamine

4-Methoxybenzyl alcohol (4.8 g, 34.7 mmol) was added to sodium (0.8 g, 34.7 mmol) in toluene (100 mL). After most of the sodium has dissolved 6-chloro-3-nitro-2-pyridineamine (5 g, 28.9 mmol) was added and the reaction was heated at 120° C. for 4 h. As there was still some starting material left, more anion of the 4-methoxybenzyl alcohol was prepared in a separate flask (0.6 g of sodium in 30 mL of toluene and 4 g of 4-methoxybenzyl alcohol were used) and added to the reaction at room temperature. The reaction was then stirred at room temperature for 5 h then water (250 mL) was added and the volume reduced to 200 mL. Diethyl ether was then added and the aqueous phase was extracted (3×500 mL). The combined organic phases were dried (MgSO$_4$), filtered and evaporated. The residue was then chromatographed on silica gel, eluting with DCM to afford 4.8 g of the title compound (60%).

$^1$H NMR (250 MHz) δ(DMSO) 3.75 (3H, s), 5.31 (2H, s), 6.14 (1H, d), 6.94 (2H, m), 7.44 (2H, m), 8.20 (2H, bs), 8.25 (1H, s).

(c) 6-({[4-(Methyloxy)phenyl]methyl}oxy)-2,3-pyridinediamine

To a suspension of 6-({[4-(methyloxy)phenyl]methyl}oxy)-3-nitro-2-pyridineamine (4.8 g, 17.5 mmol) and zinc (11 g, 175 mmol) in methanol (200 mL) was added dropwise acetic acid (5 mL) at rt. After 0.5 h the reaction was filtered through celite and then the solvent was evaporated. The residue was partitioned between water (500 mL) and ethyl acetate (500 mL), the phases were separated and the water extracted with ethyl acetate (5×500 mL). The combined organic phases were dried, filtered and evaporated to afford 3.9 g of the title compound as a black solid (91%).

MS (ES+) m/z 246 (MH+).

$^1$H NMR (250 MHz) δ(DMSO) 3.74 (3H, s), 4.12 (2H, bs), 5.03 (2H, s), 5.35 (2H, bs), 5.81 (1H, d), 6.73 (1H, d), 6.89 (2H, m), 7.32 (2H, m).

(d) Ethyl N-[2-amino-6-({[4-(methyloxy)phenyl]methyl}oxy)-3-pyridinyl]glycinate To 6-({[4-(methyloxy)phenyl]methyl}oxy)-2,3-pyridinediamine (3.9 g, 15.9 mmol) in DMF (200 mL) under Argon, potassium carbonate (4.8 g, 35 mmol) and then ethylbromo acetate (1.77 mL, 15.9 mmol) were added at rt. The reaction was stirred at rt for 2.5 h, then the solvent was removed and the residue dried under high vacuum for 1 h. The residue was subjected to column chromatography on silica gel eluting with 0-5% methanol-DCM to afford 5 g of the title compound (95%).

MS (ES+) m/z 332 (MH$^+$).

(e) 6-({[4-(Methyloxy)phenyl]methyl}oxy)pyrido[2,3-b]pyrazin-3(4H)-one

Ethyl N-[2-amino-6-({[4-(methyloxy)phenyl]methyl}oxy)-3-pyridinyl]glycinate (5 g, 15.1 mmol) was dissolved in toluene (500 mL) and heated at reflux for 2.5 days, the reaction was cooled to rt and manganese dioxide (2.4 g, 27.5 mmol) was added. After stirring for 5 h at room temperature 0.8 g of manganese dioxide were added and the reaction was stirred at room temperature overnight. The reaction was filtered through celite and the celite was washed with plenty of 20% methanol/DCM. The solvent were removed and the solid was triturated with diethyl ether, filtered off and washed with more diethyl ether to afford the title compound as a black solid (2.1 g, 50%).

$^1$H NMR (250 MHz) δ(DMSO) 3.75 (3H, s), 5.35 (2H, s), 6.77 (1H, d), 6.93 (2H, m), 7.50 (2H, m), 8.03 (1H, s), 8.08 (1H, d), 12.9 (1H, bs).

(f) 6-({[4-(methyloxy)phenyl]methyl}oxy)pyrido[2,3-b]pyrazin-3-yl trifluoromethanesulfonate A solution of 6-({[4-(methyloxy)phenyl]methyl}oxy)pyrido[2,3-b]pyrazin-3(4H)-one (1 g, 3.5 mmol) in DMF (100 mL) under argon was cooled to 0° C. and treated with sodium hydride (60% in mineral oil, 180 mg, 4.2 mmol). The reaction was stirred at rt for 0.5 h before addition of N-phenyl-bis(trifluoromethanesulfonimide) (1,1,1-trifluoro-N-phenyl-N-[(trifluoromethyl)sulfonyl]methanesulfonamide) (1.54 g, 4.2 mmol). The reaction was stirred at rt for 1 h, then water was added and the solvents were evaporated at 35° C. The residue was treated with water and extracted with DCM. The combined organic phases were dried, evaporated and subjected to column chromatography on silica gel eluting with DCM to afford 1.54 g of the title compound (100%).

¹H NMR (400 MHz) δ (CDCl₃) 3.83 (3H, s), 5.58 (2H, s), 6.94 (2H, m), 7.31 (1H, d), 7.46 (2H, m), 8.33 (1H, d), 8.71 (1H, s).

(g) 3-bromo-6-({[4-(methyloxy)phenyl]methyl}oxy)pyrido[2,3-b]pyrazine 6-({[4-(Methyloxy)phenyl]methyl}oxy)pyrido[2,3-b]pyrazin-3-yl trifluoromethanesulfonate (1.39 g, 3.35 mmol) was dissolved in dry toluene (100 mL) under argon and tetrabutylammonium bromide (2.16 g, 6.7 mmol) was added. The reaction was heated at 85° C. for 4 h; 1.08 g of tetrabutylammonium bromide were added and the reaction was heated at 90° C. for another 6 h; 0.54 g of bromide were added and the reaction was heated for 3 h. The reaction was cooled to rt, the toluene was evaporated, the residue was partitioned between water (200 mL) and diethyl ether (400 mL). The layers were separated and the aqueous was extracted with diethyl ether (2×300 mL). The organic phases were combined and washed with water (300 mL) then dried and evaporated to afford the title compound (1.19 g, 100%).

¹H NMR (250 MHz) δ (CDCl₃) 3.83 (3H, s), 5.56 (2H, s), 6.94 (2H, m), 7.27 (1H, under the solvent peak), 7.45 (2H, m), 8.57 (1H, d), 8.79 (1H, s).

(h) 3-(methyloxy)-6-({[4-(methyloxy)phenyl]methyl}oxy)pyrido[2,3-b]pyrazine

3-Bromo-6-({[4-(methyloxy)phenyl]methyl}oxy)pyrido[2,3-b]pyrazine (1.19 g, 3.44 mmol) was suspended in methanol and a solution of sodium methoxide (25% in methanol, 10.1 mL) was added at room temperature under argon. After 20 min all the solid went into solution, the reaction was stirred overnight at rt. The solvent was removed and the residue partitioned between water (250 mL) and 10% MeOH/DCM (200 mL). The aqueous phase was extracted with 10% MeOH/DCM (2×100 mL). The combined organic phases were dried, evaporated and subjected to column chromatography on silica gel eluting with DCM to afford 0.6 g of the title compound (59%).

¹H NMR (400 MHz) δ (CDCl₃) 3.83 (3H, s), 4.19 (3H, s), 5.54 (2H, s), 6.94 (2H, m), 7.04 (1H, d), 7.44 (2H, m), 8.19 (1H, d), 8.39 (1H, s).

(i) 3-(Methyloxy)pyrido[2,3-b]pyrazin-6(5H)-one 3-(Methyloxy)-6-({[4-(methyloxy)phenyl]methyl}oxy)pyrido[2,3-b]pyrazine (0.6 g, 2 mmol) was dissolved in acetonitrile (100 mL) and then ammonium cerium (IV) nitrate (1.09 g, 2 mmol) dissolved in water (50 mL) was added. The reaction was stirred at rt for 0.5 h and then 20% MeOH/DCM and water were added. The layers were separated and the aqueous was extracted with 20% MeOH/DCM twice more. The combined organic phases were dried, filtered and evaporated and the crude was purified by trituration with diethyl ether to afford the title compound (0.3 g, 85%).

MS (ES+) m/z 178 (MH⁺).

(l) 3-(Methyloxy)-5-(2-propen-1-yl)pyrido[2,3-b]pyrazin-6(5H)-one 3-(Methyloxy)pyrido[2,3-b]pyrazin-6(5H)-one (0.3 g, 1.7 mmol) was suspended in DMF (10 mL) under Argon at room temperature and then it was treated with potassium carbonate (0.47 g, 3.4 mmol) followed by allyl iodide (0.19 mL, 2.04 mmol).

After 1 h at room temperature the reaction was complete. Water (50 mL) was added followed by 10% MeOH/DCM (100 mL). Layers separated and aqueous extracted 2 more times with 10% MeOH/DCM (2×100 mL). The combined organic phases were dried (MgSO₄), filtered, evaporated and the residue was subjected to column chromatography on silica gel eluting with 0-5% methanol-DCM to afford 176 mg of pure product and 190 mg of less pure product.

MS (ES+) m/z 218 (MH⁺).

(m) [3-(Methyloxy)-6-oxopyrido[2,3-b]pyrazin-5(6H)-yl]acetaldehyde 3-(Methyloxy)-5-(2-propen-1-yl)pyrido[2,3-b]pyrazin-6(5H)-one (176 mg, 0.81 mmol) was dissolved in 1,4-dioxane (10 mL) and water (5 mL) at rt and then treated with sodium periodate (433 mg, 3.09 mmol) and 4% solution of osmium tetroxide in water (0.17 mL). The reaction was stirred at room temperature for 3 h then the 1,4-dioxane was evaporated and the aqueous phase extracted with 20% MeOH/DCM (3×50 mL). The combined organic phases were dried (MgSO₄), then toluene was added and the solvents evaporated to afford 185 mg of the title compound (100%).

¹H NMR (250 MHz) δ (CDCl₃) 3.97 (3H, s), 5.24 (2H, s), 6.83 (1H, d), 7.93 (1H, d), 8.15 (1H, s), 9.71 (1H, s).

(n) 1,1-Dimethylethyl (2,3-dihydro[1,4]dioxino[2,3-c]pyridin-7-ylmethyl)(1-{2-[3-(methyloxy)-6-oxopyrido[2,3-b]pyrazin-5(6H)-yl]ethyl}-4-piperidinyl)carbamate A suspension of [3-(methyloxy)-6-oxopyrido[2,3-b]pyrazin-5(6H)-yl]acetaldehyde (185 mg 0.84 mmol) and 1,1-dimethylethyl (2,3-dihydro[1,4]dioxino[2,3-c]pyridin-7-ylmethyl)-4-piperidinylcarbamate (for a synthesis see WO2004/058144 Example 99(h) (283 mg, 0.84 mmol) in chloroform (10 mL) and methanol (1.5 mL) was stirred at room temperature under argon for 1 h before addition of sodium triacetoxyborohydride (515 mg, 2.52 mmol). The reaction was stirred at rt overnight. A saturated solution of sodium bicarbonate (20 mL) was added to the reaction and the aqueous phase was extracted with 10% MeOH/DCM (3×50 mL). The combined organic phases were dried (MgSO₄), filtered and evaporated and the residue was subjected to column chromatography on silica gel eluting with 0-10% methanol-DCM to afford 252 mg of the title compound (60%).

MS (ES+) m/z 553 (MH⁺).

(o) Title Compound 1,1-Dimethylethyl (2,3-dihydro[1,4]dioxino[2,3-c]pyridin-7-ylmethyl)(1-{2-[3-(methyloxy)-6-oxopyrido[2,3-b]pyrazin-5(6H)-yl]ethyl}-4-piperidinyl)carbamate (250 mg, 0.45 mmol) was dissolved in chloroform (5 mL) and then treated with 4N HCl in 1,4-dioxane (5 mL). After 1.5 h the reaction was complete. Toluene was added and all the solvents were removed. The residue was dissolved in MeOH and treated with Amberlyst® A21 resin until pH was basic. The resin was filtered off, the methanol was removed and the residue was subjected to column chromatography on silica gel eluting with 0-10% 2M NH₃ in methanol-DCM to afford 141 mg of the title compound as the free base (70%).

¹H NMR (250 MHz) δ (CDCl₃) 1.40 (2H, m), 1.88 (2H, d), 2.01 (1H, bs), 2.17 (2H, m), 2.50 (1H, m), 2.70 (2H, m), 3.03

(2H, d), 3.78 (2H, s), 4.07 (3H, s), 4.30 (4H, m), 4.58 (2H, m), 6.75 (1H, d), 6.82 (1H, s), 7.83 (1H, d), 8.09 (1H, s), 8.10 (1H, s).

MS (ES+) m/z 453 (MH$^+$).

This material was converted to the hydrochloride by dissolving in dichloromethane/methanol and adding 1 equivalent of 4M HCl/1,4-dioxane then evaporating to dryness. The residue was dissolved in a minimum amount of methanol and diethyl ether added to precipitate it; solvent was then decanted and the solid dried in vacuo over $P_2O_5$ dessicant.

Example 95

5-(2-{4-[(6,7-dihydro[1,4]dioxino[2,3-c]pyridazin-3-ylmethyl)amino]-1-piperidinyl}ethyl)-3-(methyloxy)pyrido[2,3-b]pyrazin-6(5H)-one Fumarate

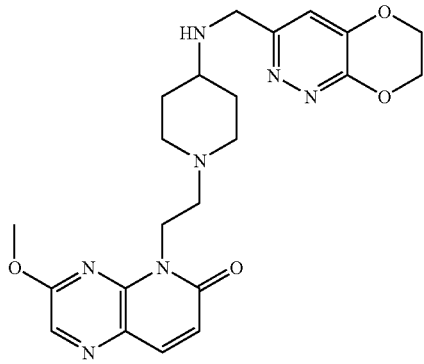

(a) 1,1-Dimethylethyl (6,7-dihydro[1,4]dioxino[2,3-c]pyridazin-3-ylmethyl)(1-{2-[3-(methyloxy)-6-oxopyrido[2,3-b]pyrazin-5(6H)-yl]ethyl}-4-piperidinyl)carbamate A suspension of [3-(methyloxy)-6-oxopyrido[2,3-b]pyrazin-5(6H)-yl]acetaldehyde (240 mg, assuming 191 mg of aldehyde) and 1,1-dimethylethyl (6,7-dihydro[1,4]dioxino[2,3-c]pyridazin-3-ylmethyl)-4-piperidinylcarbamate (305 mg) in chloroform (10 mL) and methanol (1.5 mL) was stirred at room temperature under argon for 1 h before addition of sodium triacetoxyborohydride (553 mg). The reaction was stirred at rt overnight. A saturated solution of sodium bicarbonate (20 mL) was added to the reaction and the aqueous was extracted with 10% MeOH/DCM (3×50 mL). The combined organic phases were dried (MgSO$_4$), evaporated and the residue was subjected to column chromatography on silica gel eluting with 0-10% methanol-DCM to afford 358 mg of the title compound (60%).

MS (ES+) m/z 554 (MH$^+$).

(b) Title Compound 1,1-Dimethylethyl (6,7-dihydro[1,4]dioxino[2,3-c]pyridazin-3-ylmethyl)(1-{2-[3-(methyloxy)-6-oxopyrido[2,3-b]pyrazin-5(6H)-yl]ethyl}-4-piperidinyl)carbamate (358 mg, 0.65 mmol) was dissolved in DCM (5 mL) and then trifluoroacetic acid (5 mL) was added. After 1 h all the solvents were removed and the residue was dissolved in MeOH and treated with amberlyst A21 resin until pH was basic. The resin was filtered off, the methanol was removed and the residue was subjected to column chromatography on silica gel eluting with 0-10% 2M NH$_3$ in methanol-DCM to afford 207 mg of the title compound as the free base (70%).

$^1$H NMR (250 MHz) δ (CDCl$_3$) 1.38 (2H, m), 1.89 (3H, d), 2.16 (2H, m), 2.50 (1H, m), 2.70 (2H, m), 3.03 (2H, d), 3.99 (2H, s), 4.07 (3H, s), 4.37 (2H, m), 4.50-4.60 (4H, m), 6.75 (1H, d), 7.04 (1H, s), 7.83 (1H, d), 8.11 (1H, s).

MS (ES+) m/z 454 (MH$^+$).

This material was converted to the fumarate by dissolving in methanol and adding 1 equivalent of 0.5M fumaric acid solution then evaporating to dryness.

Example 96

1-(2-{4-[(2,3-Dihydro[1,4]dioxino[2,3-c]pyridin-7-ylmethyl)amino]-1-piperidinyl}ethyl)-7-fluoro-1,5-naphthyridin-2(1H)-one 5-oxide Hydrochloride

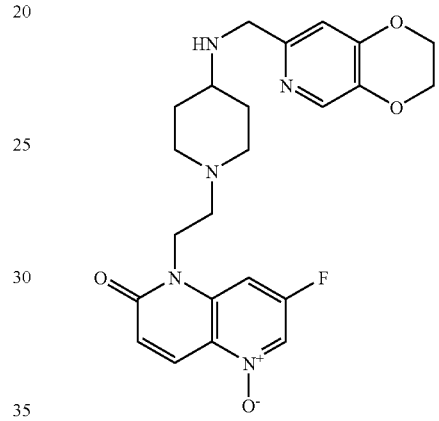

(a) 7-Fluoro-1,5-naphthyridin-2(1H)-one 5-oxide

7-Fluoro-1,5-naphthyridin-2(1H)-one (1.280 g, 7.798 mmol) and m-chloroperoxybenzoic acid (2.123 g, ca. 1.2 eq. based on an mCPBA content of 75%) were stirred in chloroform (60 mL) at reflux overnight. Further mCPBA (0.420 g) was added and the mixture was stirred at reflux for an additional 6 hours. The mixture was diluted with DCM to a total volume of ca. 100 ml and filtered with suction. The solid collected was washed with DCM (2×20 mL) and air-dried to give 7-fluoro-1,5-naphthyridin-2(1H)-one 5-oxide as a tan solid (1.045 g, contaminated with ca. 12% starting material).

MS (ES+) m/z 181 (MH$^+$).

(b) 7-Fluoro-1-(2-propen-1-yl)-1,5-naphthyridin-2(1H)-one 5-oxide

Crude 7-fluoro-1,5-naphthyridin-2(1H)-one 5-oxide (0.995 g, 5.524 mmol) and potassium carbonate were stirred in anhydrous DMF (20 mL) under argon, and allyl iodide (1.5 mL, ca. 3 eq.) was added. The mixture was stirred at rt overnight. The solvent was removed under reduced pressure and the residue was partitioned between DCM (100 mL) and water (50 mL). The organic phase was separated using a hydrophobic frit and the aqueous phase was extracted with DCM (2×50 mL). The combined organic extracts were dried over anhydrous sodium sulphate, filtered and evaporated under reduced pressure to give the crude product as a brown gum. This was purified by column chromatography on silica gel eluted with 0-10% methanol in DCM. Appropriate fractions were combined and evaporated under reduced pressure to give 7-fluoro-1-(2-propen-1-yl)-1,5-naphthyridin-2(1H)-one 5-oxide (0.341 g) as a tan amorphous solid.

MS (ES+) m/z 221 (MH+).

(c) (7-Fluoro-5-oxido-2-oxo-1,5-naphthyridin-1 (2H)-yl)acetaldehyde (as the Methyl Hemiacetal)

7-Fluoro-1-(2-propen-1-yl)-1,5-naphthyridin-2(1H)-one 5-oxide (340 mg, 1.544 mmol) was stirred in 1,4-dioxane (16 mL) and water (8 mL) was added, followed by sodium periodate (990 mg, 2.3 eq.) and osmium tetroxide (1 mL of 4% aqueous solution). The mixture was stirred at room temperature for 3 hours. The solvents were evaporated under reduced pressure (water bath temperature 30° C.) to a volume of ca. 10 mL, and the residue was extracted with 20% methanol in DCM (v:v, 3×50 mL). The combined organic extracts were dried over anhydrous sodium sulphate, filtered and evaporated under reduced pressure to give (7-fluoro-5-oxido-2-oxo-1,5-naphthyridin-1(2H)-yl)acetaldehyde largely as its methyl hemiacetal) as a tan foam (327 mg). LCMS showed major peaks for the aldehyde hydrate (32%) and the methyl hemiacetal (64%).

MS (ES+) m/z 241 (MH+ for aldehyde hydrate), m/z 255 (MH+ for Methyl Hemiacetal).

(d) 1,1-Dimethylethyl {1-[2-(7-fluoro-5-oxido-2-oxo-1,5-naphthyridin-1(2H)-yl)ethyl]-4-piperidinyl}carbamate A mixture of (7-fluoro-5-oxido-2-oxo-1,5-naphthyridin-1 (2H)-yl)acetaldehyde (as the methyl hemiacetal) (327 mg, 1.286 mmol) and 1,1-dimethylethyl 4-piperidinylcarbamate (283 mg, 1.1 eq.) in chloroform:methanol (9:1 v:v) (5 ml) was stirred for 2 h before addition of $NaBH(OAc)_3$ (481 mg, 2 eq.). The reaction was stirred for 0.5 h before addition of sat. aq $NaHCO_3$ (5 ml). The reaction was then diluted with DCM (80 mL) and the organic phase was separated using a hydrophobic frit. The aqueous phase was extracted with DCM (2×50 mL) The combined organic extracts were dried, evaporated and the crude residue purified by chromatography on silica gel using a 0-20% (2M $NH_3$ in MeOH)/DCM gradient to provide the desired compound (345 mg, 66%) as a tan foam.

MS (ES+) m/z 407 (MH+).

(e) 1-[2-(4-Amino-1-piperidinyl)ethyl]-7-fluoro-1,5-naphthyridin-2(1H)-one 5-oxide Dihydrochloride 1,1-Dimethylethyl {1-[2-(7-fluoro-5-oxido-2-oxo-1,5-naphthyridin-1(2H)-yl)ethyl]-4-piperidinyl}carbamate (335 mg, 0.824 mmol) was dissolved in DCM (3 mL) and 4M HCl in 1,4-dioxane (0.830 mL (ca. 4 eq.) was added. A further 10 mL DCM was added to disperse the solid, then a further 0.830 mL 4M HCl in 1,4-dioxane was added. The mixture was left at room temperature for 30 minutes, then the solvents were removed under reduced pressure to give title compound as a white solid (315 mg).

MS (ES+) m/z 307 (MH+).

(f) Title Compound

1-[2-(4-Amino-1-piperidinyl)ethyl]-7-fluoro-1,5-naphthyridin-2(1H)-one 5-oxide dihydrochloride (100 mg, 0.264 mmol) was stirred in chloroform (2 mL) plus methanol (0.1 mL), and triethylamine (0.130 mL) was added. After stirring for 10 minutes at room temperature 3,4-dihydro-2H-pyrano [2,3-c]pyridine-6-carbaldehyde (for a synthesis see WO2004058144, Example 126(e)) (44 mg, 1 eq.) was added and the mixture was stirred at rt for a further 3 hours before addition of sodium triacetoxyborohydride (168 mg, 3 eq.). After a further 3 hours, saturated aqueous sodium hydrogen cabonate (1 ml) was added and the organic phase was diluted with DCM to bring the total volume to ca. 50 ml. The organic phase was separated using a hydrophobic frit and the aqueous phase was extracted with DCM (2×20 ml). The combined DCM extracts were evaporated under reduced pressure and purified by MDAP to give the free base of the title compound as a tan amorphous solid (39 mg).

MS (ES+) m/z 456 (MH+).

This material was converted to the hydrochloride by dissolving in DCM and adding 1 equivalent of 1M HCl/diethyl ether then evaporating to dryness. MS as that of the free base.

Example 97

7-fluoro-1-(2-{4-[([1,3]oxathiolo[5,4-c]pyridin-6-ylmethyl)amino]-1-piperidinyl}ethyl)-1,5-naphthyridin-2(1R)-one 5-oxide Hydrochloride

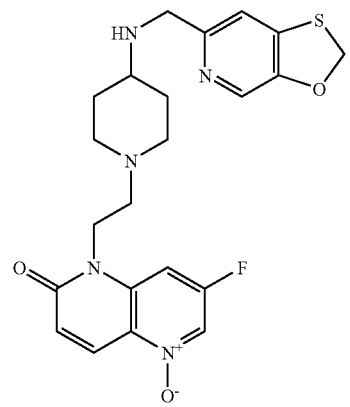

1-[2-(4-Amino-1-piperidinyl)ethyl]-7-fluoro-1,5-naphthyridin-2(1H)-one 5-oxide dihydrochloride (91 mg) was stirred in 9:1 v:v chloroform:methanol (3 mL) and triethylamine (0.117 mL) was added. After stirring for 5 minutes at room temperature[1,3]oxathiolo[5,4-c]pyridine-6-carbaldehyde (for a synthesis see WO2004058144, Example 61) (40 mg, 1 eq.) was added and the mixture was stirred at rt for a further 3 hours before addition of sodium triacetoxyborohydride (152 mg, 3 eq.). After a further 1 hour, saturated aqueous sodium hydrogen cabonate (1 ml) was added and the organic phase was diluted with DCM to bring the total volume to ca. 20 ml. The organic phase was separated using a hydrophobic frit, evaporated under reduced pressure and purified by MDAP to give the free base of the title compound as a white foam (56 mg).

MS (ES+) m/z 458 (MH+).

This material was converted to the hydrochloride by dissolving in DCM and adding 1 equivalent of 1M HCl/diethyl ether then evaporating to dryness. MS as that of the free base.

TABLE 1

Examples 98-101 were made from (7-fluoro-2-oxo-1(2H)-quinolinyl)acetaldehyde, phenylmethyl [(3R-3-pyrrolidinylmethyl]carbamate (may be prepared analogously to WO2006002047 Preparation 23(b)) and the specified aldehyde by the general method of Example 72.

| Example number | Form tested | Structure | Aldehyde |
|---|---|---|---|
| 98 | Free base MS (ES+) m/z 468 (MH+) | 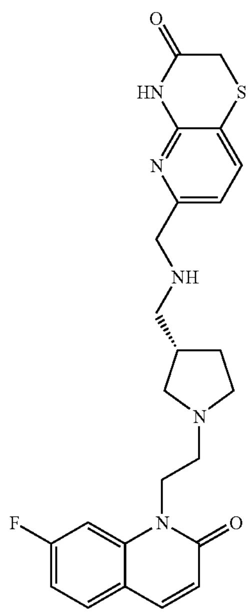 | 3-Oxo-3,4-dihydro-2H-pyrido[3,2-b][1,4]thiazine-6-carboxaldehyde (for a synthesis, see WO2004058144, Example 7(d)) |
| 99 | Free base MS (ES+) m/z 486 (MH+) | 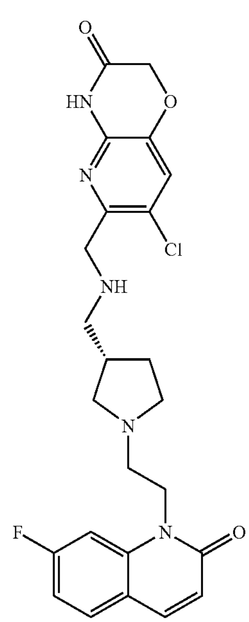 | 7-Chloro-3-oxo-3,4-dihydro-2H-pyrido[3,2-b][1,4]oxazine-6-carboxaldehyde (for a synthesis see WO2003064421, Example 15(c)) |

TABLE 1-continued

Examples 98-101 were made from (7-fluoro-2-oxo-1(2H)-quinolinyl)acetaldehyde, phenylmethyl [(3R-3-pyrrolidinylmethyl]carbamate (may be prepared analogously to WO2006002047 Preparation 23(b)) and the specified aldehyde by the general method of Example 72.

| Example number | Form tested | Structure | Aldehyde |
|---|---|---|---|
| 100 | Mono-HCl<br>MS (ES+) m/z<br>439 (MH+) | 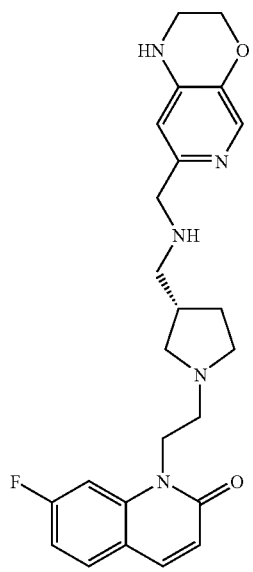 | 2,3-Dihydro[1,4]dioxino[2,3-c]pyridine-7-carboxaldehyde (for a synthesis see WO2004058144, Example 2(c) or WO03/087098, Example 19(d)) |
| 101 | Mono-HCl<br>MS (ES+) m/z<br>440 (MH+) | 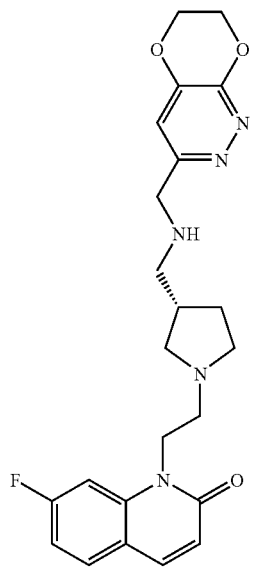 | 6,7-Dihydro[1,4]dioxino[2,3-c]pyridazine-3-carbaldehyde |

TABLE 2

Examples 102-112 were made from the specified starting materials by the general method of Example 50.

| Example number | Form tested | Structure | Starting materials |
|---|---|---|---|
| 102 | Mono-fumarate MS (ES+) m/z 481 (MH+) | 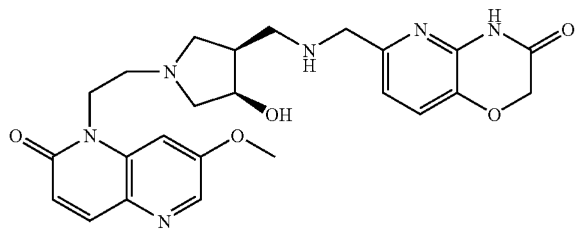 | [7-(Methoxy)-2-oxo-1,5-naphthyridin-1(2H)-yl]acetaldehyde (as the methyl hemiacetal) Phenylmethyl {[(3S,4R-4-hydroxy-3-pyrrolidinyl]methyl}carbamate 3-Oxo-3,4-dihydro-2H-pyrido[3,2-b][1,4]oxazine-6-carboxaldehyde (for a synthesis see WO2003087098, Example 31(e)) |
| 103 | Free base MS (ES+) m/z 497/499 (MH+) | 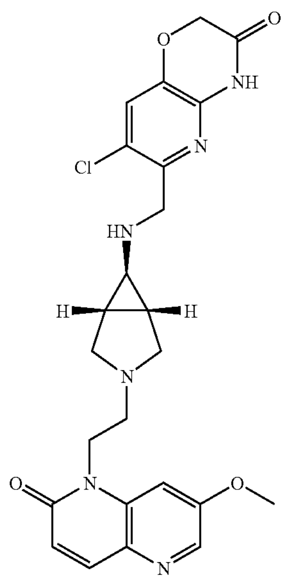 | [7-(Methoxy)-2-oxo-1,5-naphthyridin-1(2H)-yl]acetaldehyde (as the methyl hemiacetal) Exo-phenylmethyl-3-azabicyclo[3.1.0]hex-6-ylcarbamate (see Preparation 1 below for a synthesis) 7-Chloro-3-oxo-3,4-dihydro-2H-pyrido[3,2-b][1,4]oxazine-6-carboxaldehyde (for a synthesis see WO2003064421, Example 15(c)) |
| 104 | Free base MS (ES+) m/z 463 (MH+) | 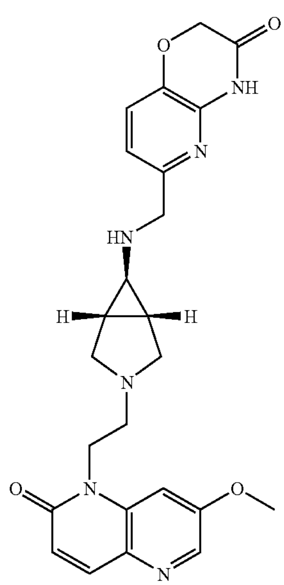 | [7-(Methoxy)-2-oxo-1,5-naphthyridin-1(2H)-yl]acetaldehyde (as the methyl hemiacetal) Exo-phenylmethyl-3-azabicyclo[3.1.0]hex-6-ylcarbamate (see Preparation 1 below for a synthesis) 3-Oxo-3,4-dihydro-2H-pyrido[3,2-b][1,4]oxazine-6-carboxaldehyde (for a synthesis see WO2003087098, Example 31(e)) |

TABLE 2-continued

Examples 102-112 were made from the specified starting materials by the general method of Example 50.

| Example number | Form tested | Structure | Starting materials |
|---|---|---|---|
| 105 | Free base<br>MS (ES+)<br>m/z 450<br>(MH+) | 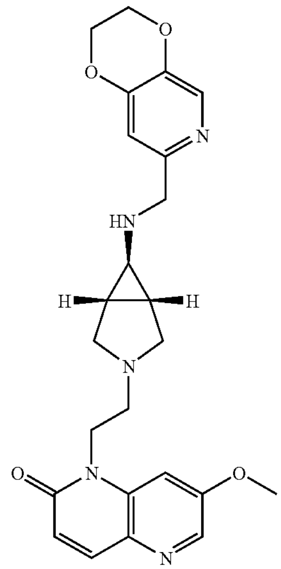 | [7-(Methoxy)-2-oxo-1,5-naphthyridin-1(2H)-yl]acetaldehyde (as the methyl hemiacetal)<br>Exo-phenylmethyl-3-azabicyclo[3.1.0]hex-6-ylcarbamate (see Preparation 1 below for a synthesis)<br>2,3-Dihydro[1,4]dioxino[2,3-c]pyridine-7-carboxaldehyde (for a synthesis see WO2004058144, Example 2(c) or WO03/087098, Example 19(d)) |
| 106 | Mono-HCl<br>MS (ES+)<br>m/z 469<br>(MH+) | 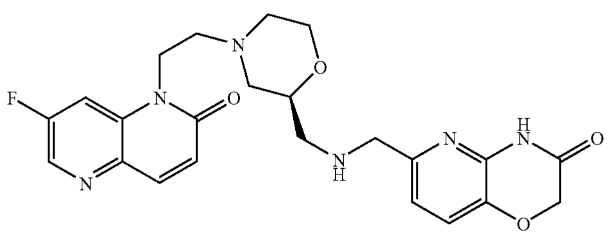 | (7-Fluoro-2-oxo-1,5-naphthyridin-1(2H)-yl)acetaldehyde (as the methyl hemiacetal)<br>1,1-Dimethylethyl [(2R)-2-morpholinyl-methyl]carbamate<br>3-Oxo-3,4-dihydro-2H-pyrido[3,2-b][1,4]oxazine-6-carboxaldehyde (for a synthesis see WO2003087098, Example 31(e)) |
| 107 | Mono-HCl<br>MS (ES+)<br>m/z 485<br>(MH+) | 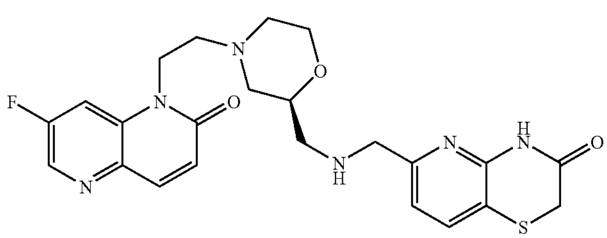 | (7-Fluoro-2-oxo-1,5-naphthyridin-1(2H)-yl)acetaldehyde (as the methyl hemiacetal)<br>1,1-Dimethylethyl [(2R)-2-morpholinyl-methyl]carbamate<br>3-Oxo-3,4-dihydro-2H-pyrido[3,2-b][1,4]thiazine-6-carboxaldehyde (for a synthesis, see WO2004058144, Example 7(d)) |
| 108 | Mono-HCl<br>MS (ES+)<br>m/z 503/505<br>(MH+) | 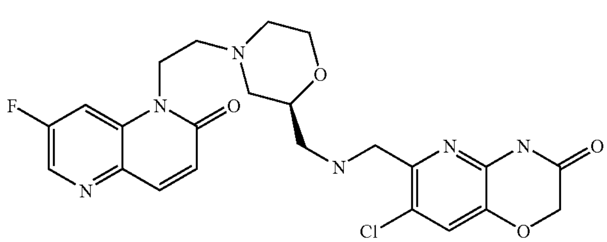 | (7-Fluoro-2-oxo-1,5-naphthyridin-1(2H)-yl)acetaldehyde (as the methyl hemiacetal)<br>1,1-Dimethylethyl [(2R)-2-morpholinyl-methyl]carbamate<br>7-Chloro-3-oxo-3,4-dihydro-2H-pyrido[3,2-b][1,4]oxazine-6-carboxaldehyde (for a synthesis, see WO2003064421, Example 15(c)) |

TABLE 2-continued

Examples 102-112 were made from the specified starting materials by the general method of Example 50.

| Example number | Form tested | Structure | Starting materials |
| --- | --- | --- | --- |
| 109 | Mono-HCl MS (ES+) m/z 466 (MH+) | 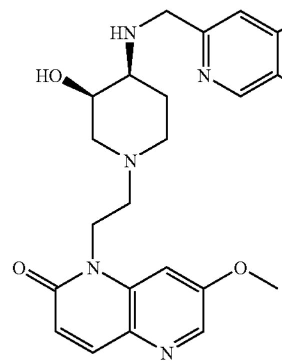 | [7-(Methoxy)-2-oxo-1,5-naphthyridin-1(2H)-yl]acetaldehyde (as the methyl hemiacetal) 1,1-Dimethylethyl[(3R,4S)-3-hydroxy-4-piperidinyl]carbamate (for a synthesis see WO2004058144, Example 5(c), cis-(3-hydroxy-piperidin-4-yl)-carbamic acid tert-butyl ester Enantiomer 1) 3,4-Dihydro-2H-pyrano[2,3-c]pyridine-6-carbaldehyde (for a synthesis see WO2004058144, Example 126(e)) |
| 110 | Mono-HCl MS (ES+) m/z 481 (MH+) | 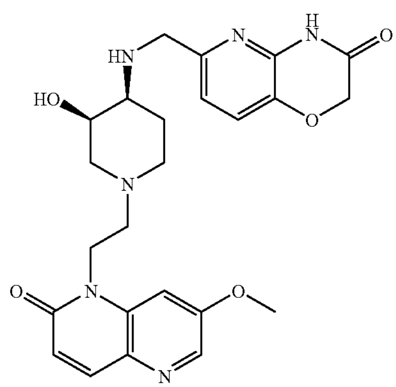 | [7-(Methoxy)-2-oxo-1,5-naphthyridin-1(2H)-yl]acetaldehyde (as the methyl hemiacetal) 1,1-Dimethylethyl[(3R,4S)-3-hydroxy-4-piperidinyl]carbamate (for a synthesis see WO2004058144, Example 5(c), cis-(3-hydroxy-piperidin-4-yl)-carbamic acid tert-butyl ester Enantiomer 1) 3-Oxo-3,4-dihydro-2H-pyrido[3,2-b][1,4]oxazine-6-carboxaldehyde (for a synthesis see WO2003087098, Example 31(e)) |
| 111 | Mono-HCl MS (ES+) m/z 454 (MH+) | 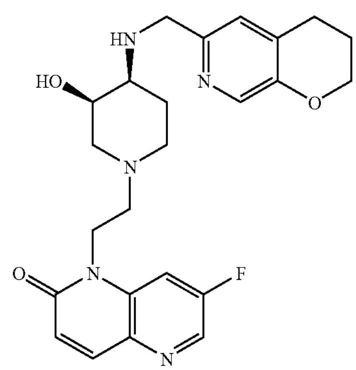 | (7-Fluoro-2-oxo-1,5-naphthyridin-1(2H)-yl)acetaldehyde (as the methyl hemiacetal) 1,1-Dimethylethyl[(3R,4S)-3-hydroxy-4-piperidinyl]carbamate (for a synthesis see WO2004058144, Example 5(c), cis-(3-hydroxy-piperidin-4-yl)-carbamic acid tert-butyl ester Enantiomer 1) 3,4-Dihydro-2H-pyrano[2,3-c]pyridine-6-carbaldehyde (for a synthesis see WO2004058144, Example 126(e)) |
| 112 | Mono-HCl MS (ES+) m/z 469 (MH+) | 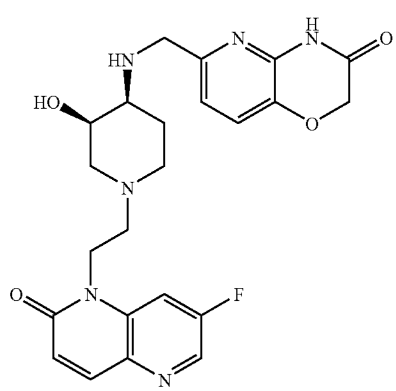 | (7-Fluoro-2-oxo-1,5-naphthyridin-1(2H)-yl)acetaldehyde (as the methyl hemiacetal) 1,1-Dimethylethyl[(3R,4S)-3-hydroxy-4-piperidinyl]carbamate (for a synthesis see WO2004058144, Example 5(c), cis-(3-hydroxy-piperidin-4-yl)-carbamic acid tert-butyl ester Enantiomer 1) 3-Oxo-3,4-dihydro-2H-pyrido[3,2-b][1,4]oxazine-6-carboxaldehyde (for a synthesis see WO2003087098, Example 31(e)) |

Preparation 1

Synthesis of exo-phenylmethyl-3-azabicyclo[3.1.0]hex-6-ylcarbamate

Exo-phenylmethyl-3-azabicyclo[3.1.0]hex-6-ylcarbamate was synthesised from the known exo-1,1-dimethylethyl 6-[bis(phenylmethyl)amino]-3-azabicyclo[3.1.0]hexane-3-carboxylate (for synthesis see De Meijere, A.; Williams, C. M.; Kourdioukov, A.; Sviridov, S, V.; Chaplinski, V,; Kordes, M,; Savchenko, A, I.; Stratmann, C,; Noltemeyer, M. Chemistry—A European Journal (2002), 8(16), 3789-3801), by the following three step sequence.

(1) Hydrogenation with Pd(OH)$_2$ catalyst to give exo-1,1-dimethylethyl 6-amino-3-azabicyclo[3.1.0]hexane-3-carboxylate, (2) Protection of the primary amine of exo-1,1-dimethylethyl 6-amino-3-azabicyclo[3.1.0]hexane-3-carboxylate with benzyl chloroformate to give exo-1,1-dimethylethyl 6-({[(phenylmethyl)oxy]carbonyl}amino)-3-azabicyclo[3.1.0]hexane-3-carboxylate and then (3) Deprotection of exo-1,1-dimethylethyl 6-({[(phenylmethyl)oxy]carbonyl}amino)-3-azabicyclo[3.1.0]hexane-3-carboxylate with HCl/DCM to give the title compound.

TABLE 3

Examples 113-118 were made from [6-(methyloxy)-3-oxopyrido[2,3-b]pyrazin-4(3H)-yl]acetaldehyde (see Example 126(e) below for a synthesis) and the specified starting materials by the general method of Example 50

| Example number | Form tested | Structure | Starting materials |
|---|---|---|---|
| 113 | Di-HCl MS (ES+) m/z 516/518 (MH$^+$) | 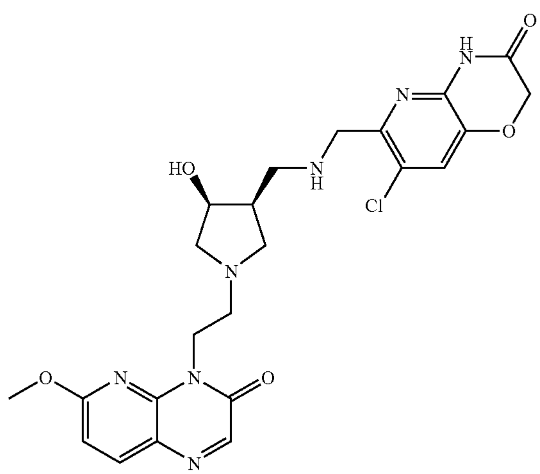 | Phenylmethyl {[(3R,4S-4-hydroxy-3-pyrrolidinyl]methyl}carbamate 7-Chloro-3-oxo-3,4-dihydro-2H-pyrido[3,2-b][1,4]oxazine-6-carboxaldehyde (for a synthesis see WO2003064421, Example 15(c)) |
| 114 | Di-HCl MS (ES+) m/z 482 (MH$^+$) | 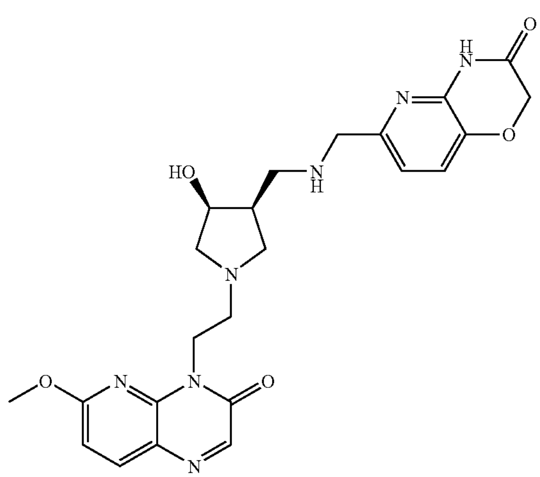 | Phenylmethyl {[(3R,4S-4-hydroxy-3-pyrrolidinyl]methyl}carbamate 3-Oxo-3,4-dihydro-2H-pyrido[3,2-b][1,4]oxazine-6-carboxaldehyde (for a synthesis see WO2003087098, Example 31(e)) |

TABLE 3-continued

Examples 113-118 were made from [6-(methyloxy)-3-oxopyrido[2,3-b]pyrazin-4(3H)-yl]acetaldehyde (see Example 126(e) below for a synthesis) and the specified starting materials by the general method of Example 50

| Example number | Form tested | Structure | Starting materials |
| --- | --- | --- | --- |
| 115 | Di-HCl MS (ES+) m/z 498 (MH+) | 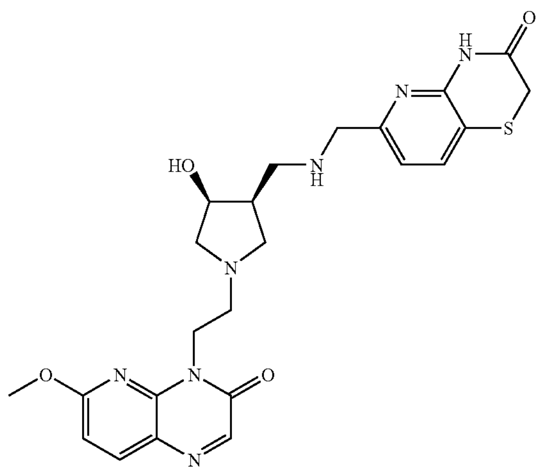 | Phenylmethyl {[(3R,4S-4-hydroxy-3-pyrrolidinyl]methyl}carbamate 3-Oxo-3,4-dihydro-2H-pyrido[3,2-b][1,4]thiazine-6-carboxaldehyde (for a synthesis, see WO2004058144, Example 7(d)) |
| 116 | Di-HCl MS (ES+) m/z 469 (MH+) | 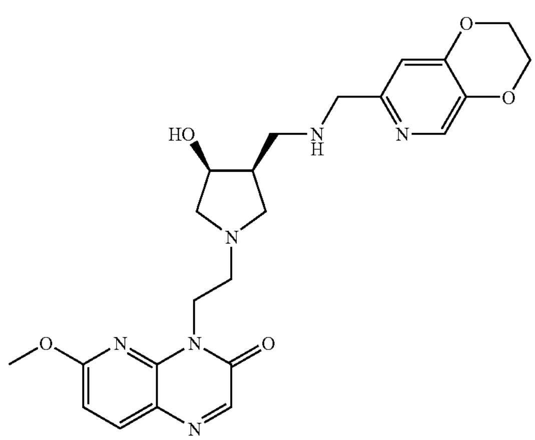 | Phenylmethyl {[(3R,4S-4-hydroxy-3-pyrrolidinyl]methyl}carbamate 2,3-Dihydro[1,4]dioxino[2,3-c]pyridine-7-carboxaldehyde (for a synthesis see WO2004058144, Example 2(c) or WO03/087098, Example 19(d)) |
| 117 | Di-HCl MS (ES+) m/z 480 (MH+) | 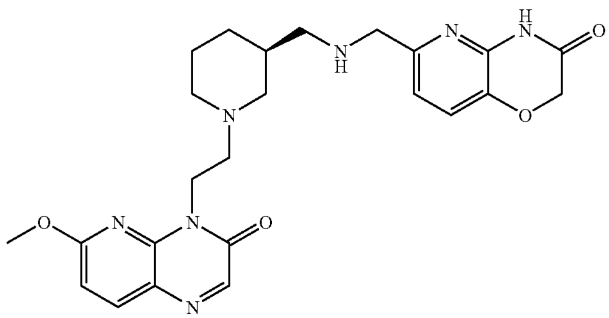 | Phenylmethyl [(3R)-3-piperidinylmethyl]carbamate 3-Oxo-3,4-dihydro-2H-pyrido[3,2-b][1,4]oxazine-6-carboxaldehyde (for a synthesis see WO2003087098, Example 31(e)) |

TABLE 3-continued

Examples 113-118 were made from [6-(methyloxy)-3-oxopyrido[2,3-b]pyrazin-4(3H)-yl]acetaldehyde (see Example 126(e) below for a synthesis) and the specified starting materials by the general method of Example 50

| Example number | Form tested | Structure | Starting materials |
|---|---|---|---|
| 118 | Di-HCl MS (ES+) m/z 514/516 (MH+) | 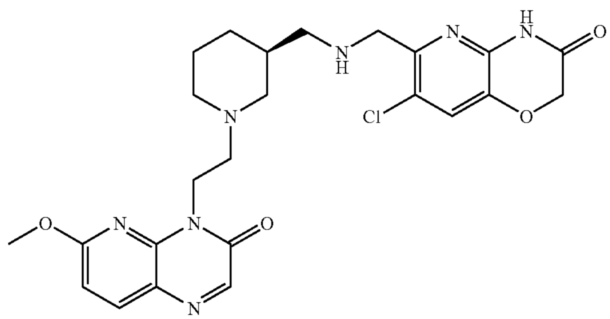 | Phenylmethyl [(3R)-3-piperidinylmethyl]carbamate 7-Chloro-3-oxo-3,4-dihydro-2H-pyrido[3,2-b][1,4]oxazine-6-carboxaldehyde (for a synthesis see WO2003064421, Example 15(c)) |

Example 116A

4-[2-((3S,4S)-3-{[(2,3-Dihydro[1,4]dioxino[2,3-c]pyridin-7-ylmethyl)amino]methyl}-4-hydroxy-1-pyrrolidinyl)ethyl]-6-(methyloxy)pyrido[2,3-b]pyrazin-3(4H)-one Dihydrochloride

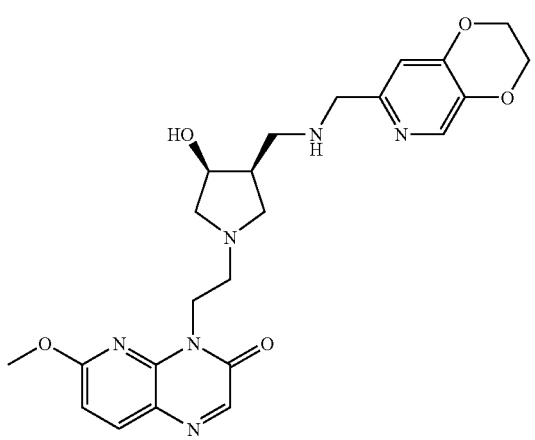

(a) Phenylmethyl [((3S,4S)-4-hydroxy-1-{2-[6-(methyloxy)-3-oxopyrido[2,3-b]pyrazin-4(3H)-yl]ethyl}-3-pyrrolidinyl)methyl]carbamate A solution of 6-(methyloxy)-3-oxopyrido[2,3-b]pyrazin-4(3H)-yl]acetaldehyde (0.348 g including some hemiacetal) (for a preparation see Example 126(e)) and phenylmethyl {[(3R,4S)-4-hydroxy-3-pyrrolidinyl]methyl}carbamate (0.395 g) (for a preparation see Example 61(a)) in methanol (2 mL) and chloroform (6 mL) was stirred at room temperature overnight. Sodium triacetoxyborohydride (0.671 g) was added and the mixture was stirred at room temperature for 1 hour. The mixture was extracted with DCM (3×), dried (sodium sulphate), evaporated, and chromatographed on silica gel, eluting with 0-10% methanol-chloroform-1% NH$_4$OH to give the product. The reaction was repeated with 0.220 g aldehyde, 0.395 g amine and 0.414 g borohydride and the batches combined (1.0 g, 85%).

LCMS: m/z 454 (MH+).

(b) 4-{2-[(3S,4S)-3-(Aminomethyl)-4-hydroxy-1-pyrrolidinyl]ethyl}-6-(methyloxy)pyrido[2,3-b]pyrazin-3(4H)-one A solution of phenylmethyl [((3S,4S)-4-hydroxy-1-{2-[6-(methyloxy)-3-oxopyrido[2,3-b]pyrazin-4(3H)-yl]ethyl}-3-pyrrolidinyl)methyl]carbamate (1.0 g, 2.2 mmol) in methanol was treated with 10% Pd/C (0.44 g) and shaken under 15 psi at room temperature for 2 hours. Pd was filtered through Celite®, the filtrate was concentrated. The residue was redissolved in DCM (20 mL) and methanol (5 mL), treated with manganese(IV) oxide (561 mg, 6.6 mmol), and stirred at room temperature for 2 hours. Solid was filtered and filtrate was concentrated to give product (0.6 g, 85%).

LCMS: m/z 320 (MH+).

(c) Title Compound

A solution of 4-{2-[(3S,4S)-3-(aminomethyl)-4-hydroxy-1-pyrrolidinyl]ethyl}-6-(methyloxy)pyrido[2,3-b]pyrazin-3(4H)-one (70 mg; 0.22 mmol) and 2,3-dihydro[1,4]dioxino[2,3-c]pyridine-7-carbaldehyde (for a synthesis see WO2004058144, Example 2(c) or WO03/087098, Example 19(d)) (36 mg, 0.22 mmol) in methanol (1 mL), DCM (5 mL) was stirred at room temperature overnight. Sodium triacetoxyborohydride (0.093 g; 0.44 mmol) was added and the mixture was stirred at room temperature for 1 hour. The solvent was evaporated and chromatographed on silica gel, eluting with 0-20% methanol-DCM-2% NH$_4$OH to give an oil.

1H NMR (400 MHz, METHANOL-d$_4$) δ ppm 2.30-2.41 (m, 1H) 2.55 (t, J=-8.97 Hz, 1H) 2.60-2.68 (m, 2H) 2.83-2.93 (m, 2H) 2.95-3.02 (m, 2H) 3.19 (dd, J=10.61, 5.56 Hz, 1H) 3.71-3.80 (m, 2H) 4.08 (s, 3H) 4.29-4.40 (m, 5H) 4.57-4.65 (m, 2H) 6.81-6.86 (m, 1H) 6.95 (s, 1H) 8.00 (s, 1H) 8.06-8.10 (m, 2H)

LCMS: m/z 469 (MH+).

The oil was treated with 1M HCl (2 eq.) to give the title compound (25 mg, 21%) as dihydrochloride salt.

Example 116B

4-[2-((3S,4S)-3-{[(2,3-Dihydro[1,4]dioxino[2,3-c]pyridin-7-ylmethyl)amino]methyl}-4-hydroxy-1-pyrrolidinyl)ethyl]-6-(methyloxy)pyrido[2,3-b]pyrazin-3(4H)-one Benzoate The benzoate salt was prepared by dissolving the free base in MeOH and adding 1 equivalent of benzoic acid. The solvent was evaporated and the benzoate salt was recovered.

(a) 6-(Methyloxy)-4-(2-propen-1-yl)-1,2,4-benzotriazin-3(4H)-one

To a solution of 6-chloro-4-(2-propen-1-yl)-1,2,4-benzotriazin-3(4H)-one 1-oxide (see Example 60(c) for a preparation) (420 mg, 1.77 mmol) in MeOH (10 ml) was added sodium methoxide solution (25% w/v, 8.84 mmol, 1.9 ml) and then the reaction was stirred at rt for 2 h. The reaction was then treated with water (100 ml) and extracted with DCM (2×100 ml). The combined organic phases were dried, evapo-

TABLE 4

Examples 119-120 were made from 5,7-difluoro-2-oxo-1(2H)-quinoxalinylacetaldehyde
(prepared from (2-amino-3,5-difluorophenyl)amine by the general method of Example 34(a)-(c))
and the specified starting material by the general method of Example 43(d)-(e).

| Example number | Form tested | Structure | Starting materials |
|---|---|---|---|
| 119 | Mono-fumarate MS (ES+) m/z 458 (MH+) | 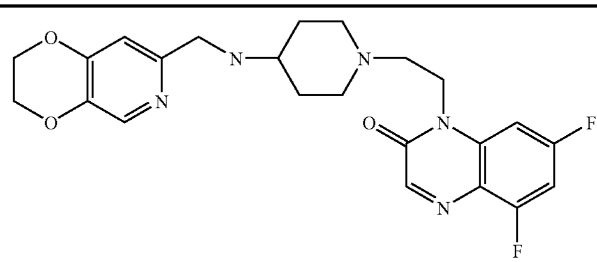 | 1,1-Dimethylethyl (2,3-dihydro[1,4]dioxino[2,3-c]pyridin-7-ylmethyl)4-piperidinylcarbamate (for a synthesis see WO2004/058144 Example 99(h) |
| 120 | Mono-fumarate MS (ES+) m/z 459 (MH+) | 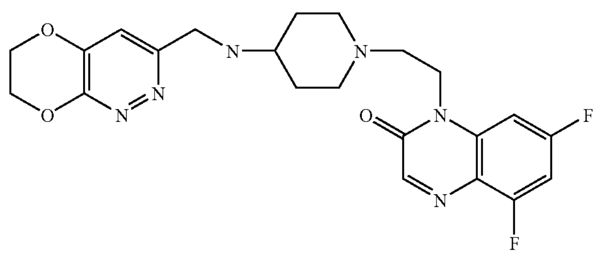 | 1,1-Dimethylethyl (6,7-dihydro[1,4]dioxino[2,3-c]pyridazin-3-ylmethyl)-4-piperidinylcarbamate |

Example 121

4-(2-{4-[(2,3-dihydro[1,4]dioxino[2,3-c]pyridin-7-ylmethyl)amino]-1-piperidinyl}ethyl)-6-(methyloxy)-1,2,4-benzotriazin-3(4H)-one Hydrochloride

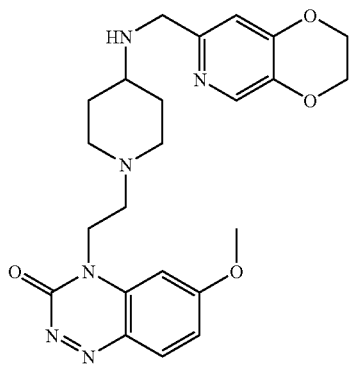

rated and the crude residue purified by chromatography on silica gel using a 0-5% MeOH/DCM gradient, followed by trituration with diethyl ether (50 ml) to provide the desired compound as a yellow foam (205 mg, 53%).
MS (ES+) m/z 218 (MH+).

(b) [6-(Methyloxy)-3-oxo-1,2,4-benzotriazin-4(3H)-yl]acetaldehyde (as the Methyl Hemiacetal)

6-(Methyloxy)-4-(2-propen-1-yl)-1,2,4-benzotriazin-3 (4H)-one (75 mg, 0.346 mmol) was dissolved in 1,4-dioxane (5 ml) and water (2 ml). Sodium periodate (185 mg, 0.865 mmol) was added, followed by osmium tetroxide (0.1 ml of 4% aqueous solution). The mixture stirred at rt for 4 h, and the 1,4-dioxane was evaporated in vacuo, then the remaining aqueous phase was extracted with 20% MeOH/DCM (3×200 ml). The organic extracts were combined, dried over anhydrous magnesium sulphate, filtered and evaporated under reduced pressure to give (6-[6-(methyloxy)-3-oxo-1,2,4-benzotriazin-4(3H)-yl]acetaldehyde (existing mostly as the methyl hemiacetal) as an impure yellow oil (89 mg, 117%).
MS (ES+) m/z 220 MH+), 252 (methyl hemiacetalH+).

(c) 1,1-Dimethylethyl (1-{2-[6-(methyloxy)-3-oxo-1,2,4-benzotriazin-4(3H)-yl]ethyl}-4-piperidinyl)carbamate A mixture of [6-(methyloxy)-3-oxo-1,2,4-benzotriazin-4 (3H)-yl]acetaldehyde (as the methyl hemiacetal) (89 mg, 0.346 mmol) and 1,1-dimethylethyl 4-piperidinylcarbamate (69 mg, 0.346 mmol) in chloroform (5 ml) and MeOH (0.5 ml) was stirred for 2 h before addition of NaBH(OAc)$_3$ (220 mg, 1.038 mmol). The reaction was stirred for 0.5 h before addition of sat. aq NaHCO$_3$ (20 ml). The reaction was then extracted with 20% MeOH in DCM (3×100 ml). The combined organic phases were dried, evaporated and the crude residue purified by chromatography on silica gel using a 0-5% MeOH/DCM gradient to provide the desired compound (48 mg, 34%).

MS (ES+) m/z 404 (MH$^+$).

(d) 4-[2-(4-Amino-1-piperidinyl)ethyl]-6-(methyloxy)-1,2,4-benzotriazin-3(4H)-one Dihydrochloride To a solution of 1,1-dimethylethyl (1-{2-[6-(methyloxy)-3-oxo-1,2,4-benzotriazin-4(3H)-yl]ethyl}-4-piperidinyl)carbamate (48 mg, 0.11 g mmol) in chloroform (2 ml) was added 4M HCl in 1,4-dioxane (2 ml). The reaction was stirred at rt for 1 h before evaporation and trituration with ethyl acetate to provide the desired compound as a yellow oil which was used without further purification (42 mg, 94%).

MS (ES+) m/z 304 (MH$^+$).

(e) Title Compound

A mixture of 4-[2-(4-amino-1-piperidinyl)ethyl]-6-(methyloxy)-1,2,4-benzotriazin-3(4H)-one dihydrochloride (42 mg, 0.112 mmol) in chloroform (2 ml) and MeOH (0.1 ml) was treated with triethylamine (50 µl, 0.358 mmol) and stirred for 0.25 h before addition of 2,3-dihydro[1,4]dioxino[2,3-c]pyridine-7-carboxaldehyde (for a synthesis see WO2004058144, Example 2(c) or WO03/087098, Example 19(d)) (18 mg, 0.112 mmol). The reaction was stirred for 0.5 h before addition of NaBH(OAc)$_3$ (71 mg, 0.336 mmol). The reaction was stirred for 1 h before addition of sat. aq NaHCO$_3$ (10 ml). The reaction was then extracted with 20% MeOH in DCM (3×200 ml). The combined organic phases were dried, evaporated and the crude residue purified by chromatography on silica gel using a 0-20% MeOH/DCM gradient to provide the free base of the title compound (26 mg, 51%).

MS (ES+) m/z 453 (MH$^+$).

$^1$H NMR (400 MHz) δ (CDCl$_3$) 1.55-1.63 (2H, m), 1.99-2.02 (2H, m), 2.27-2.32 (2H, m), 2.67-2.72 (3H, m), 3.02-3.11 (2H, m), 3.87 (2H, m), 4.02 (3H, s), 4.27-4.36 (6H, m), 6.86 (2H, br s), 7.00 (1H, dd, J 9, 2 Hz), 8.09 (1H, s), 8.29 (1H, d J 9 Hz).

The free base of the title compound was converted to the HCl salt by dissolving the obtained free base in 1:1 DCM:MeOH and adding 1 equivalent of 4M HCl in 1,4-dioxane. This was then evaporated to dryness.

Example 122

1-(2-{4-[(2,3-dihydrofuro[2,3-c]pyridin-5-ylmethyl)amino]-1-piperidinyl}ethyl)-7-(methyloxy)-2(1H)-quinoxalinone Dihydrochloride

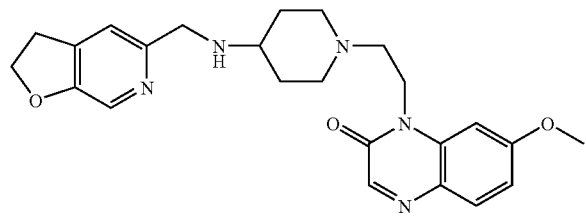

A solution of 1-[2-(4-amino-1-piperidinyl)ethyl]-7-(methyloxy)-2(1H)-quinoxalinone (see Example 47(a) for a preparation) (50 mg; 0.17 mmol) and 2,3-dihydrofuro[2,3-c]pyridine-5-carbaldehyde (see Example 38(f) for a preparation) (27 mg, 0.18 mmol) in methanol (2 mL) and chloroform (2 mL) was heated under reflux with 3A molecular sieves overnight. The mixture was cooled and sodium triacetoxyborohydride (0.18 g; 0.85 mmol) was added, and the mixture was stirred at room temperature overnight. More aldehyde (30 mg) and acetoxyborohydride (0.180 g) were added, and the mixture was stirred at room temperature overnight. Further additions of aldehyde (5.4 mg) and acetoxyborohydride (36 mg and 6 mg) were made. The mixture was stirred overnight again, then aqueous sodium bicarbonate solution was added to neutralise and the phases were separated. The aqueous phase was extracted four times with 10% methanol-dichloromethane, and the organic fractions were dried and evaporated. Chromatography on silica gel, eluting with 0-20% methanol-dichloromethane gave the free base of the title compound (56 mg, 76%).

δH (CDCl$_3$), (400 MHz) 1.50 (2H, m), 1.96 (2H, br.d, part, obscured by water), 2.20 (2H, t), 2.57 (1H, m), 2.67 (2H, t), 3.01 (2H, br. d), 3.22 (2H, t), 3.86 (2H, s), 3.93 (3H, s), 4.35 (2H, t), 4.61 (2H, t), 6.88 (1H, d), 6.92 (1H, dd), 7.20 (1H, s), 7.78 (1H, d), 8.07 (1H, s), 8.12 (1H, s)

MS (+ve ion electrospray) m/z 436 (MH+).

The free base in dichloromethane was treated with 0.4 M hydrogen chloride in 1,4-dioxane (0.70 mL) to give the dihydrochloride salt (43 mg).

Example 123

2-[({1-[2-(7-Fluoro-2-oxo-1(2H)-quinolinyl)ethyl]-4-piperidinyl}amino)methyl]-1H-pyrimido[5,4-b][1,4]oxazin-7(6H)-one Hydrochloride

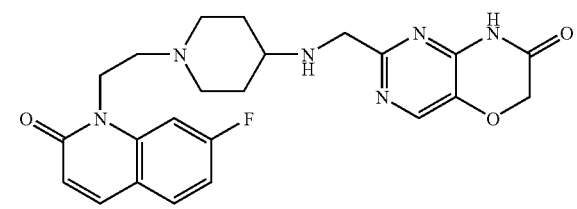

To a solution of 4-chloro-2-[({1-[2-(7-fluoro-2-oxo-1(2H)-quinolinyl)ethyl]-4-piperidinyl}amino)methyl]-1H-pyrimido[5,4-b][1,4]oxazin-7(6H)-one (see Example 124(j) for a preparation) (67 mg, 0.13 mmol) in methanol (3 mL) was added NaHCO$_3$ (40 mg) followed by 10% palladium over carbon catalyst (30 mg). The resulting mixture was stirred at room temperature under 1 atm of hydrogen (balloon) for 24 h. The reaction mixture was filtered through a nylon filter and the crude residue was purified by chromatography (silica gel) using a 0-20% MeOH/DCM gradient to provide the free base of the title compound (10 mg, 16%).

MS (ES+) m/z 453 (MH$^+$). $^1$H NMR (400 MHz, CDCl$_3$) δ 1.58 (2H, m), 1.88-2.09 (2H, m), 2.28 (2H, m), 2.60-2.72 (3H, m), 3.17 (2H, m), 3.92 (2H, s), 4.41 (2H, t), 4.72 (2H, s), 6.63 (1H, d, J=10 Hz), 6.97 (1H, m), 7.2 (1H, dd, J 10.5, 2 Hz), 7.50 (1H, dd, J=10.5 Hz, 2 Hz), 7.68 (1H, d, J=10 Hz), 7.9 (1H, s) The free base of the title compound was converted to the HCl salt by dissolving the free base in 1:1 DCM:MeOH and adding 1 equivalent of 4M HCl in 1,4-dioxane. This was then evaporated to dryness.

Example 124

4-Chloro-2-[({1-[2-(7-fluoro-2-oxo-1(2H)-quinolinyl)ethyl]-4-piperidinyl}amino)methyl]-1H-pyrimido[5,4-b][1,4]oxazin-7(6H)-one Hydrochloride The free base of the title compound was converted to the HCl salt by dissolving the free base in 1:1 DCM:MeOH and adding 1 equivalent of 4M HCl in 1,4-dioxane. This was then evaporated to dryness.

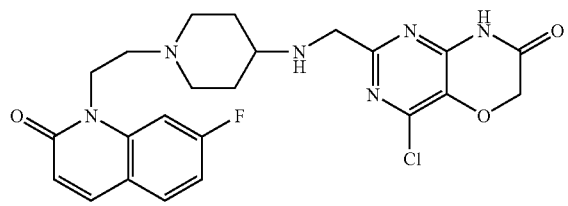

(a) Dimethyl {[2-(ethyloxy)-2-oxoethyl]oxy}propanedioate

To a solution of dimethyl diazopropanedioate (4 g, 25 mmol), prepared according to Peace, Carman, Wulfman, *Synthesis*, 658-661, (1971), in DCM (10 mL) was added ethyl glycolate (1.2 mL, 12.8 mmol) followed by rhodium (II) acetate dimer (2 g, 20% mol). The reaction mixture was stirred at room temperature for 24 h. The resulting suspension was filtered through a pad of Celite® and the solvent was removed in vacuo. The crude residue was purified by column chromatography (silica gel) using a 0-60% EtOAc/hexanes gradient to provide the desired product as an oil (3 g, 97%).

MS (ES+) m/z 235 (MH$^+$).

(b) ({4-Hydroxy-6-oxo-2-[(E)-2-phenylethenyl]-1,6-dihydro-5-pyrimidinyl}oxy)acetic Acid To a solution of dimethyl {[2-(ethyloxy)-2-oxoethyl]oxy}propanedioate (3 g, 12.8 mmol) in MeOH (10 mL) at room temperature was added (2E)-3-phenyl-2-propenimidamide (1.87 g, 12.8 mmol) (for preparation see Example 3 (g)) followed by NaOMe (8.3 g, 38.4 mmol; 25% solution in methanol). The resulting mixture was stirred at room temperature for 24 h. Solvent was removed in vacuo and the resulting solid was used in the next step without purification.

MS (ES+) m/z 288 (MH$^+$).

(c) Methyl ({4,6-dichloro-2-[(E)-2-phenylethenyl]-5-pyrimidinyl}oxy)acetate

To the crude ({4-hydroxy-6-oxo-2-[(E)-2-phenylethenyl]-1,6-dihydro-5-pyrimidinyl}oxy)acetic acid (~12.8 mmol) was added POCl$_3$ (8 mL, 76.9 mmol) followed by N,N-dimethylaniline (1.7 mL, 12.8 mmol). The resulting mixture was heated at 120° C. in a sealed tube for 3 h. The resulting mixture was cooled to 0° C. and quenched with cold methanol. The solvent was removed in vacuo and the crude residue purified by chromatography (silica gel) using a 0-30% EtOAc/hexanes gradient to provide the desired product as a solid (1.3 g, 30% for 2 steps).

MS (ES+) m/z 340 (MH$^+$).

(d) 2-({4-Amino-6-chloro-2-[(E)-2-phenylethenyl]-5-pyrimidinyl}oxy)acetamide To a solution of methyl ({4,6-dichloro-2-[(E)-2-phenylethenyl]-5-pyrimidinyl}oxy)acetate (1.1 g, 3.24 mmol) in 1,4-dioxane (10 mL) was added conc. NH$_4$OH (2 ml, 20 eq). The resulting mixture was heated at 65° C. for 4 h. After cooling to room temperature, the solvent was evaporated under reduced pressure and the residue was extracted with 10% methanol in DCM (3×300 mL). The organic extracts were combined, dried over anhydrous MgSO$_4$, filtered and concentrated to give a solid which was purified by column chromatography (silica gel) with a 0-10% methanol in DCM gradient to give the desired product as a solid (0.6 g, 61%).

MS (ES+) m/z 305 (MH$^+$). Also 0.3 g of 4-chloro-2-[(E)-2-phenylethenyl]-6H-pyrimido[5,4-b][1,4]oxazin-7(8H)-one was obtained.

(e) Ethyl ({4-amino-6-chloro-2-[(E)-2-phenylethenyl]-5-pyrimidinyl}oxy)acetate Hydrogen chloride gas was bubbled into a solution of 2-({4-amino-6-chloro-2-[(E)-2-phenylethenyl]-5-pyrimidinyl}oxy)acetamide (0.6 g, 1.97 mmol) in ethanol (20 mL). The resulting mixture was heated at 100° C. for 3 h. The mixture was evaporated under reduced pressure to give the desired product as a solid (0.55 g, 84%) which was used without purification.

MS (ES+) m/z 334 (MH$^+$).

(f) 4-Chloro-2-[(E)-2-phenylethenyl]-6H-pyrimido[5,4-b][1,4]oxazin-7(8H)-one To a solution of ethyl ({4-amino-6-chloro-2-[(E)-2-phenylethenyl]-5-pyrimidinyl}oxy)acetate (0.55 g, 1.65 mmol) in DMF (5 mL) was added solid K$_2$CO$_3$ (0.46 g, 3.3 mmol) and the resulting mixture was heated at 75° C. for 1 h. The solvent was evaporated under reduced pressure and the residue was extracted with 10% methanol in DCM (3×100 ml). The organic extracts were combined, dried over anhydrous MgSO$_4$, filtered and evaporated under reduced pressure to give a solid which was purified by column chromatography (silica gel) with a 0-10% methanol in DCM gradient to give the desired product as a solid (0.47 g, 99%).

MS (ES+) m/z 288 (MH$^+$).

(g) 4-Chloro-7-oxo-6,7-dihydro-1H-pyrimido[5,4-b][1,4]oxazine-2-carbaldehyde To a solution of 4-chloro-2-[(E)-2-phenylethenyl]-6H-pyrimido[5,4-b][1,4]oxazin-7(8H)-one (0.45 g, 1.16 mmol) in 1,4-dioxane (25 mL) and water (10 mL) was added NaIO$_4$ (1.26 g, 4.4 mmol) along with a catalytic amount of OsO$_4$ (0.36 mL, 4 wt. % in water). The resulting mixture was stirred at room temperature for 5 h. The solvent was evaporated under reduced pressure and the residue was extracted with 10% methanol in DCM (3×50 ml). The organic extracts were combined, dried over anhydrous MgSO$_4$, filtered and concentrated under reduced pressure to give a solid which was purified by column chromatography (silica gel) with a 0-10% methanol in DCM gradient to give the desired product as light yellow solid (0.28 g, 84%).

MS (ES+) m/z 214 (MH$^+$).

¹H NMR (400 MHz, CDCl₃) δ 5.03 (2H, s), 8.9 (1H, bs), 9.9 (1H, s).

(h) 1,1-Dimethylethyl {1-[2-(7-fluoro-2-oxo-1(2H)-quinolinyl)ethyl]-4-piperidinyl}carbamate (7-Fluoro-2-oxo-1(2H)-quinolinyl)acetaldehyde (0.50 g, 2.41 mmol) (for a preparation see Example 88(a)) was combined with 1,1-dimethylethyl 4-piperidinylcarbamate (0.48 g, 2.41 mmol) in 1:1 MeOH/DCM (20 mL). Excess Na₂SO₄ was added as a drying agent and the solution was stirred at ambient temperature for 16 h. NaBH(OAc)₃ (1.53 g, 7.23 mmol) was added and the reaction was stirred an additional 2 h. The solution was concentrated onto silica gel under vacuum and the crude residue purified by column chromatography (silica gel) using a DCM/DCM-MeOH—NH₄OH (90:10:1) gradient to yield the desired product as a yellow solid (0.678 g, 72%).

LCMS: m/z 390.4 (MH+).

(i) 1-[2-(4-Amino-1-piperidinyl)ethyl]-7-fluoro-2(1)-quinolinone Hydrochloride

To a solution of 1,1-dimethylethyl {1-[2-(7-fluoro-2-oxo-1(2H)-quinolinyl)ethyl]-4-piperidinyl}carbamate (0.67 g, 1.74 mmol) in DCM (20 mL), as added 4M HCl in 1,4-dioxane (2.18 mL, 8.71 mmol) and the solution was stirred at ambient temperature for 16 h. The solution was concentrated under vacuum to yield the desired product as an off white solid (0.55 g; 98%).

LCMS: m/z 290.0 (MH+).

(j) Title Compound

To a solution of 1-[2-(4-amino-1-piperidinyl)ethyl]-7-fluoro-2(1H) quinolinone hydrochloride (0.40 g, 0.12 mmol) in DCM (5 mL) and methanol (2 mL) was added 4-chloro-7-oxo-6,7-dihydro-1H-pyrimido[5,4-b][1,4]oxazine-2-carbaldehyde (0.026 g, 0.12 mmol) followed by NaHCO₃ (0.1 g, 1.2 mmol) and anhydrous Na₂SO₄ as a drying agent. The resulting mixture was stirred at room temperature for 24 h before the addition of NaBH(OAc)₃ (80 mg, 0.36 mmol). The reaction was stirred for 1 h. The reaction mixture was concentrated and the residue was extracted with 20% MeOH in DCM (3×20 ml). The combined organic phases were dried (MgSO₄), evaporated and the crude residue purified by chromatography (silica gel) using a 0-20% MeOH/DCM gradient to provide the free base of the title compound (24 mg, 40%).

MS (ES+) m/z 487 (MH+). ¹H NMR (400 MHz, CDCl₃) δ 1.58 (2H, m), 1.88-2.09 (2H, m), 2.28 (2H, m), 2.60-2.72 (3H, m), 3.17 (2H, m), 3.92 (2H, s), 4.41 (2H, t), 4.72 (2H, s), 6.63 (1H, d, J=10 Hz), 6.97 (1H, m), 7.2 (1H, dd, J 10.5, 2 Hz), 7.50 (1H, dd, J=10.5 Hz, 2 Hz), 7.68 (1H, d, J=10 Hz).

The free base of the title compound was converted to the HCl salt by dissolving the free base in 1:1 DCM:MeOH and adding 1 equivalent of 4M HCl in 1,4-dioxane. This was then evaporated to dryness.

Example 125

2-{[(1-{2-[6-(Methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one Hydrochloride

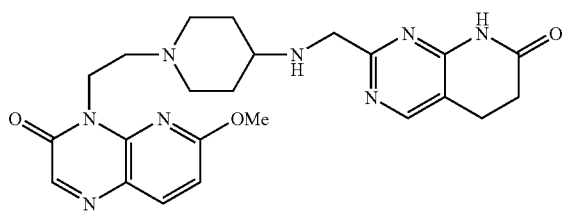

(a) 2-[Bis(methyloxy)methyl]-4-chloro-5,8-dihydropyrido[2,3-d]pyrimidin-7(6H)-one To a solution of 4-chloro-7-oxo-5,6,7,8-tetrahydropyrido[2,3-d]pyrimidine-2-carbaldehyde (for a preparation see Example 126(k)) (1.43 g, 6.78 mmol) in MeOH was added p-TsOH.H₂O (0.13 g, 0.68 mmol). The solution was heated at reflux for 2.5 h and then cooled to ambient temperature. The solution was concentrated under vacuum to yield the desired product which was used without further purification.

LCMS: m/z 257.9 (MH+).

(b) 2-[Bis(methyloxy)methyl]-5,8-dihydropyrido[2,3-d]pyrimidin-7(6H)-one

To crude 2-[bis(methyloxy)methyl]-4-chloro-5,8-dihydropyrido[2,3-d]pyrimidin-7(6H)-one (presumed 6.78 mmol) dissolved in MeOH was added 10% Pd/C (0.15 g). The solution was stirred under an atmosphere of H₂ (balloon) overnight. The Pd/C was filtered off and the solution concentrated under vacuum. The crude residue was purified by column chromatography (silica gel) using a DCM/DCM-MeOH—NH₄OH (90:10:1) gradient to yield the desired product as a white solid (0.873 g, 58% over 2 steps).

LCMS: m/z 223.9 (MH+).

(c) 7-Oxo-5,6,7,8-tetrahydropyrido[2,3-d]pyrimidine-2-carbaldehyde

To a solution of 2-[bis(methyloxy)methyl]-5,8-dihydropyrido[2,3-d]pyrimidin-7(6H)-one (0.873 g, 3.91 mmol) in 1:1 H₂O/acetone (10 mL) was added p-TsOH.H₂O (0.074 g, 0.391 mmol) and the reaction was heated to 80° C. for 3 days with additional p-TsOH.H₂O (0.20 g). After the disappearance of starting material, the solution was concentrated under vacuum to yield the desired product (1.023 g).

LCMS: m/z 178.0 (MH+).

(d) Title Compound

To a solution of 4-[2-(4-amino-1-piperidinyl)ethyl]-6-(methyloxy)pyrido[2,3-b]pyrazin-3(4H)-one hydrochloride (see Example 126(m) for a preparation) (0.600 g, 1.98 mmol)

in 1:1 MeOH/DCM, was added 7-oxo-5,6,7,8-tetrahydropyrido[2,3-d]pyrimidine-2-carbaldehyde (0.350 g, 1.98 mmol), NaHCO$_3$ (0.831 g, 9.90 mmol), and excess Na$_2$SO$_4$. The solution was stirred at ambient temperature overnight, followed by the addition of NaBH(OAc)$_3$ (1.68 g, 7.92 mmol). The resulting solution was stirred for an additional 1 h, then concentrated onto silica gel under vacuum and the crude residue purified by column chromatography (silica gel) using a DCM/DCM-MeOH—NH$_4$OH (90:10:1) gradient, followed by a further purification using 10% MeOH/DCM and then DCM/DCM-MeOH—NH$_4$OH (90:1:0.1) to yield the free base of the desired product (0.396 g, 43%). LCMS: m/z 465.2 (MH+). 1H NMR (400 MHz, CDCl$_3$) δ 1.42-1.53 (m, 2H) 1.90 (d, J=10.86 Hz, 2H) 2.18 (t, J=10.61 Hz, 2H) 2.52-2.60 (m, 1H) 2.66-2.77 (m, 5H) 2.93 (t, J=7.71 Hz, 2H) 3.07 (d, J=11.62 Hz, 2H) 3.98 (s, 2H) 4.00-4.03 (m, 3H) 4.52-4.62 (m, 2H) 6.70 (d, J=8.84 Hz, 1H) 7.99 (d, J=8.59 Hz, 1H) 8.12 (s, 1H) 8.34 (s, 1H).

The free base of the title compound was converted to the HCl salt by adding 1 equivalent of 1M HCl in ether.

Example 126

4-Chloro-2-{[(1-{2-[6-(methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one Hydrochloride

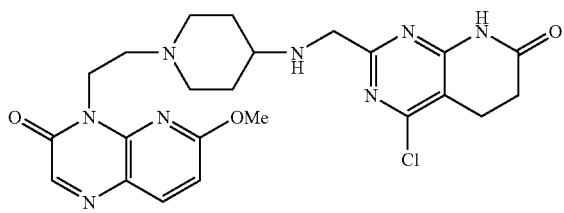

(a) N-[2,2-Bis(methyloxy)ethyl]-6-(methyloxy)-3-nitro-2-pyridineamine

A mixture of 2-chloro-6-(methyloxy)-3-nitropyridine (10 g, 53 mmol), aminoacetaldehyde dimethylacetal (5.6 g, 6.2 ml, 53 mmol) and potassium carbonate (7.4 g, 53 mmol) in acetonitrile (100 mL) and DMF (10 mL) was heated at 40° C. for 30 minutes. The mixture was filtered and extracted with DCM and brine. The organic extract was added to a silica column which was then eluted with 0-100% ethyl acetate in hexane affording a yellow solid (12.4 g, 90%).
MS (+ve ion electrospray) m/z: 258 (MH+).

(b) N$^2$-[2,2-Bis(methyloxy)ethyl]-6-(methyloxy)-2,3-pyridinediamine

A solution of N-[2,2-bis(methyloxy)ethyl]-6-(methyloxy)-3-nitro-2-pyridinamine (2.5 g, 10 mmol) in methanol was hydrogenated at 50 psi for 0.5 h over 10% palladium on charcoal (0.9 g). The mixture was filtered, evaporated, and azeotroped with chloroform affording a dark oil (2.2 g).
MS (+ve ion electrospray) m/z: 228 (MH+).

(c) Ethyl N-[2-{[2,2-bis(methyloxy)ethyl]amino}-6-(methyloxy)-3-pyridinyl]glycinate A mixture of N$^2$-[2,2-bis(methyloxy)ethyl]-6-(methyloxy)-2,3-pyridinediamine (2.2 g, 10 mmol), ethyl bromoacetate (1.1 mL, 1.65 g, 10 mmol) and potassium carbonate (2.1 g, 20 mmol) in acetonitrile (50 mL) and DMF (5 mL) was stirred at room temperature overnight. The mixture was filtered and evaporated. The residue was dissolved in ethyl acetate and washed with water and brine. The organic extract was concentrated and added to a silica column which was then eluted with 0-100% ethyl acetate in hexane affording product (2.5 g, 82%).
MS (+ve ion electrospray) m/z: 314 (MH+).

(d) 4-[2,2-Bis(methyloxy)ethyl]-6-(methyloxy)pyrido[2,3-b]pyrazin-3(4H)-one

A mixture of ethyl N-[2-{[2,2-bis(methyloxy)ethyl]amino}-6-(methyloxy)-3-pyridinyl]glycinate (1 g, 3.2 mmol) and potassium carbonate (1.3 g, 9.6 mmol) in DMF (64 mL, 0.05M) was heated at 105-110° C. for 2 h. The mixture was cooled to room temperature and MnO$_2$ (0.8 g, 11 mmol) was added and the reaction was stirred for 18 h. The reaction was filtered, concentrated, and the residue was dissolved in ethyl acetate and washed with water. The organic extract was concentrated and added to a silica column which was then eluted with 0-100% ethyl acetate in hexane affording the desired compound (0.78 g, 78%).
MS (+ve ion electrospray) m/z: 266 (MH+).

(e) [6-(Methyloxy)-3-oxopyrido[2,3-b]pyrazin-4(3H)-yl]acetaldehyde

Trifluoroacetic acid (3 mL) was added to 4-[2,2-bis(methyloxy)ethyl]-6-(methyloxy)pyrido[2,3-b]pyrazin-3(4H)-one (0.9 g, 3.4 mmol) in water (3 mL) at room temperature and stirred for 2 h. The reaction mixture was concentrated and the residue was purified by column chromatography (silica gel) using a 0-10% MeOH/DCM/1% NH$_4$OH gradient to give the product as a mixture of aldehyde and hemiacetal (0.6 g, 80%).
MS (+ve ion electrospray) m/z: 220 (MH+).

(f) 3-Ethyl 1,1-dimethyl 1,1,3-propanetricarboxylate

To a solution of dimethyl malonate (2.5 g, 18.9 mmol) in anhydrous THF (20 mL) was added NaH (0.038 g, 0.95 mmol, 60% in mineral oil). The reaction was stirred at ambient temperature for 15 minutes. In a separate flask, ethyl acrylate (1.02 mL, 9.45 mmol) was dissolved in anhydro is THF (1 mL) and then added dropwise over 30 minutes to the dimethyl malonate solution. The reaction was stirred at ambient temperature overnight and then concentrated under vacuum. The residue was dissolved in EtOAc, washed with saturated NH$_4$Cl solution and brine. The organic phase was dried over Na$_2$SO$_4$, filtered, and concentrated under vacuum. The crude residue was purified by column chromatography (silica gel) using an EtOAc/hexanes gradient to yield the desired compound (1.68 g, 77%).
$^1$H NMR (400 MHz, CDCl$_3$) δ 1.24 (t, J=7.07 Hz, 3H) 2.20 (q, J=7.24 Hz, 2H) 2.37 (t, J=7.33 Hz, 2H) 3.47 (t, J=7.33 Hz, 1H) 3.70-3.75 (m, 6H) 4.12 (q, J=7.24 Hz, 2H).

(g)(2E)-3-Phenyl-2-propenimidamide

Cinnamonitrile (25.0 g, 194 n 1 mol) was dissolved in EtOH. The solution was cooled to 0° C. and HCl gas bubbled through the solution for 30 minutes. The solution was stirred at ambient temperature for 1 h and then concentrated under vacuum. The residue was dissolved in EtOH (100 mL), cooled to 0° C. and a solution of NH$_3$/MeOH (7M, 69 mL, 484 mmol) was added dropwise through an addition funnel. Once added, the solution was allowed to warm to ambient temperature and stirred overnight and the resulting NH$_4$Cl was filtered off. The solution was concentrated under vacuum and the resulting product was used without further purification (28.6 g crude).

LCMS: m/z 147.4 (MH+).

(h) Ethyl 3-{4-hydroxy-6-oxo-2-[(E)-2-phenylethenyl]-1,6-dihydro-5-pyrimidinyl}propanoate 3-Ethyl 1,1-dimethyl 1,1,3-propanetricarboxylate (1.65 g, 7.11 mmol) and (2E)-3-phenyl-2-propenimidamide (1.04 g, 7.11 mmol) were combined in EtOH (36 mL). Triethylamine (1.98 mL, 14.2 mmol) was added and the solution was heated at reflux for 3 h with no change based on LCMS. The solution was cooled to room temperature and treated with NaOMe in MeOH (1.0 mL, 5.33 mmol, 25-30% w/w solution) and the solution was refluxed for 3 h. Another two portions of NaOMe in MeOH (2×1.0 mL) were added and the solution was refluxed overnight. After this time, a yellow precipitate had formed which was filtered off. The mother liquor was acidified to pH 2 with 1N HCl, and the solution was concentrated under vacuum. The resulting material was combined with the yellow solid and used without further purification.

LCMS: m/z 315.2 (MH+).

(i) Ethyl 3-{4,6-dichloro-2-[(E)-2-phenylethenyl]-5-pyrimidinyl}propanoate

Crude ethyl 3-{4-hydroxy-6-oxo-2-[(E)-2-phenylethenyl]-1,6-dihydro-5-pyrimidinyl}propanoate (7.1 mmol) was dissolved in POCl$_3$ (25 mL) and N,N-dimethylaniline (0.862 g, 0.9 mL, 7.1 mmol) was slowly added to the solution. The reaction was then heated at reflux for 2 h. After cooling to ambient temperature, the resulting solution was carefully and slowly added to ice water to quench the excess POCl$_3$. The mixture was extracted with EtOAc (3×) and concentrated under vacuum. The crude residue was then purified by column chromatography (silica gel) using an EtOAc/hexanes gradient to yield the desired compound as a yellow solid (0.48 g, 19% over 2 steps).

LCMS: m/z 351.4 (MH+).)

(j) 4-Chloro-2-[(E)-2-phenylethenyl]-5,8-dihydropyrido[2,3-d]pyrimidin-7(6H)-one To a solution of ethyl 3-{4,6-dichloro-2-[(E)-2-phenylethenyl]-5-pyrimidinyl}propanoate (0.42 g, 1.19 mmol) in 1,4-dioxane (5 mL) was added conc. NH$_4$OH (3.5 mL). The reaction was heated at 75° C. in a sealed tube overnight. The solution was concentrated under vacuum, diluted with water, and extracted with EtOAc/DCM. The organic layer was washed with brine, dried over Na$_2$SO$_4$, and concentrated under vacuum. The crude residue was then purified by column chromatography (silica gel) to yield the desired compound (0.072 g, 21%). LCMS: m/z 286.2 (MH+). Also obtained was 3-{4-amino-6-chloro-2-[(E)-2-phenylethenyl]-5-pyrimidinyl}propanamide (0.175 g).

LCMS: m/z 303.3 (MH+).

3-{4-Amino-6-chloro-2-[(E)-2-phenylethenyl]-5-pyrimidinyl}propanamide (0.175 g, 0.58 mmol) was dissolved in EtOH and HCl gas was bubbled through the solution until saturated. The solution was heated at reflux for 2 h, cooled to ambient temperature and concentrated under vacuum. The residue was dissolved in water, neutralised to pH9 with K$_2$CO$_3$ solution and extracted with EtOAc (3×). The organic layers were combined, dried over Na$_2$SO$_4$, filtered and concentrated under vacuum to yield ethyl 3-{4-amino-6-chloro-2-[(E)-2-phenylethenyl]-5-pyrimidinyl}propanoate as a white solid. LCMS: m/z 332.2 (MH+). This product was then dissolved in DMF (5 mL), treated with K$_2$CO$_3$ (0.16 g, 1.16 mmol) and heated at 75° C. for 30 minutes. The solution was cooled, diluted with water and extracted with Et$_2$O (3×). The organic layer was dried over Na$_2$SO$_4$, filtered, and concentrated under vacuum. The crude residue was then purified by column chromatography (silica gel) with DCM/(DCM:MeOH:NH$_4$OH) 90:10:1 to yield an additional 0.11 g of the desired compound.

LCMS: m/z 286.2 (MH+).

(k) 4-Chloro-7-oxo-5,6,7,8-tetrahydropyrido[2,3-d]pyrimidine-2-carbaldehyde

4-Chloro-2-[(E)-2-phenylethenyl]-5,8-dihydropyrido[2,3-d]pyrimidin-7(6H)-one (0.18 g, 0.64 mmol) was dissolved in a 2:1 solution of 1,4-dioxane/water (6 mL) and cooled to 0° C. NaIO$_4$ (0.314 g, 1.47 mmol) and catalytic OsO$_4$ (1 mL, 4% aq. solution) were added and the solution was then stirred at ambient temperature overnight. The reaction solution was concentrated under vacuum, diluted with water, and extracted with 10% MeOH/DCM (4×). The organic layers were combined, dried over Na$_2$SO$_4$, filtered and concentrated under vacuum. The crude residue was then purified by column chromatography (silica gel) using a DCM/DCM-MeOH—NH$_4$OH (90:10:1) gradient to yield the desired compound (0.05 g, 44%).

LCMS: m/z 212.0 (MH+).

(l) 1,1-Dimethylethyl (1-{2-[6-(methyloxy)-3-oxopyrido[2,3-b]pyrazin-4(3H)-yl]ethyl}-4-piperidinyl)carbamate

[6-(Methyloxy)-3-oxopyrido[2,3-b]pyrazin-4(3H)-yl]acetaldehyde (0.250 g, 1.14 mmol) was combined with 1,1-dimethylethyl 4-piperidinylcarbamate (0.229 g, 1.14 mmol) in a 1:1 MeOH/DCM solution. Excess Na$_2$SO$_4$ was added as a drying agent and the solution was stirred at ambient temperature overnight. NaBH(OAc)$_3$ (0.724 g, 3.42 mmol) was added and the reaction was stirred an additional 2 h. The solution was concentrated onto silica gel under vacuum and the crude residue purified by column chromatography (silica gel) using a DCM/DCM-MeOH—NH$_4$OH (90:10:1) gradient to yield the desired compound (0.271 g, 59%).

LCMS: m/z 404.6 (MH+).

(m) 4-[2-(4-Amino-1-piperidinyl)ethyl]-6-(methyloxy)pyrido[2,3-b]pyrazin-3(4H)-one To a solution of 1,1-dimethylethyl (1-{2-[6-(methyloxy)-3-oxopyrido[2,3-b]pyrazin-4(3H)-yl]ethyl}-4-piperidinyl)carbamate (0.27 g, 0.67 mmol) in DCM was added a solution of HCl in 1,4-dioxane (1.68 mL, 6.7 mmol, 4M solution). The reaction mixture was stirred at ambient temperature for 3 h. The reaction solution was concentrated under vacuum to provide the hydrochloride salt.

The hydrochloride salt was taken up in 1:1 MeOH/DCM. This solution was then treated with MP Carbonate resin (10 equivalents; Argonaut Technologies Inc.) and stirred for 1 h. The resin was filtered off and the solution was concentrated under vacuum to yield the free base as an off-white solid (0.22 g, quantitative). LCMS: m/z 304.3 (MH+).

(n) Title Compound

To a solution of 4-[2-(4-amino-1-piperidinyl)ethyl]-6-(methyloxy)pyrido[2,3-b]pyrazin-3(4H)-one (0.064 g, 0.213 mmol) in 1:1 MeOH/DCM, was added 4-chloro-7-oxo-5,6,7,8-tetrahydropyrido[2,3-d]pyrimidine-2-carbaldehyde (0.045 g, 0.213 mmol) and excess Na$_2$SO$_4$. The solution was stirred at ambient temperature overnight, followed by the addition of NaBH(OAc)$_3$ (0.135 g, 0.639 mmol). The resulting solution was stirred for an additional 2 h, concentrated onto silica gel under vacuum and the crude residue purified by column chromatography (silica gel) using a DCM/DCM-MeOH—NH$_4$OH (90:10:1) gradient to yield the free base of the title compound (0.062 g, 58%).

LCMS: m/z 499.6 (MH+). $^1$H NMR (400 MHz, CDCl$_3$) δ 1.48-1.59 (m, 2H) 1.96 (d, J=15.92 Hz, 2H) 2.28 (s, 2H) 2.58-2.69 (m, 1H) 2.73-2.84 (m, 5H) 3.03-3.15 (m, 4H) 4.01-4.06 (m, 4H) 4.54-4.65 (m, 2H) 6.66-6.76 (m, 1H) 7.96-8.05 (m, 1H) 8.09-8.15 (m, 1H).

A portion of the free base of the title compound (27 mg) was converted to the HCl salt by dissolving the free base in 1:1 DCM:MeOH and adding 1 equivalent of 1M HCl in ether. This was then evaporated to dryness (yield 25 mg).

Example 127

4-Methyl-2-{[(1-{2-[6-(methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one Hydrochloride

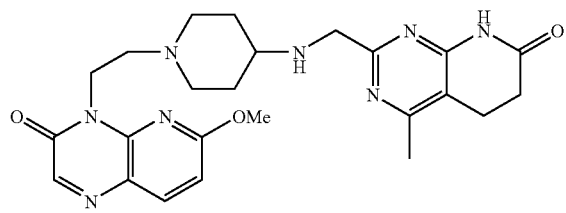

(a) Methyl 3-{4-hydroxy-6-oxo-2-[(E)-2-phenylethenyl]-1,6-dihydro-5-pyrimidinyl}propanoate 3-Ethyl 1,1-dimethyl 1,1,3-propanetricarboxylate (23.8 g; 103 mmol) and (2E)-3-phenyl-2-propenimidamide (10.0 g; 68.4 mmol) were combined in MeOH (400 mL), treated with NaOMe in MeOH (31.0 g; 143 mmol) and the solution was stirred at room temperature for 2 days. The solution turned dark, and a dark green solid was filtered off. The solution was concentrated under vacuum, diluted with water, acidified to pH 2 with 6N HCl and the resulting yellow precipitate was filtered off. The aqueous mother liquor was extracted with EtOAc. During the extraction more yellow precipitate formed and was collected. The combined yellow solids were dried under vacuum and used without further purification (12.1 g, 59%).

LCMS: m/z 301.0 (MH+).

(b) Methyl 3-{4,6-dichloro-2-[(E)-2-phenylethenyl]-5-pyrimidinyl}propanoate

Methyl 3-{4-hydroxy-6-oxo-2-[(E)-2-phenylethenyl]-1,6-dihydro-5-pyrimidinyl}propanoate was dissolved in POCl$_3$ (75 mL), treated with N,N-dimethylaniline (4.85 g, 40 mmol) and heated at reflux for 2 h. After cooling to ambient temperature, the resulting solution was carefully and slowly added to ice water to quench the excess POCl$_3$. The mixture was extracted with EtOAC (2×), dried over Na$_2$SO$_4$, filtered, and concentrated under vacuum. The crude residue was purified by column chromatography (silica gel) using an EtOAC/hexanes gradient to yield the desired product as a yellow solid (3.04 g, 23%).

LCMS: m/z 337.2 (MH+).

(c) 4-Chloro-2-[(E)-2-phenylethenyl]-5,8-dihydropyrido[2,3-d]pyrimidin-7(6H)-one To a solution of methyl 3-{4,6-dichloro-2-[(E)-2-phenylethenyl]-5-pyrimidinyl}propanoate (3.04 g, 9.02 mmol) in 1,4-dioxane (100 mL) was added conc. NH$_4$OH (20 mL). The reaction was heated at 60° C. in a sealed tube for 16 h. The solution was concentrated under vacuum, diluted with water, and extracted with EtOAc. The organic layer was washed with brine, dried over Na$_2$SO$_4$, and concentrated. The crude residue was purified by column chromatography (silica gel) using a DCM/DCM-MeOH—NH$_4$OH (90:10:1) gradient to yield a yellow solid (1.69 g) consisting of 4-chloro-2-[(E)-2-phenylethenyl]-5,8-dihydropyrido[2,3-d]pyrimidin-7(6H)-one (LCMS: m/z 285.9 (MH+)) and methyl 3-{4-amino-6-chloro-2-[(E)-2-phenylethenyl]-5-pyrimidinyl}propanoate (LCMS: m/z 317.9 (MH+)).

To the combined products (1.69 g) dissolved in DMF (20 mL) was added K$_2$CO$_3$ (0.74 g; 5.3 mmol), and the solution was heated at 70° C. for 30 minutes. The solution was concentrated under vacuum and purified by column chromatography (silica gel) using a DCM/DCM-MeOH—NH$_4$OH (90:10:1) gradient to yield the desired product as an off white solid (0.92 g, 36% over 2 steps).

LCMS: m/z 285.9 (MH+).

(d) 4-Methyl-2-[(E)-2-phenylethenyl]-5,8-dihydropyrido[2,3-d]pyrimidin-7(6H)-one 4-Chloro-2-[(E)-2-phenylethenyl]-5,8-dihydropyrido[2,3-d]pyrimidin-7(6H)-one (0.434 g, 2.05 mmol) was dissolved in DMF (5 mL) and added to a microwave vial. MeB(OH)$_2$ (0.273 g, 4.56 mmol), Pd(Ph$_3$P)$_2$Cl$_2$ (0.107 g, 0.152 mmol) and K$_2$CO$_3$ (1.05 g, 7.61 mmol) were added and the vial was capped. The reaction was heated at 140° C. in the microwave for 10 minutes. The reaction was concentrated onto silica gel and purified by column chromatography (silica gel) using a DCM/DCM-MeOH—NH$_4$OH (90:10:1) gradient to yield the desired product as an off-white solid (0.431 g, 74%).

LCMS: m/z 265.9 (MH+).

(e) 4-Methyl-7-oxo-5,6,7,8-tetrahydropyrido[2,3-d]pyrimidine-2-carbaldehyde

4-Methyl-2-[(E)-2-phenylethenyl]-5,8-dihydropyrido[2,3-d]pyrimidin-7(6H)-one (0.43 g, 1.63 mmol) was dissolved in DCM (20 mL) and the solution was cooled to −78° C. Ozone gas was bubbled through the solution until it turned a dark blue color. After stirring for an additional 10 minutes at −78° C., methyl sulfide (1.0 mL) was added in one portion. The solution was allowed to warm to ambient temperature overnight. The solution was concentrated down onto silica and purified by column chromatography (silica gel) using a DCM/DCM-MeOH—NH$_4$OH (90:10:1) gradient to yield the desired product as a yellow solid (0.178 g, 49%).

LCMS: m/z 191.9 (MH+).

(f) Title Compound

To a solution of 4-[2-(4-amino-1-piperidinyl)ethyl]-6-(methyloxy)pyrido[2,3-b]pyrazin-3(4H)-one hydrochloride (0.097 g, 0.287 mmol) in 1:1 MeOH/DCM (16 mL) was added 4-methyl-7-oxo-5,6,7,8-tetrahydropyrido[2,3-d]pyrimidine-2-carbaldehyde (0.064 g, 0.287 mmol), NaHCO$_3$ (0.12 g, 1.44 mmol) and excess Na$_2$SO$_4$. The solution was stirred at ambient temperature for 16 h followed by the addition of NaBH(OAc)$_3$ (0.182 g, 0.861 mmol). The resulting solution was stirred for an additional 2 h, then concentrated onto silica gel and the crude residue was purified by column chromatography (silica gel) using a DCM/DCM-MeOH—NH$_4$OH (90:10:1) gradient to yield the free base of the desired product as a yellowish oily film (0.072 g, 53%).

LCMS: m/z 479.2 (MH+). 1H NMR (400 MHz, CDCl$_3$) δ ppm 1.41-1.51 (m, 2H) 1.91 (d, J=11.12 Hz, 2H) 2.20 (t, J=10.61 Hz, 2H) 2.45 (s, 3H) 2.49-2.59 (m, 1H) 2.68-2.79 (m, 4H) 2.93 (t, J=7.71 Hz, 2H) 3.06 (d, J=11.62 Hz, 2H) 3.92 (s, 2H) 4.04 (s, 3H) 4.54-4.63 (m, 2H) 6.72 (d, J=8.59 Hz, 1H) 8.01 (d, J=8.59 Hz, 1H) 8.14 (s, 1H).

The free base of the title compound was converted to the HCl salt by dissolving the free base in 1:1 DCM:MeOH and adding 1 equivalent of 4M HCl in 1,4-dioxane. This was then evaporated to dryness.

Example 128

4-(Methyloxy)-2-{[(1-{2-[6-(methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one Hydrochloride

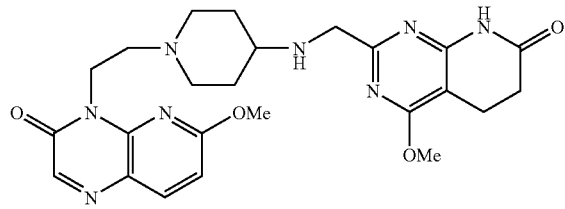

(a) 4-(Methyloxy)-2-[(E)-2-phenylethenyl]-5,8-dihydropyrido[2,3-d]pyrimidin-7(6H)-one To a suspension of 4-chloro-2-[(E)-2-phenylethenyl]-5,8-dihydropyrido[2,3-d]pyrimidin-7(6H)-one (0.45 g, 1.58 mmol) in MeOH (10 mL) was added NaOMe (0.094 g, 1.74 mmol). The reaction mixture was heated at reflux for 3 h, at which time an additional 0.10 g NaOMe was added and refluxing was continued. This was repeated two more times over 9 h. After the disappearance of all starting material (LCMS), the reaction was concentrated onto silica gel and purified by column chromatography (silica gel) using a DCM/DCM-MeOH—NH$_4$OH (90:10:1) gradient to yield the desired product as an off-white solid (0.404 g, 91%).

LCMS: m/z 282.2 (MH+).

(b) 4-(Methyloxy)-7-oxo-5,6,7,8-tetrahydropyrido[2,3-d]pyrimidine-2-carbaldehyde 4-(Methyloxy)-2-[(E)-2-phenylethenyl]-5,8-dihydropyrido[2,3-d]pyrimidin-7(6H)-one (0.40 g, 1.44 mmol) was dissolved in DCM (20 mL). The solution was cooled to −78° C. and 03 was bubbled through the solution until it turned a dark blue color. The solution was stirred an additional 10 minutes at −78° C. and then methyl sulfide (1.0 mL) was added in one portion. The solution was allowed to warm to ambient temperature over 2 days. The solution was concentrated down onto silica and purified by column chromatography (silica gel) using a DCM/DCM-MeOH—NH$_4$OH (90:10:1) gradient to yield the desired product as a yellow solid (0.216 g, 72%). LCMS: m/z 207.6 (MH+).

(c) Title Compound

To a solution of 4-[2-(4-amino-1-piperidinyl)ethyl]-6-(methyloxy)pyrido[2,3-b]pyrazin-3(4H)-one hydrochloride (0.105 g, 0.309 mmol) in 1:1 MeOH/DCM (16 mL) was added 4-(methyloxy)-7-oxo-5,6,7,8-tetrahydropyrido[2,3-d]pyrimidine-2-carbaldehyde (0.074 g, 0.309 mmol), NaHCO$_3$ (0.13 g, 1.55 mmol), and excess Na$_2$SO$_4$. The solution was stirred at ambient temperature for 16 h followed by the addition of NaBH(OAc)$_3$ (0.196 g, 0.927 mmol). The resulting solution was stirred for an additional 2 h, then concentrated onto silica gel under vacuum and the crude residue was purified by column chromatography (silica gel) using a DCM/DCM-MeOH—NH$_4$OH (90:10:1) gradient to yield the free base of the desired product as a yellowish oily film (0.114 g, 75%).

LCMS: m/z 495.3 (MH+). 1H NMR (400 MHz, CDCl$_3$) δ 1.41-1.51 (m, 2H) 1.85-1.96 (m, 2H) 2.19 (t, J=10.61 Hz, 2H) 2.55 (ddd, J=14.21, 10.29, 4.04 Hz, 2H) 2.65 (t, J=7.58 Hz, 2H) 2.71-2.78 (m, 2H) 2.83 (t, J=7.71 Hz, 2H) 3.06 (d, J=11.62 Hz, 2H) 3.84-3.90 (m, 2H) 3.98-4.01 (m, 3H) 4.01-4.04 (m, 3H) 4.54-4.62 (m, 2H) 6.72 (d, J=8.59 Hz, 1H) 8.01 (d, J=8.59 Hz, 1H) 8.14 (s, 1H) 8.73 (s, 1H).

The free base of the title compound was converted to the HCl salt by dissolving the free base in 1:1 DCM:MeOH and adding 1 equivalent of 4M HCl in 1,4-dioxane. This was then evaporated to dryness.

Example 129

7-Fluoro-2-oxo-1-[2-(4-{[(3-oxo-3,4-dihydro-2H-pyrido[3,2-b][1,4]oxazin-6-yl)methyl]amino}-1-piperidinyl)ethyl]-1,2-dihydro-4-quinolinecarbonitrile Dihydrochloride

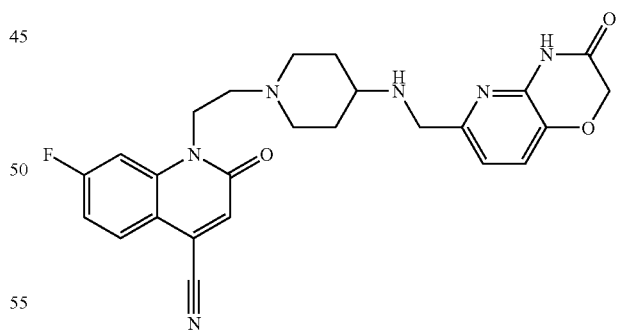

(a) 1-{2-[4-({[(1,1-Dimethylethyl)oxy]carbonyl}amino)-1-piperidinyl]ethyl}-7-fluoro-2-oxo-1,2-dihydro-4-quinolinyl Trifluoromethanesulfonate A solution of 7-fluoro-2-oxo-1-(2-oxoethyl)-1,2-dihydro-4-quinolinyl trifluoromethanesulfonate (see Example 130(e) for a preparation) (4.9 g, 12.5 mmol) and 1,1-dimethylethyl-4-piperidinylcarbamate (2.5 g, 12.5 mmol) in dichloromethane (50 ml) and methanol (50 ml) was stirred for 1 h with 3A sieves. Sodium triacetoxyborohydride (8.0 g, 37.6 mmol) added and the mixture stirred for 5 days, then sodium carbonate solution added and the mixture extracted with dichloromethane. The organics were isolated, dried and concentrated. Chromatography of the residues on silica gel, eluting with 1:1 ethyl acetate/dichloromethane provided the title compound (0.59 g, 12%).

LCMS m/z 538-[MH$^+$]

(b) 1,1-Dimethylethyl {1-[2-(4-cyano-7-fluoro-2-oxo-1(2H)-quinolinyl)ethyl]-4-piperidinyl}carbamate To a solution of 1-{2-[4-({[(1,1-dimethylethyl)oxy]carbonyl}amino)-1-piperidinyl]ethyl}-7-fluoro-2-oxo-1,2-dihydro-4-quinolinyl trifluoromethanesulfonate (0.17 g, 0.32 mmol) in DMF (10 ml) was added zinc cyanide (0.036 g, 0.3 mmol), tris(dibenzylideneacetone)dipalladium (0.022 g, 0.024 mmol) and 1,1'-bis(diphenylphosphino)ferrocene (0.056 g, 0.1 mmol) and degassed with argon. The mixture was heated at 90° C. for 18 h. The solution was allowed to cool then separated between ethyl acetate and brine. The organics were dried and concentrated then the residues combined with the crude from a similar experiment conducted on half the scale. Chromatography of the combined material over silica (10 g SPE gradient elution with ethyl acetate/methanol 0-3%) provided a brown oil which solidified as the title compound (0.113 g, 46%).

LCMS m/z 415-[MH$^+$]

(c) 1-[2-(4-Amino-1-piperidinyl)ethyl]-7-fluoro-2-oxo-1,2-dihydro-4-quinolinecarbonitrile Hydrochloride 1,1-dimethylethyl {1-[2-(4-cyano-7-fluoro-2-oxo-1 (2H)-quinolinyl)ethyl]-4-piperidinyl}carbamate (0.113 g, 0.27 mmol) was dissolved in 1,4-dioxane containing 4M HCl and stirred for 2 h. The solvent was evaporated to provide the title compound.

LCMS m/z 315-[MH$^+$]

(d) Title Compound

To a solution of 1-[2-(4-amino-1-piperidinyl)ethyl]-7-fluoro-2-oxo-1,2-dihydro-4-quinolinecarbonitrile hydrochloride (0.062 g, 0.16 mmol) and 3-oxo-3,4-dihydro-2H-pyrido[3,2-b][1,4]oxazine-6-carboxaldehyde (for a synthesis see WO2003087098, Example 31(e))(0.028 g, 0.16 mmol) in 1:1 chloroform/methanol (6 ml) was added sodium acetate (00.10 g, 12 mmol), acetic acid (0.5 ml) and 3A sieves and the mixture stirred for 1 h. Polymer supported cyanoborohydride (0.10 g) was added and the mixture stirred for 18 h, then filtered and the solid washed with dichloromethane. The organics were washed with sodium carbonate solution, dried and concentrated. Chromatography over silica (10 g SPE gradient elution with dichloromethane/methanol 0-15%) provided the product which was dissolved in dichloromethane and treated with 4M HCl in 1,4-dioxane. The precipitate was isolated and washed with ether then dried to provide the title compound (0.048 g, 55%).

LCMS m/z 477-[MH$^+$]

Free base nmr: δH (CDCl$_3$), (250 MHz) 1.55 (2H, m), 1.9 (2H, m), 2.25 (2H, m), 2.6 (3H, m), 3.05 (2H, m), 3.85 (2H, s), 4.4 (2H, t, J=7 Hz), 4.65 (2H, s), 4.8 (2H, v. br), 6.9 (1H, d, J=8 Hz), 7.07 (1H, s), 7.15 (1H, m), 7.2 (1H, d, J=8 Hz), 7.3 (1H, m), 7.9 (1H, dd, J=9.6 Hz)

Example 130

1-(2-{4-[(2,3-Dihydro[1,4]dioxino[2,3-c]pyridin-7-ylmethyl)amino]-1-piperidinyl}ethyl)-7-fluoro-2-oxo-1,2-dihydro-4-quinolinecarbonitrile Trifluoroacetate Salt

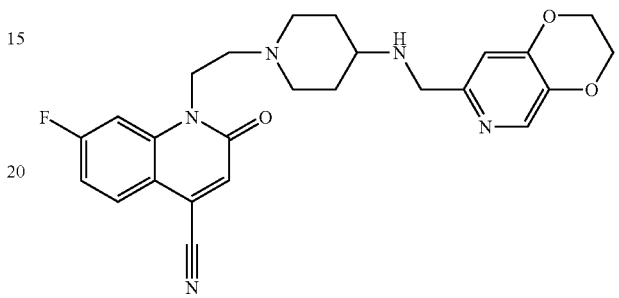

(a) 7-Fluoro-1-(2-propen-1-yl)-2H-3,1-benzoxazine-2,4(1H)-dione

To a solution of 7-fluoro-2H-3,1-benzoxazine-2,4(1H)-dione (5.01 g, 27.7 mmol) in DMF (100 ml) at 0° C. was added sodium hydride (1.11 g, 27.7 mmol, 60% in paraffin) over 15 min. Allyl iodide (2.6 ml, 27.7 mmol) was added and the solution stirred for 2 h, then poured onto ice (100 g) in water (200 ml). The precipitate was collected, washed with water, then hexane and dried under vacuum at 40° C. to yield the title compound (4.53 g, 74%) as an off-white solid.

LCMS m/z 222-[MH$^+$]

(b) Ethyl 7-fluoro-4-hydroxy-2-oxo-1-(2-propen-1-yl)-1,2-dihydro-3-quinolinecarboxylate To a solution of dimethyl malonate (2.84 g, 17.7 mmol) in DMF (50 ml) was added sodium hydride (0.71 g, 17.7 mmol, 60% in paraffin) over 5 min and the solution stirred for 0.5 h until effervescence ceased. 7-Fluoro-1-(2-propen-1-yl)-2H-3,1-benzoxazine-2,4(1H)-dione (3.92 g, 17.7 mmol) was added to the solution in one portion and the solution stirred at ambient temperature for 1 h then heated to 105° C. for 18 h. The solution was cooled and concentrated and the resulting residues separated between ethyl acetate and water. The aqueous was acidified with 2N hydrochloric acid then extracted with ethyl acetate. The organic extracts were dried and concentrated to yield the title compound as a tan solid (4.63 g, 90%).

LCMS m/z 292-[MH$^+$]

(c) 7-Fluoro-4-hydroxy-1-(2-propen-1-yl)-2(1H)-quinolinone

Ethyl 7-fluoro-4-hydroxy-2-oxo-1-(2-propen-1-yl)-1,2-dihydro-3-quinolinecarboxylate (4.46 g, 15.3 mmol) was suspended in 2N sodium hydroxide solution (70 ml) and heated at reflux for 4 h. After cooling, the pH was adjusted to ~pH6 using 2N hydrochloric acid and the resulting precipi-

205 tate filtered off, washed with water and dried under vacuum to provide the title compound as an off-white solid (2.73 g, 81%).

LCMS m/z 220-[MH$^+$]

(d) 7-Fluoro-2-oxo-1-(2-propen-1-yl)-1,2-dihydro-4-quinolinyl trifluoromethanesulfonate To a suspension of 7-fluoro-4-hydroxy-1-(2-propen-1-yl)-2(1H)-quinolinone (2.57 g, 11.7 mmol) in dichloromethane (50 ml) was added triethylamine (1.8 ml, 12.9 mmol) and the mixture cooled to 0° C. Trifluoromethanesulphonyl anhydride (2.18 ml, 12.9 mmol) was added over 15 min and the mixture stirred for 18 h, the temperature allowed to attain ambience over 1 h. The solution was washed with brine then saturated sodium bicarbonate solution, dried and concentrated to a dark oil. Chromatography (50 g silica SPE, eluting with 2:1 dichloromethane/hexane) provided the title compound as a clear oil which solidified to a white solid (2.31 g, 56%).

LCMS m/z 352-[MH$^+$]

(e) 7-Fluoro-2-oxo-1-(2-oxoethyl)-1,2-dihydro-4-quinolinyl Trifluoromethanesulfonate To a solution of 7-fluoro-2-oxo-1-(2-propen-1-yl)-1,2-dihydro-4-quinolinyl trifluoromethanesulfonate (5.6 g, 16 mmol) in 1,4-dioxane (150 ml) and water (30 ml) at 0° C. was added sodium periodate (7.96 g, 37.3 mmol) followed by osmium tetroxide (14.3 ml, 4% solution in water). The mixture was allowed to warm to ambient then stirred for 5 h. The solution was separated between water and dichloromethane and the organics isolated, dried and concentrated to provide the crude product (6.03 g, contains solvent) which was used immediately in the next stage without further purification.

LCMS m/z 372-[MH$^+$+H$_2$O]

(f) 1-{2-[4-((2,3-Dihydro[1,4]dioxino[2,3-c]pyridin-7-ylmethyl) {[(1,1-dimethylethyl)oxy]carbonyl}amino)-1-piperidinyl]ethyl}-7-fluoro-2-oxo-1,2-dihydro-4-quinolinyl Trifluoromethanesulfonate The crude 7-fluoro-2-oxo-1-(2-oxoethyl)-1,2-dihydro-4-quinolinyl trifluoromethanesulfonate (5.6 g, 15.9 mmol assumed 100% from previous step) was dissolved in THF (50 ml) and 1,1-dimethylethyl (2,3-dihydro[1,4]dioxino[2,3-c]pyridin-7-ylmethyl)-4-piperidinylcarbamate (for a synthesis see WO2004/058144 Example 99(h)) (5.60 g, 15.9 mmol) added followed by sodium sulphate (~15 g). After 2 h sodium triacetoxyborohydride (12.3 g, 58 mmol) was added portionwise over 1 h and the solution stirred for 18 h. The solution was diluted with ethyl acetate and washed with sodium bicarbonate solution, dried and concentrated. Chromatography (70 g silica SPE, eluting with ethyl acetate) provided product (4.88 g) contaminated with an impurity. Further chromatography (70 g silica SPE gradient elution with 2:1 ethyl acetate/hexane to ethyl acetate to ethyl acetate/10% methanol) provided the title compound as a clear oil (2.81 g, 26%).

LCMS m/z 687-[MH$^+$]

(g) 1,1-Dimethylethyl {1-[2-(4-cyano-7-fluoro-2-oxo-1 (2H)-quinolinyl)ethyl]-4-piperidinyl}(2,3-dihydro[1,4]dioxino[2,3-c]pyridin-7-ylmethyl)carbamate A solution of 1-{2-[4-((2,3-dihydro[1,4]dioxino[2,3-c]pyridin-7-ylmethyl){[(1,1-dimethylethyl)oxy]carbonyl}amino)-1-piperidinyl]ethyl}-7-fluoro-2-oxo-1,2-dihydro-4-quinolinyl trifluoromethanesulfonate (0.131 g, 0.19 mmol), zinc cyanide (0.027 g, 0.23 mmol), tris(dibenzylideneacetone)dipalladium (0.017 g, 0.019 mmol) and 1,1'-bis(diphenylphosphino)ferrocene (0.042 g, 0.076 mmol) in DMF (3 ml) was degassed with argon then heated at 90° C. for 18 h. The mixture was allowed to cool then separated between ethyl acetate and brine. The organics were isolated, dried and concentrated. Chromatography (10 g silica SPE gradient elution with ethyl acetate/methanol 0-3%) provided the title compound (0.062 g, 58%) as a yellow oil.

LCMS m/z 564-[MH$^+$]

(h) Title Compound 1,1-Dimethylethyl {1-[2-(4-cyano-7-fluoro-2-oxo-1(2H)-quinolinyl)ethyl]-4-piperidinyl}(2,3-dihydro[1,4]dioxino[2,3-c]pyridin-7-ylmethyl)carbamate (0.061 g, 0.11 mmol) was dissolved in trifluoroacetic acid (3 ml) and stirred for 15 min, then concentrated. The residues were dissolved in ethyl acetate and ether added which caused a precipitate to form. The precipitate was filtered off to provide the title trifluoroacetate salt as a grey solid (0.034 g, 54%).

LCMS m/z 464-[MH$^+$]δH (DMSO$_{d6}$), (400 MHz) 1.79 (2H, br), 2.33 (2H, br), 2.90-3.90 (7H, br m), 4.2 (2H, s), 4.33 (2H, m), 4.4 (2H, m), 4.57 (2H, br s), 7.11 (1H, s), 7.38 (1H, m), 7.5 (1H, s), 7.68 (1H, d, J=10 Hz), 7.93 (1H, m), 8.21 (1H, s), 9.3 (2H, br), 9.6 (1H, br).

Example 131

1-(2-{4-[(2,3-Dihydro[1,4]dioxino[2,3-c]pyridin-7-ylmethyl)amino]-1-piperidinyl}ethyl)-7-fluoro-4-methyl-2(1H)-quinolinone Dihydrochloride

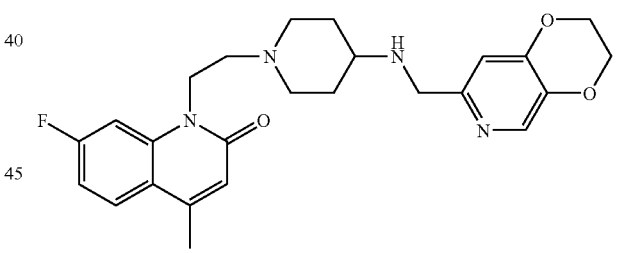

(a) 1,1-Dimethylethyl (2,3-dihydro[1,4]dioxino[2,3-c]pyridin-7-ylmethyl) {1-[2-(7-fluoro-4-methyl-2-oxo-1(2H)-quinolinyl)ethyl]-4-piperidinyl}carbamate To a solution of 1-{2-[4-((2,3-dihydro[1,4]dioxino[2,3-c]pyridin-7-ylmethyl) {[(1,1-dimethylethyl)oxy]carbonyl}amino)-1-piperidinyl]ethyl}-7-fluoro-2-oxo-1,2-dihydro-4-quinolinyl trifluoromethanesulfonate (for a preparation see Example 130(f) (0.155 g, 0.23 mmol) in 1,4-dioxane (2 ml) was added methyl boronic acid (0.05 g, 0.92 mmol), tetrakis(triphenylphosphine)palladium(0) (0.051 g, 0.004M-mol) and potassium triphosphate tribasic (0.155 g, 0.73 mmol). The mixture was degassed with argon then heated at 90° C. for 18 h. The mixture was allowed to cool then separated between ethyl acetate and water. The organics were isolated, dried and concentrated. Chromatography (10 g silica SPE elution with ethyl acetate) provided the title compound (0.062 g, 50%) as a clear oil.
LCMS m/z 553-[MH⁺]

(b) Title Compound 1,1-Dimethylethyl (2,3-dihydro[1,4]dioxino[2,3-c]pyridin-7-ylmethyl) {1-[2-(7-fluoro-4-methyl-2-oxo-1 (2H)-quinolinyl)ethyl]-4-piperidinyl}carbamate (0.061 g, 0.11 mmol) was dissolved in 1,4-dioxane containing 4M HCl and stirred for 1 h then concentrated. The solids were washed with ether and the ether decanted. The solids were dried to provide the title compound as a cream solid (0.032 g, 82%).
LCMS m/z 453-[MH⁺]
δH (DMSO$_{d6}$), (400 MHz) 2.33 (2H, m), 2.2-2.45 (2H, m), 2.49 (3H, s), 3.15 (2H, m), 3.35 (3H, m), 3.5 (1H, m), 3.7 (1H, m), 3.78 (2H, d, J=11 Hz), 4.3 (2H, m), 4.5 (2H, m), 4.65 (2H, t, J=7 Hz), 6.55 (1H, s), 7.2 (1H, m), 7.5 (1H, s), 7.75 (1H, dd, J=12, 2 Hz), 7.9 (1H, dd, J=9, 6 Hz), 8.4 (1H, s), 10.0 (2H, br), 11.0 (1H, br).

Example 132

1-(2-{4-[(2,3-Dihydro[1,4]dioxino[2,3-c]pyridin-7-ylmethyl)amino]-1-piperidinyl}ethyl)-7-fluoro-4-(methyloxy)-2(1H)-quinolinone Dihydrochloride

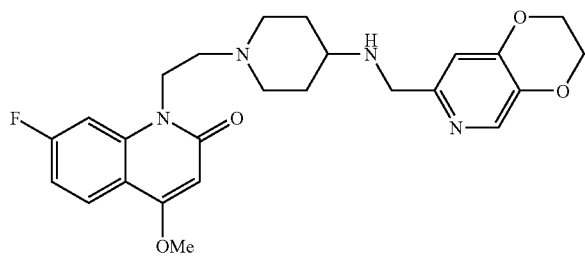

(a) 7-Fluoro-4-(methyloxy)-1-(2-propen-1-yl)-2(1H)-quinolinone

To a solution of 7-fluoro-4-hydroxy-1-(2-propen-1-yl)-2(1H)-quinolinone (see Example 130(c) for a preparation) (1.0 g, 4.56 mmol) in DMF (50 ml) at 0° C. was added sodium hydride (0.20 g, 5.0 mmol, 60% in paraffin). To the resulting solution was added methyl iodide (0.3 ml, 4.8 mmol) and stirring continued at 0° C. for 1 h, then at ambient for 18 h. The mixture was evaporated and the residues separated between dichloromethane and water. The organics were isolated, dried and concentrated. Chromatography over silica (50 g SPE, eluting with dichloromethane) provided the title compound (0.386 g, 36%).
LCMS m/z 234-[MH⁺]

(b) [7-Fluoro-4-(methyloxy)-2-oxo-1(2H)-quinolinyl]acetaldehyde

A solution of 7-fluoro-4-(methyloxy)-1-(2-propen-1-yl)-2(1H)-quinolinone (0.386 g, 1.66 mmol), sodium periodate (0.83 g, 3.7 mmol) and osmium tetroxide (1.7 ml, 4% in water) in 1,4-dioxane (15 ml) containing water (3 ml) was stirred for 5 h. The mixture was separated between dichloromethane and water. The organics were isolated, dried and concentrated to provide the title compound (0.364 g, 93%).

(c) 1,1-Dimethylethyl (1-{2-[7-fluoro-4-(methyloxy)-2-oxo-1(2H)-quinolinyl]ethyl}-4-piperidinyl)carbamate A solution of [7-fluoro-4-(methyloxy)-2-oxo-1(2H)-quinohinyl]acetaldehyde (0.364 g, 1.55 mmol) and 1,1-dimethylethyl 4-piperidinylcarbamate (0.31 g, 1.55 mmol) in dichloromethane (5 ml) and methanol (5 ml) was stirred for 0.5 h. Sodium triacetoxyborohydride (1.0 g, 4.7 mmol) added and the mixture stirred for 5 days, then sodium carbonate solution added and the mixture extracted with dichloromethane. The organics were isolated, dried and concentrated. Chromatography of the residues (20 g silica SPE, gradient elution with dichloromethane/methanol 0-2%) provided the title compound (0.407 g, 63%).
LCMS m/z 420-[MH⁺]

(d) 1-[2-(4-Amino-1-piperidinyl)ethyl]-7-fluoro-4-(methyloxy)-2(1H)-quinolinone 1,1-Dimethylethyl (1-{2-[7-fluoro-4-(methyloxy)-2-oxo-1(2H)-quinolinyl]ethyl}-4-piperidinyl)carbamate (0.40 g, 0.95 mmol) was stirred in 1,4-dioxane (15 ml) containing 4M HCl for 5 h, then concentrated. The resulting solid was portioned between ethyl acetate and sodium carbonate solution and the aqueous extracted with ethyl acetate. The organics were dried and concentrated to an oil which contained highly impure product. Analysis of the aqueous by 1 c/ms showed the product to primarily reside in the aqueous fraction. The aqueous was concentrated and the resulting solids washed with dichloromethane containing methanol (10%) which on evaporation provided material which was washed once more with dichloromethane containing methanol (10%). Concentration of the solution provided the title compound (0.114 g, 37%).
LCMS m/z 320-[MH⁺]

(e) 1-(2-{4-[(2,3-Dihydro[1,4]dioxino[2,3-c]pyridin-7-ylmethyl)amino]-1-piperidinyl}ethyl)-7-fluoro-4-(methyloxy)-2(1H)-quinolinone Dihydrochloride A solution of 1-[2-(4-amino-1-piperidinyl)ethyl]-7-fluoro-4-(methyloxy)-2(1H)-quinolinone (0.057 g, 0.18 mmol) and 2,3-dihydro[1,4]dioxino[2,3-c]pyridine-7-carbaldehyde (for a synthesis see WO2004058144, Example 2(c) or WO03/087098, Example 19(d)) (0.027 g, 0.16 mmol) in 1:1 dichloromethane/methanol (4 ml) was stirred with 3A sieves for 2 h then sodium triacetoxyborohydride (0.115 g, 0.54 mmol) added and the mixture stirred overnight. The solution was diluted with dichloromethane and washed with sodium carbonate solution. The aqueous was extracted with dichloromethane/methanol (10%) and the combined organics dried and concentrated. Chromatography over silica (20 g SPE gradient elution dichloromethane/methanol 0-20%) provided the free base of the title compound (0.022 g) which was converted to the title dihydrochloride salt by dissolving in dichloromethane and adding 4N HCl in 1,4-dioxane. Ether was added to the solution and the precipitate collected (0.022 g, 23%).
LCMS m/z 469-[MH⁺]
Free base nmr: δH (CDCl₃), (400 MHz) 1.55 (2H, m), 2.0 (3H, m), 2.25 (2H, m), 2.6 (3H, m), 3.05 (2H, m), 3.8 (2H, s), 3.95 (3H, s), 4.35 (6H, m), 5.95 (1H, s), 6.8 (1H, s), 6.9 (1H, m), 7.15 (1H, m), 7.95 (1H, m), 8.1 (1H, s)

Example 133

2-({[((3S)-1-{2-[6-(Methyloxy)-3-oxopyrido[2,3-b]pyrazin-4(3H)-yl]ethyl}-3-piperidinyl)methyl]amino}methyl)-5,6-dihydropyrido[2,3-d]pyrimidin-7(1H)-one Dihydrochloride

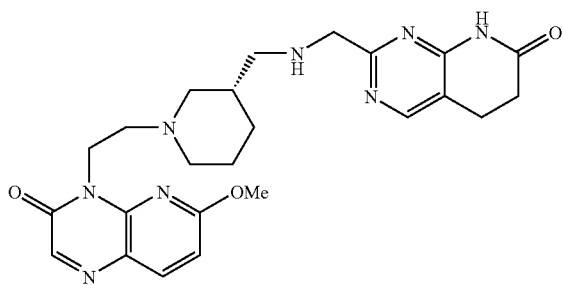

(a) Phenylmethyl [((3S)-1-{2-[6-(methyloxy)-3-oxopyrido[2,3-b]pyrazin-4(3H)-yl]ethyl}-3-piperidinyl)methyl]carbamate

[6-(Methyloxy)-3-oxopyrido[2,3-b]pyrazin-4(3H)-yl]acetaldehyde (for a preparation see Example 126(e)) (0.30 g, 1.36 mmol) was combined with phenylmethyl [(3R)-3-piperidinylmethyl]carbamate (for a preparation see Example 92(b)) (0.337 g, 1.36 mmol) in a 1:1 MeOH/DCM solution (30 mL). Excess Na$_2$SO$_4$ was added as a drying agent and the solution was stirred at ambient temperature for 16 h. NaBH(OAc)$_3$ (0.86 g, 4.08 mmol) was added and the reaction was stirred an additional 2 h. The resulting solution was concentrated onto silica gel under vacuum and the crude residue was purified by column chromatography (silica gel) using a DCM/DCM-MeOH—NH$_4$OH (90:10:1) gradient to yield the desired product as an off white solid (0.37 g, 61%).
LCMS: m/z 452.1 (MH+).

(b) 4-{2-[(3S)-3-(Aminomethyl)-1-piperidinyl]ethyl}-6-(methyloxy)pyrido[2,3-b]pyrazin-3(4H)-one To a solution of phenylmethyl [((3S)-1-{2-[6-(methyloxy)-3-oxopyrido[2,3-b]pyrazin-4(3H)-yl]ethyl}-3-piperidinyl)methyl]carbamate (0.37 g, 0.83 mmol) in MeOH (20 mL) was added 10% Pd/C (0.10 g). The solution was hydrogenated on a Parr apparatus at 50 PSI for 3 h. The Pd/C catalyst was filtered off, MnO$_2$ (0.22 g, 2.48 mmol) was added, and the solution stirred at ambient temperature for 16 h. The MnO$_2$ was filtered off and the crude material (yellowish oil) was used without further purification (0.26 g, 97% over 2 steps).
LCMS: m/z 318.1 (MH+).

(c) Title Compound

To a solution of 4-{2-[(3S)-3-(aminomethyl)-1-piperidinyl]ethyl}-6-(methyloxy)pyrido[2,3-b]pyrazin-3(4H)-one (0.072 g, 0.23 mmol) in 1:1 MeOH/DCM (20 mL), was added 7-oxo-5,6,7,8-tetrahydropyrido[2,3-d]pyrimidine-2-carbaldehyde (for a preparation see Example 125(c)) (0.04 g, 0.23 mmol), and excess Na$_2$SO$_4$. The solution was stirred at ambient temperature for 16 h followed by the addition of NaBH(OAc)$_3$ (1.68 g, 7.92 mmol). The resulting solution was stirred for an additional 2 hours. Analysis by LCMS showed only 50% product, therefore an additional portion of 7-oxo-5,6,7,8-tetrahydropyrido[2,3-d]pyrimidine-2-carbaldehyde (0.04 g, 0.23 mmol) was added and the reaction was stirred for an additional 16 h. The solution was then concentrated onto silica gel under vacuum and the crude residue purified by column chromatography (silica gel) using a DCM/DCM-MeOH—NH$_4$OH (90:10:1) gradient to yield the free base of the desired product as a yellow oily film (0.034 g, 32%). LCMS: m/z 479.2 (MH+). 1H NMR (400 MHz, CDCl$_3$) δ 1.57-1.69 (m, 2H) 1.73-1.82 (m, 1H) 1.95 (d, J=8.59 Hz, 21H) 2.18 (td, J=10.99, 3.03 Hz, 1H) 2.51-2.63 (m, 21H) 2.67-2.75 (m, 4H) 2.81-2.92 (m, 1H) 2.92-3.01 (m, 2H) 3.21-3.32 (m, 1H) 3.88-4.00 (m, 2H) 4.00-4.05 (m, 3H) 4.57-4.68 (m, 2H) 6.73 (d, J=8.59 Hz, 1H) 8.00-8.04 (m, 1H) 8.23 (s, 1H) 8.36 (s, 1H).

The compound was converted to the di-HCl salt by dissolving the free base in 1:1 DCM:MeOH and adding 2 equivalents of 4M HCl in 1,4-dioxane. This was then evaporated to dryness.

Example 134 cis-7-Chloro-6-{[({(3RS,5RS)-1-[2-(7-fluoro-2-oxo-1(2H)-quinolinyl)ethyl]-5-hydroxy-3-piperidinyl}methyl)amino]methyl}-2H-1,4-benzoxazin-3(4,H)-one Dihydrochloride

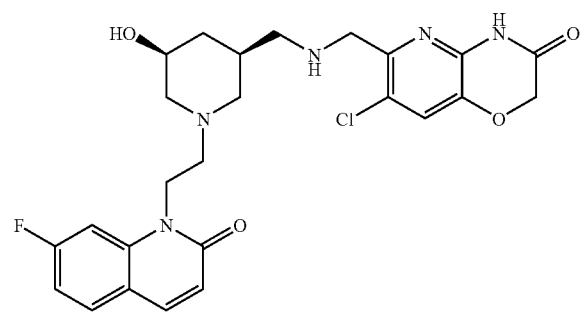

(a) cis-(3RS,5RS)-5-Hydroxy-3-piperidinecarboxylic acid

To methyl 5-hydroxy-3-pyridinecarboxylate (1.5 g; 10 mmol) in water (40 ml) was added aqueous NaOH (5 ml of a 6N solution, 30 mmol) and rhodium (750 mg, 5% wt on alumina). The reaction was hydrogenated on a Parr apparatus at 45 psi of H$_2$ for 36 hours. The hydrogen was displaced with N$_2$ and the solution was filtered through a pad of Celite® to remove the catalyst. The solution was then concentrated under reduced pressure to give the desired compound as the sodium salt (1.5 g, 90%) which was used in the next reaction without further purification.
MS (ES+) m/z 146 (MH$^+$).

(b) cis-(3RS,5RS)-5-Hydroxy 1-{[(phenylmethyl)oxy]carbonyl}-3-piperidinecarboxylic Acid To cis-(3RS,5RS)-5-hydroxy-3-piperidinecarboxylic acid sodium salt (5.2 g; 31.0 mmol) in 0.5 N NaOH (100 ml) was added benzyl chloroformate (7.0 ml; 50.0 mmol) and the reaction was allowed to stir at room temperature under N₂ for 14 hours. The reaction was extracted with diethyl ether (2×50 ml), acidified with 6N HCl (pH=2) and extracted with EtOAc (4×100 ml). The combined organic extracts were dried with Na₂SO₄, the solvents were removed to provide the desired compound (6.2 g; 72%).

MS (ES+) m/z 280 (MH⁺).

(c) cis-(3RS,5RS)-5-{[(1,1-Dimethylethyl)(dimethyl)silyl]oxy}-1-{[(phenylmethyl)oxy]carbonyl}-3-piperidinecarboxylic Acid To cis-(3RS,5RS)-5-hydroxy-1-{[(phenylmethyl)oxy]carbonyl}-3-piperidinecarboxylic acid (0.78 g; 2.8 mmol) in CHCl₃ was added Et₃N (2.0 ml; 15 mmol), and tert-butyldimethylsilyl chloride (1.06 g; 7.0 mmol). The reaction was allowed to stir for 14 hours under N₂ at room temperature. The reaction was diluted with 200 ml of CHCl₃ and washed with saturated aqueous NaHCO₃, 0.1 N aqueous HCl, saturated aqueous NH₄Cl, and brine. The organic layer was dried with Na₂SO₄, and the solvents were removed to provide the desired compound (0.80 g; 73%) as a colorless oil.

MS (ES+) m/z 394 (MH⁺).

(d) cis-Phenylmethyl (3RS,5RS)-3-{[(1,1-dimethylethyl)(dimethyl)silyl]oxy}-5-(hydroxymethyl)-1-piperidinecarboxylate To cis-(3RS,5RS)-5-{[(1,1-dimethylethyl)(dimethyl)silyl]oxy}-1-{[(phenylmethyl)oxy]carbonyl}-3-piperidinecarboxylic acid (0.80 g; 2.0 mmol) in THF (20 ml) was added 1N BH₃.THF in THF (6.0 ml; 6.0 mmol) and the reaction was allowed to stir at room temperature under N₂ for 6 h. Excess borane was quenched by the addition of MeOH and the reaction was allowed to stir for 2 hours. The reaction was partitioned between EtOAc (150 ml) and water (25 ml) the layers were separated and the organic layer was washed with brine and dried with Na₂SO₄. The solvents were removed and the crude residue was purified by chromatography on silica gel using a 0-10% MeOH/DCM gradient to provide the desired compound (550 mg; 73%) as a colorless oil.

MS (ES+) m/z 380 (MH⁺).

(e) cis-Phenylmethyl (3RS,5RS)-3-{[(1,1-dimethylethyl)(dimethyl)silyl]oxy}-5-[(1,3-dioxo-1,3-dihydro-2H-isoindol-2-yl)methyl]-1-piperidinecarboxylate To cis-phenylmethyl (3RS,5RS)-3-{[(1,1-dimethylethyl)(dimethyl)silyl]oxy}-5-(hydroxymethyl)-1-piperidinecarboxylate (550 mg; 1.4 mmol) in THF (25 ml) was added phthalimide (250 mg; 1.7 mmol), triphenylphosphine (450 mg; 1.7 mmol), and diethyl azodicarboxylate (300 mg; 1.7 mmol). The reaction was allowed to stir at room temperature under N₂ for 16 hours. The reaction was partitioned between EtOAc (150 ml) and water (50 ml), the layers were separated, the organic layer was washed with brine and dried with Na₂SO₄. The solvents were removed and the crude residue was purified by chromatography on silica gel using a 10%-100% EtOAc/hexanes gradient to provide the desired compound (690 mg; 93%) as a yellow oil.

MS (ES+) m/z 509 (MH⁺).

(f) cis-Phenylmethyl (3RS,5RS)-3-(aminomethyl)-5-{[(1,1-dimethylethyl)(dimethyl)silyl]oxy}-1-piperidinecarboxylate To cis-phenylmethyl (3RS,5RS)-3-{[(1,1-dimethylethyl)(dimethyl)silyl]oxy}-5-[(1,3-dioxo-1,3-dihydro-2H-isoindol-2-yl)methyl]-1-piperidinecarboxylate (660 mg; 1.3 mmol) in EtOH (20 ml) was added anhydrous hydrazine (0.2 ml; 6.5 mmol). The reaction was allowed to stir at room temperature under nitrogen for 14 hours, and the reaction was filtered through a pad of Celite®. The filtrate was partitioned between EtOAc (150 ml) and water (50 ml), the layers were separated, and the organic layer was washed with brine and dried with Na₂SO₄. The solvents were removed to give the desired compound (450 mg; 92%) as a pale yellow oil which was used without further purification.

MS (ES+) m/z 379 (MH⁺).

(g) cis-Phenylmethyl (3RS,5RS)-3-{[(1,1-dimethylethyl)(dimethyl)silyl]oxy}-5-[({[(1,1-dimethylethyl)oxy]carbonyl}amino)methyl]-1-piperidinecarboxylate To cis-phenylmethyl (3RS,5RS)-3-(aminomethyl)-5-{[(1,1-dimethylethyl)(dimethyl)silyl]oxy}-1-piperidinecarboxylate (450 mg; 1.2 mmol) in DCM (25 ml) was added Et₃N (0.33 ml; 2.4 mmol), and di-tert-butyl dicarbonate (315 mg; 1.4 mmol). The reaction was allowed to stir at room temperature under N₂ for 6 hours, and then was partitioned between EtOAc (150 ml) and water (50 ml), the layers were separated, and the organic layer was washed with brine and dried with Na₂SO₄. The solvents were removed and the residue was purified by chromatography on silica gel using a 5%-50% EtOAc/hexanes gradient to provide the desired compound (550 mg; 96%) as a colorless oil.

MS (ES+) m/z 479 (MH⁺).

(h) cis-1,1-Dimethylethyl [((3RS,5RS)-5-{[(1,1-dimethylethyl)(dimethyl)silyl]oxy}-3-piperidinyl)methyl]carbamate To cis-phenylmethyl (3RS,5RS)-3-{[(1,1-dimethylethyl)(dimethyl)silyl]oxy}-5-[({[(1,1-dimethylethyl)oxy]carbonyl}amino)methyl]-1-piperidinecarboxylate (550 mg; 1.1 mmol) in EtOH (50 ml) was added Pd/C (150 mg; 10%). The reaction was hydrogenated on a Parr apparatus at 40 psi of H₂ for 1.5 hours. The hydrogen was displaced with N₂ and the solution was filtered through a pad of Celite® to remove the catalyst which was washed with additional EtOH (50 ml). The filtrate was then concentrated under reduced pressure to give the desired compound (390 mg; 100%) as a pale yellow oil which was used without further purification.

(i) cis-1,1-Dimethylethyl ({(3RS,5RS)-5-{[(1,1-dimethylethyl)(dimethyl)silyl]oxy}-1-[2-(7-fluoro-2-oxo-1 (2H)-quinolinyl)ethyl]-3-piperidinyl}methyl) carbamate To cis-1,1-dimethylethyl [((3RS,5RS)-5-{[(1,1-dimethylethyl)(dimethyl)silyl]oxy}-3-piperidinyl)methyl]carbamate (350 mg; 1.0 mmol) in MeOH (2 ml) and CHCl₃ (8 ml) was added (7-fluoro-2-oxo-1(2H)-quinolinyl)acetaldehyde (for a preparation see Example 2(d) (200 mg; 1.0 mmol) and the reaction was allowed to stir at room temperature under N₂ for 8 hours. Na(OAc)₃BH (530 mg; 2.5 mmol) was added and the reaction was allowed to stir at room temperature under nitrogen for an additional 14 hours. The solvents were removed and the crude residue was purified by chromatography on silica gel using a 0-10% MeOH/DCM gradient to provide the desired compound (415 mg; 78%) as a colorless oil.
MS (ES+) m/z 534 (MH+).

(j) cis-1-{2-[(3RS,5RS)-3-(Aminomethyl)-5-hydroxy-1-piperidinyl]ethyl}-7-fluoro-2(1H)-quinolinone-hydrochloride To cis-1,1-dimethylethyl ({(3RS,5RS)-5-{[(1,1-dimethylethyl)(dimethyl)silyl]oxy}-1-[2-(7-fluoro-2-oxo-1(2H)-quinolinyl)ethyl]-3-piperidinyl}methyl)carbamate (410 mg; 0.78 mmol) in DCM (9 ml) and MeOH (1 ml) was added 4N HCl in 1,4-dioxane (1 ml; 4.0 mmol) and the reaction was allowed to stir at room temperature under nitrogen for 2 hours. The reaction was concentrated under reduced pressure to give the desired compound (270 mg; 100%) as a yellow solid which was used in the next reaction without further purification.
MS (ES+) m/z 320 (MH+).

(k) Title Compound

To a solution of cis-1-{2-[(3RS,5RS)-3-(aminomethyl)-5-hydroxy-1-piperidinyl]ethyl}-7-fluoro-2(1H)-quinolinone-hydrochloride (90 mg, 0.25 mmol) in CHCl$_3$ (10 ml) and MeOH (1 ml) was added 7-chloro-3-oxo-3,4-dihydro-2H-pyrido[3,2-b][1,4]oxazine-6-carboxaldehyde (for a synthesis, see WO2003064421, Example 15(c)) (56 mg; 0.25 mmol) and Et$_3$N (0.2 ml; 1.5 mmol). The reaction was allowed to stir at room temperature under N$_2$ for 16 hours followed by addition of NaBH$_4$ (12 mg; 0.32 mmol). The reaction was stirred for 1 hour the solvents were removed and the crude residue was purified by chromatography on silica gel using a 0-10% MeOH/DCM (1% NH$_4$OH) gradient to provide the free base of the title compound (35 mg; 27%)
MS (ES+) m/z 516, 518 (MH+). δH CDCl$_3$, (400 MHz) 1.89-2.2 (m, 5H), 2.25-2.74 (m, 4H), 2.80-3.33 (m, 3H), 4.0-4.45 (m, 4H), 4.58 (s, 2H), 4.60-4.75 (m, 2H), 6.47 (d, 1H, J=8.6), 7.10 (m, 1H), 7.16 (d, 1H, J=9.6 Hz), 7.28 (s, 1H), 7.54 (dd, 1H, J=8.6, 6.2 Hz), 7.61 (d, 1H, J=9.6 Hz).
The free base of the title compound was converted to the di-HCl salt by dissolving the obtained free base in 10% MeOH/DCM and adding 1M HCl in diethyl ether. This was then evaporated to dryness.

Example 135

6-({[((3S,4R)-4-Hydroxy-1-{2-[6-(methyloxy)-3-oxopyrido[2,3-b]pyrazin-4(3H)-yl]ethyl}-3-piperidinyl)methyl]amino}methyl)-2H-pyrido[3,2-b][1,4]thiazin-3(4H)-one Dihydrochloride

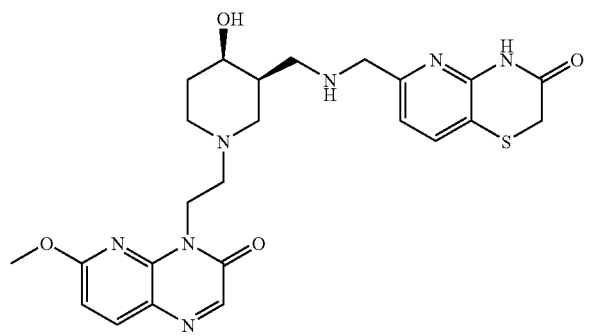

(a) 1,1-Dimethylethyl 3,6-dihydro-1(2H)-pyridinecarboxylate

A 1 L round bottom flask equipped with a stirring bar was charged with 1,2,3,6-tetrahydropyridine (20 g; 0.241 mmol) in 1,4-dioxane (300 mL). To this solution was added triethylamine (0.289 mmol; 40 mL) and cooled to 0° C. To this cooled solution di-tert-butyldicarbonate (0.265 mmol; 58 g) was added in portions. The reaction mixture was concentrated to yield 43 g (99%) of the product:
MS (ES+) m/z 127 (minus t-butyl).

(b) 1,1-Dimethylethyl 2-(phenylmethyl)hexahydroisoxazolo[4,5-c]pyridine-5(4H)-carboxylate and 1,1-dimethylethyl 2-(phenylmethyl)hexahydroisoxazolo[5,4-c]pyridine-6(2H)-carboxylate A 1 L round bottom flask equipped with a stirring bar was charged with 1,1-dimethylethyl 3,6-dihydro-1(2H)-pyridinecarboxylate (25 g; 0.136 mmol) in toluene (300 mL) and isopropanol (100 mL). To this solution was added triethylamine (0.204 mmol; 28 mL), N-benzyl hydroxylamine hydrochloride (0.204 mmol; 32.7 g and paraformaldehyde (0.682 mol; 20.5 g) and heated to 85° C. After 3 days the product was obtained as a mixture of regioisomers and (cis)-enantiomers after column chromatography ((10% MeCN: 40% DCM:50% hexanes; 12.8 g (43%)) as a yellow oil:
MS (ES+) m/z 319.2 (MH+).

(c) 1,1-Dimethylethyl 3-(aminomethyl)-4-hydroxy-1-piperidinecarboxylate and 1,1-dimethylethyl 4-(aminomethyl)-3-hydroxy-1-piperidinecarboxylate To a mixture of 1-dimethylethyl 2-(phenylmethyl)hexahydroisoxazolo[4,5-c]pyridine-5(4H)-carboxylate and 1,1-dimethylethyl 2-(phenylmethyl)hexahydroisoxazolo[5,4-c]pyridine-6(2H)-carboxylate (12.8 g; 0.04 mol) in EtOH (100 mL) was added 20% Pd(OH)$_2$/C (2 g). The mixture was hydrogenated at 55 psi at ambient temperature. The crude product was filtered through Celite and concentrated under reduced pressure to obtain the product as a mixture, yellow oil (8.8 g; 96%)
MS (ES+) m/z 231.3 (MH+).

(d) 1,1-Dimethylethyl 4-hydroxy-3-[({[(phenylmethyl)oxy]carbonyl}amino)methyl]-1-piperidinecarboxylate and 1,1-dimethylethyl 3-hydroxy-4-[({[(phenylmethyl)oxy]carbonyl}amino)methyl]-1-piperidinecarboxylate To a mixture of 1,1-dimethylethyl 3-(aminomethyl)-4-hydroxy-1-piperidinecarboxylate and 1,1-dimethylethyl 4-(aminomethyl)-3-hydroxy-1-piperidinecarboxylate (8.8 g; 0.038 mol) in dichloromethane was added triethylamine (0.046 mol; 6.4 mL) and N-benzyloxycarbonyloxy-succinimide (0.035 mol; 8.8 g) and left overnight. The reaction mixture was concentrated under reduced pressure and purified via column chromatography (50% ethyl acetate/hexanes) to obtain the product as a regiomeric mixture (11 g; 79%).

A regiomeric mixture was resolved via preparative HPLC (Chiralpak AD 20 u 101.6×250 mm column; 100% MeCN with 0.1% isopropylamine; 400 mL/min) to yield 1,1-dimethylethyl 4-hydroxy-3-[({[(phenylmethyl)oxy]carbonyl}amino)methyl]-1-piperidinecarboxylate and 1,1-dimethylethyl 3-hydroxy-4-[({[(phenylmethyl)oxy]carbonyl}amino)methyl]-1-piperidinecarboxylate as white solids. The structures of the regioisomers were confirmed by NOE (Nuclear Overhauser Effect).
MS (ES+) m/z 365.5 (MH+).

(e) 1,1-Dimethylethyl (3S,4R)-4-hydroxy-3-[({[(phenylmethyl)oxy]carbonyl}amino)methyl]-1-piperidinecarboxylate (E2) and 1,1-dimethylethyl (3R,4S)-4-hydroxy-3-[({[(phenylmethyl)oxy]carbonyl}amino)methyl]-1-piperidinecarboxylate (E1)

1,1-Dimethylethyl 4-hydroxy-3-[({[(phenylmethyl)oxy]carbonyl}amino)methyl]-1-piperidinecarboxylate was resolved via supercritical fluid chromatography (SFC) using a Chiralpak AD-H 30×250 mm column (20% Isopropanol in $CO_2$; 70 ml/min; 30 deg C.; uv 220 nm) to obtain the E1 (first eluting isomer: 98% ee) and E2 (second eluting isomer; 94% ee) enantiomers presumed 1,1-dimethylethyl (3S,4R)-4-hydroxy-3-[({[(phenylmethyl)oxy]carbonyl}amino)methyl]-1-piperidinecarboxylate (E2) and presumed 1,1-dimethylethyl (3R,4S)-4-hydroxy-3-[({[(phenylmethyl)oxy]carbonyl}amino)methyl]-1-piperidinecarboxylate (E1) as white solids.

E2 Isomer:

1H NMR (400 MHz, DMSO-$d_6$) δ ppm 1.37 (s, 9H) 1.40-1.51 (m, 2H) 1.56 (d, J=15.41 Hz, 2H) 2.90-3.02 (m, 2H) 3.06-3.15 (m, 1H) 3.59 (s, 2H) 3.80 (s, 1H) 4.65 (s, 1H) 5.02 (s, 2H) 7.21 (t, J=5.43 Hz, 1H) 7.29-7.40 (m, 5H).

MS (ES+) m/z 365.5 (MH$^+$).

Optical Rotation:

[α]d=−7.8° (methanol, C=1.00, 20° C.)

E1 Isomer:

1H NMR (400 MHz, DMSO-$d_6$) δ ppm 1.37 (s, 9H) 1.41-1.51 (m, 1H) 1.54 (s, 2H) 2.90-3.01 (m, 2H) 3.04-3.14 (m, 1H) 3.57 (d, J=17.18 Hz, 1H) 3.80 (s, 1H) 4.64 (d, J=2.27 Hz, 1H) 5.02 (s, 2H) 7.21 (t, J=5.43 Hz, 1H) 7.29-7.39 (m, 5H).

MS (ES+) m/z 365.5 (MH$^+$).

Optical Rotation:

[α]d=+7.5° (methanol, C=1.00, 20° C.)

(f) Phenylmethyl {[(3R,4R)-4-hydroxy-3-piperidinyl]methyl}carbamate

To a flask containing 1,1-dimethylethyl (3S,4R)-4-hydroxy-3-[({[(phenylmethyl)oxy]carbonyl}amino)methyl]-1-piperidinecarboxylate (E2)(500 mg; 1.37 mmol) was added 20 mL of TFA/DCM (50%). The reaction mixture was stirred for 1 h and then concentrated. The crude product was taken up in chloroform, treated with 500 mg of MP-carbonate resin (2.9 mmol/g) and stirred overnight. After filtration and concentration the product was obtained as its free base (370 mg; 100%).

MS (ES+) m/z 265.4 (MH$^+$).

(g) Phenylmethyl [((3S,4R)-4-hydroxy-1-{2-[6-(methyloxy)-3-oxopyrido[2,3-b]pyrazin-4(3H)-yl]ethyl}-3-piperidinyl)methyl]carbamate To a mixture of [6-(methyloxy)-3-oxopyrido[2,3-b]pyrazin-4(3H)-yl]acetaldehyde (for a preparation see Example 126(e) (0.278 g; 1.27 mmol) in anhydrous DCM (10 mL) and anhydrous MeOH (3 mL) was added phenylmethyl {[(3R,4R)-4-hydroxy-3-piperidinyl]methyl}carbamate. (0.37 g; 1.4 mmol) and a spatula of anhydrous sodium sulfate. The reaction was stirred overnight. The crude intermediate was treated with sodium triacetoxyborohydride (2.54 mmol; 0.538 g) and stirred for 2 h. The product was obtained as a pale yellow oil after column chromatography (90:10:0.5:DCM:MeOH:NH$_4$OH) to yield 234 mg (40%) of the product.

MS (ES+) m/z 468.3 (MH$^+$).

(h) 4-{2-[(3S,4R)-3-(Aminomethyl)-4-hydroxy-1-piperidinyl]ethyl}-6-(methyloxy)-1,4-dihydropyrido[2,3-b]pyrazin-3(2H)-one To a solution of phenylmethyl [((3S,4R)-4-hydroxy-1-{2-[6-(methyloxy)-3-oxopyrido[2,3-b]pyrazin-4(3H)-yl]ethyl}-3-piperidinyl)methyl]carbamate (234 mg; 0.502 mmol) in EtOH was added 20% Pd(OH)$_2$/C (100 mg). The mixture was hydrogenated at 1 atm of H$_2$ at ambient temperature overnight. The crude product was filtered through Celite, washed with ethanol and concentrated under reduced pressure to obtain the product (170 mg; 100%)

MS (ES+) m/z 336 (MH$^+$).

(i) 4-{2-[(3S,4R)-3-(Aminomethyl)-4-hydroxy-1-piperidinyl]ethyl}-6-(methyloxy)pyrido[2,3-b]pyrazin-3(4H)-one To a solution of 4-{2-[(3S,4R)-3-(aminomethyl)-4-hydroxy-1-piperidinyl]ethyl}-6-(methyloxy)-1,4-dihydropyrido[2,3-b]pyrazin-3(2H)-one (170 mg; 0.508 mmol) in DCM:MeOH: 10:1 was added MnO$_2$ (156 mg; 1.52 mmol). The reaction mixture was stirred at ambient temperature under N$_2$ for 2 days, filtered, and concentrated to obtain the product (142 mg; 84%).

1H NMR (400 MHz, MeOD) δ ppm 1.26-1.36 (m, 1H) 1.68-1.79 (m, 2H) 1.86-1.98 (m, 2H) 2.00-2.11 (m, 1H) 2.54 (d, J=7.33 Hz, 2H) 2.75 (td, J=12.57, 5.94 Hz, 2H) 2.87-2.98 (m, 2H) 3.13 (dd, J=12.88, 6.82 Hz, 1H) 3.37 (s, 1H) 3.90-3.98 (m, J=4.04, 3.66, 3.47, 3.47 Hz, 1H) 4.04-4.09 (m, 3H) 4.53-4.59 (m, 1H) 4.61-4.68 (m, 1H) 6.77-6.86 (m, 1H) 8.03-8.12 (m, 2H).

(j) Title Compound

To a mixture of [4-{2-[(3S,4R)-3-(aminomethyl)-4-hydroxy-1-piperidinyl]ethyl}-6-(methyloxy)pyrido[2,3-b]pyrazin-3(4H)-one (0.073 g; 0.22 mmol) in DCM (10 mL) and MeOH (3 mL) was added 3-oxo-3,4-dihydro-2H-pyrido[3,2-b][1,4]thiazine-6-carboxaldehyde see WO2004058144, Example 7(d)(0.047 g; 0.242 mmol) and sodium sulfate. The reaction was stirred for 3 days. The crude intermediate was treated with sodium triacetoxyborohydride (0.44 mmol; 93 mg) and stirred overnight. The product was obtained after column chromatography (95:5:1:DCM:MeOH:NH$_4$OH) to yield 24 mg (21%) of the product as its free base. The bis-HCl salt was made by addition of 4N HCl/1,4-dioxane (0.023 mL) to yield the title compound as a yellow solid (32.7 mg).

1H NMR (400 MHz, MeOD) δ ppm 1.67-1.78 (m, 2H) 1.86-1.97 (m, J=6.51, 6.16, 6.16, 3.16 Hz, 1H) 2.47 (d, J=9.35 Hz, 1H) 2.53 (dd, J=12.00, 6.44 Hz, 1H) 2.66 (s, 2H) 2.75 (dd, J=12.00, 6.69 Hz, 2H) 2.81 (t, J=6.95 Hz, 2H) 3.37 (s, 2H) 3.51-3.54 (m, 2H) 3.74 (s, 2H) 3.89-3.95 (m, 1H) 4.03-4.07 (m, 3H) 4.63 (td, J=12.44, 5.94 Hz, 2H) 6.81 (d, J=8.59 Hz, 1H) 7.01 (d, J=7.83 Hz, 1H) 7.68 (d, J=7.83 Hz, 1H) 8.07 (d, J=8.59 Hz, 1H) 8.09 (s, 1H).

MS (ES+) m/z 512.5 (MH$^+$).

Example 136

6-({[((3S,4R)-4-Hydroxy-1-{2-[6-(methyloxy)-3-oxopyrido[2,3-b]pyrazin-4(3H)-yl]ethyl}-3-piperidinyl)methyl]amino}methyl)-2H-pyrido[3,2-b][1,4]oxazin-3(4H)-one Dihydrochloride

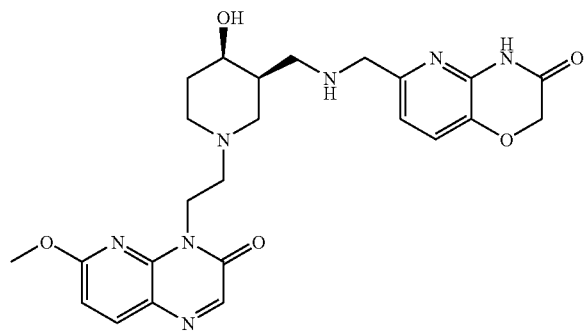

To a mixture of [4-{2-[(3S,4R)-3-(aminomethyl)-4-hydroxy-1-piperidinyl]ethyl}-6-(methyloxy)pyrido[2,3-b]pyrazin-3(4H)-one (for a preparation see Example 135(i); 0.072 g; 0.22 mmol) in anhydrous DCM (10 mL) and anhydrous MeOH (3 mL) was added 3-oxo-3,4-dihydro-2H-pyrido[3,2-b][1,4]oxazine-6-carboxaldehyde 3 (for a synthesis see WO2003087098, Example 31(e))(0.042 g; 0.238 mmol) and a spatula of anhydrous sodium sulfate. The reaction was stirred under N₂ for 18 h. The crude intermediate was treated with sodium triacetoxyborohydride (0.44 mmol; 93 mg) and stirred for 2 h. The product was obtained as a pale yellow oil after column:chromatography (95:5:1:DCM:MeOH:NH₄OH) to yield 24 mg (22%) of the free base of the title compound. The bis-HCl salt was made by addition of 4N HCl/1,4-dioxane (0.024 mL) to yield the title compound as a yellow solid.

1H NMR (400 MHz, MeOD) δ ppm 1.67-1.78 (m, 2H) 1.91 (td, J=6.25, 3.16 Hz, 1H) 2.47 (d, J=9.60 Hz, 1H) 2.53 (dd, J=12.00, 6.44 Hz, 1H) 2.68 (s, 2H) 2.75 (dd, J=12.00, 6.69 Hz, 1H) 2.81 (t, J=6.95 Hz, 2H) 3.37 (s, 2H) 3.71 (s, 2H) 3.92 (d, J=4.29 Hz, 1H) 4.03-4.08 (m, 3H) 4.59-4.66 (m, 4H) 6.81 (d, J=8.59 Hz, 1H) 6.96 (d, J=8.08 Hz, 1H) 7.26 (d, J=7.83 Hz, 1H) 8.06-8.11 (m, 2H).

MS (ES+) m/z 496.5 (MH⁺).

Example 137

4-[2-((3S,4R)-3-{[(2,3-Dihydro[1,4]dioxino[2,3-c]pyridin-7-ylmethyl)amino]methyl}-4-hydroxy-1-piperidinyl)ethyl]-6-(methyloxy)pyrido[2,3-b]pyrazin-3(4H)-one Dihydrochloride

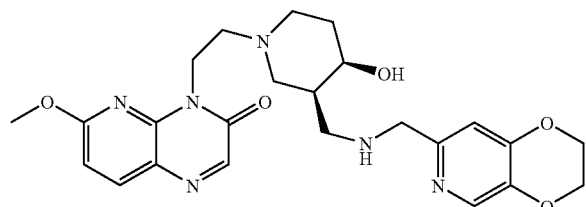

To a mixture of [4-{2-[(3S,4R)-3-(aminomethyl)-4-hydroxy-1-piperidinyl]ethyl}-6-(methyloxy)pyrido[2,3-b]pyrazin-3(4H)-one (for a preparation see Example 135(i); 0.157 g; 0.471 mmol) in anhydrous DCM (20 mL) and anhydrous MeOH (4 mL) was added 2,3-dihydro[1,4]dioxino[2,3-c]pyridine-7-carbaldehyde (for a synthesis see WO2004058144, Example 2(c) or WO03/087098, Example 19(d)) (0.042 g; 0.471 mmol) and activated 4A sieves. The reaction was stirred under N₂ for 18 h. The crude intermediate was treated with sodium triacetoxyborohydride (0.942 mmol; 199 mg) and stirred for 2 h. The product was obtained as a pale yellow oil after column:chromatography (90:10:0.5:DCM:MeOH:NH₄OH) to yield 24 mg (11%) of the free base of the title compound. The bis-HCl salt was made by addition of 1N HCl/ether (0.098 mL) to yield the title compound as a light brown solid.

1H NMR (400 MHz, MeOD) δ ppm 2.05-2.16 (m, 2H) 2.64 (d, J=6.06 Hz, 1H) 3.35-3.44 (m, 5H) 3.74 (t, J=5.94 Hz, 2H) 3.82 (d, J=11.62 Hz, 1H) 4.00 (d, J=10.36 Hz, 1H) 4.08-4.18 (m, 4H) 4.22 (s, 1H) 4.52-4.61 (m, 4H) 4.63-4.71 (m, 3H) 6.89 (d, J=8.59 Hz, 1H) 7.79-7.85 (m, 1H) 8.12-8.21 (m, 2H) 8.56-8.64 (m, 1H).

MS (ES+) m/z 492.8 (MH⁺).

Example 138

1-[2-((3S,4R)-3-{[(2,3-Dihydro[1,4]dioxino[2,3-c]pyridin-7-ylmethyl)amino]methyl}-4-hydroxy-1-piperidinyl)ethyl]-7-fluoro-2(1H)-quinolinone Dihydrochloride

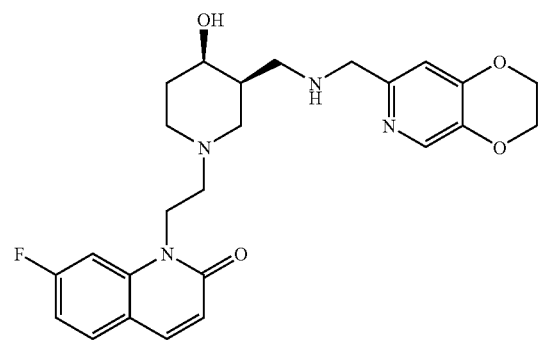

(a) Phenylmethyl ({(3S,4R)-1-[2-(7-fluoro-2-oxo-1(2H)-quinolinyl)ethyl]-4-hydroxy-3-piperidinyl}methyl)carbamate To a mixture of phenylmethyl {[(3R,4R)-4-hydroxy-3-piperidinyl]methyl}carbamate (for a preparation see Example 135(f); 0.72 g; 2.72 mmol) in anhydrous DCM (10 mL) and anhydrous MeOH (2 mL) was added (7-fluoro-2-oxo-1(2H)-quinolinyl)acetaldehyde (for a preparation see Example 88(a)) (0.559 g; 2.72 mmol) and activated 4A sieves. The reaction was stirred under N₂ for 18 h. The crude intermediate was treated with sodium triacetoxyborohydride (2.72 mmol; 577 mg) and stirred for 2 h. The product was obtained as a pale yellow oil after column:chromatography (90:10:DCM:MeOH) to yield 306 mg (25%) of the product as its free base.

MS (ES+) m/z 454.3 (MH⁺).

(b) 1-{2-[(3S,4R)-3-(Aminomethyl)-4-hydroxy-1-piperidinyl]ethyl}-7-fluoro-2(1H)-quinolinone A solution of phenylmethyl ({(3S,4R)-1-[2-(7-fluoro-2-oxo-1(2H)-quinolinyl)ethyl]-4-hydroxy-3-piperidinyl}methyl)carbamate (as prepared previously) (306 mg; 0.675 mmol) in EtOH (50 mL) was added 20% Pd(OH)₂/C (70 mg). The mixture was hydrogenated at 1 atm of H₂ at ambient temperature for 3 h. The crude product was filtered through Celite, washed with ethanol and concentrated under reduced pressure to obtain the product as a pale yellow oil (210 mg; 95%).

MS (ES+) m/z 320.3 (MH⁺).

(c) 1-[2-((3S,4R)-3-{[(2,3-dihydro[1,4]dioxino[2,3-c]pyridin-7-ylmethyl)amino]methyl}-4-hydroxy-1-piperidinyl)ethyl]-7-fluoro-2(1H)-quinolinone To a mixture of 1-{2-[(3S,4R)-3-(Aminomethyl)-4-hydroxy-1-piperidinyl]ethyl}-7-fluoro-2(1H)-quinolinone (0.210 g; 0.657 mmol) in anhydrous DCM (10 mL) and anhydrous MeOH (2 mL) was added 2,3-dihydro[1,4]dioxino[2,3-c]pyridine-7-carbaldehyde (for a synthesis see WO2004058144, Example 2(c) or WO03/087098, Example 19(d)); 0.109 g; 0.657 mmol) and 4A sieves. The reaction was stirred under N₂ for 18 h. The crude intermediate was treated with sodium triacetoxyborohydride (1.31 mmol; 278 mg) and stirred for 2 h. The product was obtained as a pale yellow oil after column chromatography (95:5:1:DCM:MeOH:NH₄OH) to yield 159 mg (52%) of the free base of the title compound. The di-HCl salt was made by addition of 4N HCl/1,4-dioxane (0.170 ml) to yield the title compound as a white solid.

1H NMR (400 MHz, MeOD) δ ppm 2.05-2.16 (m, 2H) 2.59 (d, J=6.32 Hz, 1H) 3.22-3.30 (m, 2H) 3.35-3.46 (m, 3H) 3.57-3.63 (m, 3H) 3.97-4.05 (m, 1H) 4.22 (s, 1H) 4.49-4.56 (m, 5H) 4.58-4.66 (m, 3H) 6.70 (d, J=9.35 Hz, 1H) 7.18 (td, J=8.46, 2.27 Hz, 1H) 7.57 (dd, J=11.12, 2.02 Hz, 1H) 7.66 (s, 1H) 7.83 (dd, J=8.72, 6.19 Hz, 1H) 8.00 (d, J=9.60 Hz, 1H) 8.52 (s, 1H).

MS (ES+) m/z 469.3 (MH⁺).

Example 139

6-{[({(3S,4R)-1-[2-(7-Fluoro-2-oxo-1(2H)-quinolinyl)ethyl]-4-hydroxy-3-piperidinyl}methyl)amino]methyl}-2H-pyrido[3,2-b][1,4]oxazin-3(4H)-one Dihydrochloride

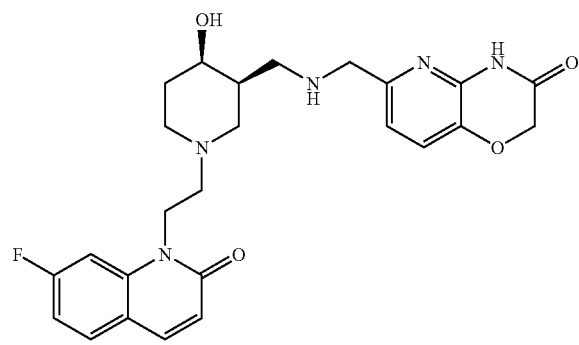

To a mixture of 1-{2-[(3S,4R)-3-(Aminomethyl)-4-hydroxy-1-piperidinyl]ethyl}-7-fluoro-2(1H)-quinolinone (for a preparation see Example 138(b); 0.066 g; 0.207 mmol) in anhydrous DCM (10 mL) and anhydrous MeOH (2 mL) was added 3-oxo-3,4-dihydro-2H-pyrido[3,2-b][1,4]oxazine-6-carboxaldehyde 3 (for a synthesis see WO2003087098, Example 31(e)) (0.037 g; 0.207 mmol) and 4A sieves. The reaction was stirred under N₂ for 18 h. The crude intermediate was treated with sodium triacetoxyborohydride (0.414 mmol; 88 mg) and stirred for 2 h. The product was obtained as a pale yellow oil after column chromatography (95:5:1:DCM:MeOH:NH₄OH) to yield 24 mg (24%) of the free base of the title compound. The bis-HCl salt was made by addition of 4N HCl/1,4-dioxane (0.025 mL) to yield the title compound as an off-white solid.

1H NMR (400 MHz, MeOD) δ ppm 1.77 (d, J=7.58 Hz, 1H) 1.82 (s, 1H) 2.29 (d, J=3.03 Hz, 2H) 2.74 (s, 1H) 2.88 (d, J=6.57 Hz, 4H) 2.98 (s, 1H) 3.11-3.20 (m, 2H) 3.93-4.02 (m, 1H) 4.44 (s, 1H) 4.60-4.69 (m, 1H) 4.72 (s, 3H) 6.66 (d, J=9.35 Hz, 1H) 7.10-7.16 (m, 3H) 7.39-7.47 (m, 3H) 7.78 (dd, J=8.59, 6.32 Hz, 1H) 7.93 (s, 1H).

MS (ES+) m/z 482.1 (MH⁺).

Example 140

1-[2-((3R,4S)-3-{[(2,3-dihydro[1,4]dioxino[2,3-c]pyridin-7-ylmethyl)amino]methyl}-4-hydroxy-1-piperidinyl)ethyl]-7-fluoro-2(1H)-quinolinone Dihydrochloride

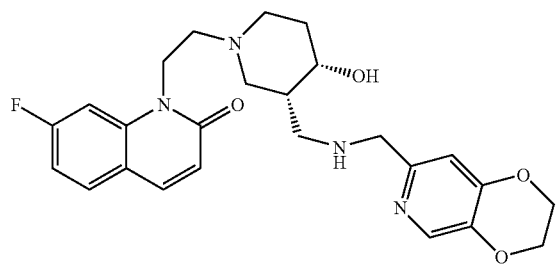

(a) Phenylmethyl {[(3S,4S)-4-hydroxy-3-piperidinyl]methyl}carbamate

To a flask containing 1,1-dimethylethyl (3R,4S)-4-hydroxy-3-[({[(phenylmethyl)oxy]carbonyl}amino)methyl]-1-piperidinecarboxylate (for a preparation see Example 135 (e)) (1 g; 2.74 mmol) was added 100 mL of TFA/DCM (50%). The reaction mixture was stirred for 1 h and then concentrated. The crude product was made basic by the addition of 6N NaOH and extracted into 10% MeOH/DCM (2×50 mL). The organic fractions were dried with anhydrous sodium sulfate, filtered and concentrated to obtain the product as a clear oil (607 mg; 84%).

MS (ES+) m/z 265.4 (MH⁺).

(b) Phenylmethyl ({(3R,4S)-1-[2-(7-fluoro-2-oxo-1(2H)-quinolinyl)ethyl]-4-hydroxy-3-piperidinyl}methyl)carbamate To a mixture of phenylmethyl {[(3S,4S)-4-hydroxy-3-piperidinyl]methyl}carbamate (0.607 g; 2.29 mmol) in anhydrous DCM (20 mL) and anhydrous MeOH (4 mL) was added (7-fluoro-2-oxo-1(2H)-quinolinyl)acetaldehyde (for a preparation see Example 88(a)) (0.471 g; 2.29 mmol) and activated 4A sieves The reaction was stirred under N₂ for 18 h. The crude intermediate was treated with sodium triacetoxyborohydride (4.48 mmol; 971 mg) and stirred for 2 h. The product was obtained as a pale yellow oil after column chromatography (95:5:0.5DCM:MeOH:NH₄OH) to yield 525 mg (50%) of the product.

MS (ES+) m/z 454.3 (MH⁺).

(c) 1-{2-[(3R,4S)-3-(Aminomethyl)-4-hydroxy-1-piperidinyl]ethyl}-7-fluoro-2(1H)-quinolinone A solution of phenylmethyl ({(3R,4S)-1-[2-(7-fluoro-2-oxo-1(2H)-quinolinyl)ethyl]-4-hydroxy-3-piperidinyl}methyl)carbamate (525 mg; 1.16 mmol) in EtOH (100 mL) was added 20% Pd(OH)₂/C (100 mg). The mixture was hydrogenated at 1 atm of $H_2$ at ambient temperature for 2 h. The crude product was filtered through Celite, washed with ethanol and concentrated under reduced pressure to obtain the product as a pale yellow oil (356 mg; 96%).

MS (ES+) m/z 320.3 (MH$^+$).

(d) Title Compound

To a mixture of 1-{2-[(3R,4S)-3-(aminomethyl)-4-hydroxy-1-piperidinyl]ethyl}-7-fluoro-2(1H)-quinolinone (0.104 g; 0.326 mmol) in anhydrous DCM (10 mL) and anhydrous MeOH (2 mL) was added 2,3-dihydro[1,4]dioxino[2,3-c]pyridine-7-carbaldehyde (for a synthesis see WO2004058144, Example 2(c) or WO03/087098, Example 19(d)) (0.054 g; 0.326 mmol) and 4A sieves. The reaction was stirred under $N_2$ for 18 h. The crude intermediate was treated with sodium triacetoxyborohydride (0.326 mmol; 72 mg) and stirred for 2 h. The product was obtained as a pale yellow oil after column chromatography (90:10:1:DCM:MeOH:NH$_4$OH) to yield 27 mg (18%) of the free base of the title compound. The bis-HCl salt was made by addition of 1N HCl/ether (0.113 mL) to yield the title compound as an off-white solid.

1H NMR (400 MHz, MeOD) δ ppm 2.11 (s, 2H) 2.59 (s, 1H) 3.60 (s, 3H) 3.69 (s, 2H) 3.99 (s, 1H) 4.21 (s, 2H) 4.50 (s, 6H) 4.60 (s, 3H) 6.70 (d, J=9.35 Hz, 1H) 7.18 (td, J=8.46, 2.27 Hz, 1H) 7.52-7.63 (m, 3H) 7.83 (dd, J=8.59, 6.32 Hz, 1H) 8.01 (d, J=9.60 Hz, 1H) 8.46 (s, 1H).

MS (ES+) m/z 469.3 (MH$^+$).

Example 141A

6-{[({(3R,4S)-1-[2-(7-Fluoro-2-oxo-1(2H)-quinolinyl)ethyl]-4-hydroxy-3-piperidinyl}methyl)amino]methyl}-2H-pyrido[3,2-b][1,4]oxazin-3(4H)-one Dihydrochloride

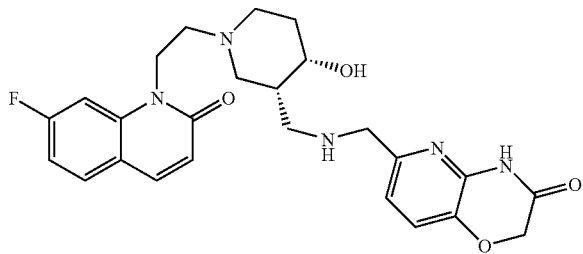

To a mixture of 1-{2-[(3R,4S)-3-(aminomethyl)-4-hydroxy-1-piperidinyl]ethyl}-7-fluoro-2(1H)-quinolinone (for a preparation see Example 140(c)) (0.106 g; 0.332 mmol) in anhydrous DCM (10 mL) and anhydrous MeOH (2 mL) was added 3-oxo-3,4-dihydro-2H-pyrido[3,2-b][1,4]oxazine-6-carbaldehyde (0.059 g; 0.332 mmol) and 4A sieves. The reaction was stirred under $N_2$ for 18 h. The crude intermediate was treated with sodium triacetoxyborohydride (0.332 mmol; 70 mg) and stirred for 2 h. The product was obtained as a pale yellow oil after column chromatography (90:10:1:DCM:MeOH:NH$_4$OH) to yield 87 mg (54%) of the free base of the title compound. The bis-HCl salt was made by addition of 1N HCl/ether (0.361 mL) to yield the title compound as an off-white solid.

1H NMR (400 MHz, MeOD) δ ppm 2.09 (s, 1H) 2.16 (s, 1H) 2.60 (s, 1H) 3.19 (s, 1H) 3.34 (s, 10H) 3.60 (s, 2H) 3.97 (s, 1H) 4.20 (s, 1H) 4.35 (s, 2H) 4.73 (s, 2H) 4.80 (s, 1H) 6.76 (d, J=9.35 Hz, 1H) 7.12-7.21 (m, 2H) 7.40 (d, J=8.08 Hz, 1H) 7.59 (dd, J=11.37, 2.02 Hz, 1H) 7.83 (dd, J=8.72, 6.19 Hz, 1H) 8.01 (d, J=9.60 Hz, 1H).

MS (ES+) m/z 482.2 (MH$^+$).

Example 141B

6-{[({(3R,4S)-1-[2-(7-Fluoro-2-oxo-1(2H)-quinolinyl)ethyl]-4-hydroxy-3-piperidinyl}methyl)amino]methyl}-2H-pyrido[3,2-b][1,4]oxazin-3(4H)-one Trifluoroacetate The product of the reaction of 1-{2-[(3R,4S)-3-(aminomethyl)-4-hydroxy-1-piperidinyl]ethyl}-7-fluoro-2(1H)-quinolinone (for a preparation see Example 140(c)) and 3-oxo-3,4-dihydro-2H-pyrido[3,2-b][1,4]oxazine-6-carbaldehyde as generally described in Example 141A, was purified by HPLC by elution with acetonitrile-water-TFA followed by evaporation of the solvent to yield the title trifluoroacetate salt.

TABLE 5

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 142 | Di-HCl MS (ES+) m/z 465 (MH$^+$) | 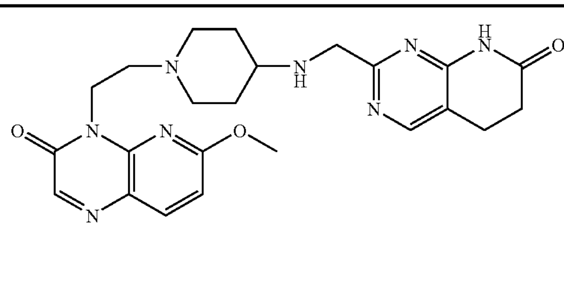 | Prepared by treatment of 2-{[(1-{2-[6-(Methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one (Example 125(d)) with 2 equivalents of HCl |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 143 | mono-HCl MS (ES+) m/z 452 (MH+) | 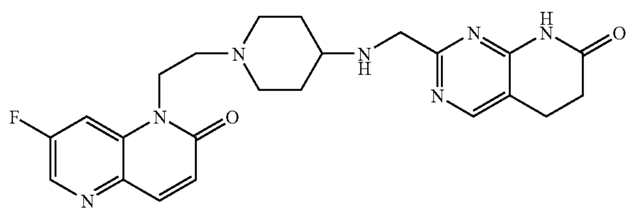 | [7-(Fluoro-2-oxo-1,5-naphthyridin-1(2H)-yl]acetaldehyde (as the methyl hemiacetal) (Example 7(d)) 1,1-Dimethylethyl 4-piperidinylcarbamate 7-Oxo-5,6,7,8-tetrahydropyrido[2,3-d]pyrimidine-2-carbaldehyde (Example 125(c)) |
| 144 | mono-HCl MS (ES+) m/z 481 (MH+) | 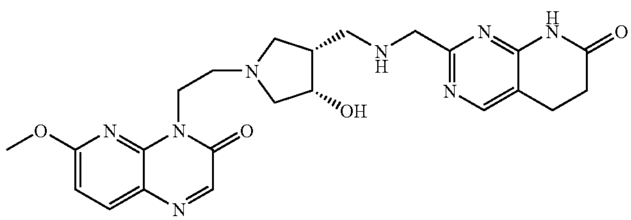 | [6-(Methyloxy)-3-oxopyrido[2,3-b]pyrazin- (Example 126(e)) Phenylmethyl {[(3R,4S)-4-hydroxy-3-pyrrolidinyl]methyl}carbamate 7-Oxo-5,6,7,8-tetrahydropyrido[2,3-d]pyrimidine-2-carbaldehyde (Example 125(c)) |
| 145 | mono-HCl MS (ES+) m/z 467 (MH+) | 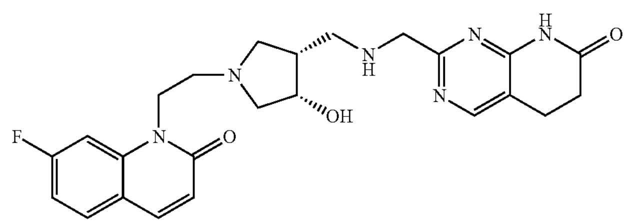 | (7-Fluoro-2-oxo-1(2H)-quinolinyl)acetaldehyde (Example 88(a)) Phenylmethyl {[(3R,4S)-4-hydroxy-3-pyrrolidinyl]methyl}carbamate 7-Oxo-5,6,7,8-tetrahydropyrido[2,3-d]pyrimidine-2-carbaldehyde (Example 125(c)) |
| 146 | mono-HCl MS (ES+) m/z 468 (MH+) | 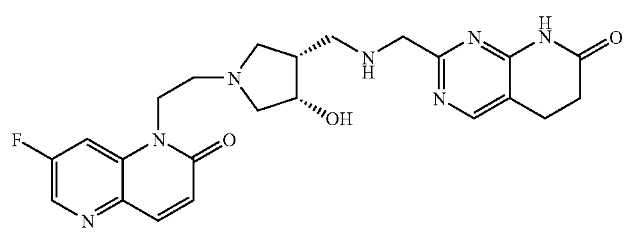 | [7-(Fluoro-2-oxo-1,5-naphthyridin-1(2H)-yl]acetaldehyde (as the methyl hemiacetal) (Example 7(d)) Phenylmethyl {[(3R,4S)-4-hydroxy-3-pyrrolidinyl]methyl}carbamate 7-oxo-5,6,7,8-tetrahydropyrido[2,3-d]pyrimidine-2-carbaldehyde (Example 125(c)) |
| 147 | mono-HCl MS (ES+) m/z 486 (MH+) | 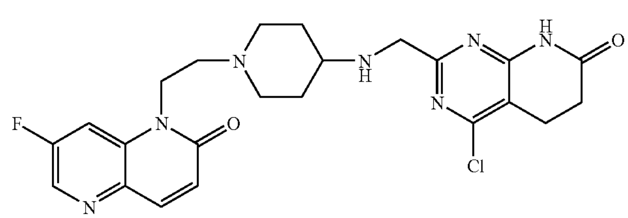 | [7-(fluoro)-2-oxo-1,5-naphthyridin-1(2H)-yl]acetaldehyde (as the methyl hemiacetal) (Example 7(d)) 1,1-Dimethylethyl 4-piperidinylcarbamate 4-Chloro-7-oxo-5,6,7,8-tetrahydropyrido[2,3-d]pyrimidine-2-carbaldehyde (Example 126(k)) |
| 148 | di-HCl MS (ES+) m/z 515/517 (MH+) | 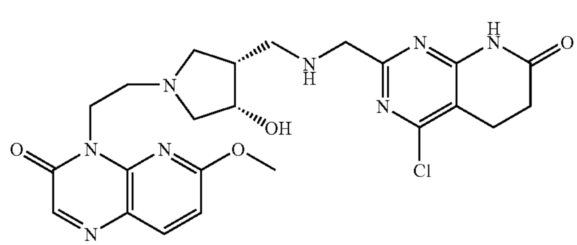 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 4-Chloro-7-oxo-5,6,7,8-tetrahydropyrido[2,3-d]pyrimidine-2-carbaldehyde (Example 126(k)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 149 | mono-HCl MS (ES+) m/z 501/503 (MH+) | 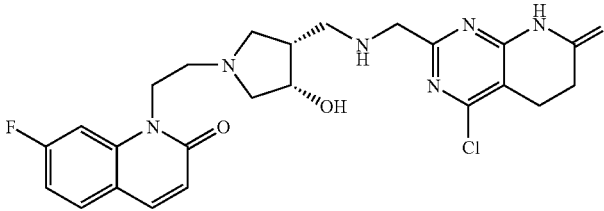 | (7-Fluoro-2-oxo-1(2H)-quinolinyl)acetaldehyde (Example 88(a)) Phenylmethyl {[(3R,4S)-4-hydroxy-3-pyrrolidinyl]methyl}carbamate 4-Chloro-7-oxo-5,6,7,8-tetrahydropyrido[2,3-d]pyrimidine-2-carbaldehyde (Example 126(k)) |
| 150 | di-HCl MS (ES+) m/z 502/503 (MH+) | 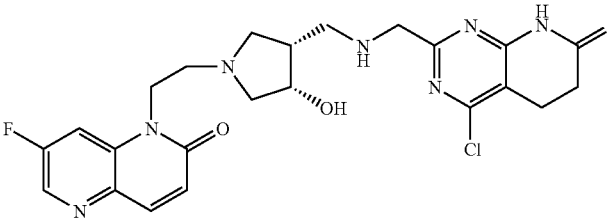 | [7-(fluoro)-2-oxo-1,5-naphthyridin-1(2H)-yl]acetaldehyde (as the methyl hemiacetal) (Example 7(d)) Phenylmethyl {[(3R,4S)-4-hydroxy-3-pyrrolidinyl]methyl}carbamate 4-Chloro-7-oxo-5,6,7,8-tetrahydropyrido[2,3-d]pyrimidine-2-carbaldehyde(Example 126(k) |
| 151 | Mono-HCl MS (ES+) m/z 465 (MH+) | 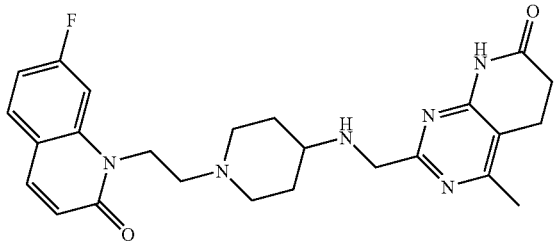 | (7-Fluoro-2-oxo-1(2H)-quinolinyl)acetaldehyde (Example 88(a)) 1,1-Dimethylethyl 4-piperidinylcarbamate 4-Methyl-7-oxo-5,6,7,8-tetrahydropyrido[2,3-d]pyrimidine-2-carbaldehyde (Example 127(e)) |
| 152 | di-HCl MS (ES+) m/z 511 (MH+) | 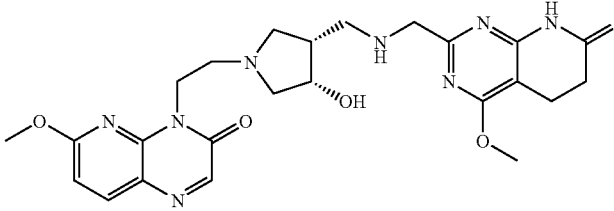 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 4-(Methyloxy)-7-oxo-5,6,7,8-tetrahydropyrido[2,3-d]pyrimidine-2-carbaldehyde (Example 128(b)) |
| 153 | Mono-HCl MS (ES+) m/z 481 (MH+) | 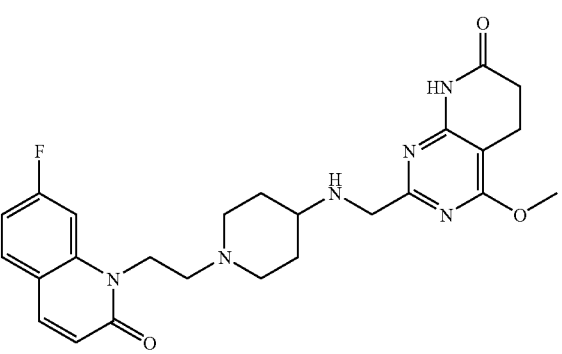 | (7-Fluoro-2-oxo-1(2H)-quinolinyl)acetaldehyde (Example 88(a)) 1,1-Dimethylethyl 4-piperidinylcarbamate 4-(Methyloxy)-7-oxo-5,6,7,8-tetrahydropyrido[2,3-d]pyrimidine-2-carbaldehyde (Example 128(b)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 154 | Mono-HCl MS (ES+) m/z 467 (MH+) | 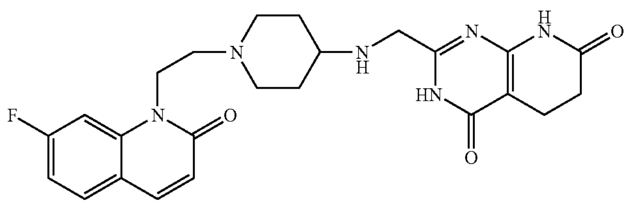 | This was made by treatment of 2-[({1-[2-(7-fluoro-2-oxo-1(2H)-quinolinyl)ethyl]-4-piperidinyl}amino)methyl]-4-(methyloxy)-5,6-dihydropyrido[2,3-d]pyrimidin-7(1H)-one (Example 153) with 33% HBr in AcOH. |
| 155 | Mono-fumarate MS (ES+) m/z 470 (MH+) | 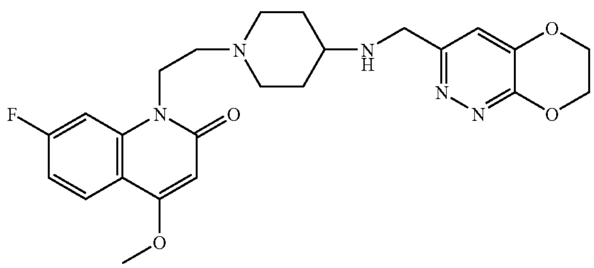 | [7-Fluoro-4-(methyloxy)-2-oxo-1(2H)-quinolinyl]acetaldehyde (Example 132(b)) 1,1-Dimethylethyl 4-piperidinylcarbamate 6,7-Dihydro[1,4]dioxino[2,3-c]pyridazine-3-carbaldehyde |
| 156 | di-HCl MS (ES+) m/z 455 (MH+) | 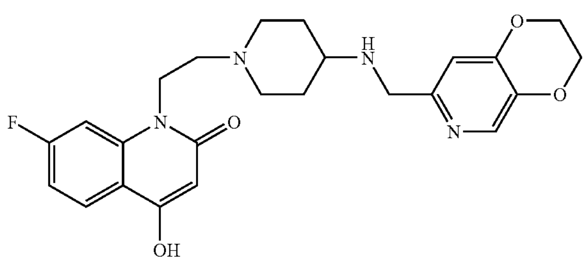 | 1-{2-[4-((2,3-Dihydro[1,4]dioxino[2,3-c]pyridin-7-ylmethyl){[(1,1-dimethylethyl)oxy]carbonyl}amino)-1-piperidinyl]ethyl}-7-fluoro-2-oxo-1,2-dihydro-4-quinolinyl trifluoromethanesulfonate (Example 130(f)) was hydrolysed to give 1,1-dimethylethyl (2,3-dihydro[1,4]dioxino[2,3-c]pyridin-7-ylmethyl){1-[2-(7-fluoro-4-hydroxy-2-oxo-1(2H)-quinolinyl)ethyl]-4-piperidinyl}carbamate which was then deprotected with 4M HCl/1,4-dioxane |
| 157 | Free base MS (ES+) m/z 482 (MH+) | 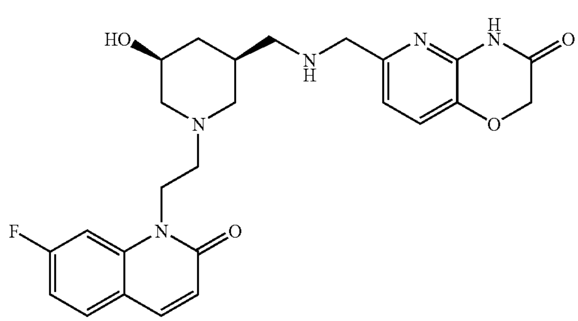 | (7-Fluoro-2-oxo-1(2H)-quinolinyl)acetaldehyde (Example 88(a)) Cis-1,1-dimethylethyl [((3RS,5RS)-5-{[(1,1-dimethylethyl)(dimethyl)silyl]oxy}-3-piperidinyl)methyl]carbamate 3-Oxo-3,4-dihydro-2H-pyrido[3,2-b][1,4]oxazine-6-carboxaldehyde (WO2003087098, Example 31(e)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 158 | free base MS (ES+) m/z 498 (MH+) | 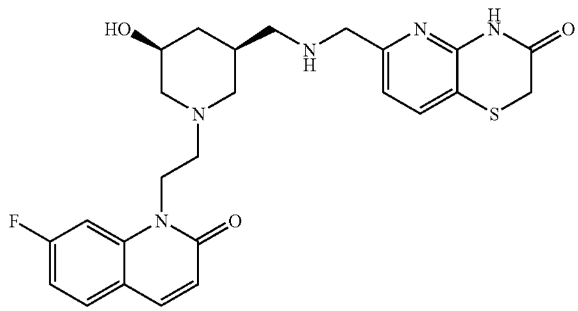 | (7-Fluoro-2-oxo-1(2H)-quinolinyl)acetaldehyde (Example 88(a)) Cis-1,1-dimethylethyl [((3RS,5RS)-5-{[(1,1-dimethylethyl)(dimethyl)silyl]oxy}-3-piperidinyl)methyl]carbamate 3-Oxo-3,4-dihydro-2H-pyrido[3,2-b][1,4]thiazine-6-carboxaldehyde (WO2004058144, Example 7(d)) |
| 159 | di-HCl MS (ES+) m/z 469 (MH+) | 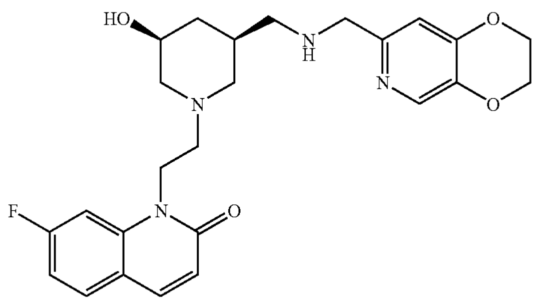 | (7-Fluoro-2-oxo-1(2H)-quinolinyl)acetaldehyde (Example 88(a)) Cis-1,1-dimethylethyl [((3RS,5RS)-5-{[(1,1-dimethylethyl)(dimethyl)silyl]oxy}-3-piperidinyl)methyl]carbamate 2,3-Dihydro[1,4]dioxino[2,3-c]pyridine-7-carboxaldehyde (WO2004058144, Example 2(c) or WO03/087098, Example 19(d)) |
| 160A and B | di-HCl (A) and benzoate (B) MS (ES+) m/z 482 (MH+) | 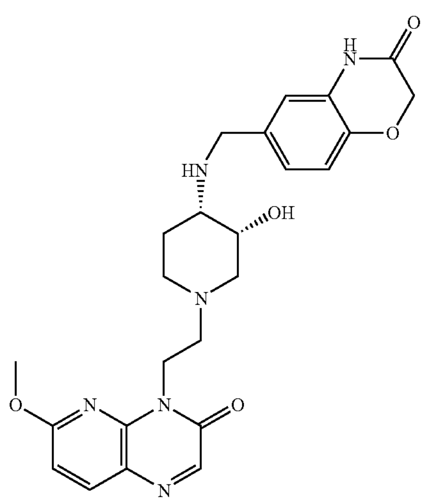 | [6-(Methyloxy)-3-oxopyrido[2,3-b]pyrazin-4(3H)-yl]acetaldehyde (Example 126(e)) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) 3-Oxo-3,4-dihydro-2H-pyrido[3,2-b][1,4]oxazine-6-carboxaldehyde (WO2003087098, Example 31(e)) |
| 161 | mono-HCl MS (ES+) m/z 443 (MH+) | 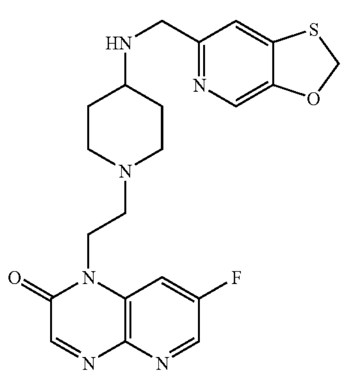 | (7-Fluoro-2-oxopyrido[2,3-b]pyrazin-1(2H)-yl)acetaldehyde (as the methyl hemiacetal) (Example 35(e)) 1,1-Dimethylethyl 4-piperidinylcarbamate [1,3]Oxathiolo[5,4-c]pyridine-6-carbaldehyde (WO2004058144, Example 61) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)- (d) for benzyl-oxycarbonyl protected central units.*

| Example number | Form tested | Structure | Starting materials (for a preparation see referenced Examples) |
|---|---|---|---|
| 162 | mono-HCl<br>MS (ES+)<br>m/z 455<br>(MH+) | 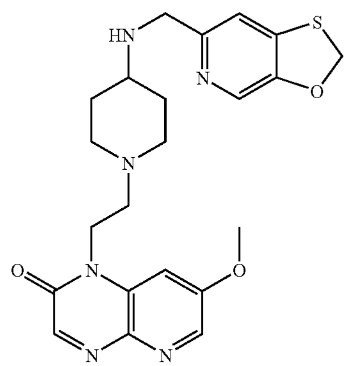 | [7-(Methyloxy)-2-oxopyrido[2,3-b]pyrazin-1(2H)-yl]acetaldehyde (as the methyl hemiacetal) (Example 51A(b))<br>1,1-Dimethylethyl 4-piperidinylcarbamate<br>[1,3]Oxathiolo[5,4-c]pyridine-6-carbaldehyde (WO2004058144, Example 61) |
| 163 | di-HCl<br>MS (ES+)<br>m/z 465<br>(MH+) | 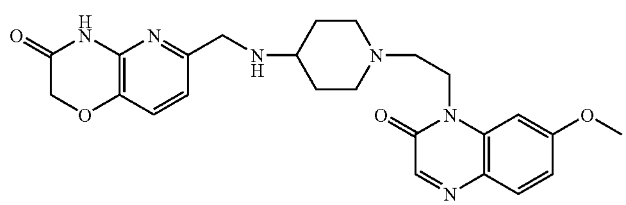 | By treatment of 1-[2-(4-amino-1-piperidinyl)ethyl]-7-fluoro-2(1H)-quinoxalinone dihydrochloride (Example 44C(g)) with NaOMe soln in MeOH and then reductive alkylation with 3-oxo-3,4-dihydro-2H-pyrido[3,2-b][1,4]oxazine-6-carboxaldehyde (WO2003087098, Example 31(e)) |
| 164A and B | Mono-HCl (A) and mono-formate (B)<br>MS (ES+)<br>m/z 451<br>(MH+) | 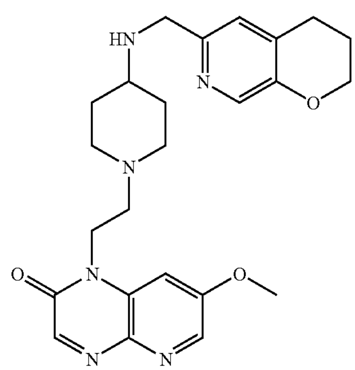 | [7-(Methyloxy)-2-oxopyrido[2,3-b]pyrazin-1(2H)-yl]acetaldehyde (as the methyl hemiacetal) (Example 51A(b))<br>1,1-Dimethylethyl 4-piperidinylcarbamate<br>3,4-Dihydro-2H-pyrano[2,3-c]pyridine-6-carbaldehyde (WO2004058144, Example 126(e)) |
| 165 | di-HCl<br>MS (ES+)<br>m/z 481<br>(MH+) | 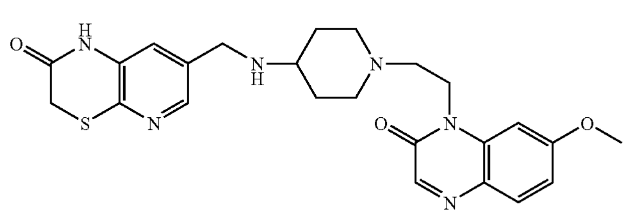 | By treatment of 1-[2-(4-amino-1-piperidinyl)ethyl]-7-fluoro-2(1H)-quinoxalinone dihydrochloride (Example 44C(g)) with NaOMe soln in MeOH and then reductive alkylation with 3-oxo-3,4-dihydro-2H-pyrido[3,2-b][1,4]thiazine-6-carboxaldehyde (WO2004058144, Example 7(d)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 166 | di-HCl<br>MS (ES+)<br>m/z 469<br>(MH+) | 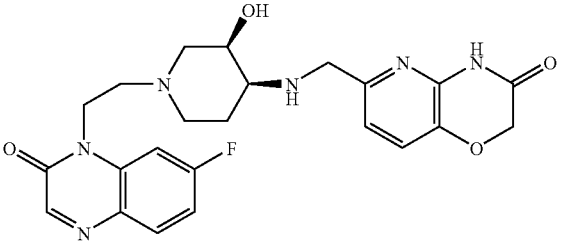 | 7-Fluoro-2-oxo-1(2H)-quinoxalinyl)acetaldehyde (Example 34(c))<br>1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1)<br>3-Oxo-3,4-dihydro-2H-pyrido[3,2-b][1,4]oxazine-6-carboxaldehyde (WO2003087098, Example 31(e)) |
| 167 | Mono-Fumarate<br>MS (ES+)<br>m/z 469<br>(MH+) | 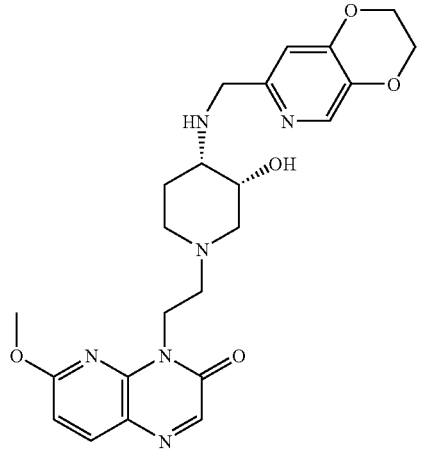 | [6-(Methyloxy)-3-oxopyrido[2,3-b]pyrazin-4(3H)-yl]acetaldehyde (Example 126(e))<br>1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1)<br>2,3-Dihydro[1,4]dioxino[2,3-c]pyridine-7-carboxaldehyde (WO2004058144, Example 2(c) or WO03/087098, Example 19(d)) |
| 168A and B | di-HCl (A) and free base (B)<br>MS (ES+)<br>m/z 456<br>(MH+) | 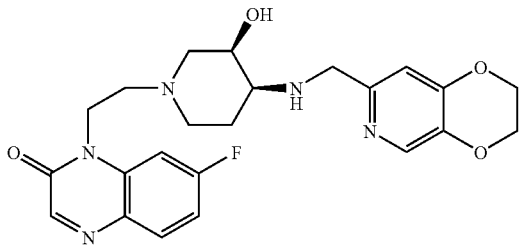 | 7-Fluoro-2-oxo-1(2H)-quinoxalinyl)acetaldehyde (Example 34(c))<br>1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1)<br>2,3-Dihydro[1,4]dioxino[2,3-c]pyridine-7-carboxaldehyde (WO2004058144, Example 2(c) or WO03/087098, Example 19(d)) |
| 169 | mono-HCl<br>MS (ES+)<br>m/z 439<br>(MH+) | 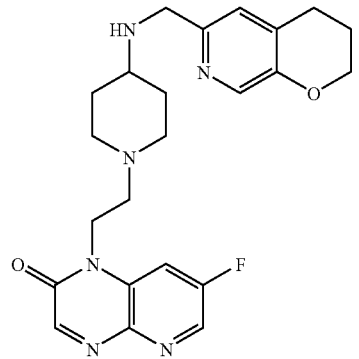 | (7-Fluoro-2-oxopyrido[2,3-b]pyrazin-1(2H)-yl)acetaldehyde (as the methyl hemiacetal) (Example 35(e))<br>1,1-Dimethylethyl 4-piperidinylcarbamate<br>3,4-Dihydro-2H-pyrano[2,3-c]pyridine-6-carbaldehyde (WO2004058144, Example 126(e)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 170A and B | di-HCl (A) and benzoate (B) MS (ES+) m/z 468 (MH+) | 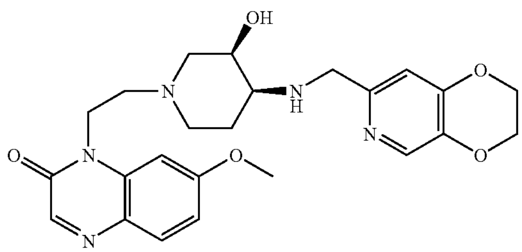 | [7-(Methyloxy)-2-oxo-1(2H)-quinoxalinyl]acetaldehyde (Preparation C) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) 2,3-Dihydro[1,4]dioxino[2,3-c]pyridine-7-carboxaldehyde (WO2004058144, Example 2(c) or WO03/087098, Example 19(d)) |
| 171 | di-HCl MS (ES+) m/z 452 (MH+) | 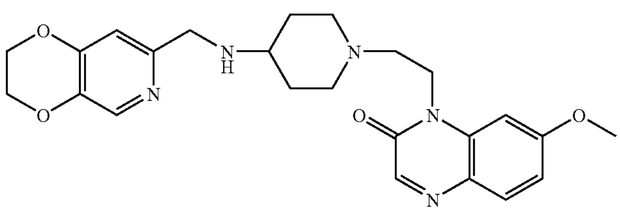 | By treatment of 1-[2-(4-amino-1-piperidinyl)ethyl]-7-fluoro-2(1H)-quinoxalinone dihydrochloride (Example 44C(g)) with NaOMe soln in MeOH and then reductive alkylation with 2,3-dihydro[1,4]dioxino[2,3-c]pyridine-7-carboxaldehyde (WO2004058144, Example 2(c) or WO03/087098, Example 19(d)) |
| 172 | Mono-HCl MS (ES+) m/z 467 (MH+) | 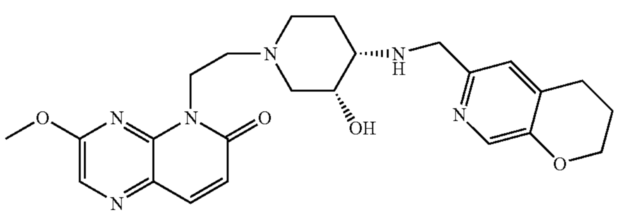 | 6-(Methyloxy)-3-oxopyrido[2,3-b]pyrazin-4(3H)-yl]acetaldehyde (Example 126(e)) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) 3,4-Dihydro-2H-pyrano[2,3-c]pyridine-6-carbaldehyde (WO2004058144, Example 126(e)) |
| 173 | Mono-HCl MS (ES+) m/z 470 (MH+) | 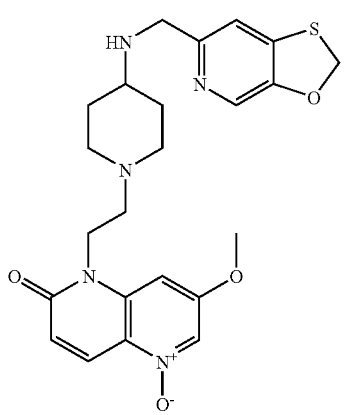 | [7-(Methyloxy)-5-oxido-2-oxo-1,5-naphthyridin-1(2H)-yl]acetaldehyde, made analogously to (7-fluoro-5-oxido-2-oxo-1,5-naphthyridin-1(2H)-yl)acetaldehyde (as the methyl hemiacetal) (Example 96(c)) from 7-(methoxy)-1,5-naphthyridin-2(1H)-one (Example 11(c)) 1,1-Dimethylethyl 4-piperidinylcarbamate [1,3]oxathiolo[5,4-c]pyridine-6-carbaldehyde (WO2004058144, Example 61) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 174 | Mono-HCl MS (ES+) m/z 497 (MH+) | 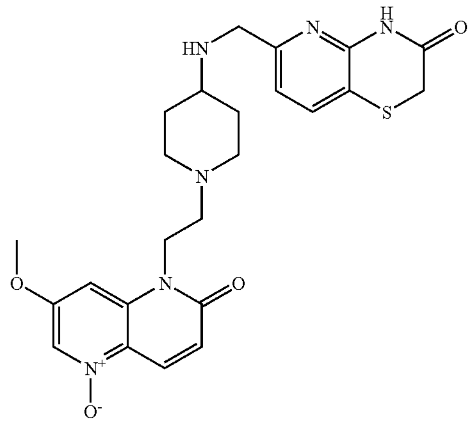 | [7-(Methyloxy)-5-oxido-2-oxo-1,5-naphthyridin-1(2H)-yl]acetaldehyde, made analogously to (7-fluoro-5-oxido-2-oxo-1,5-naphthyridin-1(2H)-yl)acetaldehyde (as the methyl hemiacetal) (Example 96(c)) from 7-(methoxy)-1,5-naphthyridin-2(1H)-one (Example 11(c)) 1,1-Dimethylethyl 4-piperidinylcarbamate 3-Oxo-3,4-dihydro-2H-pyrido[3,2-b][1,4]thiazine-6-carboxaldehyde (WO2004058144, Example 7(d)) |
| 175 | di-HCl MS (ES+) m/z 470 (MH+) | 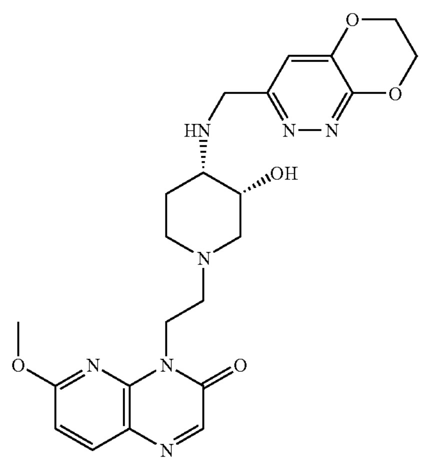 | [6-(Methyloxy)-3-oxopyrido[2,3-b]pyrazin-4(3H)-yl]acetaldehyde (Example 126(e)) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) 6,7-Dihydro[1,4]dioxino[2,3-c]pyridazine-3-carbaldehyde (Example 6(e)) |
| 176 | Mono-HCl MS (ES+) m/z 467 (MH+) | 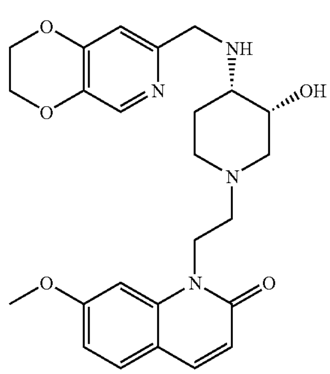 | [7-(Methyloxy)-2-oxo-1(2H)-quinolinyl]acetaldehyde (Example 1(d)) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) 2,3-Dihydro[1,4]dioxino[2,3-c]pyridine-7-carboxaldehyde (WO2004058144, Example 2(c) or WO03/087098, Example 19(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 177 | Mono-HCl<br>MS (ES+)<br>m/z 443<br>(MH+) | 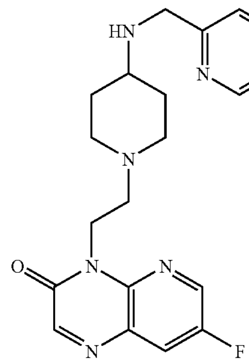 | (7-Fluoro-3-oxopyrido[2,3-b]pyrazin-4(3H)-yl)acetaldehyde (obtainable from 7-fluoropyrido[2,3-b]pyrazin-3(4H)-one, (a byproduct from Example 35(c)) by the general method of Example 35(d)-(e)<br>1,1-Dimethylethyl 4-piperidinylcarbamate<br>[1,3]Oxathiolo[5,4-c]pyridine-6-carbaldehyde<br>(WO2004058144, Example 61) |
| 178 | di-HCl<br>MS (ES+)<br>m/z 456<br>(MH+) | 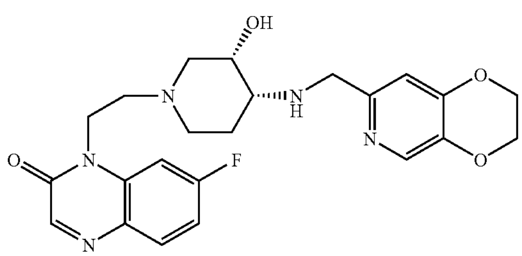 | 7-Fluoro-2-oxo-1(2H)-quinoxalinyl)acetaldehyde (Example 34(c))<br>1,1-Dimethylethyl[(3S,4R)-3-hydroxy-4-piperidinyl]carbamate (WO2004058144, Example 5(c), cis-(3-hydroxy-piperidin-4-yl)-carbamic acid tert-butyl ester Enantiomer 2)<br>2,3-Dihydro[1,4]dioxino[2,3-c]pyridine-7-carboxaldehyde (WO2004058144, Example 2(c) or WO03/087098, Example 19(d)) |
| 179 | mono-HCl<br>MS (ES+)<br>m/z 469<br>(MH+) | 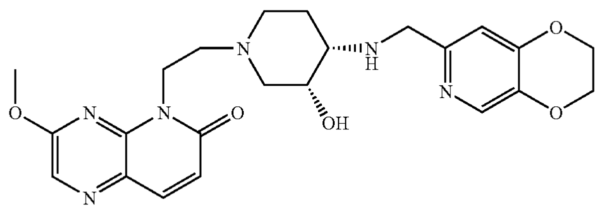 | [3-(Methyloxy)-6-oxopyrido[2,3-b]pyrazin-5(6H)-yl]acetaldehyde (Example 126(e))<br>1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1)<br>2,3-Dihydro[1,4]dioxino[2,3-c]pyridine-7-carboxaldehyde (WO2004058144, Example 2(c) or WO03/087098, Example 19(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 180 | Mono-HCl<br>MS (ES+)<br>m/z 457<br>(MH+) | 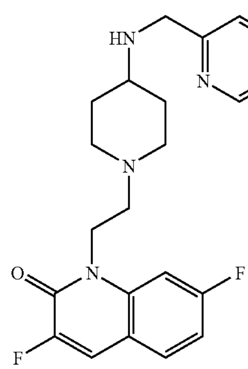 | (3,7-Difluoro-2-oxo-1(2H)-quinolinyl)acetaldehyde (obtainable by reacting 3-fluoroaniline with n-BuLi and then ethyl-2-fluoro-3-(methyloxy)-2-propenoate to give (2Z)-2-fluoro-N-(3-fluorophenyl)-3-(methloxy)-2-propenamide. This was then treated with 70% $H_2SO_4$ to give 3,7-difluoro-2(1H)-quinolinone. This was treated with sodium hydride and then allyl-iodide to give 3,7-difluoro-1-(2-propen-1-yl)-2(1H)-quinolinone which was then treated with $OsO_4/NaIO_4$. 1,1-Dimethylethyl (2,3-dihydro[1,4]dioxino[2,3-c]pyridin-7-ylmethyl)4-piperidinylcarbamate (WO2004/058144 Example 99(h))<br>Coupled by an analogous procedure to Example 7(e)-(f) |
| 181 | mono-HCl<br>MS (ES+)<br>m/z 466<br>(MH+) | 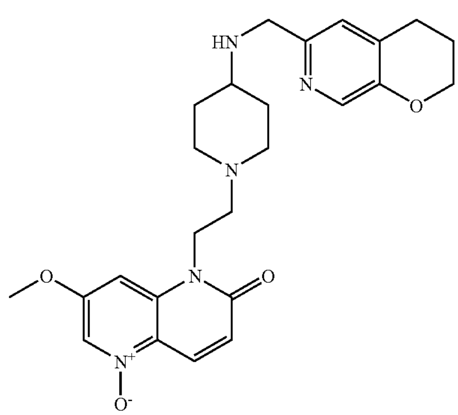 | [7-(Methyloxy)-5-oxido-2-oxo-1,5-naphthyridin-1(2H)-yl]acetalldehyde, made analogously to (7-fluoro-5-oxido-2-oxo-1,5-naphthyridin-1(2H)-yl)acetaldehyde (as the methyl hemiacetal) (Example 96(c)) from 7-(methoxy)-1,5-naphthyridin-2(1H)-one (Example 11(c))<br>1,1-Dimethylethyl 4-piperidinylcarbamate<br>3,4-Dihydro-2H-pyrano[2,3-c]pyridine-6-carbaldehyde (WO2004058144, Example 126(e)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 182 | Mono-HCl MS (ES+) m/z 479 (MH+) | 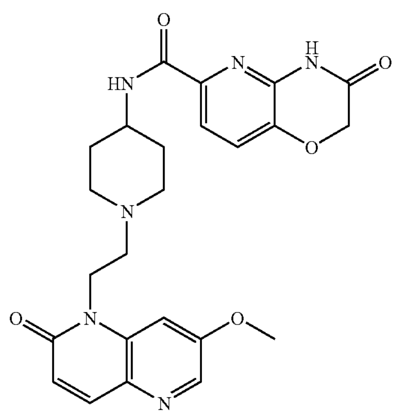 | 1-[2-(4-Amino-1-piperidinyl)ethyl]-7-(methyloxy)-1,5-naphthyridin-2(1H)-one dihydrochloride (Example 16(b)) 3-Oxo-3,4-dihydro-2H-pyrido[3,2-b][1,4]oxazine-6-carboxylic acid (WO2004058144, Example 65) Coupled using HATU (O-(7-azabenzotriazol-1-yl)-N,N,N',N'-tetramethyl-uronium-hexafluorophosphate) and triethylamine. |
| 183 | Free base MS (ES+) m/z 511 (MH+) | 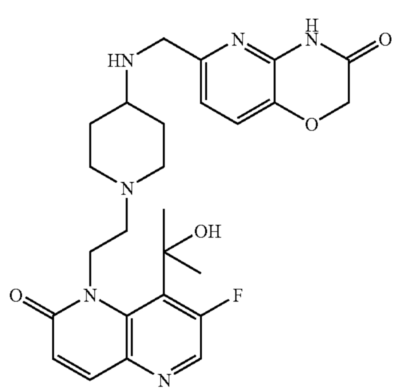 | [7-Fluoro-8-(1-hydroxy-1-methylethyl)-2-oxo-1,5-naphthyridin-1(2H)-yl]acetaldehyde (obtainable by the carbonylation of 8-bromo-7-fluoro-2-(methyloxy)-1,5-naphthyridine (WO2004058144, Example 53(g)) using Pd(OAc)$_2$, dppf and carbon monoxide gas (3 atm pressure) to give methyl 3-fluoro-6-(methyloxy)-1,5-naphthyridine-4-carboxylate. This is treated with methyl magnesium bromide to give 2-[3-fluoro-6-(methyloxy)-1,5-naphthyridin-4-yl]-2-propanol. This is treated HBr to give 7-fluoro-8-(1-hydroxy-1-methylethyl)-1,5-naphthyridin-2(1H)-one and then allyl-iodide and K$_2$CO$_3$ followed by heating with Pd(PPh$_3$)$_4$ in xylene to give 7-fluoro-8-(1-hydroxy-1-methylethyl)-1-(2-propen-1-yl)-1,5-naphthyridin-2(1H)-one. This is converted into the desired intermediate by the action of OsO$_4$ and NaIO$_4$). 1,1-Dimethylethyl 4-piperidinylcarbamate 3-Oxo-3,4-dihydro-2H-pyrido[3,2-b][1,4]oxazine-6-carboxaldehyde (WO2003087098, Example 31(e)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 184 | Tri-HCl<br>MS (ES+)<br>m/z 483<br>(MH+) | 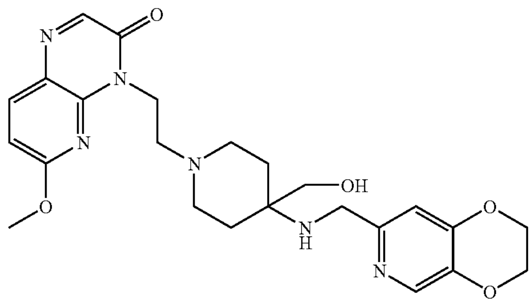 | 1-(1,1-Dimethylethyl) 4-methyl 4-amino-1,4-piperidinedicarboxylate (commercially available) was reacted with 2,3-dihydro[1,4]dioxino[2,3-c]pyridine-7-carboxaldehyde (WO2004058144, Example 2(c) or WO03/087098, Example 19(d)) to give 1-(1,1-dimethylethyl) 4-methyl 4-[(2,3-dihydro[1,4]dioxino[2,3-c]pyridin-7-ylmethyl)amino]-1,4-piperidinedicarboxylate. Deprotection with TFA gave methyl 4-[(2,3-dihydro[1,4]dioxino[2,3-c]pyridin-7-ylmethyl)amino]-4-piperidinecarboxylate. Subsequent reductive alkylation of methyl 4-[(2,3-dihydro[1,4]dioxino[2,3-c]pyridin-7-ylmethyl)amino]-4-piperidinecarboxylate with [6-(methyloxy)-3-oxopyrido[2,3-b]pyrazin-4(3H)-yl]acetaldehyde (Example 126(e)) gave methyl 4-[(2,3-dihydro[1,4]dioxino[2,3-c]pyridin-7-ylmethyl)amino]-1-{2-[6-(methyloxy)-3-oxopyrido[2,3-b]pyrazin-4(3H)-yl]ethyl}-4-piperidinecarboxylate. Reduction of the ester unit with NaBH$_4$ gave the product. |
| 185A and B | di-HCl (A) and benzoate (B)<br>MS (ES+)<br>m/z 469<br>(MH+) | 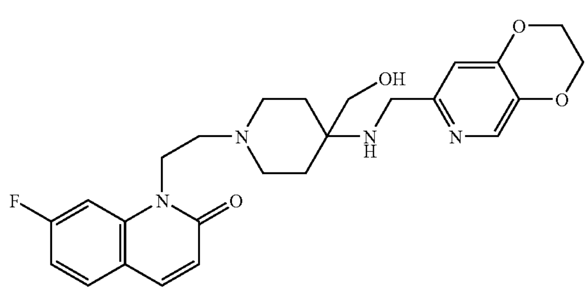 | (7-Fluoro-2-oxo-1(2H)-quinolinyl)acetaldehyde (Example 88(a))<br>Methyl 4-[(2,3-c]pyridin-7-ylmethyl)amino]-4-piperidinecarboxylate (Example 184)<br>Coupled by the general method of Example 184 |
| 186 | Free base<br>MS (ES+)<br>m/z 458<br>(MH+) | 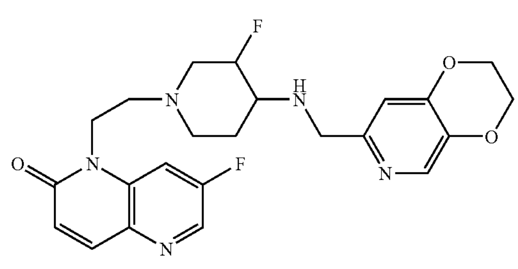 | [7-(Fluoro)-2-oxo-1,5-naphthyridin-1(2H)-yl]acetaldehyde (as the methyl hemiacetal) (Example 7(d))<br>Phenylmethyl [(cis)-3-fluoro-4-piperidinyl]carbamate (Enantiomer 1 WO2003064421 Example 6(b))<br>2,3-Dihydro[1,4]dioxino[2,3-c]pyridine-7-carboxaldehyde (WO2004058144, Example 2(c) or WO03/087098, Example 19(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 187 | mono-benzoate (ES+) m/z 470 (MH+) | 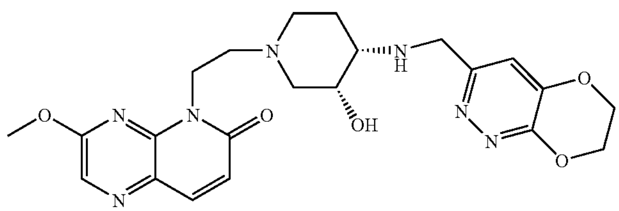 | [3-(Methyloxy)-6-oxopyrido[2,3-b]pyrazin-5(6H)-yl]acetaldehyde (Example 94(m)) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) 6,7-Dihydro[1,4]dioxino[2,3-c]pyridazine-3-carbaldehyde (Example 6(e)) |
| 188 | mono-HCl MS (ES+) m/z 435 (MH+) | 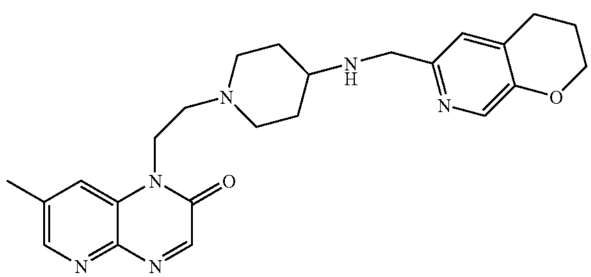 | (7-Methyl-2-oxopyrido[2,3-b]pyrazin-1(2H)-yl)acetaldehyde (obtainable by hydrogenation of 6-amino-5-nitro-picoline in the presence of 10% Pd/C paste to afford 5-methyl-2,3-pyridinediamine which is then reacted with glyoxylic acid monohydrate to afford 7-methylpyrido[2,3-b]pyrazin-2(1H)-one. This is alkylated with allyl iodide in DMF using potassium carbonate as base and the resulting 7-methyl-1-(2-propen-1-yl)pyrido[2,3-b]pyrazin-2(1H)-one is cleaved in presence of ozone to afford product) 1,1-Dimethylethyl 4-piperidinylcarbamate 3,4-Dihydro-2H-pyrano[2,3-c]pyridine-6-carbaldehyde (WO2004058144, Example 126(e)) |
| 189 | mono-HCl MS (ES+) m/z 437 (MH+) | 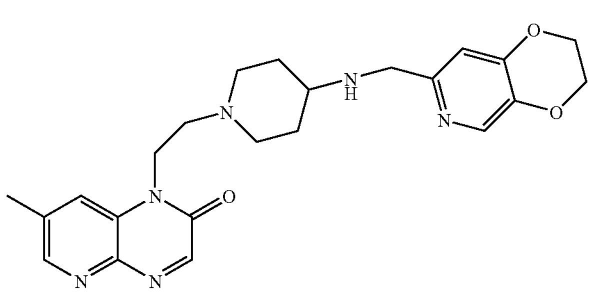 | (7-Methyl-2-oxopyrido[2,3-b]pyrazin-1(2H)-yl)acetaldehyde (Example 188) 1,1-Dimethylethyl 4-piperidinylcarbamate 2,3-Dihydro[1,4]dioxino[2,3-c]pyridine-7-carboxaldehyde (WO2004058144, Example 2(c) or WO03/087098, Example 19(d)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 190 | mono-HCl MS (ES+) m/z 482 (MH$^+$) | 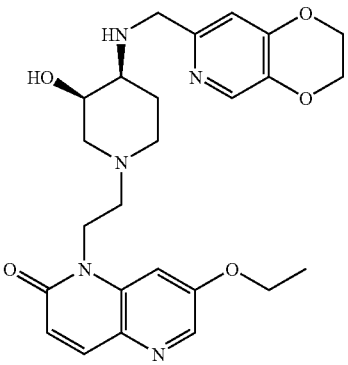 | 1-{2-[(3R,4S)-4-Amino-3-hydroxy-1-piperidinyl]ethyl}-7-fluoro-1,5-naphthyridin-2(1H)-one dihydrochloride (Example 41(b)) was treated with sodium ethoxide to form 1-{2-[(3R,4S)-4-amino-3-hydroxy-1-piperidinyl]ethyl}-7-(ethyloxy)-1,5-naphthyridin-2(1H)-one, which was then reductively alkyated with 2,3-dihydro[1,4]dioxino[2,3-c]pyridine-7-carboxaldehyde (WO2004058144, Example 2(c) or WO03/087098, Example 19(d)) by the general method of Example 4(c) |
| 191 | mono-HCl MS (ES+) m/z 484 (MH$^+$) | 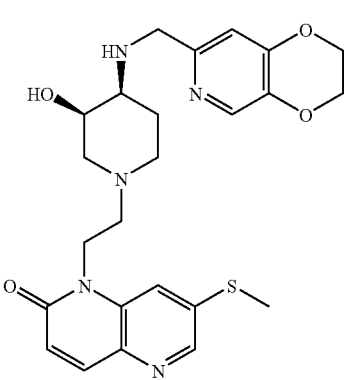 | 1-{2-[(3R,4S)-4-Amino-3-hydroxy-1-piperidinyl]ethyl}-7-fluoro-1,5-naphthyridin-2(1H)-one dihydrochloride (Example 41(b)) was treated with sodium thiomethoxide to form 1-{2-[(3R,4S)-4-amino-3-hydroxy-1-piperidinyl]ethyl}-7-(methylthio)-1,5-naphthyridin-2(1H)-one which was then reductively alklyated with 2,3-dihydro[1,4]dioxino[2,3-c]pyridine-7-carboxaldehyde (WO2004058144, Example 2(c) or WO03/087098, Example 19(d)) by the general method of Example 4(c) |
| 192 | tri-HCl MS (ES+) m/z 470 (MH$^+$) | 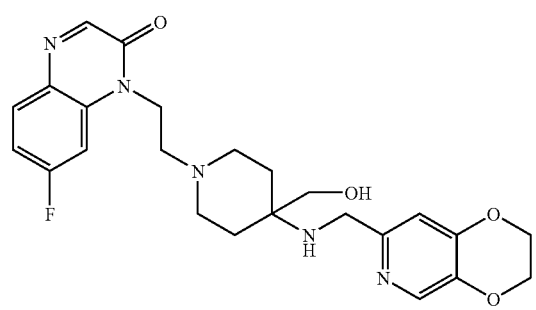 | 7-Fluoro-2-oxo-1(2H)-quinoxalinyl)acetaldehyde (Example 34(c)) Methyl 4-[(2,3-dihydro[1,4]dioxino[2,3-c]pyridin-7-ylmethyl)amino]-4-piperidinecarboxylate (Example 184) Coupled by the general method of Example 184 |
| 193 | mono-fumarate MS (ES+) m/z 457 (MH$^+$) | 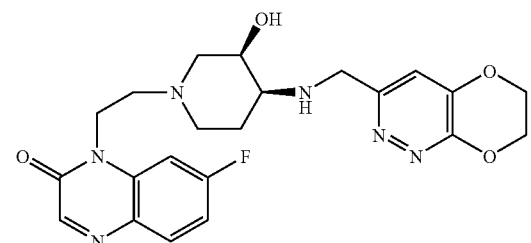 | 7-Fluoro-2-oxo-1(2H)-quinoxalinyl)acetaldehyde (Example 34(c)) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) 6,7-Dihydro[1,4]dioxino[2,3-c]pyridazine-3-carbaldehyde (Example 6(e)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 194 | Mono-HCl<br>MS (ES+)<br>m/z 441<br>(MH+) | 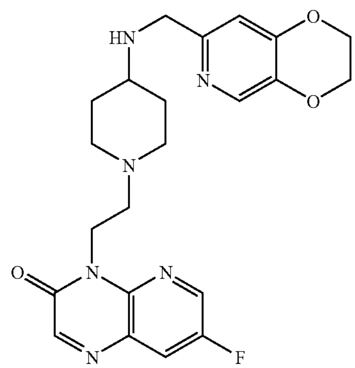 | (7-Fluoro-3-oxopyrido[2,3-b]pyrazin-4(3H)-yl)acetaldehyde (obtainable from 7-fluoropyrido[2,3-b]pyrazin-3(4H)-one, (a byproduct from Example 35(c)) by the general method of Example 35(d)-(e)<br>1,1-Dimethylethyl 4-piperidinylcarbamate<br>2,3-Dihydro[1,4]dioxino[2,3-c]pyridine-7-carboxaldehyde (WO2004058144, Example 2(c) or WO03/087098, Example 19(d)) |
| 195 | free base<br>MS (ES+)<br>m/z 458<br>(MH+) | 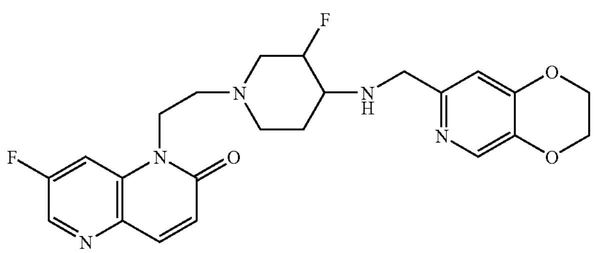 | [7-(Fluoro)-2-oxo-1,5-naphthyridin-1(2H)-yl]acetaldehyde (as the methyl hemiacetal) (Example 7(d))<br>Phenylmethyl [(cis)-3-fluoro-4-piperidinyl]carbamate (E1 isomer WO2003064421 example 6(b))<br>2,3-Dihydro[1,4]dioxino[2,3-c]pyridine-7-carboxaldehyde (WO2004058144, Example 2(c) or WO03/087098, Example 19(d)) |
| 196 | mono-trifluoroacetate<br>MS (ES+)<br>m/z 459<br>(MH+) | 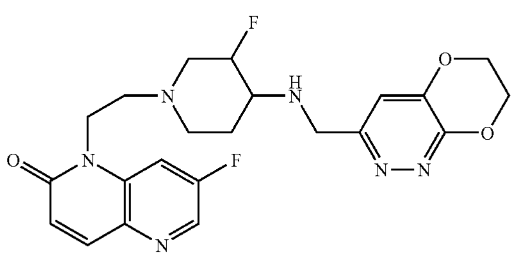 | [7-(Fluoro)-2-oxo-1,5-naphthyridin-1(2H)-yl]acetaldehyde (as the methyl hemiacetal) (Example 7(d))<br>Phenylmethyl [(cis)-3-fluoro-4-piperidinyl]carbamate (E1 isomer WO2003064421 example 6(b))<br>6,7-Dihydro[1,4]dioxino[2,3-c]pyridazine-3-carbaldehyde (Example 6(e)) |
| 197 | free base<br>MS (ES+)<br>m/z 459<br>(MH+) | 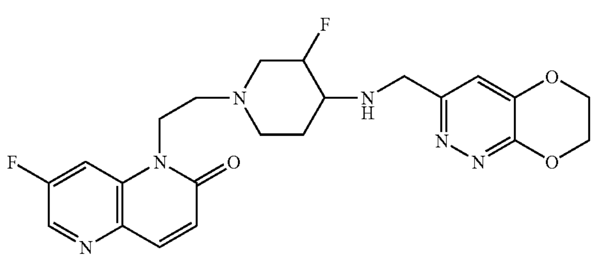 | 7-(fluoro)-2-oxo-1,5-naphthyridin-1(2H)-yl]acetaldehyde (as the methyl hemiacetal) (Example 7(d))<br>Phenylmethyl [(cis)-3-fluoro-4-piperidinyl]carbamate (E2 isomer obtainable from 1,1-dimethylethyl [(cis)-3-fluoro-4-benzylpiperidinyl]carbamate enantiomer 2 (WO2003064421 example 6(a)) by an analogous procedure to example 6(b)<br>6,7-Dihydro[1,4]dioxino[2,3-c]pyridazine-3-carbaldehyde (Example 6(e)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 198A and B | di-HCl (A) and benzoate (B) MS (ES+) m/z 467 (MH+) | 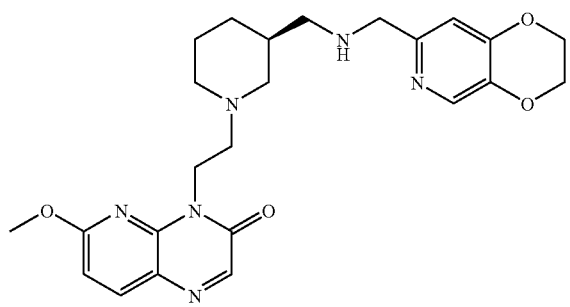 | [6-(Methyloxy)-3-oxopyrido[2,3-b]pyrazin-4(3H)-yl]acetaldehyde (Example 126(e)) Phenylmethyl [(3R)-3-piperidinylmethyl]carbamate 2,3-Dihydro[1,4]dioxino[2,3-c]pyridine-7-carboxaldehyde (WO2004058144, Example 2(c) or WO03/087098, Example 19(d)) |
| 199A and B | diHCl (A) and benzoate (B) MS (ES+) m/z 468 (MH+) | 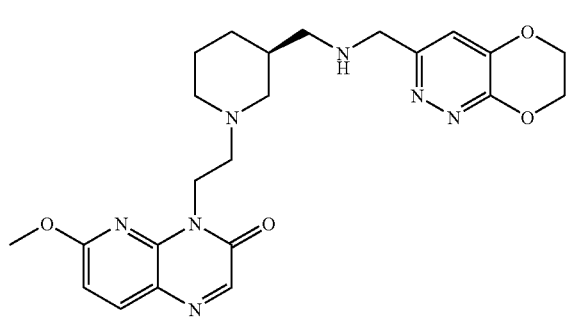 | [6-(Methyloxy)-3-oxopyrido[2,3-b]pyrazin-4(3H)-yl]acetaldehyde (Example 126(e)) Phenylmethyl [(3R)-3-piperidinylmethyl]carbamate 6,7-Dihydro[1,4]dioxino[2,3-c]pyridazine-3-carbaldehyde (Example 6(e)) |
| 200A and B | di-HCl (A) and benzoate (B) MS (ES+) m/z 468 (MH+) | 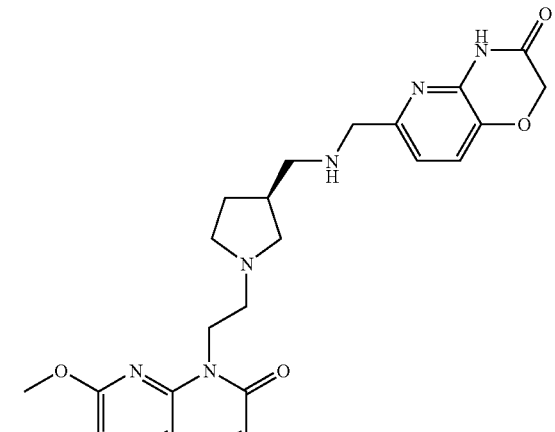 | [6-(Methloxy)-3-oxopyrido[2,3-b]pyrazin-4(3H)-yl]acetaldehyde (Example 126(e)) Phenylmethyl [(3R)-3-pyrrolidinylmethyl]carbamate (WO2006002047 Preparation 23(b)) 3-Oxo-3,4-dihydro-2H-pyrido[3,2-b][1,4]oxazine-6-carboxaldehyde (WO2003087098, Example 31(e)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 201 | Free base<br>MS (ES+)<br>m/z<br>500/502<br>(MH+) | 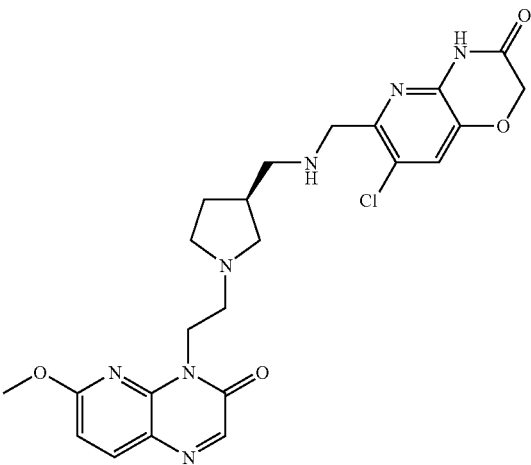 | [(6-(Methyloxy)-3-oxopyrido[2,3-b]pyrazin-4(3H)-yl]acetaldehyde (Example 126(e))<br>Phenylmethyl [(3R)-3-pyrrolidinylmethyl]carbamate (WO2006002047 Preparation 23(b))<br>7-Chloro-3-oxo-3,4-dihydro-2H-pyrido[3,2-b][1,4]oxazine-6-carbaldehyde (WO2003064421, Example 15(c)) |
| 202 | di-HCl<br>MS (ES+)<br>m/z 482<br>(MH+) | 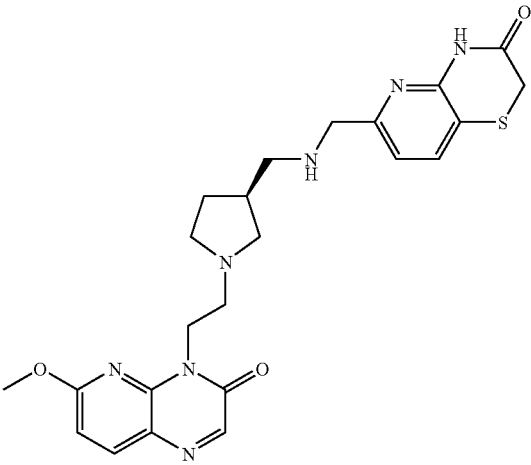 | [6-(Methyloxy)-3-oxopyrido[2,3-b]pyrazin-4(3H)-yl]acetaldehyde (Example 126(e))<br>Phenylmethyl [(3R)-3-pyrrolidinylmethyl]carbamate (WO2006002047 Preparation 23(b))<br>3-Oxo-3,4-dihydro-2H-pyrido[3,2-b][1,4]thiazine-6-carboxaldehyde (WO2004058144, Example 7(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 203 | Free base MS (ES+) m/z 482 (MH+) | 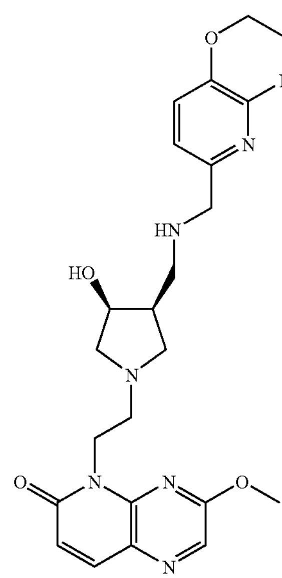 | [3-(Methyloxy)-6-oxopyrido[2,3-b]pyrazin-5(6H)-yl]acetaldehyde (Example 126(e)) Phenylmethyl {[(3R,4S)-4-hydroxy-3-pyrrolidinyl]methyl}carbamate 3-Oxo-3,4-dihydro-2H-pyrido[3,2-b][1,4]oxazine-6-carboxaldehyde (WO2003087098, Example 31(e)) |
| 204 | di-HCl MS (ES+) m/z 453 (MH+) | 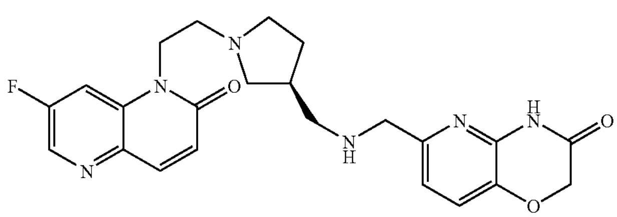 | [7-(Fluoro-2-oxo-1,5-naphthyridin-1(2H)-yl]acetaldehyde (as the methyl hemiacetal (Example 7(d)) Phenylmethyl [(3R)-3-pyrrolidinylmethyl]carbamate (WO20060020047 Preparation 23(b)) 3-Oxo-3,4-dihydro-2H-pyrido[3,2-b][1,4]oxazine-6-carboxaldehyde (WO2003087098, Example 31(e)) |
| 205 | di-HCl MS (ES+) m/z 481 (MH+) | 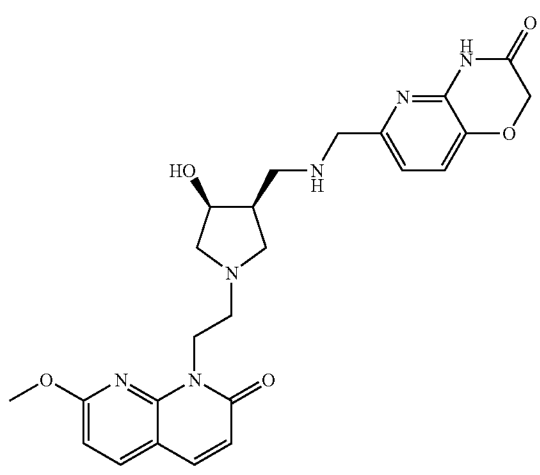 | [7-(methyloxy)-2-oxo-1,8-naphthyridin-1(2H)-yl]acetaldehyde (obtainable by treatment of 7-(methyloxy)-1-(2-propen-1-yl)-1,8-naphthyridin-2(1H)-one with OsO4/NaIO4 as in Example 17(a)) Phenylmethyl {[(3R,4S)-4-hydroxy-3-pyrrolidinyl]methyl}carbamate 3-Oxo-3,4-dihydro-2H-pyrido[3,2-b][1,4]oxazine-6-carboxaldehyde (WO2003087098, Example 31(e)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 206 | Free base<br>MS (ES+)<br>m/z<br>486/488<br>(MH+) | 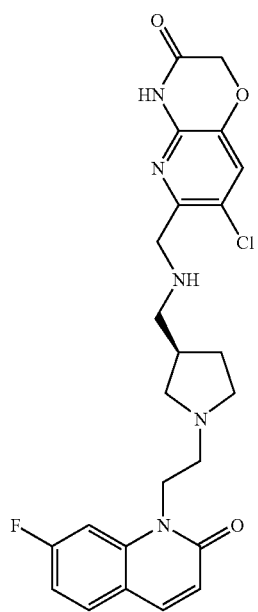 | (7-Fluoro-2-oxo-1(2H)-quinolinyl)acetaldehyde (Example 88(a))<br>Phenylmethyl [(3S)-3-pyrrolidinylmethyl]carbamate (WO2006002047 Preparation 23(b))<br>7-Chloro-3-oxo-3,4-dihydro-2H-pyrido[3,2-b][1,4]oxazine-6-carboxaldehyde (WO2003064421,Example 15(c)) |
| 207 | di-HCl<br>MS (ES+)<br>m/z 469<br>(MH+) | 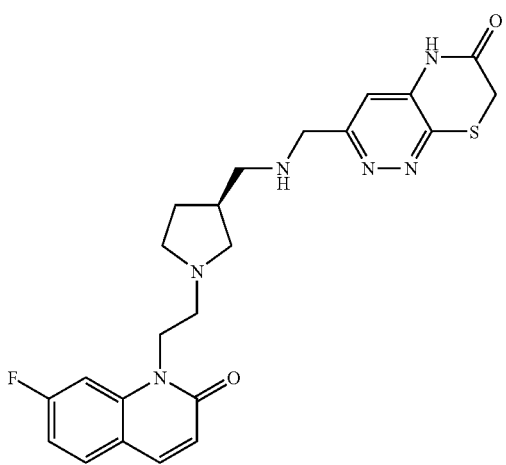 | (7-Fluoro-2-oxo-1(2H)-quinolinyl)acetaldehyde (Example 88(a))<br>Phenylmethyl ](3R)-3-pyrrolidinylmethyl]carbamate (may be prepared analogously to WO2006002047 Preparation 23(b))<br>6-Oxo-6,7-dihydro-5H-pyridazino[3,4-b][1,4]thiazine-3-carboxaldehyde (WO2003087098 Example 312(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 208 | di-HCl<br>MS (ES+)<br>m/z 469<br>(MH$^+$) | 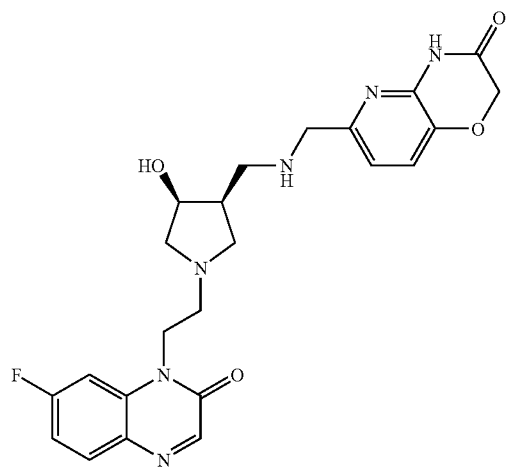 | 7-Fluoro-2-oxo-1(2H)-quinoxalinyl)acetaldehyde (Example 34(c))<br>Phenylmethyl {[(3R,4S)-4-hydroxy-3-pyrrolidinyl]methyl}carbamate<br>3-Oxo-3,4-dihydro-2H-pyrido[3,2-b][1,4]oxazine-6-carboxaldehyde (WO2003087098, Example 31(e)) |
| 209 | di-HCl<br>MS (ES+)<br>m/z 482<br>(MH$^+$) | 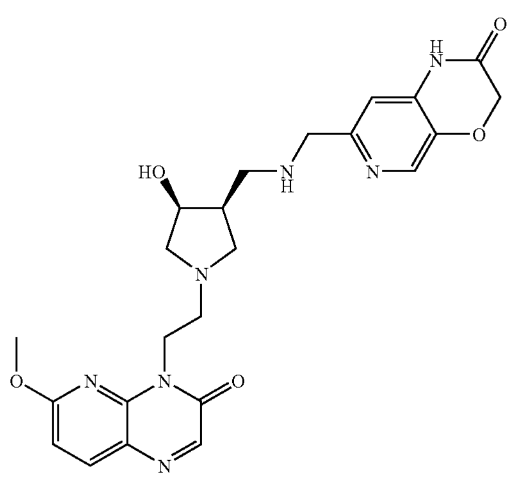 | [(6-(Methyloxy)-3-oxopyrido[2,3-b]pyrazin-4(3H)-yl]acetaldehyde (Example 126(e))<br>Phenylmethyl {[(3R,4S)-4-hydroxy-3-pyrrolidinyl]methyl}carbamate<br>2-Oxo-2,3-dihydro-1H-pyrido[3,4-b][1,4]oxazine-7-carboxaldehyde (WO2004002992, Example 22(i)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 210 | Free base MS (ES+) m/z 468 (MH+) | 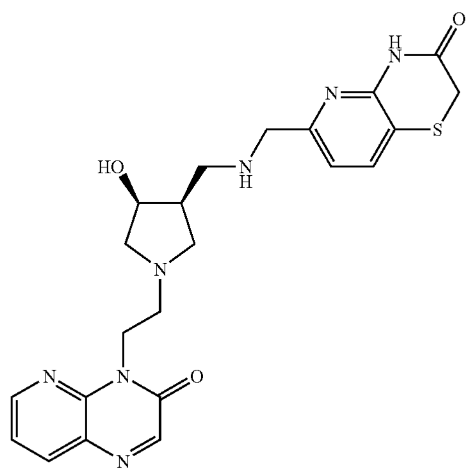 | 3-Oxopyrido[2,3-b]pyrazin-4(3H)acetaldehyde (obtainable from 2-chloro-3-nitropyridine by treatment with (a) amino acetaldehyde dimethyl acetal, potassium carbonate to form N-[2,2-bis(methyloxy)ethyl]-3-nitro-2-pyridinamine. (b) reduction of N-[2,2-bis(methyloxy)ethyl]-3-nitro-2-pyridinamine by catalytic hydrogenation to give $N^2$-[2,2-bis(methyloxy)ethyl]-3-nitro-2-pyridinamine. (c) alkylation of $N^2$-[2,2-bis(methyloxy)ethyl]-3-nitro-2-pyridinediamine with ethyl bromoacetate, potassium carbonate to give ethyl N-(2-{[2,2-bis(methyloxy)ethyl]amino}-3-pyridinyl)glycinate. (d) treatment of ethyl N-(2-{[2,2-bis(methyloxy)ethyl]amino}-3-pyridinyl)glycinate with potassium carbonate at 110°, followed by oxidation with manganese dioxide). Phenylmethyl {[(3R,4S)-4-hydroxy-3-pyrrolidinyl]methyl}carbamate 3-Oxo-3,4-dihydro-2H-pyrido[3,2-b][1,4]thiazine-6-carboxaldehyde (WO2004058144, Example 7(d) |
| 211 | free base MS (ES+) m/z 498 (MH+) | 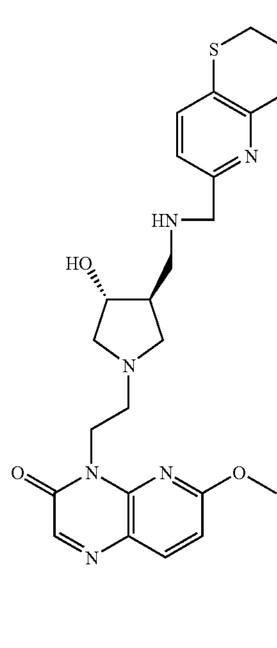 | [6-(Methyloxy)-3-oxopyrido[2,3-b]pyrazin-4(3H)-yl]acetaldehyde (Example 126(e)) Phenylmethyl {[(3R,4R)-4-hydroxy-3-pyrrolidinyl]methyl}carbamate (see Example 215) 3-Oxo-3,4-dihydro-2H-pyrido[3,2-b][1,4]thiazine-6-carboxaldehyde (WO2004058144, Example 7(d) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 212 | mono-HCl<br>MS (ES+)<br>m/z 481<br>(MH+) | 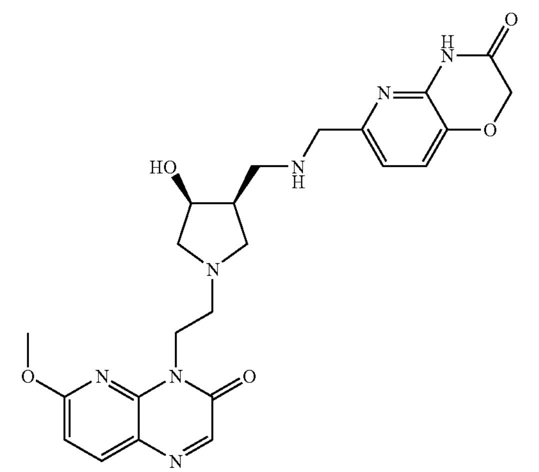 | [7-(Methyloxy)-2-oxo-1(2H)-quinoxalinyl]acetaldehyde (Preparation C)<br>Phenylmethyl {[(3R,4S)-4-hydroxy-3-pyrrolidinyl]methyl}carbamate<br>3-Oxo-3,4-dihydro-2H-pyrido[3,2-b][1,4]oxazine-6-carboxaldehyde (WO2003087098, Example 31(e)) |
| 213 | Free base<br>MS (ES+)<br>m/z 481<br>(MH+) | 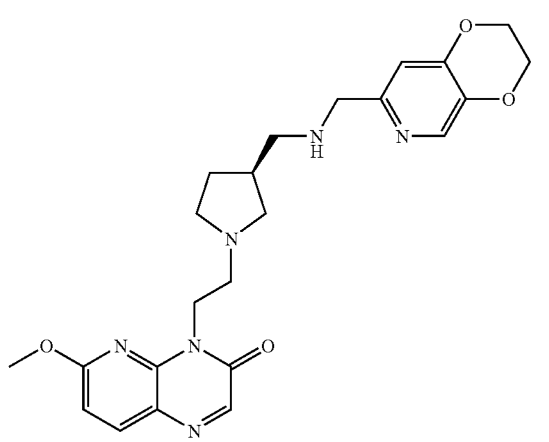 | [6-(Methyloxy)-3-oxopyrido[2,3-b]pyrazin-4(3H)-yl]acetaldehyde (Example 126(e))<br>Phenylmethyl [(3R)-3-pyrrolidinylmethyl]carbamate (may be prepared analogously to WO2006002047 Preparation 23(b))<br>2,3-Dihydro[1,4]dioxino[2,3-c]pyridine-7-carboxaldehyde (WO2004058144, Example Example 19(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 214 | Free base MS (ES+) m/z 468 (MH+) | 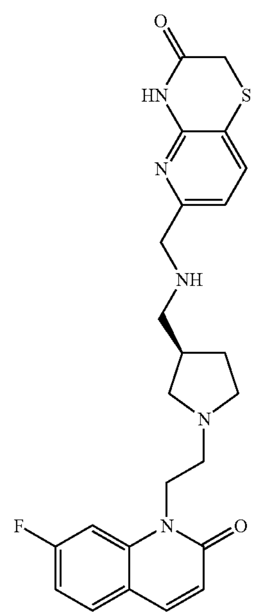 | (7-Fluoro-2-oxo-1(2H)-quinolinyl)acetaldehyde (Example 88(a)) Phenylmethyl [(3S)-3-pyrrolidinylmethyl]carbamate (WO2006002047 Preparation 23(b)) 3-Oxo-3,4-dihydro-2H-pyrido[3,2-b][1,4]thiazine-6-carboxaldehyde (WO2004058144, Example 7(d)) |
| 215 | Free base MS (ES+) m/z 484 (MH+) | 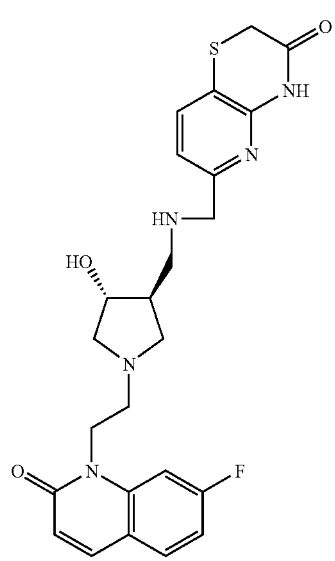 | (7-Fluoro-2-oxo-1(2H)-quinolinyl)acetaldehyde (Example 88(a)) Phenylmethyl {[(3R,4R)-4-hydroxy-3-pyrrolidinyl]methyl}carbamate (obtained from 1,1-dimethylethyl (3S,4S)-3-hydroxy-4-[({[(phenylmethyl)oxy]carbonyl}amino)methyl]-1-pyrrolidinecarboxylate (WO20062047 Preparation 24(c) E1) by Mitsunobu alcohol inversion and then acid deprotection). 3-Oxo-3,4-dihydro-2H-pyrido[3,2-b][1,4]thiazine-6-carboxaldehyde (WO2004058144, Example 7(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 216 | di-HCl<br>MS (ES+)<br>m/z 452<br>(MH+) | 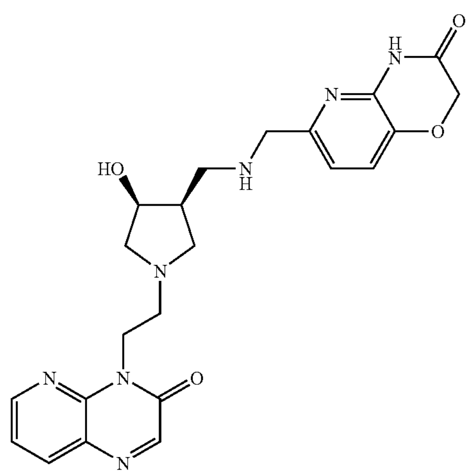 | 3-Oxopyrido[2,3-b]pyrazin-4(3H)acetaldehyde (Example 210)<br>Phenylmethyl {[(3R,4S)-4-hydroxy-3-pyrrolidinyl]methyl}carbamate<br>3-Oxo-3,4-dihydro-2H-pyrido[3,2-b][1,4]oxazine-6-carboxaldehyde (WO2003087098, Example 31(e)) |
| 217 | Free base<br>MS (ES+)<br>m/z 482<br>(MH+) | 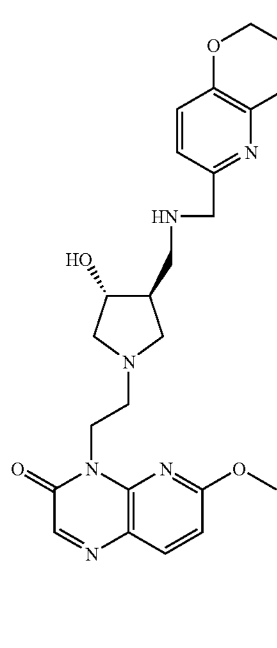 | [6-(Methyloxy)-3-oxopyrido[2,3-b]pyrazin-4(3H)-yl]acetaldehyde (Example 126(e))<br>Phenylmethyl {[(3R,4R)-4-hydroxy-3-pyrrolidinyl]methyl}carbamate (see Example 215)<br>3-Oxo-3,4-dihydro-2H-pyrido[3,2-b][1,4]oxazine-6-carboxaldehyde (WO2003087098, Example 31(e)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 218 | Mono-HCl<br>MS (ES+)<br>m/z 497<br>(MH+) | 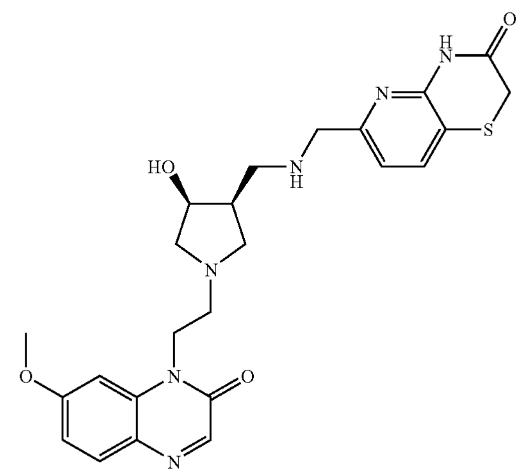 | [7-(Methyloxy)-2-oxo-1(2H)-quinoxalinyl]acetaldehyde (Preparation C)<br>Phenylmethyl {[(3R,4S)-4-hydroxy-3-pyrrolidinyl]methyl}carbamate<br>3-Oxo-3,4-dihydro-2H-pyrido[3,2-b][1,4]thiazine-6-carboxaldehyde (WO2004058144, Example 7(d) |
| 219 | di-HCl<br>MS (ES+)<br>m/z 468<br>(MH+) | 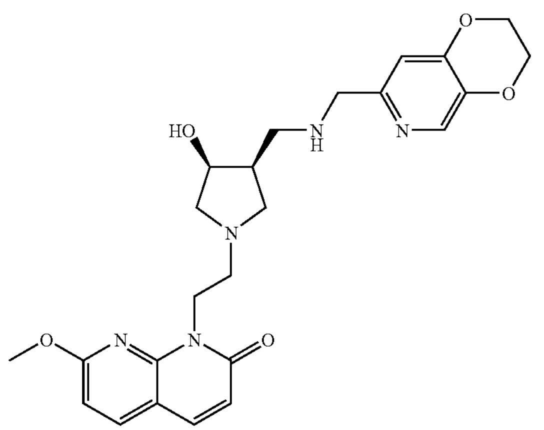 | [7-(methyloxy)-2-oxo-1,8-naphthyridin-1(2H)-yl]acetaldehyde (obtainable by treatment of 7-(methyloxy)-1-(2-propen-1-yl)-1,8-naphthyridin-2(1H)-one with OsO$_4$/NaIO$_4$ as in Example 17(a) to give intermediate aldehyde)<br>Phenylmethyl {[(3R,4S)-4-hydroxy-3-pyrrolidinyl]methyl}carbamate<br>2,3-Dihydro[1,4]dioxino[2,3-c]pyridine-7-carboxaldehyde (WO2004058144, Example 2(c) or WO03/087098, Example 19(d)) |
| 220A and B | Free base (A) and mono-HCl (B)<br>MS (ES+)<br>m/z 469<br>(MH+) | 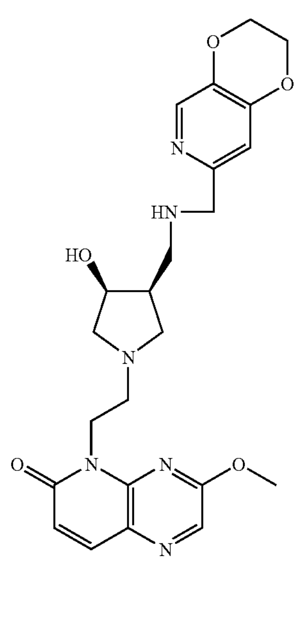 | [3-(Methyloxy)-6-oxopyrido[2,3-b]pyrazin-5(6H)-yl]acetaldehyde (Example 126(e))<br>Phenylmethyl {[(3R,4S)-4-hydroxy-3-pyrrolidinyl]methyl}carbamate<br>2,3-Dihydro[1,4]dioxino[2,3-c]pyridine-7-carboxaldehyde (WO2004058144, Example 2(c) or WO03/087098, Example 19(d)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 221 | Free base MS (ES+) m/z 468 (MH⁺) | 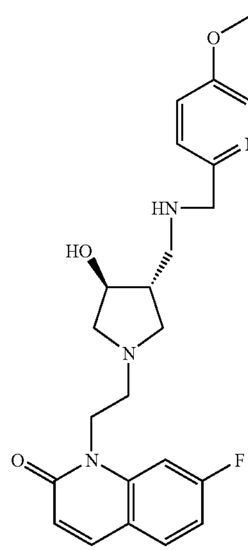 | (7-Fluoro-2-oxo-1(2H)-quinolinyl)acetaldehyde (Example 88(a)) Phenylmethyl {[(3S,4S)-4-hydroxy-3-pyrrolidinyl]methyl}carbamate (obtained from 1,1-dimethylethyl (3R,4R)-3-hydroxy-4-[({[(phenylmethyl)oxy]carbonyl}amino)methyl]-1-pyrrolidinecarboxylate (WO2006002047 Preparation 24(c) E2) by Mitsunobu alcohol inversion and then acid deprotection) 3-Oxo-3,4-dihydro-2H-pyrido[3,2-b][1,4]oxazine-6-carboxaldehyde (WO2003087098, Example 31(e)) |
| 222 | di-HCl MS (ES+) m/z 468 (MH⁺) | 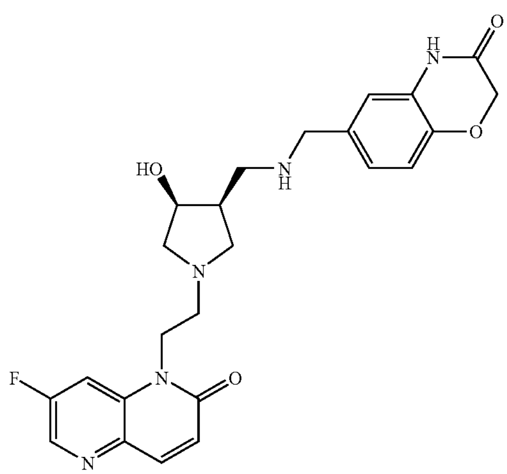 | [7-(Fluoro)-2-oxo-1,5-naphthyridin-1(2H)-yl]acetaldehyde (as the methyl hemiacetal) (Example 7(d)) Phenylmethyl {[(3R,4S)-4-hydroxy-3-pyrrolidinyl]methyl}carbamate 3-Oxo-3,4-dihydro-2H-benzo[1,4]oxazine-6-carboxaldehyde (WO2002056882, Example 5(b)) |
| 223A and B | di-trifluoroacetate (A) and di-HCl (B) MS (ES+) m/z 456 (MH⁺) | 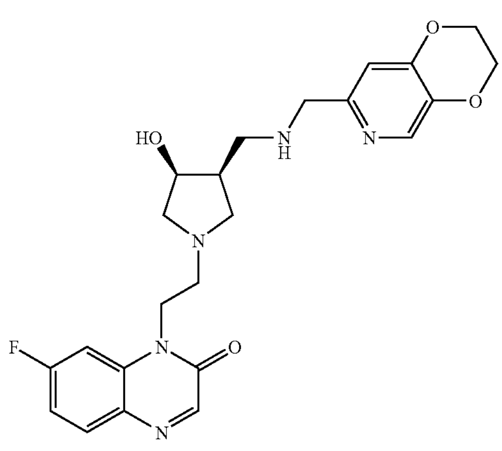 | 7-Fluoro-2-oxo-1(2H)-quinoxalinyl)acetaldehyde (Example 34(c)) Phenylmethyl {[(3R,4S)-4-hydroxy-3-pyrrolidinyl]methyl}carbamate 2,3-Dihydro[1,4]dioxino[2,3-c]pyridine-7-carboxaldehyde (WO2004058144, Example 2(c) or WO03/087098, Example 19(d)) |

US 8,071,592 B2

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 224 | di-HCl MS (ES+) m/z 478 (MH+) | 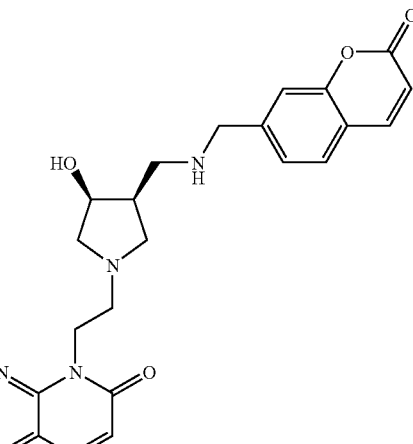 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 2-Oxo-2H-chromene-7-carbaldehyde (obtainable by heating 7-methyl-2H-chromen-2-one and SeO₂ in 1,4-dioxane at 200° C. in microwave) |
| 225 | Free base MS (ES+) m/z 469 (MH+) | 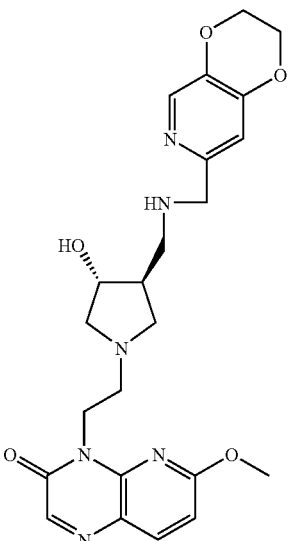 | [6-(Methyloxy)-3-oxopyrido[2,3-b]pyrazin-4(3H)-yl]acetaldehyde (Example 126(e)) Phenylmethyl {[(3R,4R)-4-hydroxy-3-pyrrolidinyl]methyl}carbamate (see Example 215) 2,3-Dihydro[1,4]dioxino[2,3-c]pyridine-7-carboxaldehyde (WO2004058144, Example 2(c) or WO03/087098, Example 19(d)) |
| 226 | Mono-HCl MS (ES+) m/z 468 (MH+) | 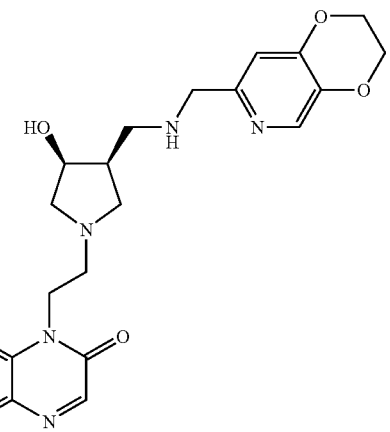 | [7-(Methyloxy)-2-oxo-1(2H)-quinoxalinyl]acetaldehyde (Preparation C) Phenylmethyl {[(3R,4S)-4-hydroxy-3-pyrrolidinyl]methyl}carbamate 2,3-Dihydro[1,4]dioxino[2,3-c]pyridine-7-carboxaldehyde (WO2004058144, Example 2(c) or WO03/087098, Example 19(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 227 | diHCl<br>MS (ES+)<br>m/z 470<br>(MH+) | 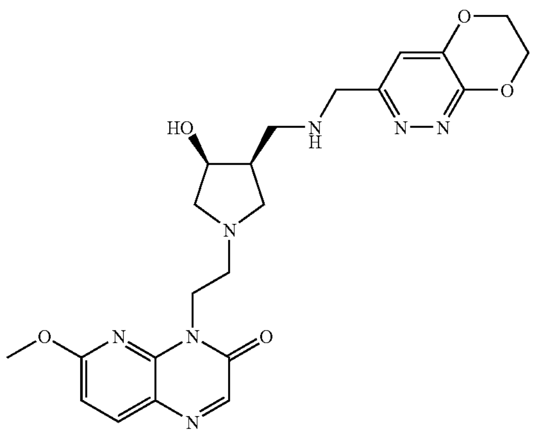 | [6-(Methyloxy)-3-oxopyrido[2,3-b]pyrazin-4(3H)-yl]acetaldehyde (Example 126(e))<br>Phenylmethyl {[(3R,4S)-4-hydroxy-3-pyrrolidinyl]methyl}carbamate<br>6,7-Dihydro[1,4]dioxino[2,3-c]pyridazine-3-carbaldehyde (Example 6(e)) |
| 228 | di-HCl<br>MS (ES+)<br>m/z 469<br>(MH+) | 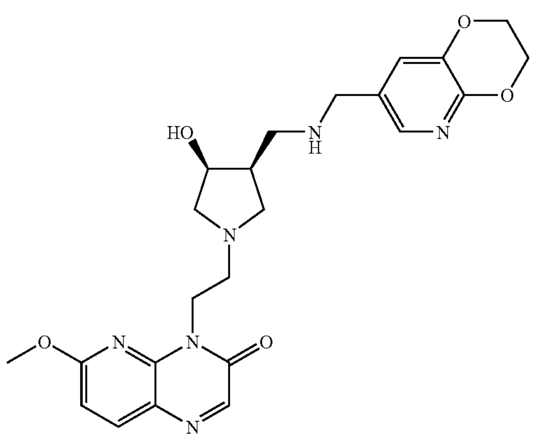 | [6-(Methyloxy)-3-oxopyrido[2,3-b]pyrazin-4(3H)-yl]acetaldehyde (Example 126(e))<br>Phenylmethyl {[(3R,4S)-4-hydroxy-3-pyrrolidinyl]methyl}carbamate<br>2,3-dihydro[1,4]dioxino[2,3-b]pyridine-7-carboxaldehyde (WO2056882 Example 40(e)) |
| 229 | di-HCl<br>MS (ES+)<br>m/z 454<br>(MH+) | 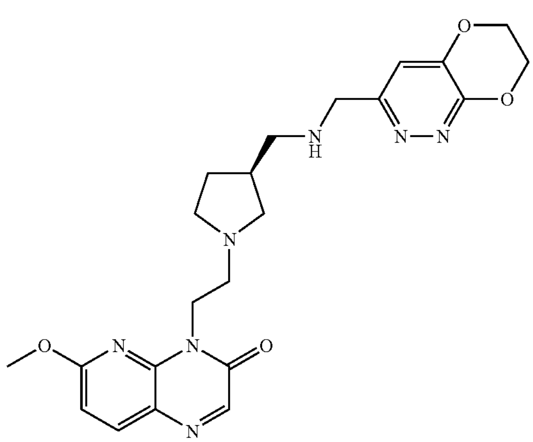 | [6-(Methyloxy)-3-oxopyrido[2,3-b]pyrazin-4(3H)-yl]acetaldehyde (Example 126(e))<br>Phenylmethyl [(3R)-3-pyrrolidinyl]carbamate (may be prepared analogously to WO2006002047 Preparation 23(b))<br>6,7-Dihydro[1,4]dioxino[2,3-c]pyridazine-3-carbaldehyde (Example 6(e)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 230 | di-trifluoroacetate MS (ES+) m/z 499 (MH+) | 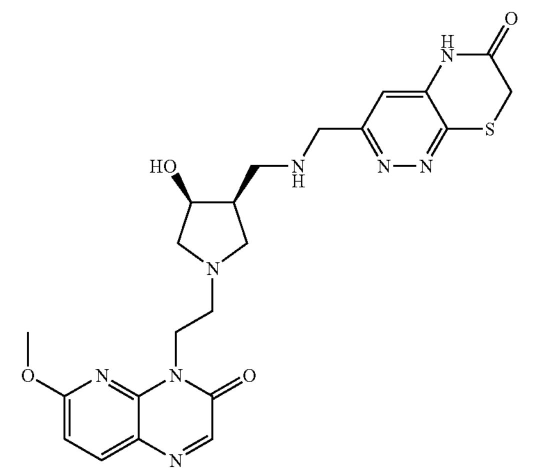 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 6-Oxo-6,7-dihydro-5H-pyridazino[3,4-b][1,4]thiazine-3-carbaldehyde (WO 2004/058144 Example 58(d)) |
| 231 | di-trifluoroacetate salt MS (ES+) m/z 478 (MH+) | 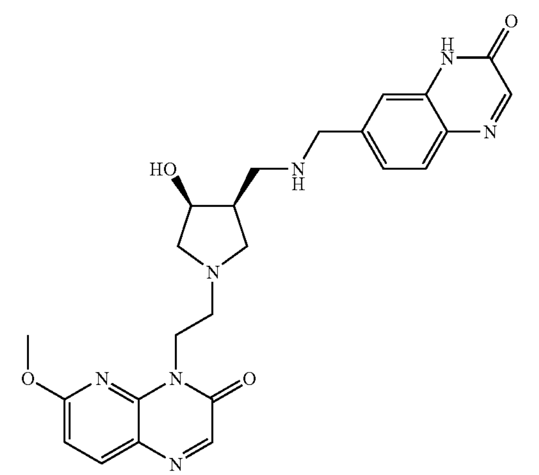 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 3-oxo-3,4-dihydro-6-quinoxalinecarbaldehyde (WO2006132739 Example 2(b)) |
| 232 | Mono-HCl MS (ES+) m/z 451 (MH+) | 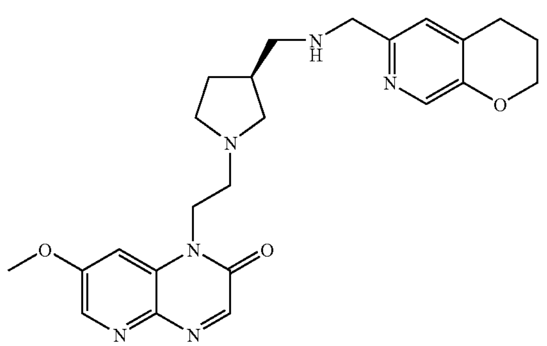 | [7-(Methyloxy)-2-oxopyrido[2,3-b]pyrazin-1(2H)-yl]acetaldehyde (as the methyl hemiacetal) (Example 51A(b)) 1,1-Dimethylethyl [(3R)-3-c]pyridine-6-carbaldehyde (WO2004058144, Example 126(e)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 233 | Free base<br>MS (ES+)<br>m/z 455<br>(MH+) | 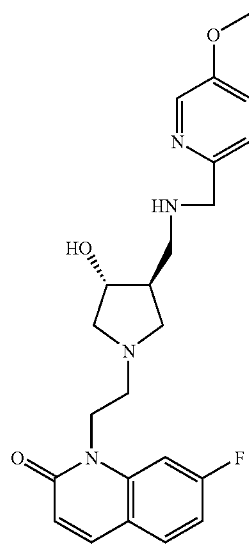 | (7-Fluoro-2-oxo-1(2H)-quinolinyl)acetaldehyde (Example 88(a))<br>Phenylmethyl {[(3R,4R)-4-hydroxy-3-pyrrolidinyl]methyl}carbamate (see Example 215)<br>2,3-Dihydro[1,4]dioxino[2,3-c]pyridine-7-carboxaldehyde (WO2004058144, Example 2(c) or WO03/087098, Example 19(d)) |
| 234 | Mono-HCl<br>MS (ES+)<br>m/z 455<br>(MH+) | 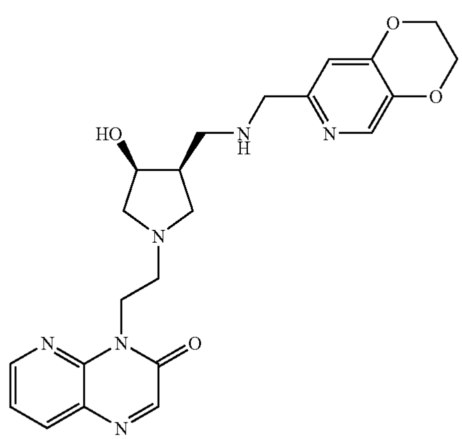 | 3-Oxopyrido[2,3-b]pyrazin-4(3H)acetaldehyde (Example 210)<br>Phenylmethyl {[(3R,4S)-4-hydroxy-3-pyrrolidinyl]methyl}carbamate<br>2,3-Dihydro[1,4]dioxino[2,3-c]pyridine-7-carboxaldehyde (WO2004058144, Example 2(c) or WO03/087098, Example 19(d)) |
| 235 | Mono-HCl<br>MS (ES+)<br>m/z 451<br>(MH+) | 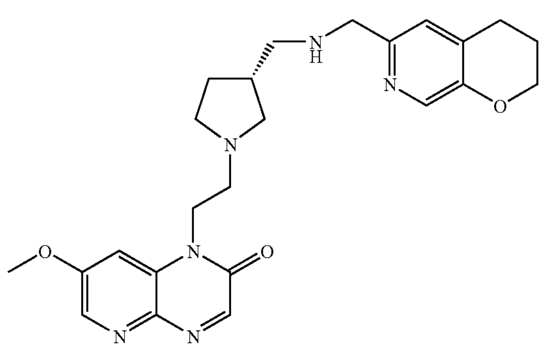 | [7-(Methyloxy)-2-oxopyrido[2,3-b]pyrazin-1(2H)-yl]acetaldehyde (as the methyl hemiacetal) (Example 51A(b))<br>1,1-Dimethylethyl [(3S)-3-pyrrolidinylmethyl]carbamate<br>3,4-Dihydro-2H-pyrano[2,3-c]pyridine-6-carbaldehyde (WO2004058144, Example 126(e)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 236 | ditrifluoro acetate MS (ES+) m/z 479 (MH+) | 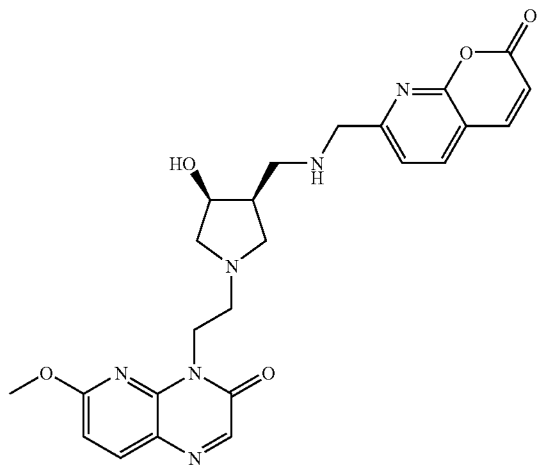 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 2-Oxo-2H-pyrano[2,3-b]pyridine-7-carbaldehyde (Preparation E) |
| 237 | Free base MS (ES+) m/z 482 (MH+) | 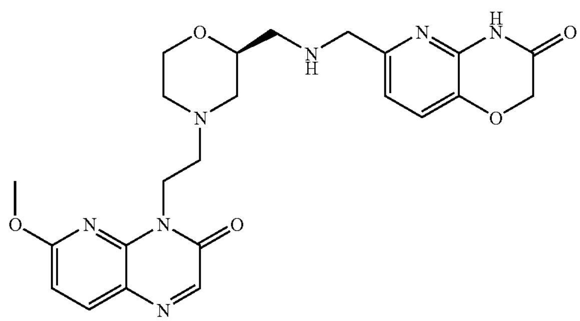 | [6-(Methyloxy)-3-oxopyrido[2,3-b]pyrazin-4(3H)-yl]acetaldehyde (Example 126(e)) 1,1-Dimethylethyl [(2R)-2-morpholinyl-methyl]carbamate 3-Oxo-3,4-dihydro-2H-pyrido[3,2-b][1,4]oxazine-6-carboxaldehyde (WO2003087098, Example 31(e)) |
| 238 | Free base MS (ES+) m/z 468 (MH+) | 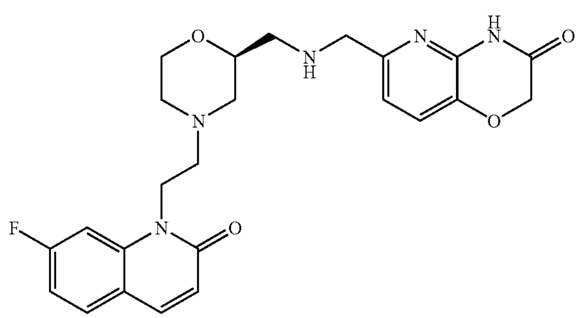 | (7-Fluoro-2-oxo-1(2H)-quinolinyl)acetaldehyde (Example 88(a)) 1,1-Dimethylethyl [(2R)-2-morpholinyl-methyl]carbamate 3-Oxo-3,4-dihydro-2H-pyrido[3,2-b][1,4]oxazine-6-carboxaldehyde (WO2003087098, Example 31(e)) |
| 239 | Free base MS (ES+) m/z 502/504 (MH+) | 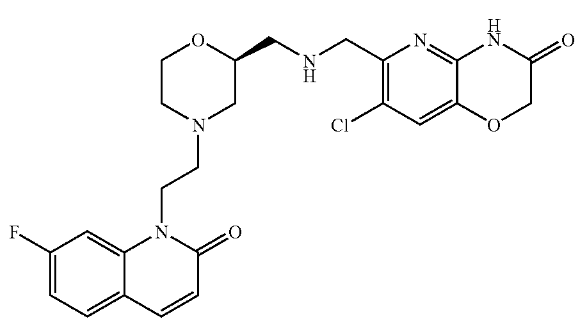 | (7-Fluoro-2-oxo-1(2H)-quinolinyl)acetaldehyde (Example 88(a)) 1,1-Dimethylethyl [(2R)-2-morpholinyl-methyl]carbamate 7-Chloro-3-oxo-3,4-dihydro-2H-pyrido[3,2-b][1,4]oxazine-6-carboxaldehyde (WO2003064421, Example 15(c)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 240A, B and C | Free base (A), mono-HCl (B) and benzoate (C) MS (ES+) m/z 484 (MH+) | 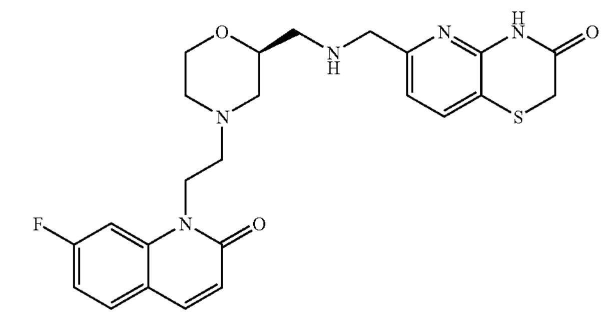 | (7-Fluoro-2-oxo-1(2H)-quinolinyl)acetaldehyde (Example 88(a)) 1,1-Dimethylethyl [(2R)-2-morpholinyl-methyl]carbamate 3-Oxo-3,4-dihydro-2H-pyrido[3,2-b][1,4]thiazine-6-carboxaldehyde (WO2004058144, Example 7(d)) |
| 241 | Free base MS (ES+) m/z 496 (MH+) | 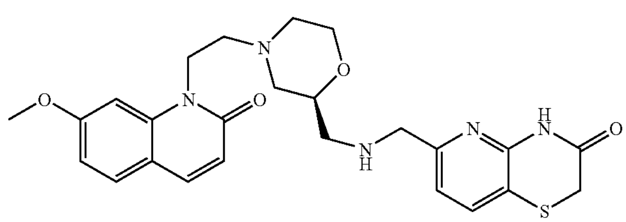 | [7-(Methyloxy)-2-oxo-1(2H)-quinolinyl]acetaldehyde (Exampole 1(d)) 1,1-Dimethylethyl [(2R)-2-morpholinyl-methyl]carbamate 3-Oxo-3,4-dihydro-2H-pyrido[3,2-b][1,4]thiazine-6-carboxaldehyde (WO2004058144, Example 7(d)) |
| 242 | Free base MS (ES+) m/z 480 (MH+) | 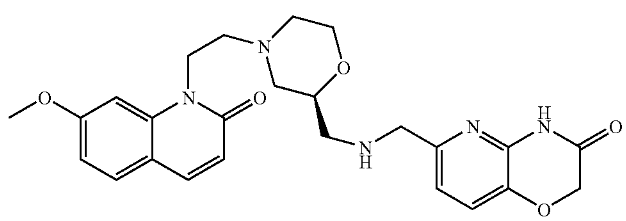 | [7-(Methyloxy)-2-oxo-1(2H)-quinolinyl]acetaldehyde (Example 1(d)) 1,1-Dimethylethyl [(2R)-2-morpholinyl-methyl]carbamate 3-Oxo-3,4-dihydro-2H-pyrido[3,2-b][1,4]oxazine-6-carboxaldehyde (WO2003087098, Example 31(e)) |
| 243 | Free base MS (ES+) m/z 484 (MH+) | 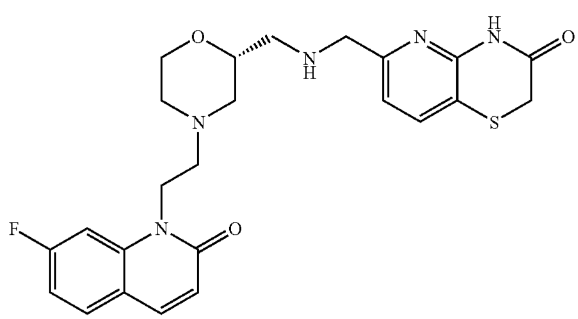 | (7-Fluoro-2-oxo-1(2H)-quinolinyl)acetaldehyde (Example 88(a)) 1,1-Dimethylethyl [(2S)-2-morpholinyl-methyl]carbamate 3-Oxo-3,4-dihydro-2H-pyrido[3,2-b][1,4]thiazine-6-carboxaldehyde (WO2004058144, Example 7(d)) |
| 244 | Mono-HCl MS (ES+) m/z 469 (MH+) | 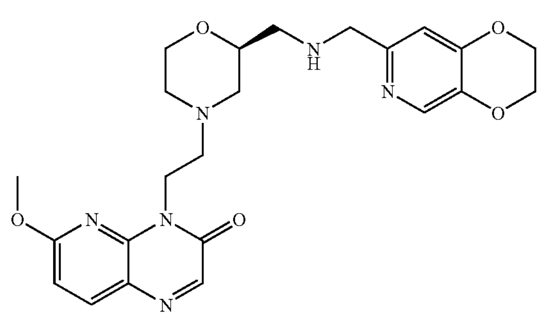 | [6-(Methyloxy)-3-oxopyrido[2,3-b]pyrazin-4(3H)-yl]acetaldehyde (Example 126(e)) 1,1-Dimethylethyl [(2R)-2-morpholinyl-methyl]carbamate 2,3-Dihydro[1,4]dioxino[2,3-c]pyridine-7-carboxaldehyde (WO2004058144, Example 2(c) or WO03/087098, Example 19(d)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 245 | Mono-HCl MS (ES+) m/z 455 (MH$^+$) | 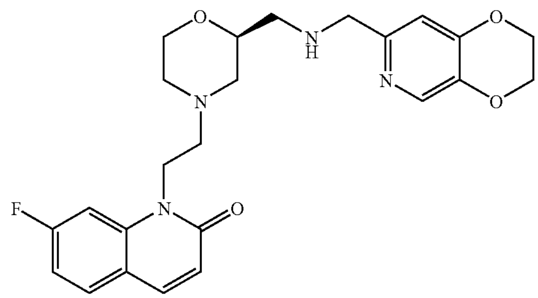 | (7-Fluoro-2-oxo-1(2H)-quinolinyl)acetaldehyde (Example 88(a)) 1,1-Dimethylethyl [(2R)-2-morpholinyl-methyl]carbamate 2,3-Dihydro[1,4]dioxino[2,3-c]pyridine-7-carboxaldehyde (WO2004058144, Example 2(c) or WO03/087098, Example 19(d)) |
| 246 | Mono-HCl MS (ES+) m/z 456 (MH$^+$) | 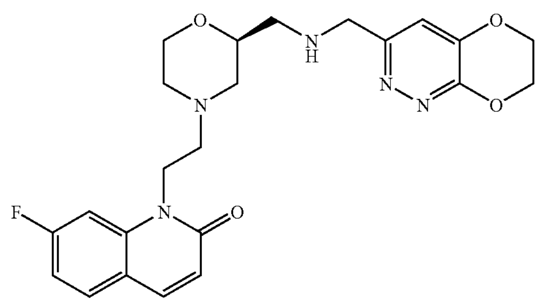 | (7-Fluoro-2-oxo-1(2H)-quinolinyl)acetaldehyde (Example 88(a)) 1,1-Dimethylethyl [(2R)-2-morpholinyl-methyl]carbamate 6,7-Dihydro[1,4]dioxino[2,3-c]pyridazine-3-carbaldehyde (Example 6(e)) |
| 247 | Mono-HCl MS (ES+) m/z 456 (MH$^+$) | 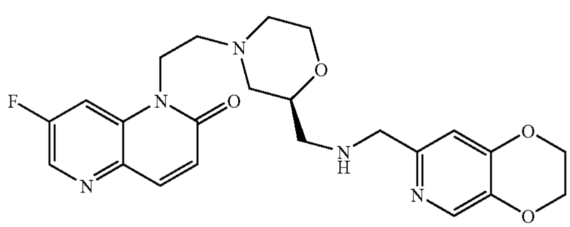 | (7-Fluoro-2-oxo-1,5-naphthyridin-1(2H)-yl)acetaldehyde(as the methyl hemiacetal) (Example 7(d)) 1,1-Dimethylethyl [(2R)-2-morpholinyl-methyl]carbamate 2,3-Dihydro[1,4]dioxino[2,3-c]pyridine-7-carboxaldehyde (WO2004058144, Example 2(c) or WO03/087098, Example 19(d)) |
| 248 | di-HCl MS (ES+) m/z 496 (MH$^+$) | 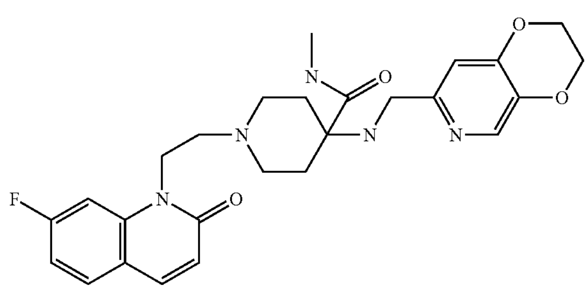 | 4-[(2,3-dihydro[1,4]dioxino[2,3-c]pyridin-7-ylmethyl)amino]-1-{[(1,1-dimethylethyl)oxy]carbonyl}-4-piperidinecarboxylic acid (WO2004058144 Example 87(c)) was converted to 1,1-dimethylethyl 4-[(2,3-dihydro[1,4]dioxino[2,3-c]pyridin-7-ylmethyl)amino]-4-[(methylamino)carbonyl]-1-piperidinecarboxylate by the action of EDC, HOBt and methylamine. This was then treated with acid to give 4-[(2,3-dihydro[1,4]dioxino[2,3-c]pyridin-7-ylmethyl)amino]-N-methyl-4-piperidinecarboxamide. This was reductively alkylated with (7-fluoro-2-oxo-1(2H)-quinolinyl)acetaldehyde (Example 88(a)) to give the product. |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 249 | Free base MS (ES+) m/z 482 (MH+) | 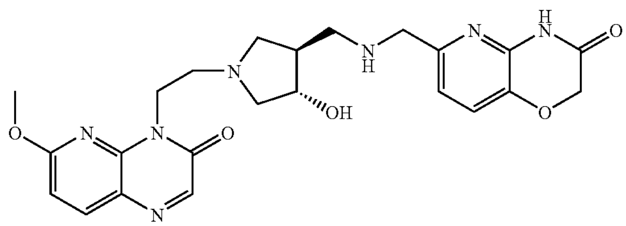 | [6-(Methyloxy)-3-oxopyrido[2,3-b]pyrazin-4(3H)-yl]acetaldehyde (Example 126(e)) Phenylmethyl {[(3S,4S)-4-hydroxy-3-pyrrolidinyl]methyl}carbamate (see Example 221) 3-Oxo-3,4-dihydro-2H-pyrido[3,2-b][1,4]oxazine-6-carboxaldehyde (WO2003087098, Example 31(e)) |
| 250 | Mono-HCl MS (ES+) m/z 434 (MH+) | 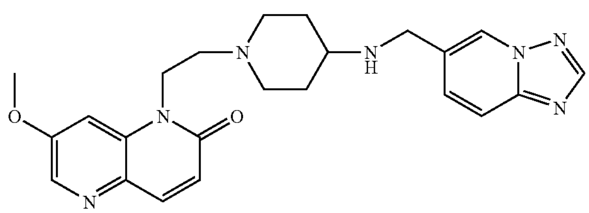 | 1-[2-(4-Amino-1-piperidinyl)ethyl]-7-(methyloxy)-1,5-naphthyridin-2(1H)-one dihydrochloride (Example 16(b)) [1,2,4]triazolo[1,5-a]pyridine-6-carbaldehyde (obtainable from 6-bromo[1,2,4]triazolo[1,5-a]pyridine (Edmondson, S. D. et al, *Journal of Medicinal Chemistry* (2006), 49(12), 3614-3627) by standard vinylation followed by cleavage with osmium tetroxide/sodium periodate. Coupled using the general method of Example 16(c) |
| 251 | Mono-HCl MS (ES+) m/z 466 (MH+) | 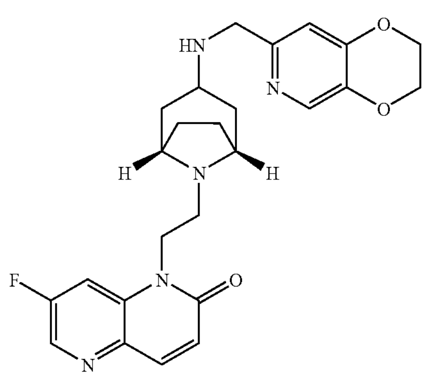 | (7-Fluoro-2-oxo-1,5-naphthyridin-1(2H)-yl)acetaldehyde (as the methyl hemiacetal) (Example 7(d)) Exo-1,1-dimethylethyl 8-azabicyclo[3.2.1]oct-3-ylcarbamate. (obtainable by reacting exo-8-(phenylmethyl)-8-azabicyclo[3.2.1]octan-3-amine (prepared according to Riley et al, *J. Heterocyclic Chem.*, (19), 1982, 485) with bis(1,1-dimethylethyl) dicarbonate to give exo-1,1-dimethylethyl [8-(phenylmethyl)-8-azabicyclo[3.2.1]oct-3-yl]carbamate. Hydrogenation of exo-1,1-dimethylethyl [8-(phenylmethyl)-8-azabicyclo[3.2.1]oct-3-yl]carbamate with Pd(OH)$_2$ gave product) 2,3-Dihydro[1,4]dioxino[2,3-c]pyridine-7-carboxaldehyde (WO2004058144, Example 2(c) or WO03/087098, Example 19(d)) |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 252 | di-HCl MS (ES+) m/z 479 (MH+) | 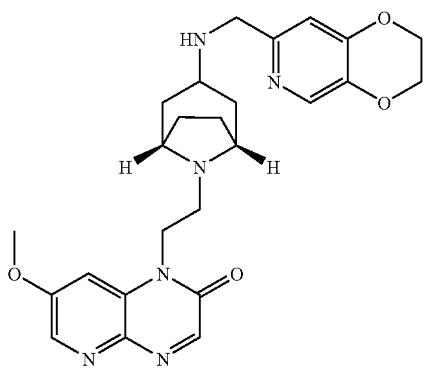 | [7-(Methyloxy)-2-oxopyrido[2,3-b]pyrazin-1(2H)-yl]acetaldehyde (as the methyl hemiacetal) (Example 51A(b)) Exo-1,1-dimethylethyl 8-azabicyclo[3.2.1]oct-3-ylcarbamate. (Example 251) 2,3-Dihydro[1,4]dioxino[2,3-c]pyridine-7-carboxaldehyde WO2004058144, Example 2(c) or WO03/087098, Example 19(d)) |
| 253 | di-HCl MS (ES+) m/z 526 (MH+) | 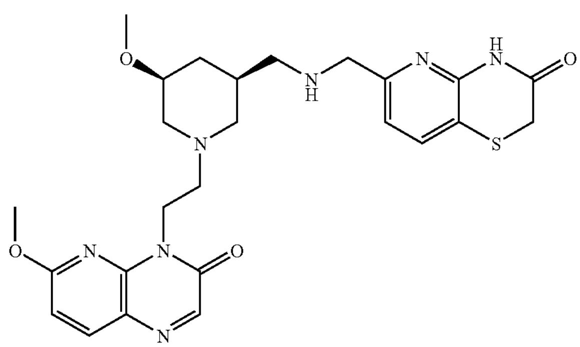 | Cis-4-{2-[(3RS,5SR)-3-(aminomethyl)-5-(methyloxy)-1-piperidinyl]ethyl}-6-(methyloxy)pyrido[2,3-b]pyrazin-3(4H)-one (Preparation B) The above intermediate was reductively alkyated with 3-oxo-3,4-dihydro-2H-pyrido[3,2-b][1,4]thiazine-6-carboxaldehyde (WO2004058144, Example 7(d)) by the general method of Example 134(k) |
| 255 | di-HCl MS (ES+) m/z 498 (MH+) | 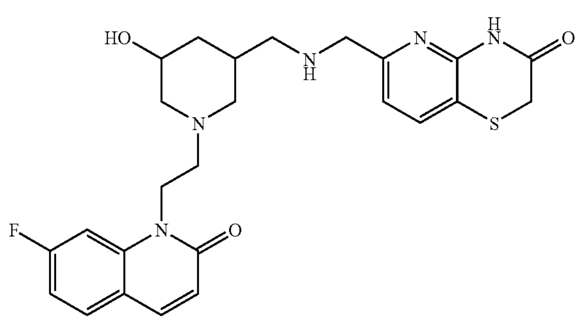 | Resolution of Example 158 by semi-preparative chiral HPLC using a 1 inch chiralpak AS-H (5 microns) column with 90:10:0.1 acetonitrile:methanol:isopropyl amine as the mobile phase. First eluting isomer E1 |
| 256 | di-HCl MS (ES+) m/z 498 (MH+) | 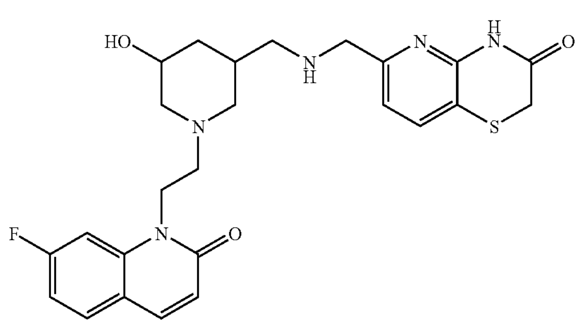 | Resolution of Example 158 by semi-preparative chiral HPLC using a 1 inch chiralpak AS-H (5 microns) column with 90:10:0.1 acetonitrile:methanol:isopropyl amine as the mobile phase. Second eluting isomer E2 |

TABLE 5-continued

Unless otherwise stated, Examples 142-253, 255-256, and 259-281 were made
from the specified starting materials by the general method of Example 121 (c)-(e) for
tert-butoxycarbonyl protected central units or by the general method of Example 61(b)-
(d) for benzyl-oxycarbonyl protected central units.

| Example number | Form tested | Structure | Starting materials (for a preparation see referenced Examples) |
|---|---|---|---|
| 259 | Mono-HCl MS (ES+) m/z 481 (MH+) | 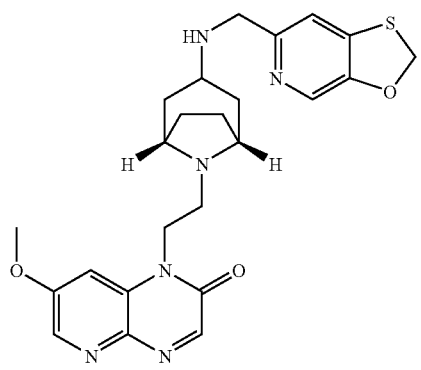 | [7-(Methyloxy)-2-oxopyrido[2,3-b]pyrazin-1(2H)-yl]acetaldehyde (as the methyl hemiacetal) (Example 51A(b)) Exo-1,1-dimethylethyl 8-azabicyclo[3.2.1]oct-3-ylcarbamate (Example 251). [1,3]oxathiolo[5,4-c]pyridine-6-carbaldehyde (WO2004058144, Example 61) |
| 260 | di-HCl MS (ES+) m/z 467 (MH+) | 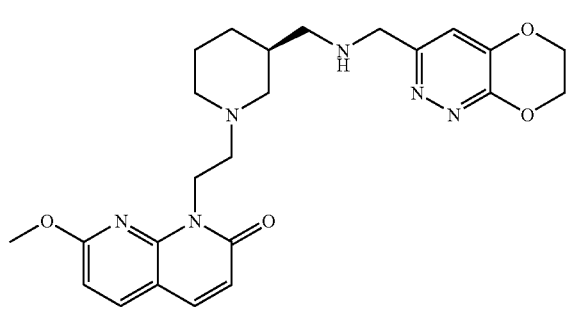 | [7-(methyloxy)-2-oxo-1,8-naphthyridin-1(2H)-yl]acetaldehyde (obtainable by treatment of 7-(methyloxy)-1-(2-propen-1-yl)-1,8-naphthyridin-2(1H)-one with OsO4/NaIO4 as in Example 17(a)) Phenylmethyl [(3R)-3-piperidinylmethyl]carbamate 6,7-Dihydro[1,4]dioxino[2,3-c]pyridazine-3-carbaldehyde (Example 6(e)) |
| 261 | di-HCl MS (ES+) m/z 498 (MH+) | 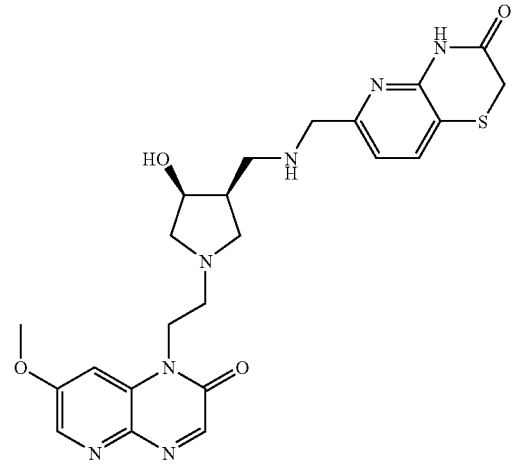 | [7-(Methyloxy)-2-oxopyrido[2,3-b]pyrazin-1(2H)-yl]acetaldehyde (as the methyl hemiacetal) (Example 51A(b)) Phenylmethyl {[(3R,4S)-4-hydroxy-3-pyrrolidinyl]methyl}carbamate 3-Oxo-3,4-dihydro-2H-pyrido[3,2-b][1,4]thiazine-6-carboxaldehyde (WO2004058144, Example 7(d)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 262 | Free base MS (ES+) m/z 502/504 (MH$^+$) | 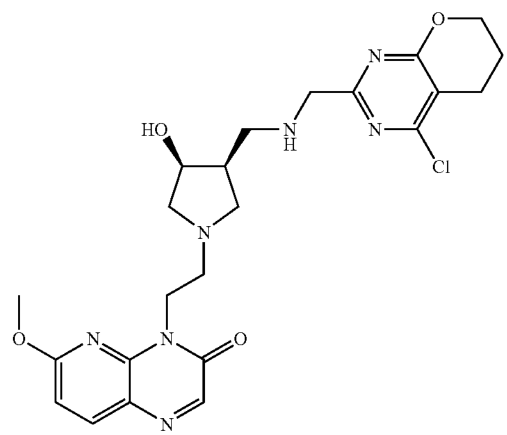 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 4-Chloro-6,7-dihydro[1,4]dioxino[2,3-d]pyrimidine-2-carbaldehyde (see preparation A below) |
| 263 | Mono-HCl MS (ES+) m/z 471 (MH$^+$) | 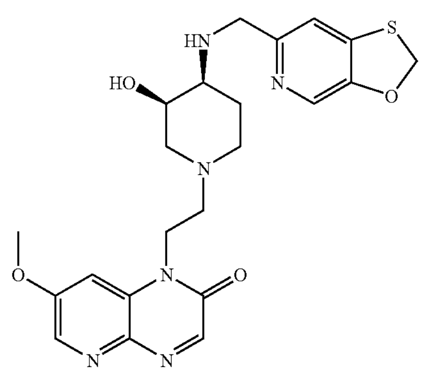 | [7-(Methyloxy)-2-oxopyrido[2,3-b]pyrazin-1(2H)-yl]acetaldehyde (as the methyl hemiacetal) (Example 51A(b)) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) [1,3]Oxathiolo[5,4-c]pyridine 6-carbaldehyde (WO2004058144, Example 61) |
| 264 | Mono-HCl MS (ES+) m/z 467 (MH$^+$) | 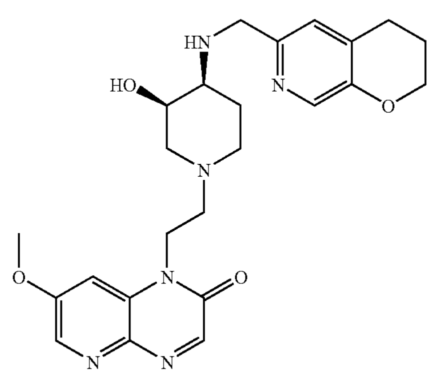 | [7-(Methyloxy)-2-oxopyrido[2,3-b]pyrazin-1(2H)-yl]acetaldehyde (as the methyl hemiacetal) (Example 51A(b)) 1,1-Dimethylethyl[(3R,4S)-3-hydroxy-4-piperidinyl]carbamate (WO2004058144, Example 5(c), cis-(3-hydroxy-piperidin-4-yl)-carbamic acid tert-butyl ester Enantiomer 1) 3,4-Dihydro-2H-pyrano[2,3-c]pyridine-6-carbaldehyde (WO2004058144, Example 126(e)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 265 | Mono-HCl MS (ES+) m/z 470 (MH+) | 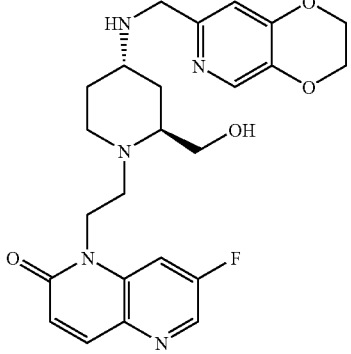 | (7-Fluoro-2-oxo-1,5-naphthyridin-1(2H)-yl)acetaldehyde (as the methyl hemiacetal) (Example 7(d)) was reductively alkylated with [(2S)-4,4-bis(ethyloxy)-2-piperidinyl]methanol (from 10% Pd/C in EtOH hydrogenolysis of {(2S)-4,4-bis(ethyloxy)-1-[(1R)-1-phenylethyl]-2-piperidinyl}methanol[1]) using NaBH(OAc)$_3$ in 1,2-dichloroethane to give 1-{2-[(2S)-4,4-bis(ethyloxy)-2-(hydroxymethyl)-1-piperidinyl]ethyl}-7-fluoro-1,5-naphthyridin-2(1H)-one. Deprotection with 2M HCl:THF 1:1 and reductive amination of the resulting product with 1-(2,3-dihydro[1,4]dioxino[2,3-c]pyridin-7-yl)methanamine[2] using NaBH(OAc)$_3$ in 1,2-dichloroethane followed by chromatographic separation of the cis and trans isomers on silica (eluted with 2%-14% (2M NH$_3$ in methanol) in DCM) gave the product, the trans isomer being eluted first. 1. Prepared by the method of J. F. Lau et al., Tet. 58(2) 7339-7344 (2002) 2 Prepared by conversion of 2,3-dihydro[1,4]dioxino[2,3-c]pyridin-7-ylmethanol (for synthesis see WO2004002490, Example 6(b)) to 7-(azidomethyl)-2,3-dihydro[1,4]dioxino[2,3-c]pyridine using diphenylphosphorylazide and then hydrogenation with Pd/C/H$_2$. |
| 266 | Mono-HCl MS (ES+) m/z 470 (MH+) | 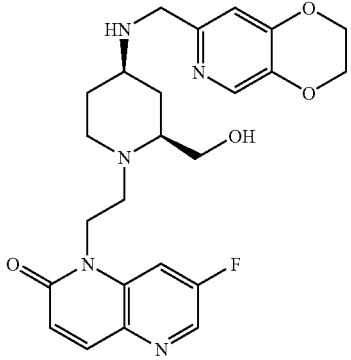 | See Example 265, the cis isomer being eluted second |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 267 | Mono-HCl MS (ES+) m/z 464 (MH+) | 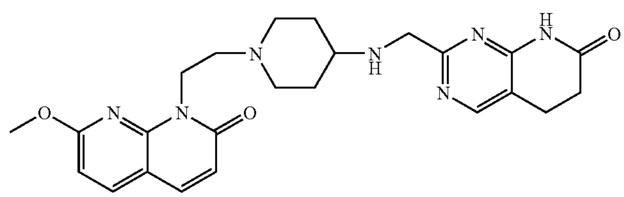 | [7-(methyloxy)-2-oxo-1,8-naphthyridin-1(2H)-yl]acetaldehyde (obtainable by treatment of 7-(methyloxy)-1-(2-propen-1-yl)-1,8-naphthyridin-2(1H)-one with $OsO_4/NaIO_4$ as in example 17(a)) 1,1-Dimethylethyl 4-piperidinylcarbamate 7-Oxo-5,6,7,8-tetrahydropyrido[2,3-d]pyrimidine-2-carbaldehyde (Example 125(c)) |
| 268 | Mono-HCl MS (ES+) m/z 485 (MH+) | 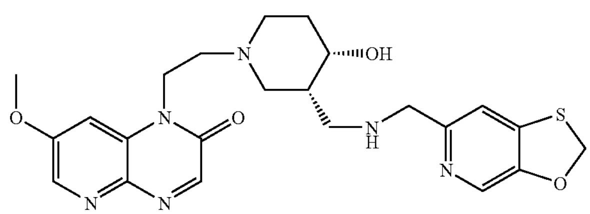 | [7-(Methyloxy)-2-oxopyrido[2,3-b]pyrazin-1(2H)-yl]acetaldehyde (as the methyl hemiacetal) (Example 51A(b)) Phenylmethyl {[(3S,4S)-4-hydroxy-3-piperidinyl]methyl}carbamate [1,3]Oxathiolo[5,4-c]pyridine-6-carbaldehyde (WO2004058144, Example 61) |
| 269 | di-trifluoro-acetate MS (ES+) m/z 464 (MH+) | 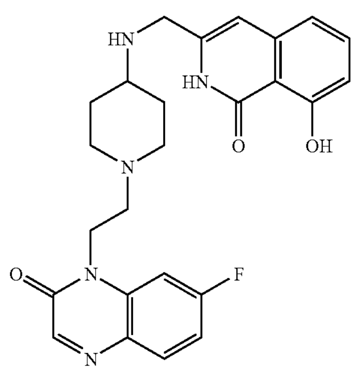 | 7-Fluoro-2-oxo-1(2H)-quinoxalinyl)acetaldehyde (Example 34(c)) 1,1-Dimethylethyl 4-piperidinylcarbamate 8-{[(Methyloxy)methyl]oxy}-1-oxo-1,2-dihydro-3-isoquinolinecarbaldehyde (WO2004058144 Example 57(e)). After coupling, deprotection of the methoxy-methyl ether with 4M HCl/1,4-1,4-dioxane and purification by HPLC gave the desired product. |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 270 | Mono-HCl MS (ES+) m/z 470 (MH+) | 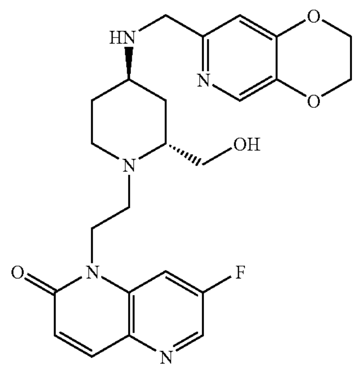 | (7-Fluoro-2-oxo-1,5-naphthyridin-1(2H)-yl)acetaldehyde (as the methyl hemiacetal) (Example 7(d)) was reductively alkylated with [(2R)-4,4-bis(ethyloxy)-2-piperidinyl]methanol (from 10% Pd/C in EtOH hydrogenolysis of {(2R)-4,4-bis(ethyloxy)-1-[(1S)-1-phenylethyl]-2-piperidinyl}methanol[1]) using NaBH(OAc)$_3$ in 1,2-dichloroethane to give 1-{2-[(2S)-4,4-bis(ethyloxy)-2-(hydroxymethyl)-1-piperidinyl]ethyl}-7-fluoro-1,5-naphthyridin-2(1H)-one. Deprotection with 2M HCl:THF 1:1 and reductive amination of the resulting product with 1-(2,3-dihydro[1,4]dioxino[2,3-c]pyridin-7-yl)methanamine[2] using NaBH(OAc)$_3$ in 1,2-dichloroethane followed by chromatographic separation of the cis and trans isomers on silica (eluted with 3%-15% (2M NH$_3$ in methanol) in DCM) gave the product, the trans isomer being eluted first. 1. Prepared by the method of J. F. Lau et al., Tet. 58(2) 7339-7344 (2002) 2 Prepared by conversio of 2,3-dihydro[1,4]dioxino[2,3-c]pyridin-7-ylmethanol (for synthesis see WO2004002490, Example 6(b)) to 7-(azidomethyl)-2,3-dihydro[1,4]dioxino[2,3-c]pyridine using diphenylphosphorylazide and then hydrogenation with Pd/C/H$_2$. |
| 271 | Mono-HCl MS (ES+) m/z 470 (MH+) | 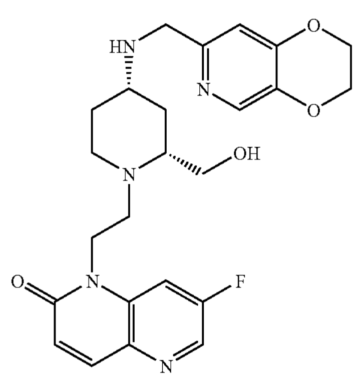 | See Example 270, the cis isomer being eluted second. |

TABLE 5-continued

Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.

| Example number | Form tested | Structure | Starting materials (for a preparation see referenced Examples) |
|---|---|---|---|
| 272 | di-HCl MS (ES+) m/z 478 (MH+) | 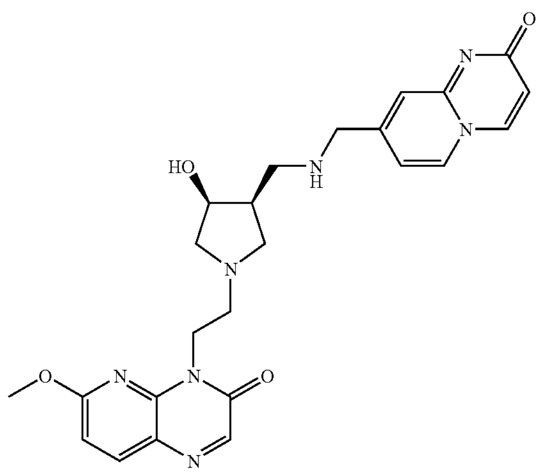 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 2-oxo-2H-pyrido[1,2-a]pyrimidine-8-carbaldehyde (obtainable by (a) treating 4-({[(1,1-dimethylethyl)(diphenyl)silyl]oxy}methyl)-2-pyridinamine and methyl-3-methoxyacrylate with 25% NaOCH$_3$ in MeOH to give N-[4-({[(1,1-dimethylethyl)(diphenyl)silyl]oxy}methyl)-2-pyridinyl]-3,3-bis(methyloxy)propanamide (b) heating -[4-({[(1,1-dimethylethyl)(diphenyl)silyl]oxy}methyl)-2-pyridinyl]-3,3-bis(methyloxy)propanamide in HOAc to give 8-({[(1,1-dimethylethyl)(diphenyl)silyl]oxy}methyl)-2H-pyrido[1,2-a]pyrimidin-2-one (c) treating 8-({[(1,1-dimethylethyl)(diphenyl)silyl]oxy}methyl)-2H-pyrido[1,2-a]pyrimidin-2-one with TBAF, followed by oxidation with manganese dioxide give the desired aldehyde) |
| 273 | Mono-Fumarate MS (ES+) m/z 465 (MH+) | 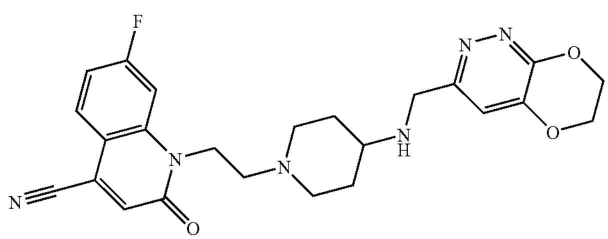 | 1-[2-(4-Amino-1-piperidinyl)ethyl]-7-fluoro-2-oxo-1,2-dihydro-4-quinolinecarbonitrile hydrochloride (Example 129(c)) 6,7-Dihydro[1,4]dioxino[2,3-c]pyridazine-3-carbaldehyde (Example 6(e)) Coupled by the general method of Example 4(c) |
| 274 | di-HCl MS (ES+) m/z 462 (MH+) | 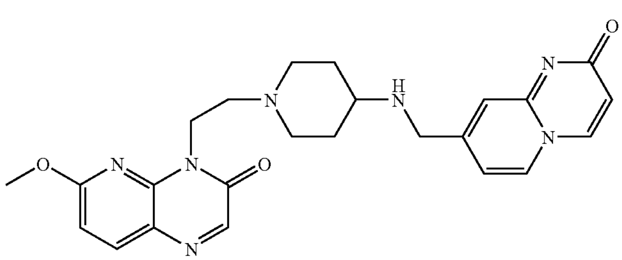 | [6-(Methyloxy)-3-oxopyrido[2,3-b]pyrazin-4(3H)-yl]acetaldehyde (Example 126(e)) 1,1-Dimethylethyl 4-piperidinylcarbamate 2-oxo-2H-pyrido[1,2-a]pyrimidine-8-carbaldehyde (see Example 272) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 275 | Free base MS (ES+) m/z 452 (MH+) | 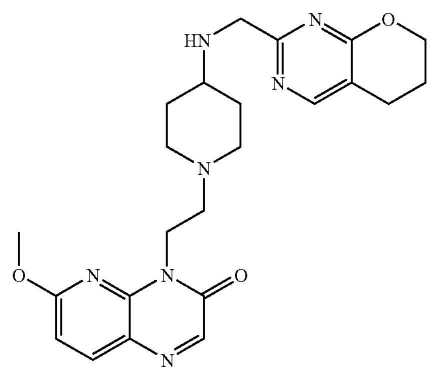 | [6-(Methyloxy)-3-oxopyrido[2,3-b]pyrazin-4(3H)-yl]acetaldehyde (Example 126(e)) 1,1-Dimethylethyl 4-piperidinylcarbamate 6,7-dihydro-5H-pyrano[2,3-d]pyrimidine-2-carbaldehyde (Preparation D) |
| 276 | Free base MS (ES+) m/z 453 (MH+) | 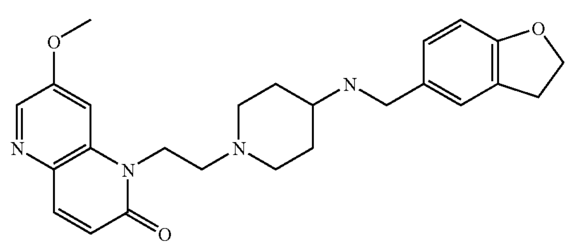 | [7-(methoxy)-2-oxo-1,5-naphthyridin-1(2H)-yl]acetaldehyde (as the methyl hemiacetal) (Example 11(e)) 1,1-Dimethylethyl 4-piperidinylcarbamate 2,3-Dihydro-1-benzofuran-5-carbaldehyde (commercially available) |
| 277 | Mono-trifluoroacetate MS (ES+) m/z 470 (MH+) | 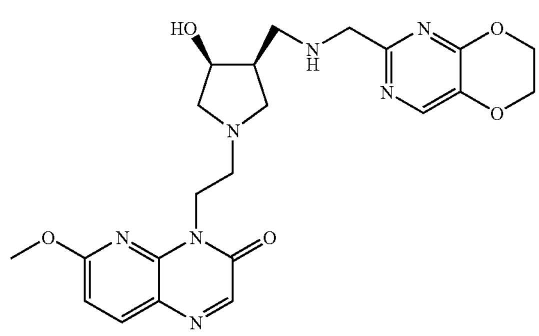 | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 6,7-Dihydro[1,4]dioxino[2,3-d]pyrimidine-2-carbaldehyde (WO2004014361, intermediate 8) |
| 278A 278B | Mono-HCl Benzoate MS (ES+) m/z 452 (MH+) | 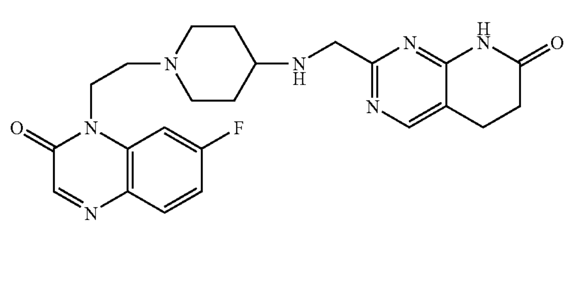 | 7-Fluoro-2-oxo-1(2H)-quinoxalinyl)acetaldehyde (Example 34(c)) 1,1-Dimethylethyl 4-piperidinylcarbamate 7-Oxo-5,6,7,8-tetrahydropyrido[2,3-d]pyrimidine-2-carbaldehyde (Example 125(c)) |

TABLE 5-continued

*Unless otherwise stated, Examples 142-253, 255-256, and 259-281 were made from the specified starting materials by the general method of Example 121 (c)-(e) for tert-butoxycarbonyl protected central units or by the general method of Example 61(b)-(d) for benzyl-oxycarbonyl protected central units.*

| Example number | Form tested | Structure | Starting materials (for a preparation see referenced Examples) |
|---|---|---|---|
| 279 | Mono-HCl<br>MS (ES+)<br>m/z 454<br>(MH+) | 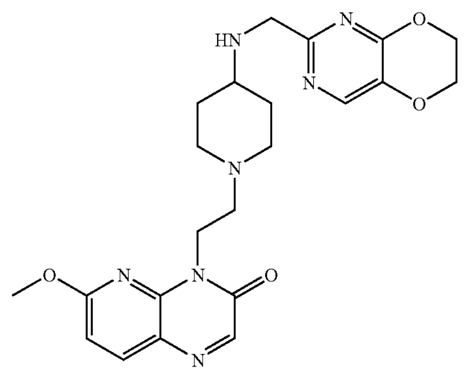 | [6-(Methyloxy)-3-oxopyrido[2,3-b]pyrazin-4(3H)-yl]acetaldehyde (Example 126(e))<br>1,1-Dimethylethyl 4-piperidinylcarbamate<br>6,7-Dihydro[1,4]dioxino[2,3-d]pyrimidine-2-carbaldehyde (WO2004014361, intermediate 8) |
| 280 | di-HCl<br>MS (ES+)<br>m/z 441<br>(MH+) | 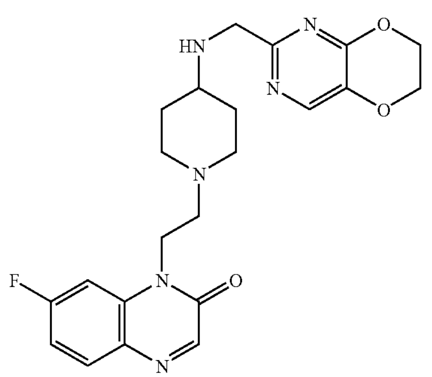 | 7-Fluoro-2-oxo-1(2H)-quinoxalinyl)acetaldehyde (Example 34(c))<br>1,1-Dimethylethyl 4-piperidinylcarbamate<br>6,7-Dihydro[1,4]dioxino[2,3-d]pyrimidine-2-carbaldehyde (WO2004014361, intermediate 8) |
| 281 | di-HCl<br>MS (ES+)<br>m/z 468<br>(MH+) | 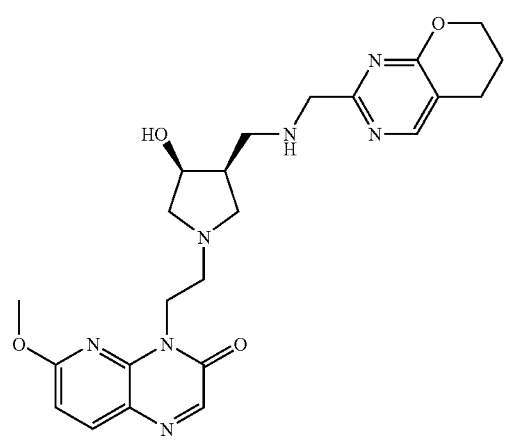 | [6-(Methyloxy)-3-oxopyrido[2,3-b]pyrazin-4(3H)-yl]acetaldehyde (Example 126(e))<br>Phenylmethyl {[(3R,4S)-4-hydroxy-3-pyrrolidinyl]methyl}carbamate<br>6,7-dihydro-5H-pyrano[2,3-d]pyrimidine-2-carbaldehyde (Preparation D) |

Preparation A

4-Chloro-6,7-dihydro[1,4]dioxino[2,3-d]pyrimidine-2-carbaldehyde

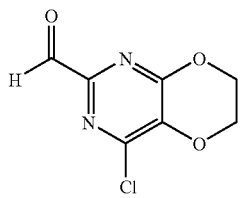

(a) 3-Ethyl 1,1-dimethyl 1,1,3-propanetricarboxylate

To a solution of dimethyl malonate (2.5 g, 18.9 mmol) in anhydrous THF (20 mL) was added NaH (0.038 g, 0.95 mmol, 60% in mineral oil). The reaction was stirred at ambient temperature for 15 minutes. In a separate flask, ethyl acrylate was dissolved in anhydrous THF (1 mL) and then added dropwise over 30 minutes to the dimethyl malonate solution. The reaction was stirred at ambient temperature for 16 h and then concentrated under vacuum. The residue was dissolved in EtOAc (ethyl acetate) and washed with saturated $NH_4Cl$ solution and brine. The organic phase was dried over $Na_2SO_4$, filtered, and concentrated under vacuum. The crude residue was purified by column chromatography (silica gel) using an EtOAc/hexanes gradient to yield the desired compound as a colorless oil (1.68 g, 77%).

$^1$H NMR (400 MHz, $CDCl_3$) δ 1.24 (t, J=7.07 Hz, 3H) 2.20 (q, J=7.24 Hz, 2H) 2.37 (t, J=7.33 Hz, 2H) 3.47 (t, J=7.33 Hz, 1H) 3.70-3.75 (m, 6H) 4.12 (q, J=7.24 Hz, 2H).

(b) (2E)-3-Phenyl-2-propenimidamide

Cinnamonitrile (25.0 g, 194 mmol) was dissolved in EtOH (ethanol) (200 mL). The solution was cooled to 0° C. and HCl gas bubbled through the solution for 30 minutes. The solution was stirred at ambient temperature for 16 h and then concentrated under vacuum. The residue was dissolved in EtOH (100 mL), cooled to 0° C. and a solution of $NH_3$/MeOH (7M, 69 mL, 484 mmol) was added dropwise through an addition funnel. Once added, the solution was allowed to warm to ambient temperature and the resulting $NH_4Cl$ was filtered off. The solution was concentrated under vacuum and the resulting white solid was used without further purification (26 g crude).

LCMS: m/z 147.4 (MH+).

(c) Ethyl 3-{4-hydroxy-6-oxo-2-[(E)-2-phenylethenyl]-1,6-dihydro-5-pyrimidinyl}propanoate 3-Ethyl 1,1-dimethyl 1,1,3-propanetricarboxylate (1.65 g, 7.1 mmol) and (2E)-3-phenyl-2-propenimidamide (1.04 g, 7.11 mmol) were combined in EtOH (36 mL). Triethylamine (1.98 mL, 14.2 mmol) was added and the solution was heated at reflux for 3 h with no change based on LCMS. The solution was cooled to room temperature and treated with NaOMe in MeOH (1.0 mL, 5.33 mmol, 25% wt solution) and the solution was refluxed for an additional 4 h. Another portion of NaOMe in MeOH (1.0 mL, 5.33 mmol, 25% wt solution) was added and the solution was refluxed for 16 h. After this time, a yellow precipitate had formed which was filtered off The mother liquor was acidified to pH2 with 1N HCl, and the solution was concentrated under vacuum. The resulting material was combined with the yellow solid and used without further purification.

LCMS: m/z 315.2 (MH+).

(d) Ethyl 3-{4,6-dichloro-2-[(E)-2-phenylethenyl]-5-pyrimidinyl}propanoate

Crude ethyl 3-{4-hydroxy-6-oxo-2-[(E)-2-phenylethenyl]-1,6-dihydro-5-pyrimidinyl}propanoate was dissolved in $POCl_3$ (25 mL) and N,N-dimethylaniline (0.9 mL, 7.1 mmol) was slowly added to the solution. The reaction was then heated at reflux for 2 h. After cooling to ambient temperature, the resulting solution was carefully and slowly added to ice water to quench the excess $POCl_3$. The mixture was extracted with EtOAc (3×), dried over $Na_2SO_4$, filtered and concentrated under vacuum. The crude residue was then purified by column chromatography (silica gel) using an EtOAc/hexanes gradient to yield the desired compound as a yellow solid (0.48 g, 19% over 2 steps).

LCMS: m/z 351.4 (MH+).

(e) 3-{4,6-dichloro-2-[(E)-2-phenylethenyl]-5-pyrimidinyl}-1-propanol

To Ethyl 3-{4,6-dichloro-2-[(E)-2-phenylethenyl]-5-pyrimidinyl}propanoate (0.35 g, 1.04 mmol) in THF (10 mL) at −78° C. was added a 1N solution of lithium aluminium hydride in THF (2.0 mL, 2.0 mmol). The reaction was allowed to stir under nitrogen for 1 h and allowed to warm to 0° C. After 2 h at 0° C. the reaction was quenched by addition of 5 mL of methanol and 2 mL of water. The reaction was concentrated under vacuum and the residue was partitioned between EtOAc and brine. The aqueous layer was extracted with EtOAc (3×), dried over $Na_2SO_4$, filtered and concentrated under vacuum to give the product as a yellow solid (275 mg, 86%) to be used without further purification.

LCMS: m/z 309.0, 311.0 (MH+).

(f) 4-Chloro-2-[(E)-2-phenylethenyl]-6,7-dihydro-5H-pyrano[2,3-d]pyrimidine To 3-{4,6-dichloro-2-[(E)-2-phenylethenyl]-5-pyrimidinyl}-1-propanol (275 mg, 0.89 mmol) in DMF (4 mL) was added $K_2CO_3$ (0.50 g, 3.6 mmol). The suspension was warmed to 60° C. and allowed to stir 16 h under nitrogen. The reaction was cooled to rt, concentrated to remove most of the DMF and the residue was partitioned between EtOAc and water. The aqueous layer was further extracted with EtOAc (2×), washed with brine, dried over $Na_2SO_4$, filtered and concentrated under vacuum. The crude residue was then purified by column chromatography (silica gel) using an EtOAc/hexanes gradient to yield the desired compound as a yellow solid (0.21 g, 88%).

LCMS: m/z 272.9 (MH+).

(g) 4-Chloro-6,7-dihydro-5H-pyrano[2,3-d]pyrimidine-2-carbaldehyde

To 4-chloro-2-[(E)-2-phenylethenyl]-6,7-dihydro-5H-pyrano[2,3-d]pyrimidine (0.21 g, 0.79 mmol) was dissolved in a 2:1 solution of 1,4-dioxane/water (6 mL) and cooled to 0° C. $NaIO_4$ (0.50 g, 2.4 mmol) and catalytic $OsO_4$ (0.25 mL, 4% aq. solution) were added and the solution was then stirred at ambient temperature for 2 h. The reaction solution was diluted with water (10 mL) and extracted with EtOAc (4×).

The organic layers were combined, dried over Na₂SO₄, filtered and concentrated under vacuum. The crude residue was then purified by column chromatography (silica gel) using a DCM-MeOH (90:10) to yield the desired compound as an off-white solid (0.055 g, 36%).

Preparation B cis-4-{2-[(3RS,5SR)-3-(Aminomethyl)-5-(methyloxy)-1-piperidinyl]ethyl}-6-(methyloxy)pyrido[2,3-b]pyrazin-3(4H)-one

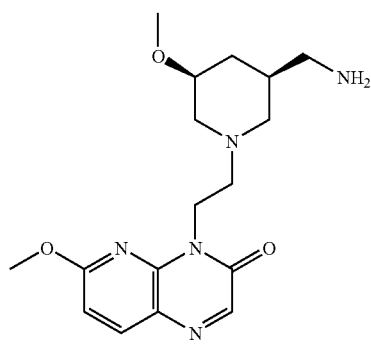

(a) Cis-phenylmethyl (3RS,5SR)-3-[(1,3-dioxo-1,3-dihydro-2H-isoindol-2-yl)methyl]-5-hydroxy-1-piperidinecarboxylate To cis-phenylmethyl (3RS,5SR)-3-{[(1,1-dimethylethyl)(dimethyl)silyl]oxy}-5-[(1,3-dioxo-1,3-dihydro-2H-isoindol-2-yl)methyl]-1-piperidinecarboxylate (for a preparation, see Example 134(e)) (0.92 g, 1.8 mmol) in 10 mL of THF at 0° C. was added a 1N solution of tetrabutyl ammonium fluoride in THF (4 mL, 4.0 mmol). The reaction was allowed to stir under nitrogen while warming to room temperature over 2 h. The reaction was partitioned between EtOAc and saturated aqueous NH₄Cl. The organic phase was separated and washed with saturated aqueous NaHCO₃, and brine, dried over Na₂SO₄, and concentrated under reduced pressure. The crude residue was purified by chromatography on silica gel using a 5-100% EtOAc/hexanes gradient to provide the desired compound (380 mg; 54%) as a colorless oil.
MS (ES+) m/z 395.1 (MH⁺).

(b) Cis-phenylmethyl (3RS,5RS)-3-[(1,3-dioxo-1,3-dihydro-2H-isoindol-2-yl)methyl]-5-(methyloxy)-1-piperidinecarboxylate To cis-phenylmethyl (3RS,5SR)-3-[(1,3-dioxo-1,3-dihydro-2H-isoindol-2-yl)methyl]-5-hydroxy-1-piperidinecarboxylate (380 mg, 0.96 mmol) in 5 mL of CH₂Cl₂ was added iodomethane (1 mL, 16.1 mmol) and Ag₂O (1.15 g, 5.0 mmol). The reaction was allowed to stir at room temperature under nitrogen for 48 h. The reaction mixture was filtered through a pad of Celite® which was washed with 25 mL CH₂Cl₂, and concentrated under reduced pressure. The crude residue was purified by chromatography on silica gel using a 10-100% EtOAc/hexanes gradient to provide the desired compound (210 mg; 53%) as a colorless oil.
MS (ES+) m/z 409.3 (MH⁺).

(c) Cis-2-{[(3RS,5SR)-5-(methyloxy)-3-piperidinyl]methyl}-1H-isoindole-1,3(2H)-dione To cis-phenylmethyl (3RS,5SR)-3-[(1,3-dioxo-1,3-dihydro-2H-isoindol-2-yl)methyl]-5-(methyloxy)-1-piperidinecarboxylate (210 mg, 0.51 mmol) in EtOH (20 mL) was added Pd/C (50 mg; 10%). The reaction was hydrogenated on a Parr apparatus at 45 psi of H₂ for 3 h. The hydrogen was displaced with N₂ and the solution was filtered through a pad of Celite® to remove the catalyst which was washed with additional EtOH (50 mL). The filtrate was then concentrated under reduced pressure to give the desired compound (125 mg; 90%) as a colorless oil which was used without further purification.
MS (ES+) m/z 274.9 (MH⁺).

(d) 2-[((3RS,5SR)-5-(methyloxy)-1-{2-[6-(methyloxy)-3-oxopyrido[2,3-b]pyrazin-4(3H)-yl]ethyl}-3-piperidinyl)methyl]-1H-isoindole-1,3(2H)-dione To cis-2-{[(3RS,5SR)-5-(methyloxy)-3-piperidinyl]methyl}-1H-isoindole-1,3(2H)-dione (125 mg, 0.43 mmol) in MeOH (1 ml) and CHCl₃ (5 ml) was added [6-(methyloxy)-3-oxopyrido[2,3-b]pyrazin-4(3H)-yl]acetaldehyde (for a preparation see Example 126(e)) (100 mg; 0.50 mmol) and the reaction was allowed to stir at room temperature under N₂ for 4 hours. Na(OAc)₃BH (210 mg; 1.0 mmol) was added and the reaction was allowed to stir at room temperature under nitrogen for an additional 14 hours. The reaction was partitioned between saturated aqueous NaHCO₃ (5 mL) and CH₂Cl₂ (20 mL), the aqueous layer was further extracted with CH₂Cl₂ (20 mL), and the combined organic layers were dried over Na₂SO₄. The solvents were removed and the crude residue was purified by chromatography on silica gel using a 0-10% MeOH/DCM gradient to provide the desired compound (10 mg; 55%) as a colorless oil.
MS (ES+) m/z 478.2 (MH⁺).

(e) cis-4-{2-[(3RS,5SR)-3-(Aminomethyl)-5-(methyloxy)-1-piperidinyl]ethyl}-6-(methyloxy)pyrido[2,3-b]pyrazin-3(4H)-one To 2-[((3RS,5SR)-5-(methyloxy) 1-{2-[6-(methyloxy)-3-oxopyrido[2,3-b]pyrazin-4(3H)-yl]ethyl}-3-piperidinyl)methyl]-1H-isoindole-1,3(2H)-dione (110 mg, 0.23 mmol) in EtOH (5 mL) was added anhydrous hydrazine (0.5 mL, 15.0 mmol). The reaction was warmed to 40° C. and allowed to stir under nitrogen for 24 h. The reaction was filtered through a pad of Celite® and the filtrate was partitioned between EtOAc (50 mL) and water (10 mL). The aqueous layer was further extracted with EtOAc (2×25 mL), and the combined organic layers were dried over Na₂SO₄. The solvents were removed to provide the desired compound (62 mg; 77%) as a tan solid which was used without further purification.
MS (ES+) m/z 348.0 (MH⁺).

Preparation C

[7-(Methyloxy)-2-oxo-1(2H)-quinoxalinyl]acetaldehyde (a) 7-(Methyloxy)-2(1H)-quinoxalinone and 6-(methyloxy)-2(1H)-quinoxalinone A mixture of 4-(methyloxy)-1,2-benzenediamine (10 g, 72.5 mmol) and ethyl glyoxalate (50% in toluene, 15.2 mL, 74.2 mmol) in ethanol (400 mL) was heated under reflux for 2 h, the cooled and refrigerated overnight. The solid was filtered off, washed with ice-cold ethanol and dried to give a mixture of 7-(methyloxy)-2(1H)-quinoxalinone and 6-(methyloxy)-2(1H)-quinoxalinone (approx. 1:1 ratio, 9.99 g). Concentration of the liquor and cooling in ice gave a second crop of mixed isomers (approx. 2:1 ratio), which was collected, washed and dried as before (1.11 g).

(b) 7-(methyloxy)-2-(2-propen-1-yloxy)quinoxaline (O-allyl 1) and 6-(methyloxy)-2-(2-propen-1-yloxy) quinoxaline (O-allyl 2)

The mixture of 7-(methyloxy)-2(1H)-quinoxalinone and 6-(methyloxy)-2(1H)-quinoxalinone (11.1 g, 63.1 mmol) was stirred with allyl iodide (6.25 mL, 69.6 mmol) and potassium carbonate (26.2 g, 189.8 mmol) in dimethylformamide (200 mL) at room temperature for 2.5 h, then evaporated. The residue was dissolved in dichloromethane and water and the phases were separated. The organic phase was extracted with dichloromethane, and the organic fractions were dried and evaporated. Chromatography on silica, eluting with 0-100% ether/petroleum ether, gave firstly O-allyl Isomer1 (1.18 g, 9%), followed by O-allyl Isomer 2 (1.99 g, 15%), and finally a mixture of two N-allyl isomers 7-(methyloxy)-1-(2-propen-1-yl)-2(1H)-quinoxalinone and 6-(methyloxy)-1-(2-propen-1-yl)-2(1H)-quinoxalinone (9.18 g, 67%).

(c) 7-(Methyloxy)-1-(2-propen-1-yl)-2(1H)-quinoxalinone

The O-allyl Isomer 1 (1.18 g, 5.45 mmol) was heated under reflux with tetrakis(triphenylphosphine)palladium(0) (120 mg) in toluene (25 mL) for 3 h. The solvent was evaporated and the residue was chromatographed on silica, eluting with 50-100% ethyl acetate/hexane to give 7-(methyloxy)-1-(2-propen-1-yl)-2(1H)-quinoxalinone (1.03 g, 87%).

(d) Title Compound

A mixture of 7-(methyloxy)-1-(2-propen-1-yl)-2(1H)-quinoxalinone (1.03 g, 4.75 mmol) and sodium periodate (4.68 g, 21.8 mmol) in 2-butanol (20 mL) and water (40 mL) was treated with osmium tetroxide (4% solution in water, 1.1 mL) and the mixture was stirred for 3.75 h. The butanol was evaporated and the residue was diluted with water and extracted with dichloromethane, then with dichloromethane/THF. The extracts were dried and evaporated, and the residue was chromatographed on silica eluted with 50-100% ethyl acetate/hexane to give the aldehyde (0.68 g, 66%).
MS (+ve ion electrospray) m/z 219 (MH+), 237 ([M+H$_2$O]H+), 233 (MCH$_3$+), 251([M+MeOH]H+).

Preparation D 6,7-dihydro-5H-pyrano[2,3-d]pyrimidine-2-carbaldehyde

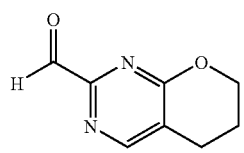

(a) 5-(3-Hydroxypropyl)-2-[(E)-2-phenylethenyl]-4(1H)-pyrimidinone

To δ-valerolactone (2.0 g; 20 mmol) in anhydrous diethyl ether (20 ml) was added ethyl formate (1.6 mL; 21 mmol) and sodium hydride (1.0 g of a 60% w:w dispersion in oil, 25 mmol). The reaction was allowed to stir at room temperature under nitrogen for 45 min. A solution of (2E)-3-phenyl-2-propenimidamide (2.92 g; 20 mmol) in EtOH (25 ml) was added, the mixture was then heated to 70° C. and stirred at this temperature for 4 hours. The reaction was cooled to room temperature, water was added (50 mL) and the mixture was extracted with EtOAc (2×200 mL). The combined organic extracts were dried with Na$_2$SO$_4$, the solvents were removed and the crude residues were purified by column chromatography on silica gel using a 0-10% MeOH/DCM gradient. Fractions containing product were concentrated to afford the desired compound (2.3 g, 45%).
MS (ES+) m/z 257 (MH+).

(b) 2-[(E)-2-Phenylethenyl]-6,7-dihydro-5H-pyrano[2,3-d]pyrimidine

To 5-(3-hydroxypropyl)-2-[(E)-2-phenylethenyl]-4(1H)-pyrimidinone (1.0 g; 4.0 mmol) in THF (20 ml) was added triphenyl phosphine (1.6 g; 6.0 mmol) and diethyl azodicarboxylate (1.0 g; 6.0 mmol). The reaction was allowed to stir at room temperature under nitrogen for 14 hours. The reaction was partitioned between water (20 ml) and EtOAc (100 ml), and the aqueous phase was further extracted with EtOAc (2×50 ml). The combined organic extracts were dried with Na$_2$SO$_4$, the solvents were removed and the crude residue was purified by column chromatography on silica gel using a 0-2.5% MeOH in DCM gradient to provide the desired compound (0.81 g; 84%).
MS (ES+) m/z 239 (MH+).

(c) 6,7-Dihydro-5H-pyrano[2,3-d]pyrimidine-2-carbaldehyde

2-[(E)-2-phenylethenyl]-6,7-dihydro-5H-pyrano[2,3-d]pyrimidine (0.5 g, 2.1 mmol) was dissolved in DCM (20 ml) and O3 was bubbled through the reaction at −78° C. for 15 mins. Nitrogen was then bubbled through for 10 mins to remove the excess O3 and the reaction was quenched with dimethyl sulfide (2.0 ml, 32.2 mmol). The reaction was allowed to warm to rt and was stirred for another 14 hours. All solvents were then removed to give the desired compound (0.28 g; 80%) which was used without further purification.
MS (ES+) m/z 165 (MH+).

Preparation E

2-Oxo-2H-pyrano[2,3-b]pyridine-7-carbaldehyde (a) 3-(Hydroxymethyl)-6-methyl-2(1H)-pyridinone 2-hydroxy-6-methylpyridine-3-carboxylic acid (2 g, 13 mmol) was dissolved in dry THF (80 ml), and this solution was cooled to −70° C. LiAlH$_4$ (32 ml, 32 mmol) was then added over a period of 20 min. The reaction mixture was warmed to room temperature and then was heated at 70° C. for 1 hour. After cooling down to 0° C., the reaction mixture was added H$_2$O (2 mL), 10% NaOH (4 mL) and finally H$_2$O (2 mL). The reaction mixture was stirred at room temperature for 1 hour. NaSO$_4$ (6 g) was added, the mixture was stirred for a further 30 min., filtered and washed with MeOH. The filtrate was concentrated to dryness to give the desired product as a solid (2 g, 100%). LCMS (ES+) m/z 140 (MH+).

(b)
6-Methyl-2-oxo-1,2-dihydro-3-pyridinecarbaldehyde 3-(hydroxymethyl)-6-methyl-2(1H)-pyridinone (2.0 g, 13 mmol) was dissolved in $CH_2Cl_2$ (80 mL), THF (80 mL) and MeOH (5 mL), $MnO_2$ (3.7 g, 43 mmol) was added. The reaction mixture was heated at 57° C. for 18 hours. The reaction was filtered through a pad of Celite® and concentrated to give a solid (1.8 g, 90%). LCMS (ES+) m/z 138 (MH+).

(c) 7-Methyl-2H-pyrano[2,3-b]pyridin-2-one

To 6-methyl-2-oxo-1,2-dihydro-3-pyridinecarbaldehyde (318 mg, 2.3 mmol) in $Ac_2O$ (3 mL) was added $Et_3N$ (1 mL). The reaction was heated at 120° C. for 18 hours. The reaction was concentrated and the resulting material was dissolved in MeOH and loaded onto silica gel and evaporated. Purification by column chromatography (silica gel) using a hexanes/ethyl acetate gradient (0-100% EtOAc) provided the desired product as a solid (80 mg, 30%). LCMS (ES+) m/z 162 (MH+).

(d) Title Compound

To a solution of 7-methyl-2H-pyrano[2,3-b]pyridin-2-one (160 mg, 0.98 mmol) in 1,4-dioxane (12 mL) in a microwave reaction vial was added $SeO_2$ (328 mg, 3.0 mmol). The reaction vial was capped and the mixture was heated in a microwave at 160° C. for 90 minutes. The reaction was diluted with DCM, filtered through a pad of Celite® and concentrated. The resulting material was dissolved in DCM and loaded onto a plug of silica gel and evaporated. Purification by column chromatography (silica gel) using a DCM/MeOH gradient (0-10% MeOH) provided the desired product as a pale yellow solid (120 mg, 40%). LCMS (ES+) m/z 176 (MH+).

Preparation F

7-Oxo-6,7-dihydro-1H-pyrimido[5,4-b][1,4]oxazine-2-carbaldehyde (a) 2-[(E)-2-Phenylethenyl]-5-(tetrahydro-2H-pyran-2-yloxy)-4(1H)-pyrimidinone NaH (0.38 g, 9.5 mmol, 60% paraffin oil) was added slowly to a THF (20 mL) solution of ethyl (tetrahydro-2H-pyran-2-yloxy)acetate (prepared by treating ethyl hydroxyacetate with 3,4-dihydro-2H-pyran and TsOH) (1.0 g, 5.3 mmol) and dry ethyl formate (3.9 g, 53 mmol). The reaction mixture was stirred at room temperature for 15 min. and then heated at 65° C. for 45 min. The reaction mixture was concentrated to dryness to give a pale yellow solid. The solid was added to a MeOH/EtOH (20 mL/20 mL) solution of (2E)-3-phenyl-2-propenimidamide (0.78 g, 5.3 mmol), the subsequent mixture was heated at 80° C. for 4 h. The resulting material was poured into DCM (10 mL) containing silica gel (3 g) and evaporated. Purification by column chromatography (silica gel) using a MeOH/DCM gradient (0-10%) provided the desired product as a pale yellow solid (1 g, 63%).
LCMS: m/z 299 (MH+).

(b) 2-[(E)-2-Phenylethenyl]-5-(tetrahydro-2H-pyran-2-yloxy)-4-pyrimidinyl Trifluoromethanesulfonate To a suspension of 2-[(E)-2-phenylethenyl]-5-(tetrahydro-2H-pyran-2-yloxy)-4(1H)-pyrimidinone (2.04 g, 6.84 mmol) in DCM (25 mL) was added pyridine (1.22 mL, 15.05 mmol). After cooling to −78° C., triflic anhydride (1.38 mL, 8.2 mmol) was slowly added via dropwise addition. The reaction was maintained at −78° C. for 10 minutes, after which time the cooling bath was replaced with a ice-water bath and the reaction was stirred for an additional 0.5 h. The reaction mixture was poured into water and the aqueous phase was extracted with DCM. The organic phase was then washed with water, saturated aq. $NaHCO_3$, and brine. The organic phase was dried over $Na_2SO_4$, filtered, and concentrated under vacuum to provide a dark reddish oil which was used directly in the next step.
LCMS: m/z 431.0 (MH+).

(c) 2-[(E)-2-Phenylethenyl]-5-(tetrahydro-2H-pyran-2-yloxy)-4-pyrimidinamine

Crude 2-[(E)-2-phenylethenyl]-5-(tetrahydro-2H-pyran-2-yloxy)-4-pyrimidinyl trifluoromethanesulfonate (6.8 mmol) was reacted with a 0.5M solution of ammonia in 1,4-dioxane (136 mL) in a pressure bottle at 60° C. for 24 h. The reaction was concentrated under vacuum, the residue was taken up in DCM and washed with water, saturated aq. $NaHCO_3$, and brine. The organic phase was dried over $Na_2SO_4$, filtered, and concentrated. The crude residue was purified by column chromatography (silica gel) using a MeOH/DCM gradient to yield the desired compound as a tan solid (1.28 g, 63% for two steps).
LCMS: m/z 298.0 (MH+).

(d) 4-Amino-2-[(E)-2-phenylethenyl]-5-pyrimidinol, Hydrochloride

2-[(E)-2-Phenylethenyl]-5-(tetrahydro-2H-pyran-2-yloxy)-4-pyrimidinamine (1.28 g, 4.3 mmol) was suspended in MeOH (25 mL) and heated in a 50° C. oil bath until fully dissolved. To this was added 4M HCl in 1,4-dioxane (0.11 mL, 0.43 mmol) and the reaction was heated at 50° C. for 1.5 h. At this time, LCMS indicated little progression, therefore an additional 1.1 mL of 4M HCl/1,4-dioxane was added and heating was continued for 3 h. The reaction was allowed to cool to room temperature resulting in the formation of a white precipitate. The solvent was removed under vacuum and the resulting tan solid was dried under high vacuum over night yielding 1.08 g (100%, for HCl salt). This material was used without further purification.
LCMS: m/z 214.0 (MH+).

(e) 2-[(E)-2-Phenylethenyl]-1H-pyrimido[5,4-b][1,4]oxazin-7(6H)-one

To a suspension of 4-amino-2-[(E)-2-phenylethenyl]-5-pyrimidinol hydrochloride (250 mg, 1.0 mmol) in absolute ethanol (5 mL) was added potassium tert-butoxide (224 mg, 2.0 mmol) at room temperature. After stirring for 5 minutes, ethyl bromoacetate (0.11 mL, 1.0 mmol) was added via dropwise addition and the reaction was stirred for 18 h. The solvent was evaporated and the residue was taken up in 10% MeOH—$CHCl_3$ and a small amount of water. The layers were separated and the aqueous phase was extracted with 10% MeOH—$CHCl_3$ (3×). The combined organic extracts were concentrated and the resulting solid was triterated with EtOAc. The white solid was collected by filtration, yielding 106 mg (42%).
LCMS: m/z 254.0 (MH+).

(f) Title Compound

To a suspension of 2-[(E)-2-phenylethenyl]-1H-pyrimido[5,4-b][1,4]oxazin-7(6H)-one (106 mg, 0.418 mmol) in 1,4- dioxane (12 mL) and water (3 mL) was added NaIO$_4$ (357 mg, 1.67 mmol) and OsO$_4$ (00.1 mL, 4% wt in water) and the reaction mixture was stirred at room temperature. After 2 h, and additional 3 mL of 1,4-dioxane and 180 mg of NaIO$_4$ were added. After a total of 7.5 h, the reaction was capped and stored in a freezer for the weekend. After warming to room temperature, additional OsO$_4$ (0.1 mL, 4% wt in water) was added and the reaction was stirred for an additional 4 h. The solvent was evaporated to give a white solid which was dissolved in DCM and water. The aqueous layer was extracted with 10% MeOH-DCM (6×). The combined organic extracts were dried over Na$_2$SO$_4$, filtered, and concentrated to give a light tan solid (92 mg) which was not purified further.

LCMS: m/z 180.0 (MH+).

Preparation G

7-Oxo-5,6,7,8-tetrahydropyrido[2,3-d]pyrimidine-2-carbaldehyde (a) Diethyl α-formylglutarate Sodium Salt Prepared from diethyl glutarate and ethyl formate in the presence of sodium metal in diethyl ether according to the literature procedure (J. Bigs, P. Sykes, *J. Chemical Society* (1959), 1849-55). Obtained solid (28 g; 45%). LCMS (ES+) m/z 238 (MH$^+$).

(b) Ethyl 3-{4-hydroxy-2-[(E)-2-phenylethenyl]-5-pyrimidinyl}propanoate

Diethyl α-formylglutarate sodium salt (1 g, 4.2 mmol) and (2E)-3-phenyl-2-propenimidamide (0.61 g, 4.2 mmol), prepared in Example 126 (g), were combined in EtOH (20 mL) and MeOH (10 mL) and heated at reflux for 12 h. The solvent was removed and the resulting solid triturated with ether and filtered to give the desired product as a yellow solid (0.75 g, 56%). The mother liquor contained additional product which was not isolated. LCMS (ES+) m/z 299 (MH$^+$).

(c) Ethyl 3-{4-chloro-2-[(E)-2-phenylethenyl]-5-pyrimidinyl}propanoate

Ethyl 3-{4-hydroxy-2-[(E)-2-phenylethenyl]-5-pyrimidinyl}propanoate (11.6 g, 38.9 mmol) in POCl$_3$ (30 mL) was heated at 120° C. for 4 h. The solvent was removed in vacuo. The crude residue was then purified by column chromatography (silica gel) using an EtOAc/hexanes (30-50%) gradient to yield the desired compound as a yellow solid (6.6 g, 53%). LCMS (ES+) m/z 317 (MH$^+$).

(d) 2-[(E)-2-Phenylethenyl]-5,8-dihydropyrido[2,3-d]pyrimidin-7(1H)-one

To a 320 mL sealed flask at room temperature was added ethyl 3-{4-chloro-2-[(E)-2-phenylethenyl]-5-pyrimidinyl}propanoate (6.6 g, 20.83 mmol) and ammonia in MeOH (59.5 mL, 417 mmol, 7M solution). The flask was sealed and the reaction was heated at 110° C. for 7 h. After 3 h a solid precipitated. The reaction was then stirred at room temperature overnight, followed by heating for an additional 5 h. The reaction mixture was filtered through a Buchner funnel and the resulting solid was washed with ethanol and dried. Obtained solid (2 g, 36.3%). LCMS (ES+) m/z 252 (MH$^+$).

(e) 7-Oxo-5,6,7,8-tetrahydropyrido[2,3-d]pyrimidine-2-carbaldehyde

To a round bottom flask was added 2-[(E)-2-phenylethenyl]-5,8-dihydropyrido[2,3-d]pyrimidin-7(6H)-one (600 mg, 2.39 mmol) in DMF (10 mL) and methanol (10 mL). Ozone was bubbled through the solution at room temperature for 20 minutes and the excess ozone was purged with a stream of nitrogen. Dimethyl sulfide (1.77 mL, 23.9 mmol) was added and the reaction was stirred at room temperature for 24 h. The solvent was evaporated and the resulting solid was dissolved in 20% MeOH-DCM. The crude product was added to a silica gel column and was eluted with 0-20% MeOH-DCM. The collected fractions gave the title compound (400 mg, 95% yield).

LCMS (ES+) m/z 177 (MH$^+$).
$^1$H NMR (400 MHz, DMSO-d6) δ 2.6 (t, 2H), 3.0 (t, 2H), 8.7 (s, 1H), 9.8 (s, 1H), 10.27 (brs, 1H).

Example 254

(+/−)1-(2-{3-(Aminomethyl)-4-[(2,3-dihydro[1,4]dioxino[2,3-c]pyridin-7-ylmethyl)amino]-1-piperidinyl}ethyl)-7-fluoro-2(1H)-quinoxalinone Isomer 1 Trihydrochloride

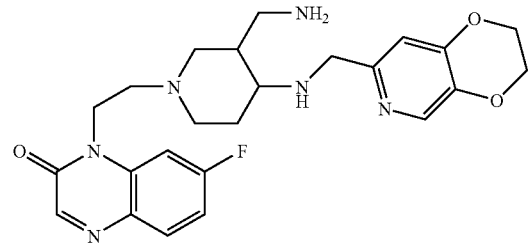

(a) Racemic ethyl 4-hydroxy-1-(phenylmethyl)-3-piperidinecarboxylate (Mixture of Cis and Trans)

To a solution of ethyl 4-oxo-1-(phenylmethyl)-3-piperidinecarboxylate hydrochloride (56.2 g, 190 mmol) in methanol (11) was added triethylamine (31.8 mL, 230 mmol) and the mixture stirred at room temperature for 10 min. Sodium borohydride (24.0 g, 630 mmol) was then added portionwise with ice cooling, and the reaction was then stirred at room temperature for 4.5 h. 5N HCl solution (200 mL) was added and the mixture was evaporated. The aqueous residue was basified with aqueous sodium bicarbonate and the extracted several times with a 9:1 dichloromethane:methanol mixture. The extracts were dried and evaporated to give the product (44.3 g, 89%) as a mixture of cis and trans isomers.

MS (+ve ion electrospray) m/z 264 (MH$^+$).

(b) Racemic 4-hydroxy-1-(phenylmethyl)-3-piperidinecarboxylic Acid

To a solution of ethyl 4-hydroxy-1-(phenylmethyl)-3-piperidinecarboxylate (30 g, 114.4 mmol) in THF/water (800 ml/80 mL) was added 2N sodium hydroxide solution (126 mL). The reaction mixture was stirred at room temperature for 5 h and then the pH was adjusted to 7 with 5N hydrochloric acid solution.

The mixture was reduced to a small volume. The residue was extracted with 10% methanol/dichloromethane and the solid was filtered off and extracted several times with 10% methanol/dichloromethane. A small volume of aqueous phase was separated from the extracts. This was evaporated to dryness and the residue was extracted as above. All the organic extracts were evaporated to give the product (25.8 g, 96%).

MS (+ve ion electrospray) m/z 236 (MH+)

(c) Racemic 4-hydroxy-1-(phenylmethyl)-3-piperidinecarboxamide

To a solution of 4-hydroxy-1-(phenylmethyl)-3-piperidinecarboxylic acid (12 g) and triethylamine (3.53 mL, 25.5 mmol) in N,N-dimethylformamide (60 mL) was added 1-hydroxy-7-azabenzotriazole (3.48 g, 25.6 mmol) and N-[3-(dimethylamino)propyl]-N'-ethylcarbodiimide hydrochloride (8.54 g, 56.2 mmol). After stirring for 5-10 min. ammonium bicarbonate (15.3 g, 204 mmol) was added. The reaction mixture was stirred at room temperature for overnight. The solvent was then removed under reduced pressure and the residue was dissolved in aqueous sodium bicarbonate and dichloromethane. The aqueous phase was extracted with 9:1 dichloromethane:methanol. The organic layer was dried and evaporated. The residue was chromatographed on silica gel, eluting with 10-20% methanol/dichloromethane, to give the desired compound (4.15 g, 35%). Impure fractions were chromatographed again to give further product (1.02 g).

MS (+ve ion electrospray) m/z 235 (MH+, 80%), 257 (100%)

(d) Racemic 3-(aminomethyl)-1-(phenylmethyl)-4-piperidinol

A suspension of 4-hydroxy-1-(phenylmethyl)-3-piperidinecarboxamide (5.62 g, 23.9 mmol) in THF (65 mL) was treated dropwise with borane-methyl sulphide complex (2M solution in THF, 26.4 mL, 52.8 mmol). After stirring for 0.5 h at room temperature, the reaction mixture was heated at 80° C. for 1.5 h. Methanol (16 mL) was added and heating continued for 0.5 h. The mixture was evaporated and the residue was chromatographed on silica gel, eluting with 10-30% (2M ammonia/methanol)/dichloromethane to give the product (2.67 g, 51%).

MS (+ve ion electrospray) m/z 221 (MH+)

(e) Racemic 1,1-dimethylethyl {[4-hydroxy-1-(phenylmethyl)-3-piperidinyl]methyl}carbamate 3-(Aminomethyl)-1-(phenylmethyl)-4-piperidinol (2.67 g, 12.1 mmol) was dissolved in dichloromethane (100 mL) and a solution of di-tert-butyl dicarbonate (2.67 g, 12.2 mmol) in dichloromethane (20 ml) was then added. The reaction mixture was stirred at room temperature for 4 h. The solvent was evaporated and the residue was chromatographed on silica gel, eluting with 0-20% (2M ammonia/methanol)/dichloromethane, to give the product (3.12 g, 81%).

MS (+ve ion electrospray) m/z 321 (MH+), 265 (loss of $C_4H_8$)

(f) Racemic 1,1-dimethylethyl {[4-hydroxy-3-piperidinyl]methyl}carbamate

A solution of 1,1-dimethylethyl {[4-hydroxy-1-(phenylmethyl)-3-piperidinyl]methyl}carbamate (3.7 g, 11.56 mmol) in methanol (70 ml) was stirred under hydrogen at room temperature with 20% palladium hydroxide/carbon (moist, 0.7 g) overnight. After filtration through kieselguhr, the methanol was evaporated to afford the desired product (2.65 g, 100%).

MS (+ve ion electrospray) m/z 231 (MH+)

(g) Racemic 1,1-dimethylethyl ({1-[2-(7-fluoro-2-oxo-1(2H)-quinoxalinyl)ethyl]-4-hydroxy-3-piperidinyl}methyl)carbamate A mixture of racemic 1,1-dimethylethyl {[4-hydroxy-3-piperidinyl]methyl}carbamate (2.65 g, 11.56 mmol) and 7-fluoro-2-oxo-1(2H)-quinoxalinyl)acetaldehyde (for a preparation see Example 34(c)) (2.39 g, 11.6 mmol) in dichloromethane (75 mL) and methanol (3.8 mL) was stirred at room temperature for 1 h. sodium triacetoxyborohydride (7.39 g, 34.67 mmol) was added and stirring was continued for 4 h. Aqueous sodium bicarbonate was added to basify and the phases were separated. The aqueous phase was extracted twice with 10% methanol/dichloromethane and the organic fractions were dried and evaporated. Chromatography on silica, eluting with 0-20% methanol/ethyl acetate gave the product (3.32 g, 68%).

MS (+ve ion electrospray) m/z 421 (MH+)

(h) Racemic 1,1-dimethylethyl ({1-[2-(7-fluoro-2-oxo-1(2H)-quinoxalinyl)ethyl]-4-oxo-3-piperidinyl}methyl)carbamate To a solution of racemic 1,1-dimethylethyl ({1-[2-(7-fluoro-2-oxo-1(2H)-quinoxalinyl)ethyl]-4-hydroxy-3-piperidinyl}methyl)carbamate (2.0 g, 4.76 mmol) in dry dichloromethane (120 mL) was added Dess-Martin periodinane (1,1,1-tris(acetyloxy)-1,1-dihydro-1,2-benziodoxol-3-(1H)-one, 3.03 g, 7.12 mmol) in portions over 5 min. The mixture was stirred for 1 h, then 10% aqueous sodium sulphite (70 mL) and aqueous sodium bicarbonate (60 mL) were added and stirring continued for 0.5 h. The phases were separated and the aqueous phase was extracted twice with dichloromethane. The organic fractions were dried and evaporated and the residue was chromatographed on silica, eluting with 50-100% ethyl acetate/hexane, to give the product (1.35 g, 68%).

MS (+ve ion electrospray) m/z 441 (Mna+), 459 ([M+$H_2O$]Na+)

(i) Racemic 1,1-dimethylethyl ({4-[(2,3-dihydro[1,4]dioxino[2,3-c]pyridin-7-ylmethyl)amino]-1-[2-(7-fluoro-2-oxo-1(2H)-quinoxalinyl)ethyl]-3-piperidinyl}methyl)carbamate Isomers 1 and 2

A mixture of racemic 1,1-dimethylethyl ({1-[2-(7-fluoro-2-oxo-1(2H)-quinoxalinyl)ethyl]-4-oxo-3-piperidinyl}methyl)carbamate (1.35 g, 3.23 mmol) and (2,3-dihydro[1,4]dioxino[2,3-c]pyridin-7-ylmethyl)amine (0.54 g, 3.23 mmol, prepared from 2,3-dihydro[1,4]dioxino[2,3-c]pyridin-7-ylmethanol (for a synthesis see WO2004002490, Example 6(b)) by reaction with diphenylphosphoryl azide and 1,8 diazabicyclo[5.4.0]undec-7-ene in toluene, 0° C.-room temperature, followed by hydrogenation of the resulting azide over 5% palladium/carbon paste in 200:1 ethanol/acetic acid) in dichloromethane (30 mL) and methanol (3 mL) was stirred with 3A molecular sieves for 1 h. Sodium triacetoxyborohydride (2.05 g, 9.69 mmol) was added and stirring continued at room temperature. More borohydride was added after 6 h (0.20 g), and after an overnight period more amine (0.20 g) and borohydride (0.80 g) were added. After stirring for a further 6 h, aqueous sodium bicarbonate was added and the phases were separated. The aqueous phase was extracted twice with 10% methanol/dichloromethane and the organic fractions were dried and evaporated. Chromatography on silica, eluting with 0-20% methanol/dichloromethane, gave firstly a major product (Isomer1, 1.12 g, 61%), followed by a minor product (Isomer 2, 0.10 g, 5% of good purity, plus 0.17 g less pure).

MS (+ve ion electrospray) m/z 569 (MH+)

(j) Title Compound

Racemic 1,1-dimethylethyl ({4-[(2,3-dihydro[1,4]dioxino[2,3-c]pyridin-7-ylmethyl)amino]-1-[2-(7-fluoro-2-oxo-1(2H)-quinoxalinyl)ethyl]-3-piperidinyl}methyl)carbamate Isomer 1 (0.05 g, 0.09 mmol) in dichloromethane (2 mL) and methanol (1 mL) was treated dropwise with 4M hydrogen chloride in 1,4-dioxane (2 mL) and the mixture was stirred at room temperature for 2.5 h, then evaporated to give the title compound (50 mg).

MS (+ve ion electrospray) m/z 469 (MH+)

Example 257

(+/−)1-(2-{3-(Aminomethyl)-4-[(2,3-dihydro [1,4]dioxino[2,3-c]pyridin-7-ylmethyl)amino]-1-piperidinyl}ethyl)-7-fluoro-2(1H)-quinoxalinone Isomer 2 trihydrochloride

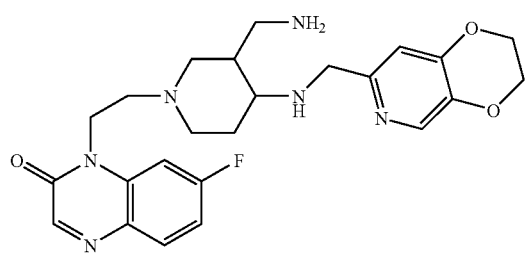

Racemic 1,1-dimethylethyl ({4-[(2,3-dihydro[1,4]dioxino[2,3-c]pyridin-7-ylmethyl)amino]-1-[2-(7-fluoro-2-oxo-1(2H)-quinoxalinyl)ethyl]-3-piperidinyl}methyl)carbamate Isomer 2 (approx. 80% pure, 0.05 g, 0.09 mmol) in dichloromethane (2 mL) and methanol (1 mL) was treated dropwise with 4M hydrogen chloride in 1,4-dioxane (2 mL) and the mixture was stirred at room temperature for 2.5 h, then evaporated. The residue was treated with aqueous sodium bicarbonate and extracted several times with 10% methanol/dichloromethane. The extracts were dried and evaporated. Chromatography on silica, eluting with 0-30% (2M ammonia in methanol)/dichloromethane, gave the free base of the title compound (29 mg. 62%).

MS (+ve ion electrospray) m/z 469 (MH+)

The free base of the title compound in dichloromethane was treated with 0.4M hydrogen chloride in 1,4-dioxane (0.46 mL) and solvent was evaporated to give the trihydrochloride salt (42 mg).

Example 258

Racemic 1-[2-(4-amino-3-{[(2,3-dihydro [1,4]dioxino [2,3-c]pyridin-7-ylmethyl)amino]methyl}-1-piperidinyl)ethyl]-7-fluoro-2(1H)-quinoxalinone Trihydrochloride

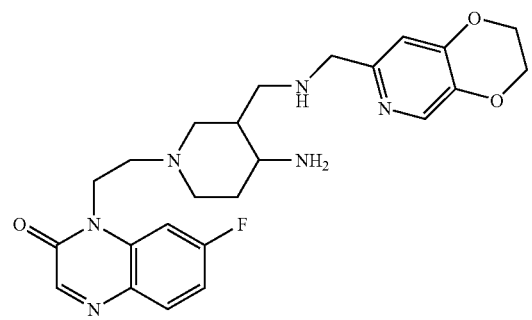

(a) 1-[2-(3-{[(2,3-Dihydro[1,4]dioxino[2,3-c]pyridin-7-ylmethyl)amino]methyl}-4-hydroxy-1-piperidinyl)ethyl]-7-fluoro-2(1H)-quinoxalinone Racemic 1,1-dimethylethyl ({1-[2-(7-fluoro-2-oxo-1(2H)-quinoxalinyl)ethyl]-4-hydroxy-3-piperidinyl}methyl)carbamate (for a preparation see Example 254(h)) (1.3 g, 3.14 mmol) was treated with trifluoroacetic acid (12 mL) in dichloromethane (30 mL) at room temperature for 1.5 h. Removal of solvent, trituration with ether and treatment with MP-carbonate resin in 10% methanol/dichloromethane gave, after removal of solvent, 1{2-[3-(aminomethyl)-4-hydroxy-1-piperidinyl]ethyl}-7-fluoro-2(1H)-quinoxalinone (1.31 g, approx. 77% pure). This material was heated under reflux with 2,3-dihydro[1,4]dioxino[2,3-c]pyridine-7-carbaldehyde (for a synthesis see WO2004058144, Example 2(c) or WO03/087098, Example 19(d)) (0.52 g, 3.14 mmol) and 3A molecular sieves in 1:1 chloroform/methanol (80 mL) overnight, then sodium triacetoxyborohydride (3.28 g, 15. mmol) was added and the mixture was stirred at room temperature for 8 h. Basification with aqueous sodium bicarbonate, extraction with 10% methanol/dichloromethane and chromatography on silica eluting with 0-20% methanol/dichloromethane, then with 0-20% (2M ammonia/methanol)/dichloromethane, gave the product (0.57 g, 37%).

MS (+ve ion electrospray) m/z 470 (MH+)

(b) 1,1-Dimethylethyl (2,3-dihydro[1,4]dioxino[2,3-c]pyridin-7-ylmethyl)({1-[2-(7-fluoro-2-oxo-1(2H)-quinoxalinyl)ethyl]-4-oxo-3-piperidinyl}methyl)carbamate 1-[2-(3-{[(2,3-Dihydro[1,4]dioxino[2,3-c]pyridin-7-ylmethyl)amino]methyl}-4-hydroxy-1-piperidinyl)ethyl]-7-fluoro-2(1H)-quinoxalinone (0.54 g, 1.15 mmol) was stirred with di-tert-butyl dicarbonate (0.27 g, 1.2 mmol) in dichloromethane (20 mL) at room temperature overnight. The mixture was washed with aqueous sodium bicarbonate, solvent was removed and the residue was chromatographed on silica, eluting with 0-10% methanol/dichloromethane, to give two isomers of 1,1-dimethylethyl (2,3-dihydro[1,4]dioxino[2,3-c]pyridin-7-ylmethyl)({1-[2-(7-fluoro-2-oxo-1(2H)-quinoxalinyl)ethyl]-4-hydroxy-3-piperidinyl}methyl)carbamate (total 0.527 g, 80%). This material was stirred with Dess-Martin periodinane (1,1,1-tris(acetyloxy)-1,1-dihydro-1,2-benziodoxol-3-(1H)-one, 0.59 g, 1.39 mmol) in dichloromethane (25 mL) at room temperature for 2.25 h. The mixture was treated with aqueous sodium sulphite and sodium bicarbonate (15 mL each) for 0.5 h. Separation of the phases, extraction of the aqueous phase with dichloromethane, and evaporation of the organic fractions gave a residue which was chromatographed on silica, eluting with 0-10% methanol/dichloromethane, then again eluting with 0-10%/meoh/ethyl acetate, to give the product 90.23 g, 44%).

MS (+ve ion electrospray) m/z 568 (MH+)

(c) 1,1-Dimethylethyl ({4-amino-1-[2-(7-fluoro-2-oxo-1(2H)-quinoxalinyl)ethyl]-3-piperidinyl}methyl)(2,3-dihydro[1,4]dioxino[2,3-c]pyridin-7-ylmethyl)carbamate A mixture of 1,1-dimethylethyl (2,3-dihydro[1,4]dioxino[2,3-c]pyridin-7-ylmethyl)({1-[2-(7-fluoro-2-oxo-1(2H)-quinoxalinyl)ethyl]-4-oxo-3-piperidinyl}methyl)carbamate (0.23 g, 0.41 mmol) and ammonium acetate (0.31 g, 4.1 mmol) in 1:1 dichloromethane/methanol (10 mL) was stirred for 4 h before addition of sodium triacetoxyborohydride (0.53 g, 2.5 mmol). Stirring was continued over two nights, with further additions of borohydride (as above) after the first overnight period, and again after another 7 h. Basification with sodium bicarbonate, extraction with 10% methanol/dichloromethane, evaporation of the organic fractions and chromatography on silica, eluting with 0-20% (2M ammonia/methanol)/dichloromethane, gave the product (0.11 g, 47%).

MS (+ve ion electrospray) m/z 569 (MH+)

(d) Title Compound 1,1-Dimethylethyl ({4-amino-1-[2-(7-fluoro-2-oxo-1(2H)-quinoxalinyl)ethyl]-3-piperidinyl}methyl)(2,3-dihydro[1,4]dioxino[2,3-c]pyridin-7-ylmethyl)carbamate (0.10 g, 0.21 mmol) was treated with trifluoroacetic acid in dichloromethane by the general method of part (a). After the treatment with MP-carbonate resin and removal of solvent, the crude material was chromatographed on silica, eluting with 0-20% (2M ammonia/methanol)/dichloromethane, to give the product free base as the second-eluted compound. This was further purified by automated HPLC with mass-directed fraction-collection (monitoring for Mw 468). After evaporation of eluent, the residue was treated with excess 0.4M hydrogen chloride in 1,4-dioxane and methanol. Evaporation of the solvent gave the title trihydrochloride salt (30 mg).

MS (+ve ion electrospray) m/z 469 (MH+)

TABLE 6

Examples 282-307 were prepared from the specified starting materials by the general method of Example 121 (c)-(e).

| Example number | Form tested | Structure | Starting materials (for a preparation see referenced Examples) |
|---|---|---|---|
| 282 | Free base MS (ES+) m/z 403 (MH+) | 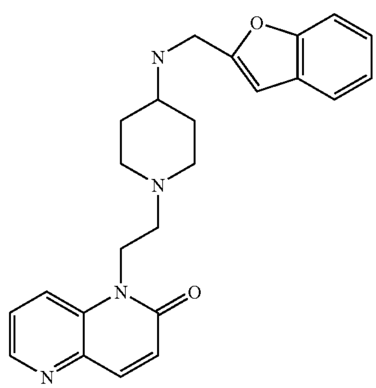 | (2-oxo-1,5-naphthyridin-1(2H)-yl)acetaldehyde (obtainable from 1,5-naphthyridin-2(1H)-one (Reference: J. Chem. Soc., 212-214, 1956)*, which was first treated with sodium hydride and then with allyl iodide to give 1-(2-propen-1-yl)-1,5-naphthyridin-2(1H)-one which was then treated with OsO4/NaIO4 to yield the title compound. 1,1-Dimethylethyl 4-piperidinylcarbamate 1-benzofuran-2-carbaldehyde (commercially available) |
| 283 | Free base MS (ES+) m/z 420 (MH+) | 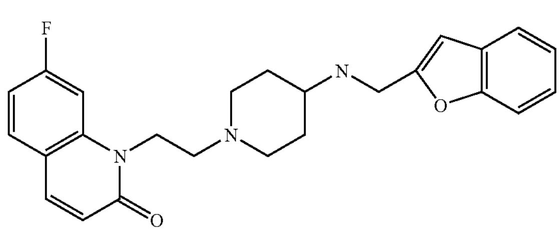 | (7-fluoro-2-oxo-1(2H)-quinolinyl)acetaldehyde (Example 2(d)) 1,1-Dimethylethyl 4-piperidinylcarbamate 1-benzofuran-2-carbaldehyde |

TABLE 6-continued

Examples 282-307 were prepared from the specified starting materials by the general method of Example 121 (c)-(e).

| Example number | Form tested | Structure | Starting materials (for a preparation see referenced Examples) |
|---|---|---|---|
| 284 | Free base MS (ES+) m/z 432 (MH+) | 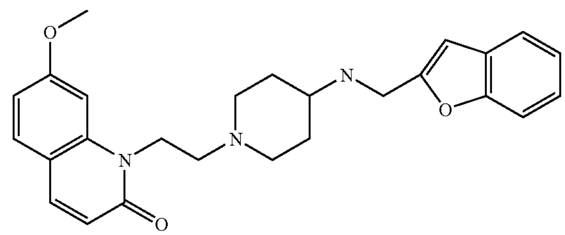 | 1-[2-(4-amino-1-piperidinyl)ethyl]-7-(methyloxy)-2(1H)-quinolinone. Obtainable as described in Example 12 (a-b)** 1-benzofuran-2-carbaldehyde(commercially available) |
| 285 | Free base MS (ES+) m/z 433 (MH+) | 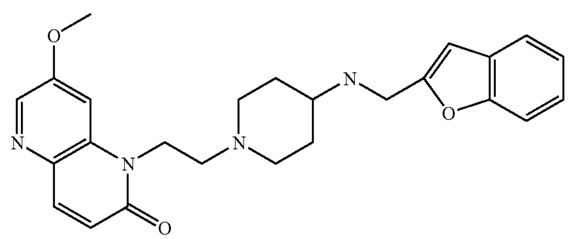 | [7-(methyloxy)-2-oxo-1,5-naphthyridin-1(2H)-yl]acetaldehyde (as the methyl hemiacetal) (Example 11(e)) 1,1-Dimethylethyl 4-piperidinylcarbamate 1-benzofuran-2-carbaldehyde(commercially available) |
| 286 | Free base MS (ES+) m/z 449 (MH+) | 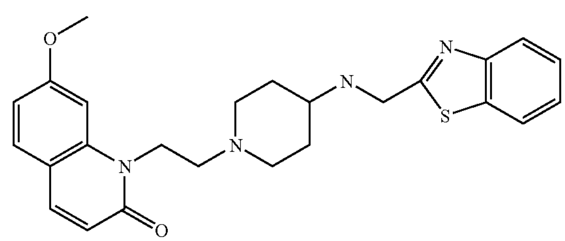 | 1-[2-(4-amino-1-piperidinyl)ethyl]-7-(methyloxy)-2(1H)-quinolinone. Obtainable as described in Example 12 (a-b)** 1,3-benzothiazole-2-carbaldehyde(commercially available) |
| 287 | Free base MS (ES+) m/z 437 (MH+) | 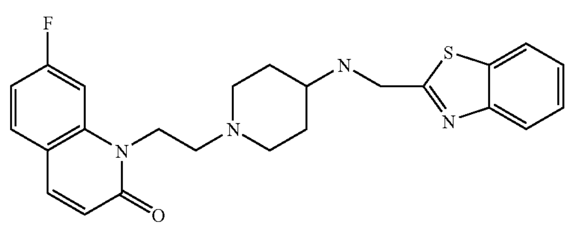 | (7-fluoro-2-oxo-1(2H)-quinolinyl)acetaldehyde (Example 2(d)) 1,1-Dimethylethyl 4-pipendinylcarbamate 1,3-benzothiazole-2-carbaldehyde(commercially available) |
| 288 | Free base MS (ES+) m/z 402 (MH+) | 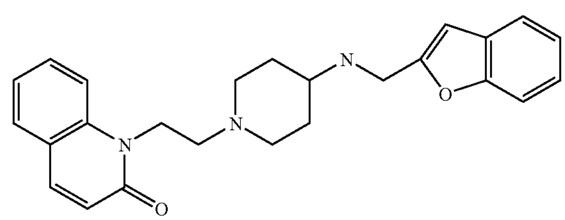 | (2-oxo-1(2H)-quinolinyl)acetaldehyde (obtainable by reacting commercially available 2(1H)-quinolinone with sodium hydride and then with ethyl iodoacetate to give ethyl (2-oxo-1(2H)-quinolinyl)acetate. This was then reduced with sodium borohydride to give 1-(2-hydroxyethyl)-2(1H)-quinolinone, which was treated with Dess-Martin periodinane to yield the title compound. 1,1-Dimethylethyl 4-piperidinylcarbamate 1-benzofuran-2-carbaldehyde(commercially available) |

TABLE 6-continued

Examples 282-307 were prepared from the specified starting materials by the general method of Example 121 (c)-(e).

| Example number | Form tested | Structure | Starting materials (for a preparation see referenced Examples) |
|---|---|---|---|
| 289 | Free base MS (ES+) m/z 452 (MH+) | 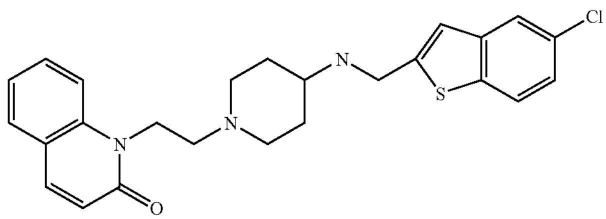 | (2-oxo-1(2H)-quinolinyl)acetaldehyde. (Obtainable as described in Example 288) 1,1-Dimethylethyl 4-piperidinylcarbamate 5-chloro-1-benzothiophene-2-carbaldehyde (Ref. Bioorganic & Medicinal Chemistry, 12(9), 2251-2273; 2004) |
| 290 | Free base MS (ES+) m/z 453 (MH+) | 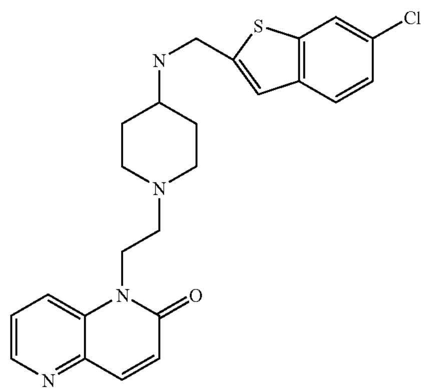 | (2-oxo-1,5-naphthyridin-1(2H)-yl)acetaldehyde. (Obtainable as described in Example 282) 1,1-Dimethylethyl 4-piperidinylcarbamate 6-chloro-1-benzothiophene-2-carbaldehyde(commercially available) |
| 291 | Free base MS (ES+) m/z 414 (MH+) | 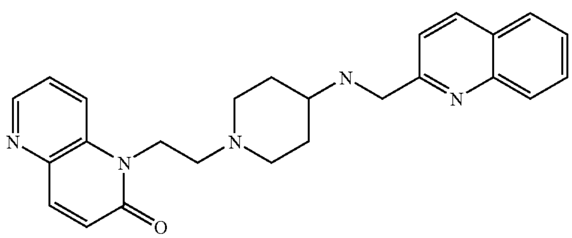 | (2-oxo-1,5-naphthyridin-1(2H)-yl)acetaldehyde. (Obtainable as described in Example 282) 1,1-Dimethylethyl 4-piperidinylcarbamate 2-quinolinecarbaldehyde |
| 292 | Free base MS (ES+) m/z 404 (MH+) | 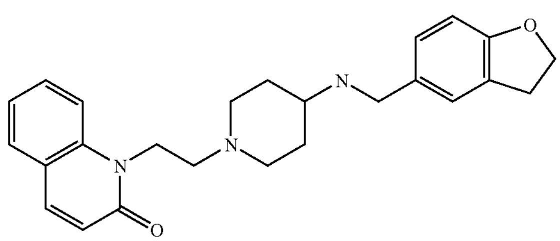 | (2-oxo-1(2H)-quinolinyl)acetaldehyde. (Obtainable as described in Example 288) 1,1-Dimethylethyl 4-piperidinylcarbamate 2,3-dihydro-1-benzofuran-5-carbaldehyde(commercially available) |
| 293 | Free base MS (ES+) m/z 422 (MH+) | 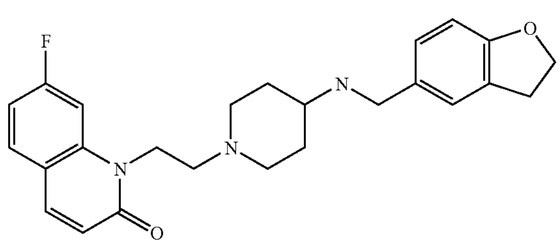 | (7-fluoro-2-oxo-1(2H)-quinolinyl)acetaldehyde (Example 2(d)) 1,1-Dimethylethyl 4-piperidinylcarbamate 2,3-dihydro-1-benzofuran-5-carbaldehyde (commercially available) |

TABLE 6-continued

Examples 282-307 were prepared from the specified starting materials by the
general method of Example 121 (c)-(e).

| Example number | Form tested | Structure | Starting materials (for a preparation see referenced Examples) |
|---|---|---|---|
| 294 | Free base MS (ES+) m/z 419 (MH+) | 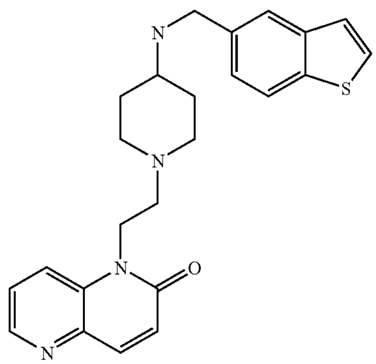 | (2-oxo-1,5-naphthyridin-1(2H)-yl)acetaldehyde. (Obtainable as described in Example 282) 1,1-Dimethylethyl 4-piperidinylcarbamate 1-benzothiophene-5-carbaldehyde(commercially available) |
| 295 | Free base MS (ES+) m/z 418 (MH+) | 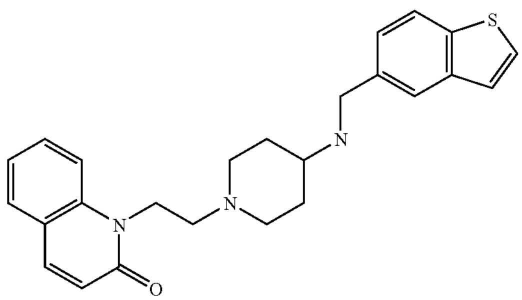 | (2-oxo-1(2H)-quinolinyl)acetaldehyde (Obtainable as described in Example 288) 1,1-Dimethylethyl 4-piperidinylcarbamate 1-benzothiophene-5-carbaldehyde(commercially available) |
| 296 | Free base MS (ES+) m/z 436 (MH+) | 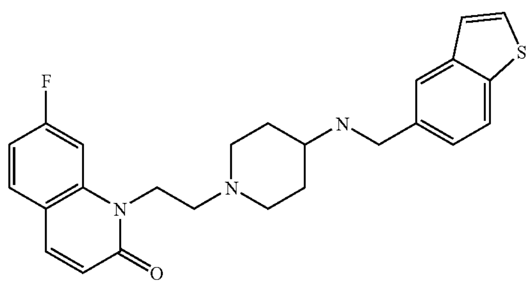 | (7-fluoro-2-oxo-1(2H)-quinolinyl)acetaldehyde (Example 2(d)) 1,1-Dimethylethyl 4-piperidinylcarbamate 1-benzothiophene-5-carbaldehyde(commercially available) |
| 297 | Free base MS (ES+) m/z 448 (MH+) | 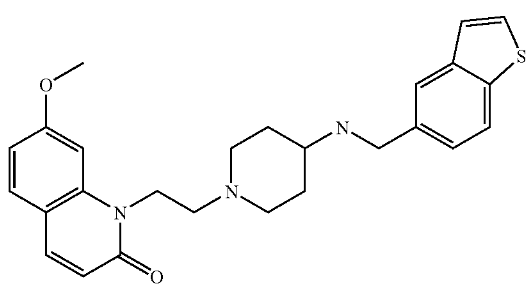 | 1-[2-(4-amino-1-piperidinyl)ethyl]-7-(methyloxy)-2(1H)-quinolinone. Obtainable as described in Example 12 (a-b)** 1-benzothiophene-5-carbaldehyde(commercially available) |
| 298 | Free base MS (ES+) m/z 449 (MH+) | 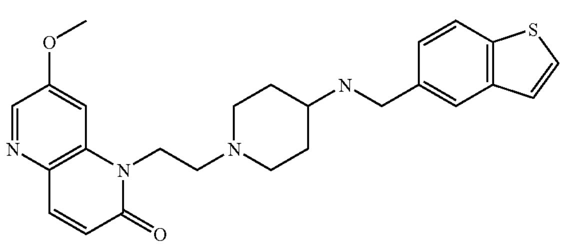 | [7-(methyloxy)-2-oxo-1,5-naphthyridin-1(2H)-yl]acetaldehyde (as the methyl hemiacetal) (Example 11(e)) 1,1-Dimethylethyl 4-piperidinylcarbamate 1-benzothiophene-5-carbaldehyde(commercially available) |

TABLE 6-continued

Examples 282-307 were prepared from the specified starting materials by the general method of Example 121 (c)-(e).

| Example number | Form tested | Structure | Starting materials (for a preparation see referenced Examples) |
|---|---|---|---|
| 299 | Free base MS (ES+) m/z 421 (MH⁺) | 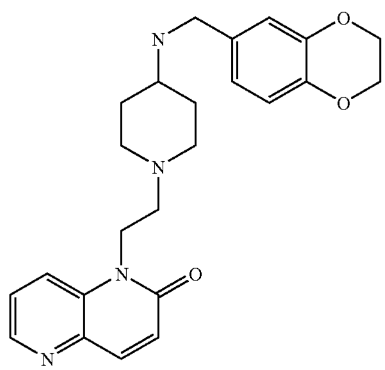 | (2-oxo-1,5-naphthyridin-1(2H)-yl)acetaldehyde. (Obtainable as described in Example 282) 1,1-Dimethylethyl 4-piperidinylcarbamate 2,3-dihydro-1,4-benzodioxin-6-carbaldehyde(commercially available) |
| 300 | Free base MS (ES+) m/z 451 (MH⁺) | 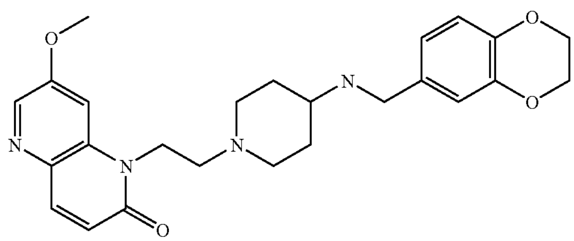 | [7-(methyloxy)-2-oxo-1,5-naphthyridin-1(2H)-yl]acetaldehyde (as the methyl hemiacetal) (Example 11(e)) 1,1-Dimethylethyl 4-piperidinylcarbamate 2,3-dihydro-1,4-benzodioxin-6-carbaldehyde(commercially available) |
| 301 | Free base MS (ES+) m/z 435 (MH⁺) | 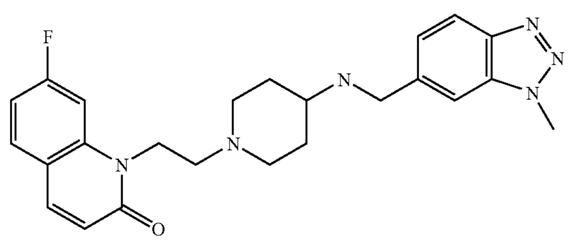 | (7-fluoro-2-oxo-1(2H)-quinolinyl)acetaldehyde (Example 2(d)) 1,1-Dimethylethyl 4-piperidinylcarbamate 1-methyl-1H-1,2,3-benzotriazole-6-carbaldehyde (Ref. WO 2004007491 A1) |
| 302 | Free base MS (ES+) m/z 447 (MH⁺) | 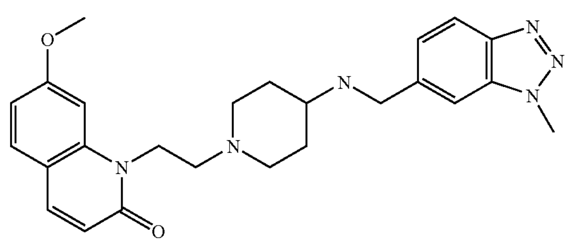 | 1-[2-(4-amino-1-piperidinyl)ethyl]-7-(methyloxy)-2(1H)-quinolinone. Obtainable as described in Example 12 (a-b)** 1-methyl-1H-1,2,3-benzotriazole-6-carbaldehyde(commercially available) |
| 303 | Free base MS (ES+) m/z 409 (MH⁺) | 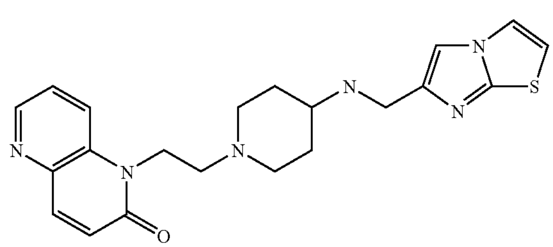 | (2-oxo-1,5-naphthyridin-1(2H)-yl)acetaldehyde. (Obtainable as described in Example 282) 1,1-Dimethylethyl 4-piperidinylcarbamate imidazo[2,1-b][1,3]thiazole-6-carbaldehyde(commercially available) |

TABLE 6-continued

Examples 282-307 were prepared from the specified starting materials by the general method of Example 121 (c)-(e).

| Example number | Form tested | Structure | Starting materials (for a preparation see referenced Examples) |
|---|---|---|---|
| 304 | Free base MS (ES+) m/z 464 (MH+) | 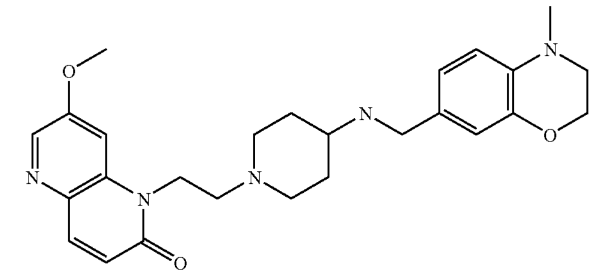 | [7-(methyloxy)-2-oxo-1,5-naphthyridin-1(2H)-yl]acetaldehyde (as the methyl hemiacetal) (Example 11(e)) 1,1-Dimethylethyl 4-piperidinylcarbamate 4-methyl-3,4-dihydro-2H-1,4-benzoxazine-7-carbaldehyde(commercially available) |
| 305 | Free base MS (ES+) m/z 461 (MH+) | 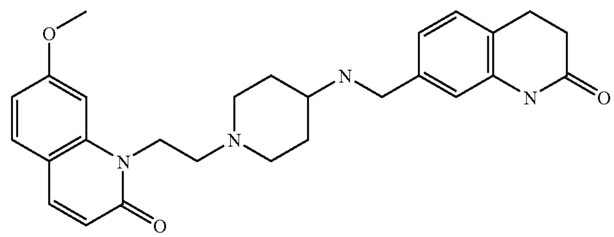 | 1-[2-(4-amino-1-piperidinyl)ethyl]-7-(methyloxy)-2(1H)-quinolinone. Obtainable as described in Example 12 (a-b)* 2-oxo-1,2,3,4-tetrahydro-7-quinolinecarbaldehyde (Ref. WO 2006137485 A1 p. 225, para [0489] 295) |
| 306 | Free base MS (ES+) m/z 462 (MH+) | 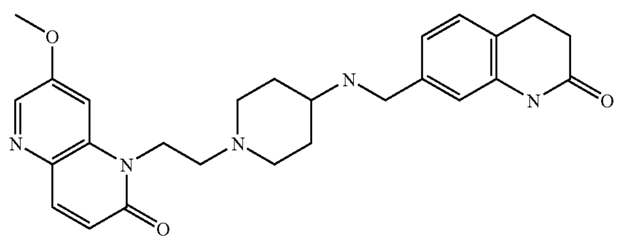 | [7-(methyloxy)-2-oxo-1,5-naphthyridin-1(2H)-yl]acetaldehyde (as the methyl hemiacetal) (Example 11(e)) 1,1-Dimethylethyl 4-piperidinylcarbamate 2-oxo-1,2,3,4-tetrahydro-7-quinolinecarbaldehyde(commercially available) |
| 307 | Free base MS (ES+) m/z 416 (MH+) | 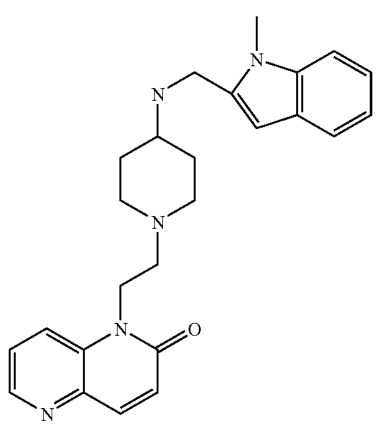 | (2-oxo-1,5-naphthyridin-1(2H)-yl)acetaldehyde. (Obtainable as described in Example 282) 1,1-Dimethylethyl 4-piperidinylcarbamate 1-methyl-1H-indole-2-carbaldehyde(commercially available) |

*1,5-naphthyridin-2(1H)-one is also obtainable by dehalogenation of 8-bromo-2-(methyloxy)-1,5-naphthyridine by treatment with 10% H2 Pd/C in EtOH and subsequent hydrolysis with 6N HCl to afford the title compound in 76% yield

**This compound can also be obtained by treatment of 7-(Methyloxy)quinoline (Example 1 (a)) with sodium hydride and then with 1,1-dimethylethyl [1-(2-chloroethyl)-4-piperidinyli-carbamate. This chloroethyl lcarbamate was obtained in a single step by reductive amination of chloroacetaldehyde and 1,1-Dimethylethyl 4-piperidinylcarbamate using NaBH(OAc)3 as reducing agent

TABLE 7

Unless otherwise stated, Examples 308-317 were made from the specified starting materials by the general method of Example 121 (c)-(e) for tert-butoxycarbonyl protected central units or by the general method of Example 61 (b)-(d) for benzyloxycarbonyl protected central units.

| Example number | Form tested | Stucture | Starting materials (for a preparation see referenced Examples) |
| --- | --- | --- | --- |
| 308 | Trifluoroacetate MS (ES+) m/z 483 (MH+) | | [3-(Methyloxy)-6-oxopyrido[2,3-b]pyrazin-5(6H)-yl]acetaldehyde (Example 94(m)) Phenylmethyl {[(3R,4R)-4-hydroxy-3-piperidinyl]methyl}carbamate (Example 135(f)) 2,3-Dihydro[1,4]dioxino[2,3-c]pyridine-7-carboxaldehyde (WO2004058144, Example 2(c) or WO03/087098, Example 19(d)) |
| 309 | Trifluoroacetate MS (ES+) m/z 450 (MH+) | | [6-(Methyloxy)-3-oxopyrido[2,3-b]pyrazin-4(3H)-yl]acetaldehyde [3 (Example 126(e)) 1,1-Dimethylethyl 4-piperidinylcarbamate 5,6,7,8-Tetrahydro-2-quinazolinecarbaldehyde (obtainable by condensation of cycloxehanone and methyl formate in the presence of sodium methoxide to give (2E)-2-(hydroxymethylidene)cyclohexanone sodium salt. Condensation of (2E)-2-(hydroxymethylidene)cyclohexanone sodium salt with (2E)-3-phenyl-2-propenimidamide (see Example 126(g)) in ethanol at 80° C. gave 2-[(E)-2-phenylethenyl]-5,6,7,8-tetrahydroquinazoline. Ozonolysis of 2-[(E)-2-phenylethenyl]-5,6,7,8-tetrahydroquinazoline gave desired 5,6,7,8-tetrahydro-2-quinazolinecarbaldehyde). |
| 310 | triftuoroacetate MS (ES+) m/z 452 (MH+) | | [7-(Methyloxy)-2-oxo-1(2H)-quinolinyl]acetaldehyde (Example 1(d)) 1,1-Dimethylethyl 4-piperidinylcarbamate 6,7-Dihydro[1,4]dioxino[2,3-d]pyrimidine-2-carbaldehyde (WO2004014361, intermediate 8) |

TABLE 7-continued

Unless otherwise stated, Examples 308-317 were made from the specified starting materials by the general method of Example 121 (c)-(e) for tert-butoxycarbonyl protected central units or by the general method of Example 61 (b)-(d) for benzyl-oxycarbonyl protected central units.

| Example number | Form tested | Structure | Starting materials (for a preparation see referenced Examples) |
|---|---|---|---|
| 311 | di-HCl<br>MS (ES+)<br>m/z 466<br>(MH+) | 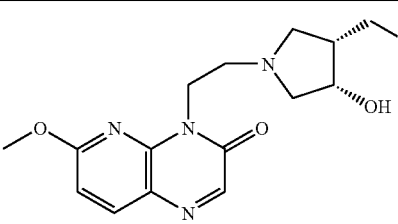 | [6-(Methyloxy)-3-oxopyrido[2,3-b]pyrazin-4(3H)-yl]acetaldehyde (Example 126(e))<br>Phenylmethyl {[(3R,4S)-4-hydroxy-3-pyrrolidinyl]methyl}carbamate 5,6,7,8-tetrahydro-2-quinazolinecarbaldehyde (Example 309) |
| 312 | di-trifluoroacetate<br>MS (ES+)<br>m/z 467<br>(MH+) | 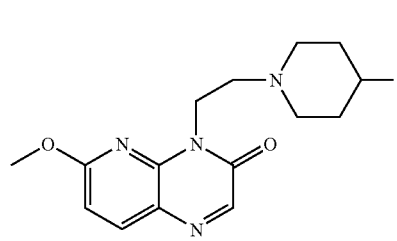 | [6-(Methyloxy)-3-oxopyrido[2,3-b]pyrazin-4(3H)-yl]acetaldehyde (Example 126(e))<br>1,1-Dimethylethyl 4-piperidinylcarbamate 7-Oxo-6,7-dihydro-1H-pyrimido[5,4-b][1,4]oxazine-2-carbaldehyde (Preparation F) |
| 313 | di-HCl<br>MS (ES+)<br>m/z 454<br>(MH+) | 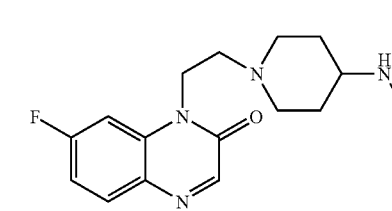 | 7-Fluoro-2-oxo-1(2H)-quinoxalinyl)acetaldehyde (Example 34(c))<br>1,1-Dimethylethyl 4-piperidinylcarbamate 7-Oxo-6,7-dihydro-1H-pyrimido[5,4-b][1,4]oxazine-2-carbaldehyde (Preparation F) |
| 314 | di-HCl<br>MS (ES+)<br>m/z 483<br>(MH+) | 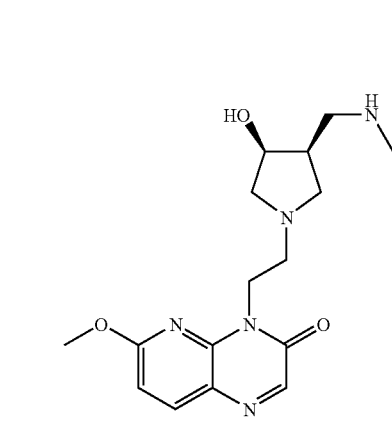 | [6-(Methyloxy)-3-oxopyrido[2,3-b]pyrazin-4(3H)-yl]acetaldehyde (Example 126(e))<br>Phenylmethyl {[(3R,4S)-4-hydroxy-3-pyrrolidinyl]methyl}carbamate 7-Oxo-6,7-dihydro-1H-pyrimido[5,4-b][1,4]oxazine-2-carbaldehyde (Preparation F) |
| 315 | Mono HCl<br>MS (ES+)<br>m/z 468<br>(MH+) | 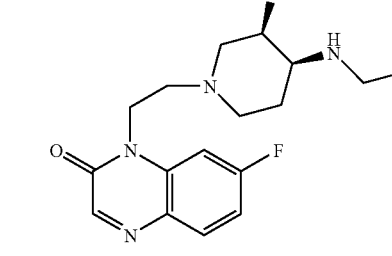 | 7-Fluoro-2-oxo-1(2H)-quinoxalinyl)acetaldehyde (Example 34(c))<br>1,1-Dimethylethyl[(3R,4S)-3-hydroxy-4-piperidinyl]carbamate (for a synthesis see WO2004058144, Example 5(c), cis-(3-hydroxy-piperidin-4-yl)-carbamic acid tert-butyl ester Enantiomer 1)<br>7-Oxo-5,6,7,8-tetrahydropyrido[2,3-d]pyrimidine-2-carbaldehyde (Example 125(c)) |

TABLE 7-continued

Unless otherwise stated, Examples 308-317 were made from the specified starting materials by the general method of Example 121 (c)-(e) for tert-butoxycarbonyl protected central units or by the general method of Example 61 (b)-(d) for benzyloxycarbonyl protected central units.

| Example number | Form tested | Stucture | Starting materials (for a preparation see referenced Examples) |
|---|---|---|---|
| 316 | di-HCl MS (ES+) m/z 483 (MH+) | | [6-(Methyloxy)-3-oxopyrido[2,3-b]pyrazin-4(3H)-yl]acetaldehyde (Example 126(e)) Phenylmethyl {[(3R,4S)-4-hydroxy-3-pyrrolidinyl]methyl}carbamate 6-Oxo-6,7-dihydro-5H-pyridazino[3,4-b][1,4]oxazine-3-carbaldehyde(made analogously to 6-oxo-6,7-dihydro-5H-pyridazino[3,4-b][1,4]thiazine-3-carbaldehyde (WO 2004/058144 Example 58(d)) but replacing methyl mercaptoacetate with methyl glycolate |
| 317 | di-HCl MS (ES+) m/z 467 (MH+) | | [6-(Methyloxy)-3-oxopyrido[2,3-b]pyrazin-4(3H)-yl]acetaldehyde (Example 126(e)) 1,1-Dimethylethyl 4-piperidinylcarbamate 6-Oxo-6,7-dihydro-5H-pyridazino[3,4-b][1,4]oxazine-3-carbaldehyde (Example 316) |

Biological Activity

Antimicrobial Activity Assay:

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically". The compounds were tested in serial two-fold dilutions ranging from 0.016 to 16 mcg/mL.

Compounds were evaluated against Gram-positive organisms, selected from *Staphylococcus aureus, Streptococcus pneumoniae, Streptococcus pyogenes, Enterococcus faecalis* and *Enterococcus faecium*.

In addition, compounds were evaluated against Gram-negative organisms selected from *Haemophilus influenzae, Moraxella catarrhalis, Escherichia coli, Pseudomonas aeruginosa, Proteus mirabilis, Legionella pneumophila, Chlamydia pneumoniae, Enterobacter cloacae, Enterobacter aerogenes, Klebsiella pneumoniae, Stenotrophomonas maltophilia* and *Mycoplasma pneumoniae*.

The *L. pneumophila* isolates were tested using a modified CLSI procedure for broth microdilution. For this assay, compounds were tested in serial doubling dilutions over a concentration range of 0.03 to 32 mcg/mL. An inoculum of each test isolate was prepared in buffered yeast broth and adjusted to a density equivalent to a 0.5 McFarland standard. After inoculation, the microtitre plates were incubated at 37° C. for 72 hours.

For the *C. pneumoniae* isolates, stocks were thawed and diluted in CCM (*Chlamydia* Culture Media) to yield an inoculum containing ~1×10$^4$ inclusion forming units/ml (IFUs/ml). A 100 µL aliquot of the inoculum was added to all wells of a microtitre plate containing HEp-2 (Human Epithelial (pharyngeal) cell line) cells grown to confluence. Microtitre plates were centrifuged for 1 hour at 1700 g., then incubated for 1 hour at 35° C. in 5% $CO_2$. One hundred microliters of diluted test compounds, prepared as a 2-fold dilution series in CCM/cycloheximide was then added to the microtiter plates. After 72 hours incubation at 35° C. in 5% $CO_2$, the microtitre plates were stained with a murine monoclonal fluorescein-conjugated antibody (Kallestad Cat. #532 Roche Biomedical Products) in accordance with the manufacturer recommendations. Upon staining, the IFUs produced an apple-green color, visible against the red counter stained HEp-2 cells when viewed at 100× magnification. The MIC was defined as the lowest concentration of compound at which no IFUs were seen.

*M. pneumoniae* MICs were determined using the method described by Tanner and Wu [1992]. This method was a modified to allow the approximate titres of the challenge inoculum to be pre-determined and set at a target of 10$^4$ cfu/mL for the assay with tolerance of 10$^3$-10$^5$ cfu/ml.

The minimum inhibitory concentration (MIC) was determined as the lowest concentration of compound that inhibited visible growth. A mirror reader was used to assist in determining the MIC endpoint.

Each of the listed Examples, as identified in the present application, was tested in at least one exemplified salt form. Unless otherwise noted, the listed Examples had a MIC≦2 μg/ml against a strain of at least one of the organisms listed above, with the exception of Examples 156, 274 and 303 which had an MIC≧8 μg/ml and Example 183 which had an MIC=16 μg/ml against a strain of at least one of the organisms listed above, and Example 272 which showed no activity against the listed organisms at ≦16 μg/ml. For at least one strain of every organism listed above, at least one Example had a MIC≦2 μg/ml.

Tanner, A. C. and WU, C. C. 1992. Adaptation of sensitive broth micro dilution technique to antimicrobial susceptibility testing of *Mycoplasma gallisepticum*. *Avian Diseases*, 36, 74-717.

*Mycobacterium tuberculosis* H37Rv Inhibition Assay

The measurement of the minimum inhibitory concentration (MIC) for each tested compound was performed in 96 wells flat-bottom, polystyrene microtiter plates. Ten two-fold drug dilutions in neat DMSO starting at 400 μM were performed. Five μl of these drug solutions were added to 95 μl of Middlebrook 7H9 medium. (Lines A-H, rows 1-10 of the plate layout). Isoniazid was used as a positive control, 8 two-fold dilution of Isoniazid starting at 160 μgml$^{-1}$ was prepared and 5 μl of this control curve was added to 95 μl of Middlebrook 7H9 (Difco catalogue Ref. 271310)+ADC medium (Becton Dickinson Catalogue Ref. 211887). (Row 11, lines A-H). Five μl of neat DMSO were added to row 12 (growth and Blank controls).

The inoculum was standardised to approximately 1×10$^7$ cfu/ml and diluted 1 in 100 in Middlebrook 7H9+ADC medium and 0.025% Tween 80 (Sigma P4780), to produce the final inoculum of H37Rv strain (ATCC25618). One hundred μl of this inoculum was added to the entire plate but G-12 and H-12 wells (Blank controls). All plates were placed in a sealed box to prevent drying out of the peripheral wells and they were incubated at 37° C. without shaking for six days. A resazurin solution was prepared by dissolving one tablet of resazurin (Resazurin Tablets for Milk Testing; Ref 330884Y VWR International Ltd) in 30 ml sterile PBS (phosphate buffered saline). 25 μl of this solution was added to each well. Fluorescence was measured (Spectramax M5 Molecular Devices, Excitation 530 nm, Emission 590 nm) after 48 hours to determine the MIC value.

Results of the *Mycobacterium tuberculosis* H37Rv Inhibition Assay

Examples 2, 4-13, 15A, 16-23, 25-28, 31, 34-39, 41, 43, 45, 46A, 49, 51B, 53, 56, 57, 64, 65, 73, 74, 77, 78, 80, 83, 86-89, 91, 94-97, 100, 101, 106, 107, 109, 110, 114, 116, 119-122, 129, 131, 134-136, 138-141A, 144, 147-149, 158, 159, 162, 164A, 165, 170A, 171, 173, 177, 179, 180, 182, 188-190, 193-194, 205, 209, 211, 212, 217-219, 225, 226, 228, 232, 237, 244, 251, 254, 257, 258, 265, 266, 270, 271, 273, 274, 276, 278 and 282-307 were tested in the *Mycobacterium tuberculosis* H37Rv inhibition assay. Examples 2, 4-13, 15A, 16-21, 27, 34, 37-39, 45, 46A, 51B, 53, 57, 65, 73, 74, 77, 80, 88, 89, 94, 95, 106, 107, 109, 110, 114, 116, 120, 122, 129, 131, 134-136, 138, 139, 144, 147-149, 158, 162, 164A, 165, 170A, 171, 173, 179, 180, 182, 190, 193, 205, 209, 211, 212, 217-219, 225, 226, 228, 237, 244, 273, 276, 278, 282-290, 292-298, 300, 302, 304-306 showed an MIC value of 4.0 μg/ml or lower. Examples 4-6, 8, 10-13, 15A, 16, 18, 19, 21, 27, 34, 39, 45, 46A, 65, 73, 77, 80, 88, 89, 94, 95, 106, 107, 109, 110, 114, 116, 122, 129, 135, 136, 139, 144, 147-149, 162, 164A, 165, 170A, 171, 173, 179, 182, 190, 205, 209, 211, 212, 217-219, 228, 237, 244, 273, 276, 278, 283-286, 290, 292-298, 300, 304-306 showed an MIC value of 1.7 μg/ml or lower.

The invention claimed is:
1. This invention provides a compound of formula (I) or a pharmaceutically acceptable salt or N-oxide thereof:

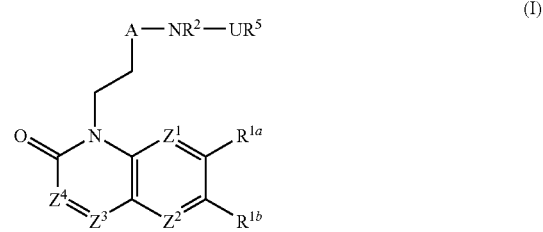

wherein:
two of $Z^1$, $Z^2$, $Z^3$ and $Z^4$ are independently $CR^{1c}$ or N and the remainder are independently $CR^{1c}$; or
$Z^3$ and $Z^4$ together represent S and one of $Z^1$ and $Z^2$ is $CR^{1c}$ or N and the other is independently $CR^{1c}$;
$R^{1a}$, $R^{1b}$ and $R^{1c}$ are independently selected from hydrogen; halogen; cyano; $(C_{1-6})$alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted$(C1-6)$alkyl; $(C_{1-6})$alkoxy-substituted$(C_{1-6})$alkyl; hydroxy $(C_{1-6})$alkyl; an amino group optionally N-substituted by one or two $(C_{1-6})$alkyl, formyl, $(C_{1-6})$alkylcarbonyl or $(C_{1-6})$alkylsulphonyl groups; or aminocarbonyl wherein the amino group is optionally substituted by $(C_{1-4})$alkyl; or two of $R^{1a}$, $R^{1b}$ and $R^{1c}$ on adjacent carbon atoms may together form an ethylenedioxy group;
$R^2$ is hydrogen, or $(C_{1-4})$alkyl, or together with $R^6$ forms Y as defined below;
A is a group (i):

in which: $R^3$ is as defined for $R^{1a}$, $R^{1b}$ and $R^{1c}$ or is oxo or aminomethyl and n is 1 or 2:

or A is a group (ii)

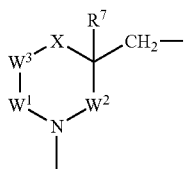

W¹, W² and W³ are CR⁴R⁸
or W² and W³ are CR⁴R⁸ and W¹ represents a bond between W³ and N;
X is O, CR⁴R⁸, or NR⁶;
one R⁴ is as defined for $R^{1a}$, $R^{1b}$ and $R^{1c}$ and the remainder and R⁸ are hydrogen or one R⁴ and R⁸ are together oxo and the remainder are hydrogen;
R⁶ is hydrogen or (C₁₋₆)alkyl; or together with R² forms Y;
R⁷ is hydrogen; halogen; hydroxy optionally substituted with (C₁₋₆)alkyl; or (C₁₋₆)alkyl;
Y is CR⁴R⁸CH₂; CH₂CR⁴R⁸; (C=O); CR⁴R⁸; CR⁴R⁸(C=O); or (C=O)CR⁴R⁸;
or when X is CR⁴R⁸, R⁸ and R⁷ together represent a bond;
U is selected from CO, and CH₂ and
R⁵ is

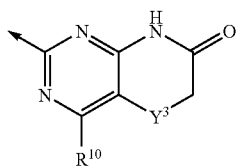

in which:
Y³ is CH₂ or O; and
R¹⁰ is independently selected from hydrogen, halogen, (C₁₋₆)alkyl and (C₁₋₆)alkoxy.

2. A compound according to claim 1 wherein each of $R^{1a}$, $R^{1b}$ and $R^{1c}$ is independently hydrogen, methoxy, methyl, ethyl, cyano, or halogen.

3. A compound according to claim 2 wherein $R^{1a}$ is methoxy, cyano, fluoro, chloro or bromo and R1b and R1c are hydrogen.

4. A compound according to claim 1 wherein R² is hydrogen.

5. A compound according to claim 1 wherein U is CH₂.

6. A compound according to claim 1 wherein R⁶ is selected from:
2-substituted 1H-pyrimido[5,4-b][1,4]oxazin-7(6H)-one;
2-substituted 4-chloro-1H-pyrimido[5,4-b][1,4]oxazin-7(6H)-one;
2-substituted 5,6-dihydropyrido[2,3-d]pyrimidin-7(1H)-one;
2-substituted 4-chloro-5,6-dihydropyrido[2,3-d]pyrimidin-7(1H)-one;
2-substituted 4-methyl-5,6-dihydropyrido[2,3-d]pyrimidin-7(1H)-one;
2-substituted 4-methyloxy-5,6-dihydropyrido[2,3-d]pyrimidin-7(1H)-one;

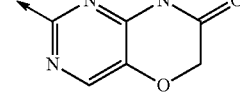 

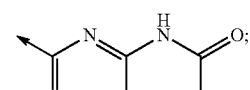 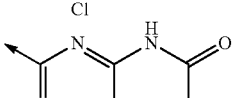

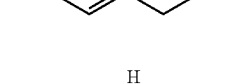 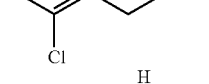

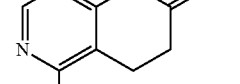 and 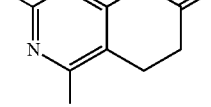

7. A compound according to claim 1 wherein:
each of Z¹, Z², Z³ and Z⁴ is independently $CR^{1c}$;
Z¹ is N and each of Z², Z³ and Z⁴ is independently $CR^{1c}$;
Z² is N and each of Z¹, Z³ and Z⁴ is independently $CR^{1c}$;
Z³ is N and each of Z¹, Z² and Z⁴ is independently $CR^{1c}$;
Z¹ and Z³ are N and Z² and Z⁴ are independently $CR^{1c}$;
Z² and Z³ are N and Z¹ and Z⁴ are independently $CR^{1c}$;
Z³ and Z⁴ are N and Z¹ and Z² are independently $CR^{1c}$;
Z³ and Z⁴ together are S and Z¹ and Z² are independently $CR^{1c}$;
Z³ and Z⁴ together are S and Z¹ is $CR^{1c}$ and Z² is N; or
Z¹ and Z² are N and Z³ and Z⁴ are independently $CR^{1c}$.

8. A compound according to claim 1 wherein A is a group (ia) in which n is 1 and R³ is hydrogen or hydroxy or A is 3-hydroxypyrrolidin-4-ylmethyl or 4-hydroxypiperidin-3-ylmethyl.

9. A compound according to claim 1 wherein A is a 4-hydroxypiperidin-3-ylmethyl.

10. A compound selected from:
2-[({1-[2-(7-Fluoro-2-oxo-1(2H)-quinolinyl)ethyl]-4-piperidinyl}amino)methyl]-1H-pyrimido[5,4-b][1,4]oxazin-7(6H)-one;
4-Chloro-2-[({1-[2-(7-fluoro-2-oxo-1(2H)-quinolinyl)ethyl]-4-piperidinyl}amino)methyl]-1H-pyrimido[5,4-b][1,4]oxazin-7(6H)-one;
2-{[(1-{2-[6-(Methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one;
4-Chloro-2-{[(1-{2-[6-(methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one;
4-Methyl-2-{[(1-{2-[6-(methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one;
4-(Methyloxy)-2-{[(1-{2-[6-(methyloxy)-3-oxopyrido[2,3-b]pyrazin-4(3H)-yl]ethyl}-4-piperidinyl)amino]methyl}-5,6-dihydropyrido[2,3-d]pyrimidin-7(1H)-one;
2-({[((3S)-1-{2-[6-(Methyloxy)-3-oxopyrido[2,3-b]pyrazin-4(3H)-yl]ethyl}-3-piperidinyl)methyl]amino}methyl)-5,6-dihydropyrido[2,3-d]pyrimidin-7(1H)-one;
the free base of a compound of the following table;

TABLE
| Example number | Structure |
|---|---|
| 142 | 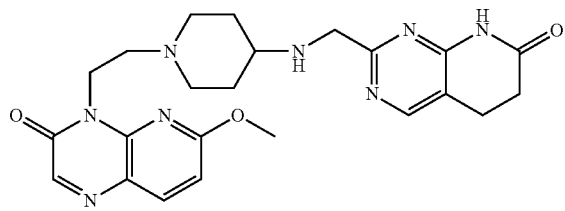 |
| 143 | 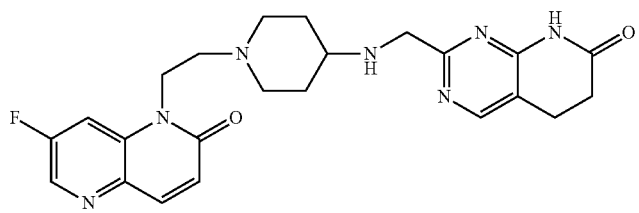 |
| 144 | 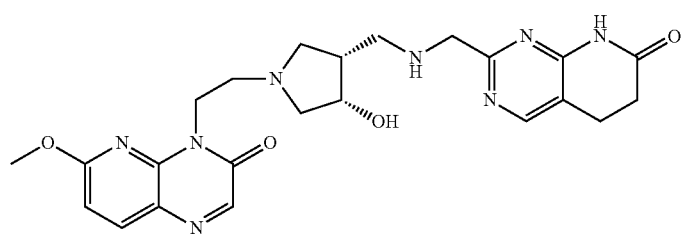 |
| 145 | 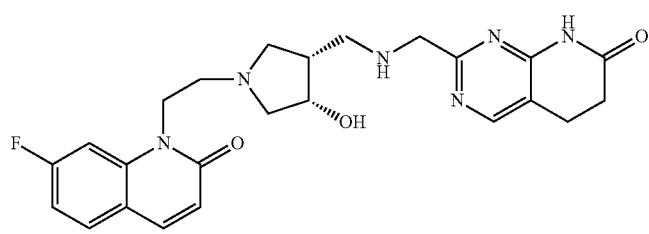 |
| 146 | 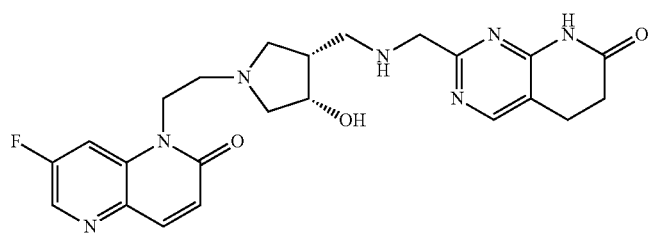 |
| 147 | 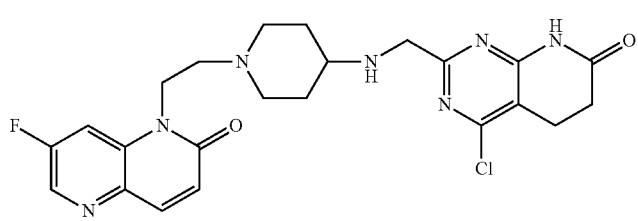 |

TABLE-continued
| Example number | Structure |
|---|---|
| 148 | 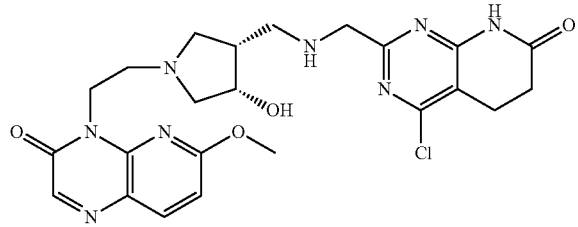 |
| 149 | 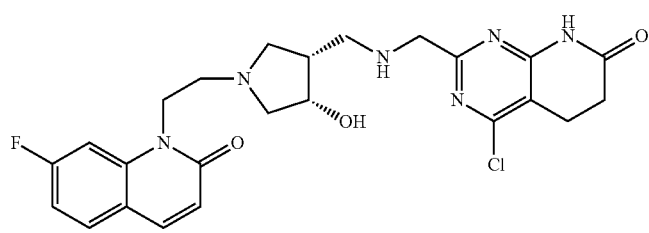 |
| 150 | 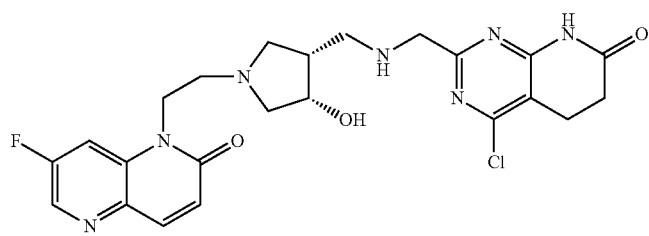 |
| 151 | 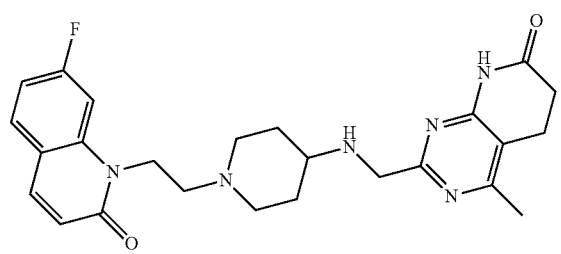 |
| 152 | 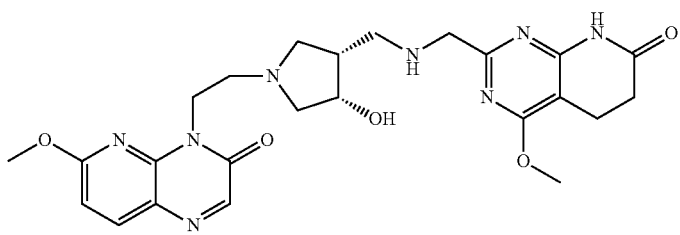 |
| 153 | 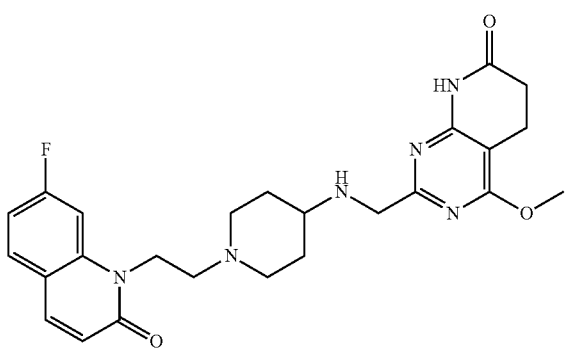 |

TABLE-continued
| Example number | Structure |
|---|---|
| 267 | 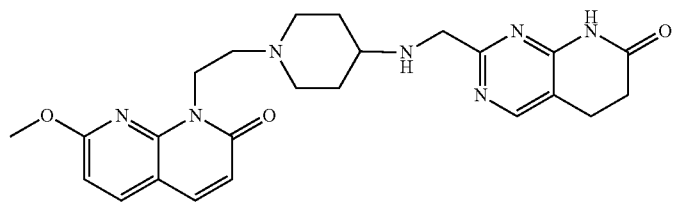 |
| 278 | 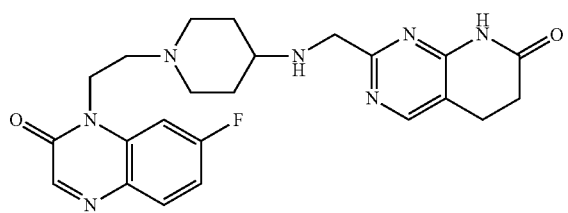 |
| 312 | 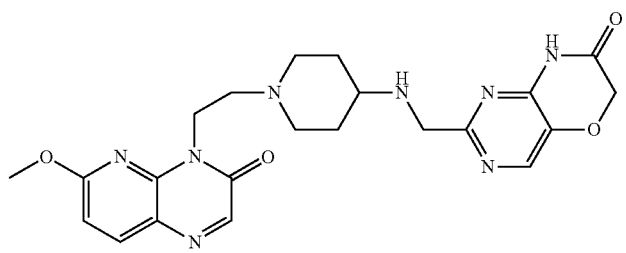 |
| 313 | 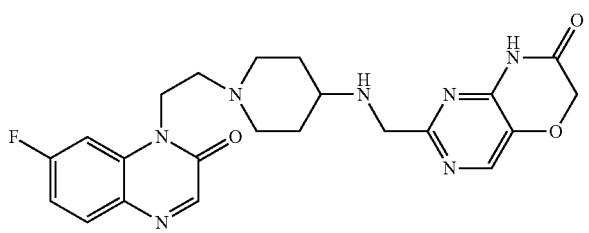 |
| 314 | 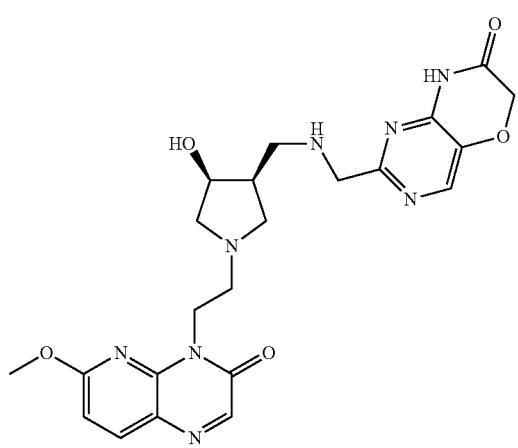 |

TABLE-continued

| Example number | Structure |
|---|---|
| 315 | 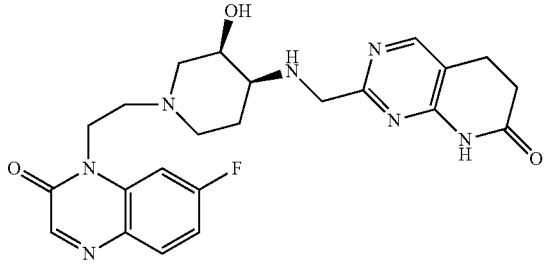 | or a pharmaceutically acceptable salt thereof.

11. A method of treatment of bacterial infections in mammals, which method comprises the administration to a mammal in need of such treatment an effective amount of a compound according to claim 1.

12. A pharmaceutical composition comprising a compound according to claim 1 and a pharmaceutically acceptable carrier.

13. A compound according to claim 6 wherein:
each of $Z^1$, $Z^2$, $Z^3$ and $Z^4$ is independently $CR^{1c}$;
$Z^1$ is N and each of $Z^2$, $Z^3$ and $Z^4$ is independently $CR^{1c}$;
$Z^2$ is N and each of $Z^1$, $Z^3$ and $Z^4$ is independently $CR^{1c}$;
$Z^3$ is N and each of $Z^1$, $Z^2$ and $Z^4$ is independently $CR^{1c}$;
$Z^1$ and $Z^3$ are N and $Z^2$ and $Z^4$ are independently $CR^{1c}$;
$Z^2$ and $Z^3$ are N and $Z^1$ and $Z^4$ are independently $CR^{1c}$;
$Z^3$ and $Z^4$ are N and $Z^1$ and $Z^2$ are independently $CR^{1c}$;
$Z^3$ and $Z^4$ together are S and $Z^1$ and $Z^2$ are independently $CR^{1c}$;
$Z^3$ and $Z^4$ together are S and $Z^1$ is $CR^{1c}$ and $Z^2$ is N; or
$Z^1$ and $Z^2$ are N and $Z^3$ and $Z^4$ are independently $CR^{1c}$.

14. A compound according to claim 6 wherein A is a group (ia) in which n is 1 and $R^3$ is hydrogen or hydroxy or A is 3-hydroxypyrrolidin-4-ylmethyl or 4-hydroxypiperidin-3-ylmethyl.

15. A compound according to claim 7 wherein A is a group (ia) in which n is 1 and $R^3$ is hydrogen or hydroxy or A is 3-hydroxypyrrolidin-4-ylmethyl or 4-hydroxypiperidin-3-ylmethyl.

16. A compound according to claim 13 wherein A is a group (ia) in which n is 1 and $R^3$ is hydrogen or hydroxy or A is 3-hydroxypyrrolidin-4-ylmethyl or 4-hydroxypiperidin-3-ylmethyl.

* * * * *